US009574204B2

(12) United States Patent
Meyer et al.

(10) Patent No.: US 9,574,204 B2
(45) Date of Patent: Feb. 21, 2017

(54) PLANT SEEDS WITH ALTERED STORAGE COMPOUND LEVELS, RELATED CONSTRUCTS AND METHODS INVOLVING GENES ENCODING PAE AND PAE-LIKE POLYPEPTIDES

(75) Inventors: Knut Meyer, Wilmington, DE (US); Brian McGonigle, Wilmington, DE (US); Kevin L Stecca, New Castle, DE (US)

(73) Assignee: E I DUPONT DE NEMOURS AND COMPANY, Wilmington, DE (US)

( * ) Notice: Subject to any disclaimer, the term of this patent is extended or adjusted under 35 U.S.C. 154(b) by 757 days.

(21) Appl. No.: 13/807,018

(22) PCT Filed: Jun. 29, 2011

(86) PCT No.: PCT/US2011/042326

§ 371 (c)(1),
(2), (4) Date: Mar. 25, 2014

(87) PCT Pub. No.: WO2012/003207

PCT Pub. Date: Jan. 5, 2012

(65) Prior Publication Data

US 2014/0304856 A1 Oct. 9, 2014

Related U.S. Application Data

(60) Provisional application No. 61/360,648, filed on Jul. 1, 2010.

(51) Int. Cl.

*C12N 15/82* (2006.01)
*C12N 9/18* (2006.01)
*A01H 5/10* (2006.01)

(52) U.S. Cl.

CPC ............. *C12N 15/8245* (2013.01); *C12N 9/18* (2013.01); *C12N 15/8234* (2013.01); *C12N 15/8246* (2013.01); *C12N 15/8247* (2013.01); *C12N 15/8251* (2013.01); *C12Y 301/01006* (2013.01)

(58) Field of Classification Search

None
See application file for complete search history.

(56) References Cited

U.S. PATENT DOCUMENTS

2006/0107345 A1 * 5/2006 Alexandrov ......... C07K 14/415
800/278

FOREIGN PATENT DOCUMENTS

| | | | |
|---|---|---|---|
| EP | 1033405 | A2 | 9/2000 |
| WO | 00/09719 | A1 | 2/2000 |
| WO | 02/10210 | A2 | 2/2000 |
| WO | 00/17368 | A1 | 3/2000 |
| WO | 01/14534 | A2 | 3/2001 |
| WO | 01/96584 | A2 | 12/2001 |
| WO | 2007/095243 | A2 | 8/2007 |
| WO | 2009/140770 | A1 | 11/2009 |

OTHER PUBLICATIONS

*Arabidopsis thaliana* At2g46930, GenBank AY052671.1, published Sep. 5, 2001.*
Al-Hadid, PhD Thesis, Purdue University, Dec. 2009.*
Schmutz et al., 2010, Nature 463: 178-183, corrigendum in Nature 465: 120.*
Glyma02g00930 sequence, SoyBase and the Soybean Breeder's Toolbox, at http://www.Soybase.org.*
Christelle Breton et al., PCR cloning and expression analysis of a cDNA encoding a pectinacetylesterase from Vigna radiata L., FEBS Letters, 1996, pp. 139-142, vol. 388.
Jin-Ying Gou et al., Characterization of Pectin Acetylesterase Reveals Critical Roles of Cell Wall Acylesterification in Plant Growth and Development, Joint Meeting, Genomics: GTL Awardee Workshop VII and USDA-DOE Plant Feedstock Genomics for Bioenergy Awardee Workshop 2009, Bethesda, Maryland, Feb. 8-11, 2009, p. 52.
Isabel Vercauteren et al., An *Arabidopsis thaliana* Pectin Acetylesterase Gene Is Upregulated in Nematode Feeding Sites Induced by Root-knot and Cyst Nematodes, Molecular Plant-Microbe Interactions, 2002, pp. 404-407, vol. 15, No. 4.
Database Accession No. AK286337, Glycine max cDNA, clone: GMFL01-26-E11, Oct. 31, 2008.
International Search Report—PCT/US2011/042326, mailed Dec. 19, 2011.

* cited by examiner

*Primary Examiner* — David T Fox
*Assistant Examiner* — Bratislav Stankovic

(57) ABSTRACT

This invention is in the field of plant molecular biology. More specifically, this invention pertains to isolated nucleic acid fragments encoding PAE or PAE-Like proteins in plants and seeds and the use of such fragments to modulate expression of a gene encoding PAE or PAE-Like protein activity in a transformed host cell.

12 Claims, 5 Drawing Sheets

FIG.1D

Figure 1A:
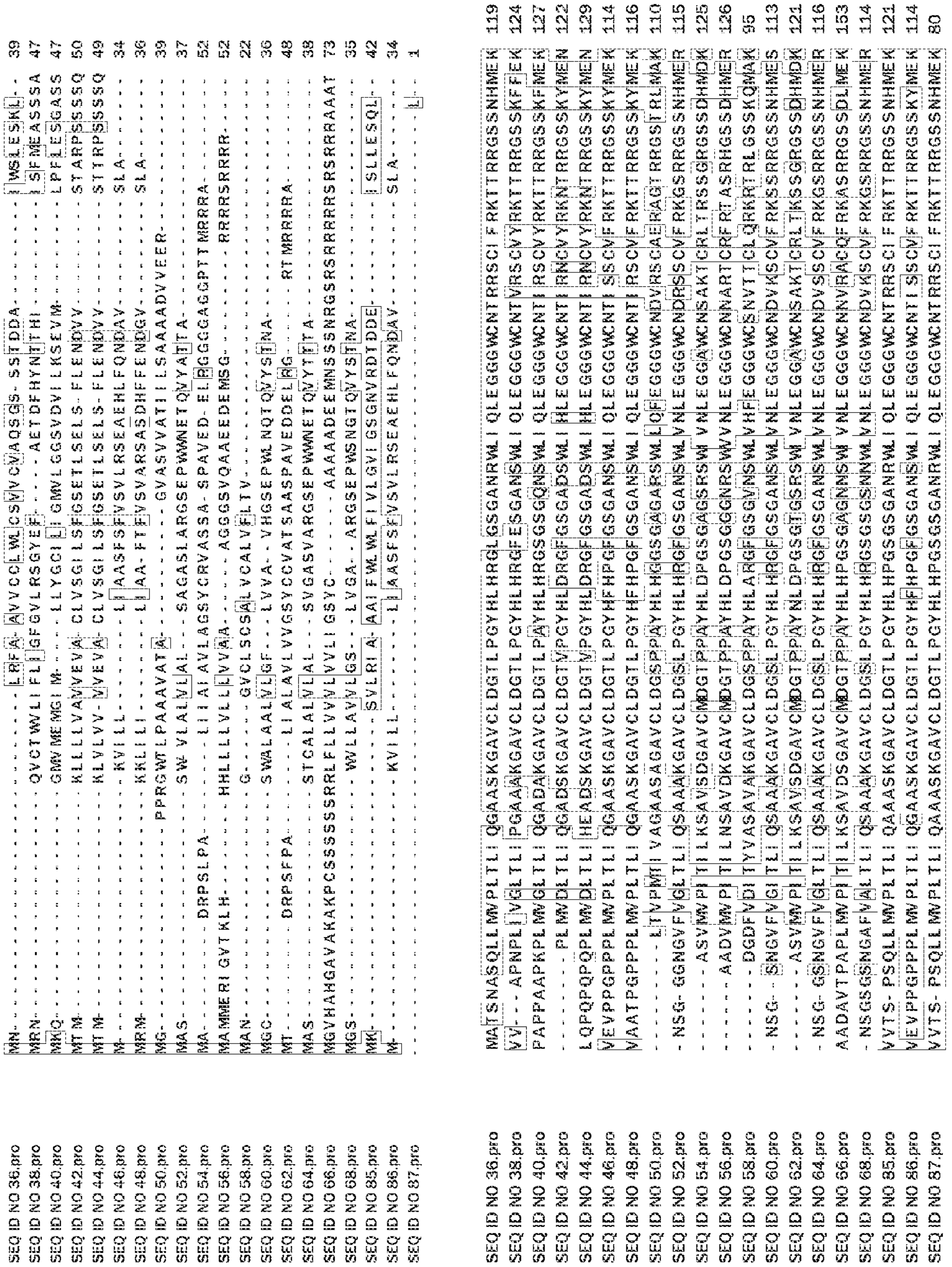

| | | |
|---|---|---|
| SEQ ID NO 36.pro | | 414 |
| SEQ ID NO 38.pro | -------------------------------------S. | 421 |
| SEQ ID NO 40.pro | | 423 |
| SEQ ID NO 42.pro | ---------------------FK. | 420 |
| SEQ ID NO 44.pro | ---------------------FK. | 427 |
| SEQ ID NO 46.pro | SDDGIPTNTMTMIYSHSTRLTFSTGLYMLRVLLAFTCS. | 460 |
| SEQ ID NO 48.pro | SDDDTPTNTMTMIYSRSTRLTFSSGLYMLSILLPFTCS. | 462 |
| SEQ ID NO 50.pro | -----PID-------------KNG----------FAGA. | 420 |
| SEQ ID NO 52.pro | ---------------RGDH. | 414 |
| SEQ ID NO 54.pro | | 422 |
| SEQ ID NO 56.pro | | 419 |
| SEQ ID NO 58.pro | | 398 |
| SEQ ID NO 60.pro | ---------------RGDY. | 412 |
| SEQ ID NO 62.pro | | 418 |
| SEQ ID NO 64.pro | ---------------RGDH. | 415 |
| SEQ ID NO 66.pro | | 454 |
| SEQ ID NO 68.pro | ---------------XGRHL. | 414 |
| SEQ ID NO 85.pro | | 417 |
| SEQ ID NO 86.pro | --------------------------------------K | 409 |
| SEQ ID NO 87.pro | --------------------------------------K | 375 |

FIG.2

Percent Identity

| | 1 | 2 | 3 | 4 | 5 | 6 | 7 | 8 | 9 | 10 | 11 | 12 | 13 | 14 | 15 | 16 | 17 | 18 | 19 | 20 | | |
|---|---|---|---|---|---|---|---|---|---|---|---|---|---|---|---|---|---|---|---|---|---|---|
| 1 | | 64.7 | 65.2 | 65.2 | 64.3 | 67.6 | 67.6 | 48.3 | 58.0 | 49.3 | 53.1 | 49.7 | 57.5 | 50.7 | 57.7 | 51.7 | 56.0 | 84.3 | 68.5 | 89.1 | 1 | SEQ ID NO 36.pro |
| 2 | 44.4 | | 65.6 | 63.3 | 63.9 | 63.7 | 64.4 | 44.8 | 58.2 | 46.8 | 48.9 | 52.0 | 59.2 | 47.4 | 57.3 | 49.6 | 55.8 | 62.6 | 65.5 | 67.5 | 2 | SEQ ID NO 38.pro |
| 3 | 43.8 | 43.1 | | 69.3 | 69.5 | 67.4 | 68.6 | 47.9 | 60.1 | 49.1 | 52.7 | 53.0 | 61.9 | 49.3 | 60.5 | 52.2 | 59.4 | 65.0 | 69.9 | 70.4 | 3 | SEQ ID NO 40.pro |
| 4 | 46.3 | 46.8 | 37.9 | | 95.2 | 72.9 | 74.0 | 46.4 | 58.2 | 49.0 | 50.8 | 51.0 | 57.8 | 49.3 | 57.8 | 50.0 | 55.3 | 62.8 | 74.6 | 68.3 | 4 | SEQ ID NO 42.pro |
| 5 | 49.1 | 47.1 | 39.1 | 2.9 | | 71.2 | 72.6 | 46.9 | 56.5 | 48.6 | 51.3 | 50.5 | 57.0 | 49.0 | 55.7 | 50.1 | 53.9 | 62.4 | 74.1 | 67.7 | 5 | SEQ ID NO 44.pro |
| 6 | 40.1 | 43.1 | 38.8 | 26.3 | 28.8 | | 91.1 | 46.9 | 59.9 | 47.2 | 51.3 | 51.3 | 59.7 | 48.1 | 59.3 | 45.6 | 57.7 | 65.7 | 99.8 | 72.0 | 6 | SEQ ID NO 46.pro |
| 7 | 38.8 | 42.4 | 38.2 | 24.1 | 27.3 | 8.1 | | 47.9 | 60.6 | 49.1 | 51.8 | 51.8 | 60.7 | 49.3 | 60.2 | 46.7 | 58.9 | 65.7 | 92.2 | 72.3 | 7 | SEQ ID NO 48.pro |
| 8 | 70.3 | 83.0 | 72.3 | 75.9 | 76.2 | 75.2 | 74.0 | | 47.8 | 41.0 | 44.4 | 47.2 | 47.8 | 43.5 | 47.5 | 43.8 | 46.9 | 48.0 | 47.9 | 52.0 | 8 | SEQ ID NO 50.pro |
| 9 | 57.6 | 56.2 | 54.7 | 57.7 | 60.3 | 53.6 | 53.7 | 74.2 | | 47.6 | 51.7 | 52.0 | 84.2 | 48.3 | 94.7 | 51.0 | 81.6 | 57.0 | 60.6 | 62.1 | 9 | SEQ ID NO 52.pro |
| 10 | 74.0 | 78.5 | 74.3 | 71.2 | 71.8 | 73.6 | 71.7 | 89.2 | 76.2 | | 64.2 | 43.0 | 50.5 | 89.5 | 48.9 | 66.8 | 48.3 | 49.9 | 48.7 | 54.1 | 10 | SEQ ID NO 54.pro |
| 11 | 63.1 | 73.4 | 65.9 | 63.6 | 64.5 | 64.5 | 63.2 | 82.6 | 65.8 | 38.1 | | 46.5 | 51.7 | 66.7 | 51.6 | 65.9 | 51.2 | 53.5 | 52.6 | 57.6 | 11 | SEQ ID NO 56.pro |
| 12 | 72.9 | 67.3 | 65.5 | 71.3 | 72.3 | 69.1 | 68.5 | 75.7 | 67.6 | 90.9 | 77.8 | | 52.8 | 43.7 | 52.8 | 45.0 | 51.8 | 50.0 | 51.0 | 52.8 | 12 | SEQ ID NO 58.pro |
| 13 | 55.6 | 55.5 | 52.1 | 56.9 | 58.6 | 54.5 | 53.9 | 73.3 | 15.1 | 73.6 | 67.5 | 65.8 | | 51.2 | 85.7 | 50.7 | 82.5 | 57.5 | 60.1 | 62.1 | 13 | SEQ ID NO 60.pro |
| 14 | 70.8 | 76.2 | 71.8 | 71.2 | 72.4 | 73.6 | 70.4 | 86.3 | 74.0 | 8.2 | 35.8 | 86.7 | 70.8 | | 49.2 | 69.1 | 48.3 | 50.6 | 49.1 | 54.7 | 14 | SEQ ID NO 62.pro |
| 15 | 58.1 | 57.5 | 54.5 | 59.0 | 62.1 | 54.9 | 55.0 | 75.8 | 4.5 | 73.0 | 66.1 | 65.8 | 13.9 | 72.1 | | 51.6 | 82.9 | 56.6 | 60.1 | 61.6 | 15 | SEQ ID NO 64.pro |
| 16 | 65.8 | 72.1 | 66.1 | 69.1 | 70.1 | 68.9 | 65.8 | 80.5 | 69.2 | 36.9 | 36.7 | 82.3 | 66.9 | 33.2 | 67.2 | | 50.2 | 53.0 | 50.6 | 57.9 | 16 | SEQ ID NO 66.pro |
| 17 | 59.9 | 61.3 | 56.9 | 61.3 | 64.2 | 57.6 | 56.2 | 74.2 | 17.6 | 75.5 | 68.4 | 69.0 | 17.9 | 74.6 | 16.3 | 69.5 | | 56.0 | 58.4 | 61.1 | 17 | SEQ ID NO 68.pro |
| 18 | 15.0 | 48.7 | 46.0 | 49.7 | 51.5 | 41.6 | 40.8 | 74.5 | 58.5 | 72.4 | 64.1 | 73.5 | 58.1 | 70.6 | 59.6 | 64.8 | 60.5 | | 67.2 | 100.0 | 18 | SEQ ID NO 85.pro |
| 19 | 40.1 | 42.9 | 38.5 | 26.2 | 28.7 | 0.0 | 6.7 | 73.8 | 52.4 | 73.6 | 64.5 | 67.7 | 53.3 | 73.6 | 53.7 | 68.9 | 56.9 | 41.4 | | 72.3 | 19 | SEQ ID NO 86.pro |
| 20 | 10.6 | 40.7 | 37.7 | 40.0 | 42.2 | 34.4 | 34.0 | 67.5 | 51.3 | 62.6 | 56.2 | 68.6 | 51.5 | 61.4 | 52.4 | 55.6 | 54.0 | 0.0 | 34.3 | | 20 | SEQ ID NO 87.pro |
| | 1 | 2 | 3 | 4 | 5 | 6 | 7 | 8 | 9 | 10 | 11 | 12 | 13 | 14 | 15 | 16 | 17 | 18 | 19 | 20 | | |

SEQUENCE LISTING

<160> NUMBER OF SEQ ID NOS: 107

<210> SEQ ID NO 1
<211> LENGTH: 18491
<212> TYPE: DNA
<213> ORGANISM: artificial sequence
<220> FEATURE:
<223> OTHER INFORMATION: pHSbarEND2s activation tagging vector

<400> SEQUENCE: 1
catgaatcaa acaaacatac acagcgactt attcacacga gctcaaatta caacggtata 60
tatcctgccg tcgacaacca tggtctagac aggatccccg ggtaccgagc tcgaatttgc 120
aggtcgactg cgtcatccct tacgtcagtg gagatatcac atcaatccac ttgctttgaa 180
gacgtggttg gaacgtcttc tttttccacg atgctcctcg tgggtggggg tccatctttg 240
ggaccactgt cggcagaggc atcttgaacg atagcctttc ctttatcgca atgatggcat 300
ttgtaggtgc caccttcctt ttctactgtc cttttgatga agtgacagat agctgggcaa 360
tggaatccga ggaggtttcc cgatattacc ctttgttgaa aagtctcaat tgccctttgg 420
tcttctgaga ctgttgcgtc atcccttacg tcagtggaga tatcacatca atccacttgc 480
tttgaagacg tggttggaac gtcttctttt tccacgatgc tcctcgtggg tgggggtcca 540
tctttgggac cactgtcggc agaggcatct tgaacgatag cctttccttt atcgcaatga 600
tggcatttgt aggtgccacc ttccttttct actgtccttt tgatgaagtg acagatagct 660
gggcaatgga atccgaggag gtttcccgat attacccttt gttgaaaagt ctcagttaac 720
ccgcgatcct gcgtcatccc ttacgtcagt ggagatatca catcaatcca cttgctttga 780
agacgtggtt ggaacgtctt ctttttccac gatgctcctc gtgggtgggg gtccatcttt 840
gggaccactg tcggcagagg catcttgaac gatagccttt cctttatcgc aatgatggca 900
tttgtaggtg ccaccttcct tttctactgt ccttttgatg aagtgacaga tagctgggca 960
atggaatccg aggaggtttc ccgatattac cctttgttga aaagtctcaa ttgccctttg 1020
gtcttctgag actgttgcgt catcccttac gtcagtggag atatcacatc aatccacttg 1080
ctttgaagac gtggttggaa cgtcttcttt ttccacgatg ctcctcgtgg gtgggggtcc 1140
atctttggga ccactgtcgg cagaggcatc ttgaacgata gcctttcctt tatcgcaatg 1200
atggcatttg taggtgccac cttccttttc tactgtcctt ttgatgaagt gacagatagc 1260
tgggcaatgg aatccgagga ggtttcccga tattaccctt tgttgaaaag tctcagttaa 1320
cccgcaattc actggccgtc gttttacaac gtcgtgactg ggaaaaccct ggcgttaccc 1380
aacttaatcg ccttgcagca catccccctt tcgccagctg gcgtaatagc gaagaggccc 1440
gcaccgatcg cccttcccaa cagttgcgca gcctgaatgg cgaatggatc gatccgtcga 1500
tcgaccaaag cggccatcgt gcctccccac tcctgcagtt cgggggcatg gatgcgcgga 1560
tagccgctgc tggtttcctg gatgccgacg gatttgcact gccggtagaa ctccgcgagg 1620
tcgtccagcc tcaggcagca gctgaaccaa ctcgcgaggg gatcgagccc ctgctgagcc 1680
tcgacatgtt gtcgcaaaat tcgccctgga cccgcccaac gatttgtcgt cactgtcaag 1740
gtttgacctg cacttcattt ggggcccaca tacaccaaaa aaatgctgca taattctcgg 1800
ggcagcaagt cggttacccg gccgccgtgc tggaccgggt tgaatggtgc ccgtaacttt 1860
cggtagagcg gacggccaat actcaacttc aaggaatctc acccatgcgc gccggcgggg 1920
aaccggagtt cccttcagtg aacgttatta gttcgccgct cggtgtgtcg tagatactag 1980
cccctggggc cttttgaaat ttgaataaga tttatgtaat cagtctttta ggtttgaccg 2040

```
gttctgccgc ttttttaaa attggatttg taataataaa acgcaattgt ttgttattgt   2100
ggcgctctat catagatgtc gctataaacc tattcagcac aatatattgt tttcatttta   2160
atattgtaca tataagtagt agggtacaat cagtaaattg aacggagaat attattcata   2220
aaaatacgat agtaacgggt gatatattca ttagaatgaa ccgaaaccgg cggtaaggat   2280
ctgagctaca catgctcagg tttttacaa cgtgcacaac agaattgaaa gcaaatatca   2340
tgcgatcata ggcgtctcgc atatctcatt aaagcagggg gtgggcgaag aactccagca   2400
tgagatcccc gcgctggagg atcatccagc cggcgtcccg gaaaacgatt ccgaagccca   2460
acctttcata gaaggcggcg gtggaatcga aatctcgtga tggcaggttg ggcgtcgctt   2520
ggtcggtcat ttcgaacccc agagtcccgc tcagaagaac tcgtcaagaa ggcgatagaa   2580
ggcgatgcgc tgcgaatcgg gagcggcgat accgtaaagc acgaggaagc ggtcagccca   2640
ttcgccgcca agctcttcag caatatcacg ggtagccaac gctatgtcct gatagcggtc   2700
cgccacaccc agccggccac agtcgatgaa tccagaaaag cggccatttt ccaccatgat   2760
attcggcaag caggcatcgc catgggtcac gacgagatcc tcgccgtcgg gcatgccccc   2820
caattcactg gccgtcgttt tacaacgtcg tgactgggaa aaccctggcg ttacccaact   2880
taatcgcctt gcagcacatc ccccttcgc cagctggcgt aatagcgaag aggcccgcac   2940
cgatcgccct tcccaacagt tgcgcagcct gaatggcgaa tggcgcctga tgcggtattt   3000
tctccttacg catctgtgcg gtatttcaca ccgcatatgg tgcactctca gtacaatctg   3060
ctctgatgcc gcatagttaa gccagccccg acacccgcca acacccgctg acgcgccctg   3120
acgggcttgt ctgctcccgg catccgctta cagacaagct gtgaccgtct ccgggagctg   3180
catgtgtcag aggttttcac cgtcatcacc gaaacgcgcg agacgaaagg gcctcgtgat   3240
acgcctattt ttataggtta atgtcatgat aataatggtt tcttagacgt caggtggcac   3300
ttttcgggga aatgtgcgcg gaacccctat ttgtttattt ttctaaatac attcaaatat   3360
gtatccgctc atgagacaat aaccctgata aatgcttcaa taatattgaa aaaggaagag   3420
tatgagtatt caacatttcc gtgtcgccct tattcccttt tttgcggcat tttgccttcc   3480
tgtttttgct cacccagaaa cgctggtgaa agtaaaagat gctgaagatc agttgggtgc   3540
acgagtgggt tacatcgaac tggatctcaa cagcggtaag atccttgaga gttttcgccc   3600
cgaagaacgt tttccaatga tgagcacttt taaagttctg ctatgtggcg cggtattatc   3660
ccgtattgac gccgggcaag agcaactcgg tcgccgcata cactattctc agaatgactt   3720
ggttgagtac tcaccagtca cagaaaagca tcttacggat ggcatgacag taagagaatt   3780
atgcagtgct gccataacca tgagtgataa cactgcggcc aacttacttc tgacaacgat   3840
cggaggaccg aaggagctaa ccgctttttt gcacaacatg ggggatcatg taactcgcct   3900
tgatcgttgg gaaccggagc tgaatgaagc cataccaaac gacgagcgtg acaccacgat   3960
gcctgtagca atggcaacaa cgttgcgcaa actattaact ggcgaactac ttactctagc   4020
ttcccggcaa caattaatag actggatgga ggcggataaa gttgcaggac cacttctgcg   4080
ctcggccctt ccggctggct ggtttattgc tgataaatct ggagccggtg agcgtgggtc   4140
tcgcggtatc attgcagcac tggggccaga tggtaagccc tcccgtatcg tagttatcta   4200
cacgacgggg agtcaggcaa ctatggatga acgaaataga cagatcgctg agataggtgc   4260
ctcactgatt aagcattggt aactgtcaga ccaagtttac tcatatatac tttagattga   4320
tttaaaactt catttttaat ttaaaaggat ctaggtgaag atcctttttg ataatctcat   4380
```

-continued

```
gaccaaaatc ccttaacgtg agttttcgtt ccactgagcg tcagaccccg tagaaaagat   4440
caaaggatct tcttgagatc cttttttctt gcgcgtaatc tgctgcttgc aaacaaaaaa   4500
accaccgcta ccagcggtgg tttgtttgcc ggatcaagag ctaccaactc tttttccgaa   4560
ggtaactggc ttcagcagag cgcagatacc aaatactgtc cttctagtgt agccgtagtt   4620
aggccaccac ttcaagaact ctgtagcacc gcctacatac ctcgctctgc taatcctgtt   4680
accagtggct gctgccagtg gcgataagtc gtgtcttacc gggttggact caagacgata   4740
gttaccggat aaggcgcagc ggtcgggctg aacggggggt tcgtgcacac agcccagctt   4800
ggagcgaacg acctacaccg aactgagata cctacagcgt gagcattgag aaagcgccac   4860
gcttcccgaa gggagaaagg cggacaggta tccggtaagc ggcagggtcg gaacaggaga   4920
gcgcacgagg gagcttccag ggggaaacgc ctggtatctt tatagtcctg tcgggtttcg   4980
ccacctctga cttgagcgtc gatttttgtg atgctcgtca ggggggcgga gcctatggaa   5040
aaacgccagc aacgcggcct ttttacggtt cctggccttt tgctggcctt ttgctcacat   5100
gttctttcct gcgttatccc ctgattctgt ggataaccgt attaccgcct ttgagtgagc   5160
tgataccgct cgccgcagcc gaacgaccga gcgcagcgag tcagtgagcg aggaagcgga   5220
agagcgccca atacgcaaac cgcctctccc cgcgcgttgg ccgattcatt aatgcagctg   5280
gcacgacagg tttcccgact ggaaagcggg cagtgagcgc aacgcaatta atgtgagtta   5340
gctcactcat taggcacccc aggctttaca ctttatgctt ccggctcgta tgttgtgtgg   5400
aattgtgagc ggataacaat ttcacacagg aaacagctat gaccatgatt acgccaagct   5460
ttctaggggg ggggtaccga tctgagatcg gtaacgaaaa cgaacgggta gggatgaaaa   5520
cggtcggtaa cggtcggtaa aatacctcta ccgttttcat tttcatattt aacttgcggg   5580
acggaaacga aaacgggata taccggtaac gaaaacgaac gggataaata cggtaatcga   5640
aaaccgatac gatccggtcg ggttaaagtc gaaatcggac gggaaccggt atttttgttc   5700
ggtaaaatca cacatgaaaa catatattca aaacttaaaa acaaatataa aaaattgtaa   5760
acacaagtct taatgatcac tagtggcgcg cctaggagat ctcgagtagg gataacaggg   5820
taatacatag ataaaatcca tataaatctg gagcacacat agtttaatgt agcacataag   5880
tgataagtct tgggctcttg gctaacataa gaagccatat aagtctacta gcacacatga   5940
cacaatataa agtttaaaac acatattcat aatcacttgc tcacatctgg atcacttagc   6000
atgctacagc tagtgcaata ttagacactt tccaatattt ctcaaacttt tcactcattg   6060
caacggccat tctcctaatg acaaattttt catgaacaca ccattggtca atcaaatcct   6120
ttatctcaca gaaacctttg taaaataaat ttgcagtgga atattgagta ccagatagga   6180
gttcagtgag atcaaaaaac ttcttcaaac acttaaaaag agttaatgcc atcttccact   6240
cctcggcttt aggacaaatt gcatcgtacc tacaataatt gacatttgat taattgagaa   6300
tttataatga tgacatgtac aacaattgag acaaacatac ctgcgaggat cacttgtttt   6360
aagccgtgtt agtgcaggct tataatataa ggcatccctc aacatcaaat aggttgaatt   6420
ccatctagtt gagacatcat atgagatccc tttagattta tccaagtcac attcactagc   6480
acacttcatt agttcttccc actgcaaagg agaagatttt acagcaagaa caatcgcttt   6540
gattttctca attgttcctg caattacagc caagccatcc tttgcaacca agttcagtat   6600
gtgacaagca cacctcacat gaaagaaagc accatcacaa actagatttg aatcagtgtc   6660
ctgcaaatcc tcaattatat cgtgcacagc tacttcattt gcactagcat tatccaaaga   6720
caaggcaaac aatttttttct caatgttcca cttaaccatg attgcagtga aggtttgtga   6780
```

-continued

```
taacctttgg ccagtgtggc gcccttcaac atgaaaaaag ccaacaattc ttttttggag   6840
acaccaatca tcatcaatcc aatggatggt gacacacatg tatgacttat tttgacaaga   6900
tgtccacata tccatagttg tactgaagcg agactgaaca tcttttagtt ttccatacaa   6960
cttttctttt tcttccaaat acaaatccat gatatatttt ctagcagtga cacgggactt   7020
tattggaaag tgagggcgca gagacttaac aaactcaaca aagtactcat gttctacaat   7080
attgaaagga tattcatgca tgattattgc caaatgaagc ttctttaggc taaccacttc   7140
atcgtactta taaggctcaa tgagatttat gtctttgcca tgatcctttt cactttttag   7200
acacaactga cctttaacta aactatgtga tgttctcaag tgatttcgaa atccgcttgt   7260
tccatgatga ccctcagccc tatacttagc cttgcaatta ggaaagttgc aatgtcccca   7320
tacctgaacg tatttctttc catcgacctc cacttcaatt tccttcttgg tgaaatgctg   7380
ccatacatcc gatgtgcact tctttgccct cttctgtggt gcttcttctt cgggttcagg   7440
ttgtggctgt ggttgtggtt ctggttgtgg ttgtggttgt ggttgtggtt catgaacaat   7500
agccatatca tcttgactcg gatctgtagc tgtaccattt gcattactac tgcttacact   7560
ctgaataaaa tgcctctcgg cctcagctgt tgatgatgat ggtgatgtgc ggccacatcc   7620
atgcccacgc gcacgtgcac gtacattctg aatccgacta gaagaggctt cagcttttct   7680
tttcaaccct gttataaaca gatttttcgt attattctac agtcaatatg atgcttccca   7740
atctacaacc aattagtaat gctaatgcta ttgctactgt ttttctaata tataccttga   7800
gcatatgcag agaatacgga atttgttttg cgagtagaag gcgctcttgt ggtagacatc   7860
aacttggcca atcttatggc tgagcctgag ggaggattat ttccaaccgg aggcgtcatc   7920
tgaggaatgg agtcgtagcc ggctagccga agtggagagc agagccctgg acagcaggtg   7980
ttcagcaatc agcttggtgc tgtactgctg tgacttgtga gcacctggac ggctggacag   8040
caatcagcag gtgttgcaga gcccctggac agcacacaaa tgacacaaca gcttggtgca   8100
atggtgctga cgtgctgtac tgctaagtgc tgtgagcctg tgagcagccg tggagacagg   8160
gagaccgcgg atggccggat gggcgagcgc cgagcagtgg aggtctggag gaccgctgac   8220
cgcagatggc ggatggcgga tgggcggacc gcggatgggc gagcagtgga gtggaggtct   8280
gggcggatgg gcggaccgcg gcgcggatgg gcgagtcgcg agcagtggag tggagggcgg   8340
accgtggatg gcggcgtctg cgtccggcgt gccgcgtcac ggccgtcacc gcgtgtggtg   8400
cctggtgcag cccagcggcc ggccggctgg gagacaggga gagtcggaga gagcaggcga   8460
gagcgagacg cgtcgccggc gtcggcgtgc ggctggcggc gtccggactc cggcgtgggc   8520
gcgtggcggc gtgtgaatgt gtgatgctgt tactcgtgtg gtgcctggcc gcctgggaga   8580
gaggcagagc agcgttcgct aggtatttct tacatgggct gggcctcagt ggttatggat   8640
gggagttgga gctggccata ttgcagtcat cccgaattag aaaatacggt aacgaaacgg   8700
gatcatcccg attaaaaacg ggatcccggt gaaacggtcg ggaaactagc tctaccgttt   8760
ccgtttccgt ttaccgtttt gtatatcccg tttccgttcc gttttcgttt tttacctcgg   8820
gttcgaaatc gatcgggata aaactaacaa aatcggttat acgataacgg tcggtacggg   8880
attttcccat cctactttca tccctgagat tattgtcgtt tctttcgcag atcggtaccc   8940
cccccctaga gtcgacatcg atctagtaac atagatgaca ccgcgcgcga taatttatcc   9000
tagtttgcgc gctatatttt gttttctatc gcgtattaaa tgtataattg cgggactcta   9060
atcataaaaa cccatctcat aaataacgtc atgcattaca tgttaattat tacatgctta   9120
```

-continued

```
acgtaattca acagaaatta tatgataatc atcgcaagac cggcaacagg attcaatctt   9180
aagaaacttt attgccaaat gtttgaacga tctgcttcga cgcactcctt ctttaggtac   9240
ggactagatc tcggtgacgg gcaggaccgg acggggcggt accggcaggc tgaagtccag   9300
ctgccagaaa cccacgtcat gccagttccc gtgcttgaag ccggccgccc gcagcatgcc   9360
gcggggggca tatccgagcg cctcgtgcat gcgcacgctc gggtcgttgg gcagcccgat   9420
gacagcgacc acgctcttga agccctgtgc ctccagggac ttcagcaggt gggtgtagag   9480
cgtggagccc agtcccgtcc gctggtggcg gggggagacg tacacggtcg actcggccgt   9540
ccagtcgtag gcgttgcgtg ccttccaggg gcccgcgtag gcgatgccgg cgacctcgcc   9600
gtccacctcg gcgacgagcc agggatagcg ctcccgcaga cggacgaggt cgtccgtcca   9660
ctcctgcggt tcctgcggct cggtacggaa gttgaccgtg cttgtctcga tgtagtggtt   9720
gacgatggtg cagaccgccg gcatgtccgc ctcggtggca cggcggatgt cggccgggcg   9780
tcgttctggg ctcatggatc tggattgaga gtgaatatga gactctaatt ggataccgag   9840
gggaatttat ggaacgtcag tggagcattt ttgacaagaa atatttgcta gctgatagtg   9900
accttaggcg acttttgaac gcgcaataat ggtttctgac gtatgtgctt agctcattaa   9960
actccagaaa cccgcggctg agtggctcct tcaatcgttg cggttctgtc agttccaaac  10020
gtaaaacggc ttgtcccgcg tcatcggcgg gggtcataac gtgactccct taattctccg  10080
ctcatgatcc ccgggtaccg agctcgaatt gcggctgagt ggctccttca atcgttgcgg  10140
ttctgtcagt tccaaacgta aaacggcttg tcccgcgtca tcggcggggg tcataacgtg  10200
actcccttaa ttctccgctc atgatcttga tcccctgcgc catcagatcc ttggcggcaa  10260
gaaagccatc cagtttactt tgcagggctt cccaacctta ccagagggcg ccccagctgg  10320
caattccggt tcgcttgctg tatcgatatg gtggatttat cacaaatggg acccgccgcc  10380
gacagaggtg tgatgttagg ccaggacttt gaaaatttgc gcaactatcg tatagtggcc  10440
gacaaattga cgccgagttg acagactgcc tagcatttga gtgaattatg tgaggtaatg  10500
ggctacactg aattggtagc tcaaactgtc agtatttatg tatatgagtg tatattttcg  10560
cataatctca gaccaatctg aagatgaaat gggtatctgg gaatggcgaa atcaaggcat  10620
cgatcgtgaa gtttctcatc taagccccca tttggacgtg aatgtagaca cgtcgaaata  10680
aagatttccg aattagaata atttgtttat tgctttcgcc tataaatacg acggatcgta  10740
atttgtcgtt ttatcaaaat gtactttcat tttataataa cgctgcggac atctacattt  10800
ttgaattgaa aaaaaattgg taattactct ttcttttct ccatattgac catcatactc  10860
attgctgatc catgtagatt tcccggacat gaagccattt acaattgaat atatcctgcc  10920
gccgctgccg ctttgcaccc ggtggagctt gcatgttggt ttctacgcag aactgagccg  10980
gttaggcaga taatttccat tgagaactga gccatgtgca ccttcccccc aacacggtga  11040
gcgacggggc aacggagtga tccacatggg acttttaaac atcatccgtc ggatggcgtt  11100
gcgagagaag cagtcgatcc gtgagatcag ccgacgcacc gggcaggcgc gcaacacgat  11160
cgcaaagtat ttgaacgcag gtacaatcga gccgacgttc accgtcaccc tggatgctgt  11220
aggcataggc ttggttatgc cggtactgcc gggcctcttg cgggatatcg tccattccga  11280
cagcatcgcc agtcactatg gcgtgctgct agcgctatat gcgttgatgc aatttctatg  11340
cgcacccgtt ctcggagcac tgtccgaccg ctttggccgc cgcccagtcc tgctcgcttc  11400
gctacttgga gccactatcg actacgcgat catggcgacc acacccgtcc tgtggtccaa  11460
cccctccgct gctatagtgc agtcggcttc tgacgttcag tgcagccgtc ttctgaaaac  11520
```

-continued gacatgtcgc acaagtccta agttacgcga caggctgccg ccctgccctt ttcctggcgt 11580
tttcttgtcg cgtgttttag tcgcataaag tagaatactt gcgactagaa ccggagacat 11640
tacgccatga acaagagcgc cgccgctggc ctgctgggct atgcccgcgt cagcaccgac 11700
gaccaggact tgaccaacca acgggccgaa ctgcacgcgg ccggctgcac caagctgttt 11760
tccgagaaga tcaccggcac caggcgcgac cgcccggagc tggccaggat gcttgaccac 11820
ctacgccctg gcgacgttgt gacagtgacc aggctagacc gcctggcccg cagcacccgc 11880
gacctactgg acattgccga gcgcatccag gaggccggcg cgggcctgcg tagcctggca 11940
gagccgtggg ccgacaccac cacgccggcc ggccgcatgg tgttgaccgt gttcgccggc 12000
attgccgagt tcgagcgttc cctaatcatc gaccgcaccc ggagcgggcg cgaggccgcc 12060
aaggcccgag gcgtgaagtt tggcccccgc cctaccctca ccccggcaca gatcgcgcac 12120
gcccgcgagc tgatcgacca ggaaggccgc accgtgaaag aggcggctgc actgcttggc 12180
gtgcatcgct cgaccctgta ccgcgcactt gagcgcagcg aggaagtgac gcccaccgag 12240
gccaggcggc gcggtgcctt ccgtgaggac gcattgaccg aggccgacgc cctggcggcc 12300
gccgagaatg aacgccaaga ggaacaagca tgaaaccgca ccaggacggc caggacgaac 12360
cgtttttcat taccgaagag atcgaggcgg agatgatcgc ggccgggtac gtgttcgagc 12420
cgcccgcgca cgtctcaacc gtgcggctgc atgaaatcct ggccggtttg tctgatgcca 12480
agctggcggc ctggccggcc agcttggccg ctgaagaaac cgagcgccgc cgtctaaaaa 12540
ggtgatgtgt atttgagtaa aacagcttgc gtcatgcggt cgctgcgtat atgatgcgat 12600
gagtaaataa acaaatacgc aagggaacgc atgaagttat cgctgtactt aaccagaaag 12660
gcgggtcagg caagacgacc atcgcaaccc atctagcccg cgccctgcaa ctcgccgggg 12720
ccgatgttct gttagtcgat tccgatcccc agggcagtgc ccgcgattgg gcggccgtgc 12780
gggaagatca accgctaacc gttgtcggca tcgaccgccc gacgattgac cgcgacgtga 12840
aggccatcgg ccggcgcgac ttcgtagtga tcgacggagc gccccaggcg gcggacttgg 12900
ctgtgtccgc gatcaaggca gccgacttcg tgctgattcc ggtgcagcca agcccttacg 12960
acatatgggc caccgccgac ctggtggagc tggttaagca gcgcattgag gtcacggatg 13020
gaaggctaca agcggccttt gtcgtgtcgc gggcgatcaa aggcacgcgc atcggcggtg 13080
aggttgccga ggcgctggcc gggtacgagc tgcccattct tgagtcccgt atcacgcagc 13140
gcgtgagcta cccaggcact gccgccgccg gcacaaccgt tcttgaatca gaacccgagg 13200
gcgacgctgc ccgcgaggtc caggcgctgg ccgctgaaat taaatcaaaa ctcatttgag 13260
ttaatgaggt aaagagaaaa tgagcaaaag cacaaacacg ctaagtgccg gccgtccgag 13320
cgcacgcagc agcaaggctg caacgttggc cagcctggca gacacgccag ccatgaagcg 13380
ggtcaacttt cagttgccgg cggaggatca caccaagctg aagatgtacg cggtacgcca 13440
aggcaagacc attaccgagc tgctatctga atacatcgcg cagctaccag agtaaatgag 13500
caaatgaata aatgagtaga tgaattttag cggctaaagg aggcggcatg gaaaatcaag 13560
aacaaccagg caccgacgcc gtggaatgcc ccatgtgtgg aggaacgggc ggttggccag 13620
gcgtaagcgg ctgggttgtc tgccggccct gcaatggcac tggaaccccc aagcccgagg 13680
aatcggcgtg agcggtcgca aaccatccgg cccggtacaa atcggcgcgg cgctgggtga 13740
tgacctggtg gagaagttga aggccgcgca ggccgcccag cggcaacgca tcgaggcaga 13800
agcacgcccc ggtgaatcgt ggcaagcggc cgctgatcga atccgcaaag aatcccggca 13860

-continued

```
accgccggca gccggtgcgc cgtcgattag gaagccgccc aagggcgacg agcaaccaga  13920
tttttcgtt ccgatgctct atgacgtggg cacccgcgat agtcgcagca tcatggacgt  13980
ggccgttttc cgtctgtcga agcgtgaccg acgagctggc gaggtgatcc gctacgagct  14040
tccagacggg cacgtagagg tttccgcagg gccggccggc atggccagtg tgtgggatta  14100
cgacctggta ctgatggcgg tttcccatct aaccgaatcc atgaaccgat accgggaagg  14160
gaagggagac aagcccggcc gcgtgttccg tccacacgtt gcggacgtac tcaagttctg  14220
ccggcgagcc gatggcggaa agcagaaaga cgacctggta gaaacctgca ttcggttaaa  14280
caccacgcac gttgccatgc agcgtacgaa gaaggccaag aacggccgcc tggtgacggt  14340
atccgagggt gaagccttga ttagccgcta caagatcgta aagagcgaaa ccgggcggcc  14400
ggagtacatc gagatcgagc tagctgattg gatgtaccgc gagatcacag aaggcaagaa  14460
cccggacgtg ctgacggttc accccgatta ctttttgatc gatcccggca tcggccgttt  14520
tctctaccgc ctggcacgcc gcgccgcagg caaggcagaa gccagatggt tgttcaagac  14580
gatctacgaa cgcagtggca gcgccggaga gttcaagaag ttctgtttca ccgtgcgcaa  14640
gctgatcggg tcaaatgacc tgccggagta cgatttgaag gaggaggcgg ggcaggctgg  14700
cccgatccta gtcatgcgct accgcaacct gatcgagggc gaagcatccg ccggttccta  14760
atgtacggag cagatgctag ggcaaattgc cctagcaggg gaaaaaggtc gaaaaggtct  14820
ctttcctgtg gatagcacgt acattgggaa cccaaagccg tacattggga accggaaccc  14880
gtacattggg aacccaaagc cgtacattgg gaaccggtca cacatgtaag tgactgatat  14940
aaaagagaaa aaaggcgatt tttccgccta aaactcttta aaacttatta aaactcttaa  15000
aacccgcctg gcctgtgcat aactgtctgg ccagcgcaca gccgaagagc tgcaaaaagc  15060
gcctaccctt cggtcgctgc gctccctacg ccccgccgct tcgcgtcggc ctatcgcggc  15120
cgctggccgc tcaaaaatgg ctggcctacg gccaggcaat ctaccagggc gcggacaagc  15180
cgcgccgtcg ccactcgacc gccggcgccc acatcaaggc accctgcctc gcgcgtttcg  15240
gtgatgacgg tgaaaacctc tgacacatgc agctcccgga gacggtcaca gcttgtctgt  15300
aagcggatgc cgggagcaga caagcccgtc agggcgcgtc agcgggtgtt ggcgggtgtc  15360
ggggcgcagc catgacccag tcacgtagcg atagcggagt gtatactggc ttaactatgc  15420
ggcatcagag cagattgtac tgagagtgca ccatatgcgg tgtgaaatac cgcacagatg  15480
cgtaaggaga aaataccgca tcaggcgctc ttccgcttcc tcgctcactg actcgctgcg  15540
ctcggtcgtt cggctgcggc gagcggtatc agctcactca aaggcggtaa tacggttatc  15600
cacagaatca ggggataacg caggaaagaa catgtgagca aaaggccagc aaaaggccag  15660
gaaccgtaaa aaggccgcgt tgctggcgtt tttccatagg ctccgccccc ctgacgagca  15720
tcacaaaaat cgacgctcaa gtcagaggtg gcgaaacccg acaggactat aaagatacca  15780
ggcgtttccc cctggaagct ccctcgtgcg ctctcctgtt ccgaccctgc cgcttaccgg  15840
atacctgtcc gcctttctcc cttcgggaag cgtggcgctt tctcatagct cacgctgtag  15900
gtatctcagt tcggtgtagg tcgttcgctc caagctgggc tgtgtgcacg aaccccccgt  15960
tcagcccgac cgctgcgcct tatccggtaa ctatcgtctt gagtccaacc cggtaagaca  16020
cgacttatcg ccactggcag cagccactgg taacaggatt agcagagcga ggtatgtagg  16080
cggtgctaca gagttcttga agtggtggcc taactacggc tacactagaa ggacagtatt  16140
tggtatctgc gctctgctga agccagttac cttcggaaaa agagttggta gctcttgatc  16200
cggcaaacaa accaccgctg gtagcggtgg tttttttgtt tgcaagcagc agattacgcg  16260
```

-continued

```
cagaaaaaaa ggatctcaag aagatccttt gatcttttct acggggtctg acgctcagtg  16320
gaacgaaaac tcacgttaag ggattttggt catgagatta tcaaaaagga tcttcaccta  16380
gatcctttta aattaaaaat gaagttttaa atcaatctaa agtatatatg agtaaacttg  16440
gtctgacagt taccaatgct taatcagtga ggcacctatc tcagcgatct gtctatttcg  16500
ttcatccata gttgcctgac tccccgtcgt gtagataact acgatacggg agggcttacc  16560
atctggcccc agtgctgcaa tgataccgcg agacccacgc tcaccggctc cagatttatc  16620
agcaataaac cagccagccg gaagggccga gcgcagaagt ggtcctgcaa ctttatccgc  16680
ctccatccag tctattaatt gttgccggga agctagagta agtagttcgc cagttaatag  16740
tttgcgcaac gttgttgcca ttgctacagg catcgtggtg tcacgctcgt cgtttggtat  16800
ggcttcattc agctccggtt cccaacgatc aaggcgagtt acatgatccc ccatgttgtg  16860
caaaaaagcg gttagctcct tcggtcctcc gatcgttgtc agaagtaagt tggccgcagt  16920
gttatcactc atggttatgg cagcactgca taattctctt actgtcatgc catccgtaag  16980
atgcttttct gtgactggtg agtactcaac caagtcattc tgagaatagt gtatgcggcg  17040
accgagttgc tcttgcccgg cgtcaacacg ggataatacc gcgccacata gcagaacttt  17100
aaaagtgctc atcattggaa aagacctgca gggggggggg ggaaagccac gttgtgtctc  17160
aaaatctctg atgttacatt gcacaagata aaaatatatc atcatgaaca ataaaactgt  17220
ctgcttacat aaacagtaat acaaggggtg ttatgagcca tattcaacgg gaaacgtctt  17280
gctcgaggcc gcgattaaat tccaacatgg atgctgattt atatgggtat aaatgggctc  17340
gcgataatgt cgggcaatca ggtgcgacaa tctatcgatt gtatgggaag cccgatgcgc  17400
cagagttgtt tctgaaacat ggcaaaggta gcgttgccaa tgatgttaca gatgagatgg  17460
tcagactaaa ctggctgacg gaatttatgc ctcttccgac catcaagcat tttatccgta  17520
ctcctgatga tgcatggtta ctcaccactg cgatccccgg gaaaacagca ttccaggtat  17580
tagaagaata tcctgattca ggtgaaaata ttgttgatgc gctggcagtg ttcctgcgcc  17640
ggttgcattc gattcctgtt tgtaattgtc cttttaacag cgatcgcgta tttcgtctcg  17700
ctcaggcgca atcacgaatg aataacggtt tggttgatgc gagtgatttt gatgacgagc  17760
gtaatggctg gcctgttgaa caagtctgga aagaaatgca taagcttttg ccattctcac  17820
cggattcagt cgtcactcat ggtgatttct cacttgataa ccttattttt gacgagggga  17880
aattaatagg ttgtattgat gttggacgag tcggaatcgc agaccgatac caggatcttg  17940
ccatcctatg gaactgcctc ggtgagtttt ctccttcatt acagaaacgg ctttttcaaa  18000
aatatggtat tgataatcct gatatgaata aattgcagtt tcatttgatg ctcgatgagt  18060
ttttctaatc agaattggtt aattggttgt aacactggca gagcattacg ctgacttgac  18120
gggacggcgg ctttgttgaa taaatcgaac ttttgctgag ttgaaggatc agatcacgca  18180
tcttcccgac aacgcagacc gttccgtggc aaagcaaaag ttcaaaatca ccaactggtc  18240
cacctacaac aaagctctca tcaaccgtgg ctccctcact ttctggctgg atgatggggc  18300
gattcaggcc tggtatgagt cagcaacacc ttcttcacga ggcagacctc agcgcccccc  18360
ccccctgca ggtcaattcg gtcgatatgg ctattacgaa gaaggctcgt gcgcggagtc  18420
ccgtgaactt tcccacgcaa caagtgaacc gcaccgggtt tgccggaggc catttcgtta  18480
aaatgcgcag c                                                   18491
```

<210> SEQ ID NO 2

<211> LENGTH: 50
<212> TYPE: DNA
<213> ORGANISM: artificial sequence
<220> FEATURE:
<223> OTHER INFORMATION: poly-linker

<400> SEQUENCE: 2
gatcactagt ggcgcgccta ggagatctcg agtagggata acagggtaat 50

<210> SEQ ID NO 3
<211> LENGTH: 7085
<212> TYPE: DNA
<213> ORGANISM: artificial sequence
<220> FEATURE:
<223> OTHER INFORMATION: plasmid pKR85

<400> SEQUENCE: 3
cgcgccaagc ttttgatcca tgcccttcat ttgccgctta ttaattaatt tggtaacagt 60
ccgtactaat cagttactta tccttccccc atcataatta atcttggtag tctcgaatgc 120
cacaacactg actagtctct tggatcataa gaaaaagcca aggaacaaaa gaagacaaaa 180
cacaatgaga gtatcctttg catagcaatg tctaagttca taaaattcaa acaaaaacgc 240
aatcacacac agtggacatc acttatccac tagctgatca ggatcgccgc gtcaagaaaa 300
aaaaactgga ccccaaaagc catgcacaac aacacgtact cacaaaggtg tcaatcgagc 360
agcccaaaac attcaccaac tcaacccatc atgagccctc acatttgttg tttctaaccc 420
aacctcaaac tcgtattctc ttccgccacc tcatttttgt ttatttcaac acccgtcaaa 480
ctgcatgcca ccccgtggcc aaatgtccat gcatgttaac aagacctatg actataaata 540
gctgcaatct cggcccaggt tttcatcatc aagaaccagt tcaatatcct agtacaccgt 600
attaaagaat ttaagatata ctgcggccgc aagtatgaac taaaatgcat gtaggtgtaa 660
gagctcatgg agagcatgga atattgtatc cgaccatgta acagtataat aactgagctc 720
catctcactt cttctatgaa taaacaaagg atgttatgat atattaacac tctatctatg 780
caccttattg ttctatgata aatttcctct tattattata aatcatctga atcgtgacgg 840
cttatggaat gcttcaaata gtacaaaaac aaatgtgtac tataagactt tctaaacaat 900
tctaacctta gcattgtgaa cgagacataa gtgttaagaa gacataacaa ttataatgga 960
agaagtttgt ctccatttat atattatata ttacccactt atgtattata ttaggatgtt 1020
aaggagacat aacaattata aagagagaag tttgtatcca tttatatatt atatactacc 1080
catttatata ttatacttat ccacttattt aatgtcttta taaggtttga tccatgatat 1140
ttctaatatt ttagttgata tgtatatgaa agggtactat ttgaactctc ttactctgta 1200
taaaggttgg atcatcctta aagtgggtct atttaatttt attgcttctt acagataaaa 1260
aaaaaattat gagttggttt gataaaatat tgaaggattt aaaataataa taaataacat 1320
ataatatatg tatataaatt tattataata taacatttat ctataaaaaa gtaaatattg 1380
tcataaatct atacaatcgt ttagccttgc tggacgaatc tcaattattt aaacgagagt 1440
aaacatattt gactttttgg ttatttaaca aattattatt taacactata tgaaattttt 1500
ttttttatca gcaaagaata aaattaaatt aagaaggaca atggtgtccc aatccttata 1560
caaccaactt ccacaagaaa gtcaagtcag agacaacaaa aaaacaagca aaggaaattt 1620
tttaatttga gttgtcttgt ttgctgcata atttatgcag taaaacacta cacataaccc 1680
ttttagcagt agagcaatgg ttgaccgtgt gcttagcttc ttttatttta ttttttttatc 1740 agcaaagaat aaataaaata aaatgagaca cttcagggat gtttcaacaa gcttggatct 1800

-continued

```
cctgcaggat ctggccggcc ggatctcgta cggatccgtc gacggcgcgc ccgatcatcc   1860
ggatatagtt cctcctttca gcaaaaaacc cctcaagacc cgtttagagg ccccaagggg   1920
ttatgctagt tattgctcag cggtggcagc agccaactca gcttcctttc gggctttgtt   1980
agcagccgga tcgatccaag ctgtacctca ctattccttt gccctcggac gagtgctggg   2040
gcgtcggttt ccactatcgg cgagtacttc tacacagcca tcggtccaga cggccgcgct   2100
tctgcgggcg atttgtgtac gcccgacagt cccggctccg gatcggacga ttgcgtcgca   2160
tcgaccctgc gcccaagctg catcatcgaa attgccgtca accaagctct gatagagttg   2220
gtcaagacca atgcggagca tatacgcccg gagccgcggc gatcctgcaa gctccggatg   2280
cctccgctcg aagtagcgcg tctgctgctc catacaagcc aaccacggcc tccagaagaa   2340
gatgttggcg acctcgtatt gggaatcccc gaacatcgcc tcgctccagt caatgaccgc   2400
tgttatgcgg ccattgtccg tcaggacatt gttggagccg aaatccgcgt gcacgaggtg   2460
ccggacttcg gggcagtcct cggcccaaag catcagctca tcgagagcct gcgcgacgga   2520
cgcactgacg gtgtcgtcca tcacagtttg ccagtgatac acatggggat cagcaatcgc   2580
gcatatgaaa tcacgccatg tagtgtattg accgattcct tgcggtccga atgggccgaa   2640
cccgctcgtc tggctaagat cggccgcagc gatcgcatcc atagcctccg cgaccggctg   2700
cagaacagcg ggcagttcgg tttcaggcag gtcttgcaac gtgacaccct gtgcacggcg   2760
ggagatgcaa taggtcaggc tctcgctgaa ttccccaatg tcaagcactt ccggaatcgg   2820
gagcgcggcc gatgcaaagt gccgataaac ataacgatct ttgtagaaac catcggcgca   2880
gctatttacc cgcaggacat atccacgccc tcctacatcg aagctgaaag cacgagattc   2940
ttcgccctcc gagagctgca tcaggtcgga gacgctgtcg aacttttcga tcagaaactt   3000
ctcgacagac gtcgcggtga gttcaggctt ttccatgggt atatctcctt cttaaagtta   3060
aacaaaatta tttctagagg gaaaccgttg tggtctccct atagtgagtc gtattaattt   3120
cgcgggatcg agatcgatcc aattccaatc ccacaaaaat ctgagcttaa cagcacagtt   3180
gctcctctca gagcagaatc gggtattcaa caccctcata tcaactacta cgttgtgtat   3240
aacggtccac atgccggtat atacgatgac tggggttgta caaaggcggc aacaaacggc   3300
gttcccggag ttgcacacaa gaaatttgcc actattacag aggcaagagc agcagctgac   3360
gcgtacacaa caagtcagca aacagacagg ttgaacttca tccccaaagg agaagctcaa   3420
ctcaagccca agagctttgc taaggcccta acaagcccac caaagcaaaa agcccactgg   3480
ctcacgctag gaaccaaaag gcccagcagt gatccagccc caaaagagat ctcctttgcc   3540
ccggagatta caatggacga tttcctctat ctttacgatc taggaaggaa gttcgaaggt   3600
gaaggtgacg acactatgtt caccactgat aatgagaagg ttagcctctt caatttcaga   3660
aagaatgctg acccacagat ggttagagag gcctacgcag caggtctcat caagacgatc   3720
tacccgagta acaatctcca ggagatcaaa taccttccca agaaggttaa agatgcagtc   3780
aaaagattca ggactaattg catcaagaac acagagaaag acatatttct caagatcaga   3840
agtactattc cagtatggac gattcaaggc ttgcttcata aaccaaggca agtaatagag   3900
attggagtct ctaaaaaggt agttcctact gaatctaagg ccatgcatgg agtctaagat   3960
tcaaatcgag gatctaacag aactcgccgt gaagactggc gaacagttca tacagagtct   4020
tttacgactc aatgacaaga agaaaatctt cgtcaacatg gtggagcacg acactctggt   4080
ctactccaaa aatgtcaaag atacagtctc agaagaccaa agggctattg agacttttca   4140
```

-continued

```
acaaaggata atttcgggaa acctcctcgg attccattgc ccagctatct gtcacttcat   4200
cgaaaggaca gtagaaaagg aaggtggctc ctacaaatgc catcattgcg ataaaggaaa   4260
ggctatcatt caagatgcct ctgccgacag tggtcccaaa gatggacccc cacccacgag   4320
gagcatcgtg gaaaaagaag acgttccaac cacgtcttca aagcaagtgg attgatgtga   4380
catctccact gacgtaaggg atgacgcaca atcccactat ccttcgcaag acccttcctc   4440
tatataagga agttcatttc atttggagag gacacgctcg agctcatttc tctattactt   4500
cagccataac aaaagaactc ttttctcttc ttattaaacc atgaaaaagc ctgaactcac   4560
cgcgacgtct gtcgagaagt ttctgatcga aaagttcgac agcgtctccg acctgatgca   4620
gctctcggag ggcgaagaat ctcgtgcttt cagcttcgat gtaggagggc gtggatatgt   4680
cctgcgggta aatagctgcg ccgatggttt ctacaaagat cgttatgttt atcggcactt   4740
tgcatcggcc gcgctcccga ttccggaagt gcttgacatt ggggaattca gcgagagcct   4800
gacctattgc atctcccgcc gtgcacaggg tgtcacgttg caagacctgc ctgaaaccga   4860
actgcccgct gttctgcagc cggtcgcgga ggccatggat gcgatcgctg cggccgatct   4920
tagccagacg agcgggttcg gcccattcgg accgcaagga atcggtcaat acactacatg   4980
gcgtgatttc atatgcgcga ttgctgatcc ccatgtgtat cactggcaaa ctgtgatgga   5040
cgacaccgtc agtgcgtccg tcgcgcaggc tctcgatgag ctgatgcttt gggccgagga   5100
ctgccccgaa gtccggcacc tcgtgcacgc ggatttcggc tccaacaatg tcctgacgga   5160
caatggccgc ataacagcgg tcattgactg gagcgaggcg atgttcgggg attcccaata   5220
cgaggtcgcc aacatcttct tctggaggcc gtggttggct tgtatggagc agcagacgcg   5280
ctacttcgag cggaggcatc cggagcttgc aggatcgccg cggctccggg cgtatatgct   5340
ccgcattggt cttgaccaac tctatcagag cttggttgac ggcaatttcg atgatgcagc   5400
ttgggcgcag ggtcgatgcg acgcaatcgt ccgatccgga gccgggactg tcgggcgtac   5460
acaaatcgcc cgcagaagcg cggccgtctg gaccgatggc tgtgtagaag tactcgccga   5520
tagtggaaac cgacgcccca gcactcgtcc gagggcaaag gaatagtgag gtacctaaag   5580
aaggagtgcg tcgaagcaga tcgttcaaac atttggcaat aaagtttctt aagattgaat   5640
cctgttgccg gtcttgcgat gattatcata taatttctgt tgaattacgt taagcatgta   5700
ataattaaca tgtaatgcat gacgttattt atgagatggg tttttatgat tagagtcccg   5760
caattataca tttaatacgc gatagaaaac aaaatatagc gcgcaaacta ggataaatta   5820
tcgcgcgcgg tgtcatctat gttactagat cgatgtcgaa tcgatcaacc tgcattaatg   5880
aatcggccaa cgcgcgggga gaggcggttt gcgtattggg cgctcttccg cttcctcgct   5940
cactgactcg ctgcgctcgg tcgttcggct gcggcgagcg gtatcagctc actcaaaggc   6000
ggtaatacgg ttatccacag aatcagggga taacgcagga aagaacatgt gagcaaaagg   6060
ccagcaaaag gccaggaacc gtaaaaaggc cgcgttgctg gcgtttttcc ataggctccg   6120
cccccctgac gagcatcaca aaaatcgacg ctcaagtcag aggtggcgaa acccgacagg   6180
actataaaga taccaggcgt ttccccctgg aagctccctc gtgcgctctc ctgttccgac   6240
cctgccgctt accggatacc tgtccgcctt tctcccttcg ggaagcgtgg cgctttctca   6300
atgctcacgc tgtaggtatc tcagttcggt gtaggtcgtt cgctccaagc tgggctgtgt   6360
gcacgaaccc cccgttcagc ccgaccgctg cgccttatcc ggtaactatc gtcttgagtc   6420
caacccggta agacacgact tatcgccact ggcagcagcc actggtaaca ggattagcag   6480
agcgaggtat gtaggcggtg ctacagagtt cttgaagtgg tggcctaact acggctacac   6540
```

tagaaggaca gtatttggta tctgcgctct gctgaagcca gttaccttcg gaaaaagagt 6600
tggtagctct tgatccggca aacaaaccac cgctggtagc ggtggttttt ttgtttgcaa 6660
gcagcagatt acgcgcagaa aaaaaggatc tcaagaagat cctttgatct tttctacggg 6720
gtctgacgct cagtggaacg aaaactcacg ttaagggatt ttggtcatga cattaaccta 6780
taaaaatagg cgtatcacga ggccctttcg tctcgcgcgt ttcggtgatg acggtgaaaa 6840
cctctgacac atgcagctcc cggagacggt cacagcttgt ctgtaagcgg atgccgggag 6900
cagacaagcc cgtcagggcg cgtcagcggg tgttggcggg tgtcggggct ggcttaacta 6960
tgcggcatca gagcagattg tactgagagt gcaccatatg gacatattgt cgttagaacg 7020
cggctacaat taatacataa ccttatgtat catacacata cgatttaggt gacactatag 7080
aacgg 7085

<210> SEQ ID NO 4
<211> LENGTH: 5303
<212> TYPE: DNA
<213> ORGANISM: artificial sequence
<220> FEATURE:
<223> OTHER INFORMATION: plasmid pKR278

<400> SEQUENCE: 4
agcttggatc tcctgcagga tctggccggc cggatctcgt acggatccgt cgacggcgcg 60
cccgatcatc cggatatagt tcctcctttc agcaaaaaac ccctcaagac ccgtttagag 120
gccccaaggg gttatgctag ttattgctca gcggtggcag cagccaactc agcttccttt 180
cgggctttgt tagcagccgg atcgatccaa gctgtacctc actattcctt tgccctcgga 240
cgagtgctgg ggcgtcggtt tccactatcg gcgagtactt ctacacagcc atcggtccag 300
acggccgcgc ttctgcgggc gatttgtgta cgcccgacag tcccggctcc ggatcggacg 360
attgcgtcgc atcgaccctg cgcccaagct gcatcatcga aattgccgtc aaccaagctc 420
tgatagagtt ggtcaagacc aatgcggagc atatacgccc ggagccgcgg cgatcctgca 480
agctccggat gcctccgctc gaagtagcgc gtctgctgct ccatacaagc caaccacggc 540
ctccagaaga agatgttggc gacctcgtat tgggaatccc cgaacatcgc ctcgctccag 600
tcaatgaccg ctgttatgcg gccattgtcc gtcaggacat tgttggagcc gaaatccgcg 660
tgcacgaggt gccggacttc ggggcagtcc tcggcccaaa gcatcagctc atcgagagcc 720
tgcgcgacgg acgcactgac ggtgtcgtcc atcacagttt gccagtgata cacatgggga 780
tcagcaatcg cgcatatgaa atcacgccat gtagtgtatt gaccgattcc ttgcggtccg 840
aatgggccga acccgctcgt ctggctaaga tcggccgcag cgatcgcatc catagcctcc 900
gcgaccggct gcagaacagc gggcagttcg gtttcaggca ggtcttgcaa cgtgacaccc 960
tgtgcacggc gggagatgca ataggtcagg ctctcgctga attccccaat gtcaagcact 1020
tccggaatcg ggagcgcggc cgatgcaaag tgccgataaa cataacgatc tttgtagaaa 1080
ccatcggcgc agctatttac ccgcaggaca tatccacgcc ctcctacatc gaagctgaaa 1140
gcacgagatt cttcgccctc cgagagctgc atcaggtcgg agacgctgtc gaacttttcg 1200
atcagaaact tctcgacaga cgtcgcggtg agttcaggct tttccatggg tatatctcct 1260
tcttaaagtt aaacaaaatt atttctagag ggaaaccgtt gtggtctccc tatagtgagt 1320
cgtattaatt tcgcgggatc gagatcgatc caattccaat cccacaaaaa tctgagctta 1380
acagcacagt tgctcctctc agagcagaat cgggtattca acaccctcat atcaactact 1440

-continued acgttgtgta taacggtcca catgccggta tatacgatga ctggggttgt acaaaggcgg 1500
caacaaacgg cgttcccgga gttgcacaca agaaatttgc cactattaca gaggcaagag 1560
cagcagctga cgcgtacaca acaagtcagc aaacagacag gttgaacttc atccccaaag 1620
gagaagctca actcaagccc aagagctttg ctaaggccct aacaagccca ccaaagcaaa 1680
aagcccactg gctcacgcta ggaaccaaaa ggcccagcag tgatccagcc ccaaaagaga 1740
tctcctttgc cccggagatt acaatggacg atttcctcta tctttacgat ctaggaagga 1800
agttcgaagg tgaaggtgac gacactatgt tcaccactga taatgagaag gttagcctct 1860
tcaatttcag aaagaatgct gacccacaga tggttagaga ggcctacgca gcaggtctca 1920
tcaagacgat ctacccgagt aacaatctcc aggagatcaa ataccttccc aagaaggtta 1980
aagatgcagt caaaagattc aggactaatt gcatcaagaa cacagagaaa gacatatttc 2040
tcaagatcag aagtactatt ccagtatgga cgattcaagg cttgcttcat aaaccaaggc 2100
aagtaataga gattggagtc tctaaaaagg tagttcctac tgaatctaag gccatgcatg 2160
gagtctaaga ttcaaatcga ggatctaaca gaactcgccg tgaagactgg cgaacagttc 2220
atacagagtc ttttacgact caatgacaag aagaaaatct tcgtcaacat ggtggagcac 2280
gacactctgg tctactccaa aaatgtcaaa gatacagtct cagaagacca aagggctatt 2340
gagacttttc aacaaaggat aatttcggga aacctcctcg gattccattg cccagctatc 2400
tgtcacttca tcgaaaggac agtagaaaag gaaggtggct cctacaaatg ccatcattgc 2460
gataaaggaa aggctatcat tcaagatgcc tctgccgaca gtggtcccaa agatggaccc 2520
ccacccacga ggagcatcgt ggaaaaagaa gacgttccaa ccacgtcttc aaagcaagtg 2580
gattgatgtg acatctccac tgacgtaagg gatgacgcac aatcccacta tccttcgcaa 2640
gacccttcct ctatataagg aagttcattt catttggaga ggacacgctc gagctcattt 2700
ctctattact tcagccataa caaaagaact cttttctctt cttattaaac catgaaaaag 2760
cctgaactca ccgcgacgtc tgtcgagaag tttctgatcg aaaagttcga cagcgtctcc 2820
gacctgatgc agctctcgga gggcgaagaa tctcgtgctt tcagcttcga tgtaggaggg 2880
cgtggatatg tcctgcgggt aaatagctgc gccgatggtt tctacaaaga tcgttatgtt 2940
tatcggcact ttgcatcggc cgcgctcccg attccggaag tgcttgacat tggggaattc 3000
agcgagagcc tgacctattg catctcccgc cgtgcacagg gtgtcacgtt gcaagacctg 3060
cctgaaaccg aactgcccgc tgttctgcag ccggtcgcgg aggccatgga tgcgatcgct 3120
gcggccgatc ttagccagac gagcgggttc ggcccattcg gaccgcaagg aatcggtcaa 3180
tacactacat ggcgtgattt catatgcgcg attgctgatc cccatgtgta tcactggcaa 3240
actgtgatgg acgacaccgt cagtgcgtcc gtcgcgcagg ctctcgatga gctgatgctt 3300
tgggccgagg actgccccga agtccggcac ctcgtgcacg cggatttcgg ctccaacaat 3360
gtcctgacgg acaatggccg cataacagcg gtcattgact ggagcgaggc gatgttcggg 3420
gattcccaat acgaggtcgc caacatcttc ttctggaggc cgtggttggc ttgtatggag 3480
cagcagacgc gctacttcga gcggaggcat ccggagcttg caggatcgcc gcggctccgg 3540
gcgtatatgc tccgcattgg tcttgaccaa ctctatcaga gcttggttga cggcaatttc 3600
gatgatgcag cttgggcgca gggtcgatgc gacgcaatcg tccgatccgg agccgggact 3660
gtcgggcgta cacaaatcgc ccgcagaagc gcggccgtct ggaccgatgg ctgtgtagaa 3720
gtactcgccg atagtggaaa ccgacgcccc agcactcgtc cgagggcaaa ggaatagtga 3780
ggtacctaaa gaaggagtgc gtcgaagcag atcgttcaaa catttggcaa taaagtttct 3840

-continued

```
taagattgaa tcctgttgcc ggtcttgcga tgattatcat ataatttctg ttgaattacg   3900

ttaagcatgt aataattaac atgtaatgca tgacgttatt tatgagatgg gtttttatga   3960

ttagagtccc gcaattatac atttaatacg cgatagaaaa caaaatatag cgcgcaaact   4020

aggataaatt atcgcgcgcg gtgtcatcta tgttactaga tcgatgtcga atcgatcaac   4080

ctgcattaat gaatcggcca acgcgcgggg agaggcggtt tgcgtattgg gcgctcttcc   4140

gcttcctcgc tcactgactc gctgcgctcg gtcgttcggc tgcggcgagc ggtatcagct   4200

cactcaaagg cggtaatacg gttatccaca gaatcagggg ataacgcagg aaagaacatg   4260

tgagcaaaag gccagcaaaa ggccaggaac cgtaaaaagg ccgcgttgct ggcgtttttc   4320

cataggctcc gcccccctga cgagcatcac aaaaatcgac gctcaagtca gaggtggcga   4380

aacccgacag gactataaag ataccaggcg tttccccctg gaagctccct cgtgcgctct   4440

cctgttccga ccctgccgct taccggatac ctgtccgcct ttctcccttc gggaagcgtg   4500

gcgctttctc aatgctcacg ctgtaggtat ctcagttcgg tgtaggtcgt tcgctccaag   4560

ctgggctgtg tgcacgaacc ccccgttcag cccgaccgct gcgccttatc cggtaactat   4620

cgtcttgagt ccaacccggt aagacacgac ttatcgccac tggcagcagc cactggtaac   4680

aggattagca gagcgaggta tgtaggcggt gctacagagt tcttgaagtg gtggcctaac   4740

tacggctaca ctagaaggac agtatttggt atctgcgctc tgctgaagcc agttaccttc   4800

ggaaaaagag ttggtagctc ttgatccggc aaacaaacca ccgctggtag cggtggtttt   4860

tttgtttgca agcagcagat tacgcgcaga aaaaaaggat ctcaagaaga tcctttgatc   4920

ttttctacgg ggtctgacgc tcagtggaac gaaaactcac gttaagggat tttggtcatg   4980

acattaacct ataaaaatag gcgtatcacg aggccctttc gtctcgcgcg tttcggtgat   5040

gacggtgaaa acctctgaca catgcagctc ccggagacgg tcacagcttg tctgtaagcg   5100

gatgccggga gcagacaagc ccgtcagggc gcgtcagcgg gtgttggcgg gtgtcggggc   5160

tggcttaact atgcggcatc agagcagatt gtactgagag tgcaccatat ggacatattg   5220

tcgttagaac gcggctacaa ttaatacata accttatgta tcatacacat acgatttagg   5280

tgacactata gaacggcgcg cca                                           5303
```

<210> SEQ ID NO 5
<211> LENGTH: 4140
<212> TYPE: DNA
<213> ORGANISM: artificial sequence
<220> FEATURE:
<223> OTHER INFORMATION: plasmid pKR407

<400> SEQUENCE: 5

```
ggccgcattt cgcaccaaat caatgaaagt aataatgaaa agtctgaata agaatactta     60

ggcttagatg cctttgttac ttgtgtaaaa taacttgagt catgtacctt tggcggaaac    120

agaataaata aaaggtgaaa ttccaatgct ctatgtataa gttagtaata cttaatgtgt    180

tctacggttg tttcaatatc atcaaactct aattgaaact ttagaaccac aaatctcaat    240

cttttcttaa tgaaatgaaa aatcttaatt gtaccatgtt tatgttaaac accttacaat    300

tggttggaga ggaggaccaa ccgatgggac aacattggga gaaagagatt caatggagat    360

ttggatagga gaacaacatt ctttttcact tcaatacaag atgagtgcaa cactaaggat    420

atgtatgaga ctttcagaag ctacgacaac atagatgagt gaggtggtga ttcctagcaa    480

gaaagacatt agaggaagcc aaaatcgaac aaggaagaca tcaagggcaa gagacaggac    540
```

-continued

```
catccatctc aggaaaagga gctttgggat agtccgagaa gttgtacaag aaatttttttg    600
gagggtgagt gatgcattgc tggtgacttt aactcaatca aaattgagaa agaaagaaaa    660
gggagggggc tcacatgtga atagaaggga aacgggagaa ttttacagtt ttgatctaat    720
gggcatccca gctagtggta acatattcac catgtttaac cttcacgtac gtctagagga    780
tcccccgggc tgcaggaatt cactggccgt cgttttacaa cgtcgtgact gggaaaaccc    840
tggcgttacc caacttaatc gccttgcagc acatccccct ttcgccagct ggcgtaatag    900
cgaagaggcc cgcaccgatc gcccttccca acagttgcgc agcctgaatg gcgaatggcg    960
cctgatgcgg tattttctcc ttacgcatct gtgcggtatt tcacaccgca tatggtgcac   1020
tctcagtaca atctgctctg atgccgcata gttaagccag ccccgacacc cgccaacacc   1080
cgctgacgcg ccctgacggg cttgtctgct cccggcatcc gcttacagac aagctgtgac   1140
cgtctccggg agctgcatgt gtcagaggtt ttcaccgtca tcaccgaaac gcgcgagacg   1200
aaagggcctc gtgatacgcc tatttttata ggttaatgtc atgataataa tggtttctta   1260
gacgtcaggt ggcacttttc ggggaaatgt gcgcggaacc cctatttgtt tatttttcta   1320
aatacattca aatatgtatc cgctcatgag acaataaccc tgataaatgc ttcaataata   1380
ttgaaaaagg aagagtatga gtattcaaca tttccgtgtc gcccttattc cctttttttgc   1440
ggcattttgc cttcctgttt ttgctcaccc agaaacgctg gtgaaagtaa aagatgctga   1500
agatcagttg ggtgcacgag tgggttacat cgaactggat ctcaacagcg gtaagatcct   1560
tgagagtttt cgccccgaag aacgttttcc aatgatgagc acttttaaag ttctgctatg   1620
tggcgcggta ttatcccgta ttgacgccgg gcaagagcaa ctcggtcgcc gcatacacta   1680
ttctcagaat gacttggttg agtactcacc agtcacagaa aagcatctta cggatggcat   1740
gacagtaaga gaattatgca gtgctgccat aaccatgagt gataacactg cggccaactt   1800
acttctgaca acgatcggag gaccgaagga gctaaccgct tttttgcaca acatggggga   1860
tcatgtaact cgccttgatc gttgggaacc ggagctgaat gaagccatac caaacgacga   1920
gcgtgacacc acgatgcctg tagcaatggc aacaacgttg cgcaaactat taactggcga   1980
actacttact ctagcttccc ggcaacaatt aatagactgg atggaggcgg ataaagttgc   2040
aggaccactt ctgcgctcgg cccttccggc tggctggttt attgctgata aatctggagc   2100
cggtgagcgt gggtctcgcg gtatcattgc agcactgggg ccagatggta agccctcccg   2160
tatcgtagtt atctacacga cggggagtca ggcaactatg gatgaacgaa atagacagat   2220
cgctgagata ggtgcctcac tgattaagca ttggtaactg tcagaccaag tttactcata   2280
tatactttag attgatttaa aacttcattt ttaatttaaa aggatctagg tgaagatcct   2340
ttttgataat ctcatgacca aaatccctta acgtgagttt tcgttccact gagcgtcaga   2400
ccccgtagaa aagatcaaag gatcttcttg agatcctttt tttctgcgcg taatctgctg   2460
cttgcaaaca aaaaaaccac cgctaccagc ggtggtttgt ttgccggatc aagagctacc   2520
aactcttttt ccgaaggtaa ctggcttcag cagagcgcag ataccaaata ctgtccttct   2580
agtgtagccg tagttaggcc accacttcaa gaactctgta gcaccgccta catacctcgc   2640
tctgctaatc ctgttaccag tggctgctgc cagtggcgat aagtcgtgtc ttaccgggtt   2700
ggactcaaga cgatagttac cggataaggc gcagcggtcg ggctgaacgg ggggttcgtg   2760
cacacagccc agcttggagc gaacgaccta caccgaactg agatacctac agcgtgagct   2820
atgagaaagc gccacgcttc ccgaagggag aaaggcggac aggtatccgg taagcggcag   2880
ggtcggaaca ggagagcgca cgagggagct tccaggggga aacgcctggt atctttatag   2940
```

```
tcctgtcggg tttcgccacc tctgacttga gcgtcgattt ttgtgatgct cgtcaggggg   3000

gcggagccta tggaaaaacg ccagcaacgc ggccttttta cggttcctgg ccttttgctg   3060

gccttttgct cacatgttct ttcctgcgtt atcccctgat tctgtggata accgtattac   3120

cgcctttgag tgagctgata ccgctcgccg cagccgaacg accgagcgca gcgagtcagt   3180

gagcgaggaa gcggaagagc gcccaatacg caaaccgcct ctccccgcgc gttggccgat   3240

tcattaatgc agctggcacg acaggtttcc cgactggaaa gcgggcagtg agcgcaacgc   3300

aattaatgtg agttagctca ctcattaggc accccaggct ttacacttta tgcttccggc   3360

tcgtatgttg tgtggaattg tgagcggata acaatttcac acaggaaaca gctatgacca   3420

tgattacgcc aagcttgcat gcctgcaggc tagcctaagt acgtactcaa aatgccaaca   3480

aataaaaaaa aagttgcttt aataatgcca aaacaaatta ataaaacact tacaacaccg   3540

gatttttttt aattaaaatg tgccatttag gataaatagt taatattttt aataattatt   3600

taaaaagccg tatctactaa aatgattttt atttggttga aatattaat atgtttaaat   3660

caacacaatc tatcaaaatt aaactaaaaa aaaaataagt gtacgtggtt aacattagta   3720

cagtaatata agaggaaaat gagaaattaa gaaattgaaa gcgagtctaa tttttaaatt   3780

atgaacctgc atatataaaa ggaaagaaag aatccaggaa gaaaagaaat gaaaccatgc   3840

atggtcccct cgtcatcacg agtttctgcc atttgcaata gaaacactga aacacctttc   3900

tctttgtcac ttaattgaga tgccgaagcc acctcacacc atgaacttca tgaggtgtag   3960

cacccaaggc ttccatagcc atgcatactg aagaatgtct caagctcagc accctacttc   4020

tgtgacgtgt ccctcattca ccttcctctc ttccctataa ataaccacgc ctcaggttct   4080

ccgcttcaca actcaaacat tctctccatt ggtccttaaa cactcatcag tcatcaccgc   4140
```

<210> SEQ ID NO 6
<211> LENGTH: 6747
<212> TYPE: DNA
<213> ORGANISM: artificial sequence
<220> FEATURE:
<223> OTHER INFORMATION: plasmid pKR1468

<400> SEQUENCE: 6

```
gatccgtcga cggcgcgccc gatcatccgg atatagttcc tcctttcagc aaaaaacccc     60

tcaagacccg tttagaggcc ccaaggggtt atgctagtta ttgctcagcg gtggcagcag    120

ccaactcagc ttcctttcgg gctttgttag cagccggatc gatccaagct gtacctcact    180

attcctttgc cctcggacga gtgctggggc gtcggtttcc actatcggcg agtacttcta    240

cacagccatc ggtccagacg gccgcgcttc tgcgggcgat ttgtgtacgc ccgacagtcc    300

cggctccgga tcggacgatt gcgtcgcatc gaccctgcgc ccaagctgca tcatcgaaat    360

tgccgtcaac caagctctga tagagttggt caagaccaat gcggagcata tacgcccgga    420

gccgcggcga tcctgcaagc tccggatgcc tccgctcgaa gtagcgcgtc tgctgctcca    480

tacaagccaa ccacggcctc cagaagaaga tgttggcgac ctcgtattgg gaatccccga    540

acatcgcctc gctccagtca atgaccgctg ttatgcggcc attgtccgtc aggacattgt    600

tggagccgaa atccgcgtgc acgaggtgcc ggacttcggg gcagtcctcg gcccaaagca    660

tcagctcatc gagagcctgc gcgacggacg cactgacggt gtcgtccatc acagtttgcc    720

agtgatacac atggggatca gcaatcgcgc atatgaaatc acgccatgta gtgtattgac    780

cgattccttg cggtccgaat gggccgaacc cgctcgtctg gctaagatcg gccgcagcga    840
```

-continued

```
tcgcatccat agcctccgcg accggctgca gaacagcggg cagttcggtt tcaggcaggt    900
cttgcaacgt gacaccctgt gcacggcggg agatgcaata ggtcaggctc tcgctgaatt    960
ccccaatgtc aagcacttcc ggaatcggga gcgcggccga tgcaaagtgc cgataaacat   1020
aacgatcttt gtagaaacca tcggcgcagc tatttacccg caggacatat ccacgccctc   1080
ctacatcgaa gctgaaagca cgagattctt cgccctccga gagctgcatc aggtcggaga   1140
cgctgtcgaa cttttcgatc agaaacttct cgacagacgt cgcggtgagt tcaggctttt   1200
ccatgggtat atctccttct taaagttaaa caaaattatt tctagaggga aaccgttgtg   1260
gtctccctat agtgagtcgt attaatttcg cgggatcgag atcgatccaa ttccaatccc   1320
acaaaaatct gagcttaaca gcacagttgc tcctctcaga gcagaatcgg gtattcaaca   1380
ccctcatatc aactactacg ttgtgtataa cggtccacat gccggtatat acgatgactg   1440
gggttgtaca aaggcggcaa caaacggcgt tcccggagtt gcacacaaga aatttgccac   1500
tattacagag gcaagagcag cagctgacgc gtacacaaca agtcagcaaa cagacaggtt   1560
gaacttcatc cccaaaggag aagctcaact caagcccaag agctttgcta aggccctaac   1620
aagcccacca aagcaaaaag cccactggct cacgctagga accaaaaggc ccagcagtga   1680
tccagcccca aaagagatct cctttgcccc ggagattaca atggacgatt tcctctatct   1740
ttacgatcta ggaaggaagt tcgaaggtga aggtgacgac actatgttca ccactgataa   1800
tgagaaggtt agcctcttca atttcagaaa gaatgctgac ccacagatgg ttagagaggc   1860
ctacgcagca ggtctcatca agacgatcta cccgagtaac aatctccagg agatcaaata   1920
ccttcccaag aaggttaaag atgcagtcaa aagattcagg actaattgca tcaagaacac   1980
agagaaagac atatttctca agatcagaag tactattcca gtatggacga ttcaaggctt   2040
gcttcataaa ccaaggcaag taatagagat tggagtctct aaaaaggtag ttcctactga   2100
atctaaggcc atgcatggag tctaagattc aaatcgagga tctaacagaa ctcgccgtga   2160
agactggcga acagttcata cagagtcttt tacgactcaa tgacaagaag aaaatcttcg   2220
tcaacatggt ggagcacgac actctggtct actccaaaaa tgtcaaagat acagtctcag   2280
aagaccaaag ggctattgag acttttcaac aaaggataat ttcgggaaac ctcctcggat   2340
tccattgccc agctatctgt cacttcatcg aaaggacagt agaaaaggaa ggtggctcct   2400
acaaatgcca tcattgcgat aaaggaaagg ctatcattca agatgcctct gccgacagtg   2460
gtcccaaaga tggaccccca cccacgagga gcatcgtgga aaaagaagac gttccaacca   2520
cgtcttcaaa gcaagtggat tgatgtgaca tctccactga cgtaagggat gacgcacaat   2580
cccactatcc ttcgcaagac ccttcctcta tataaggaag ttcatttcat ttggagagga   2640
cacgctcgag ctcatttctc tattacttca gccataacaa aagaactctt ttctcttctt   2700
attaaaccat gaaaaagcct gaactcaccg cgacgtctgt cgagaagttt ctgatcgaaa   2760
agttcgacag cgtctccgac ctgatgcagc tctcggaggg cgaagaatct cgtgctttca   2820
gcttcgatgt aggagggcgt ggatatgtcc tgcgggtaaa tagctgcgcc gatggtttct   2880
acaaagatcg ttatgtttat cggcactttg catcggccgc gctcccgatt ccggaagtgc   2940
ttgacattgg ggaattcagc gagagcctga cctattgcat ctcccgccgt gcacagggtg   3000
tcacgttgca agacctgcct gaaaccgaac tgcccgctgt tctgcagccg gtcgcggagg   3060
ccatggatgc gatcgctgcg gccgatctta gccagacgag cgggttcggc ccattcggac   3120
cgcaaggaat cggtcaatac actacatggc gtgatttcat atgcgcgatt gctgatcccc   3180
atgtgtatca ctggcaaact gtgatggacg acaccgtcag tgcgtccgtc gcgcaggctc   3240
```

-continued

```
tcgatgagct gatgctttgg gccgaggact gccccgaagt ccggcacctc gtgcacgcgg   3300
atttcggctc caacaatgtc ctgacggaca atggccgcat aacagcggtc attgactgga   3360
gcgaggcgat gttcggggat tcccaatacg aggtcgccaa catcttcttc tggaggccgt   3420
ggttggcttg tatggagcag cagacgcgct acttcgagcg gaggcatccg gagcttgcag   3480
gatcgccgcg gctccgggcg tatatgctcc gcattggtct tgaccaactc tatcagagct   3540
tggttgacgg caatttcgat gatgcagctt gggcgcaggg tcgatgcgac gcaatcgtcc   3600
gatccggagc cgggactgtc gggcgtacac aaatcgcccg cagaagcgcg gccgtctgga   3660
ccgatggctg tgtagaagta ctcgccgata gtggaaaccg acgccccagc actcgtccga   3720
gggcaaagga atagtgaggt acctaaagaa ggagtgcgtc gaagcagatc gttcaaacat   3780
ttggcaataa agtttcttaa gattgaatcc tgttgccggt cttgcgatga ttatcatata   3840
atttctgttg aattacgtta agcatgtaat aattaacatg taatgcatga cgttatttat   3900
gagatgggtt tttatgatta gagtcccgca attatacatt taatacgcga tagaaaacaa   3960
aatatagcgc gcaaactagg ataaattatc gcgcgcggtg tcatctatgt tactagatcg   4020
atgtcgaatc gatcaacctg cattaatgaa tcggccaacg cgcggggaga ggcggtttgc   4080
gtattgggcg ctcttccgct tcctcgctca ctgactcgct gcgctcggtc gttcggctgc   4140
ggcgagcggt atcagctcac tcaaaggcgg taatacggtt atccacagaa tcaggggata   4200
acgcaggaaa gaacatgtga gcaaaaggcc agcaaaaggc caggaaccgt aaaaaggccg   4260
cgttgctggc gtttttccat aggctccgcc cccctgacga gcatcacaaa aatcgacgct   4320
caagtcagag gtggcgaaac ccgacaggac tataaagata ccaggcgttt ccccctggaa   4380
gctccctcgt gcgctctcct gttccgaccc tgccgcttac cggatacctg tccgcctttc   4440
tcccttcggg aagcgtggcg ctttctcaat gctcacgctg taggtatctc agttcggtgt   4500
aggtcgttcg ctccaagctg ggctgtgtgc acgaaccccc cgttcagccc gaccgctgcg   4560
ccttatccgg taactatcgt cttgagtcca acccggtaag acacgactta tcgccactgg   4620
cagcagccac tggtaacagg attagcagag cgaggtatgt aggcggtgct acagagttct   4680
tgaagtggtg gcctaactac ggctacacta gaaggacagt atttggtatc tgcgctctgc   4740
tgaagccagt taccttcgga aaaagagttg gtagctcttg atccggcaaa caaaccaccg   4800
ctggtagcgg tggttttttt gtttgcaagc agcagattac gcgcagaaaa aaaggatctc   4860
aagaagatcc tttgatcttt tctacggggt ctgacgctca gtggaacgaa aactcacgtt   4920
aagggatttt ggtcatgaca ttaacctata aaaataggcg tatcacgagg ccctttcgtc   4980
tcgcgcgttt cggtgatgac ggtgaaaacc tctgacacat gcagctcccg gagacggtca   5040
cagcttgtct gtaagcggat gccgggagca gacaagcccg tcagggcgcg tcagcgggtg   5100
ttggcgggtg tcggggctgg cttaactatg cggcatcaga gcagattgta ctgagagtgc   5160
accatatgga catattgtcg ttagaacgcg gctacaatta atacataacc ttatgtatca   5220
tacacatacg atttaggtga cactatagaa cggcgcgcca agcttgcatg cctgcaggct   5280
agcctaagta cgtactcaaa atgccaacaa ataaaaaaaa agttgcttta ataatgccaa   5340
aacaaattaa taaaacactt acaacaccgg attttttta attaaaatgt gccatttagg   5400
ataaatagtt aatattttta ataattattt aaaaagccgt atctactaaa atgattttta   5460
tttggttgaa aatattaata tgtttaaatc aacacaatct atcaaaatta aactaaaaaa   5520
aaaataagtg tacgtggtta acattagtac agtaatataa gaggaaaatg agaaattaag   5580
```

-continued

```
aaattgaaag cgagtctaat ttttaaatta tgaacctgca tatataaaag gaaagaaaga   5640
atccaggaag aaaagaaatg aaaccatgca tggtcccctc gtcatcacga gtttctgcca   5700
tttgcaatag aaacactgaa acacctttct ctttgtcact taattgagat gccgaagcca   5760
cctcacacca tgaacttcat gaggtgtagc acccaaggct tccatagcca tgcatactga   5820
agaatgtctc aagctcagca ccctacttct gtgacgtgtc cctcattcac cttcctctct   5880
tccctataaa taaccacgcc tcaggttctc cgcttcacaa ctcaaacatt ctctccattg   5940
gtccttaaac actcatcagt catcaccgcg gccgcatttc gcaccaaatc aatgaaagta   6000
ataatgaaaa gtctgaataa gaatacttag gcttagatgc ctttgttact tgtgtaaaat   6060
aacttgagtc atgtaccttt ggcggaaaca gaataaataa aaggtgaaat tccaatgctc   6120
tatgtataag ttagtaatac ttaatgtgtt ctacggttgt ttcaatatca tcaaactcta   6180
attgaaactt tagaaccaca aatctcaatc ttttcttaat gaaatgaaaa atcttaattg   6240
taccatgttt atgttaaaca ccttacaatt ggttggagag gaggaccaac cgatgggaca   6300
acattgggag aaagagattc aatggagatt tggataggag aacaacattc tttttcactt   6360
caatacaaga tgagtgcaac actaaggata tgtatgagac tttcagaagc tacgacaaca   6420
tagatgagtg aggtggtgat tcctagcaag aaagacatta gaggaagcca aaatcgaaca   6480
aggaagacat caagggcaag agacaggacc atccatctca ggaaaaggag ctttgggata   6540
gtccgagaag ttgtacaaga aatttttttgg agggtgagtg atgcattgct ggtgacttta   6600
actcaatcaa aattgagaaa gaaagaaaag ggagggggct cacatgtgaa tagaagggaa   6660
acgggagaat tttacagttt tgatctaatg ggcatcccag ctagtggtaa catattcacc   6720
atgtttaacc ttcacgtacg tctagag                                      6747
```

```
<210> SEQ ID NO 7
<211> LENGTH: 8462
<212> TYPE: DNA
<213> ORGANISM: artificial sequence
<220> FEATURE:
<223> OTHER INFORMATION: plasmid pKR1475

<400> SEQUENCE: 7

ggccgcattt cgcaccaaat caatgaaagt aataatgaaa agtctgaata agaatactta     60
ggcttagatg cctttgttac ttgtgtaaaa taacttgagt catgtacctt tggcggaaac    120
agaataaata aaaggtgaaa ttccaatgct ctatgtataa gttagtaata cttaatgtgt    180
tctacggttg tttcaatatc atcaaactct aattgaaact ttagaaccac aaatctcaat    240
cttttcttaa tgaaatgaaa aatcttaatt gtaccatgtt tatgttaaac accttacaat    300
tggttggaga ggaggaccaa ccgatgggac aacattggga gaaagagatt caatggagat    360
ttggatagga gaacaacatt ctttttcact tcaatacaag atgagtgcaa cactaaggat    420
atgtatgaga ctttcagaag ctacgacaac atagatgagt gaggtggtga ttcctagcaa    480
gaaagacatt agaggaagcc aaaatcgaac aaggaagaca tcaagggcaa gagacaggac    540
catccatctc aggaaaagga gctttgggat agtccgagaa gttgtacaag aaatttttttg    600
gagggtgagt gatgcattgc tggtgacttt aactcaatca aaattgagaa agaaagaaaa    660
gggagggggc tcacatgtga atagaaggga aacgggagaa ttttacagtt ttgatctaat    720
gggcatccca gctagtggta acatattcac catgtttaac cttcacgtac gtctagagga    780
tccgtcgacg gcgcgcccga tcatccggat atagttcctc ctttcagcaa aaacccctc     840
aagacccgtt tagaggcccc aaggggttat gctagttatt gctcagcggt ggcagcagcc    900
```

-continued

```
aactcagctt cctttcgggc tttgttagca gccggatcga tccaagctgt acctcactat    960
tcctttgccc tcggacgagt gctggggcgt cggtttccac tatcggcgag tacttctaca   1020
cagccatcgg tccagacggc cgcgcttctg cgggcgattt gtgtacgccc gacagtcccg   1080
gctccggatc ggacgattgc gtcgcatcga ccctgcgccc aagctgcatc atcgaaattg   1140
ccgtcaacca agctctgata gagttggtca agaccaatgc ggagcatata cgcccggagc   1200
cgcggcgatc ctgcaagctc cggatgcctc cgctcgaagt agcgcgtctg ctgctccata   1260
caagccaacc acggcctcca gaagaagatg ttggcgacct cgtattggga atccccgaac   1320
atcgcctcgc tccagtcaat gaccgctgtt atgcggccat tgtccgtcag gacattgttg   1380
gagccgaaat ccgcgtgcac gaggtgccgg acttcggggc agtcctcggc ccaaagcatc   1440
agctcatcga gagcctgcgc gacggacgca ctgacggtgt cgtccatcac agtttgccag   1500
tgatacacat ggggatcagc aatcgcgcat atgaaatcac gccatgtagt gtattgaccg   1560
attccttgcg gtccgaatgg gccgaacccg ctcgtctggc taagatcggc cgcagcgatc   1620
gcatccatag cctccgcgac cggctgcaga acagcgggca gttcggtttc aggcaggtct   1680
tgcaacgtga caccctgtgc acggcgggag atgcaatagg tcaggctctc gctgaattcc   1740
ccaatgtcaa gcacttccgg aatcgggagc gcggccgatg caaagtgccg ataaacataa   1800
cgatctttgt agaaaccatc ggcgcagcta tttacccgca ggacatatcc acgccctcct   1860
acatcgaagc tgaaagcacg agattcttcg ccctccgaga gctgcatcag gtcggagacg   1920
ctgtcgaact tttcgatcag aaacttctcg acagacgtcg cggtgagttc aggcttttcc   1980
atgggtatat ctccttctta aagttaaaca aaattatttc tagagggaaa ccgttgtggt   2040
ctccctatag tgagtcgtat taatttcgcg ggatcgagat cgatccaatt ccaatcccac   2100
aaaaatctga gcttaacagc acagttgctc ctctcagagc agaatcgggt attcaacacc   2160
ctcatatcaa ctactacgtt gtgtataacg gtccacatgc cggtatatac gatgactggg   2220
gttgtacaaa ggcggcaaca aacggcgttc ccggagttgc acacaagaaa tttgccacta   2280
ttacagaggc aagagcagca gctgacgcgt acacaacaag tcagcaaaca gacaggttga   2340
acttcatccc caaaggagaa gctcaactca agcccaagag ctttgctaag gccctaacaa   2400
gcccaccaaa gcaaaaagcc cactggctca cgctaggaac caaaaggccc agcagtgatc   2460
cagccccaaa agagatctcc tttgccccgg agattacaat ggacgatttc ctctatcttt   2520
acgatctagg aaggaagttc gaaggtgaag gtgacgacac tatgttcacc actgataatg   2580
agaaggttag cctcttcaat ttcagaaaga atgctgaccc acagatggtt agagaggcct   2640
acgcagcagg tctcatcaag acgatctacc cgagtaacaa tctccaggag atcaaatacc   2700
ttcccaagaa ggttaaagat gcagtcaaaa gattcaggac taattgcatc aagaacacag   2760
agaaagacat atttctcaag atcagaagta ctattccagt atggacgatt caaggcttgc   2820
ttcataaacc aaggcaagta atagagattg gagtctctaa aaaggtagtt cctactgaat   2880
ctaaggccat gcatggagtc taagattcaa atcgaggatc taacagaact cgccgtgaag   2940
actggcgaac agttcataca gagtctttta cgactcaatg acaagaagaa aatcttcgtc   3000
aacatggtgg agcacgacac tctggtctac tccaaaaatg tcaaagatac agtctcagaa   3060
gaccaaaggg ctattgagac ttttcaacaa aggataattt cgggaaacct cctcggattc   3120
cattgcccag ctatctgtca cttcatcgaa aggacagtag aaaaggaagg tggctcctac   3180
aaatgccatc attgcgataa aggaaaggct atcattcaag atgcctctgc cgacagtggt   3240
```

-continued

```
cccaaagatg gacccccacc cacgaggagc atcgtggaaa aagaagacgt tccaaccacg   3300
tcttcaaagc aagtggattg atgtgacatc tccactgacg taagggatga cgcacaatcc   3360
cactatcctt cgcaagaccc ttcctctata taaggaagtt catttcattt ggagaggaca   3420
cgctcgagct catttctcta ttacttcagc cataacaaaa gaactctttt ctcttcttat   3480
taaaccatga aaaagcctga actcaccgcg acgtctgtcg agaagtttct gatcgaaaag   3540
ttcgacagcg tctccgacct gatgcagctc tcggagggcg aagaatctcg tgctttcagc   3600
ttcgatgtag gagggcgtgg atatgtcctg cgggtaaata gctgcgccga tggtttctac   3660
aaagatcgtt atgtttatcg gcactttgca tcggccgcgc tcccgattcc ggaagtgctt   3720
gacattgggg aattcagcga gagcctgacc tattgcatct cccgccgtgc acagggtgtc   3780
acgttgcaag acctgcctga aaccgaactg cccgctgttc tgcagccggt cgcggaggcc   3840
atggatgcga tcgctgcggc cgatcttagc cagacgagcg ggttcggccc attcggaccg   3900
caaggaatcg gtcaatacac tacatggcgt gatttcatat gcgcgattgc tgatccccat   3960
gtgtatcact ggcaaactgt gatggacgac accgtcagtg cgtccgtcgc gcaggctctc   4020
gatgagctga tgctttgggc cgaggactgc cccgaagtcc ggcacctcgt gcacgcggat   4080
ttcggctcca acaatgtcct gacggacaat ggccgcataa cagcggtcat tgactggagc   4140
gaggcgatgt tcggggattc ccaatacgag gtcgccaaca tcttcttctg gaggccgtgg   4200
ttggcttgta tggagcagca gacgcgctac ttcgagcgga ggcatccgga gcttgcagga   4260
tcgccgcggc tccgggcgta tatgctccgc attggtcttg accaactcta tcagagcttg   4320
gttgacggca atttcgatga tgcagcttgg gcgcagggtc gatgcgacgc aatcgtccga   4380
tccggagccg ggactgtcgg gcgtacacaa atcgcccgca gaagcgcggc cgtctggacc   4440
gatggctgtg tagaagtact cgccgatagt ggaaaccgac gccccagcac tcgtccgagg   4500
gcaaaggaat agtgaggtac ctaaagaagg agtgcgtcga agcagatcgt tcaaacattt   4560
ggcaataaag tttcttaaga ttgaatcctg ttgccggtct tgcgatgatt atcatataat   4620
ttctgttgaa ttacgttaag catgtaataa ttaacatgta atgcatgacg ttatttatga   4680
gatgggtttt tatgattaga gtcccgcaat tatacattta atacgcgata gaaaacaaaa   4740
tatagcgcgc aaactaggat aaattatcgc gcgcggtgtc atctatgtta ctagatcgat   4800
gtcgaatcga tcaacctgca ttaatgaatc ggccaacgcg cggggagagg cggtttgcgt   4860
attgggcgct cttccgcttc ctcgctcact gactcgctgc gctcggtcgt tcggctgcgg   4920
cgagcggtat cagctcactc aaaggcggta atacggttat ccacagaatc aggggataac   4980
gcaggaaaga acatgtgagc aaaaggccag caaaaggcca ggaaccgtaa aaaggccgcg   5040
ttgctggcgt ttttccatag gctccgcccc cctgacgagc atcacaaaaa tcgacgctca   5100
agtcagaggt ggcgaaaccc gacaggacta taaagatacc aggcgtttcc ccctggaagc   5160
tccctcgtgc gctctcctgt tccgaccctg ccgcttaccg gatacctgtc cgcctttctc   5220
ccttcgggaa gcgtggcgct ttctcaatgc tcacgctgta ggtatctcag ttcggtgtag   5280
gtcgttcgct ccaagctggg ctgtgtgcac gaaccccccg ttcagcccga ccgctgcgcc   5340
ttatccggta actatcgtct tgagtccaac ccggtaagac acgacttatc gccactggca   5400
gcagccactg gtaacaggat tagcagagcg aggtatgtag gcggtgctac agagttcttg   5460
aagtggtggc ctaactacgg ctacactaga aggacagtat ttggtatctg cgctctgctg   5520
aagccagtta ccttcggaaa aagagttggt agctcttgat ccggcaaaca aaccaccgct   5580
ggtagcggtg gtttttttgt ttgcaagcag cagattacgc gcagaaaaaa aggatctcaa   5640
```

-continued

```
gaagatcctt tgatcttttc tacggggtct gacgctcagt ggaacgaaaa ctcacgttaa   5700
gggattttgg tcatgacatt aacctataaa aataggcgta tcacgaggcc ctttcgtctc   5760
gcgcgtttcg gtgatgacgg tgaaaacctc tgacacatgc agctcccgga gacggtcaca   5820
gcttgtctgt aagcggatgc cgggagcaga caagcccgtc agggcgcgtc agcgggtgtt   5880
ggcgggtgtc ggggctggct taactatgcg gcatcagagc agattgtact gagagtgcac   5940
catatggaca tattgtcgtt agaacgcggc tacaattaat acataacctt atgtatcata   6000
cacatacgat ttaggtgaca ctatagaacg gcgcgccaag cttgcatgcc tgcaggctag   6060
cctaagtacg tactcaaaat gccaacaaat aaaaaaaaag ttgctttaat aatgccaaaa   6120
caaattaata aaacacttac aacaccggat ttttttaat taaaatgtgc catttaggat    6180
aaatagttaa tatttttaat aattatttaa aaagccgtat ctactaaaat gatttttatt   6240
tggttgaaaa tattaatatg tttaaatcaa cacaatctat caaaattaaa ctaaaaaaaa   6300
aataagtgta cgtggttaac attagtacag taatataaga ggaaaatgag aaattaagaa   6360
attgaaagcg agtctaattt ttaaattatg aacctgcata tataaaagga aagaaagaat   6420
ccaggaagaa aagaaatgaa accatgcatg gtcccctcgt catcacgagt ttctgccatt   6480
tgcaatagaa acactgaaac acctttctct ttgtcactta attgagatgc cgaagccacc   6540
tcacaccatg aacttcatga ggtgtagcac ccaaggcttc catagccatg catactgaag   6600
aatgtctcaa gctcagcacc ctacttctgt gacgtgtccc tcattcacct tcctctcttc   6660
cctataaata accacgcctc aggttctccg cttcacaact caaacattct ctccattggt   6720
ccttaaacac tcatcagtca tcaccgcggc catcacaagt ttgtacaaaa aagctgaacg   6780
agaaacgtaa aatgatataa atatcaatat attaaattag attttgcata aaaaacagac   6840
tacataatac tgtaaaacac aacatatcca gtcatattgg cggccgcatt aggcacccca   6900
ggctttacac tttatgcttc cggctcgtat aatgtgtgga ttttgagtta ggatccgtcg   6960
agattttcag gagctaagga agctaaaatg gagaaaaaaa tcactggata taccaccgtt   7020
gatatatccc aatggcatcg taaagaacat tttgaggcat ttcagtcagt tgctcaatgt   7080
acctataacc agaccgttca gctggatatt acggcctttt taaagaccgt aaagaaaaat   7140
aagcacaagt tttatccggc ctttattcac attcttgccc gcctgatgaa tgctcatccg   7200
gaattccgta tggcaatgaa agacggtgag ctggtgatat gggatagtgt tcacccttgt   7260
tacaccgttt tccatgagca aactgaaacg ttttcatcgc tctggagtga ataccacgac   7320
gatttccggc agtttctaca catatattcg caagatgtgg cgtgttacgg tgaaaacctg   7380
gcctatttcc ctaaagggtt tattgagaat atgtttttcg tctcagccaa tccctgggtg   7440
agtttcacca gttttgattt aaacgtggcc aatatggaca acttcttcgc ccccgttttc   7500
accatgggca aatattatac gcaaggcgac aaggtgctga tgccgctggc gattcaggtt   7560
catcatgccg tttgtgatgg cttccatgtc ggcagaatgc ttaatgaatt acaacagtac   7620
tgcgatgagt ggcagggcgg ggcgtaaacg cgtggatccg gcttactaaa agccagataa   7680
cagtatgcgt atttgcgcgc tgatttttgc ggtataagaa tatatactga tatgtatacc   7740
cgaagtatgt caaaaagagg tatgctatga agcagcgtat tacagtgaca gttgacagcg   7800
acagctatca gttgctcaag gcatatatga tgtcaatatc tccggtctgg taagcacaac   7860
catgcagaat gaagcccgtc gtctgcgtgc cgaacgctgg aaagcggaaa atcaggaagg   7920
gatggctgag gtcgcccggt ttattgaaat gaacggctct tttgctgacg agaacagggg   7980
```

-continued ctggtgaaat gcagtttaag gtttacacct ataaaagaga gagccgttat cgtctgtttg 8040
tggatgtaca gagtgatatt attgacacgc ccgggcgacg gatggtgatc cccctggcca 8100
gtgcacgtct gctgtcagat aaagtctccc gtgaacttta cccggtggtg catatcgggg 8160
atgaaagctg gcgcatgatg accaccgata tggccagtgt gccggtctcc gttatcgggg 8220
aagaagtggc tgatctcagc caccgcgaaa atgacatcaa aaacgccatt aacctgatgt 8280
tctggggaat ataaatgtca ggctccctta tacacagcca gtctgcaggt cgaccatagt 8340
gactggatat gttgtgtttt acagcattat gtagtctgtt ttttatgcaa aatctaattt 8400
aatatattga tatttatatc attttacgtt tctcgttcag ctttcttgta caaagtggtg 8460
at 8462

<210> SEQ ID NO 8
<211> LENGTH: 13268
<212> TYPE: DNA
<213> ORGANISM: artificial sequence
<220> FEATURE:
<223> OTHER INFORMATION: plasmid pKR92

<400> SEQUENCE: 8
cgcgcctcga gtgggcggat cccccgggct gcaggaattc actggccgtc gttttacaac 60
gtcgtgactg ggaaaaccct ggcgttaccc aacttaatcg ccttgcagca catccccctt 120
tcgccagctg gcgtaatagc gaagaggccc gcaccgatcg cccttcccaa cagttgcgca 180
gcctgaatgg cgaatggatc gatccatcgc gatgtacctt ttgttagtca gcctctcgat 240
tgctcatcgt cattacacag taccgaagtt tgatcgatct agtaacatag atgacaccgc 300
gcgcgataat ttatcctagt ttgcgcgcta tattttgttt tctatcgcgt attaaatgta 360
taattgcggg actctaatca taaaaaccca tctcataaat aacgtcatgc attacatgtt 420
aattattaca tgcttaacgt aattcaacag aaattatatg ataatcatcg caagaccggc 480
aacaggattc aatcttaaga aactttattg ccaaatgttt gaacgatctg cttcgacgca 540
ctccttcttt actccaccat ctcgtcctta ttgaaaacgt gggtagcacc aaaacgaatc 600
aagtcgctgg aactgaagtt accaatcacg ctggatgatt tgccagttgg attaatcttg 660
cctttccccg catgaataat attgatgaat gcatgcgtga ggggtagttc gatgttggca 720
atagctgcaa ttgccgcgac atcctccaac gagcataatt cttcagaaaa atagcgatgt 780
tccatgttgt cagggcatgc atgatgcacg ttatgaggtg acggtgctag gcagtattcc 840
ctcaaagttt catagtcagt atcatattca tcattgcatt cctgcaagag agaattgaga 900
cgcaatccac acgctgcggc aaccttccgg cgttcgtggt ctatttgctc ttggacgttg 960
caaacgtaag tgttggatcg atccggggtg ggcgaagaac tccagcatga gatccccgcg 1020
ctggaggatc atccagccgg cgtcccggaa aacgattccg aagcccaacc tttcatagaa 1080
ggcggcggtg gaatcgaaat ctcgtgatgg caggttgggc gtcgcttggt cggtcatttc 1140
gaaccccaga gtcccgctca gaagaactcg tcaagaaggc gatagaaggc gatgcgctgc 1200
gaatcgggag cggcgatacc gtaaagcacg aggaagcggt cagcccattc gccgccaagc 1260
tcttcagcaa tatcacgggt agccaacgct atgtcctgat agcggtccgc cacacccagc 1320
cggccacagt cgatgaatcc agaaaagcgg ccattttcca ccatgatatt cggcaagcag 1380
gcatcgccat gggtcacgac gagatcctcg ccgtcgggca tgcgcgcctt gagcctggcg 1440
aacagttcgg ctggcgcgag cccctgatgc tcttcgtcca gatcatcctg atcgacaaga 1500
ccggcttcca tccgagtacg tgctcgctcg atgcgatgtt tcgcttggtg gtcgaatggg 1560

-continued

```
caggtagccg gatcaagcgt atgcagccgc cgcattgcat cagccatgat ggatactttc   1620
tcggcaggag caaggtgaga tgacaggaga tcctgccccg gcacttcgcc caatagcagc   1680
cagtcccttc ccgcttcagt gacaacgtcg agcacagctg cgcaaggaac gcccgtcgtg   1740
gccagccacg atagccgcgc tgcctcgtcc tgcagttcat tcagggcacc ggacaggtcg   1800
gtcttgacaa aaagaaccgg gcgcccctgc gctgacagcc ggaacacggc ggcatcagag   1860
cagccgattg tctgttgtgc ccagtcatag ccgaatagcc tctccaccca agcggccgga   1920
gaacctgcgt gcaatccatc ttgttcaatc atgcgaaacg atccccgcaa gcttggagac   1980
tggtgatttc agcgtgtcct ctccaaatga aatgaacttc cttatataga ggaagggtct   2040
tgcgaaggat agtgggattg tgcgtcatcc cttacgtcag tggagatatc acatcaatcc   2100
acttgctttg aagacgtggt tggaacgtct tctttttcca cgatgctcct cgtgggtggg   2160
ggtccatctt tgggaccact gtcggcagag gcatcttcaa cgatggcctt tcctttatcg   2220
caatgatggc atttgtagga gccaccttcc ttttccacta tcttcacaat aaagtgacag   2280
atagctgggc aatggaatcc gaggaggttt ccggatatta ccctttgttg aaaagtctca   2340
attgcccttt ggtcttctga gactgtatct ttgatatttt tggagtagac aagcgtgtcg   2400
tgctccacca tgttgacgaa gattttcttc ttgtcattga gtcgtaagag actctgtatg   2460
aactgttcgc cagtctttac ggcgagttct gttaggtcct ctatttgaat ctttgactcc   2520
atggcctttg attcagtggg aactaccttt ttagagactc caatctctat tacttgcctt   2580
ggtttgtgaa gcaagccttg aatcgtccat actggaatag tacttctgat cttgagaaat   2640
atatctttct ctgtgttctt gatgcagtta gtcctgaatc ttttgactgc atctttaacc   2700
ttcttgggaa ggtatttgat ctcctggaga ttattgctcg ggtagatcgt cttgatgaga   2760
cctgctgcgt aagcctctct aaccatctgt gggttagcat tctttctgaa attgaaaagg   2820
ctaatcttct cattatcagt ggtgaacatg gtatcgtcac cttctccgtc gaacttcctg   2880
actagatcgt agagatagag gaagtcgtcc attgtgatct ctggggcaaa ggagtctgaa   2940
ttaattcgat atggtggatt tatcacaaat gggacccgcc gccgacagag gtgtgatgtt   3000
aggccaggac tttgaaaatt tgcgcaacta tcgtatagtg gccgacaaat tgacgccgag   3060
ttgacagact gcctagcatt tgagtgaatt atgtgaggta atgggctaca ctgaattggt   3120
agctcaaact gtcagtattt atgtatatga gtgtatattt tcgcataatc tcagaccaat   3180
ctgaagatga aatgggtatc tgggaatggc gaaatcaagg catcgatcgt gaagtttctc   3240
atctaagccc ccatttggac gtgaatgtag acacgtcgaa ataaagattt ccgaattaga   3300
ataatttgtt tattgctttc gcctataaat acgacggatc gtaatttgtc gttttatcaa   3360
aatgtacttt cattttataa taacgctgcg gacatctaca tttttgaatt gaaaaaaaat   3420
tggtaattac tctttctttt tctccatatt gaccatcata ctcattgctg atccatgtag   3480
atttcccgga catgaagcca tttacaattg aatatatcct gccgccgctg ccgctttgca   3540
cccggtggag cttgcatgtt ggtttctacg cagaactgag ccggttaggc agataatttc   3600
cattgagaac tgagccatgt gcaccttccc cccaacacgg tgagcgacgg ggcaacggag   3660
tgatccacat gggactttta aacatcatcc gtcggatggc gttgcgagag aagcagtcga   3720
tccgtgagat cagccgacgc accgggcagg cgcgcaacac gatcgcaaag tatttgaacg   3780
caggtacaat cgagccgacg ttcacgcgga acgaccaagc aagctagctt taatgcggta   3840
gtttatcaca gttaaattgc taacgcagtc aggcaccgtg tatgaaatct aacaatgcgc   3900
```

-continued tcatcgtcat cctcggcacc gtcaccctgg atgctgtagg cataggcttg gttatgccgg 3960
tactgccggg cctcttgcgg gatatcgtcc attccgacag catcgccagt cactatggcg 4020
tgctgctagc gctatatgcg ttgatgcaat ttctatgcgc acccgttctc ggagcactgt 4080
ccgaccgctt tggccgccgc ccagtcctgc tcgcttcgct acttggagcc actatcgact 4140
acgcgatcat ggcgaccaca cccgtcctgt ggtccaaccc ctccgctgct atagtgcagt 4200
cggcttctga cgttcagtgc agccgtcttc tgaaaacgac atgtcgcaca agtcctaagt 4260
tacgcgacag gctgccgccc tgcccttttc ctggcgtttt cttgtcgcgt gttttagtcg 4320
cataaagtag aatacttgcg actagaaccg gagacattac gccatgaaca agagcgccgc 4380
cgctggcctg ctgggctatg cccgcgtcag caccgacgac caggacttga ccaaccaacg 4440
ggccgaactg cacgcggccg gctgcaccaa gctgttttcc gagaagatca ccggcaccag 4500
gcgcgaccgc ccggagctgg ccaggatgct tgaccaccta cgccctggcg acgttgtgac 4560
agtgaccagg ctagaccgcc tggcccgcag cacccgcgac ctactggaca ttgccgagcg 4620
catccaggag gccggcgcgg gcctgcgtag cctggcagag ccgtgggccg acaccaccac 4680
gccggccggc cgcatggtgt tgaccgtgtt cgccggcatt gccgagttcg agcgttccct 4740
aatcatcgac cgcacccgga gcgggcgcga ggccgccaag gcccgaggcg tgaagtttgg 4800
cccccgccct accctcaccc cggcacagat cgcgcacgcc cgcgagctga tcgaccagga 4860
aggccgcacc gtgaaagagg cggctgcact gcttggcgtg catcgctcga ccctgtaccg 4920
cgcacttgag cgcagcgagg aagtgacgcc caccgaggcc aggcggcgcg gtgccttccg 4980
tgaggacgca ttgaccgagg ccgacgccct ggcggccgcc gagaatgaac gccaagagga 5040
acaagcatga aaccgcacca ggacggccag gacgaaccgt tttcattac cgaagagatc 5100 gaggcggaga tgatcgcggc cgggtacgtg ttcgagccgc ccgcgcacgt ctcaaccgtg 5160
cggctgcatg aaatcctggc cggtttgtct gatgccaagc tggcggcctg gccggccagc 5220
ttggccgctg aagaaaccga gcgccgccgt ctaaaaaggt gatgtgtatt tgagtaaaac 5280
agcttgcgtc atgcggtcgc tgcgtatatg atgcgatgag taaataaaca aatacgcaag 5340
ggaacgcatg aagttatcgc tgtacttaac cagaaaggcg ggtcaggcaa gacgaccatc 5400
gcaacccatc tagcccgcgc cctgcaactc gccggggccg atgttctgtt agtcgattcc 5460
gatccccagg gcagtgcccg cgattgggcg gccgtgcggg aagatcaacc gctaaccgtt 5520
gtcggcatcg accgcccgac gattgaccgc gacgtgaagg ccatcggccg gcgcgacttc 5580
gtagtgatcg acggagcgcc ccaggcggcg gacttggctg tgtccgcgat caaggcagcc 5640
gacttcgtgc tgattccggt gcagccaagc ccttacgaca tatgggccac cgccgacctg 5700
gtggagctgg ttaagcagcg cattgaggtc acggatggaa ggctacaagc ggcctttgtc 5760
gtgtcgcggg cgatcaaagg cacgcgcatc ggcggtgagg ttgccgaggc gctggccggg 5820
tacgagctgc ccattcttga gtcccgtatc acgcagcgcg tgagctaccc aggcactgcc 5880
gccgccggca caaccgttct tgaatcagaa cccgagggcg acgctgcccg cgaggtccag 5940
gcgctggccg ctgaaattaa atcaaaactc atttgagtta atgaggtaaa gagaaaatga 6000
gcaaaagcac aaacacgcta agtgccggcc gtccgagcgc acgcagcagc aaggctgcaa 6060
cgttggccag cctggcagac acgccagcca tgaagcgggt caactttcag ttgccggcgg 6120
aggatcacac caagctgaag atgtacgcgg tacgccaagg caagaccatt accgagctgc 6180
tatctgaata catcgcgcag ctaccagagt aaatgagcaa atgaataaat gagtagatga 6240
attttagcgg ctaaaggagg cggcatggaa aatcaagaac aaccaggcac cgacgccgtg 6300

```
gaatgcccca tgtgtggagg aacgggcggt tggccaggcg taagcggctg ggttgtctgc   6360
cggccctgca atggcactgg aacccccaag cccgaggaat cggcgtgagc ggtcgcaaac   6420
catccggccc ggtacaaatc ggcgcggcgc tgggtgatga cctggtggag aagttgaagg   6480
ccgcgcaggc cgcccagcgg caacgcatcg aggcagaagc acgccccggt gaatcgtggc   6540
aagcggccgc tgatcgaatc cgcaaagaat cccggcaacc gccggcagcc ggtgcgccgt   6600
cgattaggaa gccgcccaag ggcgacgagc aaccagattt tttcgttccg atgctctatg   6660
acgtgggcac ccgcgatagt cgcagcatca tggacgtggc cgttttccgt ctgtcgaagc   6720
gtgaccgacg agctggcgag gtgatccgct acgagcttcc agacgggcac gtagaggttt   6780
ccgcagggcc ggccggcatg gccagtgtgt gggattacga cctggtactg atggcggttt   6840
cccatctaac cgaatccatg aaccgatacc gggaagggaa gggagacaag cccggccgcg   6900
tgttccgtcc acacgttgcg gacgtactca agttctgccg gcgagccgat ggcggaaagc   6960
agaaagacga cctggtagaa acctgcattc ggttaaacac cacgcacgtt gccatgcagc   7020
gtacgaagaa ggccaagaac ggccgcctgg tgacggtatc cgagggtgaa gccttgatta   7080
gccgctacaa gatcgtaaag agcgaaaccg ggcggccgga gtacatcgag atcgagctag   7140
ctgattggat gtaccgcgag atcacagaag gcaagaaccc ggacgtgctg acggttcacc   7200
ccgattactt tttgatcgat cccggcatcg gccgttttct ctaccgcctg gcacgccgcg   7260
ccgcaggcaa ggcagaagcc agatggttgt tcaagacgat ctacgaacgc agtggcagcg   7320
ccggagagtt caagaagttc tgtttcaccg tgcgcaagct gatcgggtca aatgacctgc   7380
cggagtacga tttgaaggag gaggcggggc aggctggccc gatcctagtc atgcgctacc   7440
gcaacctgat cgagggcgaa gcatccgccg gttcctaatg tacggagcag atgctagggc   7500
aaattgccct agcaggggaa aaaggtcgaa aaggtctctt tcctgtggat agcacgtaca   7560
ttgggaaccc aaagccgtac attgggaacc ggaacccgta cattgggaac ccaaagccgt   7620
acattgggaa ccggtcacac atgtaagtga ctgatataaa agagaaaaaa ggcgattttt   7680
ccgcctaaaa ctctttaaaa cttattaaaa ctcttaaaac ccgcctggcc tgtgcataac   7740
tgtctggcca gcgcacagcc gaagagctgc aaaaagcgcc tacccttcgg tcgctgcgct   7800
ccctacgccc cgccgcttcg cgtcggccta tcgcggccgc tggccgctca aaaatggctg   7860
gcctacggcc aggcaatcta ccagggcgcg gacaagccgc gccgtcgcca ctcgaccgcc   7920
ggcgcccaca tcaaggcacc ctgcctcgcg cgtttcggtg atgacggtga aaacctctga   7980
cacatgcagc tcccggagac ggtcacagct tgtctgtaag cggatgccgg gagcagacaa   8040
gcccgtcagg gcgcgtcagc gggtgttggc gggtgtcggg gcgcagccat gacccagtca   8100
cgtagcgata gcggagtgta tactggctta actatgcggc atcagagcag attgtactga   8160
gagtgcacca tatgcggtgt gaaataccgc acagatgcgt aaggagaaaa taccgcatca   8220
ggcgctcttc cgcttcctcg ctcactgact cgctgcgctc ggtcgttcgg ctgcggcgag   8280
cggtatcagc tcactcaaag gcggtaatac ggttatccac agaatcaggg gataacgcag   8340
gaaagaacat gtgagcaaaa ggccagcaaa aggccaggaa ccgtaaaaag gccgcgttgc   8400
tggcgttttt ccataggctc cgcccccctg acgagcatca caaaaatcga cgctcaagtc   8460
agaggtggcg aaacccgaca ggactataaa gataccaggc gtttccccct ggaagctccc   8520
tcgtgcgctc tcctgttccg accctgccgc ttaccggata cctgtccgcc tttctccctt   8580
cgggaagcgt ggcgctttct catagctcac gctgtaggta tctcagttcg gtgtaggtcg   8640
```

-continued

```
ttcgctccaa gctgggctgt gtgcacgaac cccccgttca gcccgaccgc tgcgccttat   8700
ccggtaacta tcgtcttgag tccaacccgg taagacacga cttatcgcca ctggcagcag   8760
ccactggtaa caggattagc agagcgaggt atgtaggcgg tgctacagag ttcttgaagt   8820
ggtggcctaa ctacggctac actagaagga cagtatttgg tatctgcgct ctgctgaagc   8880
cagttacctt cggaaaaaga gttggtagct cttgatccgg caaacaaacc accgctggta   8940
gcggtggttt ttttgtttgc aagcagcaga ttacgcgcag aaaaaaagga tctcaagaag   9000
atcctttgat cttttctacg gggtctgacg ctcagtggaa cgaaaactca cgttaaggga   9060
ttttggtcat gagattatca aaaaggatct tcacctagat ccttttaaat taaaaatgaa   9120
gttttaaatc aatctaaagt atatatgagt aaacttggtc tgacagttac caatgcttaa   9180
tcagtgaggc acctatctca gcgatctgtc tatttcgttc atccatagtt gcctgactcc   9240
ccgtcgtgta gataactacg atacgggagg gcttaccatc tggccccagt gctgcaatga   9300
taccgcgaga cccacgctca ccggctccag atttatcagc aataaaccag ccagccggaa   9360
gggccgagcg cagaagtggt cctgcaactt tatccgcctc catccagtct attaattgtt   9420
gccgggaagc tagagtaagt agttcgccag ttaatagttt gcgcaacgtt gttgccattg   9480
ctacaggcat cgtggtgtca cgctcgtcgt ttggtatggc ttcattcagc tccggttccc   9540
aacgatcaag gcgagttaca tgatccccca tgttgtgcaa aaaagcggtt agctccttcg   9600
gtcctccgat cgttgtcaga agtaagttgg ccgcagtgtt atcactcatg gttatggcag   9660
cactgcataa ttctcttact gtcatgccat ccgtaagatg cttttctgtg actggtgagt   9720
actcaaccaa gtcattctga gaatagtgta tgcggcgacc gagttgctct tgcccggcgt   9780
caacacggga taataccgcg ccacatagca gaactttaaa agtgctcatc attggaaaag   9840
acctgcaggg ggggggggcg gctgaggtct gcctcgtgaa gaaggtgttg ctgactcata   9900
ccaggcctga atcgccccat catccagcca gaaagtgagg gagccacggt tgatgagagc   9960
tttgttgtag gtggaccagt tggtgatttt gaacttttgc tttgccacgg aacggtctgc  10020
gttgtcggga agatgcgtga tctgatcctt caactcagca aaagttcgat ttattcaaca  10080
aagccgccgt cccgtcaagt cagcgtaatg ctctgccagt gttacaacca attaaccaat  10140
tctgattaga aaaactcatc gagcatcaaa tgaaactgca atttattcat atcaggatta  10200
tcaataccat atttttgaaa aagccgtttc tgtaatgaag gagaaaactc accgaggcag  10260
ttccatagga tggcaagatc ctggtatcgg tctgcgattc cgactcgtcc aacatcaata  10320
caacctatta atttcccctc gtcaaaaata aggttatcaa gtgagaaatc accatgagtg  10380
acgactgaat ccggtgagaa tggcaaaagc ttatgcattt ctttccagac ttgttcaaca  10440
ggccagccat tacgctcgtc atcaaaatca ctcgcatcaa ccaaaccgtt attcattcgt  10500
gattgcgcct gagcgagacg aaatacgcga tcgctgttaa aaggacaatt acaaacagga  10560
atcgaatgca accggcgcag gaacactgcc agcgcatcaa caatattttc acctgaatca  10620
ggatattctt ctaatacctg gaatgctgtt ttcccgggga tcgcagtggt gagtaaccat  10680
gcatcatcag gagtacggat aaaatgcttg atggtcggaa gaggcataaa ttccgtcagc  10740
cagtttagtc tgaccatctc atctgtaaca tcattggcaa cgctaccttt gccatgtttc  10800
agaaacaact ctggcgcatc gggcttccca tacaatcgat agattgtcgc acctgattgc  10860
ccgacattat cgcgagccca tttataccca tataaatcag catccatgtt ggaatttaat  10920
cgcggcctcg agcaagacgt ttcccgttga atatggctca taacacccct tgtattactg  10980
tttatgtaag cagacagttt tattgttcat gatgatatat ttttatcttg tgcaatgtaa  11040
```

catcagagat tttgagacac aacgtggctt tccccccccc ccctgcaggt caattcggtc 11100
gatatggcta ttacgaagaa ggctcgtgcg cggagtcccg tgaactttcc cacgcaacaa 11160
gtgaaccgca ccgggtttgc cggaggccat ttcgttaaaa tgcgcagcca tggctgcttc 11220
gtccagcatg gcgtaatact gatcctcgtc ttcggctggc ggtatattgc cgatgggctt 11280
caaaagccgc cgtggttgaa ccagtctatc cattccaagg tagcgaactc gaccgcttcg 11340
aagctcctcc atggtccacg ccgatgaatg acctcggcct tgtaaagacc gttgatcgct 11400
tctgcgaggg cgttgtcgtg ctgtcgccga cgcttccgat agatggctcg atacctgctt 11460
ctgccaaccg ctcggaatag cgaaaggaca cgtattgaac accgcgatcc gagtgatgca 11520
ctaggccgcc atgagcggga cgccgatcat gatgagcctc ctcgagggca tcgaggacaa 11580
agcctgcatg tgctgtccgg ctcgcccgcc atccgacaat gcgacgggcg aagacgtcga 11640
tcacgaaggc cacgtagacg aagccctccc aagtggcgac ataagtacgg acatgcgcaa 11700
aggctttccc ggtttgtcgc tgatggtgca agagacgctg aagcgcgatc cgatgcgcag 11760
gcatctgttc gtcttccgcg gtcgtggcgg tggcctgatc aaggtcactc gccgaagagc 11820
tgcatgattg gctcgaaacc gagcggggga aattgtcgcg cagttctccc gtcgccgagg 11880
cgataaatta catgctcaag cgatgggatg gcattacgtc attcctcgat gacggcccga 11940
tttgcctgac gaacaatgct gccgaacgaa cgctcagagg ctatgtactc ggcaggaagt 12000
catggctgtt tgccggatcg gatcgttgtg ctgaacgtgc ggcgttcatg gcgacactga 12060
tcatgagcgc caagctcaat aacatcgatc cgcaggcctg gcttgccgac gtccgcgccg 12120
accttgcgga cgctccgatc agcaggcttg agcaacagct gccgtggaac tggacatcca 12180
agacactgag tgctcaggcg gcctgacctg cggccttcac cggatactta ccccattatc 12240
gcagattgcg atgaagcatc agcgtcattc agcaatcttg ccaaagtatg caggctcgcg 12300
agaatcgacg tgcgaaaccg gctggttgcg ccaaagatcc gcttgcggag cggtcgaaca 12360
ttcatgctgg gacttcaaga ggtcgagtag aggaagaacc ggaaaggttg caccggaaaa 12420
tatgcgttcc tttggagagc gcctcatgga cgtgaacaaa tcgcccggac caaggatgcc 12480
acggatacaa aagctcgcga agctcggtcc cgtgggtgtt ctgtcgtctc gttgtacaac 12540
gaaatccatt cccattccgc gctcaagatg gcttcccctc ggcagttcat cagggctaaa 12600
tcaatctagc cgacttgtcc ggtgaaatgg gctgcactcc aacagaaaca atcaaacaaa 12660
catacacagc gacttattca cacgagctca aattacaacg gtatatatcc tgccagtcag 12720
catcatcaca ccaaaagtta ggcccgaata gtttgaaatt agaaagctcg caattgaggt 12780
ctacaggcca aattcgctct tagccgtaca atattactca ccggtgcgat gccccccatc 12840
gtaggtgaag gtggaaatta atgatccatc ttgagaccac aggcccacaa cagctaccag 12900
tttcctcaag ggtccaccaa aaacgtaagc gcttacgtac atggtcgata agaaaaggca 12960
atttgtagat gttaacatcc aacgtcgctt tcagggatcg atccaatacg caaaccgcct 13020
ctccccgcgc gttggccgat tcattaatgc agctggcacg acaggtttcc cgactggaaa 13080
gcgggcagtg agcgcaacgc aattaatgtg agttagctca ctcattaggc accccaggct 13140
ttacacttta tgcttccggc tcgtatgttg tgtggaattg tgagcggata acaatttcac 13200
acaggaaaca gctatgacca tgattacgcc aagcttgcat gcctgcaggt cgactctaga 13260
ggatctgg 13268

<210> SEQ ID NO 9

<211> LENGTH: 16490
<212> TYPE: DNA
<213> ORGANISM: artificial sequence
<220> FEATURE:
<223> OTHER INFORMATION: pKR1478

<400> SEQUENCE: 9
cgcgccagat cctctagagt cgacctgcag gcatgcaagc ttggcgtaat catggtcata 60
gctgtttcct gtgtgaaatt gttatccgct cacaattcca cacaacatac gagccggaag 120
cataaagtgt aaagcctggg gtgcctaatg agtgagctaa ctcacattaa ttgcgttgcg 180
ctcactgccc gctttccagt cgggaaacct gtcgtgccag ctgcattaat gaatcggcca 240
acgcgcgggg agaggcggtt tgcgtattgg atcgatccct gaaagcgacg ttggatgtta 300
acatctacaa attgcctttt cttatcgacc atgtacgtaa gcgcttacgt ttttggtgga 360
cccttgagga aactggtagc tgttgtgggc ctgtggtctc aagatggatc attaatttcc 420
accttcacct acgatggggg gcatcgcacc ggtgagtaat attgtacggc taagagcgaa 480
tttggcctgt agacctcaat tgcgagcttt ctaatttcaa actattcggg cctaactttt 540
ggtgtgatga tgctgactgg caggatatat accgttgtaa tttgagctcg tgtgaataag 600
tcgctgtgta tgtttgtttg attgtttctg ttggagtgca gcccatttca ccggacaagt 660
cggctagatt gatttagccc tgatgaactg ccgaggggaa gccatcttga gcgcggaatg 720
ggaatggatt tcgttgtaca acgagacgac agaacaccca cgggaccgag cttcgcgagc 780
ttttgtatcc gtggcatcct tggtccgggc gatttgttca cgtccatgag gcgctctcca 840
aaggaacgca tattttccgg tgcaaccttt ccggttcttc ctctactcga cctcttgaag 900
tcccagcatg aatgttcgac cgctccgcaa gcggatcttt ggcgcaacca gccggtttcg 960
cacgtcgatt ctcgcgagcc tgcatacttt ggcaagattg ctgaatgacg ctgatgcttc 1020
atcgcaatct gcgataatgg ggtaagtatc cggtgaaggc cgcaggtcag gccgcctgag 1080
cactcagtgt cttggatgtc cagttccacg gcagctgttg ctcaagcctg ctgatcggag 1140
cgtccgcaag gtcggcgcgg acgtcggcaa gccaggcctg cggatcgatg ttattgagct 1200
tggcgctcat gatcagtgtc gccatgaacg ccgcacgttc agcacaacga tccgatccgg 1260
caaacagcca tgacttcctg ccgagtacat agcctctgag cgttcgttcg gcagcattgt 1320
tcgtcaggca aatcgggccg tcatcgagga atgacgtaat gccatcccat cgcttgagca 1380
tgtaatttat cgcctcggcg acgggagaac tgcgcgacaa tttcccccgc tcggtttcga 1440
gccaatcatg cagctcttcg gcgagtgacc ttgatcaggc caccgccacg accgcggaag 1500
acgaacagat gcctgcgcat cggatcgcgc ttcagcgtct cttgcaccat cagcgacaaa 1560
ccgggaaagc ctttgcgcat gtccgtactt atgtcgccac ttgggagggc ttcgtctacg 1620
tggccttcgt gatcgacgtc ttcgcccgtc gcattgtcgg atggcgggcg agccggacag 1680
cacatgcagg ctttgtcctc gatgccctcg aggaggctca tcatgatcgg cgtcccgctc 1740
atggcggcct agtgcatcac tcggatcgcg gtgttcaata cgtgtccttt cgctattccg 1800
agcggttggc agaagcaggt atcgagccat ctatcggaag cgtcggcgac agcacgacaa 1860
cgccctcgca gaagcgatca acggtcttta caaggccgag gtcattcatc ggcgtggacc 1920
atggaggagc ttcgaagcgg tcgagttcgc taccttggaa tggatagact ggttcaacca 1980
cggcggcttt tgaagcccat cggcaatata ccgccagccg aagacgagga tcagtattac 2040
gccatgctgg acgaagcagc catggctgcg cattttaacg aaatggcctc cggcaaaccc 2100
ggtgcggttc acttgttgcg tgggaaagtt cacgggactc cgcgcacgag ccttcttcgt 2160

-continued

```
aatagccata tcgaccgaat tgacctgcag gggggggggg gaaagccacg ttgtgtctca   2220
aaatctctga tgttacattg cacaagataa aaatatatca tcatgaacaa taaaactgtc   2280
tgcttacata aacagtaata caaggggtgt tatgagccat attcaacggg aaacgtcttg   2340
ctcgaggccg cgattaaatt ccaacatgga tgctgattta tatgggtata aatgggctcg   2400
cgataatgtc gggcaatcag gtgcgacaat ctatcgattg tatgggaagc ccgatgcgcc   2460
agagttgttt ctgaaacatg gcaaaggtag cgttgccaat gatgttacag atgagatggt   2520
cagactaaac tggctgacgg aatttatgcc tcttccgacc atcaagcatt ttatccgtac   2580
tcctgatgat gcatggttac tcaccactgc gatccccggg aaaacagcat tccaggtatt   2640
agaagaatat cctgattcag gtgaaaatat tgttgatgcg ctggcagtgt tcctgcgccg   2700
gttgcattcg attcctgttt gtaattgtcc ttttaacagc gatcgcgtat ttcgtctcgc   2760
tcaggcgcaa tcacgaatga ataacggttt ggttgatgcg agtgattttg atgacgagcg   2820
taatggctgg cctgttgaac aagtctggaa agaaatgcat aagcttttgc cattctcacc   2880
ggattcagtc gtcactcatg gtgatttctc acttgataac cttatttttg acgaggggaa   2940
attaataggt tgtattgatg ttggacgagt cggaatcgca gaccgatacc aggatcttgc   3000
catcctatgg aactgcctcg gtgagttttc tccttcatta cagaaacggc tttttcaaaa   3060
atatggtatt gataatcctg atatgaataa attgcagttt catttgatgc tcgatgagtt   3120
tttctaatca gaattggtta attggttgta acactggcag agcattacgc tgacttgacg   3180
ggacggcggc tttgttgaat aaatcgaact tttgctgagt tgaaggatca gatcacgcat   3240
cttcccgaca acgcagaccg ttccgtggca aagcaaaagt tcaaaatcac caactggtcc   3300
acctacaaca aagctctcat caaccgtggc tccctcactt tctggctgga tgatggggcg   3360
attcaggcct ggtatgagtc agcaacacct tcttcacgag gcagacctca gcgccccccc   3420
ccccctgcag gtcttttcca atgatgagca cttttaaagt tctgctatgt ggcgcggtat   3480
tatcccgtgt tgacgccggg caagagcaac tcggtcgccg catacactat tctcagaatg   3540
acttggttga gtactcacca gtcacagaaa agcatcttac ggatggcatg acagtaagag   3600
aattatgcag tgctgccata accatgagtg ataacactgc ggccaactta cttctgacaa   3660
cgatcggagg accgaaggag ctaaccgctt ttttgcacaa catgggggat catgtaactc   3720
gccttgatcg ttgggaaccg gagctgaatg aagccatacc aaacgacgag cgtgacacca   3780
cgatgcctgt agcaatggca acaacgttgc gcaaactatt aactggcgaa ctacttactc   3840
tagcttcccg gcaacaatta atagactgga tggaggcgga taaagttgca ggaccacttc   3900
tgcgctcggc ccttccggct ggctggttta ttgctgataa atctggagcc ggtgagcgtg   3960
ggtctcgcgg tatcattgca gcactggggc cagatggtaa gccctcccgt atcgtagtta   4020
tctacacgac ggggagtcag gcaactatgg atgaacgaaa tagacagatc gctgagatag   4080
gtgcctcact gattaagcat tggtaactgt cagaccaagt ttactcatat atactttaga   4140
ttgatttaaa acttcatttt taatttaaaa ggatctaggt gaagatcctt tttgataatc   4200
tcatgaccaa aatcccttaa cgtgagtttt cgttccactg agcgtcagac cccgtagaaa   4260
agatcaaagg atcttcttga gatccttttt ttctgcgcgt aatctgctgc ttgcaaacaa   4320
aaaaaccacc gctaccagcg gtggtttgtt tgccggatca agagctacca actctttttc   4380
cgaaggtaac tggcttcagc agagcgcaga taccaaatac tgtccttcta gtgtagccgt   4440
agttaggcca ccacttcaag aactctgtag caccgcctac atacctcgct ctgctaatcc   4500
```

-continued

```
tgttaccagt ggctgctgcc agtggcgata agtcgtgtct taccgggttg gactcaagac   4560
gatagttacc ggataaggcg cagcggtcgg gctgaacggg gggttcgtgc acacagccca   4620
gcttggagcg aacgacctac accgaactga gatacctaca gcgtgagcta tgagaaagcg   4680
ccacgcttcc cgaagggaga aaggcggaca ggtatccggt aagcggcagg gtcggaacag   4740
gagagcgcac gagggagctt ccagggggaa acgcctggta tctttatagt cctgtcgggt   4800
ttcgccacct ctgacttgag cgtcgatttt tgtgatgctc gtcagggggg cggagcctat   4860
ggaaaaacgc cagcaacgcg gcctttttac ggttcctggc cttttgctgg ccttttgctc   4920
acatgttctt tcctgcgtta tcccctgatt ctgtggataa ccgtattacc gcctttgagt   4980
gagctgatac cgctcgccgc agccgaacga ccgagcgcag cgagtcagtg agcgaggaag   5040
cggaagagcg cctgatgcgg tattttctcc ttacgcatct gtgcggtatt tcacaccgca   5100
tatggtgcac tctcagtaca atctgctctg atgccgcata gttaagccag tatacactcc   5160
gctatcgcta cgtgactggg tcatggctgc gccccgacac ccgccaacac ccgctgacgc   5220
gccctgacgg gcttgtctgc tcccggcatc cgcttacaga caagctgtga ccgtctccgg   5280
gagctgcatg tgtcagaggt tttcaccgtc atcaccgaaa cgcgcgaggc agggtgcctt   5340
gatgtgggcg ccggcggtcg agtggcgacg gcgcggcttg tccgcgccct ggtagattgc   5400
ctggccgtag gccagccatt tttgagcggc cagcggccgc gataggccga cgcgaagcgg   5460
cggggcgtag ggagcgcagc gaccgaaggg taggcgcttt ttgcagctct tcggctgtgc   5520
gctggccaga cagttatgca caggccaggc gggttttaag agttttaata agttttaaag   5580
agttttaggc ggaaaaatcg cctttttctc ttttatatc agtcacttac atgtgtgacc   5640
ggttcccaat gtacggcttt gggttcccaa tgtacgggtt ccggttccca atgtacggct   5700
ttgggttccc aatgtacgtg ctatccacag gaaagagacc ttttcgacct tttcccctg    5760
ctagggcaat ttgccctagc atctgctccg tacattagga accggcggat gcttcgccct   5820
cgatcaggtt gcggtagcgc atgactagga tcgggccagc ctgccccgcc tcctccttca   5880
aatcgtactc cggcaggtca tttgacccga tcagcttgcg cacggtgaaa cagaacttct   5940
tgaactctcc ggcgctgcca ctgcgttcgt agatcgtctt gaacaaccat ctggcttctg   6000
ccttgcctgc ggcgcggcgt gccaggcggt agagaaaacg gccgatgccg ggatcgatca   6060
aaaagtaatc ggggtgaacc gtcagcacgt ccgggttctt gccttctgtg atctcgcggt   6120
acatccaatc agctagctcg atctcgatgt actccggccg cccggtttcg ctctttacga   6180
tcttgtagcg gctaatcaag gcttcaccct cggataccgt caccaggcgg ccgttcttgg   6240
ccttcttcgt acgctgcatg gcaacgtgcg tggtgtttaa ccgaatgcag gtttctacca   6300
ggtcgtcttt ctgctttccg ccatcggctc gccggcagaa cttgagtacg tccgcaacgt   6360
gtggacggaa cacgcggccg ggcttgtctc ccttcccttc ccggtatcgg ttcatggatt   6420
cggttagatg ggaaaccgcc atcagtacca ggtcgtaatc ccacacactg gccatgccgg   6480
ccggccctgc ggaaacctct acgtgcccgt ctggaagctc gtagcggatc acctcgccag   6540
ctcgtcggtc acgcttcgac agacggaaaa cggccacgtc catgatgctg cgactatcgc   6600
gggtgcccac gtcatagagc atcggaacga aaaaatctgg ttgctcgtcg cccttgggcg   6660
gcttcctaat cgacggcgca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg ggcttggggg ttccagtgcc   6900
```

-continued

```
attgcagggc cggcagacaa cccagccgct tacgcctggc caaccgcccg ttcctccaca   6960
catggggcat tccacggcgt cggtgcctgg ttgttcttga ttttccatgc cgcctccttt   7020
agccgctaaa attcatctac tcatttattc atttgctcat ttactctggt agctgcgcga   7080
tgtattcaga tagcagctcg gtaatggtct tgccttggcg taccgcgtac atcttcagct   7140
tggtgtgatc ctccgccggc aactgaaagt tgacccgctt catggctggc gtgtctgcca   7200
ggctggccaa cgttgcagcc ttgctgctgc gtgcgctcgg acggccggca cttagcgtgt   7260
ttgtgctttt gctcattttc tctttacctc attaactcaa atgagttttg atttaatttc   7320
agcggccagc gcctggacct cgcgggcagc gtcgccctcg ggttctgatt caagaacggt   7380
tgtgccggcg gcggcagtgc ctgggtagct cacgcgctgc gtgatacggg actcaagaat   7440
gggcagctcg tacccggcca gcgcctcggc aacctcaccg ccgatgcgcg tgcctttgat   7500
cgcccgcgac acgacaaagg ccgcttgtag ccttccatcc gtgacctcaa tgcgctgctt   7560
aaccagctcc accaggtcgg cggtggccca tatgtcgtaa gggcttggct gcaccggaat   7620
cagcacgaag tcggctgcct tgatcgcgga cacagccaag tccgccgcct ggggcgctcc   7680
gtcgatcact acgaagtcgc gccggccgat ggccttcacg tcgcggtcaa tcgtcgggcg   7740
gtcgatgccg acaacggtta gcggttgatc ttcccgcacg gccgcccaat cgcgggcact   7800
gccctgggga tcggaatcga ctaacagaac atcggccccg gcgagttgca gggcgcgggc   7860
tagatgggtt gcgatggtcg tcttgcctga cccgcctttc tggttaagta cagcgataac   7920
ttcatgcgtt cccttgcgta tttgtttatt tactcatcgc atcatatacg cagcgaccgc   7980
atgacgcaag ctgttttact caaatacaca tcaccttttt agacggcggc gctcggtttc   8040
ttcagcggcc aagctggccg gccaggccgc cagcttggca tcagacaaac cggccaggat   8100
ttcatgcagc cgcacggttg agacgtgcgc gggcggctcg aacacgtacc cggccgcgat   8160
catctccgcc tcgatctctt cggtaatgaa aaacggttcg tcctggccgt cctggtgcgg   8220
tttcatgctt gttcctcttg gcgttcattc tcggcggccg ccagggcgtc ggcctcggtc   8280
aatgcgtcct cacggaaggc accgcgccgc ctggcctcgg tgggcgtcac ttcctcgctg   8340
cgctcaagtg cgcggtacag ggtcgagcga tgcacgccaa gcagtgcagc cgcctctttc   8400
acggtgcggc cttcctggtc gatcagctcg cgggcgtgcg cgatctgtgc cggggtgagg   8460
gtagggcggg ggccaaactt cacgcctcgg gccttggcgg cctcgcgccc gctccgggtg   8520
cggtcgatga ttagggaacg ctcgaactcg gcaatgccgg cgaacacggt caacaccatg   8580
cggccggccg gcgtggtggt gtcggcccac ggctctgcca ggctacgcag gcccgcgccg   8640
gcctcctgga tgcgctcggc aatgtccagt aggtcgcggg tgctgcgggc caggcggtct   8700
agcctggtca ctgtcacaac gtcgccaggg cgtaggtggt caagcatcct ggccagctcc   8760
gggcggtcgc gcctggtgcc ggtgatcttc tcggaaaaca gcttggtgca gccggccgcg   8820
tgcagttcgg cccgttggtt ggtcaagtcc tggtcgtcgg tgctgacgcg ggcatagccc   8880
agcaggccag cggcggcgct cttgttcatg gcgtaatgtc tccggttcta gtcgcaagta   8940
ttctacttta tgcgactaaa acacgcgaca agaaaacgcc aggaaaaggg cagggcggca   9000
gcctgtcgcg taacttagga cttgtgcgac atgtcgtttt cagaagacgg ctgcactgaa   9060
cgtcagaagc cgactgcact atagcagcgg aggggttgga ccacaggacg ggtgtggtcg   9120
ccatgatcgc gtagtcgata gtggctccaa gtagcgaagc gagcaggact gggcggcggc   9180
caaagcggtc ggacagtgct ccgagaacgg gtgcgcatag aaattgcatc aacgcatata   9240
```

-continued gcgctagcag cacgccatag tgactggcga tgctgtcgga atggacgata tcccgcaaga 9300
ggcccggcag taccggcata accaagccta tgcctacagc atccagggtg acggtgccga 9360
ggatgacgat gagcgcattg ttagatttca tacacggtgc ctgactgcgt tagcaattta 9420
actgtgataa actaccgcat taaagctagc ttgcttggtc gttccgcgtg aacgtcggct 9480
cgattgtacc tgcgttcaaa tactttgcga tcgtgttgcg cgcctgcccg gtgcgtcggc 9540
tgatctcacg gatcgactgc ttctctcgca acgccatccg acggatgatg tttaaaagtc 9600
ccatgtggat cactccgttg ccccgtcgct caccgtgttg gggggaaggt gcacatggct 9660
cagttctcaa tggaaattat ctgcctaacc ggctcagttc tgcgtagaaa ccaacatgca 9720
agctccaccg ggtgcaaagc ggcagcggcg gcaggatata ttcaattgta aatggcttca 9780
tgtccgggaa atctacatgg atcagcaatg agtatgatgg tcaatatgga gaaaaagaaa 9840
gagtaattac caattttttt tcaattcaaa aatgtagatg tccgcagcgt tattataaaa 9900
tgaaagtaca ttttgataaa acgacaaatt acgatccgtc gtatttatag gcgaaagcaa 9960
taaacaaatt attctaattc ggaaatcttt atttcgacgt gtctacattc acgtccaaat 10020
gggggcttag atgagaaact tcacgatcga tgccttgatt tcgccattcc cagataccca 10080
tttcatcttc agattggtct gagattatgc gaaaatatac actcatatac ataaatactg 10140
acagtttgag ctaccaattc agtgtagccc attacctcac ataattcact caaatgctag 10200
gcagtctgtc aactcggcgt caatttgtcg gccactatac gatagttgcg caaattttca 10260
aagtcctggc ctaacatcac acctctgtcg gcggcgggtc ccatttgtga taaatccacc 10320
atatcgaatt aattcagact cctttgcccc agagatcaca atggacgact tcctctatct 10380
ctacgatcta gtcaggaagt tcgacggaga aggtgacgat accatgttca ccactgataa 10440
tgagaagatt agccttttca atttcagaaa gaatgctaac ccacagatgg ttagagaggc 10500
ttacgcagca ggtctcatca agacgatcta cccgagcaat aatctccagg agatcaaata 10560
ccttcccaag aaggttaaag atgcagtcaa aagattcagg actaactgca tcaagaacac 10620
agagaaagat atatttctca agatcagaag tactattcca gtatggacga ttcaaggctt 10680
gcttcacaaa ccaaggcaag taatagagat tggagtctct aaaaaggtag ttcccactga 10740
atcaaaggcc atggagtcaa agattcaaat agaggaccta acagaactcg ccgtaaagac 10800
tggcgaacag ttcatacaga gtctcttacg actcaatgac aagaagaaaa tcttcgtcaa 10860
catggtggag cacgacacgc ttgtctactc caaaaatatc aaagatacag tctcagaaga 10920
ccaaagggca attgagactt ttcaacaaag ggtaatatcc ggaaacctcc tcggattcca 10980
ttgcccagct atctgtcact ttattgtgaa gatagtggaa aaggaaggtg gctcctacaa 11040
atgccatcat tgcgataaag gaaaggccat cgttgaagat gcctctgccg acagtggtcc 11100
caaagatgga cccccaccca cgaggagcat cgtggaaaaa gaagacgttc caaccacgtc 11160
ttcaaagcaa gtggattgat gtgatatctc cactgacgta agggatgacg cacaatccca 11220
ctatccttcg caagaccctt cctctatata aggaagttca tttcatttgg agaggacacg 11280
ctgaaatcac cagtctccaa gcttgcgggg atcgtttcgc atgattgaac aagatggatt 11340
gcacgcaggt tctccggccg cttgggtgga gaggctattc ggctatgact gggcacaaca 11400
gacaatcggc tgctctgatg ccgccgtgtt ccggctgtca gcgcaggggc gcccggttct 11460
ttttgtcaag accgacctgt ccggtgccct gaatgaactg caggacgagg cagcgcggct 11520
atcgtggctg gccacgacgg gcgttccttg cgcagctgtg ctcgacgttg tcactgaagc 11580
gggaagggac tggctgctat tgggcgaagt gccggggcag gatctcctgt catctcacct 11640

-continued

```
tgctcctgcc gagaaagtat ccatcatggc tgatgcaatg cggcggctgc atacgcttga  11700
tccggctacc tgcccattcg accaccaagc gaaacatcgc atcgagcgag cacgtactcg  11760
gatggaagcc ggtcttgtcg atcaggatga tctggacgaa gagcatcagg ggctcgcgcc  11820
agccgaactg ttcgccaggc tcaaggcgcg catgcccgac ggcgaggatc tcgtcgtgac  11880
ccatggcgat gcctgcttgc cgaatatcat ggtggaaaat ggccgctttt ctggattcat  11940
cgactgtggc cggctgggtg tggcggaccg ctatcaggac atagcgttgg ctacccgtga  12000
tattgctgaa gagcttggcg gcgaatgggc tgaccgcttc ctcgtgcttt acggtatcgc  12060
cgctcccgat tcgcagcgca tcgccttcta tcgccttctt gacgagttct tctgagcggg  12120
actctggggt tcgaaatgac cgaccaagcg acgcccaacc tgccatcacg agatttcgat  12180
tccaccgccg ccttctatga aaggttgggc ttcggaatcg ttttccggga cgccggctgg  12240
atgatcctcc agcgcgggga tctcatgctg gagttcttcg cccaccccgg atcgatccaa  12300
cacttacgtt tgcaacgtcc aagagcaaat agaccacgaa cgccggaagg ttgccgcagc  12360
gtgtggattg cgtctcaatt ctctcttgca ggaatgcaat gatgaatatg atactgacta  12420
tgaaactttg agggaatact gcctagcacc gtcacctcat aacgtgcatc atgcatgccc  12480
tgacaacatg gaacatcgct atttttctga agaattatgc tcgttggagg atgtcgcggc  12540
aattgcagct attgccaaca tcgaactacc cctcacgcat gcattcatca atattattca  12600
tgcggggaaa ggcaagatta atccaactgg caaatcatcc agcgtgattg gtaacttcag  12660
ttccagcgac ttgattcgtt ttggtgctac ccacgttttc aataaggacg agatggtgga  12720
gtaaagaagg agtgcgtcga agcagatcgt tcaaacattt ggcaataaag tttcttaaga  12780
ttgaatcctg ttgccggtct tgcgatgatt atcatataat ttctgttgaa ttacgttaag  12840
catgtaataa ttaacatgta atgcatgacg ttatttatga gatgggtttt tatgattaga  12900
gtcccgcaat tatacattta atacgcgata gaaaacaaaa tatagcgcgc aaactaggat  12960
aaattatcgc gcgcggtgtc atctatgtta ctagatcgat caaacttcgg tactgtgtaa  13020
tgacgatgag caatcgagag gctgactaac aaaaggtaca tcgcgatgga tcgatccatt  13080
cgccattcag gctgcgcaac tgttgggaag ggcgatcggt gcgggcctct tcgctattac  13140
gccagctggc gaaaggggga tgtgctgcaa ggcgattaag ttgggtaacg ccagggtttt  13200
cccagtcacg acgttgtaaa acgacggcca gtgaattcct gcagcccggg ggatccgccc  13260
actcgaggcg cgccaagctt gcatgcctgc aggctagcct aagtacgtac tcaaaatgcc  13320
aacaaataaa aaaaaagttg ctttaataat gccaaaacaa attaataaaa cacttacaac  13380
accggatttt ttttaattaa aatgtgccat ttaggataaa tagttaatat ttttaataat  13440
tatttaaaaa gccgtatcta ctaaaatgat tttatttgg ttgaaaatat taatatgttt  13500
aaatcaacac aatctatcaa aattaaacta aaaaaaaaat aagtgtacgt ggttaacatt  13560
agtacagtaa tataagagga aaatgagaaa ttaagaaatt gaaagcgagt ctaattttta  13620
aattatgaac ctgcatatat aaaaggaaag aaagaatcca ggaagaaaag aaatgaaacc  13680
atgcatggtc ccctcgtcat cacgagtttc tgccatttgc aatagaaaca ctgaaacacc  13740
tttctctttg tcacttaatt gagatgccga agccacctca caccatgaac ttcatgaggt  13800
gtagcaccca aggcttccat agccatgcat actgaagaat gtctcaagct cagcacccta  13860
cttctgtgac gtgtccctca ttcaccttcc tctcttccct ataaataacc acgcctcagg  13920
ttctccgctt cacaactcaa acattctctc cattggtcct taaacactca tcagtcatca  13980
```

-continued

```
ccgcggccat cacaagtttg tacaaaaaag ctgaacgaga aacgtaaaat gatataaata  14040
tcaatatatt aaattagatt ttgcataaaa aacagactac ataatactgt aaaacacaac  14100
atatccagtc atattggcgg ccgcattagg caccccaggc tttacacttt atgcttccgg  14160
ctcgtataat gtgtggattt tgagttagga tccgtcgaga ttttcaggag ctaaggaagc  14220
taaaatggag aaaaaaatca ctggatatac caccgttgat atatcccaat ggcatcgtaa  14280
agaacatttt gaggcatttc agtcagttgc tcaatgtacc tataaccaga ccgttcagct  14340
ggatattacg gcctttttaa agaccgtaaa gaaaaataag cacaagtttt atccggcctt  14400
tattcacatt cttgcccgcc tgatgaatgc tcatccggaa ttccgtatgg caatgaaaga  14460
cggtgagctg gtgatatggg atagtgttca cccttgttac accgttttcc atgagcaaac  14520
tgaaacgttt tcatcgctct ggagtgaata ccacgacgat ttccggcagt ttctacacat  14580
atattcgcaa gatgtggcgt gttacggtga aaacctggcc tatttcccta aagggtttat  14640
tgagaatatg tttttcgtct cagccaatcc ctgggtgagt ttcaccagtt ttgatttaaa  14700
cgtggccaat atggacaact tcttcgcccc cgttttcacc atgggcaaat attatacgca  14760
aggcgacaag gtgctgatgc cgctggcgat tcaggttcat catgccgttt gtgatggctt  14820
ccatgtcggc agaatgctta atgaattaca acagtactgc gatgagtggc agggcggggc  14880
gtaaacgcgt ggatccggct tactaaaagc cagataacag tatgcgtatt tgcgcgctga  14940
tttttgcggt ataagaatat atactgatat gtatacccga agtatgtcaa aaagaggtat  15000
gctatgaagc agcgtattac agtgacagtt gacagcgaca gctatcagtt gctcaaggca  15060
tatatgatgt caatatctcc ggtctggtaa gcacaaccat gcagaatgaa gcccgtcgtc  15120
tgcgtgccga acgctggaaa gcggaaaatc aggaagggat ggctgaggtc gcccggttta  15180
ttgaaatgaa cggctctttt gctgacgaga acaggggctg gtgaaatgca gtttaaggtt  15240
tacacctata aaagagagag ccgttatcgt ctgtttgtgg atgtacagag tgatattatt  15300
gacacgcccg ggcgacggat ggtgatcccc ctggccagtg cacgtctgct gtcagataaa  15360
gtctcccgtg aactttaccc ggtggtgcat atcggggatg aaagctggcg catgatgacc  15420
accgatatgg ccagtgtgcc ggtctccgtt atcggggaag aagtggctga tctcagccac  15480
cgcgaaaatg acatcaaaaa cgccattaac ctgatgttct ggggaatata aatgtcaggc  15540
tcccttatac acagccagtc tgcaggtcga ccatagtgac tggatatgtt gtgttttaca  15600
gcattatgta gtctgttttt tatgcaaaat ctaatttaat atattgatat ttatatcatt  15660
ttacgtttct cgttcagctt tcttgtacaa agtggtgatg gccgcatttc gcaccaaatc  15720
aatgaaagta ataatgaaaa gtctgaataa gaatacttag gcttagatgc ctttgttact  15780
tgtgtaaaat aacttgagtc atgtaccttt ggcggaaaca gaataaataa aaggtgaaat  15840
tccaatgctc tatgtataag ttagtaatac ttaatgtgtt ctacggttgt ttcaatatca  15900
tcaaactcta attgaaactt tagaaccaca aatctcaatc ttttcttaat gaaatgaaaa  15960
atcttaattg taccatgttt atgttaaaca ccttacaatt ggttggagag gaggaccaac  16020
cgatgggaca acattgggag aaagagattc aatggagatt tggataggag aacaacattc  16080
tttttcactt caatacaaga tgagtgcaac actaaggata tgtatgagac tttcagaagc  16140
tacgacaaca tagatgagtg aggtggtgat tcctagcaag aaagacatta gaggaagcca  16200
aaatcgaaca aggaagacat caagggcaag agacaggacc atccatctca ggaaaaggag  16260
ctttgggata gtccgagaag ttgtacaaga aatttttgg agggtgagtg atgcattgct  16320
ggtgacttta actcaatcaa aattgagaaa gaaagaaaag ggagggggct cacatgtgaa  16380
```

-continued tagaagggaa acgggagaat tttacagttt tgatctaatg ggcatcccag ctagtggtaa 16440
catattcacc atgtttaacc ttcacgtacg tctagaggat ccgtcgacgg 16490

<210> SEQ ID NO 10
<211> LENGTH: 552
<212> TYPE: DNA
<213> ORGANISM: artificial sequence
<220> FEATURE:
<223> OTHER INFORMATION: SAIFF and genomic DNA of lo22730

<400> SEQUENCE: 10
atgtaaaagc gaaagatcgt ctttttagag ttcttatttt tattttcctc ttacatctga 60
tttattggat attttttaca agaattgata cattaaaagt acttttttttt ttacgtacat 120 tcttagagag taaatacata accgatcatt aaaaagaaga gatgaagaag tgaatttcca 180
caatgtttta aaccttcaga atttatatta atggggtttg caaatgattg gaggtataca 240
attacaggtg attcacgtca ttattgttct catcgatgga ccctttgcat ggtttcaatt 300
ttttctatgc gggtcccgtt ttttattcac acccatttta tcaatgtttt ttttttgtta 360
tggtcttcaa ttttttatat ttggttgcat tgaatcttgc tcctcataat cggaagattt 420
gaccagtgtt aatgatatta tatagtttga acgttaaagt atgttaacat gttagtcttc 480
ttttttaatg ttatcatatt ctgtttacca agtaggttta ttttaaatct caatgctcta 540
tatactatct ta 552

<210> SEQ ID NO 11
<211> LENGTH: 27
<212> TYPE: DNA
<213> ORGANISM: artificial sequence
<220> FEATURE:
<223> OTHER INFORMATION: primer

<400> SEQUENCE: 11
caccatgaag agtgtgttgc gtattgc 27

<210> SEQ ID NO 12
<211> LENGTH: 21
<212> TYPE: DNA
<213> ORGANISM: artificial sequence
<220> FEATURE:
<223> OTHER INFORMATION: primer

<400> SEQUENCE: 12
tcacttgaag atgagattgt g 21

<210> SEQ ID NO 13
<211> LENGTH: 3831
<212> TYPE: DNA
<213> ORGANISM: artificial sequence
<220> FEATURE:
<223> OTHER INFORMATION: vector pENTR-PAE

<400> SEQUENCE: 13
aagggtgggc gcgccgaccc agctttcttg tacaaagttg gcattataag aaagcattgc 60
ttatcaattt gttgcaacga acaggtcact atcagtcaaa ataaaatcat tatttgccat 120
ccagctgata tcccctatag tgagtcgtat tacatggtca tagctgtttc ctggcagctc 180
tggcccgtgt ctcaaaatct ctgatgttac attgcacaag ataaaaatat atcatcatga 240
acaataaaac tgtctgctta cataaacagt aatacaaggg gtgttatgag ccatattcaa 300

-continued

```
cgggaaacgt cgaggccgcg attaaattcc aacatggatg ctgatttata tgggtataaa    360
tgggctcgcg ataatgtcgg gcaatcaggt gcgacaatct atcgcttgta tgggaagccc    420
gatgcgccag agttgtttct gaaacatggc aaaggtagcg ttgccaatga tgttacagat    480
gagatggtca gactaaactg gctgacggaa tttatgcctc ttccgaccat caagcatttt    540
atccgtactc ctgatgatgc atggttactc accactgcga tccccggaaa aacagcattc    600
caggtattag aagaatatcc tgattcaggt gaaaatattg ttgatgcgct ggcagtgttc    660
ctgcgccggt tgcattcgat tcctgtttgt aattgtcctt ttaacagcga tcgcgtattt    720
cgtctcgctc aggcgcaatc acgaatgaat aacggtttgg ttgatgcgag tgattttgat    780
gacgagcgta atggctggcc tgttgaacaa gtctggaaag aaatgcataa acttttgcca    840
ttctcaccgg attcagtcgt cactcatggt gatttctcac ttgataacct tatttttgac    900
gaggggaaat taataggttg tattgatgtt ggacgagtcg gaatcgcaga ccgataccag    960
gatcttgcca tcctatggaa ctgcctcggt gagttttctc cttcattaca gaaacggctt   1020
tttcaaaaat atggtattga taatcctgat atgaataaat tgcagtttca tttgatgctc   1080
gatgagtttt tctaatcaga attggttaat tggttgtaac actggcagag cattacgctg   1140
acttgacggg acggcgcaag ctcatgacca aaatccctta acgtgagtta cgcgtcgttc   1200
cactgagcgt cagaccccgt agaaaagatc aaaggatctt cttgagatcc tttttttctg   1260
cgcgtaatct gctgcttgca aacaaaaaaa ccaccgctac cagcggtggt ttgtttgccg   1320
gatcaagagc taccaactct ttttccgaag gtaactggct tcagcagagc gcagatacca   1380
aatactgtcc ttctagtgta gccgtagtta ggccaccact tcaagaactc tgtagcaccg   1440
cctacatacc tcgctctgct aatcctgtta ccagtggctg ctgccagtgg cgataagtcg   1500
tgtcttaccg ggttggactc aagacgatag ttaccggata aggcgcagcg gtcgggctga   1560
acggggggtt cgtgcacaca gcccagcttg gagcgaacga cctacaccga actgagatac   1620
ctacagcgtg agcattgaga aagcgccacg cttcccgaag ggagaaaggc ggacaggtat   1680
ccggtaagcg gcagggtcgg aacaggagag cgcacgaggg agcttccagg gggaaacgcc   1740
tggtatcttt atagtcctgt cgggtttcgc cacctctgac ttgagcgtcg atttttgtga   1800
tgctcgtcag gggggcggag cctatggaaa aacgccagca acgcggcctt tttacggttc   1860
ctggcctttt gctggccttt tgctcacatg ttctttcctg cgttatcccc tgattctgtg   1920
gataaccgta ttaccgcctt tgagtgagct gataccgctc gccgcagccg aacgaccgag   1980
cgcagcgagt cagtgagcga ggaagcggaa gagcgcccaa tacgcaaacc gcctctcccc   2040
gcgcgttggc cgattcatta atgcagctgg cacgacaggt ttcccgactg gaaagcgggc   2100
agtgagcgca acgcaattaa tacgcgtacc gctagccagg aagagtttgt agaaacgcaa   2160
aaaggccatc cgtcaggatg gccttctgct tagtttgatg cctggcagtt tatggcgggc   2220
gtcctgcccg ccaccctccg ggccgttgct tcacaacgtt caaatccgct cccggcggat   2280
ttgtcctact caggagagcg ttcaccgaca aacaacagat aaaacgaaag gcccagtctt   2340
ccgactgagc ctttcgtttt atttgatgcc tggcagttcc ctactctcgc gttaacgcta   2400
gcatggatgt tttcccagtc acgacgttgt aaaacgacgg ccagtcttaa gctcgggccc   2460
caaataatga ttttattttg actgatagtg acctgttcgt tgcaacaaat tgatgagcaa   2520
tgctttttta taatgccaac tttgtacaaa aaagcaggct ccgcggccgc ccccttcacc   2580
atgaagagtg tgttgcgtat tgcggcggcg atattctggc tttggctgtt tatcgtgtta   2640
ggtgtgattg ggagtgggaa tgtgagagat acagacgatg agatctcgtt actcgaaagt   2700
```

caattggtgg tgacatctcc gtcgcagctt cttatggtgc ctctcacttt gattcaggct 2760
gctgcctcca aaggagctgt gtgcctggat ggaacactac ctggttatca tctacaccct 2820
ggttctggat caggagctaa ccggtggctc atccaactcg agggtggagg atggtgcaac 2880
acacgtagga gctgtatctt ccggaaaacc actcgccgtg gttcatcaaa tcatatggag 2940
aaagttttgg ccttcactgg aatattgagc aataaatcta atgagaatcc tgacttcttc 3000
aactggaaca gagtcaaatt gcgttactgc gatggtgcct ctttcaccgg cgatagtcag 3060
gatgagagct cacaacttta ctatagagga caacgaatct ggcattcagc tatggaagaa 3120
ctactctcta aaggcatgca aaaagcagaa caggctctac tttctggatg ttcagctggg 3180
ggattagctt ccatcctaca ctgcgatcag ttcaaggaac tatttccggg cactacgaca 3240
gtgaaatgct taagtgatgc tggaatgttt atggatgcag tggatgtctc tgggggccac 3300
tcgctccgga aaatgttcca aggtgttgtt acagtacaga acctccaaaa ggaactgtcc 3360
actgcttgta caaagcattt ggatccaact tcgtgcttct ttccccagaa cttggtttca 3420
ggcattaaga ctccaatgtt tcttctcaat gcagcatatg acgcttggca ggtacaagag 3480
agtttagctc caccatcagt tgacctaagc ggctcttgga aggcatgcaa atctgatcac 3540
tcgcattgta attcatctca gatccagttc ttccaagact tcaggactca tatggtagat 3600
gctgtaaagt ctttcgcgac atcgacacat aacggtgtgt tcataaactc atgcttcgct 3660
cactgccaat ctgaaagaca ggacacttgg tatgcaccag attctcctac tcttcatggc 3720
aagaccgttg ctgaatctgt tggtgattgg tactttgaca gaacaacagt gaaagccatt 3780
gactgtcctt acccctgtga caaaacatgt cacaatctca tcttcaagtg a 3831

<210> SEQ ID NO 14
<211> LENGTH: 16122
<212> TYPE: DNA
<213> ORGANISM: artificial sequence
<220> FEATURE:
<223> OTHER INFORMATION: vector pKR1478-PAE

<400> SEQUENCE: 14
acccagcttt cttgtacaaa gtggtgatgg ccgcatttcg caccaaatca atgaaagtaa 60
taatgaaaag tctgaataag aatacttagg cttagatgcc tttgttactt gtgtaaaata 120
acttgagtca tgtacctttg gcggaaacag aataaataaa aggtgaaatt ccaatgctct 180
atgtataagt tagtaatact taatgtgttc tacggttgtt tcaatatcat caaactctaa 240
ttgaaacttt agaaccacaa atctcaatct tttcttaatg aaatgaaaaa tcttaattgt 300
accatgttta tgttaaacac cttacaattg gttggagagg aggaccaacc gatgggacaa 360
cattgggaga aagagattca atggagattt ggataggaga acaacattct ttttcacttc 420
aatacaagat gagtgcaaca ctaaggatat gtatgagact ttcagaagct acgacaacat 480
agatgagtga ggtggtgatt cctagcaaga aagacattag aggaagccaa aatcgaacaa 540
ggaagacatc aagggcaaga gacaggacca tccatctcag gaaaaggagc tttgggatag 600
tccgagaagt tgtacaagaa attttttgga gggtgagtga tgcattgctg gtgactttaa 660
ctcaatcaaa attgagaaag aaagaaaagg gagggggctc acatgtgaat agaagggaaa 720
cgggagaatt ttacagtttt gatctaatgg gcatcccagc tagtggtaac atattcacca 780
tgtttaacct tcacgtacgt ctagaggatc cgtcgacggc gcgccagatc ctctagagtc 840
gacctgcagg catgcaagct tggcgtaatc atggtcatag ctgtttcctg tgtgaaattg 900

-continued

```
ttatccgctc acaattccac acaacatacg agccggaagc ataaagtgta aagcctgggg    960
tgcctaatga gtgagctaac tcacattaat tgcgttgcgc tcactgcccg ctttccagtc   1020
gggaaacctg tcgtgccagc tgcattaatg aatcggccaa cgcgcgggga gaggcggttt   1080
gcgtattgga tcgatccctg aaagcgacgt tggatgttaa catctacaaa ttgccttttc   1140
ttatcgacca tgtacgtaag cgcttacgtt tttggtggac ccttgaggaa actggtagct   1200
gttgtgggcc tgtggtctca agatggatca ttaatttcca ccttcaccta cgatgggggg   1260
catcgcaccg gtgagtaata ttgtacggct aagagcgaat ttggcctgta gacctcaatt   1320
gcgagctttc taatttcaaa ctattcgggc ctaacttttg gtgtgatgat gctgactggc   1380
aggatatata ccgttgtaat ttgagctcgt gtgaataagt cgctgtgtat gtttgtttga   1440
ttgtttctgt tggagtgcag cccatttcac cggacaagtc ggctagattg atttagccct   1500
gatgaactgc cgaggggaag ccatcttgag cgcggaatgg gaatggattt cgttgtacaa   1560
cgagacgaca gaacacccac gggaccgagc ttcgcgagct tttgtatccg tggcatcctt   1620
ggtccgggcg atttgttcac gtccatgagg cgctctccaa aggaacgcat attttccggt   1680
gcaacctttc cggttcttcc tctactcgac ctcttgaagt cccagcatga atgttcgacc   1740
gctccgcaag cggatctttg gcgcaaccag ccggtttcgc acgtcgattc tcgcgagcct   1800
gcatactttg gcaagattgc tgaatgacgc tgatgcttca tcgcaatctg cgataatggg   1860
gtaagtatcc ggtgaaggcc gcaggtcagg ccgcctgagc actcagtgtc ttggatgtcc   1920
agttccacgg cagctgttgc tcaagcctgc tgatcggagc gtccgcaagg tcggcgcgga   1980
cgtcggcaag ccaggcctgc ggatcgatgt tattgagctt ggcgctcatg atcagtgtcg   2040
ccatgaacgc cgcacgttca gcacaacgat ccgatccggc aaacagccat gacttcctgc   2100
cgagtacata gcctctgagc gttcgttcgg cagcattgtt cgtcaggcaa atcgggccgt   2160
catcgaggaa tgacgtaatg ccatcccatc gcttgagcat gtaatttatc gcctcggcga   2220
cgggagaact gcgcgacaat ttcccccgct cggtttcgag ccaatcatgc agctcttcgg   2280
cgagtgacct tgatcaggcc accgccacga ccgcggaaga cgaacagatg cctgcgcatc   2340
ggatcgcgct tcagcgtctc ttgcaccatc agcgacaaac cgggaaagcc tttgcgcatg   2400
tccgtactta tgtcgccact tgggagggct tcgtctacgt ggccttcgtg atcgacgtct   2460
tcgcccgtcg cattgtcgga tggcgggcga gccggacagc acatgcaggc tttgtcctcg   2520
atgccctcga ggaggctcat catgatcggc gtcccgctca tggcggccta gtgcatcact   2580
cggatcgcgg tgttcaatac gtgtcctttc gctattccga gcggttggca gaagcaggta   2640
tcgagccatc tatcggaagc gtcggcgaca gcacgacaac gccctcgcag aagcgatcaa   2700
cggtctttac aaggccgagg tcattcatcg gcgtggacca tggaggagct tcgaagcggt   2760
cgagttcgct accttggaat ggatagactg gttcaaccac ggcggctttt gaagcccatc   2820
ggcaatatac cgccagccga agacgaggat cagtattacg ccatgctgga cgaagcagcc   2880
atggctgcgc attttaacga aatggcctcc ggcaaacccg gtgcggttca cttgttgcgt   2940
gggaaagttc acgggactcc gcgcacgagc cttcttcgta atagccatat cgaccgaatt   3000
gacctgcagg gggggggggg aaagccacgt tgtgtctcaa aatctctgat gttacattgc   3060
acaagataaa aatatatcat catgaacaat aaaactgtct gcttacataa acagtaatac   3120
aaggggtgtt atgagccata ttcaacggga aacgtcttgc tcgaggccgc gattaaattc   3180
caacatggat gctgatttat atgggtataa atgggctcgc gataatgtcg ggcaatcagg   3240
tgcgacaatc tatcgattgt atgggaagcc cgatgcgcca gagttgtttc tgaaacatgg   3300
```

-continued

```
caaaggtagc gttgccaatg atgttacaga tgagatggtc agactaaact ggctgacgga   3360
atttatgcct cttccgacca tcaagcattt tatccgtact cctgatgatg catggttact   3420
caccactgcg atccccggga aaacagcatt ccaggtatta gaagaatatc ctgattcagg   3480
tgaaaatatt gttgatgcgc tggcagtgtt cctgcgccgg ttgcattcga ttcctgtttg   3540
taattgtcct tttaacagcg atcgcgtatt tcgtctcgct caggcgcaat cacgaatgaa   3600
taacggtttg gttgatgcga gtgattttga tgacgagcgt aatggctggc ctgttgaaca   3660
agtctggaaa gaaatgcata agcttttgcc attctcaccg gattcagtcg tcactcatgg   3720
tgatttctca cttgataacc ttatttttga cgaggggaaa ttaataggtt gtattgatgt   3780
tggacgagtc ggaatcgcag accgatacca ggatcttgcc atcctatgga actgcctcgg   3840
tgagttttct ccttcattac agaaacggct ttttcaaaaa tatggtattg ataatcctga   3900
tatgaataaa ttgcagtttc atttgatgct cgatgagttt ttctaatcag aattggttaa   3960
ttggttgtaa cactggcaga gcattacgct gacttgacgg gacggcggct ttgttgaata   4020
aatcgaactt ttgctgagtt gaaggatcag atcacgcatc ttcccgacaa cgcagaccgt   4080
tccgtggcaa agcaaaagtt caaaatcacc aactggtcca cctacaacaa agctctcatc   4140
aaccgtggct ccctcacttt ctggctggat gatggggcga ttcaggcctg gtatgagtca   4200
gcaacacctt cttcacgagg cagacctcag cgcccccccc cccctgcagg tcttttccaa   4260
tgatgagcac ttttaaagtt ctgctatgtg gcgcggtatt atcccgtgtt gacgccgggc   4320
aagagcaact cggtcgccgc atacactatt ctcagaatga cttggttgag tactcaccag   4380
tcacagaaaa gcatcttacg gatggcatga cagtaagaga attatgcagt gctgccataa   4440
ccatgagtga taacactgcg gccaacttac ttctgacaac gatcggagga ccgaaggagc   4500
taaccgcttt tttgcacaac atgggggatc atgtaactcg ccttgatcgt tgggaaccgg   4560
agctgaatga agccatacca aacgacgagc gtgacaccac gatgcctgta gcaatggcaa   4620
caacgttgcg caaactatta actggcgaac tacttactct agcttcccgg caacaattaa   4680
tagactggat ggaggcggat aaagttgcag gaccacttct gcgctcggcc cttccggctg   4740
gctggtttat tgctgataaa tctggagccg gtgagcgtgg gtctcgcggt atcattgcag   4800
cactggggcc agatggtaag ccctcccgta tcgtagttat ctacacgacg gggagtcagg   4860
caactatgga tgaacgaaat agacagatcg ctgagatagg tgcctcactg attaagcatt   4920
ggtaactgtc agaccaagtt tactcatata tactttagat tgatttaaaa cttcattttt   4980
aatttaaaag gatctaggtg aagatccttt ttgataatct catgaccaaa atcccttaac   5040
gtgagttttc gttccactga gcgtcagacc ccgtagaaaa gatcaaagga tcttcttgag   5100
atcctttttt tctgcgcgta atctgctgct tgcaaacaaa aaaaccaccg ctaccagcgg   5160
tggtttgttt gccggatcaa gagctaccaa ctctttttcc gaaggtaact ggcttcagca   5220
gagcgcagat accaaatact gtccttctag tgtagccgta gttaggccac cacttcaaga   5280
actctgtagc accgcctaca tacctcgctc tgctaatcct gttaccagtg gctgctgcca   5340
gtggcgataa gtcgtgtctt accgggttgg actcaagacg atagttaccg gataaggcgc   5400
agcggtcggg ctgaacgggg ggttcgtgca cacagcccag cttggagcga acgacctaca   5460
ccgaactgag atacctacag cgtgagctat gagaaagcgc cacgcttccc gaagggagaa   5520
aggcggacag gtatccggta agcggcaggg tcggaacagg agagcgcacg agggagcttc   5580
caggggggaaa cgcctggtat ctttatagtc ctgtcgggtt tcgccacctc tgacttgagc   5640
```

-continued

```
gtcgattttt gtgatgctcg tcaggggggc ggagcctatg gaaaaacgcc agcaacgcgg   5700
cctttttacg gttcctggcc ttttgctggc cttttgctca catgttcttt cctgcgttat   5760
cccctgattc tgtggataac cgtattaccg cctttgagtg agctgatacc gctcgccgca   5820
gccgaacgac cgagcgcagc gagtcagtga gcgaggaagc ggaagagcgc ctgatgcggt   5880
attttctcct tacgcatctg tgcggtattt cacaccgcat atggtgcact ctcagtacaa   5940
tctgctctga tgccgcatag ttaagccagt atacactccg ctatcgctac gtgactgggt   6000
catggctgcg ccccgacacc cgccaacacc cgctgacgcg ccctgacggg cttgtctgct   6060
cccggcatcc gcttacagac aagctgtgac cgtctccggg agctgcatgt gtcagaggtt   6120
ttcaccgtca tcaccgaaac gcgcgaggca gggtgccttg atgtgggcgc cggcggtcga   6180
gtggcgacgg cgcggcttgt ccgcgccctg gtagattgcc tggccgtagg ccagccattt   6240
ttgagcggcc agcggccgcg ataggccgac gcgaagcggc ggggcgtagg gagcgcagcg   6300
accgaagggt aggcgctttt tgcagctctt cggctgtgcg ctggccagac agttatgcac   6360
aggccaggcg ggttttaaga gttttaataa gttttaaaga gttttaggcg gaaaaatcgc   6420
ctttttctc ttttatatca gtcacttaca tgtgtgaccg gttcccaatg tacggctttg   6480
ggttcccaat gtacgggttc cggttcccaa tgtacggctt tgggttccca atgtacgtgc   6540
tatccacagg aaagagacct tttcgacctt tttcccctgc tagggcaatt tgccctagca   6600
tctgctccgt acattaggaa ccggcggatg cttcgccctc gatcaggttg cggtagcgca   6660
tgactaggat cgggccagcc tgccccgcct cctccttcaa atcgtactcc ggcaggtcat   6720
ttgacccgat cagcttgcgc acggtgaaac agaacttctt gaactctccg gcgctgccac   6780
tgcgttcgta gatcgtcttg aacaaccatc tggcttctgc cttgcctgcg gcgcggcgtg   6840
ccaggcggta gagaaaacgg ccgatgccgg gatcgatcaa aaagtaatcg gggtgaaccg   6900
tcagcacgtc cgggttcttg ccttctgtga tctcgcggta catccaatca gctagctcga   6960
tctcgatgta ctccggccgc ccggtttcgc tctttacgat cttgtagcgg ctaatcaagg   7020
cttcaccctc ggataccgtc accaggcggc cgttcttggc cttcttcgta cgctgcatgg   7080
caacgtgcgt ggtgtttaac cgaatgcagg tttctaccag gtcgtctttc tgctttccgc   7140
catcggctcg ccggcagaac ttgagtacgt ccgcaacgtg tggacggaac acgcggccgg   7200
gcttgtctcc cttcccttcc cggtatcggt tcatggattc ggttagatgg gaaaccgcca   7260
tcagtaccag gtcgtaatcc cacacactgg ccatgccggc cggccctgcg gaaacctcta   7320
cgtgcccgtc tggaagctcg tagcggatca cctcgccagc tcgtcggtca cgcttcgaca   7380
gacggaaaac ggccacgtcc atgatgctgc gactatcgcg ggtgcccacg tcatagagca   7440
tcggaacgaa aaaatctggt tgctcgtcgc ccttgggcgg cttcctaatc gacggcgcac   7500
cggctgccgg cggttgccgg gattctttgc ggattcgatc agcggccgct tgccacgatt   7560
caccggggcg tgcttctgcc tcgatgcgtt gccgctgggc ggcctgcgcg gccttcaact   7620
tctccaccag gtcatcaccc agcgccgcgc cgatttgtac cgggccggat ggtttgcgac   7680
cgctcacgcc gattcctcgg gcttgggggt tccagtgcca ttgcagggcc ggcagacaac   7740
ccagccgctt acgcctggcc aaccgcccgt tcctccacac atggggcatt ccacggcgtc   7800
ggtgcctggt tgttcttgat ttccatgcc gcctccttta gccgctaaaa ttcatctact   7860
catttattca tttgctcatt tactctggta gctgcgcgat gtattcagat agcagctcgg   7920
taatggtctt gccttggcgt accgcgtaca tcttcagctt ggtgtgatcc tccgccggca   7980
actgaaagtt gacccgcttc atggctggcg tgtctgccag gctggccaac gttgcagcct   8040
```

-continued

```
tgctgctgcg tgcgctcgga cggccggcac ttagcgtgtt tgtgcttttg ctcattttct   8100
ctttacctca ttaactcaaa tgagttttga tttaatttca gcggccagcg cctggacctc   8160
gcgggcagcg tcgccctcgg gttctgattc aagaacggtt gtgccggcgg cggcagtgcc   8220
tgggtagctc acgcgctgcg tgatacggga ctcaagaatg ggcagctcgt acccggccag   8280
cgcctcggca acctcaccgc cgatgcgcgt gcctttgatc gcccgcgaca cgacaaaggc   8340
cgcttgtagc cttccatccg tgacctcaat gcgctgctta accagctcca ccaggtcggc   8400
ggtggcccat atgtcgtaag ggcttggctg caccggaatc agcacgaagt cggctgcctt   8460
gatcgcggac acagccaagt ccgccgcctg ggcgctccg tcgatcacta cgaagtcgcg   8520
ccggccgatg gccttcacgt cgcggtcaat cgtcgggcgg tcgatgccga caacggttag   8580
cggttgatct tcccgcacgg ccgcccaatc gcgggcactg ccctggggat cggaatcgac   8640
taacagaaca tcggccccgg cgagttgcag ggcgcgggct agatgggttg cgatggtcgt   8700
cttgcctgac ccgcctttct ggttaagtac agcgataact tcatgcgttc ccttgcgtat   8760
ttgtttattt actcatcgca tcatatacgc agcgaccgca tgacgcaagc tgttttactc   8820
aaatacacat cacctttttta gacggcggcg ctcggtttct tcagcggcca agctggccgg   8880
ccaggccgcc agcttggcat cagacaaacc ggccaggatt tcatgcagcc gcacggttga   8940
gacgtgcgcg ggcggctcga acacgtaccc ggccgcgatc atctccgcct cgatctcttc   9000
ggtaatgaaa aacggttcgt cctggccgtc ctggtgcggt ttcatgcttg ttcctcttgg   9060
cgttcattct cggcggccgc cagggcgtcg gcctcggtca atgcgtcctc acggaaggca   9120
ccgcgccgcc tggcctcggt gggcgtcact tcctcgctgc gctcaagtgc gcggtacagg   9180
gtcgagcgat gcacgccaag cagtgcagcc gcctctttca cggtgcggcc ttcctggtcg   9240
atcagctcgc gggcgtgcgc gatctgtgcc ggggtgaggg tagggcgggg gccaaacttc   9300
acgcctcggg ccttggcggc ctcgcgcccg ctccgggtgc ggtcgatgat tagggaacgc   9360
tcgaactcgg caatgccggc gaacacggtc aacaccatgc ggccggccgg cgtggtggtg   9420
tcggcccacg gctctgccag gctacgcagg cccgcgccgg cctcctggat gcgctcggca   9480
atgtccagta ggtcgcgggt gctgcgggcc aggcggtcta gcctggtcac tgtcacaacg   9540
tcgccagggc gtaggtggtc aagcatcctg gccagctccg ggcggtcgcg cctggtgccg   9600
gtgatcttct cggaaaacag cttggtgcag ccggccgcgt gcagttcggc ccgttggttg   9660
gtcaagtcct ggtcgtcggt gctgacgcgg gcatagccca gcaggccagc ggcggcgctc   9720
ttgttcatgg cgtaatgtct ccggttctag tcgcaagtat tctactttat gcgactaaaa   9780
cacgcgacaa gaaaacgcca ggaaaagggc agggcggcag cctgtcgcgt aacttaggac   9840
ttgtgcgaca tgtcgttttc agaagacggc tgcactgaac gtcagaagcc gactgcacta   9900
tagcagcgga ggggttggac cacaggacgg gtgtggtcgc catgatcgcg tagtcgatag   9960
tggctccaag tagcgaagcg agcaggactg ggcggcggcc aaagcggtcg gacagtgctc  10020
cgagaacggg tgcgcataga aattgcatca acgcatatag cgctagcagc acgccatagt  10080
gactggcgat gctgtcggaa tggacgatat cccgcaagag gcccggcagt accggcataa  10140
ccaagcctat gcctacagca tccagggtga cggtgccgag gatgacgatg agcgcattgt  10200
tagatttcat acacggtgcc tgactgcgtt agcaatttaa ctgtgataaa ctaccgcatt  10260
aaagctagct tgcttggtcg ttccgcgtga acgtcggctc gattgtacct gcgttcaaat  10320
actttgcgat cgtgttgcgc gcctgcccgg tgcgtcggct gatctcacgg atcgactgct  10380
```

-continued

```
tctctcgcaa cgccatccga cggatgatgt ttaaaagtcc catgtggatc actccgttgc  10440
cccgtcgctc accgtgttgg ggggaaggtg cacatggctc agttctcaat ggaaattatc  10500
tgcctaaccg gctcagttct gcgtagaaac caacatgcaa gctccaccgg gtgcaaagcg  10560
gcagcggcgg caggatatat tcaattgtaa atggcttcat gtccgggaaa tctacatgga  10620
tcagcaatga gtatgatggt caatatggag aaaaagaaag agtaattacc aatttttttt  10680
caattcaaaa atgtagatgt ccgcagcgtt attataaaat gaaagtacat tttgataaaa  10740
cgacaaatta cgatccgtcg tatttatagg cgaaagcaat aaacaaatta ttctaattcg  10800
gaaatcttta tttcgacgtg tctacattca cgtccaaatg gggggcttaga tgagaaactt  10860
cacgatcgat gccttgattt cgccattccc agatacccat ttcatcttca gattggtctg  10920
agattatgcg aaaatataca ctcatataca taaatactga cagtttgagc taccaattca  10980
gtgtagccca ttacctcaca taattcactc aaatgctagg cagtctgtca actcggcgtc  11040
aatttgtcgg ccactatacg atagttgcgc aaattttcaa agtcctggcc taacatcaca  11100
cctctgtcgg cggcgggtcc catttgtgat aaatccacca tatcgaatta attcagactc  11160
ctttgcccca gagatcacaa tggacgactt cctctatctc tacgatctag tcaggaagtt  11220
cgacggagaa ggtgacgata ccatgttcac cactgataat gagaagatta gccttttcaa  11280
tttcagaaag aatgctaacc cacagatggt tagagaggct tacgcagcag gtctcatcaa  11340
gacgatctac ccgagcaata atctccagga gatcaaatac cttcccaaga aggttaaaga  11400
tgcagtcaaa agattcagga ctaactgcat caagaacaca gagaaagata tatttctcaa  11460
gatcagaagt actattccag tatggacgat tcaaggcttg cttcacaaac caaggcaagt  11520
aatagagatt ggagtctcta aaaaggtagt tcccactgaa tcaaaggcca tggagtcaaa  11580
gattcaaata gaggacctaa cagaactcgc cgtaaagact ggcgaacagt tcatacagag  11640
tctcttacga ctcaatgaca agaagaaaat cttcgtcaac atggtggagc acgacacgct  11700
tgtctactcc aaaaatatca aagatacagt ctcagaagac caaagggcaa ttgagacttt  11760
tcaacaaagg gtaatatccg gaaacctcct cggattccat tgcccagcta tctgtcactt  11820
tattgtgaag atagtggaaa aggaaggtgg ctcctacaaa tgccatcatt gcgataaagg  11880
aaaggccatc gttgaagatg cctctgccga cagtggtccc aaagatggac ccccacccac  11940
gaggagcatc gtggaaaaag aagacgttcc aaccacgtct tcaaagcaag tggattgatg  12000
tgatatctcc actgacgtaa gggatgacgc acaatcccac tatccttcgc aagacccttc  12060
ctctatataa ggaagttcat ttcatttgga gaggacacgc tgaaatcacc agtctccaag  12120
cttgcgggga tcgtttcgca tgattgaaca agatggattg cacgcaggtt ctccggccgc  12180
ttgggtggag aggctattcg gctatgactg ggcacaacag acaatcggct gctctgatgc  12240
cgccgtgttc cggctgtcag cgcaggggcg cccggttctt tttgtcaaga ccgacctgtc  12300
cggtgccctg aatgaactgc aggacgaggc agcgcggcta tcgtggctgg ccacgacggg  12360
cgttccttgc gcagctgtgc tcgacgttgt cactgaagcg ggaagggact ggctgctatt  12420
gggcgaagtg ccggggcagg atctcctgtc atctcacctt gctcctgccg agaaagtatc  12480
catcatggct gatgcaatgc ggcggctgca tacgcttgat ccggctacct gcccattcga  12540
ccaccaagcg aaacatcgca tcgagcgagc acgtactcgg atggaagccg gtcttgtcga  12600
tcaggatgat ctggacgaag agcatcaggg gctcgcgcca gccgaactgt tcgccaggct  12660
caaggcgcgc atgcccgacg gcgaggatct cgtcgtgacc catggcgatg cctgcttgcc  12720
gaatatcatg gtggaaaatg gccgcttttc tggattcatc gactgtggcc ggctgggtgt  12780
```

```
ggcggaccgc tatcaggaca tagcgttggc tacccgtgat attgctgaag agcttggcgg  12840
cgaatgggct gaccgcttcc tcgtgcttta cggtatcgcc gctcccgatt cgcagcgcat  12900
cgccttctat cgccttcttg acgagttctt ctgagcggga ctctggggtt cgaaatgacc  12960
gaccaagcga cgcccaacct gccatcacga gatttcgatt ccaccgccgc cttctatgaa  13020
aggttgggct tcggaatcgt tttccgggac gccggctgga tgatcctcca gcgcggggat  13080
ctcatgctgg agttcttcgc ccaccccgga tcgatccaac acttacgttt gcaacgtcca  13140
agagcaaata gaccacgaac gccggaaggt tgccgcagcg tgtggattgc gtctcaattc  13200
tctcttgcag gaatgcaatg atgaatatga tactgactat gaaactttga gggaatactg  13260
cctagcaccg tcacctcata acgtgcatca tgcatgccct gacaacatgg aacatcgcta  13320
tttttctgaa gaattatgct cgttggagga tgtcgcggca attgcagcta ttgccaacat  13380
cgaactaccc ctcacgcatg cattcatcaa tattattcat gcggggaaag gcaagattaa  13440
tccaactggc aaatcatcca gcgtgattgg taacttcagt tccagcgact tgattcgttt  13500
tggtgctacc cacgttttca ataaggacga gatggtggag taaagaagga gtgcgtcgaa  13560
gcagatcgtt caaacatttg gcaataaagt ttcttaagat tgaatcctgt tgccggtctt  13620
gcgatgatta tcatataatt tctgttgaat tacgttaagc atgtaataat taacatgtaa  13680
tgcatgacgt tatttatgag atgggttttt atgattagag tcccgcaatt atacatttaa  13740
tacgcgatag aaaacaaaat atagcgcgca aactaggata aattatcgcg cgcggtgtca  13800
tctatgttac tagatcgatc aaacttcggt actgtgtaat gacgatgagc aatcgagagg  13860
ctgactaaca aaaggtacat cgcgatggat cgatccattc gccattcagg ctgcgcaact  13920
gttgggaagg gcgatcggtg cgggcctctt cgctattacg ccagctggcg aaagggggat  13980
gtgctgcaag gcgattaagt tgggtaacgc cagggttttc ccagtcacga cgttgtaaaa  14040
cgacggccag tgaattcctg cagcccgggg gatccgccca ctcgaggcgc gccaagcttg  14100
catgcctgca ggctagccta agtacgtact caaaatgcca acaaataaaa aaaaagttgc  14160
tttaataatg ccaaaacaaa ttaataaaac acttacaaca ccggattttt tttaattaaa  14220
atgtgccatt taggataaat agttaatatt tttaataatt atttaaaaag ccgtatctac  14280
taaaatgatt tttatttggt tgaaaatatt aatatgttta aatcaacaca atctatcaaa  14340
attaaactaa aaaaaaaata agtgtacgtg gttaacatta gtacagtaat ataagaggaa  14400
aatgagaaat taagaaattg aaagcgagtc taatttttaa attatgaacc tgcatatata  14460
aaaggaaaga aagaatccag gaagaaaaga aatgaaacca tgcatggtcc cctcgtcatc  14520
acgagtttct gccatttgca atagaaacac tgaaacacct ttctctttgt cacttaattg  14580
agatgccgaa gccacctcac accatgaact tcatgaggtg tagcacccaa ggcttccata  14640
gccatgcata ctgaagaatg tctcaagctc agcaccctac ttctgtgacg tgtccctcat  14700
tcaccttcct ctcttcccta taaataacca cgcctcaggt tctccgcttc acaactcaaa  14760
cattctctcc attggtcctt aaacactcat cagtcatcac cgcggccatc acaagtttgt  14820
acaaaaaagc aggctccgcg gccgccccct tcaccatgaa gagtgtgttg cgtattgcgg  14880
cggcgatatt ctggctttgg ctgtttatcg tgttaggtgt gattgggagt gggaatgtga  14940
gagatacaga cgatgagatc tcgttactcg aaagtcaatt ggtggtgaca tctccgtcgc  15000
agcttcttat ggtgcctctc actttgattc aggctgctgc ctccaaagga gctgtgtgcc  15060
tggatggaac actacctggt tatcatctac accctggttc tggatcagga gctaaccggt  15120
```

```
ggctcatcca actcgagggt ggaggatggt gcaacacacg taggagctgt atcttccgga  15180
aaaccactcg ccgtggttca tcaaatcata tggagaaagt tttggccttc actggaatat  15240
tgagcaataa atctaatgag aatcctgact tcttcaactg gaacagagtc aaattgcgtt  15300
actgcgatgg tgcctctttc accggcgata gtcaggatga gagctcacaa ctttactata  15360
gaggacaacg aatctggcat tcagctatgg aagaactact ctctaaaggc atgcaaaaag  15420
cagaacaggc tctactttct ggatgttcag ctgggggatt agcttccatc ctacactgcg  15480
atcagttcaa ggaactattt ccgggcacta cgacagtgaa atgcttaagt gatgctggaa  15540
tgtttatgga tgcagtggat gtctctgggg gccactcgct ccggaaaatg ttccaaggtg  15600
ttgttacagt acagaacctc caaaaggaac tgtccactgc ttgtacaaag catttggatc  15660
caacttcgtg cttctttccc cagaacttgg tttcaggcat taagactcca atgtttcttc  15720
tcaatgcagc atatgacgct tggcaggtac aagagagttt agctccacca tcagttgacc  15780
taagcggctc ttggaaggca tgcaaatctg atcactcgca ttgtaattca tctcagatcc  15840
agttcttcca agacttcagg actcatatgg tagatgctgt aaagtctttc gcgacatcga  15900
cacataacgg tgtgttcata aactcatgct tcgctcactg ccaatctgaa agacaggaca  15960
cttggtatgc accagattct cctactcttc atggcaagac cgttgctgaa tctgttggtg  16020
attggtactt tgacagaaca acagtgaaag ccattgactg tccttacccc tgtgacaaaa  16080
catgtcacaa tctcatcttc aagtgaaagg gtgggcgcgc cg                     16122
```

<210> SEQ ID NO 15
<211> LENGTH: 18657
<212> TYPE: DNA
<213> ORGANISM: artificial sequence
<220> FEATURE:
<223> OTHER INFORMATION: vector pKR1481

<400> SEQUENCE: 15

```
cgcgccagat cctctagagt cgacctgcag gcatgcaagc ttggcgtaat catggtcata     60
gctgtttcct gtgtgaaatt gttatccgct cacaattcca cacaacatac gagccggaag    120
cataaagtgt aaagcctggg gtgcctaatg agtgagctaa ctcacattaa ttgcgttgcg    180
ctcactgccc gctttccagt cgggaaacct gtcgtgccag ctgcattaat gaatcggcca    240
acgcgcgggg agaggcggtt tgcgtattgg atcgatccct gaaagcgacg ttggatgtta    300
acatctacaa attgcctttt cttatcgacc atgtacgtaa gcgcttacgt ttttggtgga    360
cccttgagga aactggtagc tgttgtgggc ctgtggtctc aagatggatc attaatttcc    420
accttcacct acgatggggg gcatcgcacc ggtgagtaat attgtacggc taagagcgaa    480
tttggcctgt agacctcaat tgcgagcttt ctaatttcaa actattcggg cctaactttt    540
ggtgtgatga tgctgactgg caggatatat accgttgtaa tttgagctcg tgtgaataag    600
tcgctgtgta tgtttgtttg attgtttctg ttggagtgca gcccatttca ccggacaagt    660
cggctagatt gatttagccc tgatgaactg ccgaggggaa gccatcttga gcgcggaatg    720
ggaatggatt tcgttgtaca acgagacgac agaacaccca cgggaccgag cttcgcgagc    780
ttttgtatcc gtggcatcct tggtccgggc gatttgttca cgtccatgag gcgctctcca    840
aaggaacgca tatttttccgg tgcaaccttt ccggttcttc ctctactcga cctcttgaag    900
tcccagcatg aatgttcgac cgctccgcaa gcggatcttt ggcgcaacca gccggtttcg    960
cacgtcgatt ctcgcgagcc tgcatacttt ggcaagattg ctgaatgacg ctgatgcttc   1020
atcgcaatct gcgataatgg ggtaagtatc cggtgaaggc cgcaggtcag gccgcctgag   1080
```

-continued cactcagtgt cttggatgtc cagttccacg gcagctgttg ctcaagcctg ctgatcggag 1140
cgtccgcaag gtcggcgcgg acgtcggcaa gccaggcctg cggatcgatg ttattgagct 1200
tggcgctcat gatcagtgtc gccatgaacg ccgcacgttc agcacaacga tccgatccgg 1260
caaacagcca tgacttcctg ccgagtacat agcctctgag cgttcgttcg gcagcattgt 1320
tcgtcaggca aatcgggccg tcatcgagga atgacgtaat gccatcccat cgcttgagca 1380
tgtaatttat cgcctcggcg acgggagaac tgcgcgacaa tttcccccgc tcggtttcga 1440
gccaatcatg cagctcttcg gcgagtgacc ttgatcaggc caccgccacg accgcggaag 1500
acgaacagat gcctgcgcat cggatcgcgc ttcagcgtct cttgcaccat cagcgacaaa 1560
ccgggaaagc ctttgcgcat gtccgtactt atgtcgccac ttgggagggc ttcgtctacg 1620
tggccttcgt gatcgacgtc ttcgcccgtc gcattgtcgg atggcgggcg agccggacag 1680
cacatgcagg ctttgtcctc gatgccctcg aggaggctca tcatgatcgg cgtcccgctc 1740
atggcggcct agtgcatcac tcggatcgcg gtgttcaata cgtgtccttt cgctattccg 1800
agcggttggc agaagcaggt atcgagccat ctatcggaag cgtcggcgac agcacgacaa 1860
cgccctcgca gaagcgatca acggtcttta caaggccgag gtcattcatc ggcgtggacc 1920
atggaggagc ttcgaagcgg tcgagttcgc taccttggaa tggatagact ggttcaacca 1980
cggcggcttt tgaagcccat cggcaatata ccgccagccg aagacgagga tcagtattac 2040
gccatgctgg acgaagcagc catggctgcg cattttaacg aaatggcctc cggcaaaccc 2100
ggtgcggttc acttgttgcg tgggaaagtt cacgggactc cgcgcacgag ccttcttcgt 2160
aatagccata tcgaccgaat tgacctgcag gggggggggg gaaagccacg ttgtgtctca 2220
aaatctctga tgttacattg cacaagataa aaatatatca tcatgaacaa taaaactgtc 2280
tgcttacata aacagtaata caaggggtgt tatgagccat attcaacggg aaacgtcttg 2340
ctcgaggccg cgattaaatt ccaacatgga tgctgattta tatgggtata aatgggctcg 2400
cgataatgtc gggcaatcag gtgcgacaat ctatcgattg tatgggaagc ccgatgcgcc 2460
agagttgttt ctgaaacatg gcaaaggtag cgttgccaat gatgttacag atgagatggt 2520
cagactaaac tggctgacgg aatttatgcc tcttccgacc atcaagcatt ttatccgtac 2580
tcctgatgat gcatggttac tcaccactgc gatccccggg aaaacagcat tccaggtatt 2640
agaagaatat cctgattcag gtgaaaatat tgttgatgcg ctggcagtgt tcctgcgccg 2700
gttgcattcg attcctgttt gtaattgtcc ttttaacagc gatcgcgtat ttcgtctcgc 2760
tcaggcgcaa tcacgaatga ataacggttt ggttgatgcg agtgattttg atgacgagcg 2820
taatggctgg cctgttgaac aagtctggaa agaaatgcat aagcttttgc cattctcacc 2880
ggattcagtc gtcactcatg gtgatttctc acttgataac cttatttttg acgaggggaa 2940
attaataggt tgtattgatg ttggacgagt cggaatcgca gaccgatacc aggatcttgc 3000
catcctatgg aactgcctcg gtgagttttc tccttcatta cagaaacggc tttttcaaaa 3060
atatggtatt gataatcctg atatgaataa attgcagttt catttgatgc tcgatgagtt 3120
tttctaatca gaattggtta attggttgta acactggcag agcattacgc tgacttgacg 3180
ggacggcggc tttgttgaat aaatcgaact tttgctgagt tgaaggatca gatcacgcat 3240
cttcccgaca acgcagaccg ttccgtggca aagcaaaagt tcaaaatcac caactggtcc 3300
acctacaaca aagctctcat caaccgtggc tccctcactt tctggctgga tgatggggcg 3360
attcaggcct ggtatgagtc agcaacacct tcttcacgag gcagacctca gcgccccccc 3420

-continued

```
ccccctgcag gtcttttcca atgatgagca cttttaaagt tctgctatgt ggcgcggtat   3480
tatcccgtgt tgacgccggg caagagcaac tcggtcgccg catacactat tctcagaatg   3540
acttggttga gtactcacca gtcacagaaa agcatcttac ggatggcatg acagtaagag   3600
aattatgcag tgctgccata accatgagtg ataacactgc ggccaactta cttctgacaa   3660
cgatcggagg accgaaggag ctaaccgctt ttttgcacaa catgggggat catgtaactc   3720
gccttgatcg ttgggaaccg gagctgaatg aagccatacc aaacgacgag cgtgacacca   3780
cgatgcctgt agcaatggca acaacgttgc gcaaactatt aactggcgaa ctacttactc   3840
tagcttcccg gcaacaatta atagactgga tggaggcgga taaagttgca ggaccacttc   3900
tgcgctcggc ccttccggct ggctggttta ttgctgataa atctggagcc ggtgagcgtg   3960
ggtctcgcgg tatcattgca gcactggggc cagatggtaa gccctcccgt atcgtagtta   4020
tctacacgac ggggagtcag gcaactatgg atgaacgaaa tagacagatc gctgagatag   4080
gtgcctcact gattaagcat tggtaactgt cagaccaagt ttactcatat atactttaga   4140
ttgatttaaa acttcatttt taatttaaaa ggatctaggt gaagatcctt tttgataatc   4200
tcatgaccaa aatcccttaa cgtgagtttt cgttccactg agcgtcagac cccgtagaaa   4260
agatcaaagg atcttcttga gatccttttt ttctgcgcgt aatctgctgc ttgcaaacaa   4320
aaaaaccacc gctaccagcg gtggtttgtt tgccggatca agagctacca actctttttc   4380
cgaaggtaac tggcttcagc agagcgcaga taccaaatac tgtccttcta gtgtagccgt   4440
agttaggcca ccacttcaag aactctgtag caccgcctac atacctcgct ctgctaatcc   4500
tgttaccagt ggctgctgcc agtggcgata agtcgtgtct taccgggttg gactcaagac   4560
gatagttacc ggataaggcg cagcggtcgg gctgaacggg gggttcgtgc acacagccca   4620
gcttggagcg aacgacctac accgaactga gatacctaca gcgtgagcta tgagaaagcg   4680
ccacgcttcc cgaagggaga aaggcggaca ggtatccggt aagcggcagg gtcggaacag   4740
gagagcgcac gagggagctt ccagggggaa acgcctggta tctttatagt cctgtcgggt   4800
ttcgccacct ctgacttgag cgtcgatttt tgtgatgctc gtcagggggg cggagcctat   4860
ggaaaaacgc cagcaacgcg gcctttttac ggttcctggc cttttgctgg ccttttgctc   4920
acatgttctt tcctgcgtta tcccctgatt ctgtggataa ccgtattacc gcctttgagt   4980
gagctgatac cgctcgccgc agccgaacga ccgagcgcag cgagtcagtg agcgaggaag   5040
cggaagagcg cctgatgcgg tattttctcc ttacgcatct gtgcggtatt tcacaccgca   5100
tatggtgcac tctcagtaca atctgctctg atgccgcata gttaagccag tatacactcc   5160
gctatcgcta cgtgactggg tcatggctgc gccccgacac ccgccaacac ccgctgacgc   5220
gccctgacgg gcttgtctgc tcccggcatc cgcttacaga caagctgtga ccgtctccgg   5280
gagctgcatg tgtcagaggt tttcaccgtc atcaccgaaa cgcgcgaggc agggtgcctt   5340
gatgtgggcg ccggcggtcg agtggcgacg gcgcggcttg tccgcgccct ggtagattgc   5400
ctggccgtag gccagccatt tttgagcggc cagcggccgc gataggccga cgcgaagcgg   5460
cggggcgtag ggagcgcagc gaccgaaggg taggcgcttt ttgcagctct tcggctgtgc   5520
gctggccaga cagttatgca caggccaggc gggttttaag agttttaata agttttaaag   5580
agttttaggc ggaaaaatcg cctttttttct cttttatatc agtcacttac atgtgtgacc   5640
ggttcccaat gtacggcttt gggttcccaa tgtacgggtt ccggttccca atgtacggct   5700
ttgggttccc aatgtacgtg ctatccacag gaaagagacc ttttcgacct tttcccctg   5760
ctagggcaat ttgccctagc atctgctccg tacattagga accggcggat gcttcgccct   5820
```

-continued

```
cgatcaggtt gcggtagcgc atgactagga tcgggccagc ctgccccgcc tcctccttca   5880
aatcgtactc cggcaggtca tttgacccga tcagcttgcg cacggtgaaa cagaacttct   5940
tgaactctcc ggcgctgcca ctgcgttcgt agatcgtctt gaacaaccat ctggcttctg   6000
ccttgcctgc ggcgcggcgt gccaggcggt agagaaaacg gccgatgccg ggatcgatca   6060
aaaagtaatc ggggtgaacc gtcagcacgt ccgggttctt gccttctgtg atctcgcggt   6120
acatccaatc agctagctcg atctcgatgt actccggccg cccggtttcg ctctttacga   6180
tcttgtagcg gctaatcaag gcttcaccct cggataccgt caccaggcgg ccgttcttgg   6240
ccttcttcgt acgctgcatg gcaacgtgcg tggtgtttaa ccgaatgcag gtttctacca   6300
ggtcgtcttt ctgctttccg ccatcggctc gccggcagaa cttgagtacg tccgcaacgt   6360
gtggacggaa cacgcggccg ggcttgtctc ccttcccttc ccggtatcgg ttcatggatt   6420
cggttagatg ggaaaccgcc atcagtacca ggtcgtaatc ccacacactg gccatgccgg   6480
ccggccctgc ggaaacctct acgtgcccgt ctggaagctc gtagcggatc acctcgccag   6540
ctcgtcggtc acgcttcgac agacggaaaa cggccacgtc catgatgctg cgactatcgc   6600
gggtgcccac gtcatagagc atcggaacga aaaaatctgg ttgctcgtcg cccttgggcg   6660
gcttcctaat cgacggcgca ccggctgccg gcggttgccg ggattctttg cggattcgat   6720
cagcggccgc ttgccacgat tcaccggggc gtgcttctgc ctcgatgcgt tgccgctggg   6780
cggcctgcgc ggccttcaac ttctccacca ggtcatcacc cagcgccgcg ccgatttgta   6840
ccgggccgga tggtttgcga ccgctcacgc cgattcctcg ggcttggggg ttccagtgcc   6900
attgcagggc cggcagacaa cccagccgct tacgcctggc caaccgcccg ttcctccaca   6960
catggggcat tccacggcgt cggtgcctgg ttgttcttga ttttccatgc cgcctccttt   7020
agccgctaaa attcatctac tcatttattc atttgctcat ttactctggt agctgcgcga   7080
tgtattcaga tagcagctcg gtaatggtct tgccttggcg taccgcgtac atcttcagct   7140
tggtgtgatc ctccgccggc aactgaaagt tgacccgctt catggctggc gtgtctgcca   7200
ggctggccaa cgttgcagcc ttgctgctgc gtgcgctcgg acggccggca cttagcgtgt   7260
ttgtgctttt gctcattttc tctttacctc attaactcaa atgagttttg atttaatttc   7320
agcggccagc gcctggacct cgcgggcagc gtcgccctcg ggttctgatt caagaacggt   7380
tgtgccggcg gcggcagtgc ctgggtagct cacgcgctgc gtgatacggg actcaagaat   7440
gggcagctcg tacccggcca gcgcctcggc aacctcaccg ccgatgcgcg tgcctttgat   7500
cgcccgcgac acgacaaagg ccgcttgtag ccttccatcc gtgacctcaa tgcgctgctt   7560
aaccagctcc accaggtcgg cggtggccca tatgtcgtaa gggcttggct gcaccggaat   7620
cagcacgaag tcggctgcct tgatcgcgga cacagccaag tccgccgcct ggggcgctcc   7680
gtcgatcact acgaagtcgc gccggccgat ggccttcacg tcgcggtcaa tcgtcgggcg   7740
gtcgatgccg acaacggtta gcggttgatc ttcccgcacg gccgcccaat cgcgggcact   7800
gccctgggga tcggaatcga ctaacagaac atcggccccg gcgagttgca gggcgcgggc   7860
tagatgggtt gcgatggtcg tcttgcctga cccgcctttc tggttaagta cagcgataac   7920
ttcatgcgtt cccttgcgta tttgtttatt tactcatcgc atcatatacg cagcgaccgc   7980
atgacgcaag ctgttttact caaatacaca tcaccttttt agacggcggc gctcggtttc   8040
ttcagcggcc aagctggccg gccaggccgc cagcttggca tcagacaaac cggccaggat   8100
ttcatgcagc cgcacggttg agacgtgcgc gggcggctcg aacacgtacc cggccgcgat   8160
```

catctccgcc tcgatctctt cggtaatgaa aaacggttcg tcctggccgt cctggtgcgg 8220
tttcatgctt gttcctcttg gcgttcattc tcggcggccg ccagggcgtc ggcctcggtc 8280
aatgcgtcct cacggaaggc accgcgccgc ctggcctcgg tgggcgtcac ttcctcgctg 8340
cgctcaagtg cgcggtacag ggtcgagcga tgcacgccaa gcagtgcagc cgcctctttc 8400
acggtgcggc cttcctggtc gatcagctcg cgggcgtgcg cgatctgtgc cggggtgagg 8460
gtagggcggg ggccaaactt cacgcctcgg gccttggcgg cctcgcgccc gctccgggtg 8520
cggtcgatga ttagggaacg ctcgaactcg gcaatgccgg cgaacacggt caacaccatg 8580
cggccggccg gcgtggtggt gtcggcccac ggctctgcca ggctacgcag gcccgcgccg 8640
gcctcctgga tgcgctcggc aatgtccagt aggtcgcggg tgctgcgggc caggcggtct 8700
agcctggtca ctgtcacaac gtcgccaggg cgtaggtggt caagcatcct ggccagctcc 8760
gggcggtcgc gcctggtgcc ggtgatcttc tcggaaaaca gcttggtgca gccggccgcg 8820
tgcagttcgg cccgttggtt ggtcaagtcc tggtcgtcgg tgctgacgcg ggcatagccc 8880
agcaggccag cggcggcgct cttgttcatg gcgtaatgtc tccggttcta gtcgcaagta 8940
ttctacttta tgcgactaaa acacgcgaca agaaaacgcc aggaaaaggg cagggcggca 9000
gcctgtcgcg taacttagga cttgtgcgac atgtcgtttt cagaagacgg ctgcactgaa 9060
cgtcagaagc cgactgcact atagcagcgg aggggttgga ccacaggacg ggtgtggtcg 9120
ccatgatcgc gtagtcgata gtggctccaa gtagcgaagc gagcaggact gggcggcggc 9180
caaagcggtc ggacagtgct ccgagaacgg gtgcgcatag aaattgcatc aacgcatata 9240
gcgctagcag cacgccatag tgactggcga tgctgtcgga atggacgata tcccgcaaga 9300
ggcccggcag taccggcata accaagccta tgcctacagc atccagggtg acggtgccga 9360
ggatgacgat gagcgcattg ttagatttca tacacggtgc ctgactgcgt tagcaattta 9420
actgtgataa actaccgcat taaagctagc ttgcttggtc gttccgcgtg aacgtcggct 9480
cgattgtacc tgcgttcaaa tactttgcga tcgtgttgcg cgcctgcccg gtgcgtcggc 9540
tgatctcacg gatcgactgc ttctctcgca acgccatccg acggatgatg tttaaaagtc 9600
ccatgtggat cactccgttg ccccgtcgct caccgtgttg gggggaaggt gcacatggct 9660
cagttctcaa tggaaattat ctgcctaacc ggctcagttc tgcgtagaaa ccaacatgca 9720
agctccaccg ggtgcaaagc ggcagcggcg gcaggatata ttcaattgta aatggcttca 9780
tgtccgggaa atctacatgg atcagcaatg agtatgatgg tcaatatgga gaaaaagaaa 9840
gagtaattac caattttttt tcaattcaaa aatgtagatg tccgcagcgt tattataaaa 9900
tgaaagtaca ttttgataaa acgacaaatt acgatccgtc gtatttatag gcgaaagcaa 9960
taaacaaatt attctaattc ggaaatcttt atttcgacgt gtctacattc acgtccaaat 10020
gggggcttag atgagaaact tcacgatcga tgccttgatt tcgccattcc cagataccca 10080
tttcatcttc agattggtct gagattatgc gaaaatatac actcatatac ataaatactg 10140
acagtttgag ctaccaattc agtgtagccc attacctcac ataattcact caaatgctag 10200
gcagtctgtc aactcggcgt caatttgtcg gccactatac gatagttgcg caaattttca 10260
aagtcctggc ctaacatcac acctctgtcg gcggcgggtc ccatttgtga taaatccacc 10320
atatcgaatt aattcagact cctttgcccc agagatcaca atggacgact tcctctatct 10380
ctacgatcta gtcaggaagt tcgacggaga aggtgacgat accatgttca ccactgataa 10440
tgagaagatt agccttttca atttcagaaa gaatgctaac ccacagatgg ttagagaggc 10500
ttacgcagca ggtctcatca agacgatcta cccgagcaat aatctccagg agatcaaata 10560
ccttcccaag aaggttaaag atgcagtcaa aagattcagg actaactgca tcaagaacac 10620
agagaaagat atatttctca agatcagaag tactattcca gtatggacga ttcaaggctt 10680
gcttcacaaa ccaaggcaag taatagagat tggagtctct aaaaaggtag ttcccactga 10740
atcaaaggcc atggagtcaa agattcaaat agaggaccta acagaactcg ccgtaaagac 10800
tggcgaacag ttcatacaga gtctcttacg actcaatgac aagaagaaaa tcttcgtcaa 10860
catggtggag cacgacacgc ttgtctactc caaaaatatc aaagatacag tctcagaaga 10920
ccaaagggca attgagactt ttcaacaaag ggtaatatcc ggaaacctcc tcggattcca 10980
ttgcccagct atctgtcact ttattgtgaa gatagtggaa aaggaaggtg gctcctacaa 11040
atgccatcat tgcgataaag gaaaggccat cgttgaagat gcctctgccg acagtggtcc 11100
caaagatgga cccccaccca cgaggagcat cgtggaaaaa gaagacgttc caaccacgtc 11160
ttcaaagcaa gtggattgat gtgatatctc cactgacgta agggatgacg cacaatccca 11220
ctatccttcg caagaccctt cctctatata aggaagttca tttcatttgg agaggacacg 11280
ctgaaatcac cagtctccaa gcttgcgggg atcgtttcgc atgattgaac aagatggatt 11340
gcacgcaggt tctccggccg cttgggtgga gaggctattc ggctatgact gggcacaaca 11400
gacaatcggc tgctctgatg ccgccgtgtt ccggctgtca gcgcaggggc gcccggttct 11460
ttttgtcaag accgacctgt ccggtgccct gaatgaactg caggacgagg cagcgcggct 11520
atcgtggctg gccacgacgg gcgttccttg cgcagctgtg ctcgacgttg tcactgaagc 11580
gggaagggac tggctgctat tgggcgaagt gccggggcag gatctcctgt catctcacct 11640
tgctcctgcc gagaaagtat ccatcatggc tgatgcaatg cggcggctgc atacgcttga 11700
tccggctacc tgcccattcg accaccaagc gaaacatcgc atcgagcgag cacgtactcg 11760
gatggaagcc ggtcttgtcg atcaggatga tctggacgaa gagcatcagg ggctcgcgcc 11820
agccgaactg ttcgccaggc tcaaggcgcg catgcccgac ggcgaggatc tcgtcgtgac 11880
ccatggcgat gcctgcttgc cgaatatcat ggtggaaaat ggccgctttt ctggattcat 11940
cgactgtggc cggctgggtg tggcggaccg ctatcaggac atagcgttgg ctacccgtga 12000
tattgctgaa gagcttggcg gcgaatgggc tgaccgcttc ctcgtgcttt acggtatcgc 12060
cgctcccgat tcgcagcgca tcgccttcta tcgccttctt gacgagttct tctgagcggg 12120
actctggggt tcgaaatgac cgaccaagcg acgcccaacc tgccatcacg agatttcgat 12180
tccaccgccg ccttctatga aaggttgggc ttcggaatcg ttttccggga cgccggctgg 12240
atgatcctcc agcgcgggga tctcatgctg gagttcttcg cccaccccgg atcgatccaa 12300
cacttacgtt tgcaacgtcc aagagcaaat agaccacgaa cgccggaagg ttgccgcagc 12360
gtgtggattg cgtctcaatt ctctcttgca ggaatgcaat gatgaatatg atactgacta 12420
tgaaactttg agggaatact gcctagcacc gtcacctcat aacgtgcatc atgcatgccc 12480
tgacaacatg gaacatcgct atttttctga agaattatgc tcgttggagg atgtcgcggc 12540
aattgcagct attgccaaca tcgaactacc cctcacgcat gcattcatca atattattca 12600
tgcggggaaa ggcaagatta atccaactgg caaatcatcc agcgtgattg gtaacttcag 12660
ttccagcgac ttgattcgtt ttggtgctac ccacgttttc aataaggacg agatggtgga 12720
gtaaagaagg agtgcgtcga agcagatcgt tcaaacattt ggcaataaag tttcttaaga 12780
ttgaatcctg ttgccggtct tgcgatgatt atcatataat ttctgttgaa ttacgttaag 12840
catgtaataa ttaacatgta atgcatgacg ttatttatga gatgggtttt tatgattaga 12900

-continued

```
gtcccgcaat tatacattta atacgcgata gaaaacaaaa tatagcgcgc aaactaggat  12960
aaattatcgc gcgcggtgtc atctatgtta ctagatcgat caaacttcgg tactgtgtaa  13020
tgacgatgag caatcgagag gctgactaac aaaaggtaca tcgcgatgga tcgatccatt  13080
cgccattcag gctgcgcaac tgttgggaag ggcgatcggt gcgggcctct tcgctattac  13140
gccagctggc gaaaggggga tgtgctgcaa ggcgattaag ttgggtaacg ccagggtttt  13200
cccagtcacg acgttgtaaa acgacggcca gtgaattcct gcagcccggg ggatccgccc  13260
actcgaggcg cgccaagctt ggatctcctg caggatctgg ccggccggat ctcgtaccga  13320
gctcggatcc actagtaacg gccgccagtg tgctggaatt caggtcctgc aggtctactc  13380
tttacatgtt ctttactccg tctcaaaatt tcctttttt gttggctctc tccgaacgag  13440
ttggagaaat cgttaaccct aatcgaagat ctagattcct ctacatacgt ttgatctctc  13500
tctcagtatg gattacaaag cgccaaggag atactactca cacggagttg ttgcgagaca  13560
gcaagatttc gcaacagata tagttacgag aagaagacct tatgtccctt acgaccgtcc  13620
aaataagttt tcaaggagtc tggtttggac gtcaaaagag tacaaatcac ccgagggcaa  13680
taatatgcca aggaccaatg atgtgtcacc gaaaccacca gttttaggtt tggcgaggaa  13740
gaatgctgct tgtgggccaa tgagatcttc tagtctcaga aaatgggtat gtaagtattg  13800
gaaagatgga aagtgcaaga ggggtgagca gtgccagttc ttacactctt ggtcttgttt  13860
ccctggattg gccatggtag cttctcttga agggcacaat aaggaactaa aggggatcgc  13920
tctccctgag ggttcagata aactcttttc agtcagtatt gatggtacat tgcgagtttg  13980
ggactgcaat tctggtcagt gtgtacattc catcaacctt gacgcagaag cagggtctct  14040
aatcagtgaa ggcccttggg ttttccttgg cttgccaaac gctataaagg cttttaacgt  14100
tcaaaccagt caagatttgc atcttcaagc agcaggggtg gttggtcagg tgaatgcaat  14160
gactattgca aacggaatgc tttttgctgg aacaagttct ggtagtatct tagtctggaa  14220
agctactaca gactctgagt ctgatccatt caaatacttg acatctcttg agggacatag  14280
tggtgaagtc acttgttttg ctgttggagg tcaaatgcta tactctggtt ctgtcgataa  14340
aacaatcaag atgtgggatc tcaacaccct gcaatgtata atgaccctga agcaacatac  14400
cggcactgtc acttcactct tatgttggga taaatgtttg atatcgtctt ccttggatgg  14460
gaccataaaa gtttgggctt attctgaaaa cggaatcttg aaagttgttc aaactcgcag  14520
acaagaacag agtagtgttc atgctctttc tggtatgcat gatgcagaag ccaaaccgat  14580
aatattctgc tcttaccaaa acggaaccgt tggcattttc gacctaccat cttttcaaga  14640
aagaggaagg atgttctcta cgcacacgat cgccacactc acaattggtc ctcaaggatt  14700
gttattcagt ggagacgaga gtggtaactt gcgtgtatgg accttagctg ctggcaacaa  14760
agtttagtct tttcgactaa agaattctga tttaattttg tggtttatat gttgagttaa  14820
ctgttaagag agttttattt tgtaataggt gtatcagtca ataaacaatc tttgtatcaa  14880
ccaaatgtaa tttttctcgt taattcgatt tcagagtttt tactttaaga taaacaaact  14940
ctttcacaca tcatttaatg aaagtggaga agcttaaaaa acaaacaaag aaactgatcc  15000
atttttggcg ggtcttcttc tactcttatt catatgtgtt aacgaactat agcgtaaaat  15060
tcagagcaag cgatctccga tttgaacgtg gctatcaccg gaggcccacc actacgggcg  15120
atacgctcta agtgaggatt aaagtgctct ggtggtgacg ttgaagaaac tcgcccatgg  15180
tttttgttat ctctgcagcc aagtgtcgtt ctttcttcgc cacttctcat caagctacag  15240
tgaatttaaa aatggcgtct ttctttgatc tcgtatacat aagctggatt ggtttcttaa  15300
```

-continued

```
acaaattcct ctccttttgg gtcttctggg tttgccttgt aagtgtttgt gtttttgcct  15360
ctgagaaaaa atcgcggccc tagacgccca tcacaagttt gtacaaaaaa gctgaacgag  15420
aaacgtaaaa tgatataaat atcaatatat taaattagat tttgcataaa aaacagacta  15480
cataatactg taaaacacaa catatccagt catattggcg gccgcattag gcaccccagg  15540
ctttacactt tatgcttccg gctcgtataa tgtgtggatt ttgagttagg atccgtcgag  15600
attttcagga gctaaggaag ctaaaatgga gaaaaaaatc actggatata ccaccgttga  15660
tatatcccaa tggcatcgta aagaacattt tgaggcattt cagtcagttg ctcaatgtac  15720
ctataaccag accgttcagc tggatattac ggccttttta aagaccgtaa agaaaaataa  15780
gcacaagttt tatccggcct ttattcacat tcttgcccgc ctgatgaatg ctcatccgga  15840
attccgtatg gcaatgaaag acggtgagct ggtgatatgg gatagtgttc acccttgtta  15900
caccgttttc catgagcaaa ctgaaacgtt ttcatcgctc tggagtgaat accacgacga  15960
tttccggcag tttctacaca tatattcgca agatgtggcg tgttacggtg aaaacctggc  16020
ctatttccct aaagggttta ttgagaatat gtttttcgtc tcagccaatc cctgggtgag  16080
tttcaccagt tttgatttaa acgtggccaa tatggacaac ttcttcgccc ccgttttcac  16140
catgggcaaa tattatacgc aaggcgacaa ggtgctgatg ccgctggcga ttcaggttca  16200
tcatgccgtt tgtgatggct tccatgtcgg cagaatgctt aatgaattac aacagtactg  16260
cgatgagtgg cagggcgggg cgtaaacgcg tggatccggc ttactaaaag ccagataaca  16320
gtatgcgtat ttgcgcgctg atttttgcgg tataagaata tatactgata tgtatacccg  16380
aagtatgtca aaaagaggta tgctatgaag cagcgtatta cagtgacagt tgacagcgac  16440
agctatcagt tgctcaaggc atatatgatg tcaatatctc cggtctggta agcacaacca  16500
tgcagaatga agcccgtcgt ctgcgtgccg aacgctggaa agcggaaaat caggaaggga  16560
tggctgaggt cgcccggttt attgaaatga acggctcttt tgctgacgag aacaggggct  16620
ggtgaaatgc agtttaaggt ttacacctat aaaagagaga gccgttatcg tctgtttgtg  16680
gatgtacaga gtgatattat tgacacgccc gggcgacgga tggtgatccc cctggccagt  16740
gcacgtctgc tgtcagataa agtctcccgt gaactttacc cggtggtgca tatcggggat  16800
gaaagctggc gcatgatgac caccgatatg gccagtgtgc cggtctccgt tatcggggaa  16860
gaagtggctg atctcagcca ccgcgaaaat gacatcaaaa acgccattaa cctgatgttc  16920
tggggaatat aaatgtcagg ctcccttata cacagccagt ctgcaggtcg accatagtga  16980
ctggatatgt tgtgttttac agcattatgt agtctgtttt ttatgcaaaa tctaatttaa  17040
tatattgata tttatatcat tttacgtttc tcgttcagct ttcttgtaca aagtggtgat  17100
gataaccaag tttaacgtga gtttatatat tcacagttcc atttacagat cttatgctga  17160
ttgcagcata taacatagtc gcaacttaac tttatccctg cttacgtaaa gaaacataca  17220
tattgtttgt ggcttcgtag tggaacatat gcaattatgt aatctttata ttatgagcct  17280
ttacttacaa agattacttg agatttatgt acgtgtgcta ttttcacttt tcaaacatga  17340
atttcctacg tttacaatca tttaatgtaa aagggatgat ataatgtatt tacgtacatg  17400
tgaacaacca agcatgttat tttttccttt tttgttgcaa cttacaatca agtaatgatt  17460
atggttatga ttatgatatt ggtgtgtgtc ttttgcctta tatatatatt tatccctttc  17520
gtttaacttt gcaatataat tattactgat cactatattt tggtttgaaa tggcgcaggt  17580
tgtaatgatc gatcatcacc actttgtaca agaaagctga acgagaaacg taaaatgata  17640
```

-continued

```
taaatatcaa tatattaaat tagattttgc ataaaaaaca gactacataa tgctgtaaaa  17700

cacaacatat ccagtcacta tggtcgacct gcagactggc tgtgtataag ggagcctgac  17760

atttatattc cccagaacat caggttaatg gcgtttttga tgtcattttc gcggtggctg  17820

agatcagcca cttcttcccc gataacggag accggcacac tggccatatc ggtggtcatc  17880

atgcgccagc tttcatcccc gatatgcacc accgggtaaa gttcacggga gactttatct  17940

gacagcagac gtgcactggc cagggggatc accatccgtc gcccgggcgt gtcaataata  18000

tcactctgta catccacaaa cagacgataa cggctctctc ttttataggt gtaaacctta  18060

aactgcattt caccagcccc tgttctcgtc agcaaaagag ccgttcattt caataaaccg  18120

ggcgacctca gccatccctt cctgattttc cgctttccag cgttcggcac gcagacgacg  18180

ggcttcattc tgcatggttg tgcttaccag accggagata ttgacatcat atatgccttg  18240

agcaactgat agctgtcgct gtcaactgtc actgtaatac gctgcttcat agcatacctc  18300

tttttgacat acttcgggta tacatatcag tatatattct tataccgcaa aaatcagcgc  18360

gcaaatacgc atactgttat ctggctttta gtaagccgga tcctaactca aaatccacac  18420

attatacgag ccggaagcat aaagtgtaaa gcctggggtg cctaatgcgg ccgccaatat  18480

gactggatat gttgtgtttt acagtattat gtagtctgtt ttttatgcaa aatctaattt  18540

aatatattga tatttatatc attttacgtt tctcgttcag ctttttttgta caaacttgtg  18600

atgggcgtct agcgaactag aggatccccg ggtaccgagg tacggatccg tcgacgg     18657
```

<210> SEQ ID NO 16
<211> LENGTH: 38
<212> TYPE: DNA
<213> ORGANISM: artificial sequence
<220> FEATURE:
<223> OTHER INFORMATION: primer

<400> SEQUENCE: 16

```
cctagggtta accaagttta acgtgagttt atatattc                          38
```

<210> SEQ ID NO 17
<211> LENGTH: 38
<212> TYPE: DNA
<213> ORGANISM: artificial sequence
<220> FEATURE:
<223> OTHER INFORMATION: primer

<400> SEQUENCE: 17

```
actagttcgc gatcattaca acctgcgcca tttcaaac                          38
```

<210> SEQ ID NO 18
<211> LENGTH: 506
<212> TYPE: DNA
<213> ORGANISM: artificial sequence
<220> FEATURE:
<223> OTHER INFORMATION: CR product w laccase intron

<400> SEQUENCE: 18

```
cctagggtta accaagttta acgtgagttt atatattcac agttccattt acagatctta    60

tgctgattgc agcatataac atagtcgcaa cttaacttta tccctgctta cgtaaagaaa   120

catacatatt gtttgtggct tcgtagtgga acatatgcaa ttatgtaatc tttatattat   180

gagcctttac ttacaaagat tacttgagat ttatgtacgt gtgctatttt cacttttcaa   240

acatgaattt cctacgttta caatcattta atgtaaaagg gatgatataa tgtatttacg   300

tacatgtgaa caaccaagca tgttattttt tcctttttttg ttgcaactta caatcaagta   360
```

atgattatgg ttatgattat gatattggtg tgtgtctttt gccttatata tatatttatc 420
cctttcgttt aactttgcaa tataattatt actgatcact atattttggt ttgaaatggc 480
gcaggttgta atgatcgcga actagt 506

<210> SEQ ID NO 19
<211> LENGTH: 1724
<212> TYPE: DNA
<213> ORGANISM: artificial sequence
<220> FEATURE:
<223> OTHER INFORMATION: plasmid PSM1318

<400> SEQUENCE: 19
ctagacgccc atcacaagtt tgtacaaaaa agctgaacga gaaacgtaaa atgatataaa 60
tatcaatata ttaaattaga ttttgcataa aaaacagact acataatact gtaaaacaca 120
acatatccag tcatattggc ggccgcatta ggcaccccag gctttacact ttatgcttcc 180
ggctcgtata atgtgtggat tttgagttag gatccgtcga gattttcagg agctaaggaa 240
gctaaaatgg agaaaaaaat cactggatat accaccgttg atatatccca atggcatcgt 300
aaagaacatt ttgaggcatt tcagtcagtt gctcaatgta cctataacca gaccgttcag 360
ctggatatta cggccttttt aaagaccgta aagaaaaata agcacaagtt ttatccggcc 420
tttattcaca ttcttgcccg cctgatgaat gctcatccgg aattccgtat ggcaatgaaa 480
gacggtgagc tggtgatatg ggatagtgtt cacccttgtt acaccgtttt ccatgagcaa 540
actgaaacgt tttcatcgct ctggagtgaa taccacgacg atttccggca gtttctacac 600
atatattcgc aagatgtggc gtgttacggt gaaaacctgg cctatttccc taaagggttt 660
attgagaata tgtttttcgt ctcagccaat ccctgggtga gtttcaccag ttttgattta 720
aacgtggcca atatggacaa cttcttcgcc cccgttttca ccatgggcaa atattatacg 780
caaggcgaca aggtgctgat gccgctggcg attcaggttc atcatgccgt ttgtgatggc 840
ttccatgtcg gcagaatgct taatgaatta caacagtact gcgatgagtg gcagggcggg 900
gcgtaaacgc gtggatccgg cttactaaaa gccagataac agtatgcgta tttgcgcgct 960
gatttttgcg gtataagaat atatactgat atgtataccc gaagtatgtc aaaaagaggt 1020
atgctatgaa gcagcgtatt acagtgacag ttgacagcga cagctatcag ttgctcaagg 1080
catatatgat gtcaatatct ccggtctggt aagcacaacc atgcagaatg aagcccgtcg 1140
tctgcgtgcc gaacgctgga aagcggaaaa tcaggaaggg atggctgagg tcgccccggtt 1200 tattgaaatg aacggctctt ttgctgacga gaacaggggc tggtgaaatg cagtttaagg 1260
tttacaccta taaaagagag agccgttatc gtctgtttgt ggatgtacag agtgatatta 1320
ttgacacgcc cgggcgacgg atggtgatcc ccctggccag tgcacgtctg ctgtcagata 1380
aagtctcccg tgaactttac ccggtggtgc atatcgggga tgaaagctgg cgcatgatga 1440
ccaccgatat ggccagtgtg ccggtctccg ttatcgggga agaagtggct gatctcagcc 1500
accgcgaaaa tgacatcaaa aacgccatta acctgatgtt ctggggaata taaatgtcag 1560
gctcccttat acacagccag tctgcaggtc gaccatagtg actggatatg ttgtgtttta 1620
cagcattatg tagtctgttt tttatgcaaa atctaattta atatattgat atttatatca 1680
ttttacgttt ctcgttcagc tttcttgtac aaagtggtga tgat 1724

<210> SEQ ID NO 20
<211> LENGTH: 4934
<212> TYPE: DNA

<213> ORGANISM: artificial sequence
<220> FEATURE:
<223> OTHER INFORMATION: plasmid pMBL18 ATTR12 INT

<400> SEQUENCE: 20
ctagaggatc cccgggtacc gagctcgaat tcgtaatcat ggtcatagct gtttcctgtg 60
tgaaattgtt atccgctcac aattccacac aacatacgag ccggaagcat aaagtgtaaa 120
gcctggggtg cctaatgagt gagctaactc acattaattg cgttgcgctc actgcccgct 180
ttccagtcgg gaaacctgtc gtgccagctg cattaatgaa tcggccaacg cgcggggaga 240
ggcggtttgc gtattgggcg ctagcggagt gtatactggc ttactatgtt ggcactgatg 300
agggtgtcag tgaagtgctt catgtggcag gagaaaaaag gctgcaccgg tgcgtcagca 360
gaatatgtga tacaggatat attccgcttc ctcgctcact gactcgctac gctcggtcgt 420
tcgactgcgg cgagcggaaa tggcttacga acggggcgga gatttcctgg aagatgccag 480
gaagatactt aacagggaag tgagagggcc gcggcaaagc cgtttttcca taggctccgc 540
ccccctgaca agcatcacga aatctgacgc tcaaatcagt ggtggcgaaa cccgacagga 600
ctataaagat accaggcgtt tccccctggc ggctccctcg tgcgctctcc tgttcctgcc 660
tttcggttta ccggtgtcat tccgctgtta tggccgcgtt tgtctcattc cacgcctgac 720
actcagttcc gggtaggcag ttcgctccaa gctggactgt atgcacgaac cccccgttca 780
gtccgaccgc tgcgccttat ccggtaacta tcgtcttgag tccaacccgg aaagacatgc 840
aaaagcacca ctggcagcag ccactggtaa ttgatttaga ggagttagtc ttgaagtcat 900
gcgccggtta aggctaaact gaaaggacaa gttttggtga ctgcgctcct ccaagccagt 960
tacctcggtt caaagagttg gtagctcaga gaaccttcga aaaaccgccc tgcaaggcgg 1020 tttttcgtt ttcagagcaa gagattacgc gcagaccaaa acgatctcaa gaagatcatc 1080
ttattaaggg gtctgacgct cagtggaacg aaaactcacg ttaagggatt ttggtcatga 1140
gattatcaaa aaggatcttc acctagatcc ttttaaatta aaaatgaagt tttaaatcaa 1200
tctaaagtat atatgagtaa acttggtctg acagttacca atgcttaatc agtgaggcac 1260
ctatctcagc gatctgtcta tttcgttcat ccatagttgc ctgactcccc gtcgtgtaga 1320
taactacgat acgggagggc ttaccatctg gccccagtgc tgcaatgata ccgcgagacc 1380
cacgctcacc ggctccagat ttatcagcaa taaaccagcc agccggaagg gccgagcgca 1440
gaagtggtcc tgcaacttta tccgcctcca tccagtctat taattgttgc cgggaagcta 1500
gagtaagtag ttcgccagtt aatagtttgc gcaacgttgt tgccattgct acaggcatcg 1560
tggtgtcacg ctcgtcgttt ggtatggctt cattcagctc cggttcccaa cgatcaaggc 1620
gagttacatg atcccccatg ttgtgcaaaa aagcggttag ctccttcggt cctccgatcg 1680
ttgtcagaag taagttggcc gcagtgttat cactcatggt tatggcagca ctgcataatt 1740
ctcttactgt catgccatcc gtaagatgct tttctgtgac tggtgagtac tcaaccaagt 1800
cattctgaga atagtgtatg cggcgaccga gttgctcttg cccggcgtca atacgggata 1860
ataccgcgcc acatagcaga actttaaaag tgctcatcat tggaaaacgt tcttcggggc 1920
gaaaactctc aaggatctta ccgctgttga gatccagttc gatgtaaccc actcgtgcac 1980
ccaactgatc ttcagcatct tttactttca ccagcgtttc tgggtgagca aaaacaggaa 2040
ggcaaaatgc cgcaaaaaag ggaataaggg cgacacggaa atgttgaata ctcatactct 2100
tcctttttca atattattga agcatttatc agggttattg tctcatgagc ggatacatat 2160
ttgaatgtat ttagaaaaat aaacaaatag gggttccgcg cacatttccc cgaaaagtgc 2220

```
cacctgacgt ctaagaaacc attattatca tgacattaac ctataaaaat aggcgtatca   2280
cgaggccctt tcgtctcgcg cgtttcggtg atgacggtga aaacctctga cacatgcagc   2340
tcccggagac ggtcacagct tgtctgtaag cggatgccgg gagcagacaa gcccgtcagg   2400
gcgcgtcagc gggtgttggc gggtgtcggg gctggcttaa ctatgcggca tcagagcaga   2460
ttgtactgag agtgcaccat atgcggtgtg aaataccgca cagatgcgta aggagaaaat   2520
accgcatcag gcgccattcg ccattcaggc tgcgcaactg ttgggaaggg cgatcggtgc   2580
gggcctcttc gctattacgc cagctggcga aagggggatg tgctgcaagg cgattaagtt   2640
gggtaacgcc agggttttcc cagtcacgac gttgtaaaac gacggccagt gccaagcttg   2700
catgcctgca ggtcgactct agacgcccat cacaagtttg tacaaaaaag ctgaacgaga   2760
aacgtaaaat gatataaata tcaatatatt aaattagatt ttgcataaaa aacagactac   2820
ataatactgt aaaacacaac atatccagtc atattggcgg ccgcattagg caccccaggc   2880
tttacacttt atgcttccgg ctcgtataat gtgtggattt tgagttagga tccgtcgaga   2940
ttttcaggag ctaaggaagc taaaatggag aaaaaaatca ctggatatac caccgttgat   3000
atatcccaat ggcatcgtaa agaacatttt gaggcatttc agtcagttgc tcaatgtacc   3060
tataaccaga ccgttcagct ggatattacg gcctttttaa agaccgtaaa gaaaaataag   3120
cacaagtttt atccggcctt tattcacatt cttgcccgcc tgatgaatgc tcatccggaa   3180
ttccgtatgg caatgaaaga cggtgagctg gtgatatggg atagtgttca cccttgttac   3240
accgttttcc atgagcaaac tgaaacgttt tcatcgctct ggagtgaata ccacgacgat   3300
ttccggcagt ttctacacat atattcgcaa gatgtggcgt gttacggtga aaacctggcc   3360
tatttcccta aagggtttat tgagaatatg tttttcgtct cagccaatcc ctgggtgagt   3420
ttcaccagtt ttgatttaaa cgtggccaat atggacaact tcttcgcccc cgttttcacc   3480
atgggcaaat attatacgca aggcgacaag gtgctgatgc cgctggcgat tcaggttcat   3540
catgccgttt gtgatggctt ccatgtcggc agaatgctta atgaattaca acagtactgc   3600
gatgagtggc agggcggggc gtaaacgcgt ggatccggct tactaaaagc cagataacag   3660
tatgcgtatt tgcgcgctga tttttgcggt ataagaatat atactgatat gtatacccga   3720
agtatgtcaa aaagaggtat gctatgaagc agcgtattac agtgacagtt gacagcgaca   3780
gctatcagtt gctcaaggca tatatgatgt caatatctcc ggtctggtaa gcacaaccat   3840
gcagaatgaa gcccgtcgtc tgcgtgccga acgctggaaa gcggaaaatc aggaagggat   3900
ggctgaggtc gcccggttta ttgaaatgaa cggctctttt gctgacgaga acaggggctg   3960
gtgaaatgca gtttaaggtt tacacctata aaagagagag ccgttatcgt ctgtttgtgg   4020
atgtacagag tgatattatt gacacgcccg ggcgacggat ggtgatcccc ctggccagtg   4080
cacgtctgct gtcagataaa gtctcccgtg aactttaccc ggtggtgcat atcggggatg   4140
aaagctggcg catgatgacc accgatatgg ccagtgtgcc ggtctccgtt atcggggaag   4200
aagtggctga tctcagccac cgcgaaaatg acatcaaaaa cgccattaac ctgatgttct   4260
ggggaatata aatgtcaggc tcccttatac acagccagtc tgcaggtcga ccatagtgac   4320
tggatatgtt gtgttttaca gcattatgta gtctgttttt tatgcaaaat ctaatttaat   4380
atattgatat ttatatcatt ttacgtttct cgttcagctt tcttgtacaa agtggtgatg   4440
ataaccaagt ttaacgtgag tttatatatt cacagttcca tttacagatc ttatgctgat   4500
tgcagcatat aacatagtcg caacttaact ttatccctgc ttacgtaaag aaacatacat   4560
```

-continued attgtttgtg gcttcgtagt ggaacatatg caattatgta atctttatat tatgagcctt 4620
tacttacaaa gattacttga gatttatgta cgtgtgctat tttcactttt caaacatgaa 4680
tttcctacgt ttacaatcat ttaatgtaaa agggatgata taatgtattt acgtacatgt 4740
gaacaaccaa gcatgttatt ttttcctttt ttgttgcaac ttacaatcaa gtaatgatta 4800
tggttatgat tatgatattg gtgtgtgtct tttgccttat atatatattt atccctttcg 4860
tttaactttg caatataatt attactgatc actatatttt ggtttgaaat ggcgcaggtt 4920
gtaatgatcg cgaa 4934

<210> SEQ ID NO 21
<211> LENGTH: 1021
<212> TYPE: DNA
<213> ORGANISM: artificial sequence
<220> FEATURE:
<223> OTHER INFORMATION: plasmid PSM1789

<400> SEQUENCE: 21
ctagacgccc atcacaagtt tgtacaaaaa agctgaacga gaaacgtaaa atgatataaa 60
tatcaatata ttaaattaga ttttgcataa aaaacagact acataatact gtaaaacaca 120
acatatccag tcatattggc ggccgcatta ggcaccccag gctttacact ttatgcttcc 180
ggctcgtata atgtgtggat tttgagttag gatccggctt actaaaagcc agataacagt 240
atgcgtattt gcgcgctgat ttttgcggta taagaatata tactgatatg tatacccgaa 300
gtatgtcaaa aagaggtatg ctatgaagca gcgtattaca gtgacagttg acagcgacag 360
ctatcagttg ctcaaggcat atatgatgtc aatatctccg gtctggtaag cacaaccatg 420
cagaatgaag cccgtcgtct gcgtgccgaa cgctggaaag cggaaaatca ggaagggatg 480
gctgaggtcg cccggtttat tgaaatgaac ggctcttttg ctgacgagaa caggggctgg 540
tgaaatgcag tttaaggttt acacctataa aagagagagc cgttatcgtc tgtttgtgga 600
tgtacagagt gatattattg acacgcccgg gcgacggatg gtgatccccc tggccagtgc 660
acgtctgctg tcagataaag tctcccgtga actttacccg gtggtgcata tcggggatga 720
aagctggcgc atgatgacca ccgatatggc cagtgtgccg gtctccgtta tcggggaaga 780
agtggctgat ctcagccacc gcgaaaatga catcaaaaac gccattaacc tgatgttctg 840
gggaatataa atgtcaggct cccttataca cagccagtct gcaggtcgac catagtgact 900
ggatatgttg tgttttacag cattatgtag tctgtttttt atgcaaaatc taatttaata 960
tattgatatt tatatcattt tacgtttctc gttcagcttt cttgtacaaa gtggtgatga 1020
t 1021

<210> SEQ ID NO 22
<211> LENGTH: 5955
<212> TYPE: DNA
<213> ORGANISM: artificial sequence
<220> FEATURE:
<223> OTHER INFORMATION: plasmid pMBL18 ATTR12 INT ATTR21

<400> SEQUENCE: 22
atcatcacca ctttgtacaa gaaagctgaa cgagaaacgt aaaatgatat aaatatcaat 60
atattaaatt agattttgca taaaaaacag actacataat gctgtaaaac acaacatatc 120
cagtcactat ggtcgacctg cagactggct gtgtataagg gagcctgaca tttatattcc 180
ccagaacatc aggttaatgg cgtttttgat gtcattttcg cggtggctga gatcagccac 240
ttcttccccg ataacggaga ccggcacact ggccatatcg gtggtcatca tgcgccagct 300

```
ttcatccccg atatgcacca ccgggtaaag ttcacgggag actttatctg acagcagacg    360
tgcactggcc agggggatca ccatccgtcg cccgggcgtg tcaataatat cactctgtac    420
atccacaaac agacgataac ggctctctct tttataggtg taaaccttaa actgcatttc    480
accagcccct gttctcgtca gcaaaagagc cgttcatttc aataaaccgg gcgacctcag    540
ccatcccttc ctgattttcc gctttccagc gttcggcacg cagacgacgg gcttcattct    600
gcatggttgt gcttaccaga ccggagatat tgacatcata tatgccttga gcaactgata    660
gctgtcgctg tcaactgtca ctgtaatacg ctgcttcata gcatacctct ttttgacata    720
cttcgggtat acatatcagt atatattctt ataccgcaaa aatcagcgcg caaatacgca    780
tactgttatc tggcttttag taagccggat cctaactcaa aatccacaca ttatacgagc    840
cggaagcata aagtgtaaag cctggggtgc ctaatgcggc cgccaatatg actggatatg    900
ttgtgtttta cagtattatg tagtctgttt tttatgcaaa atctaattta atatattgat    960
atttatatca ttttacgttt ctcgttcagc ttttttgtac aaacttgtga tgggcgtcta   1020
gcgaactaga ggatccccgg gtaccgagct cgaattcgta atcatggtca tagctgtttc   1080
ctgtgtgaaa ttgttatccg ctcacaattc cacacaacat acgagccgga agcataaagt   1140
gtaaagcctg gggtgcctaa tgagtgagct aactcacatt aattgcgttg cgctcactgc   1200
ccgctttcca gtcgggaaac ctgtcgtgcc agctgcatta atgaatcggc caacgcgcgg   1260
ggagaggcgg tttgcgtatt gggcgctagc ggagtgtata ctggcttact atgttggcac   1320
tgatgagggt gtcagtgaag tgcttcatgt ggcaggagaa aaaaggctgc accggtgcgt   1380
cagcagaata tgtgatacag gatatattcc gcttcctcgc tcactgactc gctacgctcg   1440
gtcgttcgac tgcggcgagc ggaaatggct tacgaacggg gcggagattt cctggaagat   1500
gccaggaaga tacttaacag ggaagtgaga gggccgcggc aaagccgttt ttccataggc   1560
tccgcccccc tgacaagcat cacgaaatct gacgctcaaa tcagtggtgg cgaaacccga   1620
caggactata aagataccag gcgtttcccc ctggcggctc cctcgtgcgc tctcctgttc   1680
ctgcctttcg gtttaccggt gtcattccgc tgttatggcc gcgtttgtct cattccacgc   1740
ctgacactca gttccgggta ggcagttcgc tccaagctgg actgtatgca cgaacccccc   1800
gttcagtccg accgctgcgc cttatccggt aactatcgtc ttgagtccaa cccggaaaga   1860
catgcaaaag caccactggc agcagccact ggtaattgat ttagaggagt tagtcttgaa   1920
gtcatgcgcc ggttaaggct aaactgaaag gacaagtttt ggtgactgcg ctcctccaag   1980
ccagttacct cggttcaaag agttggtagc tcagagaacc ttcgaaaaac cgccctgcaa   2040
ggcggttttt tcgttttcag agcaagagat tacgcgcaga ccaaaacgat ctcaagaaga   2100
tcatcttatt aaggggtctg acgctcagtg gaacgaaaac tcacgttaag ggattttggt   2160
catgagatta tcaaaaagga tcttcaccta gatcctttta aattaaaaat gaagttttaa   2220
atcaatctaa agtatatatg agtaaacttg gtctgacagt taccaatgct taatcagtga   2280
ggcacctatc tcagcgatct gtctatttcg ttcatccata gttgcctgac tccccgtcgt   2340
gtagataact acgatacggg agggcttacc atctggcccc agtgctgcaa tgataccgcg   2400
agacccacgc tcaccggctc cagatttatc agcaataaac cagccagccg gaagggccga   2460
gcgcagaagt ggtcctgcaa ctttatccgc ctccatccag tctattaatt gttgccggga   2520
agctagagta agtagttcgc cagttaatag tttgcgcaac gttgttgcca ttgctacagg   2580
catcgtggtg tcacgctcgt cgtttggtat ggcttcattc agctccggtt cccaacgatc   2640
```

aaggcgagtt acatgatccc ccatgttgtg caaaaaagcg gttagctcct tcggtcctcc 2700
gatcgttgtc agaagtaagt tggccgcagt gttatcactc atggttatgg cagcactgca 2760
taattctctt actgtcatgc catccgtaag atgcttttct gtgactggtg agtactcaac 2820
caagtcattc tgagaatagt gtatgcggcg accgagttgc tcttgcccgg cgtcaatacg 2880
ggataatacc gcgccacata gcagaacttt aaaagtgctc atcattggaa aacgttcttc 2940
ggggcgaaaa ctctcaagga tcttaccgct gttgagatcc agttcgatgt aacccactcg 3000
tgcacccaac tgatcttcag catcttttac tttcaccagc gtttctgggt gagcaaaaac 3060
aggaaggcaa aatgccgcaa aaaagggaat aagggcgaca cggaaatgtt gaatactcat 3120
actcttcctt tttcaatatt attgaagcat ttatcagggt tattgtctca tgagcggata 3180
catatttgaa tgtatttaga aaaataaaca aataggggtt ccgcgcacat ttccccgaaa 3240
agtgccacct gacgtctaag aaaccattat tatcatgaca ttaacctata aaaataggcg 3300
tatcacgagg ccctttcgtc tcgcgcgttt cggtgatgac ggtgaaaacc tctgacacat 3360
gcagctcccg gagacggtca cagcttgtct gtaagcggat gccgggagca gacaagcccg 3420
tcagggcgcg tcagcgggtg ttggcgggtg tcggggctgg cttaactatg cggcatcaga 3480
gcagattgta ctgagagtgc accatatgcg gtgtgaaata ccgcacagat gcgtaaggag 3540
aaaataccgc atcaggcgcc attcgccatt caggctgcgc aactgttggg aagggcgatc 3600
ggtgcgggcc tcttcgctat tacgccagct ggcgaaaggg ggatgtgctg caaggcgatt 3660
aagttgggta acgccagggt tttcccagtc acgacgttgt aaaacgacgg ccagtgccaa 3720
gcttgcatgc ctgcaggtcg actctagacg cccatcacaa gtttgtacaa aaaagctgaa 3780
cgagaaacgt aaaatgatat aaatatcaat atattaaatt agattttgca taaaaaacag 3840
actacataat actgtaaaac acaacatatc cagtcatatt ggcggccgca ttaggcaccc 3900
caggctttac actttatgct tccggctcgt ataatgtgtg gattttgagt taggatccgt 3960
cgagattttc aggagctaag gaagctaaaa tggagaaaaa aatcactgga tataccaccg 4020
ttgatatatc ccaatggcat cgtaaagaac attttgaggc atttcagtca gttgctcaat 4080
gtacctataa ccagaccgtt cagctggata ttacggcctt tttaaagacc gtaaagaaaa 4140
ataagcacaa gttttatccg gcctttattc acattcttgc ccgcctgatg aatgctcatc 4200
cggaattccg tatggcaatg aaagacggtg agctggtgat atgggatagt gttcaccctt 4260
gttacaccgt tttccatgag caaactgaaa cgttttcatc gctctggagt gaataccacg 4320
acgatttccg gcagtttcta cacatatatt cgcaagatgt ggcgtgttac ggtgaaaacc 4380
tggcctattt ccctaaaggg tttattgaga atatgttttt cgtctcagcc aatccctggg 4440
tgagtttcac cagttttgat ttaaacgtgg ccaatatgga caacttcttc gcccccgttt 4500
tcaccatggg caaatattat acgcaaggcg acaaggtgct gatgccgctg gcgattcagg 4560
ttcatcatgc cgtttgtgat ggcttccatg tcggcagaat gcttaatgaa ttacaacagt 4620
actgcgatga gtggcagggc ggggcgtaaa cgcgtggatc cggcttacta aaagccagat 4680
aacagtatgc gtatttgcgc gctgattttt gcggtataag aatatatact gatatgtata 4740
cccgaagtat gtcaaaaaga ggtatgctat gaagcagcgt attacagtga cagttgacag 4800
cgacagctat cagttgctca aggcatatat gatgtcaata tctccggtct ggtaagcaca 4860
accatgcaga atgaagcccg tcgtctgcgt gccgaacgct ggaaagcgga aaatcaggaa 4920
gggatggctg aggtcgcccg gtttattgaa atgaacggct cttttgctga cgagaacagg 4980
ggctggtgaa atgcagttta aggtttacac ctataaaaga gagagccgtt atcgtctgtt 5040

-continued tgtggatgta cagagtgata ttattgacac gcccgggcga cggatggtga tccccctggc 5100
cagtgcacgt ctgctgtcag ataaagtctc ccgtgaactt tacccggtgg tgcatatcgg 5160
ggatgaaagc tggcgcatga tgaccaccga tatggccagt gtgccggtct ccgttatcgg 5220
ggaagaagtg gctgatctca gccaccgcga aaatgacatc aaaaacgcca ttaacctgat 5280
gttctgggga atataaatgt caggctccct tatacacagc cagtctgcag gtcgaccata 5340
gtgactggat atgttgtgtt ttacagcatt atgtagtctg tttttatgc aaaatctaat 5400 ttaatatatt gatatttata tcattttacg tttctcgttc agctttcttg tacaaagtgg 5460
tgatgataac caagtttaac gtgagtttat atattcacag ttccatttac agatcttatg 5520
ctgattgcag catataacat agtcgcaact taactttatc cctgcttacg taaagaaaca 5580
tacatattgt ttgtggcttc gtagtggaac atatgcaatt atgtaatctt tatattatga 5640
gcctttactt acaaagatta cttgagattt atgtacgtgt gctattttca cttttcaaac 5700
atgaatttcc tacgtttaca atcatttaat gtaaaaggga tgatataatg tatttacgta 5760
catgtgaaca accaagcatg ttattttttc ctttttgtt gcaacttaca atcaagtaat 5820
gattatggtt atgattatga tattggtgtg tgtcttttgc cttatatata tatttatccc 5880
tttcgtttaa ctttgcaata taattattac tgatcactat attttggttt gaaatggcgc 5940
aggttgtaat gatcg 5955

<210> SEQ ID NO 23
<211> LENGTH: 35
<212> TYPE: DNA
<213> ORGANISM: artificial sequence
<220> FEATURE:
<223> OTHER INFORMATION: primer

<400> SEQUENCE: 23
tcctgcaggt ctactcttta catgttcttt actcc 35

<210> SEQ ID NO 24
<211> LENGTH: 34
<212> TYPE: DNA
<213> ORGANISM: artificial sequence
<220> FEATURE:
<223> OTHER INFORMATION: primer

<400> SEQUENCE: 24
agcggccgcg atttttctc agaggcaaaa acac 34

<210> SEQ ID NO 25
<211> LENGTH: 5531
<212> TYPE: DNA
<213> ORGANISM: artificial sequence
<220> FEATURE:
<223> OTHER INFORMATION: plasmid pLF122

<400> SEQUENCE: 25
cctgaattct gcagatatcc atcacactgg cggccgctcg agcatgcatc tagagggccc 60
aattcgccct atagtgagtc gtattacaat tcactggccg tcgttttaca acgtcgtgac 120
tgggaaaacc ctggcgttac ccaacttaat cgccttgcag cacatccccc tttcgccagc 180
tggcgtaata gcgaagaggc ccgcaccgat cgcccttccc aacagttgcg cagcctatac 240
gtacggcagt ttaaggttta cacctataaa agagagagcc gttatcgtct gtttgtggat 300
gtacagagtg atattattga cacgccgggg cgacggatgg tgatccccct ggccagtgca 360

-continued

```
cgtctgctgt cagataaagt ctcccgtgaa ctttacccgg tggtgcatat cggggatgaa    420
agctggcgca tgatgaccac cgatatggcc agtgtgccgg tctccgttat cggggaagaa    480
gtggctgatc tcagccaccg cgaaaatgac atcaaaaacg ccattaacct gatgttctgg    540
ggaatataaa tgtcaggcat gagattatca aaaaggatct tcacctagat ccttttcacg    600
tagaaagcca gtccgcagaa acggtgctga ccccggatga atgtcagcta ctgggctatc    660
tggacaaggg aaaacgcaag cgcaaagaga aagcaggtag cttgcagtgg gcttacatgg    720
cgatagctag actgggcggt tttatggaca gcaagcgaac cggaattgcc agctggggcg    780
ccctctggta aggttgggaa gccctgcaaa gtaaactgga tggctttctc gccgccaagg    840
atctgatggc gcaggggatc aagctctgat caagagacag gatgaggatc gtttcgcatg    900
attgaacaag atggattgca cgcaggttct ccggccgctt gggtggagag gctattcggc    960
tatgactggg cacaacagac aatcggctgc tctgatgccg ccgtgttccg gctgtcagcg   1020
caggggcgcc cggttctttt tgtcaagacc gacctgtccg gtgccctgaa tgaactgcaa   1080
gacgaggcag cgcggctatc gtggctggcc acgacgggcg ttccttgcgc agctgtgctc   1140
gacgttgtca ctgaagcggg aagggactgg ctgctattgg gcgaagtgcc ggggcaggat   1200
ctcctgtcat ctcaccttgc tcctgccgag aaagtatcca tcatggctga tgcaatgcgg   1260
cggctgcata cgcttgatcc ggctacctgc ccattcgacc accaagcgaa acatcgcatc   1320
gagcgagcac gtactcggat ggaagccggt cttgtcgatc aggatgatct ggacgaagag   1380
catcaggggc tcgcgccagc cgaactgttc gccaggctca aggcgagcat gcccgacggc   1440
gaggatctcg tcgtgaccca tggcgatgcc tgcttgccga atatcatggt ggaaaatggc   1500
cgcttttctg gattcatcga ctgtggccgg ctgggtgtgg cggaccgcta tcaggacata   1560
gcgttggcta cccgtgatat tgctgaagag cttggcggcg aatgggctga ccgcttcctc   1620
gtgctttacg gtatcgccgc tcccgattcg cagcgcatcg ccttctatcg ccttcttgac   1680
gagttcttct gaattattaa cgcttacaat ttcctgatgc ggtattttct ccttacgcat   1740
ctgtgcggta tttcacaccg catacaggtg gcacttttcg gggaaatgtg cgcggaaccc   1800
ctatttgttt atttttctaa atacattcaa atatgtatcc gctcatgaga caataaccct   1860
gataaatgct tcaataatag cacgtgagga gggccaccat ggccaagttg accagtgccg   1920
ttccggtgct caccgcgcgc gacgtcgccg gagcggtcga gttctggacc gaccggctcg   1980
ggttctcccg ggacttcgtg gaggacgact tcgccggtgt ggtccgggac gacgtgaccc   2040
tgttcatcag cgcggtccag gaccaggtgg tgccggacaa caccctggcc tgggtgtggg   2100
tgcgcggcct ggacgagctg tacgccgagt ggtcggaggt cgtgtccacg aacttccggg   2160
acgcctccgg gccggccatg accgagatcg gcgagcagcc gtgggggcgg gagttcgccc   2220
tgcgcgaccc ggccggcaac tgcgtgcact tcgtggccga ggagcaggac tgacacgtgc   2280
taaaacttca tttttaattt aaaaggatct aggtgaagat cctttttgat aatctcatga   2340
ccaaaatccc ttaacgtgag ttttcgttcc actgagcgtc agaccccgta gaaaagatca   2400
aaggatcttc ttgagatcct ttttttctgc gcgtaatctg ctgcttgcaa acaaaaaaac   2460
caccgctacc agcggtggtt tgtttgccgg atcaagagct accaactctt tttccgaagg   2520
taactggctt cagcagagcg cagataccaa atactgtcct tctagtgtag ccgtagttag   2580
gccaccactt caagaactct gtagcaccgc ctacatacct cgctctgcta atcctgttac   2640
cagtggctgc tgccagtggc gataagtcgt gtcttaccgg gttggactca agacgatagt   2700
taccggataa ggcgcagcgg tcgggctgaa cggggggttc gtgcacacag cccagcttgg   2760
```

-continued

```
agcgaacgac ctacaccgaa ctgagatacc tacagcgtga gctatgagaa agcgccacgc   2820
ttcccgaagg gagaaaggcg gacaggtatc cggtaagcgg cagggtcgga acaggagagc   2880
gcacgaggga gcttccaggg ggaaacgcct ggtatcttta tagtcctgtc gggtttcgcc   2940
acctctgact tgagcgtcga tttttgtgat gctcgtcagg ggggcggagc ctatggaaaa   3000
acgccagcaa cgcggccttt ttacggttcc tgggcttttg ctggcctttt gctcacatgt   3060
tctttcctgc gttatcccct gattctgtgg ataaccgtat taccgccttt gagtgagctg   3120
ataccgctcg ccgcagccga acgaccgagc gcagcgagtc agtgagcgag gaagcggaag   3180
agcgcccaat acgcaaaccg cctctccccg cgcgttggcc gattcattaa tgcagctggc   3240
acgacaggtt tcccgactgg aaagcgggca gtgagcgcaa cgcaattaat gtgagttagc   3300
tcactcatta ggcaccccag gctttacact ttatgcttcc ggctcgtatg ttgtgtggaa   3360
ttgtgagcgg ataacaattt cacacaggaa acagctatga ccatgattac gccaagctat   3420
ttaggtgacg cgttagaata ctcaagctat gcatcaagct tggtaccgag ctcggatcca   3480
ctagtaacgg ccgccagtgt gctggaattc aggtcctgca ggtctactct ttacatgttc   3540
tttactccgt ctcaaaattt ccttttttttg ttggctctct ccgaacgagt tggagaaatc   3600
gttaacccta atcgaagatc tagattcctc tacatacgtt tgatctctct ctcagtatgg   3660
attacaaagc gccaaggaga tactactcac acggagttgt tgcgagacag caagatttcg   3720
caacagatat agttacgaga agaagacctt atgtccctta cgaccgtcca aataagtttt   3780
caaggagtct ggtttggacg tcaaaagagt acaaatcacc cgagggcaat aatatgccaa   3840
ggaccaatga tgtgtcaccg aaaccaccag ttttaggttt ggcgaggaag aatgctgctt   3900
gtgggccaat gagatcttct agtctcagaa aatgggtatg taagtattgg aaagatggaa   3960
agtgcaagag gggtgagcag tgccagttct tacactcttg gtcttgtttc cctggattgg   4020
ccatggtagc ttctcttgaa gggcacaata aggaactaaa ggggatcgct ctccctgagg   4080
gttcagataa actcttttca gtcagtattg atggtacatt gcgagtttgg gactgcaatt   4140
ctggtcagtg tgtacattcc atcaaccttg acgcagaagc agggtctcta atcagtgaag   4200
gcccttgggt tttccttggc ttgccaaacg ctataaaggc ttttaacgtt caaaccagtc   4260
aagatttgca tcttcaagca gcaggggtgg ttggtcaggt gaatgcaatg actattgcaa   4320
acggaatgct ttttgctgga acaagttctg gtagtatctt agtctggaaa gctactacag   4380
actctgagtc tgatccattc aaatacttga catctcttga gggacatagt ggtgaagtca   4440
cttgttttgc tgttggaggt caaatgctat actctggttc tgtcgataaa acaatcaaga   4500
tgtgggatct caacaccctg caatgtataa tgaccctgaa gcaacatacc ggcactgtca   4560
cttcactctt atgttgggat aaatgtttga tatcgtcttc cttggatggg accataaaag   4620
tttgggctta ttctgaaaac ggaatcttga aagttgttca aactcgcaga caagaacaga   4680
gtagtgttca tgctctttct ggtatgcatg atgcagaagc caaaccgata atattctgct   4740
cttaccaaaa cggaaccgtt ggcattttcg acctaccatc ttttcaagaa agaggaagga   4800
tgttctctac gcacacgatc gccacactca caattggtcc tcaaggattg ttattcagtg   4860
gagacgagag tggtaacttg cgtgtatgga ccttagctgc tggcaacaaa gtttagtctt   4920
ttcgactaaa gaattctgat ttaattttgt ggtttatatg ttgagttaac tgttaagaga   4980
gttttatttt gtaataggtg tatcagtcaa taaacaatct ttgtatcaac caaatgtaat   5040
ttttctcgtt aattcgattt cagagttttt actttaagat aaacaaactc tttcacacat   5100
```

```
catttaatga aagtggagaa gcttaaaaaa caaacaaaga aactgatcca tttttggcgg   5160

gtcttcttct actcttattc atatgtgtta acgaactata gcgtaaaatt cagagcaagc   5220

gatctccgat ttgaacgtgg ctatcaccgg aggcccacca ctacgggcga tacgctctaa   5280

gtgaggatta aagtgctctg gtggtgacgt tgaagaaact cgcccatggt tttgttatc    5340

tctgcagcca agtgtcgttc tttcttcgcc acttctcatc aagctacagt gaatttaaaa   5400

atggcgtctt tctttgatct cgtatacata agctggattg gtttcttaaa caaattcctc   5460

tccttttggg tcttctgggt ttgccttgta agtgtttgtg tttttgcctc tgagaaaaaa   5520

tcgcggccgc t                                                        5531
```

```
<210> SEQ ID NO 26
<211> LENGTH: 5195
<212> TYPE: DNA
<213> ORGANISM: artificial sequence
<220> FEATURE:
<223> OTHER INFORMATION: plasmid pKR1142

<400> SEQUENCE: 26
```

```
ctagagggcc caattcgccc tatagtgagt cgtattacaa ttcactggcc gtcgttttac     60

aacgtcgtga ctgggaaaac cctggcgtta cccaacttaa tcgccttgca gcacatcccc    120

ctttcgccag ctggcgtaat agcgaagagg cccgcaccga tcgcccttcc caacagttgc    180

gcagcctata cgtacggcag tttaaggttt acacctataa aagagagagc cgttatcgtc    240

tgtttgtgga tgtacagagt gatattattg acacgccggg gcgacggatg gtgatccccc    300

tggccagtgc acgtctgctg tcagataaag tctcccgtga actttacccg gtggtgcata    360

tcggggatga aagctggcgc atgatgacca ccgatatggc cagtgtgccg gtctccgtta    420

tcggggaaga agtggctgat ctcagccacc gcgaaaatga catcaaaaac gccattaacc    480

tgatgttctg gggaatataa atgtcaggca tgagattatc aaaaaggatc ttcacctaga    540

tccttttcac gtagaaagcc agtccgcaga aacggtgctg accccggatg aatgtcagct    600

actgggctat ctggacaagg gaaaacgcaa gcgcaaagag aaagcaggta gcttgcagtg    660

ggcttacatg gcgatagcta gactgggcgg ttttatggac agcaagcgaa ccggaattgc    720

cagctggggc gccctctggt aaggttggga agccctgcaa agtaaactgg atggctttct    780

cgccgccaag gatctgatgg cgcaggggat caagctctga tcaagagaca ggatgaggat    840

cgtttcgcat gattgaacaa gatggattgc acgcaggttc tccggccgct tgggtggaga    900

ggctattcgg ctatgactgg gcacaacaga caatcggctg ctctgatgcc gccgtgttcc    960

ggctgtcagc gcaggggcgc ccggttcttt ttgtcaagac cgacctgtcc ggtgccctga   1020

atgaactgca agacgaggca gcgcggctat cgtggctggc cacgacgggc gttccttgcg   1080

cagctgtgct cgacgttgtc actgaagcgg gaagggactg gctgctattg ggcgaagtgc   1140

cggggcagga tctcctgtca tctcaccttg ctcctgccga gaaagtatcc atcatggctg   1200

atgcaatgcg gcggctgcat acgcttgatc cggctacctg cccattcgac caccaagcga   1260

aacatcgcat cgagcgagca cgtactcgga tggaagccgg tcttgtcgat caggatgatc   1320

tggacgaaga gcatcagggg ctcgcgccag ccgaactgtt cgccaggctc aaggcgagca   1380

tgcccgacgg cgaggatctc gtcgtgaccc atggcgatgc ctgcttgccg aatatcatgg   1440

tggaaaatgg ccgcttttct ggattcatcg actgtggccg gctgggtgtg gcggaccgct   1500

atcaggacat agcgttggct acccgtgata ttgctgaaga gcttggcggc gaatgggctg   1560

accgcttcct cgtgctttac ggtatcgccg ctcccgattc gcagcgcatc gccttctatc   1620
```

-continued

```
gccttcttga cgagttcttc tgaattatta acgcttacaa tttcctgatg cggtattttc   1680
tccttacgca tctgtgcggt atttcacacc gcatacaggt ggcacttttc ggggaaatgt   1740
gcgcggaacc cctatttgtt tatttttcta aatacattca aatatgtatc cgctcatgag   1800
acaataaccc tgataaatgc ttcaataata gcacgtgagg agggccacca tggccaagtt   1860
gaccagtgcc gttccggtgc tcaccgcgcg cgacgtcgcc ggagcggtcg agttctggac   1920
cgaccggctc gggttctccc gggacttcgt ggaggacgac ttcgccggtg tggtccggga   1980
cgacgtgacc ctgttcatca gcgcggtcca ggaccaggtg gtgccggaca acaccctggc   2040
ctgggtgtgg gtgcgcggcc tggacgagct gtacgccgag tggtcggagg tcgtgtccac   2100
gaacttccgg gacgcctccg ggccggccat gaccgagatc ggcgagcagc cgtgggggcg   2160
ggagttcgcc ctgcgcgacc cggccggcaa ctgcgtgcac ttcgtggccg aggagcagga   2220
ctgacacgtg ctaaaacttc atttttaatt taaaaggatc taggtgaaga tcctttttga   2280
taatctcatg accaaaatcc cttaacgtga gttttcgttc cactgagcgt cagaccccgt   2340
agaaaagatc aaaggatctt cttgagatcc tttttttctg cgcgtaatct gctgcttgca   2400
aacaaaaaaa ccaccgctac cagcggtggt ttgtttgccg gatcaagagc taccaactct   2460
ttttccgaag gtaactggct tcagcagagc gcagatacca aatactgtcc ttctagtgta   2520
gccgtagtta ggccaccact tcaagaactc tgtagcaccg cctacatacc tcgctctgct   2580
aatcctgtta ccagtggctg ctgccagtgg cgataagtcg tgtcttaccg ggttggactc   2640
aagacgatag ttaccggata aggcgcagcg gtcgggctga acggggggtt cgtgcacaca   2700
gcccagcttg gagcgaacga cctacaccga actgagatac ctacagcgtg agctatgaga   2760
aagcgccacg cttcccgaag ggagaaaggc ggacaggtat ccggtaagcg gcagggtcgg   2820
aacaggagag cgcacgaggg agcttccagg gggaaacgcc tggtatcttt atagtcctgt   2880
cgggtttcgc cacctctgac ttgagcgtcg atttttgtga tgctcgtcag gggggcggag   2940
cctatggaaa aacgccagca acgcggcctt tttacggttc ctgggctttt gctggccttt   3000
tgctcacatg ttctttcctg cgttatcccc tgattctgtg gataaccgta ttaccgcctt   3060
tgagtgagct gataccgctc gccgcagccg aacgaccgag cgcagcgagt cagtgagcga   3120
ggaagcggaa gagcgcccaa tacgcaaacc gcctctcccc gcgcgttggc cgattcatta   3180
atgcagctgg cacgacaggt ttcccgactg gaaagcgggc agtgagcgca acgcaattaa   3240
tgtgagttag ctcactcatt aggcacccca ggctttacac tttatgcttc cggctcgtat   3300
gttgtgtgga attgtgagcg gataacaatt tcacacagga aacagctatg accatgatta   3360
cgccaagcta tttaggtgac gcgttagaat actcaagcta tgcatcaagc ttggtaccga   3420
gctcggatcc tctagaaatc cgtcaacatg gtggagcacg acactctcgt ctactccaag   3480
aatatcaaag atacagtctc agaagaccaa agggctattg agacttttca acaaagggta   3540
atatcgggaa acctcctcgg attccattgc ccagctatct gtcacttcat caaaaggaca   3600
gtagaaaagg aaggtggcac ctacaaatgc catcattgcg ataaaggaaa ggctatcgtt   3660
caagatgcct ctgccgacag tggtcccaaa gatggacccc cacccacgag gagcatcgtg   3720
gaaaaagaag acgttccaac cacgtcttca aagcaagtgg attgatgtga tgatcctatg   3780
cgtatggtat gacgtgtgtt caagatgatg acttcaaacc tacctatgac gtatggtatg   3840
aacgtgtgtc gactgatgac ttagatccac tcgagcggct ataaatacgt acctacgcac   3900
cctgcgctac catccctaga gctgcagctt atttttacaa caattaccaa caacaacaaa   3960
```

caacaaacaa cattacaatt actatttaca attacagtcg acccgggatc gtacctctag 4020
ggtggcggcc gcaagtatga actaaaatgc atgtaggtgt aagagctcat ggagagcatg 4080
gaatattgta tccgaccatg taacagtata ataactgagc tccatctcac ttcttctatg 4140
aataaacaaa ggatgttatg atatattaac actctatcta tgcaccttat tgttctatga 4200
taaatttcct cttattatta taaatcatct gaatcgtgac ggcttatgga atgcttcaaa 4260
tagtacaaaa acaaatgtgt actataagac tttctaaaca attctaacct tagcattgtg 4320
aacgagacat aagtgttaag aagacataac aattataatg gaagaagttt gtctccattt 4380
atatattata tattacccac ttatgtatta tattaggatg ttaaggagac ataacaatta 4440
taaagagaga agtttgtatc catttatata ttatatacta cccatttata tattatactt 4500
atccacttat ttaatgtctt tataaggttt gatccatgat atttctaata ttttagttga 4560
tatgtatatg aaagggtact atttgaactc tcttactctg tataaaggtt ggatcatcct 4620
taaagtgggt ctatttaatt ttattgcttc ttacagataa aaaaaaaatt atgagttggt 4680
ttgataaaat attgaaggat ttaaaataat aataaataac atataatata tgtatataaa 4740
tttattataa tataacattt atctataaaa aagtaaatat tgtcataaat ctatacaatc 4800
gtttagcctt gctggacgaa tctcaattat ttaaacgaga gtaaacatat ttgacttttt 4860
ggttatttaa caaattatta tttaacacta tatgaaattt tttttttat cagcaaagaa 4920 taaaattaaa ttaagaagga caatggtgtc ccaatcctta tacaaccaac ttccacaaga 4980
aagtcaagtc agagacaaca aaaaaacaag caaaggaaat tttttaattt gagttgtctt 5040
gtttgctgca taatttatgc agtaaaacac tacacataac ccttttagca gtagagcaat 5100
ggttgaccgt gtgcttagct tcttttattt tattttttta tcagcaaaga ataaataaaa 5160
taaaatgaga cacttcaggg atgtttcaac aagct 5195

<210> SEQ ID NO 27
<211> LENGTH: 6644
<212> TYPE: DNA
<213> ORGANISM: artificial sequence
<220> FEATURE:
<223> OTHER INFORMATION: plasmid pKR1155

<400> SEQUENCE: 27
ggccgcaagt atgaactaaa atgcatgtag gtgtaagagc tcatggagag catggaatat 60
tgtatccgac catgtaacag tataataact gagctccatc tcacttcttc tatgaataaa 120
caaaggatgt tatgatatat taacactcta tctatgcacc ttattgttct atgataaatt 180
tcctcttatt attataaatc atctgaatcg tgacggctta tggaatgctt caaatagtac 240
aaaaacaaat gtgtactata agactttcta aacaattcta accttagcat tgtgaacgag 300
acataagtgt taagaagaca taacaattat aatggaagaa gtttgtctcc atttatatat 360
tatatattac ccacttatgt attatattag gatgttaagg agacataaca attataaaga 420
gagaagtttg tatccattta tatattatat actacccatt tatatattat acttatccac 480
ttatttaatg tctttataag gtttgatcca tgatatttct aatattttag ttgatatgta 540
tatgaaaggg tactatttga actctcttac tctgtataaa ggttggatca tccttaaagt 600
gggtctattt aattttattg cttcttacag ataaaaaaaa aattatgagt tggtttgata 660
aaatattgaa ggatttaaaa taataataaa taacatataa tatatgtata taaatttatt 720
ataatataac atttatctat aaaaaagtaa atattgtcat aaatctatac aatcgtttag 780
ccttgctgga cgaatctcaa ttatttaaac gagagtaaac atatttgact tttggttat 840

-continued ttaacaaatt attatttaac actatatgaa attttttttt ttatcagcaa agaataaaat 900
taaattaaga aggacaatgg tgtcccaatc cttatacaac caacttccac aagaaagtca 960
agtcagagac aacaaaaaaa caagcaaagg aaatttttta atttgagttg tcttgtttgc 1020
tgcataattt atgcagtaaa acactacaca taaccctttt agcagtagag caatggttga 1080
ccgtgtgctt agcttctttt attttatttt tttatcagca aagaataaat aaaataaaat 1140
gagacacttc agggatgttt caacaagctc tagagggccc aattcgccct atagtgagtc 1200
gtattacaat tcactggccg tcgttttaca acgtcgtgac tgggaaaacc ctggcgttac 1260
ccaacttaat cgccttgcag cacatccccc tttcgccagc tggcgtaata gcgaagaggc 1320
ccgcaccgat cgcccttccc aacagttgcg cagcctatac gtacggcagt ttaaggttta 1380
cacctataaa agagagagcc gttatcgtct gtttgtggat gtacagagtg atattattga 1440
cacgccgggg cgacggatgg tgatccccct ggccagtgca cgtctgctgt cagataaagt 1500
ctcccgtgaa ctttacccgg tggtgcatat cggggatgaa agctggcgca tgatgaccac 1560
cgatatggcc agtgtgccgg tctccgttat cggggaagaa gtggctgatc tcagccaccg 1620
cgaaaatgac atcaaaaacg ccattaacct gatgttctgg ggaatataaa tgtcaggcat 1680
gagattatca aaaaggatct tcacctagat ccttttcacg tagaaagcca gtccgcagaa 1740
acggtgctga ccccggatga atgtcagcta ctgggctatc tggacaaggg aaaacgcaag 1800
cgcaaagaga aagcaggtag cttgcagtgg gcttacatgg cgatagctag actgggcggt 1860
tttatggaca gcaagcgaac cggaattgcc agctggggcg ccctctggta aggttgggaa 1920
gccctgcaaa gtaaactgga tggctttctc gccgccaagg atctgatggc gcaggggatc 1980
aagctctgat caagagacag gatgaggatc gtttcgcatg attgaacaag atggattgca 2040
cgcaggttct ccggccgctt gggtggagag gctattcggc tatgactggg cacaacagac 2100
aatcggctgc tctgatgccg ccgtgttccg gctgtcagcg caggggcgcc cggttctttt 2160
tgtcaagacc gacctgtccg gtgccctgaa tgaactgcaa gacgaggcag cgcggctatc 2220
gtggctggcc acgacgggcg ttccttgcgc agctgtgctc gacgttgtca ctgaagcggg 2280
aagggactgg ctgctattgg gcgaagtgcc ggggcaggat ctcctgtcat ctcaccttgc 2340
tcctgccgag aaagtatcca tcatggctga tgcaatgcgg cggctgcata cgcttgatcc 2400
ggctacctgc ccattcgacc accaagcgaa acatcgcatc gagcgagcac gtactcggat 2460
ggaagccggt cttgtcgatc aggatgatct ggacgaagag catcaggggc tcgcgccagc 2520
cgaactgttc gccaggctca aggcgagcat gcccgacggc gaggatctcg tcgtgaccca 2580
tggcgatgcc tgcttgccga atatcatggt ggaaaatggc cgcttttctg gattcatcga 2640
ctgtggccgg ctgggtgtgg cggaccgcta tcaggacata gcgttggcta cccgtgatat 2700
tgctgaagag cttggcggcg aatgggctga ccgcttcctc gtgctttacg gtatcgccgc 2760
tcccgattcg cagcgcatcg ccttctatcg ccttcttgac gagttcttct gaattattaa 2820
cgcttacaat ttcctgatgc ggtattttct ccttacgcat ctgtgcggta tttcacaccg 2880
catacaggtg gcacttttcg gggaaatgtg cgcggaaccc ctatttgttt atttttctaa 2940
atacattcaa atatgtatcc gctcatgaga caataaccct gataaatgct tcaataatag 3000
cacgtgagga gggccaccat ggccaagttg accagtgccg ttccggtgct caccgcgcgc 3060
gacgtcgccg gagcggtcga gttctggacc gaccggctcg ggttctcccg ggacttcgtg 3120
gaggacgact tcgccggtgt ggtccgggac gacgtgaccc tgttcatcag cgcggtccag 3180

-continued

```
gaccaggtgg tgccggacaa caccctggcc tgggtgtggg tgcgcggcct ggacgagctg   3240
tacgccgagt ggtcggaggt cgtgtccacg aacttccggg acgcctccgg gccggccatg   3300
accgagatcg gcgagcagcc gtgggggcgg gagttcgccc tgcgcgaccc ggccggcaac   3360
tgcgtgcact tcgtggccga ggagcaggac tgacacgtgc taaaacttca tttttaattt   3420
aaaaggatct aggtgaagat cctttttgat aatctcatga ccaaaatccc ttaacgtgag   3480
ttttcgttcc actgagcgtc agaccccgta gaaaagatca aaggatcttc ttgagatcct   3540
tttttctgc gcgtaatctg ctgcttgcaa acaaaaaaac caccgctacc agcggtggtt   3600
tgtttgccgg atcaagagct accaactctt tttccgaagg taactggctt cagcagagcg   3660
cagataccaa atactgtcct tctagtgtag ccgtagttag gccaccactt caagaactct   3720
gtagcaccgc ctacatacct cgctctgcta atcctgttac cagtggctgc tgccagtggc   3780
gataagtcgt gtcttaccgg gttggactca agacgatagt taccggataa ggcgcagcgg   3840
tcgggctgaa cggggggttc gtgcacacag cccagcttgg agcgaacgac ctacaccgaa   3900
ctgagatacc tacagcgtga gctatgagaa agcgccacgc ttcccgaagg gagaaaggcg   3960
gacaggtatc cggtaagcgg cagggtcgga acaggagagc gcacgaggga gcttccaggg   4020
ggaaacgcct ggtatcttta tagtcctgtc gggtttcgcc acctctgact tgagcgtcga   4080
tttttgtgat gctcgtcagg ggggcggagc ctatggaaaa acgccagcaa cgcggccttt   4140
ttacggttcc tgggcttttg ctggcctttt gctcacatgt tctttcctgc gttatcccct   4200
gattctgtgg ataaccgtat taccgccttt gagtgagctg ataccgctcg ccgcagccga   4260
acgaccgagc gcagcgagtc agtgagcgag gaagcggaag agcgcccaat acgcaaaccg   4320
cctctccccg cgcgttggcc gattcattaa tgcagctggc acgacaggtt tcccgactgg   4380
aaagcgggca gtgagcgcaa cgcaattaat gtgagttagc tcactcatta ggcaccccag   4440
gctttacact ttatgcttcc ggctcgtatg ttgtgtggaa ttgtgagcgg ataacaattt   4500
cacacaggaa acagctatga ccatgattac gccaagctat ttaggtgacg cgttagaata   4560
ctcaagctat gcatcaagct tggtaccgag ctcggatcca ctagtaacgg ccgccagtgt   4620
gctggaattc aggtcctgca ggtctactct ttacatgttc tttactccgt ctcaaaattt   4680
cctttttttg ttggctctct ccgaacgagt tggagaaatc gttaacccta atcgaagatc   4740
tagattcctc tacatacgtt tgatctctct ctcagtatgg attacaaagc gccaaggaga   4800
tactactcac acggagttgt tgcgagacag caagatttcg caacagatat agttacgaga   4860
agaagacctt atgtccctta cgaccgtcca aataagtttt caaggagtct ggtttggacg   4920
tcaaaagagt acaaatcacc cgagggcaat aatatgccaa ggaccaatga tgtgtcaccg   4980
aaaccaccag ttttaggttt ggcgaggaag aatgctgctt gtgggccaat gagatcttct   5040
agtctcagaa aatgggtatg taagtattgg aaagatggaa agtgcaagag gggtgagcag   5100
tgccagttct tacactcttg gtcttgtttc cctggattgg ccatggtagc ttctcttgaa   5160
gggcacaata aggaactaaa ggggatcgct ctccctgagg gttcagataa actcttttca   5220
gtcagtattg atggtacatt gcgagtttgg gactgcaatt ctggtcagtg tgtacattcc   5280
atcaaccttg acgcagaagc agggtctcta atcagtgaag gcccttgggt tttccttggc   5340
ttgccaaacg ctataaaggc ttttaacgtt caaaccagtc aagatttgca tcttcaagca   5400
gcaggggtgg ttggtcaggt gaatgcaatg actattgcaa acggaatgct tttgctgga   5460
acaagttctg gtagtatctt agtctggaaa gctactacag actctgagtc tgatccattc   5520
aaatacttga catctcttga gggacatagt ggtgaagtca cttgttttgc tgttggaggt   5580
```

```
caaatgctat actctggttc tgtcgataaa acaatcaaga tgtgggatct caacaccctg   5640
caatgtataa tgaccctgaa gcaacatacc ggcactgtca cttcactctt atgttgggat   5700
aaatgtttga tatcgtcttc cttggatggg accataaaag tttgggctta ttctgaaaac   5760
ggaatcttga aagttgttca aactcgcaga caagaacaga gtagtgttca tgctctttct   5820
ggtatgcatg atgcagaagc caaaccgata atattctgct cttaccaaaa cggaaccgtt   5880
ggcattttcg acctaccatc ttttcaagaa agaggaagga tgttctctac gcacacgatc   5940
gccacactca caattggtcc tcaaggattg ttattcagtg gagacgagag tggtaacttg   6000
cgtgtatgga ccttagctgc tggcaacaaa gtttagtctt ttcgactaaa gaattctgat   6060
ttaattttgt ggtttatatg ttgagttaac tgttaagaga gttttatttt gtaataggtg   6120
tatcagtcaa taaacaatct ttgtatcaac caaatgtaat tttctcgtt aattcgattt   6180
cagagttttt actttaagat aaacaaactc tttcacacat catttaatga aagtggagaa   6240
gcttaaaaaa caaacaaaga aactgatcca tttttggcgg gtcttcttct actcttattc   6300
atatgtgtta acgaactata gcgtaaaatt cagagcaagc gatctccgat ttgaacgtgg   6360
ctatcaccgg aggcccacca ctacgggcga tacgctctaa gtgaggatta aagtgctctg   6420
gtggtgacgt tgaagaaact cgcccatggt ttttgttatc tctgcagcca agtgtcgttc   6480
tttcttcgcc acttctcatc aagctacagt gaatttaaaa atggcgtctt tctttgatct   6540
cgtatacata agctggattg gtttcttaaa caaattcctc tcctttttggg tcttctgggt   6600
ttgccttgta agtgtttgtg tttttgcctc tgagaaaaaa tcgc                    6644
```

<210> SEQ ID NO 28
<211> LENGTH: 4330
<212> TYPE: DNA
<213> ORGANISM: artificial sequence
<220> FEATURE:
<223> OTHER INFORMATION: plasmid KS294

<400> SEQUENCE: 28

```
agcttggaat tcgggatctg agtctagaaa tccgtcaaca tggtggagca cgacactctc     60
gtctactcca agaatatcaa agatacagtc tcagaagacc aaagggctat tgagactttt    120
caacaaaggg taatatcggg aaacctcctc ggattccatt gcccagctat ctgtcacttc    180
atcaaaagga cagtagaaaa ggaaggtggc acctacaaat gccatcattg cgataaagga    240
aaggctatcg ttcaagatgc ctctgccgac agtggtccca aagatggacc cccacccacg    300
aggagcatcg tggaaaaaga agacgttcca accacgtctt caaagcaagt ggattgatgt    360
gatgatccta tgcgtatggt atgacgtgtg ttcaagatga tgacttcaaa cctacctatg    420
acgtatggta tgaacgtgtg tcgactgatg acttagatcc actcgagcgg ctataaatac    480
gtacctacgc accctgcgct accatcccta gagctgcagc ttattttac aacaattacc    540
aacaacaaca aacaacaaac aacattacaa ttactattta caattacagt cgacccggga    600
tcgtacctct agggtggcgg ccgcaagtat gaactaaaat gcatgtaggt gtaagagctc    660
atggagagca tggaatattg tatccgacca tgtaacagta taataactga gctccatctc    720
acttcttcta tgaataaaca aaggatgtta tgatatatta acactctatc tatgcacctt    780
attgttctat gataaatttc ctcttattat tataaatcat ctgaatcgtg acggcttatg    840
gaatgcttca aatagtacaa aaacaaatgt gtactataag actttctaaa caattctaac    900
cttagcattg tgaacgagac ataagtgtta agaagacata acaattataa tggaagaagt    960
```

-continued

```
ttgtctccat ttatatatta tatattaccc acttatgtat tatattagga tgttaaggag   1020
acataacaat tataaagaga gaagtttgta tccatttata tattatatac tacccattta   1080
tatattatac ttatccactt atttaatgtc tttataaggt ttgatccatg atatttctaa   1140
tattttagtt gatatgtata tgaaagggta ctatttgaac tctcttactc tgtataaagg   1200
ttggatcatc cttaaagtgg gtctatttaa ttttattgct tcttacagat aaaaaaaaaa   1260
ttatgagttg gtttgataaa atattgaagg atttaaaata ataataaata acatataata   1320
tatgtatata aatttattat aatataacat ttatctataa aaaagtaaat attgtcataa   1380
atctatacaa tcgtttagcc ttgctggacg aatctcaatt atttaaacga gagtaaacat   1440
atttgacttt ttggttattt aacaaattat tatttaacac tatatgaaat ttttttttt   1500
atcagcaaag aataaaatta aattaagaag gacaatggtg tcccaatcct tatacaacca   1560
acttccacaa gaaagtcaag tcagagacaa caaaaaaaca agcaaaggaa attttttaat   1620
ttgagttgtc ttgtttgctg cataatttat gcagtaaaac actacacata accctttag   1680
cagtagagca atggttgacc gtgtgcttag cttcttttat tttatttttt tatcagcaaa   1740
gaataaataa aataaaatga gacacttcag ggatgtttca acaagctcta gactggaatt   1800
cgtcgacggc gcgcccgatc atccggatat agttcctcct ttcagcaaaa aacccctcaa   1860
gacccgttta gaggccccaa ggggttatgc tagttattgc tcagcggtgg cagcagccaa   1920
ctcagcttcc tttcgggctt tgttagcagc cggatcgatc caagctgtac ctcactattc   1980
ctttgccctc ggacgagtgc tggggcgtcg gtttccacta tcggcgagta cttctacaca   2040
gccatcggtc cagacggccg cgcttctgcg ggcgatttgt gtacgcccga cagtcccggc   2100
tccggatcgg acgattgcgt cgcatcgacc ctgcgcccaa gctgcatcat cgaaattgcc   2160
gtcaaccaag ctctgataga gttggtcaag accaatgcgg agcatatacg cccggagccg   2220
cggcgatcct gcaagctccg gatgcctccg ctcgaagtag cgcgtctgct gctccataca   2280
agccaaccac ggcctccaga agaagatgtt ggcgacctcg tattgggaat ccccgaacat   2340
cgcctcgctc cagtcaatga ccgctgttat gcggccattg tccgtcagga cattgttgga   2400
gccgaaatcc gcgtgcacga ggtgccggac ttcggggcag tcctcggccc aaagcatcag   2460
ctcatcgaga gcctgcgcga cggacgcact gacggtgtcg tccatcacag tttgccagtg   2520
atacacatgg ggatcagcaa tcgcgcatat gaaatcacgc catgtagtgt attgaccgat   2580
tccttgcggt ccgaatgggc cgaacccgct cgtctggcta agatcggccg cagcgatcgc   2640
atccatagcc tccgcgaccg gctgcagaac agcgggcagt tcggtttcag gcaggtcttg   2700
caacgtgaca ccctgtgcac ggcgggagat gcaataggtc aggctctcgc tgaattcccc   2760
aatgtcaagc acttccggaa tcgggagcgc ggccgatgca aagtgccgat aaacataacg   2820
atctttgtag aaaccatcgg cgcagctatt tacccgcagg acatatccac gccctcctac   2880
atcgaagctg aaagcacgag attcttcgcc ctccgagagc tgcatcaggt cggagacgct   2940
gtcgaacttt tcgatcagaa acttctcgac agacgtcgcg gtgagttcag gcttttccat   3000
gggtatatct ccttcttaaa gttaaacaaa attatttcta gagggaaacc gttgtggtct   3060
ccctatagtg agtcgtatta atttcgcggg atcgagatct gatcaacctg cattaatgaa   3120
tcggccaacg cgcggggaga ggcggtttgc gtattgggcg ctcttccgct tcctcgctca   3180
ctgactcgct gcgctcggtc gttcggctgc ggcgagcggt atcagctcac tcaaaggcgg   3240
taatacggtt atccacagaa tcaggggata acgcaggaaa gaacatgtga gcaaaaggcc   3300
agcaaaaggc caggaaccgt aaaaaggccg cgttgctggc gtttttccat aggctccgcc   3360
```

-continued

```
cccctgacga gcatcacaaa aatcgacgct caagtcagag gtggcgaaac ccgacaggac   3420

tataaagata ccaggcgttt ccccctggaa gctccctcgt gcgctctcct gttccgaccc   3480

tgccgcttac cggatacctg tccgcctttc tcccttcggg aagcgtggcg ctttctcaat   3540

gctcacgctg taggtatctc agttcggtgt aggtcgttcg ctccaagctg ggctgtgtgc   3600

acgaaccccc cgttcagccc gaccgctgcg ccttatccgg taactatcgt cttgagtcca   3660

acccggtaag acacgactta tcgccactgg cagcagccac tggtaacagg attagcagag   3720

cgaggtatgt aggcggtgct acagagttct tgaagtggtg gcctaactac ggctacacta   3780

gaaggacagt atttggtatc tgcgctctgc tgaagccagt taccttcgga aaaagagttg   3840

gtagctcttg atccggcaaa caaaccaccg ctggtagcgg tggttttttt gtttgcaagc   3900

agcagattac gcgcagaaaa aaaggatctc aagaagatcc tttgatcttt tctacggggt   3960

ctgacgctca gtggaacgaa aactcacgtt aagggatttt ggtcatgaca ttaacctata   4020

aaaataggcg tatcacgagg ccctttcgtc tcgcgcgttt cggtgatgac ggtgaaaacc   4080

tctgacacat gcagctcccg gagacggtca cagcttgtct gtaagcggat gccgggagca   4140

gacaagcccg tcagggcgcg tcagcgggtg ttggcgggtg tcggggctgg cttaactatg   4200

cggcatcaga gcagattgta ctgagagtgc accatatgga catattgtcg ttagaacgcg   4260

gctacaatta atacataacc ttatgtatca tacacatacg atttaggtga cactatagaa   4320

cggcgcgcca                                                          4330
```

<210> SEQ ID NO 29
<211> LENGTH: 4746
<212> TYPE: DNA
<213> ORGANISM: artificial sequence
<220> FEATURE:
<223> OTHER INFORMATION: plasmid pKR627

<400> SEQUENCE: 29

```
gatcctctag acctgcaggc caactgcgtt tggggctcca gattaaacga cgccgtttcg     60

ttcctttcgc ttcacggctt aacgatgtcg tttctgtctg tgcccaaaaa ataaaggcat    120

ttgttatttg caccagatat ttactaagtg caccctagtt tgacaagtag gcgataatta    180

caaatagatg cggtgcaaat aataaatttt gaaggaaata attacaaaag aacagaactt    240

atatttactt tattttaaaa aactaaaatg aaagaacaaa aaaagtaaaa aatacaaaaa    300

atgtgcttta accactttca ttatttgtta cagaaagtat gattctactc aaattgatct    360

gttgtatctg gtgctgcctt gtcacactgg cgatttcaat cccctaaaga tatggtgcaa    420

actgcgaagt gatcaatatc tgctcggtta atttagatta attaataata ttcaacgtga    480

tgtaccaaaa aaagacaatt ttttgctcca ttgacaaatt aaacctcatc aaggtaattt    540

ccaaacctat aagcaaaaaa atttcacatt aattggcccg caatcctatt agtcttatta    600

tactagagta ggaaaaaaaa caattacaca acttgtctta ttattctcta tgctaatgaa    660

tatttttccc ttttgttaga aatcagtgtt tcctaattta ttgagtatta attccactca    720

ccgcatatat ttaccgttga ataagaaaat tttacacata attcttttta agataaataa    780

tttttttata ctagatctta tatgattacg tgaagccaag tgggttatac taatgatata    840

taatgtttga tagtaatcag tttataaacc aaatgcatgg aaatgttacg tggaagcacg    900

taaattaaca agcattgaag caaatgcagc caccgcacca aaaccacccc acttcacttc    960

cacgtaccat attccatgca actacaacac cctaaaactt caataaatgc cccccacttc   1020
```

-continued

```
acttcacttc acccatcaat agcaagcggc cgcgaagtta aaagcaatgt tgtcacttgt   1080
cgtactaaca catgatgtga tagtttatgc tagctagcta taacataagc tgtctctgag   1140
tgtgttgtat attaataaag atcatcactg gtgaatggtg atcgtgtacg taccctactt   1200
agtaggcaat ggaagcactt agagtgtgct ttgtgcatgg ccttgcctct gttttgagac   1260
ttttgtaatg ttttcgagtt taaatctttg cctttgcgta cgtctagagt cgagcatgca   1320
tctagagggc ccaattcgcc ctatagtgag tcgtattaca attcactggc cgtcgtttta   1380
caacgtcgtg actgggaaaa ccctggcgtt acccaactta atcgccttgc agcacatccc   1440
cctttcgcca gctggcgtaa tagcgaagag gcccgcaccg atcgcccttc ccaacagttg   1500
cgcagcctat acgtacggca gtttaaggtt tacacctata aaagagagag ccgttatcgt   1560
ctgtttgtgg atgtacagag tgatattatt gacacgccgg ggcgacggat ggtgatcccc   1620
ctggccagtg cacgtctgct gtcagataaa gtctcccgtg aactttaccc ggtggtgcat   1680
atcggggatg aaagctggcg catgatgacc accgatatgg ccagtgtgcc ggtctccgtt   1740
atcggggaag aagtggctga tctcagccac cgcgaaaatg acatcaaaaa cgccattaac   1800
ctgatgttct ggggaatata aatgtcaggc atgagattat caaaaaggat cttcacctag   1860
atccttttca cgtagaaagc cagtccgcag aaacggtgct gaccccggat gaatgtcagc   1920
tactgggcta tctggacaag ggaaaacgca agcgcaaaga gaaagcaggt agcttgcagt   1980
gggcttacat ggcgatagct agactgggcg gttttatgga cagcaagcga accggaattg   2040
ccagctgggg cgccctctgg taaggttggg aagccctgca aagtaaactg gatggctttc   2100
tcgccgccaa ggatctgatg gcgcagggga tcaagctctg atcaagagac aggatgagga   2160
tcgtttcgca tgattgaaca agatggattg cacgcaggtt ctccggccgc ttgggtggag   2220
aggctattcg gctatgactg ggcacaacag acaatcggct gctctgatgc cgccgtgttc   2280
cggctgtcag cgcaggggcg cccggttctt tttgtcaaga ccgacctgtc cggtgccctg   2340
aatgaactgc aagacgaggc agcgcggcta tcgtggctgg ccacgacggg cgttccttgc   2400
gcagctgtgc tcgacgttgt cactgaagcg ggaagggact ggctgctatt gggcgaagtg   2460
ccggggcagg atctcctgtc atctcacctt gctcctgccg agaaagtatc catcatggct   2520
gatgcaatgc ggcggctgca tacgcttgat ccggctacct gcccattcga ccaccaagcg   2580
aaacatcgca tcgagcgagc acgtactcgg atggaagccg gtcttgtcga tcaggatgat   2640
ctggacgaag agcatcaggg gctcgcgcca gccgaactgt tcgccaggct caaggcgagc   2700
atgcccgacg gcgaggatct cgtcgtgacc catggcgatg cctgcttgcc gaatatcatg   2760
gtggaaaatg gccgcttttc tggattcatc gactgtggcc ggctgggtgt ggcggaccgc   2820
tatcaggaca tagcgttggc tacccgtgat attgctgaag agcttggcgg cgaatgggct   2880
gaccgcttcc tcgtgcttta cggtatcgcc gctcccgatt cgcagcgcat cgccttctat   2940
cgccttcttg acgagttctt ctgaattatt aacgcttaca atttcctgat gcggtatttt   3000
ctccttacgc atctgtgcgg tatttcacac cgcatacagg tggcactttt cggggaaatg   3060
tgcgcggaac ccctatttgt ttatttttct aaatacattc aaatatgtat ccgctcatga   3120
gacaataacc ctgataaatg cttcaataat agcacgtgag gagggccacc atggccaagt   3180
tgaccagtgc cgttccggtg ctcaccgcgc gcgacgtcgc cggagcggtc gagttctgga   3240
ccgaccggct cgggttctcc cgggacttcg tggaggacga cttcgccggt gtggtccggg   3300
acgacgtgac cctgttcatc agcgcggtcc aggaccaggt ggtgccggac aacaccctgg   3360
cctgggtgtg ggtgcgcggc ctggacgagc tgtacgccga gtggtcggag gtcgtgtcca   3420
```

cgaacttccg ggacgcctcc gggccggcca tgaccgagat cggcgagcag ccgtgggggc 3480
gggagttcgc cctgcgcgac ccggccggca actgcgtgca cttcgtggcc gaggagcagg 3540
actgacacgt gctaaaactt catttttaat ttaaaaggat ctaggtgaag atcctttttg 3600
ataatctcat gaccaaaatc ccttaacgtg agttttcgtt ccactgagcg tcagaccccg 3660
tagaaaagat caaaggatct tcttgagatc cttttttct gcgcgtaatc tgctgcttgc 3720
aaacaaaaaa accaccgcta ccagcggtgg tttgtttgcc ggatcaagag ctaccaactc 3780
tttttccgaa ggtaactggc ttcagcagag cgcagatacc aaatactgtc cttctagtgt 3840
agccgtagtt aggccaccac ttcaagaact ctgtagcacc gcctacatac ctcgctctgc 3900
taatcctgtt accagtggct gctgccagtg gcgataagtc gtgtcttacc gggttggact 3960
caagacgata gttaccggat aaggcgcagc ggtcgggctg aacggggggt tcgtgcacac 4020
agcccagctt ggagcgaacg acctacaccg aactgagata cctacagcgt gagctatgag 4080
aaagcgccac gcttcccgaa gggagaaagg cggacaggta tccggtaagc ggcagggtcg 4140
gaacaggaga gcgcacgagg gagcttccag ggggaaacgc ctggtatctt tatagtcctg 4200
tcgggtttcg ccacctctga cttgagcgtc gatttttgtg atgctcgtca ggggggcgga 4260
gcctatggaa aaacgccagc aacgcggcct ttttacggtt cctggccttt tgctggcctt 4320
ttgctcacat gttctttcct gcgttatccc ctgattctgt ggataaccgt attaccgcct 4380
ttgagtgagc tgataccgct cgccgcagcc gaacgaccga gcgcagcgag tcagtgagcg 4440
aggaagcgga agagcgccca atacgcaaac cgcctctccc cgcgcgttgg ccgattcatt 4500
aatgcagctg gcacgacagg tttcccgact ggaaagcggg cagtgagcgc aacgcaatta 4560
atgtgagtta gctcactcat taggcacccc aggctttaca ctttatgctt ccggctcgta 4620
tgttgtgtgg aattgtgagc ggataacaat ttcacacagg aaacagctat gaccatgatt 4680
acgccaagct atttaggtga cgcgttagaa tactcaagct atgcatcaag cttggtaccg 4740
agctcg 4746

<210> SEQ ID NO 30
<211> LENGTH: 3983
<212> TYPE: DNA
<213> ORGANISM: artificial sequence
<220> FEATURE:
<223> OTHER INFORMATION: plasmid pKR132

<400> SEQUENCE: 30
ctagagtcga cctgcaggca tgcaagcttg gcgtaatcat ggtcatagct gtttcctgtg 60
tgaaattgtt atccgctcac aattccacac aacatacgag ccggaagcat aaagtgtaaa 120
gcctggggtg cctaatgagt gagctaactc acattaattg cgttgcgctc actgcccgct 180
ttccagtcgg gaaacctgtc gtgccagctg cattaatgaa tcggccaacg cgcggggaga 240
ggcggtttgc gtattgggcg ctcttccgct tcctcgctca ctgactcgct gcgctcggtc 300
gttcggctgc ggcgagcggt atcagctcac tcaaaggcgg taatacggtt atccacagaa 360
tcaggggata acgcaggaaa gaacatgtga gcaaaaggcc agcaaaaggc caggaaccgt 420
aaaaaggccg cgttgctggc gtttttccat aggctccgcc cccctgacga gcatcacaaa 480
aatcgacgct caagtcagag gtggcgaaac ccgacaggac tataaagata ccaggcgttt 540
ccccctggaa gctccctcgt gcgctctcct gttccgaccc tgccgcttac cggatacctg 600
tccgcctttc tcccttcggg aagcgtggcg ctttctcata gctcacgctg taggtatctc 660

-continued

```
agttcggtgt aggtcgttcg ctccaagctg ggctgtgtgc acgaaccccc cgttcagccc    720
gaccgctgcg ccttatccgg taactatcgt cttgagtcca acccggtaag acacgactta    780
tcgccactgg cagcagccac tggtaacagg attagcagag cgaggtatgt aggcggtgct    840
acagagttct tgaagtggtg gcctaactac ggctacacta gaaggacagt atttggtatc    900
tgcgctctgc tgaagccagt taccttcgga aaaagagttg gtagctcttg atccggcaaa    960
caaaccaccg ctggtagcgg tggttttttt gtttgcaagc agcagattac gcgcagaaaa   1020
aaaggatctc aagaagatcc tttgatcttt tctacggggt ctgacgctca gtggaacgaa   1080
aactcacgtt aagggatttt ggtcatgaga ttatcaaaaa ggatcttcac ctagatcctt   1140
ttaaattaaa aatgaagttt taaatcaatc taaagtatat atgagtaaac ttggtctgac   1200
agttaccaat gcttaatcag tgaggcacct atctcagcga tctgtctatt tcgttcatcc   1260
atagttgcct gactccccgt cgtgtagata actacgatac gggagggctt accatctggc   1320
cccagtgctg caatgatacc gcgagaccca cgctcaccgg ctccagattt atcagcaata   1380
aaccagccag ccggaagggc cgagcgcaga agtggtcctg caactttatc cgcctccatc   1440
cagtctatta attgttgccg ggaagctaga gtaagtagtt cgccagttaa tagtttgcgc   1500
aacgttgttg ccattgctac aggcatcgtg gtgtcacgct cgtcgtttgg tatggcttca   1560
ttcagctccg gttcccaacg atcaaggcga gttacatgat cccccatgtt gtgcaaaaaa   1620
gcggttagct ccttcggtcc tccgatcgtt gtcagaagta agttggccgc agtgttatca   1680
ctcatggtta tggcagcact gcataattct cttactgtca tgccatccgt aagatgcttt   1740
tctgtgactg gtgagtactc aaccaagtca ttctgagaat agtgtatgcg gcgaccgagt   1800
tgctcttgcc cggcgtcaat acgggataat accgcgccac atagcagaac tttaaaagtg   1860
ctcatcattg gaaaacgttc ttcggggcga aaactctcaa ggatcttacc gctgttgaga   1920
tccagttcga tgtaacccac tcgtgcaccc aactgatctt cagcatcttt tactttcacc   1980
agcgtttctg ggtgagcaaa aacaggaagg caaaatgccg caaaaaaggg aataagggcg   2040
acacggaaat gttgaatact catactcttc ctttttcaat attattgaag catttatcag   2100
ggttattgtc tcatgagcgg atacatattt gaatgtattt agaaaaataa acaaataggg   2160
gttccgcgca catttccccg aaaagtgcca cctgacgtct aagaaaccat tattatcatg   2220
acattaacct ataaaaatag gcgtatcacg aggccctttc gtctcgcgcg tttcggtgat   2280
gacggtgaaa acctctgaca catgcagctc ccggagacgg tcacagcttg tctgtaagcg   2340
gatgccggga gcagacaagc ccgtcagggc gcgtcagcgg gtgttggcgg gtgtcggggc   2400
tggcttaact atgcggcatc agagcagatt gtactgagag tgcaccatat gcggtgtgaa   2460
ataccgcaca gatgcgtaag gagaaaatac cgcatcaggc gccattcgcc attcaggctg   2520
cgcaactgtt gggaagggcg atcggtgcgg gcctcttcgc tattacgcca gctggcgaaa   2580
gggggatgtg ctgcaaggcg attaagttgg gtaacgccag ggttttccca gtcacgacgt   2640
tgtaaaacga cggccagtga attcgagctc ggtacccggg gatcctctag acctgcaggc   2700
caactgcgtt tggggctcca gattaaacga cgccgtttcg ttcctttcgc ttcacggctt   2760
aacgatgtcg tttctgtctg tgcccaaaaa ataaaggcat ttgttatttg caccagatat   2820
ttactaagtg caccctagtt tgacaagtag gcgataatta caaatagatg cggtgcaaat   2880
aataaatttt gaaggaaata attacaaaag aacagaactt atatttactt tattttaaaa   2940
aactaaaatg aaagaacaaa aaaagtaaaa aatacaaaaa atgtgcttta accactttca   3000
ttatttgtta cagaaagtat gattctactc aaattgatct gttgtatctg gtgctgcctt   3060
```

gtcacactgg cgatttcaat cccctaaaga tatggtgcaa actgcgaagt gatcaatatc 3120
tgctcggtta atttagatta attaataata ttcaacgtga tgtaccaaaa aaagacaatt 3180
ttttgctcca ttgacaaatt aaacctcatc aaggtaattt ccaaacctat aagcaaaaaa 3240
atttcacatt aattggcccg caatcctatt agtcttatta tactagagta ggaaaaaaaa 3300
caattacaca acttgtctta ttattctcta tgctaatgaa tatttttccc ttttgttaga 3360
aatcagtgtt tcctaattta ttgagtatta attccactca ccgcatatat ttaccgttga 3420
ataagaaaat tttacacata attcttttta agataaataa ttttttttata ctagatctta 3480 tatgattacg tgaagccaag tgggttatac taatgatata taatgtttga tagtaatcag 3540
tttataaacc aaatgcatgg aaatgttacg tggaagcacg taaattaaca agcattgaag 3600
caaatgcagc caccgcacca aaaccacccc acttcacttc cacgtaccat attccatgca 3660
actacaacac cctaaaactt caataaatgc ccccaccttc acttcacttc acccatcaat 3720
agcaagcggc cgcgaagtta aaagcaatgt tgtcacttgt cgtactaaca catgatgtga 3780
tagtttatgc tagctagcta taacataagc tgtctctgag tgtgttgtat attaataaag 3840
atcatcactg gtgaatggtg atcgtgtacg taccctactt agtaggcaat ggaagcactt 3900
agagtgtgct ttgtgcatgg ccttgcctct gttttgagac ttttgtaatg ttttcgagtt 3960
taaatctttg cctttgcgta cgt 3983

<210> SEQ ID NO 31
<211> LENGTH: 5303
<212> TYPE: DNA
<213> ORGANISM: artificial sequence
<220> FEATURE:
<223> OTHER INFORMATION: plasmid pKR278

<400> SEQUENCE: 31
agcttggatc tcctgcagga tctggccggc cggatctcgt acggatccgt cgacggcgcg 60
cccgatcatc cggatatagt tcctcctttc agcaaaaaac ccctcaagac ccgtttagag 120
gccccaaggg gttatgctag ttattgctca gcggtggcag cagccaactc agcttccttt 180
cgggctttgt tagcagccgg atcgatccaa gctgtacctc actattcctt tgccctcgga 240
cgagtgctgg ggcgtcggtt tccactatcg gcgagtactt ctacacagcc atcggtccag 300
acggccgcgc ttctgcgggc gatttgtgta cgcccgacag tcccggctcc ggatcggacg 360
attgcgtcgc atcgaccctg cgcccaagct gcatcatcga aattgccgtc aaccaagctc 420
tgatagagtt ggtcaagacc aatgcggagc atatacgccc ggagccgcgg cgatcctgca 480
agctccggat gcctccgctc gaagtagcgc gtctgctgct ccatacaagc caaccacggc 540
ctccagaaga agatgttggc gacctcgtat tgggaatccc cgaacatcgc ctcgctccag 600
tcaatgaccg ctgttatgcg gccattgtcc gtcaggacat tgttggagcc gaaatccgcg 660
tgcacgaggt gccggacttc ggggcagtcc tcggcccaaa gcatcagctc atcgagagcc 720
tgcgcgacgg acgcactgac ggtgtcgtcc atcacagttt gccagtgata cacatgggga 780
tcagcaatcg cgcatatgaa atcacgccat gtagtgtatt gaccgattcc ttgcggtccg 840
aatgggccga acccgctcgt ctggctaaga tcggccgcag cgatcgcatc catagcctcc 900
gcgaccggct gcagaacagc gggcagttcg gtttcaggca ggtcttgcaa cgtgacaccc 960
tgtgcacggc gggagatgca ataggtcagg ctctcgctga attccccaat gtcaagcact 1020
tccggaatcg ggagcgcggc cgatgcaaag tgccgataaa cataacgatc tttgtagaaa 1080

-continued

```
ccatcggcgc agctatttac ccgcaggaca tatccacgcc ctcctacatc gaagctgaaa   1140
gcacgagatt cttcgccctc cgagagctgc atcaggtcgg agacgctgtc gaacttttcg   1200
atcagaaact tctcgacaga cgtcgcggtg agttcaggct tttccatggg tatatctcct   1260
tcttaaagtt aaacaaaatt atttctagag ggaaaccgtt gtggtctccc tatagtgagt   1320
cgtattaatt tcgcgggatc gagatcgatc caattccaat cccacaaaaa tctgagctta   1380
acagcacagt tgctcctctc agagcagaat cgggtattca acaccctcat atcaactact   1440
acgttgtgta taacggtcca catgccggta tatacgatga ctggggttgt acaaaggcgg   1500
caacaaacgg cgttcccgga gttgcacaca agaaatttgc cactattaca gaggcaagag   1560
cagcagctga cgcgtacaca acaagtcagc aaacagacag gttgaacttc atccccaaag   1620
gagaagctca actcaagccc aagagctttg ctaaggccct aacaagccca ccaaagcaaa   1680
aagcccactg gctcacgcta ggaaccaaaa ggcccagcag tgatccagcc ccaaaagaga   1740
tctcctttgc cccggagatt acaatggacg atttcctcta tctttacgat ctaggaagga   1800
agttcgaagg tgaaggtgac gacactatgt tcaccactga taatgagaag gttagcctct   1860
tcaatttcag aaagaatgct gacccacaga tggttagaga ggcctacgca gcaggtctca   1920
tcaagacgat ctacccgagt aacaatctcc aggagatcaa ataccttccc aagaaggtta   1980
aagatgcagt caaaagattc aggactaatt gcatcaagaa cacagagaaa gacatatttc   2040
tcaagatcag aagtactatt ccagtatgga cgattcaagg cttgcttcat aaaccaaggc   2100
aagtaataga gattggagtc tctaaaaagg tagttcctac tgaatctaag gccatgcatg   2160
gagtctaaga ttcaaatcga ggatctaaca gaactcgccg tgaagactgg cgaacagttc   2220
atacagagtc ttttacgact caatgacaag aagaaaatct tcgtcaacat ggtggagcac   2280
gacactctgg tctactccaa aaatgtcaaa gatacagtct cagaagacca aagggctatt   2340
gagacttttc aacaaaggat aatttcggga aacctcctcg gattccattg cccagctatc   2400
tgtcacttca tcgaaaggac agtagaaaag gaaggtggct cctacaaatg ccatcattgc   2460
gataaaggaa aggctatcat tcaagatgcc tctgccgaca gtggtcccaa agatggaccc   2520
ccacccacga ggagcatcgt ggaaaaagaa gacgttccaa ccacgtcttc aaagcaagtg   2580
gattgatgtg acatctccac tgacgtaagg gatgacgcac aatcccacta tccttcgcaa   2640
gacccttcct ctatataagg aagttcattt catttggaga ggacacgctc gagctcattt   2700
ctctattact tcagccataa caaaagaact cttttctctt cttattaaac catgaaaaag   2760
cctgaactca ccgcgacgtc tgtcgagaag tttctgatcg aaaagttcga cagcgtctcc   2820
gacctgatgc agctctcgga gggcgaagaa tctcgtgctt tcagcttcga tgtaggaggg   2880
cgtggatatg tcctgcgggt aaatagctgc gccgatggtt tctacaaaga tcgttatgtt   2940
tatcggcact ttgcatcggc cgcgctcccg attccggaag tgcttgacat tggggaattc   3000
agcgagagcc tgacctattg catctcccgc cgtgcacagg gtgtcacgtt gcaagacctg   3060
cctgaaaccg aactgcccgc tgttctgcag ccggtcgcgg aggccatgga tgcgatcgct   3120
gcggccgatc ttagccagac gagcgggttc ggcccattcg gaccgcaagg aatcggtcaa   3180
tacactacat ggcgtgattt catatgcgcg attgctgatc cccatgtgta tcactggcaa   3240
actgtgatgg acgacaccgt cagtgcgtcc gtcgcgcagg ctctcgatga gctgatgctt   3300
tgggccgagg actgccccga agtccggcac ctcgtgcacg cggatttcgg ctccaacaat   3360
gtcctgacgg acaatggccg cataacagcg gtcattgact ggagcgaggc gatgttcggg   3420
gattcccaat acgaggtcgc caacatcttc ttctggaggc cgtggttggc ttgtatggag   3480
```

```
cagcagacgc gctacttcga gcggaggcat ccggagcttg caggatcgcc gcggctccgg   3540

gcgtatatgc tccgcattgg tcttgaccaa ctctatcaga gcttggttga cggcaatttc   3600

gatgatgcag cttgggcgca gggtcgatgc gacgcaatcg tccgatccgg agccgggact   3660

gtcgggcgta cacaaatcgc ccgcagaagc gcggccgtct ggaccgatgg ctgtgtagaa   3720

gtactcgccg atagtggaaa ccgacgcccc agcactcgtc cgagggcaaa ggaatagtga   3780

ggtacctaaa gaaggagtgc gtcgaagcag atcgttcaaa catttggcaa taaagtttct   3840

taagattgaa tcctgttgcc ggtcttgcga tgattatcat ataatttctg ttgaattacg   3900

ttaagcatgt aataattaac atgtaatgca tgacgttatt tatgagatgg gtttttatga   3960

ttagagtccc gcaattatac atttaatacg cgatagaaaa caaaatatag cgcgcaaact   4020

aggataaatt atcgcgcgcg gtgtcatcta tgttactaga tcgatgtcga atcgatcaac   4080

ctgcattaat gaatcggcca acgcgcgggg agaggcggtt tgcgtattgg gcgctcttcc   4140

gcttcctcgc tcactgactc gctgcgctcg gtcgttcggc tgcggcgagc ggtatcagct   4200

cactcaaagg cggtaatacg gttatccaca gaatcagggg ataacgcagg aaagaacatg   4260

tgagcaaaag gccagcaaaa ggccaggaac cgtaaaaagg ccgcgttgct ggcgtttttc   4320

cataggctcc gcccccctga cgagcatcac aaaaatcgac gctcaagtca gaggtggcga   4380

aacccgacag gactataaag ataccaggcg tttccccctg gaagctccct cgtgcgctct   4440

cctgttccga ccctgccgct taccggatac ctgtccgcct ttctcccttc gggaagcgtg   4500

gcgctttctc aatgctcacg ctgtaggtat ctcagttcgg tgtaggtcgt tcgctccaag   4560

ctgggctgtg tgcacgaacc ccccgttcag cccgaccgct gcgccttatc cggtaactat   4620

cgtcttgagt ccaacccggt aagacacgac ttatcgccac tggcagcagc cactggtaac   4680

aggattagca gagcgaggta tgtaggcggt gctacagagt tcttgaagtg gtggcctaac   4740

tacggctaca ctagaaggac agtatttggt atctgcgctc tgctgaagcc agttaccttc   4800

ggaaaaagag ttggtagctc ttgatccggc aaacaaacca ccgctggtag cggtggtttt   4860

tttgtttgca agcagcagat tacgcgcaga aaaaaaggat ctcaagaaga tcctttgatc   4920

ttttctacgg ggtctgacgc tcagtggaac gaaaactcac gttaagggat tttggtcatg   4980

acattaacct ataaaaatag gcgtatcacg aggccctttc gtctcgcgcg tttcggtgat   5040

gacggtgaaa acctctgaca catgcagctc ccggagacgg tcacagcttg tctgtaagcg   5100

gatgccggga gcagacaagc ccgtcagggc gcgtcagcgg gtgttggcgg gtgtcggggc   5160

tggcttaact atgcggcatc agagcagatt gtactgagag tgcaccatat ggacatattg   5220

tcgttagaac gcggctacaa ttaatacata accttatgta tcatacacat acgatttagg   5280

tgacactata gaacggcgcg cca                                           5303
```

<210> SEQ ID NO 32
<211> LENGTH: 8725
<212> TYPE: DNA
<213> ORGANISM: artificial sequence
<220> FEATURE:
<223> OTHER INFORMATION: plasmid pKR1157

<400> SEQUENCE: 32

```
gtacggatcc gtcgacggcg cgcccgatca tccggatata gttcctcctt tcagcaaaaa     60

acccctcaag acccgtttag aggccccaag gggttatgct agttattgct cagcggtggc    120

agcagccaac tcagcttcct ttcgggcttt gttagcagcc ggatcgatcc aagctgtacc    180
```

-continued

```
tcactattcc tttgccctcg gacgagtgct ggggcgtcgg tttccactat cggcgagtac    240
ttctacacag ccatcggtcc agacggccgc gcttctgcgg gcgatttgtg tacgcccgac    300
agtcccggct ccggatcgga cgattgcgtc gcatcgaccc tgcgcccaag ctgcatcatc    360
gaaattgccg tcaaccaagc tctgatagag ttggtcaaga ccaatgcgga gcatatacgc    420
ccggagccgc ggcgatcctg caagctccgg atgcctccgc tcgaagtagc gcgtctgctg    480
ctccatacaa gccaaccacg gcctccagaa gaagatgttg gcgacctcgt attgggaatc    540
cccgaacatc gcctcgctcc agtcaatgac cgctgttatg cggccattgt ccgtcaggac    600
attgttggag ccgaaatccg cgtgcacgag gtgccggact tcggggcagt cctcggccca    660
aagcatcagc tcatcgagag cctgcgcgac ggacgcactg acggtgtcgt ccatcacagt    720
ttgccagtga tacacatggg gatcagcaat cgcgcatatg aaatcacgcc atgtagtgta    780
ttgaccgatt ccttgcggtc cgaatgggcc gaacccgctc gtctggctaa gatcggccgc    840
agcgatcgca tccatagcct ccgcgaccgg ctgcagaaca gcgggcagtt cggtttcagg    900
caggtcttgc aacgtgacac cctgtgcacg gcgggagatg caataggtca ggctctcgct    960
gaattcccca atgtcaagca cttccggaat cgggagcgcg gccgatgcaa agtgccgata   1020
aacataacga tctttgtaga aaccatcggc gcagctattt acccgcagga catatccacg   1080
ccctcctaca tcgaagctga aagcacgaga ttcttcgccc tccgagagct gcatcaggtc   1140
ggagacgctg tcgaactttt cgatcagaaa cttctcgaca gacgtcgcgg tgagttcagg   1200
cttttccatg ggtatatctc cttcttaaag ttaaacaaaa ttatttctag agggaaaccg   1260
ttgtggtctc cctatagtga gtcgtattaa tttcgcggga tcgagatcga tccaattcca   1320
atcccacaaa aatctgagct taacagcaca gttgctcctc tcagagcaga atcgggtatt   1380
caacaccctc atatcaacta ctacgttgtg tataacggtc cacatgccgg tatatacgat   1440
gactggggtt gtacaaaggc ggcaacaaac ggcgttcccg gagttgcaca caagaaattt   1500
gccactatta cagaggcaag agcagcagct gacgcgtaca caacaagtca gcaaacagac   1560
aggttgaact tcatccccaa aggagaagct caactcaagc ccaagagctt tgctaaggcc   1620
ctaacaagcc caccaaagca aaaagcccac tggctcacgc taggaaccaa aaggcccagc   1680
agtgatccag ccccaaaaga gatctccttt gccccggaga ttacaatgga cgatttcctc   1740
tatctttacg atctaggaag gaagttcgaa ggtgaaggtg acgacactat gttcaccact   1800
gataatgaga aggttagcct cttcaatttc agaaagaatg ctgacccaca gatggttaga   1860
gaggcctacg cagcaggtct catcaagacg atctacccga gtaacaatct ccaggagatc   1920
aaataccttc ccaagaaggt taaagatgca gtcaaaagat tcaggactaa ttgcatcaag   1980
aacacagaga aagacatatt tctcaagatc agaagtacta ttccagtatg gacgattcaa   2040
ggcttgcttc ataaaccaag gcaagtaata gagattggag tctctaaaaa ggtagttcct   2100
actgaatcta aggccatgca tggagtctaa gattcaaatc gaggatctaa cagaactcgc   2160
cgtgaagact ggcgaacagt tcatacagag tcttttacga ctcaatgaca agaagaaaat   2220
cttcgtcaac atggtggagc acgacactct ggtctactcc aaaaatgtca aagatacagt   2280
ctcagaagac caaagggcta ttgagacttt tcaacaaagg ataatttcgg gaaacctcct   2340
cggattccat tgcccagcta tctgtcactt catcgaaagg acagtagaaa aggaaggtgg   2400
ctcctacaaa tgccatcatt gcgataaagg aaaggctatc attcaagatg cctctgccga   2460
cagtggtccc aaagatggac ccccacccac gaggagcatc gtggaaaaag aagacgttcc   2520
aaccacgtct tcaaagcaag tggattgatg tgacatctcc actgacgtaa gggatgacgc   2580
```

```
acaatcccac tatccttcgc aagacccttc ctctatataa ggaagttcat ttcatttgga   2640
gaggacacgc tcgagctcat ttctctatta cttcagccat aacaaaagaa ctcttttctc   2700
ttcttattaa accatgaaaa agcctgaact caccgcgacg tctgtcgaga agtttctgat   2760
cgaaaagttc gacagcgtct ccgacctgat gcagctctcg gagggcgaag aatctcgtgc   2820
tttcagcttc gatgtaggag ggcgtggata tgtcctgcgg gtaaatagct gcgccgatgg   2880
tttctacaaa gatcgttatg tttatcggca ctttgcatcg gccgcgctcc cgattccgga   2940
agtgcttgac attggggaat tcagcgagag cctgacctat tgcatctccc gccgtgcaca   3000
gggtgtcacg ttgcaagacc tgcctgaaac cgaactgccc gctgttctgc agccggtcgc   3060
ggaggccatg gatgcgatcg ctgcggccga tcttagccag acgagcgggt tcggcccatt   3120
cggaccgcaa ggaatcggtc aatacactac atggcgtgat ttcatatgcg cgattgctga   3180
tccccatgtg tatcactggc aaactgtgat ggacgacacc gtcagtgcgt ccgtcgcgca   3240
ggctctcgat gagctgatgc tttgggccga ggactgcccc gaagtccggc acctcgtgca   3300
cgcggatttc ggctccaaca atgtcctgac ggacaatggc cgcataacag cggtcattga   3360
ctggagcgag gcgatgttcg gggattccca atacgaggtc gccaacatct tcttctggag   3420
gccgtggttg gcttgtatgg agcagcagac gcgctacttc gagcggaggc atccggagct   3480
tgcaggatcg ccgcggctcc gggcgtatat gctccgcatt ggtcttgacc aactctatca   3540
gagcttggtt gacggcaatt tcgatgatgc agcttgggcg cagggtcgat gcgacgcaat   3600
cgtccgatcc ggagccggga ctgtcgggcg tacacaaatc gcccgcagaa gcgcggccgt   3660
ctggaccgat ggctgtgtag aagtactcgc cgatagtgga aaccgacgcc ccagcactcg   3720
tccgagggca aaggaatagt gaggtaccta aagaaggagt gcgtcgaagc agatcgttca   3780
aacatttggc aataaagttt cttaagattg aatcctgttg ccggtcttgc gatgattatc   3840
atataatttc tgttgaatta cgttaagcat gtaataatta acatgtaatg catgacgtta   3900
tttatgagat gggtttttat gattagagtc ccgcaattat acatttaata cgcgatagaa   3960
aacaaaatat agcgcgcaaa ctaggataaa ttatcgcgcg cggtgtcatc tatgttacta   4020
gatcgatgtc gaatcgatca acctgcatta atgaatcggc caacgcgcgg ggagaggcgg   4080
tttgcgtatt gggcgctctt ccgcttcctc gctcactgac tcgctgcgct cggtcgttcg   4140
gctgcggcga gcggtatcag ctcactcaaa ggcggtaata cggttatcca cagaatcagg   4200
ggataacgca ggaaagaaca tgtgagcaaa aggccagcaa aaggccagga accgtaaaaa   4260
ggccgcgttg ctggcgtttt tccataggct ccgcccccct gacgagcatc acaaaaatcg   4320
acgctcaagt cagaggtggc gaaacccgac aggactataa agataccagg cgtttccccc   4380
tggaagctcc ctcgtgcgct ctcctgttcc gaccctgccg cttaccggat acctgtccgc   4440
ctttctccct tcgggaagcg tggcgctttc tcaatgctca cgctgtaggt atctcagttc   4500
ggtgtaggtc gttcgctcca agctgggctg tgtgcacgaa ccccccgttc agcccgaccg   4560
ctgcgcctta tccggtaact atcgtcttga gtccaacccg gtaagacacg acttatcgcc   4620
actggcagca gccactggta acaggattag cagagcgagg tatgtaggcg gtgctacaga   4680
gttcttgaag tggtggccta actacggcta cactagaagg acagtatttg gtatctgcgc   4740
tctgctgaag ccagttacct tcggaaaaag agttggtagc tcttgatccg gcaaacaaac   4800
caccgctggt agcggtggtt tttttgtttg caagcagcag attacgcgca gaaaaaaagg   4860
atctcaagaa gatcctttga tcttttctac ggggtctgac gctcagtgga acgaaaactc   4920
```

-continued

```
acgttaaggg attttggtca tgacattaac ctataaaaat aggcgtatca cgaggccctt   4980
tcgtctcgcg cgtttcggtg atgacggtga aaacctctga cacatgcagc tcccggagac   5040
ggtcacagct tgtctgtaag cggatgccgg gagcagacaa gcccgtcagg gcgcgtcagc   5100
gggtgttggc gggtgtcggg gctggcttaa ctatgcggca tcagagcaga ttgtactgag   5160
agtgcaccat atggacatat tgtcgttaga acgcggctac aattaataca taaccttatg   5220
tatcatacac atacgattta ggtgacacta tagaacggcg cgccaagctt ggatctcctg   5280
caggatctgg ccggccggat ctcgtaccga gctcggatcc actagtaacg gccgccagtg   5340
tgctggaatt caggtcctgc aggtctactc tttacatgtt ctttactccg tctcaaaatt   5400
tcctttttt gttggctctc tccgaacgag ttggagaaat cgttaaccct aatcgaagat   5460
ctagattcct ctacatacgt ttgatctctc tctcagtatg gattacaaag cgccaaggag   5520
atactactca cacggagttg ttgcgagaca gcaagatttc gcaacagata tagttacgag   5580
aagaagacct tatgtccctt acgaccgtcc aaataagttt tcaaggagtc tggtttggac   5640
gtcaaaagag tacaaatcac ccgagggcaa taatatgcca aggaccaatg atgtgtcacc   5700
gaaaccacca gttttaggtt tggcgaggaa gaatgctgct tgtgggccaa tgagatcttc   5760
tagtctcaga aaatgggtat gtaagtattg gaaagatgga aagtgcaaga ggggtgagca   5820
gtgccagttc ttacactctt ggtcttgttt ccctggattg gccatggtag cttctcttga   5880
agggcacaat aaggaactaa aggggatcgc tctccctgag ggttcagata aactcttttc   5940
agtcagtatt gatggtacat tgcgagtttg ggactgcaat tctggtcagt gtgtacattc   6000
catcaacctt gacgcagaag cagggtctct aatcagtgaa ggcccttggg ttttccttgg   6060
cttgccaaac gctataaagg cttttaacgt tcaaaccagt caagatttgc atcttcaagc   6120
agcaggggtg gttggtcagg tgaatgcaat gactattgca aacggaatgc tttttgctgg   6180
aacaagttct ggtagtatct tagtctggaa agctactaca gactctgagt ctgatccatt   6240
caaatacttg acatctcttg agggacatag tggtgaagtc acttgttttg ctgttggagg   6300
tcaaatgcta tactctggtt ctgtcgataa aacaatcaag atgtgggatc tcaacaccct   6360
gcaatgtata atgaccctga agcaacatac cggcactgtc acttcactct tatgttggga   6420
taaatgtttg atatcgtctt ccttggatgg gaccataaaa gtttgggctt attctgaaaa   6480
cggaatcttg aaagttgttc aaactcgcag acaagaacag agtagtgttc atgctctttc   6540
tggtatgcat gatgcagaag ccaaaccgat aatattctgc tcttaccaaa acggaaccgt   6600
tggcattttc gacctaccat cttttcaaga aagaggaagg atgttctcta cgcacacgat   6660
cgccacactc acaattggtc ctcaaggatt gttattcagt ggagacgaga gtggtaactt   6720
gcgtgtatgg accttagctg ctggcaacaa agtttagtct tttcgactaa agaattctga   6780
tttaattttg tggtttatat gttgagttaa ctgttaagag agttttattt tgtaataggt   6840
gtatcagtca ataaacaatc tttgtatcaa ccaaatgtaa tttttctcgt taattcgatt   6900
tcagagtttt tactttaaga taaacaaact ctttcacaca tcatttaatg aaagtggaga   6960
agcttaaaaa acaaacaaag aaactgatcc atttttggcg ggtcttcttc tactcttatt   7020
catatgtgtt aacgaactat agcgtaaaat tcagagcaag cgatctccga tttgaacgtg   7080
gctatcaccg gaggcccacc actacgggcg atacgctcta agtgaggatt aaagtgctct   7140
ggtggtgacg ttgaagaaac tcgcccatgg tttttgttat ctctgcagcc aagtgtcgtt   7200
ctttcttcgc cacttctcat caagctacag tgaatttaaa aatggcgtct ttctttgatc   7260
tcgtatacat aagctggatt ggtttcttaa acaaattcct ctccttttgg gtcttctggg   7320
```

```
tttgccttgt aagtgtttgt gtttttgcct ctgagaaaaa atcgcggccg caagtatgaa   7380
ctaaaatgca tgtaggtgta agagctcatg gagagcatgg aatattgtat ccgaccatgt   7440
aacagtataa taactgagct ccatctcact tcttctatga ataaacaaag gatgttatga   7500
tatattaaca ctctatctat gcaccttatt gttctatgat aaatttcctc ttattattat   7560
aaatcatctg aatcgtgacg gcttatggaa tgcttcaaat agtacaaaaa caaatgtgta   7620
ctataagact ttctaaacaa ttctaacctt agcattgtga acgagacata agtgttaaga   7680
agacataaca attataatgg aagaagtttg tctccattta tatattatat attacccact   7740
tatgtattat attaggatgt taaggagaca taacaattat aaagagagaa gtttgtatcc   7800
atttatatat tatatactac ccatttatat attatactta tccacttatt taatgtcttt   7860
ataaggtttg atccatgata tttctaatat tttagttgat atgtatatga aagggtacta   7920
tttgaactct cttactctgt ataaaggttg gatcatcctt aaagtgggtc tatttaattt   7980
tattgcttct tacagataaa aaaaaaatta tgagttggtt tgataaaata ttgaaggatt   8040
taaaataata ataaataaca tataatatat gtatataaat ttattataat ataacattta   8100
tctataaaaa agtaaatatt gtcataaatc tatacaatcg tttagccttg ctggacgaat   8160
ctcaattatt taaacgagag taaacatatt tgacttttg gttatttaac aaattattat   8220
ttaacactat atgaaatttt ttttttatc agcaaagaat aaaattaaat taagaaggac   8280
aatggtgtcc caatccttat acaaccaact tccacaagaa agtcaagtca gagacaacaa   8340
aaaaacaagc aaaggaaatt ttttaatttg agttgtcttg tttgctgcat aatttatgca   8400
gtaaaacact acacataacc cttttagcag tagagcaatg gttgaccgtg tgcttagctt   8460
cttttatttt atttttttat cagcaaagaa taaataaaat aaaatgagac acttcaggga   8520
tgtttcaaca agctctagag ggcccaattc gccctatagt gagtcgtatt acaattcact   8580
ggccgtcgtt ttacaacgtc gtgactggga aaaccctggc gttacccaac ttaatcgcct   8640
tgcagcacat ccccctttcg ccagctggcg taatagcgaa gaggcccgca ccgatcgccc   8700
ttcccaacag ttgcgcagcc tatac                                        8725
```

<210> SEQ ID NO 33
<211> LENGTH: 10629
<212> TYPE: DNA
<213> ORGANISM: artificial sequence
<220> FEATURE:
<223> OTHER INFORMATION: pKR1479

<400> SEQUENCE: 33

```
gtacggatcc gtcgacggcg cgcccgatca tccggatata gttcctcctt tcagcaaaaa     60
acccctcaag acccgtttag aggccccaag gggttatgct agttattgct cagcggtggc    120
agcagccaac tcagcttcct ttcgggcttt gttagcagcc ggatcgatcc aagctgtacc    180
tcactattcc tttgccctcg gacgagtgct ggggcgtcgg tttccactat cggcgagtac    240
ttctacacag ccatcggtcc agacggccgc gcttctgcgg gcgatttgtg tacgcccgac    300
agtcccggct ccggatcgga cgattgcgtc gcatcgaccc tgcgcccaag ctgcatcatc    360
gaaattgccg tcaaccaagc tctgatagag ttggtcaaga ccaatgcgga gcatatacgc    420
ccggagccgc ggcgatcctg caagctccgg atgcctccgc tcgaagtagc gcgtctgctg    480
ctccatacaa gccaaccacg gcctccagaa gaagatgttg gcgacctcgt attgggaatc    540
cccgaacatc gcctcgctcc agtcaatgac cgctgttatg cggccattgt ccgtcaggac    600
```

-continued attgttggag ccgaaatccg cgtgcacgag gtgccggact tcggggcagt cctcggccca 660
aagcatcagc tcatcgagag cctgcgcgac ggacgcactg acggtgtcgt ccatcacagt 720
ttgccagtga tacacatggg gatcagcaat cgcgcatatg aaatcacgcc atgtagtgta 780
ttgaccgatt ccttgcggtc cgaatgggcc gaacccgctc gtctggctaa gatcggccgc 840
agcgatcgca tccatagcct ccgcgaccgg ctgcagaaca gcgggcagtt cggtttcagg 900
caggtcttgc aacgtgacac cctgtgcacg gcgggagatg caataggtca ggctctcgct 960
gaattcccca atgtcaagca cttccggaat cgggagcgcg gccgatgcaa agtgccgata 1020
aacataacga tctttgtaga aaccatcggc gcagctattt acccgcagga catatccacg 1080
ccctcctaca tcgaagctga aagcacgaga ttcttcgccc tccgagagct gcatcaggtc 1140
ggagacgctg tcgaactttt cgatcagaaa cttctcgaca gacgtcgcgg tgagttcagg 1200
cttttccatg ggtatatctc cttcttaaag ttaaacaaaa ttatttctag agggaaaccg 1260
ttgtggtctc cctatagtga gtcgtattaa tttcgcggga tcgagatcga tccaattcca 1320
atcccacaaa aatctgagct taacagcaca gttgctcctc tcagagcaga atcgggtatt 1380
caacaccctc atatcaacta ctacgttgtg tataacggtc cacatgccgg tatatacgat 1440
gactggggtt gtacaaaggc ggcaacaaac ggcgttcccg gagttgcaca caagaaattt 1500
gccactatta cagaggcaag agcagcagct gacgcgtaca caacaagtca gcaaacagac 1560
aggttgaact tcatccccaa aggagaagct caactcaagc ccaagagctt tgctaaggcc 1620
ctaacaagcc caccaaagca aaaagcccac tggctcacgc taggaaccaa aaggcccagc 1680
agtgatccag ccccaaaaga gatctccttt gccccggaga ttacaatgga cgatttcctc 1740
tatctttacg atctaggaag gaagttcgaa ggtgaaggtg acgacactat gttcaccact 1800
gataatgaga aggttagcct cttcaatttc agaaagaatg ctgacccaca gatggttaga 1860
gaggcctacg cagcaggtct catcaagacg atctacccga gtaacaatct ccaggagatc 1920
aaataccttc ccaagaaggt taaagatgca gtcaaaagat tcaggactaa ttgcatcaag 1980
aacacagaga aagacatatt tctcaagatc agaagtacta ttccagtatg gacgattcaa 2040
ggcttgcttc ataaaccaag gcaagtaata gagattggag tctctaaaaa ggtagttcct 2100
actgaatcta aggccatgca tggagtctaa gattcaaatc gaggatctaa cagaactcgc 2160
cgtgaagact ggcgaacagt tcatacagag tcttttacga ctcaatgaca agaagaaaat 2220
cttcgtcaac atggtggagc acgacactct ggtctactcc aaaaatgtca aagatacagt 2280
ctcagaagac caaagggcta ttgagacttt tcaacaaagg ataatttcgg gaaacctcct 2340
cggattccat tgcccagcta tctgtcactt catcgaaagg acagtagaaa aggaaggtgg 2400
ctcctacaaa tgccatcatt gcgataaagg aaaggctatc attcaagatg cctctgccga 2460
cagtggtccc aaagatggac ccccacccac gaggagcatc gtggaaaaag aagacgttcc 2520
aaccacgtct tcaaagcaag tggattgatg tgacatctcc actgacgtaa gggatgacgc 2580
acaatcccac tatccttcgc aagacccttc ctctatataa ggaagttcat ttcatttgga 2640
gaggacacgc tcgagctcat ttctctatta cttcagccat aacaaaagaa ctcttttctc 2700
ttcttattaa accatgaaaa agcctgaact caccgcgacg tctgtcgaga agtttctgat 2760
cgaaaagttc gacagcgtct ccgacctgat gcagctctcg gagggcgaag aatctcgtgc 2820
tttcagcttc gatgtaggag ggcgtggata tgtcctgcgg gtaaatagct gcgccgatgg 2880
tttctacaaa gatcgttatg tttatcggca ctttgcatcg gccgcgctcc cgattccgga 2940
agtgcttgac attggggaat tcagcgagag cctgacctat tgcatctccc gccgtgcaca 3000

-continued gggtgtcacg ttgcaagacc tgcctgaaac cgaactgccc gctgttctgc agccggtcgc 3060
ggaggccatg gatgcgatcg ctgcggccga tcttagccag acgagcgggt tcggcccatt 3120
cggaccgcaa ggaatcggtc aatacactac atggcgtgat ttcatatgcg cgattgctga 3180
tccccatgtg tatcactggc aaactgtgat ggacgacacc gtcagtgcgt ccgtcgcgca 3240
ggctctcgat gagctgatgc tttgggccga ggactgcccc gaagtccggc acctcgtgca 3300
cgcggatttc ggctccaaca atgtcctgac ggacaatggc cgcataacag cggtcattga 3360
ctggagcgag gcgatgttcg gggattccca atacgaggtc gccaacatct tcttctggag 3420
gccgtggttg gcttgtatgg agcagcagac gcgctacttc gagcggaggc atccggagct 3480
tgcaggatcg ccgcggctcc gggcgtatat gctccgcatt ggtcttgacc aactctatca 3540
gagcttggtt gacggcaatt tcgatgatgc agcttgggcg cagggtcgat gcgacgcaat 3600
cgtccgatcc ggagccggga ctgtcgggcg tacacaaatc gcccgcagaa gcgcggccgt 3660
ctggaccgat ggctgtgtag aagtactcgc cgatagtgga aaccgacgcc ccagcactcg 3720
tccgagggca aaggaatagt gaggtaccta aagaaggagt gcgtcgaagc agatcgttca 3780
aacatttggc aataaagttt cttaagattg aatcctgttg ccggtcttgc gatgattatc 3840
atataatttc tgttgaatta cgttaagcat gtaataatta acatgtaatg catgacgtta 3900
tttatgagat gggtttttat gattagagtc ccgcaattat acatttaata cgcgatagaa 3960
aacaaaatat agcgcgcaaa ctaggataaa ttatcgcgcg cggtgtcatc tatgttacta 4020
gatcgatgtc gaatcgatca acctgcatta atgaatcggc caacgcgcgg ggagaggcgg 4080
tttgcgtatt gggcgctctt ccgcttcctc gctcactgac tcgctgcgct cggtcgttcg 4140
gctgcggcga gcggtatcag ctcactcaaa ggcggtaata cggttatcca cagaatcagg 4200
ggataacgca ggaaagaaca tgtgagcaaa aggccagcaa aaggccagga accgtaaaaa 4260
ggccgcgttg ctggcgtttt tccataggct ccgcccccct gacgagcatc acaaaaatcg 4320
acgctcaagt cagaggtggc gaaacccgac aggactataa agataccagg cgtttccccc 4380
tggaagctcc ctcgtgcgct ctcctgttcc gaccctgccg cttaccggat acctgtccgc 4440
ctttctccct tcgggaagcg tggcgctttc tcaatgctca cgctgtaggt atctcagttc 4500
ggtgtaggtc gttcgctcca agctgggctg tgtgcacgaa ccccccgttc agcccgaccg 4560
ctgcgcctta tccggtaact atcgtcttga gtccaacccg gtaagacacg acttatcgcc 4620
actggcagca gccactggta acaggattag cagagcgagg tatgtaggcg gtgctacaga 4680
gttcttgaag tggtggccta actacggcta cactagaagg acagtatttg gtatctgcgc 4740
tctgctgaag ccagttacct tcggaaaaag agttggtagc tcttgatccg gcaaacaaac 4800
caccgctggt agcggtggtt tttttgtttg caagcagcag attacgcgca gaaaaaaagg 4860
atctcaagaa gatcctttga tcttttctac ggggtctgac gctcagtgga acgaaaactc 4920
acgttaaggg attttggtca tgacattaac ctataaaaat aggcgtatca cgaggccctt 4980
tcgtctcgcg cgtttcggtg atgacggtga aaacctctga cacatgcagc tcccggagac 5040
ggtcacagct tgtctgtaag cggatgccgg gagcagacaa gcccgtcagg gcgcgtcagc 5100
gggtgttggc gggtgtcggg gctggcttaa ctatgcggca tcagagcaga ttgtactgag 5160
agtgcaccat atggacatat tgtcgttaga acgcggctac aattaataca taaccttatg 5220
tatcatacac atacgattta ggtgacacta tagaacggcg cgccaagctt ggatctcctg 5280
caggatctgg ccggccggat ctcgtaccga gctcggatcc actagtaacg gccgccagtg 5340

-continued tgctggaatt caggtcctgc aggtctactc tttacatgtt ctttactccg tctcaaaatt 5400 tcctttttttt gttggctctc tccgaacgag ttggagaaat cgttaaccct aatcgaagat 5460
ctagattcct ctacatacgt ttgatctctc tctcagtatg gattacaaag cgccaaggag 5520
atactactca cacggagttg ttgcgagaca gcaagatttc gcaacagata tagttacgag 5580
aagaagacct tatgtccctt acgaccgtcc aaataagttt tcaaggagtc tggtttggac 5640
gtcaaaagag tacaaatcac ccgagggcaa taatatgcca aggaccaatg atgtgtcacc 5700
gaaaccacca gttttaggtt tggcgaggaa gaatgctgct tgtgggccaa tgagatcttc 5760
tagtctcaga aaatgggtat gtaagtattg gaaagatgga aagtgcaaga ggggtgagca 5820
gtgccagttc ttacactctt ggtcttgttt ccctggattg gccatggtag cttctcttga 5880
agggcacaat aaggaactaa aggggatcgc tctccctgag ggttcagata aactcttttc 5940
agtcagtatt gatggtacat tgcgagtttg ggactgcaat tctggtcagt gtgtacattc 6000
catcaacctt gacgcagaag cagggtctct aatcagtgaa ggcccttggg ttttccttgg 6060
cttgccaaac gctataaagg cttttaacgt tcaaaccagt caagatttgc atcttcaagc 6120
agcaggggtg gttggtcagg tgaatgcaat gactattgca aacggaatgc tttttgctgg 6180
aacaagttct ggtagtatct tagtctggaa agctactaca gactctgagt ctgatccatt 6240
caaatacttg acatctcttg agggacatag tggtgaagtc acttgttttg ctgttggagg 6300
tcaaatgcta tactctggtt ctgtcgataa aacaatcaag atgtgggatc tcaacaccct 6360
gcaatgtata atgaccctga agcaacatac cggcactgtc acttcactct tatgttggga 6420
taaatgtttg atatcgtctt ccttggatgg gaccataaaa gtttgggctt attctgaaaa 6480
cggaatcttg aaagttgttc aaactcgcag acaagaacag agtagtgttc atgctctttc 6540
tggtatgcat gatgcagaag ccaaaccgat aatattctgc tcttaccaaa acggaaccgt 6600
tggcattttc gacctaccat cttttcaaga aagaggaagg atgttctcta cgcacacgat 6660
cgccacactc acaattggtc ctcaaggatt gttattcagt ggagacgaga gtggtaactt 6720
gcgtgtatgg accttagctg ctggcaacaa agtttagtct tttcgactaa agaattctga 6780
tttaattttg tggtttatat gttgagttaa ctgttaagag agttttattt tgtaataggt 6840
gtatcagtca ataaacaatc tttgtatcaa ccaaatgtaa tttttctcgt taattcgatt 6900
tcagagtttt tactttaaga taaacaaact ctttcacaca tcatttaatg aaagtggaga 6960
agcttaaaaa acaaacaaag aaactgatcc atttttggcg ggtcttcttc tactcttatt 7020
catatgtgtt aacgaactat agcgtaaaat tcagagcaag cgatctccga tttgaacgtg 7080
gctatcaccg gaggcccacc actacgggcg atacgctcta agtgaggatt aaagtgctct 7140
ggtggtgacg ttgaagaaac tcgcccatgg tttttgttat ctctgcagcc aagtgtcgtt 7200
ctttcttcgc cacttctcat caagctacag tgaatttaaa aatggcgtct ttctttgatc 7260
tcgtatacat aagctggatt ggtttcttaa acaaattcct ctccttttgg gtcttctggg 7320
tttgccttgt aagtgtttgt gtttttgcct ctgagaaaaa atcgcggccc tagacgccca 7380
tcacaagttt gtacaaaaaa gctgaacgag aaacgtaaaa tgatataaat atcaatatat 7440
taaattagat tttgcataaa aaacagacta cataatactg taaaacacaa catatccagt 7500
catattggcg gccgcattag gcaccccagg ctttacactt tatgcttccg gctcgtataa 7560
tgtgtggatt ttgagttagg atccgtcgag attttcagga gctaaggaag ctaaaatgga 7620
gaaaaaaatc actggatata ccaccgttga tatatcccaa tggcatcgta aagaacattt 7680
tgaggcattt cagtcagttg ctcaatgtac ctataaccag accgttcagc tggatattac 7740

-continued

```
ggccttttta aagaccgtaa agaaaaataa gcacaagttt tatccggcct ttattcacat   7800
tcttgcccgc ctgatgaatg ctcatccgga attccgtatg gcaatgaaag acggtgagct   7860
ggtgatatgg gatagtgttc acccttgtta caccgttttc catgagcaaa ctgaaacgtt   7920
ttcatcgctc tggagtgaat accacgacga tttccggcag tttctacaca tatattcgca   7980
agatgtggcg tgttacggtg aaaacctggc ctatttccct aaagggttta ttgagaatat   8040
gtttttcgtc tcagccaatc cctgggtgag tttcaccagt tttgatttaa acgtggccaa   8100
tatggacaac ttcttcgccc ccgttttcac catgggcaaa tattatacgc aaggcgacaa   8160
ggtgctgatg ccgctggcga ttcaggttca tcatgccgtt tgtgatggct tccatgtcgg   8220
cagaatgctt aatgaattac aacagtactg cgatgagtgg cagggcgggg cgtaaacgcg   8280
tggatccggc ttactaaaag ccagataaca gtatgcgtat ttgcgcgctg atttttgcgg   8340
tataagaata tatactgata tgtatacccg aagtatgtca aaaagaggta tgctatgaag   8400
cagcgtatta cagtgacagt tgacagcgac agctatcagt tgctcaaggc atatatgatg   8460
tcaatatctc cggtctggta agcacaacca tgcagaatga agcccgtcgt ctgcgtgccg   8520
aacgctggaa agcggaaaat caggaaggga tggctgaggt cgcccggttt attgaaatga   8580
acggctcttt tgctgacgag aacaggggct ggtgaaatgc agtttaaggt ttacacctat   8640
aaaagagaga gccgttatcg tctgtttgtg gatgtacaga gtgatattat tgacacgccc   8700
gggcgacgga tggtgatccc cctggccagt gcacgtctgc tgtcagataa agtctcccgt   8760
gaactttacc cggtggtgca tatcggggat gaaagctggc gcatgatgac caccgatatg   8820
gccagtgtgc cggtctccgt tatcggggaa gaagtggctg atctcagcca ccgcgaaaat   8880
gacatcaaaa acgccattaa cctgatgttc tggggaatat aaatgtcagg ctcccttata   8940
cacagccagt ctgcaggtcg accatagtga ctggatatgt tgtgttttac agcattatgt   9000
agtctgtttt ttatgcaaaa tctaatttaa tatattgata tttatatcat tttacgtttc   9060
tcgttcagct ttcttgtaca aagtggtgat gataaccaag tttaacgtga gtttatatat   9120
tcacagttcc atttacagat cttatgctga ttgcagcata taacatagtc gcaacttaac   9180
tttatccctg cttacgtaaa gaaacataca tattgtttgt ggcttcgtag tggaacatat   9240
gcaattatgt aatctttata ttatgagcct ttacttacaa agattacttg agatttatgt   9300
acgtgtgcta ttttcacttt tcaaacatga atttcctacg tttacaatca tttaatgtaa   9360
aagggatgat ataatgtatt tacgtacatg tgaacaacca agcatgttat tttttccttt   9420
tttgttgcaa cttacaatca agtaatgatt atggttatga ttatgatatt ggtgtgtgtc   9480
ttttgcctta tatatatatt tatccctttc gtttaacttt gcaatataat tattactgat   9540
cactatattt tggtttgaaa tggcgcaggt tgtaatgatc gatcatcacc actttgtaca   9600
agaaagctga acgagaaacg taaaatgata taaatatcaa tatattaaat tagattttgc   9660
ataaaaaaca gactacataa tgctgtaaaa cacaacatat ccagtcacta tggtcgacct   9720
gcagactggc tgtgtataag ggagcctgac atttatattc cccagaacat caggttaatg   9780
gcgtttttga tgtcattttc gcggtggctg agatcagcca cttcttcccc gataacggag   9840
accggcacac tggccatatc ggtggtcatc atgcgccagc tttcatcccc gatatgcacc   9900
accgggtaaa gttcacggga gactttatct gacagcagac gtgcactggc caggggggatc   9960
accatccgtc gcccgggcgt gtcaataata tcactctgta catccacaaa cagacgataa  10020
cggctctctc ttttataggt gtaaacctta aactgcattt caccagcccc tgttctcgtc  10080
```

-continued

```
agcaaaagag ccgttcattt caataaaccg ggcgacctca gccatccctt cctgattttc  10140

cgctttccag cgttcggcac gcagacgacg ggcttcattc tgcatggttg tgcttaccag  10200

accggagata ttgacatcat atatgccttg agcaactgat agctgtcgct gtcaactgtc  10260

actgtaatac gctgcttcat agcatacctc tttttgacat acttcgggta tacatatcag  10320

tatatattct tataccgcaa aaatcagcgc gcaaatacgc atactgttat ctggctttta  10380

gtaagccgga tcctaactca aaatccacac attatacgag ccggaagcat aaagtgtaaa  10440

gcctggggtg cctaatgcgg ccgccaatat gactggatat gttgtgtttt acagtattat  10500

gtagtctgtt ttttatgcaa aatctaattt aatatattga tatttatatc attttacgtt  10560

tctcgttcag ctttttgta caaacttgtg atgggcgtct agcgaactag aggatccccg  10620

ggtaccgag                                                           10629
```

<210> SEQ ID NO 34
<211> LENGTH: 18587
<212> TYPE: DNA
<213> ORGANISM: artificial sequence
<220> FEATURE:
<223> OTHER INFORMATION: plasmid pKR1481-PAE

<400> SEQUENCE: 34

```
ccgcggccgc ccccttcacc atgaagagtg tgttgcgtat tgcggcggcg atattctggc     60

tttggctgtt tatcgtgtta ggtgtgattg ggagtgggaa tgtgagagat acagacgatg    120

agatctcgtt actcgaaagt caattggtgg tgacatctcc gtcgcagctt cttatggtgc    180

ctctcacttt gattcaggct gctgcctcca aaggagctgt gtgcctggat ggaacactac    240

ctggttatca tctacaccct ggttctggat caggagctaa ccggtggctc atccaactcg    300

agggtggagg atggtgcaac acacgtagga gctgtatctt ccggaaaacc actcgccgtg    360

gttcatcaaa tcatatggag aaagttttgg ccttcactgg aatattgagc aataaatcta    420

atgagaatcc tgacttcttc aactggaaca gagtcaaatt gcgttactgc gatggtgcct    480

ctttcaccgg cgatagtcag gatgagagct cacaacttta ctatagagga caacgaatct    540

ggcattcagc tatggaagaa ctactctcta aaggcatgca aaaagcagaa caggctctac    600

tttctggatg ttcagctggg ggattagctt ccatcctaca ctgcgatcag ttcaaggaac    660

tatttccggg cactacgaca gtgaaatgct taagtgatgc tggaatgttt atggatgcag    720

tggatgtctc tgggggccac tcgctccgga aaatgttcca aggtgttgtt acagtacaga    780

acctccaaaa ggaactgtcc actgcttgta caaagcattt ggatccaact tcgtgcttct    840

ttccccagaa cttggtttca ggcattaaga ctccaatgtt tcttctcaat gcagcatatg    900

acgcttggca ggtacaagag agtttagctc caccatcagt tgacctaagc ggctcttgga    960

aggcatgcaa atctgatcac tcgcattgta attcatctca gatccagttc ttccaagact   1020

tcaggactca tatggtagat gctgtaaagt ctttcgcgac atcgacacat aacggtgtgt   1080

tcataaactc atgcttcgct cactgccaat ctgaaagaca ggacacttgg tatgcaccag   1140

attctcctac tcttcatggc aagaccgttg ctgaatctgt tggtgattgg tactttgaca   1200

gaacaacagt gaaagccatt gactgtcctt acccctgtga caaaacatgt cacaatctca   1260

tcttcaagtg aaagggtggg cgcgccgacc cagctttctt gtacaaagtg gtgtgagttt   1320

atatattcac agttccattt acagatctta tgctgattgc agcatataac atagtcgcaa   1380

cttaacttta tccctgctta cgtaaagaaa catacatatt gtttgtggct tcgtagtgga   1440

acatatgcaa ttatgtaatc tttatattat gagcctttac ttacaaagat tacttgagat   1500
```

ttatgtacgt gtgctatttt cacttttcaa acatgaattt cctacgttta caatcattta 1560
atgtaaaagg gatgatataa tgtatttacg tacatgtgaa caaccaagca tgttattttt 1620
tcctttttg ttgcaactta caatcaagta atgattatgg ttatgattat gatattggtg 1680
tgtgtctttt gccttatata tatatttatc cctttcgttt aactttgcaa tataattatt 1740
actgatcact atattttggt ttgaaatggc gcagaccact ttgtacaaga aagctgggtc 1800
ggcgcgccca ccctttcact tgaagatgag attgtgacat gttttgtcac aggggtaagg 1860
acagtcaatg gctttcactg ttgttctgtc aaagtaccaa tcaccaacag attcagcaac 1920
ggtcttgcca tgaagagtag gagaatctgg tgcataccaa gtgtcctgtc tttcagattg 1980
gcagtgagcg aagcatgagt ttatgaacac accgttatgt gtcgatgtcg cgaaagactt 2040
tacagcatct accatatgag tcctgaagtc ttggaagaac tggatctgag atgaattaca 2100
atgcgagtga tcagatttgc atgccttcca agagccgctt aggtcaactg atggtggagc 2160
taaactctct tgtacctgcc aagcgtcata tgctgcattg agaagaaaca ttggagtctt 2220
aatgcctgaa accaagttct ggggaaagaa gcacgaagtt ggatccaaat gctttgtaca 2280
agcagtggac agttcctttt ggaggttctg tactgtaaca acaccttgga acattttccg 2340
gagcgagtgg cccccagaga catccactgc atccataaac attccagcat cacttaagca 2400
tttcactgtc gtagtgcccg gaaatagttc cttgaactga tcgcagtgta ggatggaagc 2460
taatccccca gctgaacatc cagaaagtag agcctgttct gctttttgca tgcctttaga 2520
gagtagttct tccatagctg aatgccagat tcgttgtcct ctatagtaaa gttgtgagct 2580
ctcatcctga ctatcgccgg tgaaagaggc accatcgcag taacgcaatt tgactctgtt 2640
ccagttgaag aagtcaggat tctcattaga tttattgctc aatattccag tgaaggccaa 2700
aactttctcc atatgatttg atgaaccacg gcgagtggtt ttccggaaga tacagctcct 2760
acgtgtgttg caccatcctc caccctcgag ttggatgagc caccggttag ctcctgatcc 2820
agaaccaggg tgtagatgat aaccaggtag tgttccatcc aggcacacag ctcctttgga 2880
ggcagcagcc tgaatcaaag tgagaggcac cataagaagc tgcgacggag atgtcaccac 2940
caattgactt tcgagtaacg agatctcatc gtctgtatct ctcacattcc cactcccaat 3000
cacacctaac acgataaaca gccaaagcca gaatatcgcc gccgcaatac gcaacacact 3060
cttcatggtg aagggggcgg ccgcggagcc tgcttttttg tacaaacttg tgatgggcgt 3120
ctagcgaact agaggatccc cgggtaccga ggtacggatc cgtcgacggc gcgccagatc 3180
ctctagagtc gacctgcagg catgcaagct tggcgtaatc atggtcatag ctgtttcctg 3240
tgtgaaattg ttatccgctc acaattccac acaacatacg agccggaagc ataaagtgta 3300
aagcctgggg tgcctaatga gtgagctaac tcacattaat tgcgttgcgc tcactgcccg 3360
ctttccagtc gggaaacctg tcgtgccagc tgcattaatg aatcggccaa cgcgcgggga 3420
gaggcggttt gcgtattgga tcgatccctg aaagcgacgt tggatgttaa catctacaaa 3480
ttgccttttc ttatcgacca tgtacgtaag cgcttacgtt tttggtggac ccttgaggaa 3540
actggtagct gttgtgggcc tgtggtctca agatggatca ttaatttcca ccttcaccta 3600
cgatgggggg catcgcaccg gtgagtaata ttgtacggct aagagcgaat ttggcctgta 3660
gacctcaatt gcgagctttc taatttcaaa ctattcgggc ctaacttttg gtgtgatgat 3720
gctgactggc aggatatata ccgttgtaat ttgagctcgt gtgaataagt cgctgtgtat 3780
gtttgtttga ttgtttctgt tggagtgcag cccatttcac cggacaagtc ggctagattg 3840

-continued

```
atttagccct gatgaactgc cgaggggaag ccatcttgag cgcggaatgg gaatggattt   3900
cgttgtacaa cgagacgaca gaacacccac gggaccgagc ttcgcgagct tttgtatccg   3960
tggcatcctt ggtccgggcg atttgttcac gtccatgagg cgctctccaa aggaacgcat   4020
attttccggt gcaacctttc cggttcttcc tctactcgac ctcttgaagt cccagcatga   4080
atgttcgacc gctccgcaag cggatctttg gcgcaaccag ccggtttcgc acgtcgattc   4140
tcgcgagcct gcatactttg gcaagattgc tgaatgacgc tgatgcttca tcgcaatctg   4200
cgataatggg gtaagtatcc ggtgaaggcc gcaggtcagg ccgcctgagc actcagtgtc   4260
ttggatgtcc agttccacgg cagctgttgc tcaagcctgc tgatcggagc gtccgcaagg   4320
tcggcgcgga cgtcggcaag ccaggcctgc ggatcgatgt tattgagctt ggcgctcatg   4380
atcagtgtcg ccatgaacgc cgcacgttca gcacaacgat ccgatccggc aaacagccat   4440
gacttcctgc cgagtacata gcctctgagc gttcgttcgg cagcattgtt cgtcaggcaa   4500
atcgggccgt catcgaggaa tgacgtaatg ccatcccatc gcttgagcat gtaatttatc   4560
gcctcggcga cgggagaact gcgcgacaat ttcccccgct cggtttcgag ccaatcatgc   4620
agctcttcgg cgagtgacct tgatcaggcc accgccacga ccgcggaaga cgaacagatg   4680
cctgcgcatc ggatcgcgct tcagcgtctc ttgcaccatc agcgacaaac cgggaaagcc   4740
tttgcgcatg tccgtactta tgtcgccact tgggagggct tcgtctacgt ggccttcgtg   4800
atcgacgtct tcgcccgtcg cattgtcgga tggcgggcga gccggacagc acatgcaggc   4860
tttgtcctcg atgccctcga ggaggctcat catgatcggc gtcccgctca tggcggccta   4920
gtgcatcact cggatcgcgg tgttcaatac gtgtcctttc gctattccga gcggttggca   4980
gaagcaggta tcgagccatc tatcggaagc gtcggcgaca gcacgacaac gccctcgcag   5040
aagcgatcaa cggtctttac aaggccgagg tcattcatcg gcgtggacca tggaggagct   5100
tcgaagcggt cgagttcgct accttggaat ggatagactg gttcaaccac ggcggctttt   5160
gaagcccatc ggcaatatac cgccagccga agacgaggat cagtattacg ccatgctgga   5220
cgaagcagcc atggctgcgc attttaacga aatggcctcc ggcaaacccg gtgcggttca   5280
cttgttgcgt gggaaagttc acgggactcc gcgcacgagc cttcttcgta atagccatat   5340
cgaccgaatt gacctgcagg gggggggggg aaagccacgt tgtgtctcaa aatctctgat   5400
gttacattgc acaagataaa aatatatcat catgaacaat aaaactgtct gcttacataa   5460
acagtaatac aaggggtgtt atgagccata ttcaacggga aacgtcttgc tcgaggccgc   5520
gattaaattc caacatggat gctgatttat atgggtataa atgggctcgc gataatgtcg   5580
ggcaatcagg tgcgacaatc tatcgattgt atgggaagcc cgatgcgcca gagttgtttc   5640
tgaaacatgg caaaggtagc gttgccaatg atgttacaga tgagatggtc agactaaact   5700
ggctgacgga atttatgcct cttccgacca tcaagcattt tatccgtact cctgatgatg   5760
catggttact caccactgcg atccccggga aaacagcatt ccaggtatta gaagaatatc   5820
ctgattcagg tgaaaatatt gttgatgcgc tggcagtgtt cctgcgccgg ttgcattcga   5880
ttcctgtttg taattgtcct tttaacagcg atcgcgtatt tcgtctcgct caggcgcaat   5940
cacgaatgaa taacggtttg gttgatgcga gtgattttga tgacgagcgt aatggctggc   6000
ctgttgaaca agtctggaaa gaaatgcata agcttttgcc attctcaccg gattcagtcg   6060
tcactcatgg tgatttctca cttgataacc ttatttttga cgaggggaaa ttaataggtt   6120
gtattgatgt tggacgagtc ggaatcgcag accgatacca ggatcttgcc atcctatgga   6180
actgcctcgg tgagttttct ccttcattac agaaacggct tttcaaaaa tatggtattg   6240
```

-continued

```
ataatcctga tatgaataaa ttgcagtttc atttgatgct cgatgagttt ttctaatcag   6300
aattggttaa ttggttgtaa cactggcaga gcattacgct gacttgacgg gacggcggct   6360
ttgttgaata aatcgaactt ttgctgagtt gaaggatcag atcacgcatc ttcccgacaa   6420
cgcagaccgt tccgtggcaa agcaaaagtt caaaatcacc aactggtcca cctacaacaa   6480
agctctcatc aaccgtggct ccctcacttt ctggctggat gatggggcga ttcaggcctg   6540
gtatgagtca gcaacacctt cttcacgagg cagacctcag cgcccccccc cccctgcagg   6600
tcttttccaa tgatgagcac ttttaaagtt ctgctatgtg gcgcggtatt atcccgtgtt   6660
gacgccgggc aagagcaact cggtcgccgc atacactatt ctcagaatga cttggttgag   6720
tactcaccag tcacagaaaa gcatcttacg gatggcatga cagtaagaga attatgcagt   6780
gctgccataa ccatgagtga taacactgcg gccaacttac ttctgacaac gatcggagga   6840
ccgaaggagc taaccgcttt tttgcacaac atgggggatc atgtaactcg ccttgatcgt   6900
tgggaaccgg agctgaatga agccatacca aacgacgagc gtgacaccac gatgcctgta   6960
gcaatggcaa caacgttgcg caaactatta actggcgaac tacttactct agcttcccgg   7020
caacaattaa tagactggat ggaggcggat aaagttgcag gaccacttct gcgctcggcc   7080
cttccggctg gctggtttat tgctgataaa tctggagccg gtgagcgtgg gtctcgcggt   7140
atcattgcag cactggggcc agatggtaag ccctcccgta tcgtagttat ctacacgacg   7200
gggagtcagg caactatgga tgaacgaaat agacagatcg ctgagatagg tgcctcactg   7260
attaagcatt ggtaactgtc agaccaagtt tactcatata tactttagat tgatttaaaa   7320
cttcattttt aatttaaaag gatctaggtg aagatccttt ttgataatct catgaccaaa   7380
atcccttaac gtgagttttc gttccactga gcgtcagacc ccgtagaaaa gatcaaagga   7440
tcttcttgag atcctttttt tctgcgcgta atctgctgct tgcaaacaaa aaaaccaccg   7500
ctaccagcgg tggtttgttt gccggatcaa gagctaccaa ctctttttcc gaaggtaact   7560
ggcttcagca gagcgcagat accaaatact gtccttctag tgtagccgta gttaggccac   7620
cacttcaaga actctgtagc accgcctaca tacctcgctc tgctaatcct gttaccagtg   7680
gctgctgcca gtggcgataa gtcgtgtctt accgggttgg actcaagacg atagttaccg   7740
gataaggcgc agcggtcggg ctgaacgggg ggttcgtgca cacagcccag cttggagcga   7800
acgacctaca ccgaactgag atacctacag cgtgagctat gagaaagcgc cacgcttccc   7860
gaagggagaa aggcggacag gtatccggta agcggcaggg tcggaacagg agagcgcacg   7920
agggagcttc caggggggaaa cgcctggtat ctttatagtc ctgtcgggtt tcgccacctc   7980
tgacttgagc gtcgattttt gtgatgctcg tcaggggggc ggagcctatg gaaaaacgcc   8040
agcaacgcgg cctttttacg gttcctggcc ttttgctggc cttttgctca catgttcttt   8100
cctgcgttat cccctgattc tgtggataac cgtattaccg cctttgagtg agctgatacc   8160
gctcgccgca gccgaacgac cgagcgcagc gagtcagtga gcgaggaagc ggaagagcgc   8220
ctgatgcggt attttctcct tacgcatctg tgcggtattt cacaccgcat atggtgcact   8280
ctcagtacaa tctgctctga tgccgcatag ttaagccagt atacactccg ctatcgctac   8340
gtgactgggt catggctgcg ccccgacacc cgccaacacc cgctgacgcg ccctgacggg   8400
cttgtctgct cccggcatcc gcttacagac aagctgtgac cgtctccggg agctgcatgt   8460
gtcagaggtt ttcaccgtca tcaccgaaac gcgcgaggca gggtgccttg atgtgggcgc   8520
cggcggtcga gtggcgacgg cgcggcttgt ccgcgccctg gtagattgcc tggccgtagg   8580
```

-continued

```
ccagccattt ttgagcggcc agcggccgcg ataggccgac gcgaagcggc ggggcgtagg   8640
gagcgcagcg accgaagggt aggcgctttt tgcagctctt cggctgtgcg ctggccagac   8700
agttatgcac aggccaggcg ggttttaaga gttttaataa gttttaaaga gttttaggcg   8760
gaaaaatcgc ctttttctc ttttatatca gtcacttaca tgtgtgaccg gttcccaatg   8820
tacggctttg ggttcccaat gtacgggttc cggttcccaa tgtacggctt tgggttccca   8880
atgtacgtgc tatccacagg aaagagacct tttcgacctt tttcccctgc tagggcaatt   8940
tgccctagca tctgctccgt acattaggaa ccggcggatg cttcgccctc gatcaggttg   9000
cggtagcgca tgactaggat cgggccagcc tgccccgcct cctccttcaa atcgtactcc   9060
ggcaggtcat ttgacccgat cagcttgcgc acggtgaaac agaacttctt gaactctccg   9120
gcgctgccac tgcgttcgta gatcgtcttg aacaaccatc tggcttctgc cttgcctgcg   9180
gcgcggcgtg ccaggcggta gagaaaacgg ccgatgccgg gatcgatcaa aaagtaatcg   9240
gggtgaaccg tcagcacgtc cgggttcttg ccttctgtga tctcgcggta catccaatca   9300
gctagctcga tctcgatgta ctccggccgc ccggtttcgc tctttacgat cttgtagcgg   9360
ctaatcaagg cttcaccctc ggataccgtc accaggcggc cgttcttggc cttcttcgta   9420
cgctgcatgg caacgtgcgt ggtgtttaac cgaatgcagg tttctaccag gtcgtctttc   9480
tgctttccgc catcggctcg ccggcagaac ttgagtacgt ccgcaacgtg tggacggaac   9540
acgcggccgg gcttgtctcc cttcccttcc cggtatcggt tcatggattc ggttagatgg   9600
gaaaccgcca tcagtaccag gtcgtaatcc cacacactgg ccatgccggc cggccctgcg   9660
gaaacctcta cgtgcccgtc tggaagctcg tagcggatca cctcgccagc tcgtcggtca   9720
cgcttcgaca gacggaaaac ggccacgtcc atgatgctgc gactatcgcg ggtgcccacg   9780
tcatagagca tcggaacgaa aaaatctggt tgctcgtcgc ccttgggcgg cttcctaatc   9840
gacggcgcac cggctgccgg cggttgccgg gattctttgc ggattcgatc agcggccgct   9900
tgccacgatt caccggggcg tgcttctgcc tcgatgcgtt gccgctgggc ggcctgcgcg   9960
gccttcaact tctccaccag gtcatcaccc agcgccgcgc cgatttgtac cgggccggat  10020
ggtttgcgac cgctcacgcc gattcctcgg gcttgggggt tccagtgcca ttgcagggcc  10080
ggcagacaac ccagccgctt acgcctggcc aaccgcccgt tcctccacac atggggcatt  10140
ccacggcgtc ggtgcctggt tgttcttgat tttccatgcc gcctccttta gccgctaaaa  10200
ttcatctact catttattca tttgctcatt tactctggta gctgcgcgat gtattcagat  10260
agcagctcgg taatggtctt gccttggcgt accgcgtaca tcttcagctt ggtgtgatcc  10320
tccgccggca actgaaagtt gacccgcttc atggctggcg tgtctgccag gctggccaac  10380
gttgcagcct tgctgctgcg tgcgctcgga cggccggcac ttagcgtgtt tgtgcttttg  10440
ctcattttct ctttacctca ttaactcaaa tgagttttga tttaatttca gcggccagcg  10500
cctggacctc gcgggcagcg tcgccctcgg gttctgattc aagaacggtt gtgccggcgg  10560
cggcagtgcc tgggtagctc acgcgctgcg tgatacggga ctcaagaatg ggcagctcgt  10620
acccggccag cgcctcggca acctcaccgc cgatgcgcgt gcctttgatc gcccgcgaca  10680
cgacaaaggc cgcttgtagc cttccatccg tgacctcaat gcgctgctta accagctcca  10740
ccaggtcggc ggtggcccat atgtcgtaag ggcttggctg caccggaatc agcacgaagt  10800
cggctgcctt gatcgcggac acagccaagt ccgccgcctg ggcgctccg tcgatcacta  10860
cgaagtcgcg ccggccgatg gccttcacgt cgcggtcaat cgtcgggcgg tcgatgccga  10920
caacggttag cggttgatct tcccgcacgg ccgcccaatc gcgggcactg ccctggggat  10980
```

cggaatcgac taacagaaca tcggccccgg cgagttgcag ggcgcgggct agatgggttg 11040
cgatggtcgt cttgcctgac ccgcctttct ggttaagtac agcgataact tcatgcgttc 11100
ccttgcgtat ttgtttattt actcatcgca tcatatacgc agcgaccgca tgacgcaagc 11160
tgttttactc aaatacacat caccttttta gacggcggcg ctcggtttct tcagcggcca 11220
agctggccgg ccaggccgcc agcttggcat cagacaaacc ggccaggatt tcatgcagcc 11280
gcacggttga gacgtgcgcg ggcggctcga acacgtaccc ggccgcgatc atctccgcct 11340
cgatctcttc ggtaatgaaa aacggttcgt cctggccgtc ctggtgcggt ttcatgcttg 11400
ttcctcttgg cgttcattct cggcggccgc cagggcgtcg gcctcggtca atgcgtcctc 11460
acggaaggca ccgcgccgcc tggcctcggt gggcgtcact tcctcgctgc gctcaagtgc 11520
gcggtacagg gtcgagcgat gcacgccaag cagtgcagcc gcctctttca cggtgcggcc 11580
ttcctggtcg atcagctcgc gggcgtgcgc gatctgtgcc ggggtgaggg tagggcgggg 11640
gccaaacttc acgcctcggg ccttggcggc ctcgcgcccg ctccgggtgc ggtcgatgat 11700
tagggaacgc tcgaactcgg caatgccggc gaacacggtc aacaccatgc ggccggccgg 11760
cgtggtggtg tcggcccacg gctctgccag gctacgcagg cccgcgccgg cctcctggat 11820
gcgctcggca atgtccagta ggtcgcgggt gctgcgggcc aggcggtcta gcctggtcac 11880
tgtcacaacg tcgccagggc gtaggtggtc aagcatcctg gccagctccg ggcggtcgcg 11940
cctggtgccg gtgatcttct cggaaaacag cttggtgcag ccggccgcgt gcagttcggc 12000
ccgttggttg gtcaagtcct ggtcgtcggt gctgacgcgg gcatagccca gcaggccagc 12060
ggcggcgctc ttgttcatgg cgtaatgtct ccggttctag tcgcaagtat tctactttat 12120
gcgactaaaa cacgcgacaa gaaaacgcca ggaaaagggc agggcggcag cctgtcgcgt 12180
aacttaggac ttgtgcgaca tgtcgttttc agaagacggc tgcactgaac gtcagaagcc 12240
gactgcacta tagcagcgga ggggttggac cacaggacgg gtgtggtcgc catgatcgcg 12300
tagtcgatag tggctccaag tagcgaagcg agcaggactg ggcggcggcc aaagcggtcg 12360
gacagtgctc cgagaacggg tgcgcataga aattgcatca acgcatatag cgctagcagc 12420
acgccatagt gactggcgat gctgtcggaa tggacgatat cccgcaagag gcccggcagt 12480
accggcataa ccaagcctat gcctacagca tccagggtga cggtgccgag gatgacgatg 12540
agcgcattgt tagatttcat acacggtgcc tgactgcgtt agcaatttaa ctgtgataaa 12600
ctaccgcatt aaagctagct tgcttggtcg ttccgcgtga acgtcggctc gattgtacct 12660
gcgttcaaat actttgcgat cgtgttgcgc gcctgcccgg tgcgtcggct gatctcacgg 12720
atcgactgct tctctcgcaa cgccatccga cggatgatgt ttaaaagtcc catgtggatc 12780
actccgttgc cccgtcgctc accgtgttgg ggggaaggtg cacatggctc agttctcaat 12840
ggaaattatc tgcctaaccg gctcagttct gcgtagaaac caacatgcaa gctccaccgg 12900
gtgcaaagcg gcagcggcgg caggatatat tcaattgtaa atggcttcat gtccgggaaa 12960
tctacatgga tcagcaatga gtatgatggt caatatggag aaaaagaaag agtaattacc 13020
aatttttttt caattcaaaa atgtagatgt ccgcagcgtt attataaaat gaaagtacat 13080
tttgataaaa cgacaaatta cgatccgtcg tatttatagg cgaaagcaat aaacaaatta 13140
ttctaattcg gaaatcttta tttcgacgtg tctacattca cgtccaaatg ggggcttaga 13200
tgagaaactt cacgatcgat gccttgattt cgccattccc agatacccat ttcatcttca 13260
gattggtctg agattatgcg aaaatataca ctcatataca taaatactga cagtttgagc 13320

-continued

```
taccaattca gtgtagccca ttacctcaca taattcactc aaatgctagg cagtctgtca  13380
actcggcgtc aatttgtcgg ccactatacg atagttgcgc aaattttcaa agtcctggcc  13440
taacatcaca cctctgtcgg cggcgggtcc catttgtgat aaatccacca tatcgaatta  13500
attcagactc ctttgcccca gagatcacaa tggacgactt cctctatctc tacgatctag  13560
tcaggaagtt cgacggagaa ggtgacgata ccatgttcac cactgataat gagaagatta  13620
gcctttttcaa tttcagaaag aatgctaacc cacagatggt tagagaggct tacgcagcag  13680
gtctcatcaa gacgatctac ccgagcaata atctccagga gatcaaatac cttcccaaga  13740
aggttaaaga tgcagtcaaa agattcagga ctaactgcat caagaacaca gagaaagata  13800
tatttctcaa gatcagaagt actattccag tatggacgat tcaaggcttg cttcacaaac  13860
caaggcaagt aatagagatt ggagtctcta aaaaggtagt tcccactgaa tcaaaggcca  13920
tggagtcaaa gattcaaata gaggacctaa cagaactcgc cgtaaagact ggcgaacagt  13980
tcatacagag tctcttacga ctcaatgaca agaagaaaat cttcgtcaac atggtggagc  14040
acgacacgct tgtctactcc aaaaatatca aagatacagt ctcagaagac caaagggcaa  14100
ttgagacttt tcaacaaagg gtaatatccg gaaacctcct cggattccat tgcccagcta  14160
tctgtcactt tattgtgaag atagtggaaa aggaaggtgg ctcctacaaa tgccatcatt  14220
gcgataaagg aaaggccatc gttgaagatg cctctgccga cagtggtccc aaagatggac  14280
ccccacccac gaggagcatc gtggaaaaag aagacgttcc aaccacgtct tcaaagcaag  14340
tggattgatg tgatatctcc actgacgtaa gggatgacgc acaatcccac tatccttcgc  14400
aagacccttc ctctatataa ggaagttcat ttcatttgga gaggacacgc tgaaatcacc  14460
agtctccaag cttgcgggga tcgtttcgca tgattgaaca agatggattg cacgcaggtt  14520
ctccggccgc ttgggtggag aggctattcg gctatgactg ggcacaacag acaatcggct  14580
gctctgatgc cgccgtgttc cggctgtcag cgcaggggcg cccggttctt tttgtcaaga  14640
ccgacctgtc cggtgccctg aatgaactgc aggacgaggc agcgcggcta tcgtggctgg  14700
ccacgacggg cgttccttgc gcagctgtgc tcgacgttgt cactgaagcg ggaagggact  14760
ggctgctatt gggcgaagtg ccggggcagg atctcctgtc atctcacctt gctcctgccg  14820
agaaagtatc catcatggct gatgcaatgc ggcggctgca tacgcttgat ccggctacct  14880
gcccattcga ccaccaagcg aaacatcgca tcgagcgagc acgtactcgg atggaagccg  14940
gtcttgtcga tcaggatgat ctggacgaag agcatcaggg gctcgcgcca gccgaactgt  15000
tcgccaggct caaggcgcgc atgcccgacg gcgaggatct cgtcgtgacc catggcgatg  15060
cctgcttgcc gaatatcatg gtggaaaatg gccgcttttc tggattcatc gactgtggcc  15120
ggctgggtgt ggcggaccgc tatcaggaca tagcgttggc tacccgtgat attgctgaag  15180
agcttggcgg cgaatgggct gaccgcttcc tcgtgcttta cggtatcgcc gctcccgatt  15240
cgcagcgcat cgccttctat cgccttcttg acgagttctt ctgagcggga ctctggggtt  15300
cgaaatgacc gaccaagcga cgcccaacct gccatcacga gatttcgatt ccaccgccgc  15360
cttctatgaa aggttgggct tcggaatcgt tttccgggac gccggctgga tgatcctcca  15420
gcgcggggat ctcatgctgg agttcttcgc ccaccccgga tcgatccaac acttacgttt  15480
gcaacgtcca agagcaaata gaccacgaac gccggaaggt tgccgcagcg tgtggattgc  15540
gtctcaattc tctcttgcag gaatgcaatg atgaatatga tactgactat gaaactttga  15600
gggaatactg cctagcaccg tcacctcata acgtgcatca tgcatgccct gacaacatgg  15660
aacatcgcta tttttctgaa gaattatgct cgttggagga tgtcgcggca attgcagcta  15720
```

-continued

```
ttgccaacat cgaactaccc ctcacgcatg cattcatcaa tattattcat gcggggaaag  15780
gcaagattaa tccaactggc aaatcatcca gcgtgattgg taacttcagt tccagcgact  15840
tgattcgttt tggtgctacc cacgttttca ataaggacga gatggtggag taaagaagga  15900
gtgcgtcgaa gcagatcgtt caaacatttg gcaataaagt ttcttaagat tgaatcctgt  15960
tgccggtctt gcgatgatta tcatataatt tctgttgaat tacgttaagc atgtaataat  16020
taacatgtaa tgcatgacgt tatttatgag atgggttttt atgattagag tcccgcaatt  16080
atacatttaa tacgcgatag aaaacaaaat atagcgcgca aactaggata aattatcgcg  16140
cgcggtgtca tctatgttac tagatcgatc aaacttcggt actgtgtaat gacgatgagc  16200
aatcgagagg ctgactaaca aaaggtacat cgcgatggat cgatccattc gccattcagg  16260
ctgcgcaact gttgggaagg gcgatcggtg cgggcctctt cgctattacg ccagctggcg  16320
aaagggggat gtgctgcaag gcgattaagt tgggtaacgc cagggttttc ccagtcacga  16380
cgttgtaaaa cgacggccag tgaattcctg cagcccgggg gatccgccca ctcgaggcgc  16440
gccaagcttg gatctcctgc aggatctggc cggccggatc tcgtaccgag ctcggatcca  16500
ctagtaacgg ccgccagtgt gctggaattc aggtcctgca ggtctactct ttacatgttc  16560
tttactccgt ctcaaaattt cctttttttg ttggctctct ccgaacgagt tggagaaatc  16620
gttaacccta atcgaagatc tagattcctc tacatacgtt tgatctctct ctcagtatgg  16680
attacaaagc gccaaggaga tactactcac acggagttgt tgcgagacag caagatttcg  16740
caacagatat agttacgaga agaagacctt atgtccctta cgaccgtcca aataagtttt  16800
caaggagtct ggtttggacg tcaaaagagt acaaatcacc cgagggcaat aatatgccaa  16860
ggaccaatga tgtgtcaccg aaaccaccag ttttaggttt ggcgaggaag aatgctgctt  16920
gtgggccaat gagatcttct agtctcagaa aatgggtatg taagtattgg aaagatggaa  16980
agtgcaagag gggtgagcag tgccagttct tacactcttg gtcttgtttc cctggattgg  17040
ccatggtagc ttctcttgaa gggcacaata aggaactaaa ggggatcgct ctccctgagg  17100
gttcagataa actcttttca gtcagtattg atggtacatt gcgagtttgg gactgcaatt  17160
ctggtcagtg tgtacattcc atcaaccttg acgcagaagc agggtctcta atcagtgaag  17220
gcccttgggt tttccttggc ttgccaaacg ctataaaggc ttttaacgtt caaaccagtc  17280
aagatttgca tcttcaagca gcaggggtgg ttggtcaggt gaatgcaatg actattgcaa  17340
acggaatgct ttttgctgga acaagttctg gtagtatctt agtctggaaa gctactacag  17400
actctgagtc tgatccattc aaatacttga catctcttga gggacatagt ggtgaagtca  17460
cttgttttgc tgttggaggt caaatgctat actctggttc tgtcgataaa acaatcaaga  17520
tgtgggatct caacaccctg caatgtataa tgaccctgaa gcaacatacc ggcactgtca  17580
cttcactctt atgttgggat aaatgtttga tatcgtcttc cttggatggg accataaaag  17640
tttgggctta ttctgaaaac ggaatcttga aagttgttca aactcgcaga caagaacaga  17700
gtagtgttca tgctctttct ggtatgcatg atgcagaagc caaaccgata atattctgct  17760
cttaccaaaa cggaaccgtt ggcattttcg acctaccatc ttttcaagaa agaggaagga  17820
tgttctctac gcacacgatc gccacactca caattggtcc tcaaggattg ttattcagtg  17880
gagacgagag tggtaacttg cgtgtatgga ccttagctgc tggcaacaaa gtttagtctt  17940
ttcgactaaa gaattctgat ttaattttgt ggtttatatg ttgagttaac tgttaagaga  18000
gttttatttt gtaataggtg tatcagtcaa taaacaatct ttgtatcaac caaatgtaat  18060
```

```
ttttctcgtt aattcgattt cagagttttt actttaagat aaacaaactc tttcacacat  18120

catttaatga aagtggagaa gcttaaaaaa caaacaaaga aactgatcca tttttggcgg  18180

gtcttcttct actcttattc atatgtgtta acgaactata gcgtaaaatt cagagcaagc  18240

gatctccgat ttgaacgtgg ctatcaccgg aggcccacca ctacgggcga tacgctctaa  18300

gtgaggatta aagtgctctg gtggtgacgt tgaagaaact cgcccatggt ttttgttatc  18360

tctgcagcca agtgtcgttc tttcttcgcc acttctcatc aagctacagt gaatttaaaa  18420

atggcgtctt tctttgatct cgtatacata agctggattg gtttcttaaa caaattcctc  18480

tccttttggg tcttctgggt ttgccttgta agtgtttgtg tttttgcctc tgagaaaaaa  18540

tcgcggccct agacgcccat caacaagttt gtacaaaaaa gcaggct                18587
```

<210> SEQ ID NO 35
<211> LENGTH: 1502
<212> TYPE: DNA
<213> ORGANISM: Brassica rapa

<400> SEQUENCE: 35

```
ggacatgcat tttaaaagat tccttccatc tgaaccgatc ttattaagct caactcaata     60

gctccggtct ctgctcacct cagctcttac gacgccggcg gagatgaatt tgcgttttgc    120

ggcggtggta tgctgtcttt ggctgtgttc tgtcgtgtgt gtggctcaga gcggatctag    180

cagtactgac gatgcgatct ggtcgctgga aagtaaattg atggcgacat ctaatgcttc    240

acagcttctc atggtgcctc tcactttgat tcaaggagct gcctccaaag gagctgtgtg    300

tctggatggg acactacctg gttaccatct ccaccgtggt ttgggatcag gtgctaaccg    360

ctggctcatc caactcgagg gaggaggatg gtgcaacacg cggaggagct gtatcttcag    420

gaaaaccaca cgccgtggct catcaaacca catggagaaa gtcttggcct tcactggaat    480

cttaagcaac aaagctaacg agaaccctga cttcttcaac tggaacagag tcaaattgcg    540

ttactgtgat ggcgcatctt tcacaggcga tagtgaagac cagagttcac aactatacta    600

tagaggacaa agaatctggc aagtggctat ggaagaactg ctctctaaag gcatgcagaa    660

agcagatcag gctctgctct ctggatgttc agctggagga ttagcttcca tcctgcactg    720

tgatcagttc aaggcagtct tacctggtac tacgaaagtc aaatgcttaa gtgatgctgg    780

aatgtttatg gatgcagtgg atgtctctgg aggccactcg ctgaggaaca tgttccaagg    840

tgttgttaca gtacagaatc tccaaaagga actgtccact acttgtacta agcatttgga    900

tccaacttcg tgttttttc ctcagaactt ggtttcagag atcaagactc ccatgtttct    960

tctaaatgca gcttacgacg cttggcaggt acaagagagc ttagctcctc catctgctga   1020

cagaaccggc tcttggaaag catgcaaatc agatcactcc cattgtaact catctcaaat   1080

ccacttcttc caagacttca ggagtcaaat ggtgaatgct gtaaagactt tctcggcctc   1140

ggctcacaac ggtctgttca taaactcatg cttcgcccac tgccaatccg agagacagga   1200

cacttggttt gcaccagatt ctcctaagct ttatggcaag acggtagctg aatctgttgg   1260

tgattggtac tttgacagga aaacagtcaa ggccattgac tgtccttacc cttgtgacaa   1320

aacatgtcac gatctcacct tctgagttta acaacaacat cctcaaactc aaacagcttc   1380

ttgatttttt ttttttttta cataatttat gatgcttatc ttctccttgt cgttgtgttt   1440

gttatctgtg tttgagtata tgcattggat ttgaaagctg aaaaaaaaaa aaaaaaaaaa   1500

aa                                                                  1502
```

```
<210> SEQ ID NO 36
<211> LENGTH: 413
<212> TYPE: PRT
<213> ORGANISM: Brassica rapa

<400> SEQUENCE: 36

Met Asn Leu Arg Phe Ala Ala Val Val Cys Cys Leu Trp Leu Cys Ser
1               5                   10                  15

Val Val Cys Val Ala Gln Ser Gly Ser Ser Ser Thr Asp Asp Ala Ile
            20                  25                  30

Trp Ser Leu Glu Ser Lys Leu Met Ala Thr Ser Asn Ala Ser Gln Leu
        35                  40                  45

Leu Met Val Pro Leu Thr Leu Ile Gln Gly Ala Ala Ser Lys Gly Ala
    50                  55                  60

Val Cys Leu Asp Gly Thr Leu Pro Gly Tyr His Leu His Arg Gly Leu
65                  70                  75                  80

Gly Ser Gly Ala Asn Arg Trp Leu Ile Gln Leu Glu Gly Gly Gly Trp
                85                  90                  95

Cys Asn Thr Arg Arg Ser Cys Ile Phe Arg Lys Thr Thr Arg Arg Gly
            100                 105                 110

Ser Ser Asn His Met Glu Lys Val Leu Ala Phe Thr Gly Ile Leu Ser
        115                 120                 125

Asn Lys Ala Asn Glu Asn Pro Asp Phe Phe Asn Trp Asn Arg Val Lys
    130                 135                 140

Leu Arg Tyr Cys Asp Gly Ala Ser Phe Thr Gly Asp Ser Glu Asp Gln
145                 150                 155                 160

Ser Ser Gln Leu Tyr Tyr Arg Gly Gln Arg Ile Trp Gln Val Ala Met
                165                 170                 175

Glu Glu Leu Leu Ser Lys Gly Met Gln Lys Ala Asp Gln Ala Leu Leu
            180                 185                 190

Ser Gly Cys Ser Ala Gly Gly Leu Ala Ser Ile Leu His Cys Asp Gln
        195                 200                 205

Phe Lys Ala Val Leu Pro Gly Thr Thr Lys Val Lys Cys Leu Ser Asp
    210                 215                 220

Ala Gly Met Phe Met Asp Ala Val Asp Val Ser Gly Gly His Ser Leu
225                 230                 235                 240

Arg Asn Met Phe Gln Gly Val Val Thr Val Gln Asn Leu Gln Lys Glu
                245                 250                 255

Leu Ser Thr Thr Cys Thr Lys His Leu Asp Pro Thr Ser Cys Phe Phe
            260                 265                 270

Pro Gln Asn Leu Val Ser Glu Ile Lys Thr Pro Met Phe Leu Leu Asn
        275                 280                 285

Ala Ala Tyr Asp Ala Trp Gln Val Gln Glu Ser Leu Ala Pro Pro Ser
    290                 295                 300

Ala Asp Arg Thr Gly Ser Trp Lys Ala Cys Lys Ser Asp His Ser His
305                 310                 315                 320

Cys Asn Ser Ser Gln Ile His Phe Phe Gln Asp Phe Arg Ser Gln Met
                325                 330                 335

Val Asn Ala Val Lys Thr Phe Ser Ala Ser Ala His Asn Gly Leu Phe
            340                 345                 350

Ile Asn Ser Cys Phe Ala His Cys Gln Ser Glu Arg Gln Asp Thr Trp
        355                 360                 365

Phe Ala Pro Asp Ser Pro Lys Leu Tyr Gly Lys Thr Val Ala Glu Ser
    370                 375                 380
```

-continued

```
Val Gly Asp Trp Tyr Phe Asp Arg Lys Thr Val Lys Ala Ile Asp Cys
385                 390                 395                 400

Pro Tyr Pro Cys Asp Lys Thr Cys His Asp Leu Thr Phe
                405                 410
```

<210> SEQ ID NO 37
<211> LENGTH: 1616
<212> TYPE: DNA
<213> ORGANISM: Helianthus annuus

<400> SEQUENCE: 37

```
gcggggggct tcccccgtgc agaaaacata tatgggctct ctctctctct cgtctctctc     60

tctctctctc ctcttgcttc tgttctaaac ttaacataga ttctgattcc tgttgataag    120

gtacaaagat ttcacaatca aatcccacac atcattcagt tcttaactaa aagaaaaaac    180

aattatatct atctctctag tacacataac aaatcactgt cagaggtcca agatttgaga    240

atgaggaacc aggtttgtac atgggttttg atattcttga ttggattcgg tgttttgcga    300

agtgggtatg agtttgctga gacagatttc cattacaata ccacccatat tatttcattc    360

atggaagctt cttcttctgc tgttgttgcc cctaatcctc ttattgttgg tctcactctt    420

attccaggag ctgctgctaa aggagctgta tgtttggatg gaacattacc cgggtatcat    480

ttgcaccgag gattcgaatc gggcgcaaac agttggctca ttcaattgga gggtggagga    540

tggtgtaaca ctgttagatc ttgtgtttac cggaaaacaa ccaggcgtgg atcatcaaaa    600

ttttttgaga aacagttggc gtttaccgga attttgagca ataaagctga agataatcca    660

gatttttca actggaatcg agtaaaggtc cgctattgtg atggtgcatc atttgccggg    720

gatgcagaag ataaggctaa tgacctccaa tttagaggcc acaaaatatt cttggcagca    780

atggaagact tgatgtcaaa gggattgcga aatgctgatc aagcacttct ttctgggtgc    840

tcggcaggcg gtttggcatc tattttacac tgtgacgagt ttagttcttt attccccgga    900

agcactaaag tcaagtgttt ggctgatgct ggaatgttta tggacgcgat tgatgttgct    960

ggtgcacgta cactaaggaa catgtatgaa ggtgttgtaa ccttgcaggg ggttgctaaa   1020

aacttatcgc cggcatgtat cagccaactc gacccaacct cgtgcttttt tcctcagaac   1080

atagttcccc acattaagac tcctatgttc atcctcaatg ctgcatacga ttcttggcag   1140

gttgtttcca gtttatgcac tccacccgcg gatcctactg gtgcttggaa ggcatgcaag   1200

cacaacactg acagttgttc accatctcag atgaacttct ttcaagattt cagaaaccag   1260

atgctgaatg cacttaaagg attctctacg tccaaacaaa acgggctgtt tataaattct   1320

tgtttcgcgc attgccaaac agagaggcag gatacatggt ttgcagatga ttctccgatt   1380

attaacaaca agccggtagc gttggcggtg ggagactggt atttcgatag atcaagcgtg   1440

aaagaaacag actgcccgta tccatgtgac aagagttgtc acaatctgca atttagatca   1500

taaatttatg taacatcttc gtatatttta tttgaatgaa attaataaac tgcatttccc   1560

attgtttggt caagaacaag ttgggatatt attattatta acaaaattat tgtgat       1616
```

<210> SEQ ID NO 38
<211> LENGTH: 420
<212> TYPE: PRT
<213> ORGANISM: Helianthus annuus

<400> SEQUENCE: 38

```
Met Arg Asn Gln Val Cys Thr Trp Val Leu Ile Phe Leu Ile Gly Phe
1               5                   10                  15
```

-continued

```
Gly Val Leu Arg Ser Gly Tyr Glu Phe Ala Glu Thr Asp Phe His Tyr
            20                  25                  30

Asn Thr Thr His Ile Ile Ser Phe Met Glu Ala Ser Ser Ser Ala Val
        35                  40                  45

Val Ala Pro Asn Pro Leu Ile Val Gly Leu Thr Leu Ile Pro Gly Ala
    50                  55                  60

Ala Ala Lys Gly Ala Val Cys Leu Asp Gly Thr Leu Pro Gly Tyr His
65                  70                  75                  80

Leu His Arg Gly Phe Glu Ser Gly Ala Asn Ser Trp Leu Ile Gln Leu
                85                  90                  95

Glu Gly Gly Gly Trp Cys Asn Thr Val Arg Ser Cys Val Tyr Arg Lys
            100                 105                 110

Thr Thr Arg Arg Gly Ser Ser Lys Phe Phe Glu Lys Gln Leu Ala Phe
        115                 120                 125

Thr Gly Ile Leu Ser Asn Lys Ala Glu Asp Asn Pro Asp Phe Phe Asn
    130                 135                 140

Trp Asn Arg Val Lys Val Arg Tyr Cys Asp Gly Ala Ser Phe Ala Gly
145                 150                 155                 160

Asp Ala Glu Asp Lys Ala Asn Asp Leu Gln Phe Arg Gly His Lys Ile
                165                 170                 175

Phe Leu Ala Ala Met Glu Asp Leu Met Ser Lys Gly Leu Arg Asn Ala
            180                 185                 190

Asp Gln Ala Leu Leu Ser Gly Cys Ser Ala Gly Gly Leu Ala Ser Ile
        195                 200                 205

Leu His Cys Asp Glu Phe Ser Ser Leu Phe Pro Gly Ser Thr Lys Val
    210                 215                 220

Lys Cys Leu Ala Asp Ala Gly Met Phe Met Asp Ala Ile Asp Val Ala
225                 230                 235                 240

Gly Ala Arg Thr Leu Arg Asn Met Tyr Glu Gly Val Val Thr Leu Gln
                245                 250                 255

Gly Val Ala Lys Asn Leu Ser Pro Ala Cys Ile Ser Gln Leu Asp Pro
            260                 265                 270

Thr Ser Cys Phe Phe Pro Gln Asn Ile Val Pro His Ile Lys Thr Pro
        275                 280                 285

Met Phe Ile Leu Asn Ala Ala Tyr Asp Ser Trp Gln Val Val Ser Ser
    290                 295                 300

Leu Cys Thr Pro Pro Ala Asp Pro Thr Gly Ala Trp Lys Ala Cys Lys
305                 310                 315                 320

His Asn Thr Asp Ser Cys Ser Pro Ser Gln Met Asn Phe Phe Gln Asp
                325                 330                 335

Phe Arg Asn Gln Met Leu Asn Ala Leu Lys Gly Phe Ser Thr Ser Lys
            340                 345                 350

Gln Asn Gly Leu Phe Ile Asn Ser Cys Phe Ala His Cys Gln Thr Glu
        355                 360                 365

Arg Gln Asp Thr Trp Phe Ala Asp Asp Ser Pro Ile Ile Asn Asn Lys
    370                 375                 380

Pro Val Ala Leu Ala Val Gly Asp Trp Tyr Phe Asp Arg Ser Ser Val
385                 390                 395                 400

Lys Glu Thr Asp Cys Pro Tyr Pro Cys Asp Lys Ser Cys His Asn Leu
                405                 410                 415

Gln Phe Arg Ser
            420
```

<210> SEQ ID NO 39
<211> LENGTH: 1627
<212> TYPE: DNA
<213> ORGANISM: Ricinus communis

<400> SEQUENCE: 39

```
ctgtaagctc tgaggagcag tgggtggcga gctcaaaata agggaaaaag cagagtctag     60

gccctgtgct tctctcctct gcactctgaa cttgtgcatt tgagagaatg aagcaaggga    120

tggtgatgga gatggggata atgctgttat acggttgtat tttgattgga atggttttgg    180

gcggatctgt tgatgttatt ctaaaatcag aagtcatgtt gccttttctg gagagcggtg    240

cttcttcccc tgctcctcct gctgctccca aacctcttat ggtcggcctt actcttattc    300

agggagctga cgccaaagga gctgtctgct tggatggaac attgcctgcc taccacttgc    360

atcgtgggtc tggatcgggt caaaacagtt ggctcattca attagaggga ggcgggtggt    420

gtaataccat caggagctgt gtttaccgca aaactacacg acgtggttca tccaaattta    480

tggaaaaagt attacctttc actggaatat taagcaataa accagacgaa aatccagatt    540

tctttaattg gaacagagtc aagttacgat attgtgatgg ggcatctttc agtggggatt    600

atcatgatga ggctgcacag ctttattttc gaggacaacg aatctggtca gctgctatgg    660

agaatctaat ggctgaagga atgctaaatg ccactcaggc tcttctttct ggatgctctg    720

ctggaggtct ggcatccata ttacactgtg atgagttcag ggacttgttt ccacaatcta    780

caaaagtgaa atgcttaagt gatgctggac tttttcttga tgcaattgat gtgtctggca    840

atcgcacgct acggaatatg tatgaaggtg tagttagctt acagaaagtg caaaagaatc    900

taccgagcac gtgtaccagc cgactggatc caacttcatg cttcttcccc cagaatttga    960

ttgctaatat taagactcca ttgtttattc tcaatgcagc ctatgataca tggcaggttc   1020

aagctagttt ggctccacct acagctgatc ctcaaggttc ttggaatgaa tgcaaacaaa   1080

atcatgcaca atgtaattca tcccaaatcc aatttttgca agacttcagg aatcaaatgc   1140

tagatgccat aaacgtcttc tcaatgacaa ctcaaaatgg tttattcata aattcttgct   1200

tttctcattg ccaatctgag agacaagata catggtttgc cactgattct ccagtcattc   1260

gggacaagag gatctcacaa tctgttggag actggtattt tgatcgagtt gatgttaaag   1320

ccattgactg tgcatatccc tgtgatagta gctgccataa tctagtattc aagtgagtgg   1380

aaatcttatc tgctcttcat tatcttgtct tcatttattt ccccatttgt catatgtaga   1440

aattgtaaca tttatttgtg aagtcatctc taatgtgccc tgatatgtga tttattagtt   1500

tgtcgttatc tcagaagaac ttataagttc actgagctca aaaatgtaac atagttgaga   1560

tgtttcaaga aagctataag ctttatggtt ctgtcatttt cagtattgcc attattttcc   1620

tttggta                                                             1627
```

<210> SEQ ID NO 40
<211> LENGTH: 422
<212> TYPE: PRT
<213> ORGANISM: Ricinus communis

<400> SEQUENCE: 40

```
Met Lys Gln Gly Met Val Met Glu Met Gly Ile Met Leu Leu Tyr Gly
1               5                   10                  15

Cys Ile Leu Ile Gly Met Val Leu Gly Gly Ser Val Asp Val Ile Leu
            20                  25                  30

Lys Ser Glu Val Met Leu Pro Phe Leu Glu Ser Gly Ala Ser Ser Pro
        35                  40                  45
```

```
Ala Pro Pro Ala Ala Pro Lys Pro Leu Met Val Gly Leu Thr Leu Ile
    50                  55                  60

Gln Gly Ala Asp Ala Lys Gly Ala Val Cys Leu Asp Gly Thr Leu Pro
65                  70                  75                  80

Ala Tyr His Leu His Arg Gly Ser Gly Ser Gly Gln Asn Ser Trp Leu
                85                  90                  95

Ile Gln Leu Glu Gly Gly Gly Trp Cys Asn Thr Ile Arg Ser Cys Val
            100                 105                 110

Tyr Arg Lys Thr Thr Arg Arg Gly Ser Ser Lys Phe Met Glu Lys Val
        115                 120                 125

Leu Pro Phe Thr Gly Ile Leu Ser Asn Lys Pro Asp Glu Asn Pro Asp
    130                 135                 140

Phe Phe Asn Trp Asn Arg Val Lys Leu Arg Tyr Cys Asp Gly Ala Ser
145                 150                 155                 160

Phe Ser Gly Asp Tyr His Asp Glu Ala Ala Gln Leu Tyr Phe Arg Gly
                165                 170                 175

Gln Arg Ile Trp Ser Ala Ala Met Glu Asn Leu Met Ala Glu Gly Met
            180                 185                 190

Leu Asn Ala Thr Gln Ala Leu Leu Ser Gly Cys Ser Ala Gly Gly Leu
        195                 200                 205

Ala Ser Ile Leu His Cys Asp Glu Phe Arg Asp Leu Phe Pro Gln Ser
    210                 215                 220

Thr Lys Val Lys Cys Leu Ser Asp Ala Gly Leu Phe Leu Asp Ala Ile
225                 230                 235                 240

Asp Val Ser Gly Asn Arg Thr Leu Arg Asn Met Tyr Glu Gly Val Val
                245                 250                 255

Ser Leu Gln Lys Val Gln Lys Asn Leu Pro Ser Thr Cys Thr Ser Arg
            260                 265                 270

Leu Asp Pro Thr Ser Cys Phe Phe Pro Gln Asn Leu Ile Ala Asn Ile
        275                 280                 285

Lys Thr Pro Leu Phe Ile Leu Asn Ala Ala Tyr Asp Thr Trp Gln Val
    290                 295                 300

Gln Ala Ser Leu Ala Pro Pro Thr Ala Asp Pro Gln Gly Ser Trp Asn
305                 310                 315                 320

Glu Cys Lys Gln Asn His Ala Gln Cys Asn Ser Ser Gln Ile Gln Phe
                325                 330                 335

Leu Gln Asp Phe Arg Asn Gln Met Leu Asp Ala Ile Asn Val Phe Ser
            340                 345                 350

Met Thr Thr Gln Asn Gly Leu Phe Ile Asn Ser Cys Phe Ser His Cys
        355                 360                 365

Gln Ser Glu Arg Gln Asp Thr Trp Phe Ala Thr Asp Ser Pro Val Ile
    370                 375                 380

Arg Asp Lys Arg Ile Ser Gln Ser Val Gly Asp Trp Tyr Phe Asp Arg
385                 390                 395                 400

Val Asp Val Lys Ala Ile Asp Cys Ala Tyr Pro Cys Asp Ser Ser Cys
                405                 410                 415

His Asn Leu Val Phe Lys
            420
```

<210> SEQ ID NO 41
<211> LENGTH: 1564
<212> TYPE: DNA
<213> ORGANISM: Glycine max

<400> SEQUENCE: 41
ggctttgatt cctccacatg agaagagaaa cgaccaacgg ttcttattta aagcaaataa 60
taaatactga aagacaagac aagagataaa taataactag ttgtagctgc tggggagagt 120
ggaacataat aaacatgaca atgaagctgc tgcttttggt agccgttgtt gaagttgcat 180
gcttagtttc tgggatcttg tcctttggat ctgagacact ctctgagctt tctttcttag 240
aaaacgatgt cgtctcaaca gcaagacctt cctcttcatc tcaacctctt atggtcgacc 300
tcactctcat tcaaggagct gattctaaag gagctgtctg tttggatgga acggtgcctg 360
gataccattt ggatcgtgga tttggatctg gtgcagatag ttggctaatt catttggagg 420
gaggaggatg gtgtaatacc atcagaaact gtgtctatag aaaaaatact cgtcgtggat 480
cctcgaaata catggaaaat caaataccat tcacgggaat attgagcaac aaacctgaag 540
aaaaccctga tttctttaac tggaatagag ttaaattacg gtactgtgat ggggcgtctt 600
tcagtggaga tagtgaagat gagtctgcac agcttcaatt tcgaggacaa aaaatatggc 660
tagctgcaat ggaggaatta atgtccaaag gaatgcagaa agccgatcag gcacttctct 720
ctggatgctc tgcgggtggt ctggcatcga taatacactg tgatgagttc cggagcttgt 780
ttccaaaatc ttccaaagtc aaatgtttga gtgatggagg tttttttctt gacgtaatgg 840
atgtatctgg gggacgcaca ctgaggactc tttttggagg tgtggttcag ttgcaggagt 900
tacaaaaaaa tctgccaaaa agttgtcttg accaactaga cccaacttcg tgcttctttc 960
ctcagaatat gatcgaacat gttgagaccc cattgtttct actcaacgct gcttatgatg 1020
tgtggcaggt ccaagctagt ttagccccac cttcagctga ccgccttggc tcttggaatg 1080
aatgcaaatc gaaccatgca aattgtagct catctcaaat gcagttcctc caagacttca 1140
gaaatcaaat gcttagtgac attaaagact tctcgagctc atctcaaact gggctattca 1200
taaattcttg ttttgctcat tgtcagtctg agagacagga gacatggttt gctgatgact 1260
ctccccttat cgaggacaag ccaattgcag ttgctattgg agactggtat tttgatcgag 1320
aagttgtcaa agctattgac tgtgcttacc cgtgtgacaa cagctgccat aatctggtgt 1380
ttaactttaa gtgaacaaaa tttgttgtct cctcgttcca ctttaatcct tgtaactgca 1440
atgagtattc cacaattacc attcattgat tattatggaa agaccattct tagtttatca 1500
gcattttcat tagtagtcat ttatctactt ttggttagaa tataaaaaaa tggacagtga 1560
tttt 1564

<210> SEQ ID NO 42
<211> LENGTH: 419
<212> TYPE: PRT
<213> ORGANISM: Glycine max

<400> SEQUENCE: 42

Met Thr Met Lys Leu Leu Leu Leu Val Ala Val Val Glu Val Ala Cys
1 5 10 15

Leu Val Ser Gly Ile Leu Ser Phe Gly Ser Glu Thr Leu Ser Glu Leu
20 25 30

Ser Phe Leu Glu Asn Asp Val Val Ser Thr Ala Arg Pro Ser Ser Ser
35 40 45

Ser Gln Pro Leu Met Val Asp Leu Thr Leu Ile Gln Gly Ala Asp Ser
50 55 60

Lys Gly Ala Val Cys Leu Asp Gly Thr Val Pro Gly Tyr His Leu Asp
65 70 75 80

-continued

```
Arg Gly Phe Gly Ser Gly Ala Asp Ser Trp Leu Ile His Leu Glu Gly
                85                  90                  95

Gly Gly Trp Cys Asn Thr Ile Arg Asn Cys Val Tyr Arg Lys Asn Thr
            100                 105                 110

Arg Arg Gly Ser Ser Lys Tyr Met Glu Asn Gln Ile Pro Phe Thr Gly
        115                 120                 125

Ile Leu Ser Asn Lys Pro Glu Glu Asn Pro Asp Phe Phe Asn Trp Asn
    130                 135                 140

Arg Val Lys Leu Arg Tyr Cys Asp Gly Ala Ser Phe Ser Gly Asp Ser
145                 150                 155                 160

Glu Asp Glu Ser Ala Gln Leu Gln Phe Arg Gly Gln Lys Ile Trp Leu
                165                 170                 175

Ala Ala Met Glu Glu Leu Met Ser Lys Gly Met Gln Lys Ala Asp Gln
            180                 185                 190

Ala Leu Leu Ser Gly Cys Ser Ala Gly Gly Leu Ala Ser Ile Ile His
        195                 200                 205

Cys Asp Glu Phe Arg Ser Leu Phe Pro Lys Ser Ser Lys Val Lys Cys
    210                 215                 220

Leu Ser Asp Gly Gly Phe Phe Leu Asp Val Met Asp Val Ser Gly Gly
225                 230                 235                 240

Arg Thr Leu Arg Thr Leu Phe Gly Gly Val Val Gln Leu Gln Glu Leu
                245                 250                 255

Gln Lys Asn Leu Pro Lys Ser Cys Leu Asp Gln Leu Asp Pro Thr Ser
            260                 265                 270

Cys Phe Phe Pro Gln Asn Met Ile Glu His Val Glu Thr Pro Leu Phe
        275                 280                 285

Leu Leu Asn Ala Ala Tyr Asp Val Trp Gln Val Gln Ala Ser Leu Ala
    290                 295                 300

Pro Pro Ser Ala Asp Arg Leu Gly Ser Trp Asn Glu Cys Lys Ser Asn
305                 310                 315                 320

His Ala Asn Cys Ser Ser Ser Gln Met Gln Phe Leu Gln Asp Phe Arg
                325                 330                 335

Asn Gln Met Leu Ser Asp Ile Lys Asp Phe Ser Ser Ser Ser Gln Thr
            340                 345                 350

Gly Leu Phe Ile Asn Ser Cys Phe Ala His Cys Gln Ser Glu Arg Gln
        355                 360                 365

Glu Thr Trp Phe Ala Asp Asp Ser Pro Leu Ile Glu Asp Lys Pro Ile
    370                 375                 380

Ala Val Ala Ile Gly Asp Trp Tyr Phe Asp Arg Glu Val Val Lys Ala
385                 390                 395                 400

Ile Asp Cys Ala Tyr Pro Cys Asp Asn Ser Cys His Asn Leu Val Phe
                405                 410                 415

Asn Phe Lys
```

<210> SEQ ID NO 43
<211> LENGTH: 1691
<212> TYPE: DNA
<213> ORGANISM: Glycine max

<400> SEQUENCE: 43

```
gtgtctgtta cttagtatca gtaagatagg ctttgtttcc tccacatgag aagagaaagt      60

gagaaactac caatggttct tatttaaagc aaataaatat tgaaagacaa gaggtaacag     120

ataaatagag tgtgtgaata ataataagta gttgtagctg ggagagtggg aacattgtca     180
```

-continued

```
gcttcataat aaagatgaca atgaagctgg ttttggtagt tgttgttgaa gttgcatgct    240
tagtttctgg gatcttgtcc tttggatctg agacactctc tgagctttct ttcttagaaa    300
atgatgtcgt ctcaacaaca agaccttcct cttcatctca acttcaacct caacctcaac    360
ctcaacctct tatggtggac ctcactctca ttcatgaagc tgattctaaa ggagctgtct    420
gtttggatgg aacggtgcct ggataccatt tggatcgtgg atttggatct ggtgcagata    480
gttggcttat tcatttggag ggaggaggat ggtgtaatac catcagaaac tgtgtctata    540
gaaaaaatac tcgtcgtgga tcctcaaaat acatggaaaa tcaaatacca ttcacgggaa    600
tattgagcaa caaacctgaa gaaaaccctg atttctttaa ctggaataga gttaaattac    660
ggtactgtga tggagcatct ttcagtggag atagtgaaga tgagtctgca cagctccagt    720
ttcgaggaca aaaaatatgg ctagctgcaa tggaggaatt aatgtccaaa ggaatgcaga    780
aagccgatca ggcacttctc tctggatgct ctgcgggtgg tctggcatcc ataatacact    840
gtgatgagtt cgggagcttg tttggaaaat cttccaaagt taaatgtttg agcgatggag    900
gtttttttct tgatgcaatg gatgtatctg gggacgcac actgaggact cttttcggag    960
gtgtggttca gttgcaggat gtacaaaaaa atctgccaaa aagttgtctc gaccaactag   1020
acccaacttc gtgcttcttt cctcagaata tgatcgaaca tgttgagacc ccattgtttc   1080
tactcaatgc tgcttatgat gtgtggcagg tccaagccag tttagcccca ccttcagctg   1140
accgccttgg ttcttggaat gaatgcaaat cgaaccatgc aaattgtagc tcatctcaaa   1200
tgcagttcct tcaagacttc agaaatcaaa tgctgggtga cattaaagac ttctcaagct   1260
catctcaaac tgggctattc ataaattctt gttttgctca ttgtcagtct gagagacagg   1320
agacatggtt tgctgatgac tctcccctta tcgaggacaa gccaattgca gttgctgttg   1380
gagactggta ttttgatcga gaagttgtca aagctattga ctgtgcttac ccatgtgaca   1440
acagctgcca taatctggtg tttaacttta agtgaacaaa atttgttgtc tcctcattac   1500
actttaatcc ttgtaattgc aatgagtatt caacaatcaa cattcattaa ttattatgga   1560
aggacaattc ttggttatca tcattttcac tgatattaag ttatgtcaat aagattcatt   1620
agtagtcatt tatctactct tggttataaa tatccaaaaa tggacaatga attcgtgcat   1680
tggttgctac c                                                        1691
```

```
<210> SEQ ID NO 44
<211> LENGTH: 426
<212> TYPE: PRT
<213> ORGANISM: Glycine max

<400> SEQUENCE: 44

Met Thr Met Lys Leu Val Leu Val Val Val Val Glu Val Ala Cys Leu
1               5                   10                  15

Val Ser Gly Ile Leu Ser Phe Gly Ser Glu Thr Leu Ser Glu Leu Ser
            20                  25                  30

Phe Leu Glu Asn Asp Val Val Ser Thr Thr Arg Pro Ser Ser Ser Ser
        35                  40                  45

Gln Leu Gln Pro Gln Pro Gln Pro Gln Pro Leu Met Val Asp Leu Thr
    50                  55                  60

Leu Ile His Glu Ala Asp Ser Lys Gly Ala Val Cys Leu Asp Gly Thr
65                  70                  75                  80

Val Pro Gly Tyr His Leu Asp Arg Gly Phe Gly Ser Gly Ala Asp Ser
                85                  90                  95

Trp Leu Ile His Leu Glu Gly Gly Gly Trp Cys Asn Thr Ile Arg Asn
```

-continued

```
            100                 105                 110

Cys Val Tyr Arg Lys Asn Thr Arg Arg Gly Ser Ser Lys Tyr Met Glu
        115                 120                 125

Asn Gln Ile Pro Phe Thr Gly Ile Leu Ser Asn Lys Pro Glu Glu Asn
    130                 135                 140

Pro Asp Phe Phe Asn Trp Asn Arg Val Lys Leu Arg Tyr Cys Asp Gly
145                 150                 155                 160

Ala Ser Phe Ser Gly Asp Ser Glu Asp Glu Ser Ala Gln Leu Gln Phe
                165                 170                 175

Arg Gly Gln Lys Ile Trp Leu Ala Ala Met Glu Glu Leu Met Ser Lys
            180                 185                 190

Gly Met Gln Lys Ala Asp Gln Ala Leu Leu Ser Gly Cys Ser Ala Gly
        195                 200                 205

Gly Leu Ala Ser Ile Ile His Cys Asp Glu Phe Gly Ser Leu Phe Gly
    210                 215                 220

Lys Ser Ser Lys Val Lys Cys Leu Ser Asp Gly Gly Phe Phe Leu Asp
225                 230                 235                 240

Ala Met Asp Val Ser Gly Gly Arg Thr Leu Arg Thr Leu Phe Gly Gly
                245                 250                 255

Val Val Gln Leu Gln Asp Val Gln Lys Asn Leu Pro Lys Ser Cys Leu
            260                 265                 270

Asp Gln Leu Asp Pro Thr Ser Cys Phe Phe Pro Gln Asn Met Ile Glu
        275                 280                 285

His Val Glu Thr Pro Leu Phe Leu Leu Asn Ala Ala Tyr Asp Val Trp
    290                 295                 300

Gln Val Gln Ala Ser Leu Ala Pro Pro Ser Ala Asp Arg Leu Gly Ser
305                 310                 315                 320

Trp Asn Glu Cys Lys Ser Asn His Ala Asn Cys Ser Ser Ser Gln Met
                325                 330                 335

Gln Phe Leu Gln Asp Phe Arg Asn Gln Met Leu Gly Asp Ile Lys Asp
            340                 345                 350

Phe Ser Ser Ser Ser Gln Thr Gly Leu Phe Ile Asn Ser Cys Phe Ala
        355                 360                 365

His Cys Gln Ser Glu Arg Gln Glu Thr Trp Phe Ala Asp Asp Ser Pro
    370                 375                 380

Leu Ile Glu Asp Lys Pro Ile Ala Val Ala Val Gly Asp Trp Tyr Phe
385                 390                 395                 400

Asp Arg Glu Val Val Lys Ala Ile Asp Cys Ala Tyr Pro Cys Asp Asn
                405                 410                 415

Ser Cys His Asn Leu Val Phe Asn Phe Lys
            420                 425
```

<210> SEQ ID NO 45
<211> LENGTH: 1467
<212> TYPE: DNA
<213> ORGANISM: Glycine max

<400> SEQUENCE: 45

```
atgaaggtga ttctattact catagcagca tcattttcct ttgtttctgt acttagatct      60

gaggctgagc atttgttcca aaacgatgcc gtttcactgg cagtggaagt accgcccgga     120

cctccacctc tcatggtccc cctcactctc attcagggag ctgcttccaa aggagccgtc     180

tgtttggatg gaacattgcc tggttaccac tttcatcctg gatttggatc tggggcaaat     240

agttggctca ttcaattgga gggaggagga tggtgtaata ccatcagtag ttgtgtcttt     300
```

```
agaaaaacta ctcgtcgtgg ttcctcaaaa tacatggaaa agcaactagc attcacaggg    360

ttgttgagca ataaagctga agaaaaccct gatttcttta actggaacag agttaaagta    420

cggtactgtg atggagcatc tttcagtgga gatagtcaaa acgaggttgc acagcttcaa    480

tttcgaggac aaaaaatatg gcaagctgca atgcaggaat tattgttcaa gggaatgcag    540

aaggccaacc aggccctttt gtctggatgc tctgcaggtg gtctggcatc tataatacat    600

tgtgatgagt tccggagctt gtttcctaca tctaccaaag tgaaatgttt gagtgacgcc    660

gggtttttcc tagatgcagt tgatgtatct gggggtcaca cactgaggaa tctgtttgga    720

ggtgtagtta agttacagga ggtgcaaaaa aatctgccaa atagttgtct caaccaactg    780

gacccaactt cgtgtttttt tcctcagaat ttgatcaact atgttgagac tccactgttt    840

ctgctcaatg cagcttatga tgcatggcag gtccaagaaa gtttggtccc acattcagca    900

gatccccatg gctcttggaa tgattgtaaa gcaaatcatg cacactgtaa ctcatctcaa    960

attcagttcc tccaagactt cagaaatcaa atgctaaatg atgtgaaagg cttctctgag   1020

acatctcaaa ctgggttatt cataaattct tgttttgctc attgccagtc tgagagacaa   1080

gatacatggt ttgctgatga ctctccactc attaacaacg tgccagttgc aattgctgtt   1140

ggagactggt tttggatcgg gaaaactgtc aaagctatcg actgtgctta cccctgtgac   1200

aatacctgcc ataatctggt cttcaatgct ggtaaatctg ctgcggtgga ctaccagtcc   1260

acaagtgatg atggcatacc taccaatacc atgaccatga tatattccca ctccacgagg   1320

ctgactttta gtactggcct atatatgcta cgtgttttat tggcatttac atgttcctag   1380

tgcactatgg acagttttag cccagaaaaa caaatgtact atgggcagat tcgttagtcc   1440

ctattcaatc ttccatttaa gccactt                                       1467
```

```
<210> SEQ ID NO 46
<211> LENGTH: 459
<212> TYPE: PRT
<213> ORGANISM: Glycine max

<400> SEQUENCE: 46

Met Lys Val Ile Leu Leu Leu Ile Ala Ala Ser Phe Ser Phe Val Ser
1               5                   10                  15

Val Leu Arg Ser Glu Ala Glu His Leu Phe Gln Asn Asp Ala Val Ser
            20                  25                  30

Leu Ala Val Glu Val Pro Pro Gly Pro Pro Pro Leu Met Val Pro Leu
        35                  40                  45

Thr Leu Ile Gln Gly Ala Ala Ser Lys Gly Ala Val Cys Leu Asp Gly
    50                  55                  60

Thr Leu Pro Gly Tyr His Phe His Pro Gly Phe Gly Ser Gly Ala Asn
65                  70                  75                  80

Ser Trp Leu Ile Gln Leu Glu Gly Gly Gly Trp Cys Asn Thr Ile Ser
                85                  90                  95

Ser Cys Val Phe Arg Lys Thr Thr Arg Arg Gly Ser Ser Lys Tyr Met
            100                 105                 110

Glu Lys Gln Leu Ala Phe Thr Gly Leu Leu Ser Asn Lys Ala Glu Glu
        115                 120                 125

Asn Pro Asp Phe Phe Asn Trp Asn Arg Val Lys Val Arg Tyr Cys Asp
    130                 135                 140

Gly Ala Ser Phe Ser Gly Asp Ser Gln Asn Glu Val Ala Gln Leu Gln
145                 150                 155                 160
```

```
Phe Arg Gly Gln Lys Ile Trp Gln Ala Ala Met Gln Glu Leu Leu Phe
                165                 170                 175

Lys Gly Met Gln Lys Ala Asn Gln Ala Leu Leu Ser Gly Cys Ser Ala
            180                 185                 190

Gly Gly Leu Ala Ser Ile Ile His Cys Asp Glu Phe Arg Ser Leu Phe
        195                 200                 205

Pro Thr Ser Thr Lys Val Lys Cys Leu Ser Asp Ala Gly Phe Phe Leu
    210                 215                 220

Asp Ala Val Asp Val Ser Gly Gly His Thr Leu Arg Asn Leu Phe Gly
225                 230                 235                 240

Gly Val Val Lys Leu Gln Glu Val Gln Lys Asn Leu Pro Asn Ser Cys
                245                 250                 255

Leu Asn Gln Leu Asp Pro Thr Ser Cys Phe Phe Pro Gln Asn Leu Ile
            260                 265                 270

Asn Tyr Val Glu Thr Pro Leu Phe Leu Leu Asn Ala Ala Tyr Asp Ala
        275                 280                 285

Trp Gln Val Gln Glu Ser Leu Val Pro His Ser Ala Asp Pro His Gly
    290                 295                 300

Ser Trp Asn Asp Cys Lys Ala Asn His Ala His Cys Asn Ser Ser Gln
305                 310                 315                 320

Ile Gln Phe Leu Gln Asp Phe Arg Asn Gln Met Leu Asn Asp Val Lys
                325                 330                 335

Gly Phe Ser Glu Thr Ser Gln Thr Gly Leu Phe Ile Asn Ser Cys Phe
            340                 345                 350

Ala His Cys Gln Ser Glu Arg Gln Asp Thr Trp Phe Ala Asp Asp Ser
        355                 360                 365

Pro Leu Ile Asn Asn Val Pro Val Ala Ile Ala Val Gly Asp Trp Phe
    370                 375                 380

Leu Asp Arg Lys Thr Val Lys Ala Ile Asp Cys Ala Tyr Pro Cys Asp
385                 390                 395                 400

Asn Thr Cys His Asn Leu Val Phe Asn Ala Gly Lys Ser Ala Ala Val
                405                 410                 415

Asp Tyr Gln Ser Thr Ser Asp Asp Gly Ile Pro Thr Asn Thr Met Thr
            420                 425                 430

Met Ile Tyr Ser His Ser Thr Arg Leu Thr Phe Ser Thr Gly Leu Tyr
        435                 440                 445

Met Leu Arg Val Leu Leu Ala Phe Thr Cys Ser
    450                 455


<210> SEQ ID NO 47
<211> LENGTH: 1756
<212> TYPE: DNA
<213> ORGANISM: Glycine max

<400> SEQUENCE: 47

gtttctgttt ctgtataaat aaataacaaa acagacgagt gagtgaatag tgtgattaag      60

cttttgaggt tgttgcgaga aatgagaatg aagaagctga ttttaatact catagcagca     120

tttaccttcg tttctgtggc tagatctgcg tctgatcatt tcttcgaaaa cgatggcgtt     180

tcactggcag ttgctgcaac gcccggacct ccacctctca tggtccccct cactcttatt     240

cagggagctg cttccaaagg agccgtctgt ttggatggaa cattgcctgg ttaccacttt     300

catcctggat ttggatctgg ggcaaatagt tggctcattc aattggaggg aggaggatgg     360

tgtaatacca tcagaagttg tgtctttaga aaaactactc gtcgtggttc ctcaaaatac     420
```

-continued

```
atggaaaaac aactagcatt cacagggata ttgagcaata aagctgaaga aaaccctgat    480
ttctttaact ggaacagagt tatagtacgt tactgtgatg gggcatcttt cagtggagat    540
agtcaaaatg aggctgcaca gcttcaattc cgaggacaaa aaatatggca agctgcaatg    600
caggaattat tgttcaaggg aatgcagaag gccaaccagg ccctttgtc cggatgctct    660
gcgggtggtc tggcatctat aatacattgt gatgagttcc ggagcttgtt tcctacatct    720
accaaagtga aatgtttgag tgatgcaggg tttttcctag atgcggttga catatctggg    780
ggtcacacac tgaggaatct gtttggaggt gtagttaaat tacaggaggt gcaaaaaaat    840
ctgccaaaca gttgtctcaa ccaactggac ccaacttcgt gctttttcc tcagaatttg    900
atcaaccatg ttgaaactcc attgtttcta ctcaatgcag cttatgatgc atggcaggtc    960
caagaaagtt tggccccaca ttcagcagat ccccatggct cttggaatga ttgtaaatca   1020
aatcatgcac gctgtaactc atctcaaatt cagttcctcc aagacttcag aaatcaaatg   1080
ctaaatgatg tgaaaggctt ctcagggaca tctcaaactg ggttattcat aaattcttgt   1140
tttgctcatt gccagtctga gagacaagat acatggtttg ctgatgactc tccactaatt   1200
aacaacatgc caattgcaat tgctgttgga gactggtttt ttgatcggaa aactgtcaaa   1260
gctatcgact gtgcttaccc ctgtgacaat acatgccata atctggtctt caatgctgtt   1320
aaatctgctg tggtggacta ccagtccaca agtgatgatg acacacctac caataccatg   1380
accatgatat attcccgctc cacaaggctg acttttagta gtggcctata tatgctaagt   1440
attttattgc catttacatg ttcctagtgc actatggata gtttcagccc agaaaagcaa   1500
atgcactata ggcaggttcg ttagtcccta ttcaatcttc catttaagcc acttatggtt   1560
atctgtgtca gctattaatt acaggtcaag acctggattc agcaatagat agtttaggac   1620
ttgaagaacc aatttggtta aggaaaaaca acctgtaact atgtaggtac ctcctccgat   1680
cttctaaata ttttagcgaa ttgcacagtt cactttgtaa tctcaagttt gttataatgg   1740
agtttaagaa atgatt                                                   1756
```

<210> SEQ ID NO 48
<211> LENGTH: 461
<212> TYPE: PRT
<213> ORGANISM: Glycine max

<400> SEQUENCE: 48

```
Met Arg Met Lys Lys Leu Ile Leu Ile Leu Ile Ala Ala Phe Thr Phe
1               5                   10                  15

Val Ser Val Ala Arg Ser Ala Ser Asp His Phe Phe Glu Asn Asp Gly
            20                  25                  30

Val Ser Leu Ala Val Ala Ala Thr Pro Gly Pro Pro Pro Leu Met Val
        35                  40                  45

Pro Leu Thr Leu Ile Gln Gly Ala Ala Ser Lys Gly Ala Val Cys Leu
    50                  55                  60

Asp Gly Thr Leu Pro Gly Tyr His Phe His Pro Gly Phe Gly Ser Gly
65                  70                  75                  80

Ala Asn Ser Trp Leu Ile Gln Leu Glu Gly Gly Gly Trp Cys Asn Thr
                85                  90                  95

Ile Arg Ser Cys Val Phe Arg Lys Thr Thr Arg Arg Gly Ser Ser Lys
            100                 105                 110

Tyr Met Glu Lys Gln Leu Ala Phe Thr Gly Ile Leu Ser Asn Lys Ala
        115                 120                 125

Glu Glu Asn Pro Asp Phe Phe Asn Trp Asn Arg Val Ile Val Arg Tyr
```

-continued

```
    130                 135                 140

Cys Asp Gly Ala Ser Phe Ser Gly Asp Ser Gln Asn Glu Ala Ala Gln
145                 150                 155                 160

Leu Gln Phe Arg Gly Gln Lys Ile Trp Gln Ala Ala Met Gln Glu Leu
                165                 170                 175

Leu Phe Lys Gly Met Gln Lys Ala Asn Gln Ala Leu Leu Ser Gly Cys
            180                 185                 190

Ser Ala Gly Gly Leu Ala Ser Ile Ile His Cys Asp Glu Phe Arg Ser
        195                 200                 205

Leu Phe Pro Thr Ser Thr Lys Val Lys Cys Leu Ser Asp Ala Gly Phe
    210                 215                 220

Phe Leu Asp Ala Val Asp Ile Ser Gly Gly His Thr Leu Arg Asn Leu
225                 230                 235                 240

Phe Gly Gly Val Val Lys Leu Gln Glu Val Gln Lys Asn Leu Pro Asn
                245                 250                 255

Ser Cys Leu Asn Gln Leu Asp Pro Thr Ser Cys Phe Phe Pro Gln Asn
            260                 265                 270

Leu Ile Asn His Val Glu Thr Pro Leu Phe Leu Leu Asn Ala Ala Tyr
        275                 280                 285

Asp Ala Trp Gln Val Gln Glu Ser Leu Ala Pro His Ser Ala Asp Pro
    290                 295                 300

His Gly Ser Trp Asn Asp Cys Lys Ser Asn His Ala Arg Cys Asn Ser
305                 310                 315                 320

Ser Gln Ile Gln Phe Leu Gln Asp Phe Arg Asn Gln Met Leu Asn Asp
                325                 330                 335

Val Lys Gly Phe Ser Gly Thr Ser Gln Thr Gly Leu Phe Ile Asn Ser
            340                 345                 350

Cys Phe Ala His Cys Gln Ser Glu Arg Gln Asp Thr Trp Phe Ala Asp
        355                 360                 365

Asp Ser Pro Leu Ile Asn Asn Met Pro Ile Ala Ile Ala Val Gly Asp
    370                 375                 380

Trp Phe Phe Asp Arg Lys Thr Val Lys Ala Ile Asp Cys Ala Tyr Pro
385                 390                 395                 400

Cys Asp Asn Thr Cys His Asn Leu Val Phe Asn Ala Val Lys Ser Ala
                405                 410                 415

Val Val Asp Tyr Gln Ser Thr Ser Asp Asp Asp Thr Pro Thr Asn Thr
            420                 425                 430

Met Thr Met Ile Tyr Ser Arg Ser Thr Arg Leu Thr Phe Ser Ser Gly
        435                 440                 445

Leu Tyr Met Leu Ser Ile Leu Leu Pro Phe Thr Cys Ser
    450                 455                 460
```

<210> SEQ ID NO 49
<211> LENGTH: 1593
<212> TYPE: DNA
<213> ORGANISM: Zea mays

<400> SEQUENCE: 49

```
gtcgccacaa cgcacccttt ttgttggctg cacgcatacg cacacggcac atacaccctt      60

ctgtctgtcc tgtggcgcca tccatccgtt cgttacaggt gcgccggccc ggtctctcct     120

cctcccagcc ggccggcggc ctccgcttcg ctcgcccgtc cctgggttct cggttccgcg     180

gcaccaccgc gtgccatggg gcctccgcgg ggctggacac tgcctgccgc cgccgttgcc     240

acggccggcg tcgcctcggt ggtggccacc atcatcttgt ccgcggcggc ggccgatgtg     300
```

```
gtcgaggaga ggctgacggt gcccatgacg atcgtcgctg gcgcagcgtc ggcgggggca    360
gtgtgcctcg acgggagccc gccggcgtac cacctgcacg gcggctccgg cgcgggcgcg    420
cggagctggc tgctccagtt cgagggcggc ggctggtgca acgacgtgcg gtcgtgcgcg    480
gagagggccg ggacgcgccg gggatcgacg cgcctcatgg caaaggccga gtccttctcc    540
ggcatcctca gcaaccgtcc ggccatgaat ccagactttt acaactggaa ccgtgtgaag    600
ctgcgttact gcgacggcgg gtccttcatg ggcgattcag cagtgtatat aaacagctcc    660
tcggtgctct acttcagtgg ccagaggata tgggacgcta ttgtcgccga tctgctcagg    720
aagggactgg cgagagccga caaggttctg ctctcaggct gttcggcagg aggcctagct    780
acgttcttcc actgcgacgg ccttaagcag cggcttggag ccgcagccac ggtgaaatgc    840
ctgagcgacg ccggattttt ccttgatctg agtgacattt ctgggagcaa caccataagg    900
caattcttta gcagcctagt atccctgcag ggaatccaga agaatttgaa catggactgc    960
ctgagttcaa cttcaacaga caatgcatac ctgtgtttct ttccacagtt cgcgcttgcg   1020
aacatccgaa ccccgttttt catcttgaat tcagcttatg atgtatacca gttccaccac   1080
attctggtgc cgccttcgtc tgatcctgga ggccattgga gccgctgcaa gtcggatcct   1140
ggtggatgca acgcaacaca gatcgcaacc ctccaaggac tgagaagtgg aatgctgaca   1200
tctctgagac agtttaaaag caaaccggag gcagggatgt tcatcaactc ctgcttcgcg   1260
cattgccaga gtgagctgca ggacacatgg ttcgcaccaa attctccatc catagataac   1320
aagaaaattg cagaggtggt aggtgattgg tacttcgaaa gaggagctgc cgtggagatt   1380
gactgcgcct atccctgtga ttcaacttgt cgcaacctta taccaattga taagaatggg   1440
ttcgctggcg catgaagtgg acctcgattc agagccatca acatttgccc aaacatgatt   1500
gattacctgt atatattgca cattgcatca caattcaact tggcacatgg atgaataaaa   1560
tgtagagcca gtgctctcga aagatatgca aaa                                1593

<210> SEQ ID NO 50
<211> LENGTH: 419
<212> TYPE: PRT
<213> ORGANISM: Zea mays

<400> SEQUENCE: 50

Met Gly Pro Pro Arg Gly Trp Thr Leu Pro Ala Ala Ala Val Ala Thr
1               5                   10                  15

Ala Gly Val Ala Ser Val Val Ala Thr Ile Ile Leu Ser Ala Ala Ala
            20                  25                  30

Ala Asp Val Val Glu Glu Arg Leu Thr Val Pro Met Thr Ile Val Ala
        35                  40                  45

Gly Ala Ala Ser Ala Gly Ala Val Cys Leu Asp Gly Ser Pro Pro Ala
    50                  55                  60

Tyr His Leu His Gly Gly Ser Gly Ala Gly Ala Arg Ser Trp Leu Leu
65                  70                  75                  80

Gln Phe Glu Gly Gly Gly Trp Cys Asn Asp Val Arg Ser Cys Ala Glu
                85                  90                  95

Arg Ala Gly Thr Arg Arg Gly Ser Thr Arg Leu Met Ala Lys Ala Glu
            100                 105                 110

Ser Phe Ser Gly Ile Leu Ser Asn Arg Pro Ala Met Asn Pro Asp Phe
        115                 120                 125

Tyr Asn Trp Asn Arg Val Lys Leu Arg Tyr Cys Asp Gly Gly Ser Phe
    130                 135                 140
```

```
Met Gly Asp Ser Ala Val Tyr Ile Asn Ser Ser Ser Val Leu Tyr Phe
145                 150                 155                 160

Ser Gly Gln Arg Ile Trp Asp Ala Ile Val Ala Asp Leu Leu Arg Lys
                165                 170                 175

Gly Leu Ala Arg Ala Asp Lys Val Leu Leu Ser Gly Cys Ser Ala Gly
            180                 185                 190

Gly Leu Ala Thr Phe Phe His Cys Asp Gly Leu Lys Gln Arg Leu Gly
        195                 200                 205

Ala Ala Ala Thr Val Lys Cys Leu Ser Asp Ala Gly Phe Phe Leu Asp
    210                 215                 220

Leu Ser Asp Ile Ser Gly Ser Asn Thr Ile Arg Gln Phe Phe Ser Ser
225                 230                 235                 240

Leu Val Ser Leu Gln Gly Ile Gln Lys Asn Leu Asn Met Asp Cys Leu
                245                 250                 255

Ser Ser Thr Ser Thr Asp Asn Ala Tyr Leu Cys Phe Phe Pro Gln Phe
            260                 265                 270

Ala Leu Ala Asn Ile Arg Thr Pro Phe Phe Ile Leu Asn Ser Ala Tyr
        275                 280                 285

Asp Val Tyr Gln Phe His His Ile Leu Val Pro Pro Ser Ser Asp Pro
    290                 295                 300

Gly Gly His Trp Ser Arg Cys Lys Ser Asp Pro Gly Gly Cys Asn Ala
305                 310                 315                 320

Thr Gln Ile Ala Thr Leu Gln Gly Leu Arg Ser Gly Met Leu Thr Ser
                325                 330                 335

Leu Arg Gln Phe Lys Ser Lys Pro Glu Ala Gly Met Phe Ile Asn Ser
            340                 345                 350

Cys Phe Ala His Cys Gln Ser Glu Leu Gln Asp Thr Trp Phe Ala Pro
        355                 360                 365

Asn Ser Pro Ser Ile Asp Asn Lys Lys Ile Ala Glu Val Val Gly Asp
    370                 375                 380

Trp Tyr Phe Glu Arg Gly Ala Ala Val Glu Ile Asp Cys Ala Tyr Pro
385                 390                 395                 400

Cys Asp Ser Thr Cys Arg Asn Leu Ile Pro Ile Asp Lys Asn Gly Phe
                405                 410                 415

Ala Gly Ala
```

<210> SEQ ID NO 51
<211> LENGTH: 1812
<212> TYPE: DNA
<213> ORGANISM: Zea mays

<400> SEQUENCE: 51

```
tttcattccg ggagatactt tacttcacgc acctgtaacg ccgcaccatt gcaccaacac      60

caggcaacgg cacgccgcgt tatgcgttac acgtcgcagc tagcactagc actgtacact     120

acagaaacct ccattgccag ccagctgcgc agtgcgcttg cctctgctgc gttgagcggg     180

gacgccgtgg aggggcgagg gggagccaga ttgagccatg gcctcctcct gggttcttgc     240

cctggttctt gcgctgtcgg caggcgcaag cctggcgcgt ggctcagagc cgtggtggaa     300

cgagacacag gtgtacgcca ccaccgccaa ctccggtggc ggcaacggcg tcttcgtcgg     360

cctcacgctc atccagtcgg cggcggccaa gggagcggtg tgcttggatg gaagcttacc     420

aggttaccac ctccacagag ggtttggatc aggagcaaac agttggctcg tcaatctcga     480

gggtggaggc tggtgcaatg atcgcagcag ctgtgtgttc cgcaagggca gtcgtcgtgg     540
```

```
atcatcaaat cacatggaga ggcaactcca gtttacaggg atattgagta acaaacctga    600

agagaatccc gatttctaca actggaatag agtgaaggtc cggtactgtg atggtggatc    660

tttcactggt gatggctctg atgcggctgc aggcctttat ttccgaggtc agcgcatttg    720

gcaggccgct atggatgacc taatggccca aggaatgcgt tatgctaatc aggccccttct   780

ttctggatgc tctgccggtg gtgtttctac catacttcac tgtgatgaat tccatggatt    840

gtttccctcg aataccagag tcaaatgcct agctgatgct ggaatgtttc ttgacactgt    900

tgatgtttct ggccgtcggg aaatgagatc ctttttcaat ggcattgtga gattgcaggg    960

ttctggaaga agcttgccta ggtcttgcac ctcacacatg gacaaaacct cgtgcttttt   1020

cccccagaat gtgttgccaa ccatccgaac cccaactttt gttttgaaca ctgcctatga   1080

cgtgtggcag cttcaacaaa gtgtggcccc tagaacagct gatccccaag gtctttggtc   1140

aaagtgtagg acgaaccatg ccttctgtaa tagcaaccag ctccagtttt tgcaagggtt   1200

caggaaccag atgcttgatg ccgtgagggg tttctctgca tcaaggcaaa atggtctgtt   1260

catcaactca tgttttgctc attgccagag cgagagacag gatacttggt acgcgaacaa   1320

ctcgccacgt cttggtaaca agaaaatcgc tgacgctgtt ggggactggt tcttcgagag   1380

ggggaacgcc aagtacacag actgcccata cccttgcgat ggcacttgcc atcaccttgt   1440

gttcagggga gaccactaag atcattcttc agcaccaaca aattcatcag atggtacaag   1500

gatcaaaccc caatgggtac agaatggaaa acaggatata gatacagata aggtgcaagt   1560

ggtcggcttg cccatgtttg ttcatcagtg agtcatatga ttgatagtgc gaggacctca   1620

cccgcgaacg cgcggaggag gcctctgcat tagattcaca taccgtcatg atatcgatta   1680

ttttcattgg aaaagcgtcc atgattacgt accagaacaa ttgagttaca tactcatttc   1740

gtgtactgta ttaataacac tagaacgtta catattcatt tgtcctgaag atcgtactac   1800

ttggcatgag ta                                                       1812
```

```
<210> SEQ ID NO 52
<211> LENGTH: 413
<212> TYPE: PRT
<213> ORGANISM: Zea mays

<400> SEQUENCE: 52

Met Ala Ser Ser Trp Val Leu Ala Leu Val Leu Ala Leu Ser Ala Gly
1               5                   10                  15

Ala Ser Leu Ala Arg Gly Ser Glu Pro Trp Trp Asn Glu Thr Gln Val
            20                  25                  30

Tyr Ala Thr Thr Ala Asn Ser Gly Gly Gly Asn Gly Val Phe Val Gly
        35                  40                  45

Leu Thr Leu Ile Gln Ser Ala Ala Ala Lys Gly Ala Val Cys Leu Asp
    50                  55                  60

Gly Ser Leu Pro Gly Tyr His Leu His Arg Gly Phe Gly Ser Gly Ala
65                  70                  75                  80

Asn Ser Trp Leu Val Asn Leu Glu Gly Gly Gly Trp Cys Asn Asp Arg
                85                  90                  95

Ser Ser Cys Val Phe Arg Lys Gly Ser Arg Arg Gly Ser Ser Asn His
            100                 105                 110

Met Glu Arg Gln Leu Gln Phe Thr Gly Ile Leu Ser Asn Lys Pro Glu
        115                 120                 125

Glu Asn Pro Asp Phe Tyr Asn Trp Asn Arg Val Lys Val Arg Tyr Cys
    130                 135                 140
```

-continued

Asp Gly Gly Ser Phe Thr Gly Asp Gly Ser Asp Ala Ala Ala Gly Leu
145 150 155 160

Tyr Phe Arg Gly Gln Arg Ile Trp Gln Ala Ala Met Asp Asp Leu Met
165 170 175

Ala Gln Gly Met Arg Tyr Ala Asn Gln Ala Leu Leu Ser Gly Cys Ser
180 185 190

Ala Gly Gly Val Ser Thr Ile Leu His Cys Asp Glu Phe His Gly Leu
195 200 205

Phe Pro Ser Asn Thr Arg Val Lys Cys Leu Ala Asp Ala Gly Met Phe
210 215 220

Leu Asp Thr Val Asp Val Ser Gly Arg Arg Glu Met Arg Ser Phe Phe
225 230 235 240

Asn Gly Ile Val Arg Leu Gln Gly Ser Gly Arg Ser Leu Pro Arg Ser
245 250 255

Cys Thr Ser His Met Asp Lys Thr Ser Cys Phe Phe Pro Gln Asn Val
260 265 270

Leu Pro Thr Ile Arg Thr Pro Thr Phe Val Leu Asn Thr Ala Tyr Asp
275 280 285

Val Trp Gln Leu Gln Gln Ser Val Ala Pro Arg Thr Ala Asp Pro Gln
290 295 300

Gly Leu Trp Ser Lys Cys Arg Thr Asn His Ala Phe Cys Asn Ser Asn
305 310 315 320

Gln Leu Gln Phe Leu Gln Gly Phe Arg Asn Gln Met Leu Asp Ala Val
325 330 335

Arg Gly Phe Ser Ala Ser Arg Gln Asn Gly Leu Phe Ile Asn Ser Cys
340 345 350

Phe Ala His Cys Gln Ser Glu Arg Gln Asp Thr Trp Tyr Ala Asn Asn
355 360 365

Ser Pro Arg Leu Gly Asn Lys Lys Ile Ala Asp Ala Val Gly Asp Trp
370 375 380

Phe Phe Glu Arg Gly Asn Ala Lys Tyr Thr Asp Cys Pro Tyr Pro Cys
385 390 395 400

Asp Gly Thr Cys His His Leu Val Phe Arg Gly Asp His
405 410

<210> SEQ ID NO 53
<211> LENGTH: 1753
<212> TYPE: DNA
<213> ORGANISM: Zea mays

<400> SEQUENCE: 53
atatattcac ctgagccagg tcgctgtttc atcatcgtgc ttgactgcag tctgcagggg 60
gtgtggccgc gctgcagcct gcctgtcaat ctcgatcgat caaggggtgg cgtgccgaga 120
tggcggaccg gccgtcgctt cctgctctca ttattgctat cgccgttctt gctggcagtt 180
actgccgcgt ggcgagctcg gcctcgccgg cggtggaaga tgagctgcgc ggtggaggag 240
gagccggcgg tccgacgacg atgcggcggc gcgcggcgtc ggtgatggtg cccatcacca 300
tcctcaagtc cgctgttagc gacggagctg tgtgcatgga tggaacgcca cctgcttacc 360
acttggatcc tggctccgga gcgggcagca gaagctggat tgtgaactta gagggaggtg 420
cgtggtgcaa cagcgccaag acatgccggc tcaccaggag ctccggccgt ggctcgtcgg 480
accacatgga caaagagatc cccttcaccg gcatcatgag cagtagccgt gccgtgaatc 540
ctgatttcta caactggaac cgggtcaagg ttcgctactg tgacggtgga tcttttgccg 600

-continued

```
gcgaggcctt cgacaaggac actgggatct acttccgagg gcagcgcatc tggaacgcgg    660

tcatccggca cctcctctcc attgggatgg ccaacgctga ccaggtgctg ctcgccggct    720

gctcctcggg cggtctggcg gtgatactgc actgcgacca gctccgcgcc ttcttcccgt    780

ccggctccac cgtcgtcaag tgcatctccg acggcggcct ctacctcgac gccgtggacg    840

tctccggggg ccgcagcctg agatcctact tcggagacat tgtggccatg caaggaatag    900

ctcagaacct gccgccggct tgcaccgccc gcctcgacgc cacctcgtgc ttcttcccgc    960

agaacataat cgacggcgtt aaaaccccac tgttcctgct aaatgccgca tacgacttca   1020

ttcagattgt gctcagcctg gcgccagaca gagctgaccc aagcggcgct tggcgagcct   1080

gcaagtccaa ccgcacggcc tgcagcgcat cccagatgag tttcctgcaa gatttcaggg   1140

accagatggt agcgtccgtc aaaggcttct ccggttccag gagcaacggg gtcttcctaa   1200

gctcctgctt cgcgcactgc cagtccgagc agctgggcac ctggaacacc aaaccaggtg   1260

gctcccccac cattcaaaac aaggggattt caaaatccgt tggcgactgg tactttgatc   1320

gagctgaggt gaaggcggtc gactgccgct atccctgcga caacacttgc caccacatta   1380

tatgagagga tccacgtttt tttattattt tatgcatagg gaagaacatt cgctctctca   1440

acgaagtgta catcgtattt gattttggga atgcaattgg atacagccat caaatgaaca   1500

caacacgcga aaataaatgg taatggcgtg ttccagtaag acaattgagt gattcaacag   1560

ctgttgttta gcatttgatc catgcaatgg agttcctctg tattatcatt ctagtcagtt   1620

ggcactgcta ccagcaaata tcttctacta gtacattcgg aattctgcgt gcctgttcat   1680

gctaatcctg caaaaactga aggattgagc tttcagtaat cagtgccgat aagaatgaat   1740

tacattatta tac                                                      1753
```

<210> SEQ ID NO 54
<211> LENGTH: 421
<212> TYPE: PRT
<213> ORGANISM: Zea mays

<400> SEQUENCE: 54

```
Met Ala Asp Arg Pro Ser Leu Pro Ala Leu Ile Ile Ala Ile Ala Val
1               5                   10                  15

Leu Ala Gly Ser Tyr Cys Arg Val Ala Ser Ser Ala Ser Pro Ala Val
            20                  25                  30

Glu Asp Glu Leu Arg Gly Gly Gly Gly Ala Gly Gly Pro Thr Thr Met
        35                  40                  45

Arg Arg Arg Ala Ala Ser Val Met Val Pro Ile Thr Ile Leu Lys Ser
    50                  55                  60

Ala Val Ser Asp Gly Ala Val Cys Met Asp Gly Thr Pro Pro Ala Tyr
65                  70                  75                  80

His Leu Asp Pro Gly Ser Gly Ala Gly Ser Arg Ser Trp Ile Val Asn
                85                  90                  95

Leu Glu Gly Gly Ala Trp Cys Asn Ser Ala Lys Thr Cys Arg Leu Thr
            100                 105                 110

Arg Ser Ser Gly Arg Gly Ser Ser Asp His Met Asp Lys Glu Ile Pro
        115                 120                 125

Phe Thr Gly Ile Met Ser Ser Ser Arg Ala Val Asn Pro Asp Phe Tyr
    130                 135                 140

Asn Trp Asn Arg Val Lys Val Arg Tyr Cys Asp Gly Gly Ser Phe Ala
145                 150                 155                 160
```

-continued

```
Gly Glu Ala Phe Asp Lys Asp Thr Gly Ile Tyr Phe Arg Gly Gln Arg
                165                 170                 175

Ile Trp Asn Ala Val Ile Arg His Leu Leu Ser Ile Gly Met Ala Asn
            180                 185                 190

Ala Asp Gln Val Leu Leu Ala Gly Cys Ser Ser Gly Gly Leu Ala Val
        195                 200                 205

Ile Leu His Cys Asp Gln Leu Arg Ala Phe Phe Pro Ser Gly Ser Thr
    210                 215                 220

Val Val Lys Cys Ile Ser Asp Gly Gly Leu Tyr Leu Asp Ala Val Asp
225                 230                 235                 240

Val Ser Gly Gly Arg Ser Leu Arg Ser Tyr Phe Gly Asp Ile Val Ala
                245                 250                 255

Met Gln Gly Ile Ala Gln Asn Leu Pro Pro Ala Cys Thr Ala Arg Leu
            260                 265                 270

Asp Ala Thr Ser Cys Phe Phe Pro Gln Asn Ile Ile Asp Gly Val Lys
        275                 280                 285

Thr Pro Leu Phe Leu Leu Asn Ala Ala Tyr Asp Phe Ile Gln Ile Val
    290                 295                 300

Leu Ser Leu Ala Pro Asp Arg Ala Asp Pro Ser Gly Ala Trp Arg Ala
305                 310                 315                 320

Cys Lys Ser Asn Arg Thr Ala Cys Ser Ala Ser Gln Met Ser Phe Leu
                325                 330                 335

Gln Asp Phe Arg Asp Gln Met Val Ala Ser Val Lys Gly Phe Ser Gly
            340                 345                 350

Ser Arg Ser Asn Gly Val Phe Leu Ser Ser Cys Phe Ala His Cys Gln
        355                 360                 365

Ser Glu Gln Leu Gly Thr Trp Asn Thr Lys Pro Gly Gly Ser Pro Thr
    370                 375                 380

Ile Gln Asn Lys Gly Ile Ser Lys Ser Val Gly Asp Trp Tyr Phe Asp
385                 390                 395                 400

Arg Ala Glu Val Lys Ala Val Asp Cys Arg Tyr Pro Cys Asp Asn Thr
                405                 410                 415

Cys His His Ile Ile
            420


<210> SEQ ID NO 55
<211> LENGTH: 2340
<212> TYPE: DNA
<213> ORGANISM: Oryza sativa

<400> SEQUENCE: 55

atgcctacac agtacacaca gtgcgtttcc attttgttct ttcttccaac actttgggag      60

agagctatac cacgttgctc tctcttgctt tgcttgattt gcgtatcata atctttttat     120

aattcgtgct gtttaaaatt ttaattagga ggtgaattaa aagccgtcct cgtacgtaca     180

taaattagct ggcgaatctg gccagtcttt aattctgcca tatatgtgca tgtgtgtgta     240

catgtatgga aggatagtat tctctcctta atttcttgaa ttgctatccg atcctgagca     300

atatatgtcc ctagctagct agctgggcgt ccgccataat ttgctgccaa taataattag     360

ccccatatat ccttgtagct aggtgaatca tccccttgat atgccttgtt aaatatgtag     420

ctccgattta agctctcttg cccatttttt tttcagagtt tatagtttca ttttgattct     480

tccgctctct gctagcttcc acacaccaag ttcatcagcc aatttcttcc tgacgagaag     540

gccgtgtaag aattttagtg aagtgagtgt cttttttgtt tttcgattgg tcgatcgagt     600
```

```
gctggtacaa gctagaggat ggcgatgatg gagaggattg gggtcaccaa gcttcatcat    660
catcttcttc ttcttgttct tcttctcgtc gtcgccgccg ccggcggcgg cagcgtacag    720
gcggcggagg aggatgagat gagcggccgg aggaggagaa gcaggcggcg gcgtgcggcg    780
gacgtgatgg tgcccatcac catcctcaac tccgccgtcg acaagggagc cgtgtgcatg    840
gacgggacgc cgccggcgta ccacctggac ccgggctccg gcggcggcaa ccggagctgg    900
gtggtcaacc tggagggcgg cgggtggtgc aacaacgccc gcacgtgccg cttccgcacc    960
gccagccgcc acggctcctc cgaccacatg gagcgccgca tcgccttcac cggcatcatg   1020
agctccgccg ccgccgacaa ccccgatttc cacagctgga accgcgtcaa gatccgctac   1080
tgcgacagcg ggtccttcgc cggcgacgcc ttcaacgagg gattgaagct gcaattccgg   1140
gggcagcgca tctggggggc ggtgatccag cacctgctcg acgtcggcat ggcctccgcc   1200
gagcatgtgc tgctcaccgg ctgctccgcc ggcggcctcg ccgcgatcct ccactgcgac   1260
cagctccgcg ccctcctccc cgccgccgcc accgtcaagt gcctctccga cggcggcctc   1320
ttcctcgacg ccgtggacgt cgccggcggc aggagcctga ggtcatacta cggcgacgtc   1380
gtcggcctgc aggcggtggc gcccaacctt cccgagacct gcaccgacca tctcgacgcc   1440
acctcgtgct tcttccctca gaacataatc gacggcataa agacacccat cttcctgctg   1500
aatgcggcgt acgacgtctg gcagatcgag cagagcctgg cccctaacgc agctgacacc   1560
agcggcacct ggcgagtctg caagttcaac cgcgcagcct gcaacgcgtc tcagctgcag   1620
ttcctgcaag gtttcagaga tcagatggtg gcagcggtga gagtcttctc cgagtcgagg   1680
agcaacgggc tgttcatcaa ctcgtgcttc gctcactgcc agtccgagct gacggccacc   1740
tggaatggtg gctctcctgc tctccagaac aagggaattg caaagtctgt tggtgactgg   1800
tactttggtc gagctgaggt gaaggccatc gattgcccct acccctgtga caaaacatgc   1860
cacaacatca tatgacatca tgtactgacg tttactcgtc tcgaccgaat ggagtgacac   1920
acatttttgc ctcgaagtcc tctcaagttc ttcactctag ctagtagcta tatacatgta   1980
gaactatcga gttcagagcc aaaacataca aaacagagaa cctcacacaa acagatacaa   2040
aggaagcaaa acaaagttaa caaaagcaaa taggaagggg gagaggggca gggcacatta   2100
atatcgggaa gcagtgtggt ggagtcatgg gtgtataatt tcacctatta agaataaatt   2160
acagtattca caaacatagt atgggattag aaaggagagc taatacgtta gctccatctc   2220
tttaagcatg tgttagggca ttcgtggaag tgtgtctgat gtcgcgtgta cagtggtctg   2280
cggtgtaatc gccaaaaaca aaaaaaaggt agtatgtttg acatagatct cttagacatc   2340
```

<210> SEQ ID NO 56
<211> LENGTH: 418
<212> TYPE: PRT
<213> ORGANISM: Oryza sativa

<400> SEQUENCE: 56

```
Met Ala Met Met Glu Arg Ile Gly Val Thr Lys Leu His His His Leu
1               5                   10                  15

Leu Leu Leu Val Leu Leu Leu Val Val Ala Ala Ala Gly Gly Gly Ser
            20                  25                  30

Val Gln Ala Ala Glu Glu Asp Glu Met Ser Gly Arg Arg Arg Arg Ser
        35                  40                  45

Arg Arg Arg Arg Ala Ala Asp Val Met Val Pro Ile Thr Ile Leu Asn
    50                  55                  60

Ser Ala Val Asp Lys Gly Ala Val Cys Met Asp Gly Thr Pro Pro Ala
```

-continued

```
65                  70                  75                  80

Tyr His Leu Asp Pro Gly Ser Gly Gly Gly Asn Arg Ser Trp Val Val
                85                  90                  95

Asn Leu Glu Gly Gly Gly Trp Cys Asn Asn Ala Arg Thr Cys Arg Phe
            100                 105                 110

Arg Thr Ala Ser Arg His Gly Ser Ser Asp His Met Glu Arg Arg Ile
        115                 120                 125

Ala Phe Thr Gly Ile Met Ser Ser Ala Ala Ala Asp Asn Pro Asp Phe
    130                 135                 140

His Ser Trp Asn Arg Val Lys Ile Arg Tyr Cys Asp Ser Gly Ser Phe
145                 150                 155                 160

Ala Gly Asp Ala Phe Asn Glu Gly Leu Lys Leu Gln Phe Arg Gly Gln
                165                 170                 175

Arg Ile Trp Gly Ala Val Ile Gln His Leu Leu Asp Val Gly Met Ala
            180                 185                 190

Ser Ala Glu His Val Leu Leu Thr Gly Cys Ser Ala Gly Gly Leu Ala
        195                 200                 205

Ala Ile Leu His Cys Asp Gln Leu Arg Ala Leu Leu Pro Ala Ala Ala
    210                 215                 220

Thr Val Lys Cys Leu Ser Asp Gly Gly Leu Phe Leu Asp Ala Val Asp
225                 230                 235                 240

Val Ala Gly Gly Arg Ser Leu Arg Ser Tyr Tyr Gly Asp Val Val Gly
                245                 250                 255

Leu Gln Ala Val Ala Pro Asn Leu Pro Glu Thr Cys Thr Asp His Leu
            260                 265                 270

Asp Ala Thr Ser Cys Phe Phe Pro Gln Asn Ile Ile Asp Gly Ile Lys
        275                 280                 285

Thr Pro Ile Phe Leu Leu Asn Ala Ala Tyr Asp Val Trp Gln Ile Glu
    290                 295                 300

Gln Ser Leu Ala Pro Asn Ala Ala Asp Thr Ser Gly Thr Trp Arg Val
305                 310                 315                 320

Cys Lys Phe Asn Arg Ala Ala Cys Asn Ala Ser Gln Leu Gln Phe Leu
                325                 330                 335

Gln Gly Phe Arg Asp Gln Met Val Ala Ala Val Arg Val Phe Ser Glu
            340                 345                 350

Ser Arg Ser Asn Gly Leu Phe Ile Asn Ser Cys Phe Ala His Cys Gln
        355                 360                 365

Ser Glu Leu Thr Ala Thr Trp Asn Gly Gly Ser Pro Ala Leu Gln Asn
    370                 375                 380

Lys Gly Ile Ala Lys Ser Val Gly Asp Trp Tyr Phe Gly Arg Ala Glu
385                 390                 395                 400

Val Lys Ala Ile Asp Cys Pro Tyr Pro Cys Asp Lys Thr Cys His Asn
                405                 410                 415

Ile Ile
```

<210> SEQ ID NO 57
<211> LENGTH: 2059
<212> TYPE: DNA
<213> ORGANISM: Oryza sativa

<400> SEQUENCE: 57

```
ggggccgccc actctgcgtt ttgcatcggc agaggcgcgg tggagaaaaa aaaaggccga      60

gcttggatgg aaagctccaa gcttttgcgc tgttcgcttg cctgagcccc ccgtcccgtc     120
```

```
ccgtcccctc gcctcggcaa gaacaaagag catgcgagat tagatcgaga cggcgtatcc    180
ggtaagcgct gttccatctc cggcacaaaa gggatggcga atgggggtgt ctgcctctcg    240
tgctctgcac ttgtctgcgc gctggtgttt ctcacggtgg atggtgattt cgtggacatt    300
acttacgtag cgagcgctgt ggccaaaggc gcagtctgtt tggatgggag ccccccggcc    360
taccatctcg cccggggttt tggctccggc gtgaatagtt ggctggttca tttcgaggga    420
ggaggatggt gcagcaatgt gacgacctgc ctgcaacgca aacgcactcg gttaggatca    480
tcgaagcaga tggcaaagca gattgccttc tctggaatac tgagcaacac ccctgattac    540
aacccggatt tctacaattg gaacaaggtc aaggttcggt actgtgatgg gtcatctttc    600
accggcgatg tggaaaaagt agatcctgca acaaagcttc actacagagg tgctagggtg    660
tggcaagcag ttatggatga tctgcttgcg aaaggaatga acagtgccaa taatgctcta    720
atttcgggct gttctgctgg tggtttaact tccatactac actgtgacag atttcgtgac    780
cttttcccag tggataccaa agttaaatgc ctttctgatg ctggtttctt catcaatgag    840
aaggatattg ctggagtgga gtacattgtg gcctttttca atggcgtagc tacaacccat    900
ggatcagcga agaatttacc ttctgcttgc acctccagat tgtccccagg catgtgcttt    960
tttcctcaga atgaggtgaa acagattcag acacctttgt tcattctcaa cgcagcgtat   1020
gattcctggc aggtaaggaa catcttggtg ccaggatttg cagaccctca tggtaaatgg   1080
catagctgta agcatgatat agatcaatgt cctgcatcgc aacttcaaat cttgcaagga   1140
ttcagagacg attttctgaa agcactgaag gaacaaggga ctccctccac cagaggattg   1200
tttataaact catgcttcgt gcattgccaa tctgagacgc aggagacatg gtttgcatct   1260
ggttccccca tgcttgaaac caaaacaata gcggatgcag ttggagattg gttctacgac   1320
cgcaatccgt ttcagaagat tgattgccct tacccttgcg attcaacctg ccacaaccga   1380
atctacgacg accccctcaga agcatagcaa ttacagaaac ctcacctcgt actaccattc   1440
atcacattgt tatatttgat gcacccttat tgctcgcaat agggcaatcc gtgggcaacc   1500
attgattttc aggaataact gcagatgatg gcttaaagct catctgatgc ctggaggctg   1560
gatgcagctt ccaacagtag ttacaggtgt ctccaacatt tgattcgctt tgtcggcaat   1620
attttgccat atcttcgata atcatcgaca aagtccacat taatgttact gaagtgacat   1680
tggacgaaca cgaaacacga aaagtttatc tggtgagggg atggataatg ctattttctc   1740
gaaattagct caaaattcaa gtacgttcag tgagattttc gaaatcaaag tggagcctaa   1800
ccaaactgcg ctctgttaac ctgtcaacgg cgcctcgccg ccgccgttgc gcgtccccgc   1860
cggccatcga tgaagagctc cggcgtgaga tcccccgtat ctccaccgca tatcaccacg   1920
tctgcacgtc aacgagtgcc agatccattt ctgccctcgt cggcgtgacg aacgacggcg   1980
gacgtacggg cggcgctgat gagcagagcg agggatgcag cacgagctcg aggaggggat   2040
gatatttcgt cgattcatg                                                2059
```

<210> SEQ ID NO 58
<211> LENGTH: 397
<212> TYPE: PRT
<213> ORGANISM: oryza sativa

<400> SEQUENCE: 58

```
Met Ala Asn Gly Gly Val Cys Leu Ser Cys Ser Ala Leu Val Cys Ala
1               5                   10                  15

Leu Val Phe Leu Thr Val Asp Gly Asp Phe Val Asp Ile Thr Tyr Val
            20                  25                  30
```

```
Ala Ser Ala Val Ala Lys Gly Ala Val Cys Leu Asp Gly Ser Pro Pro
        35                  40                  45

Ala Tyr His Leu Ala Arg Gly Phe Gly Ser Gly Val Asn Ser Trp Leu
    50                  55                  60

Val His Phe Glu Gly Gly Gly Trp Cys Ser Asn Val Thr Thr Cys Leu
65                  70                  75                  80

Gln Arg Lys Arg Thr Arg Leu Gly Ser Ser Lys Gln Met Ala Lys Gln
                85                  90                  95

Ile Ala Phe Ser Gly Ile Leu Ser Asn Thr Pro Asp Tyr Asn Pro Asp
            100                 105                 110

Phe Tyr Asn Trp Asn Lys Val Lys Val Arg Tyr Cys Asp Gly Ser Ser
        115                 120                 125

Phe Thr Gly Asp Val Glu Lys Val Asp Pro Ala Thr Lys Leu His Tyr
    130                 135                 140

Arg Gly Ala Arg Val Trp Gln Ala Val Met Asp Asp Leu Leu Ala Lys
145                 150                 155                 160

Gly Met Asn Ser Ala Asn Asn Ala Leu Ile Ser Gly Cys Ser Ala Gly
                165                 170                 175

Gly Leu Thr Ser Ile Leu His Cys Asp Arg Phe Arg Asp Leu Phe Pro
            180                 185                 190

Val Asp Thr Lys Val Lys Cys Leu Ser Asp Ala Gly Phe Phe Ile Asn
        195                 200                 205

Glu Lys Asp Ile Ala Gly Val Glu Tyr Ile Val Ala Phe Phe Asn Gly
    210                 215                 220

Val Ala Thr Thr His Gly Ser Ala Lys Asn Leu Pro Ser Ala Cys Thr
225                 230                 235                 240

Ser Arg Leu Ser Pro Gly Met Cys Phe Phe Pro Gln Asn Glu Val Lys
                245                 250                 255

Gln Ile Gln Thr Pro Leu Phe Ile Leu Asn Ala Ala Tyr Asp Ser Trp
            260                 265                 270

Gln Val Arg Asn Ile Leu Val Pro Gly Phe Ala Asp Pro His Gly Lys
        275                 280                 285

Trp His Ser Cys Lys His Asp Ile Asp Gln Cys Pro Ala Ser Gln Leu
    290                 295                 300

Gln Ile Leu Gln Gly Phe Arg Asp Asp Phe Leu Lys Ala Leu Lys Glu
305                 310                 315                 320

Gln Gly Thr Pro Ser Thr Arg Gly Leu Phe Ile Asn Ser Cys Phe Val
                325                 330                 335

His Cys Gln Ser Glu Thr Gln Glu Thr Trp Phe Ala Ser Gly Ser Pro
            340                 345                 350

Met Leu Glu Thr Lys Thr Ile Ala Asp Ala Val Gly Asp Trp Phe Tyr
        355                 360                 365

Asp Arg Asn Pro Phe Gln Lys Ile Asp Cys Pro Tyr Pro Cys Asp Ser
    370                 375                 380

Thr Cys His Asn Arg Ile Tyr Asp Asp Pro Ser Glu Ala
385                 390                 395
```

<210> SEQ ID NO 59
<211> LENGTH: 2209
<212> TYPE: DNA
<213> ORGANISM: oryza sativa

<400> SEQUENCE: 59

```
gcgaagaagc gcaagcgagg aagtgaccag cctgcctacg gccgctgctc agctcagctc      60
```

```
ccagctgtca cttgctccaa tggagacgag tacgcccacc aaaaaagcag taattgcact    120
tcacagtttt ccccaccctt tcgccgccct cccctggatt ccgtagttcc gtcatcacca    180
ccaccacgtt ccgggcgact ccttccattg cttcttttct tcttcttctt cttctccatt    240
tctacagcct cacaagatag ggagatgctt tgcttcacaa ctgtaattgc actacacgtt    300
ttttcactgg aagcactagt gcagctgcac tagtagcagt gcacaccgct ccacagaatc    360
tcccagaagc agccgctttt gttttgtcag ccattgccag catccagctg cacttggctc    420
cgcgtataac ttcctttctt gcttggccgc ttctgctcct ccattcttcc ctcctcctct    480
tccccttctt ccagatccat tcctcaggaa gaaggcagag gctgggagtg ggaggaaggc    540
ccaagaacca gcaaagaaag aagagaacca tcaaccatgg gttgttcttg ggctcttgct    600
gctctggttc ttggcttctt ggtggtggca gtccatggct ctgagccgtg gctgaatcag    660
acgcaggtct actccaccaa tgccaactct ggtagcaatg gcgtcttcgt cgggattacg    720
ctcatccagt cggcggccgc caagggagcc gtatgcttgg atgggagctt accagggtat    780
cacctacacc gagggtttgg atcaggggca aacagttggc ttgtcaattt ggagggtgga    840
ggctggtgca acgatgttaa aagctgcgtg tttcgcaaga gcagtcggcg tggttcatca    900
aatcacatgg agagccaact ccagtttact gggataatga gtaacaggcc tgaagaaaat    960
cctgatttct acaactggaa cagagtgaag gttcgatatt gtgatggcgg atccttcact   1020
ggtgatgggg ctgatgcgtc tgcaggcctt tatttccgag gtcagcgtat ttggcaggct   1080
gctatggatg atctgatggc ccaaggaatg agatatgcta accaggcact tctttctgga   1140
tgctctgctg gtggtgtttc aaccatactt cactgtgacg agttccgtgg attgtttagc   1200
ggcagtacaa acgtgaagtg ccttgctgat gctggaatgt ttctggactt tgttgatgtt   1260
tctgggcaac gagaaatgag ggacttcttc aatggtattg tgagattgca gggttccgga   1320
agaagcctgc ctaggtcttg tacctcccgc atggataaaa cttcgtgctt tttcccccag   1380
aatgtggtgc caaacattca aactccaact tttattttga acactgctta tgatgtgtgg   1440
cagcttcaac aaagtgtggc ccccaaaagg gctgatccgc aaggtctatg gcgaggatgt   1500
aggatgaatc atgcctcctg taatagcaac caactgcaat ttttacaagg tttcaggaat   1560
caaatgctcg atgcggtgag ggtttctcc ggcgcaaggc agaacggtct ttttatcaac   1620
tcctgtttcg cacattgcca aagtgagaga caggacacat ggtacgcagg ggattctcct   1680
cgtctcggta acaagagaat tgctgaagca gtaggcgact ggtttttcga tagggcagac   1740
gcgaagtaca cagactgtgc ataccccttgt gatggtacct gccatcatct tacattcagg   1800
ggagattact aagattcatt cttagaccac caccaaatgt aggtggcaaa aagaggggaa   1860
aaaagggaca cccaatggga atatatacag aataagagga aggtatagat agaggatgca   1920
aagctagtga cttgcatgga catgttcatc attactcaga tatgatctta gggcagggcc   1980
tggtgtgctt gctaatgtgg catgatcagg cctctgcatt tagctccaca caccgattga   2040
ttcttttcca ttgcctgaat tccctggatg atgtatctct gaacatttgg accccaatgg   2100
tgtatctgta tcataaattt acatatccat gtactaaacg tgataatatg aatgaaataa   2160
gtaatgtgcc tgcaagaaac ccaatcattt gtcaggcaaa tatctacca                2209
```

<210> SEQ ID NO 60
<211> LENGTH: 411
<212> TYPE: PRT
<213> ORGANISM: Oryza sativa

<400> SEQUENCE: 60

```
Met Gly Cys Ser Trp Ala Leu Ala Ala Leu Val Leu Gly Phe Leu Val
1               5                   10                  15

Val Ala Val His Gly Ser Glu Pro Trp Leu Asn Gln Thr Gln Val Tyr
            20                  25                  30

Ser Thr Asn Ala Asn Ser Gly Ser Asn Gly Val Phe Val Gly Ile Thr
        35                  40                  45

Leu Ile Gln Ser Ala Ala Ala Lys Gly Ala Val Cys Leu Asp Gly Ser
    50                  55                  60

Leu Pro Gly Tyr His Leu His Arg Gly Phe Gly Ser Gly Ala Asn Ser
65                  70                  75                  80

Trp Leu Val Asn Leu Glu Gly Gly Gly Trp Cys Asn Asp Val Lys Ser
                85                  90                  95

Cys Val Phe Arg Lys Ser Ser Arg Arg Gly Ser Ser Asn His Met Glu
            100                 105                 110

Ser Gln Leu Gln Phe Thr Gly Ile Met Ser Asn Arg Pro Glu Glu Asn
        115                 120                 125

Pro Asp Phe Tyr Asn Trp Asn Arg Val Lys Val Arg Tyr Cys Asp Gly
    130                 135                 140

Gly Ser Phe Thr Gly Asp Gly Ala Asp Ala Ser Ala Gly Leu Tyr Phe
145                 150                 155                 160

Arg Gly Gln Arg Ile Trp Gln Ala Ala Met Asp Asp Leu Met Ala Gln
                165                 170                 175

Gly Met Arg Tyr Ala Asn Gln Ala Leu Leu Ser Gly Cys Ser Ala Gly
            180                 185                 190

Gly Val Ser Thr Ile Leu His Cys Asp Glu Phe Arg Gly Leu Phe Ser
        195                 200                 205

Gly Ser Thr Asn Val Lys Cys Leu Ala Asp Ala Gly Met Phe Leu Asp
    210                 215                 220

Phe Val Asp Val Ser Gly Gln Arg Glu Met Arg Asp Phe Phe Asn Gly
225                 230                 235                 240

Ile Val Arg Leu Gln Gly Ser Gly Arg Ser Leu Pro Arg Ser Cys Thr
                245                 250                 255

Ser Arg Met Asp Lys Thr Ser Cys Phe Phe Pro Gln Asn Val Val Pro
            260                 265                 270

Asn Ile Gln Thr Pro Thr Phe Ile Leu Asn Thr Ala Tyr Asp Val Trp
        275                 280                 285

Gln Leu Gln Gln Ser Val Ala Pro Lys Arg Ala Asp Pro Gln Gly Leu
    290                 295                 300

Trp Arg Gly Cys Arg Met Asn His Ala Ser Cys Asn Ser Asn Gln Leu
305                 310                 315                 320

Gln Phe Leu Gln Gly Phe Arg Asn Gln Met Leu Asp Ala Val Arg Gly
                325                 330                 335

Phe Ser Gly Ala Arg Gln Asn Gly Leu Phe Ile Asn Ser Cys Phe Ala
            340                 345                 350

His Cys Gln Ser Glu Arg Gln Asp Thr Trp Tyr Ala Gly Asp Ser Pro
        355                 360                 365

Arg Leu Gly Asn Lys Arg Ile Ala Glu Ala Val Gly Asp Trp Phe Phe
    370                 375                 380

Asp Arg Ala Asp Ala Lys Tyr Thr Asp Cys Ala Tyr Pro Cys Asp Gly
385                 390                 395                 400

Thr Cys His His Leu Thr Phe Arg Gly Asp Tyr
                405                 410
```

<210> SEQ ID NO 61
<211> LENGTH: 1254
<212> TYPE: DNA
<213> ORGANISM: Sorghum bicolor

<400> SEQUENCE: 61

```
atgacggatc ggccgtcgtt tccggctctc attgctctcg ccgttcttgt ggtgggcagc     60
tactgctgcg tggcgacctc ggccgcctcg ccggcggtgg aagatgatga gctgcgtggt    120
cggacgatgc ggcggcgccg cgcggcgtcg gtgatggtgc ccatcaccat cctcaagtcc    180
gcagtcagcg acggagctgt gtgcatggat ggaacgccac ctgcttacaa cttggatcct    240
ggctccggaa cgggtagcag aagctggatt gtgaacttag agggaggtgc atggtgcaac    300
agcgccaaga catgccggct taccaagagc tccgggcgcg gctcgtcgga ccacatggat    360
aaagagatcc ccttcaccgg catcatgagc agcagcagcg ccgtcaatcc tgatttctac    420
aattggaacc gggtaaagat tcgctactgc gacggtggat cttttgccgg cgaggccttt    480
gataagaaca ctgggattta tttccgaggg cagcgcatct ggaacgcggt catccggcac    540
ctcctctcca ttgggatggc ctctgctgat cgtgtgctgc tcaccggctg ctcctcgggg    600
ggtctggcgg tgatcctgca ctgcgaccag ttgcgcgcct tcttcccgtc cggcaccacc    660
gtcgtcaagt gcatctccga cggcggcctc tacctcgacg ccgtggatgt ctccggtggc    720
cggagcctga gatcctactt ccgtgacatc gtggccatgc aaggaatagc tcagaacctg    780
ccgccggctt gcaccgcccg tctcgacgcc acctcgtgct tcttcccgca aaacataatc    840
gatggcatca agaccccact gtttctgcta aatgcagcat acgacttcat tcagattgtg    900
ctcagcctgg cgccagacag agctgaccca aacggcgctt ggcgagcctg caagtccaac    960
cgcacggcct gcagtgcatc ccagatgagt ttcctgcaag atttcaggga ccagatggta   1020
gcatccgtca gaggcttctc cggttccagg agcaacgggc tcttcataag ctcctgcttc   1080
gcgcactgcc agtcggagca gctgggcacc tggaacacca aaccaggtgg ctccccccacc   1140
attcaaaaca aggggattgc aaaatccgtt ggtgactggt actttgatcg agctgaagtg   1200
aaggcgatcg actgccgcta tccctgcgac aacacttgcc accatatcat atga          1254
```

<210> SEQ ID NO 62
<211> LENGTH: 417
<212> TYPE: PRT
<213> ORGANISM: Sorghum bicolor

<400> SEQUENCE: 62

```
Met Thr Asp Arg Pro Ser Phe Pro Ala Leu Ile Ala Leu Ala Val Leu
1               5                   10                  15

Val Val Gly Ser Tyr Cys Cys Val Ala Thr Ser Ala Ala Ser Pro Ala
            20                  25                  30

Val Glu Asp Asp Glu Leu Arg Gly Arg Thr Met Arg Arg Arg Arg Ala
        35                  40                  45

Ala Ser Val Met Val Pro Ile Thr Ile Leu Lys Ser Ala Val Ser Asp
    50                  55                  60

Gly Ala Val Cys Met Asp Gly Thr Pro Pro Ala Tyr Asn Leu Asp Pro
65                  70                  75                  80

Gly Ser Gly Thr Gly Ser Arg Ser Trp Ile Val Asn Leu Glu Gly Gly
                85                  90                  95

Ala Trp Cys Asn Ser Ala Lys Thr Cys Arg Leu Thr Lys Ser Ser Gly
            100                 105                 110
```

```
Arg Gly Ser Ser Asp His Met Asp Lys Glu Ile Pro Phe Thr Gly Ile
        115                 120                 125

Met Ser Ser Ser Ser Ala Val Asn Pro Asp Phe Tyr Asn Trp Asn Arg
    130                 135                 140

Val Lys Ile Arg Tyr Cys Asp Gly Gly Ser Phe Ala Gly Glu Ala Phe
145                 150                 155                 160

Asp Lys Asn Thr Gly Ile Tyr Phe Arg Gly Gln Arg Ile Trp Asn Ala
                165                 170                 175

Val Ile Arg His Leu Leu Ser Ile Gly Met Ala Ser Ala Asp Arg Val
            180                 185                 190

Leu Leu Thr Gly Cys Ser Ser Gly Gly Leu Ala Val Ile Leu His Cys
        195                 200                 205

Asp Gln Leu Arg Ala Phe Phe Pro Ser Gly Thr Thr Val Val Lys Cys
    210                 215                 220

Ile Ser Asp Gly Gly Leu Tyr Leu Asp Ala Val Asp Val Ser Gly Gly
225                 230                 235                 240

Arg Ser Leu Arg Ser Tyr Phe Arg Asp Ile Val Ala Met Gln Gly Ile
                245                 250                 255

Ala Gln Asn Leu Pro Pro Ala Cys Thr Ala Arg Leu Asp Ala Thr Ser
            260                 265                 270

Cys Phe Phe Pro Gln Asn Ile Ile Asp Gly Ile Lys Thr Pro Leu Phe
        275                 280                 285

Leu Leu Asn Ala Ala Tyr Asp Phe Ile Gln Ile Val Leu Ser Leu Ala
    290                 295                 300

Pro Asp Arg Ala Asp Pro Asn Gly Ala Trp Arg Ala Cys Lys Ser Asn
305                 310                 315                 320

Arg Thr Ala Cys Ser Ala Ser Gln Met Ser Phe Leu Gln Asp Phe Arg
                325                 330                 335

Asp Gln Met Val Ala Ser Val Arg Gly Phe Ser Gly Ser Arg Ser Asn
            340                 345                 350

Gly Leu Phe Ile Ser Ser Cys Phe Ala His Cys Gln Ser Glu Gln Leu
        355                 360                 365

Gly Thr Trp Asn Thr Lys Pro Gly Gly Ser Pro Thr Ile Gln Asn Lys
    370                 375                 380

Gly Ile Ala Lys Ser Val Gly Asp Trp Tyr Phe Asp Arg Ala Glu Val
385                 390                 395                 400

Lys Ala Ile Asp Cys Arg Tyr Pro Cys Asp Asn Thr Cys His His Ile
                405                 410                 415

Ile
```

<210> SEQ ID NO 63
<211> LENGTH: 1245
<212> TYPE: DNA
<213> ORGANISM: Sorghum bicolor

<400> SEQUENCE: 63

```
atggcctcct ccacttgcgc tcttgccctg gttcttgcgc tgtcggtcgg tgcaagcgtg     60

gcgcgtggct ccgagccctg gtggaacgag acgcaggtgt acaccaccac cgccaactcc    120

ggtggcagca acggcgtctt cgtcggcctc accctcatcc agtcggcggc ggccaaggga    180

gcggtgtgct tggatggaag cttaccaggt taccacctgc acagagggtt tggatcagga    240

gcgaacagtt ggcttgtcaa tctcgagggt ggaggctggt gcaatgatgt cagcagctgt    300

gtgttccgca agggtagtcg tcgtggatca tcaaatcaca tggagcggca actccagttt    360
```

```
acagggataa tgagtaacag acctgatgag aatcctgatt tctacaactg gaatagagtg    420

aaggtccggt actgtgacgg tggatccttc actggtgatg gctctgatgc ggctgcaggc    480

ctttatttcc gaggtcagcg tatttggcag gccgctatgg atgacctaat ggcccaagga    540

atgcgttatg ctaatcaggc ccttctttct ggatgctctg ccggtggtgt ttctaccata    600

cttcactgtg atgaattccg tggattgttt ccatcaaata ccagagtcaa atgcctggct    660

gatgctggaa tgtttcttga cactgttgat gtttctggcc gtcgggaaat gagatctttt    720

ttcaatggca ttgtgagatt gcagggttct ggaagaagct tgcctaggtc ttgcaccgca    780

cgcatggaca aaacctcgtg ctttttcccg cagaacgtgt taccaaacat tcaaacccca    840

acttttgttt tgaacactgc ctatgacgtg tggcagcttc aacaaagtgt ggcccccaga    900

acagctgatc cccaaggtct ttggtcaaag tgtaggacga accacgcttt ctgtaatagc    960

aaccagcttc agtttttgca agggtttagg aaccaaatgc ttgatgccgt gaagggtttt   1020

tctgcgtcaa ggcgaaatgg tttgttcatc aactcatgtt ttgctcattg ccagagcgag   1080

agacaggata cttggtatgc gaacaactcg ccacgtcttg gtaacaagaa aatcgctgac   1140

gctgtcggtg attggttctt tgagagggga gacgccaagt acacagactg cccataccct   1200

tgcgatggca cttgccatca tcttgtgttc aggggagacc attaa                   1245
```

<210> SEQ ID NO 64
<211> LENGTH: 414
<212> TYPE: PRT
<213> ORGANISM: Sorghum bicolor

<400> SEQUENCE: 64

```
Met Ala Ser Ser Thr Cys Ala Leu Ala Leu Val Leu Ala Leu Ser Val
1               5                   10                  15

Gly Ala Ser Val Ala Arg Gly Ser Glu Pro Trp Trp Asn Glu Thr Gln
            20                  25                  30

Val Tyr Thr Thr Thr Ala Asn Ser Gly Gly Ser Asn Gly Val Phe Val
        35                  40                  45

Gly Leu Thr Leu Ile Gln Ser Ala Ala Ala Lys Gly Ala Val Cys Leu
    50                  55                  60

Asp Gly Ser Leu Pro Gly Tyr His Leu His Arg Gly Phe Gly Ser Gly
65                  70                  75                  80

Ala Asn Ser Trp Leu Val Asn Leu Glu Gly Gly Gly Trp Cys Asn Asp
                85                  90                  95

Val Ser Ser Cys Val Phe Arg Lys Gly Ser Arg Arg Gly Ser Ser Asn
            100                 105                 110

His Met Glu Arg Gln Leu Gln Phe Thr Gly Ile Met Ser Asn Arg Pro
        115                 120                 125

Asp Glu Asn Pro Asp Phe Tyr Asn Trp Asn Arg Val Lys Val Arg Tyr
    130                 135                 140

Cys Asp Gly Gly Ser Phe Thr Gly Asp Gly Ser Asp Ala Ala Ala Gly
145                 150                 155                 160

Leu Tyr Phe Arg Gly Gln Arg Ile Trp Gln Ala Ala Met Asp Asp Leu
                165                 170                 175

Met Ala Gln Gly Met Arg Tyr Ala Asn Gln Ala Leu Leu Ser Gly Cys
            180                 185                 190

Ser Ala Gly Gly Val Ser Thr Ile Leu His Cys Asp Glu Phe Arg Gly
        195                 200                 205

Leu Phe Pro Ser Asn Thr Arg Val Lys Cys Leu Ala Asp Ala Gly Met
```

```
    210                 215                 220

Phe Leu Asp Thr Val Asp Val Ser Gly Arg Arg Glu Met Arg Ser Phe
225                 230                 235                 240

Phe Asn Gly Ile Val Arg Leu Gln Gly Ser Gly Arg Ser Leu Pro Arg
                245                 250                 255

Ser Cys Thr Ala Arg Met Asp Lys Thr Ser Cys Phe Phe Pro Gln Asn
            260                 265                 270

Val Leu Pro Asn Ile Gln Thr Pro Thr Phe Val Leu Asn Thr Ala Tyr
        275                 280                 285

Asp Val Trp Gln Leu Gln Gln Ser Val Ala Pro Arg Thr Ala Asp Pro
    290                 295                 300

Gln Gly Leu Trp Ser Lys Cys Arg Thr Asn His Ala Phe Cys Asn Ser
305                 310                 315                 320

Asn Gln Leu Gln Phe Leu Gln Gly Phe Arg Asn Gln Met Leu Asp Ala
                325                 330                 335

Val Lys Gly Phe Ser Ala Ser Arg Arg Asn Gly Leu Phe Ile Asn Ser
            340                 345                 350

Cys Phe Ala His Cys Gln Ser Glu Arg Gln Asp Thr Trp Tyr Ala Asn
        355                 360                 365

Asn Ser Pro Arg Leu Gly Asn Lys Lys Ile Ala Asp Ala Val Gly Asp
    370                 375                 380

Trp Phe Phe Glu Arg Gly Asp Ala Lys Tyr Thr Asp Cys Pro Tyr Pro
385                 390                 395                 400

Cys Asp Gly Thr Cys His His Leu Val Phe Arg Gly Asp His
                405                 410


<210> SEQ ID NO 65
<211> LENGTH: 1362
<212> TYPE: DNA
<213> ORGANISM: Sorghum bicolor

<400> SEQUENCE: 65

atgggggtgc atgcgcatgg ggctgttgcc aaagccaaac cctgcagcag cagcagcagc     60

agcaggcggc ttttcctgtt ggttgttgta ctcgtcgtcc tcataggtag ctactgcgcc    120

gccgccgctg cagatgagga gatgaacagc agcagtaata ggggcagccg gagccggagg    180

aggaggagga gcaggagcag gagacgggcc gctgccacgg cggccgacgc ggtgacgccg    240

gcgccgctca tggtgcccat caccatcctc aagtccgccg tcgactcggg agccgtgtgc    300

atggacggaa caccgcctgc ttaccaccta caccctggct ccggggctgg caacaatagc    360

tggatcgtca acctggaggg aggcggttgg tgcaacaacg ttcgggcgtg ccagttccgc    420

aaggccagcc gccgcggctc gtcggacctc atggagaagg agatcccctt cggcggcatc    480

atgagcagca gccctgtcga taaccctgat ttctacaagt ggaaccgggt gaagatccgc    540

tactgcgacg gcgcgtcctt cgccggagaa ggcttcgaca aggagaacgg gttttacttc    600

cgcgggcagc gcatctggga cgccaccgtc cggcacctcc tctccatcgg gatggcctcc    660

gcagagcagg tgctgctcac cggctgctcc gccggcggcc tggccgtcat actgcactgc    720

gaccagttcc aggccttctt ccctcgctcc accaccgtcg tcaagtgcct cgccgacgcc    780

ggcctcttcc tcgacgcctc cgatgtctcc ggcggccgca gccttcgttc ctactactcc    840

gacatcgtgg ccatgcaggg cgtggctccc aacctgccgc cggcctgcac tgcccgtctc    900

gacaccacct cgtgcttctt cccgcagaat gtaatcgatg gcatcaacac ccccatcttc    960

ctgctcaacg cagcatacga cgtatggcag atacaggaga gcctggcacc caccggagct   1020
```

```
gaccccagcg gagcctggcg ggcctgcaag tccaaccact ctgcctgcga cgcatcccag   1080

atgaaattcc tgcaagattt cagagaccag atggtagcat cggtgaacaa cggcttcgct   1140

ggctccagga gcaacgggct cttcatcaac tcctgcttcg cgcactgcca gtccgagctg   1200

ccgatgacat ggagcgacaa cgcggcaggt ggtggtgcct ccccggccat tcaaagcagg   1260

gggattgcca agtcagtggg cgactggtac tttggtcgag ctcaagttaa ggccatcgac   1320

tgcccctacc catgcgaccg aacatgccgc aacatcatat ga                      1362
```

<210> SEQ ID NO 66
<211> LENGTH: 453
<212> TYPE: PRT
<213> ORGANISM: Sorghum bicolor

<400> SEQUENCE: 66

```
Met Gly Val His Ala His Gly Ala Val Ala Lys Ala Lys Pro Cys Ser
1               5                   10                  15

Ser Ser Ser Ser Ser Arg Arg Leu Phe Leu Leu Val Val Val Leu Val
            20                  25                  30

Val Leu Ile Gly Ser Tyr Cys Ala Ala Ala Ala Ala Asp Glu Glu Met
        35                  40                  45

Asn Ser Ser Ser Asn Arg Gly Ser Arg Ser Arg Arg Arg Arg Arg Ser
    50                  55                  60

Arg Ser Arg Arg Arg Ala Ala Ala Thr Ala Ala Asp Ala Val Thr Pro
65                  70                  75                  80

Ala Pro Leu Met Val Pro Ile Thr Ile Leu Lys Ser Ala Val Asp Ser
                85                  90                  95

Gly Ala Val Cys Met Asp Gly Thr Pro Pro Ala Tyr His Leu His Pro
            100                 105                 110

Gly Ser Gly Ala Gly Asn Asn Ser Trp Ile Val Asn Leu Glu Gly Gly
        115                 120                 125

Gly Trp Cys Asn Asn Val Arg Ala Cys Gln Phe Arg Lys Ala Ser Arg
    130                 135                 140

Arg Gly Ser Ser Asp Leu Met Glu Lys Glu Ile Pro Phe Gly Gly Ile
145                 150                 155                 160

Met Ser Ser Ser Pro Val Asp Asn Pro Asp Phe Tyr Lys Trp Asn Arg
                165                 170                 175

Val Lys Ile Arg Tyr Cys Asp Gly Ala Ser Phe Ala Gly Glu Gly Phe
            180                 185                 190

Asp Lys Glu Asn Gly Phe Tyr Phe Arg Gly Gln Arg Ile Trp Asp Ala
        195                 200                 205

Thr Val Arg His Leu Leu Ser Ile Gly Met Ala Ser Ala Glu Gln Val
    210                 215                 220

Leu Leu Thr Gly Cys Ser Ala Gly Gly Leu Ala Val Ile Leu His Cys
225                 230                 235                 240

Asp Gln Phe Gln Ala Phe Phe Pro Arg Ser Thr Thr Val Val Lys Cys
                245                 250                 255

Leu Ala Asp Ala Gly Leu Phe Leu Asp Ala Ser Asp Val Ser Gly Gly
            260                 265                 270

Arg Ser Leu Arg Ser Tyr Tyr Ser Asp Ile Val Ala Met Gln Gly Val
        275                 280                 285

Ala Pro Asn Leu Pro Pro Ala Cys Thr Ala Arg Leu Asp Thr Thr Ser
    290                 295                 300

Cys Phe Phe Pro Gln Asn Val Ile Asp Gly Ile Asn Thr Pro Ile Phe
```

-continued

```
305                 310                 315                 320

Leu Leu Asn Ala Ala Tyr Asp Val Trp Gln Ile Gln Glu Ser Leu Ala
                325                 330                 335

Pro Thr Gly Ala Asp Pro Ser Gly Ala Trp Arg Ala Cys Lys Ser Asn
            340                 345                 350

His Ser Ala Cys Asp Ala Ser Gln Met Lys Phe Leu Gln Asp Phe Arg
        355                 360                 365

Asp Gln Met Val Ala Ser Val Asn Asn Gly Phe Ala Gly Ser Arg Ser
    370                 375                 380

Asn Gly Leu Phe Ile Asn Ser Cys Phe Ala His Cys Gln Ser Glu Leu
385                 390                 395                 400

Pro Met Thr Trp Ser Asp Asn Ala Ala Gly Gly Gly Ala Ser Pro Ala
                405                 410                 415

Ile Gln Ser Arg Gly Ile Ala Lys Ser Val Gly Asp Trp Tyr Phe Gly
            420                 425                 430

Arg Ala Gln Val Lys Ala Ile Asp Cys Pro Tyr Pro Cys Asp Arg Thr
        435                 440                 445

Cys Arg Asn Ile Ile
    450


<210> SEQ ID NO 67
<211> LENGTH: 1592
<212> TYPE: DNA
<213> ORGANISM: Triticum avestinum
<220> FEATURE:
<221> NAME/KEY: misc_feature
<223> OTHER INFORMATION: n=a, c, g, or t
<220> FEATURE:
<221> NAME/KEY: misc_feature
<222> LOCATION: (1401)..(1402)
<223> OTHER INFORMATION: n=a, c, g, or t
<220> FEATURE:
<221> NAME/KEY: misc_feature
<222> LOCATION: (1467)..(1468)
<223> OTHER INFORMATION: n=a, c, g, or t
<220> FEATURE:
<221> NAME/KEY: misc_feature
<222> LOCATION: (1531)..(1532)
<223> OTHER INFORMATION: n=a, c, g, or t

<400> SEQUENCE: 67

gagctgcgct tgcacttgcg ctcggccggc ctccgctccg cgtataagtt ccttccttgc     60

tttggccact tccgccacga tcccttctcc ctcttccaga tccattcctc tcccagcccc    120

aggcctcgct cgcctccccc gttgggacgg agagagctcg gaagggcagg gagccatggg    180

ttcctgggtc cttcttgctg tggttctcgg gtccttggtg ggagctgcgc gcggctccga    240

gccgtggtcg aacggcacgc aggtctactc caccaatgcc aactccggca gcggcagcaa    300

cggcgccttc gtcgccctca ctctcatcca gtccgcggcc gccaagggag ccgtatgctt    360

ggatggaagt ttaccgggtt accacctaca ccggggatct ggatcagggt caaacaattg    420

gcttgtcaat ctggagggtg gaggatggtg caatgatgtt aaaagctgtg tgttccgcaa    480

gggcagtcgg cgtgggtcat cgaaccacat ggagaggcaa ctccagttta caggcataat    540

gagtaacagg cctgaagaaa atcctgattt ctacaactgg aacagagtga aggttcggta    600

ttgtgatggt ggatccttca ccggtgatgg ggctgacgcg gcttcaggcc tttatttccg    660

aggtcagcgt atttggcagg ctgctatcga tgacttgatg gcccaaggaa tgcgttctgc    720

tactcaggcc cttctttcgg gatgctctgc tgggggtgct tctgccatac ttcactgtga    780

tcagttccgt ggaatgtttc catcaaatac cagagtcaag tgcctcgctg atgctcgaat    840
```

```
gttccttgac tctgttgaca ttgcgggtcg tcgagaaatg agagacttat tcaatggcat    900

tgtgagattg caggcttctg gaagaagctt gcctcggtct tgtacctctc gcatggataa    960

aacctcatgc tttttccgc agaacgtgtt gccaaacatt caaactccga cttttatctt   1020

gaacactgct tatgatgtgt ggcagcttca agaaagtctg gctcccagaa cggctgatcc   1080

ccggggtcta tggcaaagtt gcaagcagaa ttacgcctct tgcaatagca atcaacttca   1140

gtttttaaat ggctttagga atgaaatgct taacgctgtg aagggtttct ccgggtcagg   1200

gcagaatggg gtattcatca actcttgttt cgcgcattgc cagagcgaga gacaggatac   1260

atggtactcg agcaactccc ctcgtcttgg caacaagaga atcgcagaag cggtcggtga   1320

ctggttcttc gagaggggca acgccaagta caccgactgc gcgtaccctt gcgacggcac   1380

gtgccatcac cttgtgttca nggggaggca tctctaatac gatcatatcc tttgatacca   1440

gcagcccagt gagtgggcac aaccganagg gaggtataga tagaagaaga tgggtgcaag   1500

ttggtggctt gccccgcggt catcgcctga natagatatg ataggccagg acctcgcacg   1560

caaacgcagc gaggccctct gcgttatttt ag                                 1592
```

<210> SEQ ID NO 68
<211> LENGTH: 413
<212> TYPE: PRT
<213> ORGANISM: Triticum avestinum
<220> FEATURE:
<221> NAME/KEY: MISC_FEATURE
<222> LOCATION: (409)..(410)
<223> OTHER INFORMATION: X=any aa

<400> SEQUENCE: 68

```
Met Gly Ser Trp Val Leu Leu Ala Val Val Leu Gly Ser Leu Val Gly
1               5                   10                  15

Ala Ala Arg Gly Ser Glu Pro Trp Ser Asn Gly Thr Gln Val Tyr Ser
            20                  25                  30

Thr Asn Ala Asn Ser Gly Ser Gly Ser Asn Gly Ala Phe Val Ala Leu
        35                  40                  45

Thr Leu Ile Gln Ser Ala Ala Ala Lys Gly Ala Val Cys Leu Asp Gly
    50                  55                  60

Ser Leu Pro Gly Tyr His Leu His Arg Gly Ser Gly Ser Gly Ser Asn
65                  70                  75                  80

Asn Trp Leu Val Asn Leu Glu Gly Gly Gly Trp Cys Asn Asp Val Lys
                85                  90                  95

Ser Cys Val Phe Arg Lys Gly Ser Arg Arg Gly Ser Ser Asn His Met
            100                 105                 110

Glu Arg Gln Leu Gln Phe Thr Gly Ile Met Ser Asn Arg Pro Glu Glu
        115                 120                 125

Asn Pro Asp Phe Tyr Asn Trp Asn Arg Val Lys Val Arg Tyr Cys Asp
    130                 135                 140

Gly Gly Ser Phe Thr Gly Asp Gly Ala Asp Ala Ala Ser Gly Leu Tyr
145                 150                 155                 160

Phe Arg Gly Gln Arg Ile Trp Gln Ala Ala Ile Asp Asp Leu Met Ala
                165                 170                 175

Gln Gly Met Arg Ser Ala Thr Gln Ala Leu Leu Ser Gly Cys Ser Ala
            180                 185                 190

Gly Gly Ala Ser Ala Ile Leu His Cys Asp Gln Phe Arg Gly Met Phe
        195                 200                 205

Pro Ser Asn Thr Arg Val Lys Cys Leu Ala Asp Ala Arg Met Phe Leu
```

```
    210                 215                 220

Asp Ser Val Asp Ile Ala Gly Arg Arg Glu Met Arg Asp Leu Phe Asn
225                 230                 235                 240

Gly Ile Val Arg Leu Gln Ala Ser Gly Arg Ser Leu Pro Arg Ser Cys
                245                 250                 255

Thr Ser Arg Met Asp Lys Thr Ser Cys Phe Phe Pro Gln Asn Val Leu
            260                 265                 270

Pro Asn Ile Gln Thr Pro Thr Phe Ile Leu Asn Thr Ala Tyr Asp Val
        275                 280                 285

Trp Gln Leu Gln Glu Ser Leu Ala Pro Arg Thr Ala Asp Pro Arg Gly
    290                 295                 300

Leu Trp Gln Ser Cys Lys Gln Asn Tyr Ala Ser Cys Asn Ser Asn Gln
305                 310                 315                 320

Leu Gln Phe Leu Asn Gly Phe Arg Asn Glu Met Leu Asn Ala Val Lys
                325                 330                 335

Gly Phe Ser Gly Ser Gly Gln Asn Gly Val Phe Ile Asn Ser Cys Phe
            340                 345                 350

Ala His Cys Gln Ser Glu Arg Gln Asp Thr Trp Tyr Ser Ser Asn Ser
        355                 360                 365

Pro Arg Leu Gly Asn Lys Arg Ile Ala Glu Ala Val Gly Asp Trp Phe
    370                 375                 380

Phe Glu Arg Gly Asn Ala Lys Tyr Thr Asp Cys Ala Tyr Pro Cys Asp
385                 390                 395                 400

Gly Thr Cys His His Leu Val Phe Xaa Gly Arg His Leu
                405                 410


<210> SEQ ID NO 69
<211> LENGTH: 34
<212> TYPE: DNA
<213> ORGANISM: artificial sequence
<220> FEATURE:
<223> OTHER INFORMATION: linker

<400> SEQUENCE: 69

ggcgcgccaa gcttggatcc gtcgacggcg cgcc                                34


<210> SEQ ID NO 70
<211> LENGTH: 4974
<212> TYPE: DNA
<213> ORGANISM: artificial sequence
<220> FEATURE:
<223> OTHER INFORMATION: plasmid KS133
<220> FEATURE:
<221> NAME/KEY: misc_feature
<222> LOCATION: (3951)..(3952)
<223> OTHER INFORMATION: n=a, c, g, or t

<400> SEQUENCE: 70

ggccgccgac tcgacgatga gcgagatgac cagctccggc cgcgacacaa gtgtgagagt      60

actaaataaa tgctttggtt gtacgaaatc attacactaa ataaaataat caaagcttat     120

atatgccttc cgctaaggcc gaatgcaaag aaattggttc tttctcgtta tcttttgcca     180

cttttactag tacgtattaa ttactactta atcatctttg tttacggctc attatatccg     240

tcgacggcgc gcccgatcat ccggatatag ttcctccttt cagcaaaaaa cccctcaaga     300

cccgtttaga ggccccaagg ggttatgcta gttattgctc agcggtggca gcagccaact     360

cagcttcctt tcgggctttg ttagcagccg gatcgatcca agctgtacct cactattcct     420

ttgccctcgg acgagtgctg gggcgtcggt ttccactatc ggcgagtact tctacacagc     480
```

catcggtcca gacggccgcg cttctgcggg cgatttgtgt acgcccgaca gtcccggctc 540
cggatcggac gattgcgtcg catcgaccct gcgcccaagc tgcatcatcg aaattgccgt 600
caaccaagct ctgatagagt tggtcaagac caatgcggag catatacgcc cggagccgcg 660
gcgatcctgc aagctccgga tgcctccgct cgaagtagcg cgtctgctgc tccatacaag 720
ccaaccacgg cctccagaag aagatgttgg cgacctcgta ttgggaatcc ccgaacatcg 780
cctcgctcca gtcaatgacc gctgttatgc ggccattgtc cgtcaggaca ttgttggagc 840
cgaaatccgc gtgcacgagg tgccggactt cggggcagtc ctcggcccaa agcatcagct 900
catcgagagc ctgcgcgacg gacgcactga cggtgtcgtc catcacagtt tgccagtgat 960
acacatgggg atcagcaatc gcgcatatga aatcacgcca tgtagtgtat tgaccgattc 1020
cttgcggtcc gaatgggccg aacccgctcg tctggctaag atcggccgca gcgatcgcat 1080
ccatagcctc cgcgaccggc tgcagaacag cgggcagttc ggtttcaggc aggtcttgca 1140
acgtgacacc ctgtgcacgg cgggagatgc aataggtcag gctctcgctg aattccccaa 1200
tgtcaagcac ttccggaatc gggagcgcgg ccgatgcaaa gtgccgataa acataacgat 1260
ctttgtagaa accatcggcg cagctattta cccgcaggac atatccacgc cctcctacat 1320
cgaagctgaa agcacgagat tcttcgccct ccgagagctg catcaggtcg gagacgctgt 1380
cgaacttttc gatcagaaac ttctcgacag acgtcgcggt gagttcaggc ttttccatgg 1440
gtatatctcc ttcttaaagt taaacaaaat tatttctaga gggaaaccgt tgtggtctcc 1500
ctatagtgag tcgtattaat ttcgcgggat cgagatctga tcaacctgca ttaatgaatc 1560
ggccaacgcg cggggagagg cggtttgcgt attgggcgct cttccgcttc ctcgctcact 1620
gactcgctgc gctcggtcgt tcggctgcgg cgagcggtat cagctcactc aaaggcggta 1680
atacggttat ccacagaatc aggggataac gcaggaaaga acatgtgagc aaaaggccag 1740
caaaaggcca ggaaccgtaa aaaggccgcg ttgctggcgt ttttccatag gctccgcccc 1800
cctgacgagc atcacaaaaa tcgacgctca agtcagaggt ggcgaaaccc gacaggacta 1860
taaagatacc aggcgtttcc ccctggaagc tccctcgtgc gctctcctgt tccgaccctg 1920
ccgcttaccg gatacctgtc cgcctttctc ccttcgggaa gcgtggcgct ttctcaatgc 1980
tcacgctgta ggtatctcag ttcggtgtag gtcgttcgct ccaagctggg ctgtgtgcac 2040
gaaccccccg ttcagcccga ccgctgcgcc ttatccggta actatcgtct tgagtccaac 2100
ccggtaagac acgacttatc gccactggca gcagccactg gtaacaggat tagcagagcg 2160
aggtatgtag gcggtgctac agagttcttg aagtggtggc ctaactacgg ctacactaga 2220
aggacagtat ttggtatctg cgctctgctg aagccagtta ccttcggaaa aagagttggt 2280
agctcttgat ccggcaaaca aaccaccgct ggtagcggtg gtttttttgt ttgcaagcag 2340
cagattacgc gcagaaaaaa aggatctcaa gaagatcctt tgatcttttc tacggggtct 2400
gacgctcagt ggaacgaaaa ctcacgttaa gggattttgg tcatgacatt aacctataaa 2460
aataggcgta tcacgaggcc ctttcgtctc gcgcgtttcg gtgatgacgg tgaaaacctc 2520
tgacacatgc agctcccgga gacggtcaca gcttgtctgt aagcggatgc cgggagcaga 2580
caagcccgtc agggcgcgtc agcgggtgtt ggcgggtgtc ggggctggct taactatgcg 2640
gcatcagagc agattgtact gagagtgcac catatggaca tattgtcgtt agaacgcggc 2700
tacaattaat acataacctt atgtatcata cacatacgat ttaggtgaca ctatagaacg 2760
gcgcgccaag cttggatcct cgaagagaag ggttaataac acatttttta acatttttaa 2820

-continued

```
cacaaatttt agttatttaa aaatttatta aaaaatttaa aataagaaga ggaactcttt   2880
aaataaatct aacttacaaa atttatgatt tttaataagt tttcaccaat aaaaaatgtc   2940
ataaaaatat gttaaaaagt atattatcaa tattctcttt atgataaata aaaagaaaaa   3000
aaaaataaaa gttaagtgaa aatgagattg aagtgacttt aggtgtgtat aaatatatca   3060
accccgccaa caatttattt aatccaaata tattgaagta tattattcca tagcctttat   3120
ttatttatat atttattata taaaagcttt atttgttcta ggttgttcat gaaatatttt   3180
tttggtttta tctccgttgt aagaaaatca tgtgctttgt gtcgccactc actattgcag   3240
ctttttcatg cattggtcag attgacggtt gattgtattt ttgtttttta tggttttgtg   3300
ttatgactta agtcttcatc tctttatctc ttcatcaggt ttgatggtta cctaatatgg   3360
tccatgggta catgcatggt taaattaggt ggccaacttt gttgtgaacg atagaatttt   3420
ttttatatta agtaaactat ttttatatta tgaaataata ataaaaaaaa tattttatca   3480
ttattaacaa aatcatatta gttaatttgt taactctata ataaaagaaa tactgtaaca   3540
ttcacattac atggtaacat ctttccaccc tttcatttgt tttttgtttg atgacttttt   3600
ttcttgttta aatttatttc ccttctttta aatttggaat acattatcat catatataaa   3660
ctaaaatact aaaaacagga ttacacaaat gataaataat aacacaaata tttataaatc   3720
tagctgcaat atatttaaac tagctatatc gatattgtaa aataaaacta gctgcattga   3780
tactgataaa aaaatatcat gtgctttctg gactgatgat gcagtatact tttgacattg   3840
cctttatttt atttttcaga aaagctttct tagttctggg ttcttcatta tttgtttccc   3900
atctccattg tgaattgaat catttgcttc gtgtcacaaa tacaatttag ntaggtacat   3960
gcattggtca gattcacggt ttattatgtc atgacttaag ttcatggtag tacattacct   4020
gccacgcatg cattatattg gttagatttg ataggcaaat ttggttgtca acaatataaa   4080
tataaataat gtttttatat tacgaaataa cagtgatcaa aacaaacagt tttatcttta   4140
ttaacaagat tttgtttttg tttgatgacg ttttttaatg tttacgcttt ccccccttctt   4200
ttgaatttag aacactttat catcataaaa tcaaatacta aaaaaattac atatttcata   4260
aataataaca caaatatttt taaaaaatct gaaataataa tgaacaatat tacatattat   4320
cacgaaaatt cattaataaa aatattatat aaataaaatg taatagtagt tatatgtagg   4380
aaaaaagtac tgcacgcata atatatacaa aaagattaaa atgaactatt ataaataata   4440
acactaaatt aatggtgaat catatcaaaa taatgaaaaa gtaaataaaa tttgtaatta   4500
acttctatat gtattacaca cacaaataat aaataatagt aaaaaaaatt atgataaata   4560
tttaccatct cataagatat ttaaaataat gataaaaata tagattattt tttatgcaac   4620
tagctagcca aaaagagaac acgggtatat ataaaaagag tacctttaaa ttctactgta   4680
cttcctttat tcctgacgtt tttatatcaa gtggacatac gtgaagattt taattatcag   4740
tctaaatatt tcattagcac ttaatacttt tctgttttat tcctatccta taagtagtcc   4800
cgattctccc aacattgctt attcacacaa ctaactaaga aagtcttcca tagcccccca   4860
agcggccgga gctggtcatc tcgctcatcg tcgagtcggc ggccggagct ggtcatctcg   4920
ctcatcgtcg agtcggcggc cgccgactcg acgatgagcg agatgaccag ctcc         4974
```

<210> SEQ ID NO 71
<211> LENGTH: 80
<212> TYPE: DNA
<213> ORGANISM: artificial sequence
<220> FEATURE:
<223> OTHER INFORMATION: nucleotide fragment

<400> SEQUENCE: 71
cggccggagc tggtcatctc gctcatcgtc gagtcggcgg ccgccgactc gacgatgagc 60
gagatgacca gctccggccg 80

<210> SEQ ID NO 72
<211> LENGTH: 118
<212> TYPE: DNA
<213> ORGANISM: artificial sequence
<220> FEATURE:
<223> OTHER INFORMATION: nucleotide fragment

<400> SEQUENCE: 72
cggccggagc tggtcatctc gctcatcgtc gagtcggcgg ccggagctgg tcatctcgct 60
catcgtcgag tcggcggccg ccgactcgac gatgagcgag atgaccagct ccggccgc 118

<210> SEQ ID NO 73
<211> LENGTH: 92
<212> TYPE: DNA
<213> ORGANISM: artificial sequence
<220> FEATURE:
<223> OTHER INFORMATION: primer

<400> SEQUENCE: 73
gaattccggc cggagctggt catctcgctc atcgtcgagt cggcggccgc cgactcgacg 60
atgagcgaga tgaccagctc cggccggaat tc 92

<210> SEQ ID NO 74
<211> LENGTH: 15
<212> TYPE: DNA
<213> ORGANISM: artificial sequence
<220> FEATURE:
<223> OTHER INFORMATION: primer

<400> SEQUENCE: 74
gaattccggc cggag 15

<210> SEQ ID NO 75
<211> LENGTH: 31
<212> TYPE: DNA
<213> ORGANISM: artificial sequence
<220> FEATURE:
<223> OTHER INFORMATION: primer

<400> SEQUENCE: 75
gcggccgcaa ttattgttca agggaatgca g 31

<210> SEQ ID NO 76
<211> LENGTH: 30
<212> TYPE: DNA
<213> ORGANISM: artificial sequence
<220> FEATURE:
<223> OTHER INFORMATION: primer

<400> SEQUENCE: 76
ctgatcggct ttctgtagtt gatcaaattc 30

<210> SEQ ID NO 77
<211> LENGTH: 30
<212> TYPE: DNA
<213> ORGANISM: artificial sequence
<220> FEATURE:
<223> OTHER INFORMATION: primer

<400> SEQUENCE: 77
gaatttgatc aactacagaa agccgatcag 30

<210> SEQ ID NO 78
<211> LENGTH: 30
<212> TYPE: DNA
<213> ORGANISM: artificial sequence
<220> FEATURE:
<223> OTHER INFORMATION: primer

<400> SEQUENCE: 78
cgaacatgtt gagacaaacc atgtctcctg 30

<210> SEQ ID NO 79
<211> LENGTH: 30
<212> TYPE: DNA
<213> ORGANISM: artificial sequence
<220> FEATURE:
<223> OTHER INFORMATION: primer

<400> SEQUENCE: 79
caggagacat ggtttgtctc aacatgttcg 30

<210> SEQ ID NO 80
<211> LENGTH: 3899
<212> TYPE: DNA
<213> ORGANISM: artificial sequence
<220> FEATURE:
<223> OTHER INFORMATION: plasmid pGEM T-Easy D

<400> SEQUENCE: 80
gggcgaattg ggcccgacgt cgcatgctcc cggccgccat ggcggccgcg ggaattcgat 60
tgcggccgca attattgttc aagggaatgc agaaggccaa ccaggccctt ttgtctggat 120
gctctgcagg tggtctggca tctataatac attgtgatga gttccggagc ttgtttccta 180
catctaccaa agtgaaatgt ttgagtgacg ccgggttttt cctagatgca gttgatgtat 240
ctgggggtca cacactgagg aatctgtttg gaggtgtagt taagttacag gaggtgcaaa 300
aaaatctgcc aaatagttgt ctcaaccaac tggacccaac ttcgtgtttt tttcctcaga 360
atttgatcaa ctacagaaag ccgatcaggc acttctctct ggatgctctg cgggtggtct 420
ggcatccata atacactgtg atgagttcgg gagcttgttt ggaaaatctt ccaaagtcaa 480
atgtttgagc gatggaggtt tttttcttga tgcaatggat gtatctgggg gacgcacact 540
gaggactctt ttcggaggtg tggttcagtt gcaggatgta caaaaaaatc tgccaaaaag 600
ttgtctcgac caactagacc caacttcgtg cttctttcct cagaatatga tcgaacatgt 660
tgagacccca ttgtttctac tcaatgctgc ttatgatgtg tggcaggtcc aagccagttt 720
agccccacct tcagctgacc gccttggttc ttggaatgaa tgcaaatcga accatgcaaa 780
ttgtagctca tctcaaatgc agttccttca agacttcaga aatcaaatgc tgggtgacat 840
taaagacttc tcaagctcat ctcaaactgg gctattcata aattcttgtt ttgctcattg 900
tcagtctgag agacaggaga catggtttgt ctcaacatgt tcgaatcact agtgaattcg 960
cggccgcctg caggtcgacc atatgggaga gctcccaacg cgttggatgc atagcttgag 1020
tattctatag tgtcacctaa atagcttggc gtaatcatgg tcatagctgt ttcctgtgtg 1080
aaattgttat ccgctcacaa ttccacacaa catacgagcc ggaagcataa agtgtaaagc 1140
ctggggtgcc taatgagtga gctaactcac attaattgcg ttgcgctcac tgcccgcttt 1200
ccagtcggga aacctgtcgt gccagctgca ttaatgaatc ggccaacgcg cggggagagg 1260

-continued cggtttgcgt attgggcgct cttccgcttc ctcgctcact gactcgctgc gctcggtcgt 1320
tcggctgcgg cgagcggtat cagctcactc aaaggcggta atacggttat ccacagaatc 1380
aggggataac gcaggaaaga acatgtgagc aaaaggccag caaaaggcca ggaaccgtaa 1440
aaaggccgcg ttgctggcgt ttttccatag gctccgcccc cctgacgagc atcacaaaaa 1500
tcgacgctca agtcagaggt ggcgaaaccc gacaggacta taaagatacc aggcgtttcc 1560
ccctggaagc tccctcgtgc gctctcctgt tccgaccctg ccgcttaccg gatacctgtc 1620
cgcctttctc ccttcgggaa gcgtggcgct ttctcatagc tcacgctgta ggtatctcag 1680
ttcggtgtag gtcgttcgct ccaagctggg ctgtgtgcac gaaccccccg ttcagcccga 1740
ccgctgcgcc ttatccggta actatcgtct tgagtccaac ccggtaagac acgacttatc 1800
gccactggca gcagccactg gtaacaggat tagcagagcg aggtatgtag gcggtgctac 1860
agagttcttg aagtggtggc ctaactacgg ctacactaga agaacagtat ttggtatctg 1920
cgctctgctg aagccagtta ccttcggaaa aagagttggt agctcttgat ccggcaaaca 1980
aaccaccgct ggtagcggtg gtttttttgt ttgcaagcag cagattacgc gcagaaaaaa 2040
aggatctcaa gaagatcctt tgatcttttc tacggggtct gacgctcagt ggaacgaaaa 2100
ctcacgttaa gggattttgg tcatgagatt atcaaaaagg atcttcacct agatcctttt 2160
aaattaaaaa tgaagtttta aatcaatcta aagtatatat gagtaaactt ggtctgacag 2220
ttaccaatgc ttaatcagtg aggcacctat ctcagcgatc tgtctatttc gttcatccat 2280
agttgcctga ctccccgtcg tgtagataac tacgatacgg gagggcttac catctggccc 2340
cagtgctgca atgataccgc gagacccacg ctcaccggct ccagatttat cagcaataaa 2400
ccagccagcc ggaagggccg agcgcagaag tggtcctgca actttatccg cctccatcca 2460
gtctattaat tgttgccggg aagctagagt aagtagttcg ccagttaata gtttgcgcaa 2520
cgttgttgcc attgctacag gcatcgtggt gtcacgctcg tcgtttggta tggcttcatt 2580
cagctccggt tcccaacgat caaggcgagt tacatgatcc cccatgttgt gcaaaaaagc 2640
ggttagctcc ttcggtcctc cgatcgttgt cagaagtaag ttggccgcag tgttatcact 2700
catggttatg gcagcactgc ataattctct tactgtcatg ccatccgtaa gatgcttttc 2760
tgtgactggt gagtactcaa ccaagtcatt ctgagaatag tgtatgcggc gaccgagttg 2820
ctcttgcccg gcgtcaatac gggataatac cgcgccacat agcagaactt taaaagtgct 2880
catcattgga aaacgttctt cggggcgaaa actctcaagg atcttaccgc tgttgagatc 2940
cagttcgatg taacccactc gtgcacccaa ctgatcttca gcatctttta ctttcaccag 3000
cgtttctggg tgagcaaaaa caggaaggca aaatgccgca aaaaagggaa taagggcgac 3060
acggaaatgt tgaatactca tactcttcct ttttcaatat tattgaagca tttatcaggg 3120
ttattgtctc atgagcggat acatatttga atgtatttag aaaaataaac aaataggggt 3180
tccgcgcaca tttccccgaa aagtgccacc tgatgcggtg tgaaataccg cacagatgcg 3240
taaggagaaa ataccgcatc aggaaattgt aagcgttaat attttgttaa aattcgcgtt 3300
aaatttttgt taaatcagct cattttttaa ccaataggcc gaaatcggca aaatccctta 3360
taaatcaaaa gaatagaccg agatagggtt gagtgttgtt ccagtttgga acaagagtcc 3420
actattaaag aacgtggact ccaacgtcaa agggcgaaaa accgtctatc agggcgatgg 3480
cccactacgt gaaccatcac cctaatcaag ttttttgggg tcgaggtgcc gtaaagcact 3540
aaatcggaac cctaaaggga gcccccgatt tagagcttga cggggaaagc cggcgaacgt 3600
ggcgagaaag gaagggaaga aagcgaaagg agcgggcgct agggcgctgg caagtgtagc 3660
ggtcacgctg cgcgtaacca ccacacccgc cgcgcttaat gcgccgctac agggcgcgtc 3720
cattcgccat tcaggctgcg caactgttgg gaagggcgat cggtgcgggc ctcttcgcta 3780
ttacgccagc tggcgaaagg gggatgtgct gcaaggcgat taagttgggt aacgccaggg 3840
ttttcccagt cacgacgttg taaaacgacg gccagtgaat tgtaatacga ctcactata 3899

<210> SEQ ID NO 81
<211> LENGTH: 3637
<212> TYPE: DNA
<213> ORGANISM: artificial sequence
<220> FEATURE:
<223> OTHER INFORMATION: plasmid pGEM T-Easy F

<400> SEQUENCE: 81
tcaggagaca tggtttgtct caacatgttc gatcatattc tgaggaaaga agcacgaagt 60
tgggtctagt tggtcgagac aactttttgg cagatttttt tgtacatcct gcaactgaac 120
cacacctccg aaaagagtcc tcagtgtgcg tcccccagat acatccattg catcaagaaa 180
aaaacctcca tcgctcaaac atttgacttt ggaagatttt ccaaacaagc tcccgaactc 240
atcacagtgt attatggatg ccagaccacc cgcagagcat ccagagagaa gtgcctgatc 300
ggctttctgt agttgatcaa attctgagga aaaaaacacg aagttgggtc cagttggttg 360
agacaactat ttggcagatt tttttgcacc tcctgtaact taactacacc tccaaacaga 420
ttcctcagtg tgtgaccccc agatacatca actgcatcta ggaaaaaccc ggcgtcactc 480
aaacatttca ctttggtaga tgtaggaaac aagctccgga actcatcaca atgtattata 540
gatgccagac cacctgcaga gcatccagac aaaagggcct ggttggcctt ctgcattccc 600
ttgaacaata attgcggccg caatcgaatt cccgcggccg ccatggcggc cgggagcatg 660
cgacgtcggg cccaattcgc cctatagtga gtcgtattac aattcactgg ccgtcgtttt 720
acaacgtcgt gactgggaaa accctggcgt tacccaactt aatcgccttg cagcacatcc 780
ccctttcgcc agctggcgta atagcgaaga ggcccgcacc gatcgccctt cccaacagtt 840
gcgcagcctg aatggcgaat ggacgcgccc tgtagcggcg cattaagcgc ggcgggtgtg 900
gtggttacgc gcagcgtgac cgctacactt gccagcgccc tagcgcccgc tcctttcgct 960
ttcttccctt cctttctcgc cacgttcgcc ggctttcccc gtcaagctct aaatcggggg 1020
ctccctttag ggttccgatt tagtgcttta cggcacctcg accccaaaaa acttgattag 1080
ggtgatggtt cacgtagtgg gccatcgccc tgatagacgg tttttcgccc tttgacgttg 1140
gagtccacgt tctttaatag tggactcttg ttccaaactg gaacaacact caaccctatc 1200
tcggtctatt cttttgattt ataagggatt ttgccgattt cggcctattg gttaaaaaat 1260
gagctgattt aacaaaaatt taacgcgaat tttaacaaaa tattaacgct tacaatttcc 1320
tgatgcggta ttttctcctt acgcatctgt gcggtatttc acaccgcatc aggtggcact 1380
tttcggggaa atgtgcgcgg aacccctatt tgtttatttt tctaaataca ttcaaatatg 1440
tatccgctca tgagacaata accctgataa atgcttcaat aatattgaaa aaggaagagt 1500
atgagtattc aacatttccg tgtcgccctt attccctttt ttgcggcatt ttgccttcct 1560
gtttttgctc acccagaaac gctggtgaaa gtaaaagatg ctgaagatca gttgggtgca 1620
cgagtgggtt acatcgaact ggatctcaac agcggtaaga tccttgagag ttttcgcccc 1680
gaagaacgtt ttccaatgat gagcactttt aaagttctgc tatgtggcgc ggtattatcc 1740
cgtattgacg ccgggcaaga gcaactcggt cgccgcatac actattctca gaatgacttg 1800

```
gttgagtact caccagtcac agaaaagcat cttacggatg gcatgacagt aagagaatta   1860
tgcagtgctg ccataaccat gagtgataac actgcggcca acttacttct gacaacgatc   1920
ggaggaccga aggagctaac cgcttttttg cacaacatgg gggatcatgt aactcgcctt   1980
gatcgttggg aaccggagct gaatgaagcc ataccaaacg acgagcgtga caccacgatg   2040
cctgtagcaa tggcaacaac gttgcgcaaa ctattaactg gcgaactact tactctagct   2100
tcccggcaac aattaataga ctggatggag gcggataaag ttgcaggacc acttctgcgc   2160
tcggcccttc cggctggctg gtttattgct gataaatctg gagccggtga gcgtgggtct   2220
cgcggtatca ttgcagcact ggggccagat ggtaagccct cccgtatcgt agttatctac   2280
acgacgggga gtcaggcaac tatggatgaa cgaaatagac agatcgctga gataggtgcc   2340
tcactgatta agcattggta actgtcagac caagtttact catatatact ttagattgat   2400
ttaaaacttc atttttaatt taaaaggatc taggtgaaga tcctttttga taatctcatg   2460
accaaaatcc cttaacgtga gttttcgttc cactgagcgt cagaccccgt agaaaagatc   2520
aaaggatctt cttgagatcc tttttttctg cgcgtaatct gctgcttgca aacaaaaaaa   2580
ccaccgctac cagcggtggt ttgtttgccg gatcaagagc taccaactct ttttccgaag   2640
gtaactggct tcagcagagc gcagatacca aatactgttc ttctagtgta gccgtagtta   2700
ggccaccact tcaagaactc tgtagcaccg cctacatacc tcgctctgct aatcctgtta   2760
ccagtggctg ctgccagtgg cgataagtcg tgtcttaccg ggttggactc aagacgatag   2820
ttaccggata aggcgcagcg gtcgggctga acggggggtt cgtgcacaca gcccagcttg   2880
gagcgaacga cctacaccga actgagatac ctacagcgtg agctatgaga aagcgccacg   2940
cttcccgaag ggagaaaggc ggacaggtat ccggtaagcg gcagggtcgg aacaggagag   3000
cgcacgaggg agcttccagg gggaaacgcc tggtatcttt atagtcctgt cgggtttcgc   3060
cacctctgac ttgagcgtcg atttttgtga tgctcgtcag gggggcggag cctatggaaa   3120
aacgccagca acgcggcctt tttacggttc ctggcctttt gctggccttt tgctcacatg   3180
ttctttcctg cgttatcccc tgattctgtg gataaccgta ttaccgcctt tgagtgagct   3240
gataccgctc gccgcagccg aacgaccgag cgcagcgagt cagtgagcga ggaagcggaa   3300
gagcgcccaa tacgcaaacc gcctctcccc gcgcgttggc cgattcatta atgcagctgg   3360
cacgacaggt ttcccgactg gaaagcgggc agtgagcgca acgcaattaa tgtgagttag   3420
ctcactcatt aggcacccca ggctttacac tttatgcttc cggctcgtat gttgtgtgga   3480
attgtgagcg gataacaatt tcacacagga aacagctatg accatgatta cgccaagcta   3540
tttaggtgac actatagaat actcaagcta tgcatccaac gcgttgggag ctctcccata   3600
tggtcgacct gcaggcggcc gcgaattcac tagtgat                            3637
```

<210> SEQ ID NO 82
<211> LENGTH: 9062
<212> TYPE: DNA
<213> ORGANISM: artificial sequence
<220> FEATURE:
<223> OTHER INFORMATION: plasmid pKS426
<220> FEATURE:
<221> NAME/KEY: misc_feature
<222> LOCATION: (6642)..(6643)
<223> OTHER INFORMATION: n=a, c, g, or t

<400> SEQUENCE: 82

```
ggccgcgaca caagtgtgag agtactaaat aaatgctttg gttgtacgaa atcattacac     60
```

-continued

```
taaataaaat aatcaaagct tatatatgcc ttccgctaag gccgaatgca aagaaattgg    120
ttctttctcg ttatcttttg ccacttttac tagtacgtat taattactac ttaatcatct    180
ttgtttacgg ctcattatat ccgtcgacgg cgcgcccgat catccggata tagttcctcc    240
tttcagcaaa aaacccctca agacccgttt agaggcccca aggggttatg ctagttattg    300
ctcagcggtg gcagcagcca actcagcttc ctttcgggct ttgttagcag ccggatcgat    360
ccaagctgta cctcactatt cctttgccct cggacgagtg ctggggcgtc ggtttccact    420
atcggcgagt acttctacac agccatcggt ccagacggcc gcgcttctgc gggcgatttg    480
tgtacgcccg acagtcccgg ctccggatcg gacgattgcg tcgcatcgac cctgcgccca    540
agctgcatca tcgaaattgc cgtcaaccaa gctctgatag agttggtcaa gaccaatgcg    600
gagcatatac gcccggagcc gcggcgatcc tgcaagctcc ggatgcctcc gctcgaagta    660
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc cgcgtgcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac accctgtgca cggcgggaga tgcaataggt   1140
caggctctcg ctgaattccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt ttcgatcaga aacttctcga cagacgtcgc   1380
ggtgagttca ggcttttcca tgggtatatc tccttcttaa agttaaacaa aattatttct   1440
agagggaaac cgttgtggtc tccctatagt gagtcgtatt aatttcgcgg gatcgagatc   1500
gatccaattc caatcccaca aaaatctgag cttaacagca cagttgctcc tctcagagca   1560
gaatcgggta ttcaacaccc tcatatcaac tactacgttg tgtataacgg tccacatgcc   1620
ggtatatacg atgactgggg ttgtacaaag gcggcaacaa acggcgttcc cggagttgca   1680
cacaagaaat ttgccactat tacagaggca agagcagcag ctgacgcgta cacaacaagt   1740
cagcaaacag acaggttgaa cttcatcccc aaaggagaag ctcaactcaa gcccaagagc   1800
tttgctaagg ccctaacaag cccaccaaag caaaaagccc actggctcac gctaggaacc   1860
aaaaggccca gcagtgatcc agccccaaaa gagatctcct ttgccccgga gattacaatg   1920
gacgatttcc tctatcttta cgatctagga aggaagttcg aaggtgaagg tgacgacact   1980
atgttcacca ctgataatga gaaggttagc ctcttcaatt tcagaaagaa tgctgaccca   2040
cagatggtta gagaggccta cgcagcaggt ctcatcaaga cgatctaccc gagtaacaat   2100
ctccaggaga tcaaatacct tcccaagaag gttaaagatg cagtcaaaag attcaggact   2160
aattgcatca agaacacaga gaaagacata tttctcaaga tcagaagtac tattccagta   2220
tggacgattc aaggcttgct tcataaacca aggcaagtaa tagagattgg agtctctaaa   2280
aaggtagttc ctactgaatc taaggccatg catggagtct aagattcaaa tcgaggatct   2340
aacagaactc gccgtgaaga ctggcgaaca gttcatacag agtcttttac gactcaatga   2400
caagaagaaa atcttcgtca acatggtgga gcacgacact ctggtctact ccaaaaatgt   2460
```

-continued

```
caaagataca gtctcagaag accaaagggc tattgagact tttcaacaaa ggataatttc   2520
gggaaacctc ctcggattcc attgcccagc tatctgtcac ttcatcgaaa ggacagtaga   2580
aaaggaaggt ggctcctaca aatgccatca ttgcgataaa ggaaaggcta tcattcaaga   2640
tgcctctgcc gacagtggtc ccaaagatgg acccccaccc acgaggagca tcgtggaaaa   2700
agaagacgtt ccaaccacgt cttcaaagca agtggattga tgtgacatct ccactgacgt   2760
aagggatgac gcacaatccc actatccttc gcaagaccct tcctctatat aaggaagttc   2820
atttcatttg gagaggacac gctcgagctc atttctctat tacttcagcc ataacaaaag   2880
aactcttttc tcttcttatt aaaccatgaa aaagcctgaa ctcaccgcga cgtctgtcga   2940
gaagtttctg atcgaaaagt tcgacagcgt ctccgacctg atgcagctct cggagggcga   3000
agaatctcgt gctttcagct tcgatgtagg agggcgtgga tatgtcctgc gggtaaatag   3060
ctgcgccgat ggtttctaca aagatcgtta tgtttatcgg cactttgcat cggccgcgct   3120
cccgattccg gaagtgcttg acattgggga attcagcgag agcctgacct attgcatctc   3180
ccgccgtgca cagggtgtca cgttgcaaga cctgcctgaa accgaactgc ccgctgttct   3240
gcagccggtc gcggaggcca tggatgcgat cgctgcggcc gatcttagcc agacgagcgg   3300
gttcggccca ttcggaccgc aaggaatcgg tcaatacact acatggcgtg atttcatatg   3360
cgcgattgct gatccccatg tgtatcactg gcaaactgtg atggacgaca ccgtcagtgc   3420
gtccgtcgcg caggctctcg atgagctgat gctttgggcc gaggactgcc ccgaagtccg   3480
gcacctcgtg cacgcggatt tcggctccaa caatgtcctg acggacaatg gccgcataac   3540
agcggtcatt gactggagcg aggcgatgtt cggggattcc caatacgagg tcgccaacat   3600
cttcttctgg aggccgtggt tggcttgtat ggagcagcag acgcgctact tcgagcggag   3660
gcatccggag cttgcaggat cgccgcggct ccgggcgtat atgctccgca ttggtcttga   3720
ccaactctat cagagcttgg ttgacggcaa tttcgatgat gcagcttggg cgcagggtcg   3780
atgcgacgca atcgtccgat ccggagccgg gactgtcggg cgtacacaaa tcgcccgcag   3840
aagcgcggcc gtctggaccg atggctgtgt agaagtactc gccgatagtg gaaaccgacg   3900
ccccagcact cgtccgaggg caaaggaata gtgaggtacc taaagaagga gtgcgtcgaa   3960
gcagatcgtt caaacatttg gcaataaagt ttcttaagat tgaatcctgt tgccggtctt   4020
gcgatgatta tcatataatt tctgttgaat tacgttaagc atgtaataat taacatgtaa   4080
tgcatgacgt tatttatgag atgggttttt atgattagag tcccgcaatt atacatttaa   4140
tacgcgatag aaaacaaaat atagcgcgca aactaggata aattatcgcg cgcggtgtca   4200
tctatgttac tagatcgatg tcgaatctga tcaacctgca ttaatgaatc ggccaacgcg   4260
cggggagagg cggtttgcgt attgggcgct cttccgcttc ctcgctcact gactcgctgc   4320
gctcggtcgt tcggctgcgg cgagcggtat cagctcactc aaaggcggta atacggttat   4380
ccacagaatc aggggataac gcaggaaaga acatgtgagc aaaaggccag caaaaggcca   4440
ggaaccgtaa aaaggccgcg ttgctggcgt ttttccatag gctccgcccc cctgacgagc   4500
atcacaaaaa tcgacgctca agtcagaggt ggcgaaaccc gacaggacta taaagatacc   4560
aggcgtttcc ccctggaagc tccctcgtgc gctctcctgt tccgaccctg ccgcttaccg   4620
gatacctgtc cgcctttctc ccttcgggaa gcgtggcgct ttctcaatgc tcacgctgta   4680
ggtatctcag ttcggtgtag gtcgttcgct ccaagctggg ctgtgtgcac gaaccccccg   4740
ttcagcccga ccgctgcgcc ttatccggta actatcgtct tgagtccaac ccggtaagac   4800
```

-continued

```
acgacttatc gccactggca gcagccactg gtaacaggat tagcagagcg aggtatgtag   4860
gcggtgctac agagttcttg aagtggtggc ctaactacgg ctacactaga aggacagtat   4920
ttggtatctg cgctctgctg aagccagtta ccttcggaaa aagagttggt agctcttgat   4980
ccggcaaaca aaccaccgct ggtagcggtg gtttttttgt ttgcaagcag cagattacgc   5040
gcagaaaaaa aggatctcaa gaagatcctt tgatcttttc tacggggtct gacgctcagt   5100
ggaacgaaaa ctcacgttaa gggattttgg tcatgacatt aacctataaa aataggcgta   5160
tcacgaggcc ctttcgtctc gcgcgtttcg gtgatgacgg tgaaaacctc tgacacatgc   5220
agctcccgga gacggtcaca gcttgtctgt aagcggatgc cgggagcaga caagcccgtc   5280
agggcgcgtc agcgggtgtt ggcgggtgtc ggggctggct taactatgcg gcatcagagc   5340
agattgtact gagagtgcac catatggaca tattgtcgtt agaacgcggc tacaattaat   5400
acataacctt atgtatcata cacatacgat ttaggtgaca ctatagaacg gcgcgccaag   5460
cttggatcct cgaagagaag ggttaataac acactttttt aacattttta acacaaattt   5520
tagttattta aaaatttatt aaaaaattta aaataagaag aggaactctt taaataaatc   5580
taacttacaa aatttatgat ttttaataag ttttcaccaa taaaaaatgt cataaaaata   5640
tgttaaaaag tatattatca atattctctt tatgataaat aaaaagaaaa aaaaaataaa   5700
agttaagtga aaatgagatt gaagtgactt taggtgtgta taaatatatc aaccccgcca   5760
acaatttatt taatccaaat atattgaagt atattattcc atagccttta tttatttata   5820
tatttattat ataaaagctt tatttgttct aggttgttca tgaaatattt ttttggtttt   5880
atctccgttg taagaaaatc atgtgctttg tgtcgccact cactattgca gctttttcat   5940
gcattggtca gattgacggt tgattgtatt tttgtttttt atggttttgt gttatgactt   6000
aagtcttcat ctctttatct cttcatcagg tttgatggtt acctaatatg gtccatgggt   6060
acatgcatgg ttaaattagg tggccaactt tgttgtgaac gatagaattt tttttatatt   6120
aagtaaacta tttttatatt atgaaataat aataaaaaaa atattttatc attattaaca   6180
aaatcatatt agttaatttg ttaactctat aataaaagaa atactgtaac attcacatta   6240
catggtaaca tctttccacc ctttcatttg tttttttgttt gatgactttt tttcttgttt   6300
aaatttattt cccttctttt aaatttggaa tacattatca tcatatataa actaaaatac   6360
taaaaacagg attacacaaa tgataaataa taacacaaat atttataaat ctagctgcaa   6420
tatatttaaa ctagctatat cgatattgta aaataaaact agctgcattg atactgataa   6480
aaaaatatca tgtgctttct ggactgatga tgcagtatac ttttgacatt gcctttattt   6540
tatttttcag aaaagctttc ttagttctgg gttcttcatt atttgtttcc catctccatt   6600
gtgaattgaa tcatttgctt cgtgtcacaa atacaattta gntaggtaca tgcattggtc   6660
agattcacgg tttattatgt catgacttaa gttcatggta gtacattacc tgccacgcat   6720
gcattatatt ggttagattt gataggcaaa tttggttgtc aacaatataa atataaataa   6780
tgtttttata ttacgaaata acagtgatca aaacaaacag ttttatcttt attaacaaga   6840
ttttgttttt gtttgatgac gtttttttaat gtttacgctt tccccccttct tttgaattta   6900
gaacacttta tcatcataaa atcaaatact aaaaaaatta catatttcat aaataataac   6960
acaaatattt ttaaaaaatc tgaaataata atgaacaata ttacatatta tcacgaaaat   7020
tcattaataa aaatattata taaataaaat gtaatagtag ttatatgtag gaaaaaagta   7080
ctgcacgcat aatatataca aaaagattaa aatgaactat tataaataat aacactaaat   7140
taatggtgaa tcatatcaaa ataatgaaaa agtaaataaa atttgtaatt aacttctata   7200
```

```
tgtattacac acacaaataa taaataatag taaaaaaaat tatgataaat atttaccatc   7260

tcataagata tttaaaataa tgataaaaat atagattatt ttttatgcaa ctagctagcc   7320

aaaaagagaa cacgggtata tataaaaaga gtacctttaa attctactgt acttccttta   7380

ttcctgacgt ttttatatca agtggacata cgtgaagatt ttaattatca gtctaaatat   7440

ttcattagca cttaatactt ttctgtttta ttcctatcct ataagtagtc ccgattctcc   7500

caacattgct tattcacaca actaactaag aaagtcttcc atagcccccc aagcggccgc   7560

aattattgtt caagggaatg cagaaggcca accaggccct tttgtctgga tgctctgcag   7620

gtggtctggc atctataata cattgtgatg agttccggag cttgtttcct acatctacca   7680

aagtgaaatg tttgagtgac gccgggtttt tcctagatgc agttgatgta tctgggggtc   7740

acacactgag gaatctgttt ggaggtgtag ttaagttaca ggaggtgcaa aaaaatctgc   7800

caaatagttg tctcaaccaa ctggacccaa cttcgtgttt ttttcctcag aatttgatca   7860

actacagaaa gccgatcagg cacttctctc tggatgctct gcgggtggtc tggcatccat   7920

aatacactgt gatgagttcg ggagcttgtt tggaaaatct tccaaagtca aatgtttgag   7980

cgatggaggt ttttttcttg atgcaatgga tgtatctggg ggacgcacac tgaggactct   8040

tttcggaggt gtggttcagt tgcaggatgt acaaaaaaat ctgccaaaaa gttgtctcga   8100

ccaactagac ccaacttcgt gcttctttcc tcagaatatg atcgaacatg ttgagacccc   8160

attgtttcta ctcaatgctg cttatgatgt gtggcaggtc caagccagtt tagccccacc   8220

ttcagctgac cgccttggtt cttggaatga atgcaaatcg aaccatgcaa attgtagctc   8280

atctcaaatg cagttccttc aagacttcag aaatcaaatg ctgggtgaca ttaaagactt   8340

ctcaagctca tctcaaactg ggctattcat aaattcttgt tttgctcatt gtcagtctga   8400

gagacaggag acatggtttg tctcaacatg ttcgaatcac tagtgattca ggagacatgg   8460

tttgtctcaa catgttcgat catattctga ggaaagaagc acgaagttgg gtctagttgg   8520

tcgagacaac tttttggcag attttttgt acatcctgca actgaaccac acctccgaaa   8580

agagtcctca gtgtgcgtcc cccagataca tccattgcat caagaaaaaa acctccatcg   8640

ctcaaacatt tgactttgga agattttcca aacaagctcc cgaactcatc acagtgtatt   8700

atggatgcca gaccacccgc agagcatcca gagagaagtg cctgatcggc tttctgtagt   8760

tgatcaaatt ctgaggaaaa aaacacgaag ttgggtccag ttggttgaga caactatttg   8820

gcagattttt ttgcacctcc tgtaacttaa ctacacctcc aaacagattc ctcagtgtgt   8880

gacccccaga tacatcaact gcatctagga aaaacccggc gtcactcaaa catttcactt   8940

tggtagatgt aggaaacaag ctccggaact catcacaatg tattatagat gccagaccac   9000

ctgcagagca tccagacaaa agggcctggt tggccttctg cattcccttg aacaataatt   9060

gc                                                                  9062
```

<210> SEQ ID NO 83
<211> LENGTH: 5267
<212> TYPE: DNA
<213> ORGANISM: artificial sequence
<220> FEATURE:
<223> OTHER INFORMATION: plasmid pKS120

<400> SEQUENCE: 83

```
atctgatcaa cctgcattaa tgaatcggcc aacgcgcggg gagaggcggt ttgcgtattg     60

ggcgctcttc cgcttcctcg ctcactgact cgctgcgctc ggtcgttcgg ctgcggcgag    120
```

-continued

```
cggtatcagc tcactcaaag gcggtaatac ggttatccac agaatcaggg gataacgcag    180
gaaagaacat gtgagcaaaa ggccagcaaa aggccaggaa ccgtaaaaag gccgcgttgc    240
tggcgttttt ccataggctc cgcccccctg acgagcatca caaaaatcga cgctcaagtc    300
agaggtggcg aaacccgaca ggactataaa gataccaggc gtttccccct ggaagctccc    360
tcgtgcgctc tcctgttccg accctgccgc ttaccggata cctgtccgcc tttctccctt    420
cgggaagcgt ggcgctttct caatgctcac gctgtaggta tctcagttcg gtgtaggtcg    480
ttcgctccaa gctgggctgt gtgcacgaac cccccgttca gcccgaccgc tgcgccttat    540
ccggtaacta tcgtcttgag tccaacccgg taagacacga cttatcgcca ctggcagcag    600
ccactggtaa caggattagc agagcgaggt atgtaggcgg tgctacagag ttcttgaagt    660
ggtggcctaa ctacggctac actagaagga cagtatttgg tatctgcgct ctgctgaagc    720
cagttacctt cggaaaaaga gttggtagct cttgatccgg caaacaaacc accgctggta    780
gcggtggttt ttttgtttgc aagcagcaga ttacgcgcag aaaaaaagga tctcaagaag    840
atcctttgat cttttctacg gggtctgacg ctcagtggaa cgaaaactca cgttaaggga    900
ttttggtcat gacattaacc tataaaaata ggcgtatcac gaggcccttt cgtctcgcgc    960
gtttcggtga tgacggtgaa aacctctgac acatgcagct cccggagacg gtcacagctt   1020
gtctgtaagc ggatgccggg agcagacaag cccgtcaggg cgcgtcagcg ggtgttggcg   1080
ggtgtcgggg ctggcttaac tatgcggcat cagagcagat tgtactgaga gtgcaccata   1140
tggacatatt gtcgttagaa cgcggctaca attaatacat aaccttatgt atcatacaca   1200
tacgatttag gtgacactat agaacggcgc gccaagcttg gatccgtcga cggcgcgccc   1260
gatcatccgg atatagttcc tcctttcagc aaaaaacccc tcaagacccg tttagaggcc   1320
ccaaggggtt atgctagtta ttgctcagcg gtggcagcag ccaactcagc ttcctttcgg   1380
gctttgttag cagccggatc gatccaagct gtacctcact attcctttgc cctcggacga   1440
gtgctggggc gtcggtttcc actatcggcg agtacttcta cacagccatc ggtccagacg   1500
gccgcgcttc tgcgggcgat ttgtgtacgc ccgacagtcc cggctccgga tcggacgatt   1560
gcgtcgcatc gaccctgcgc ccaagctgca tcatcgaaat tgccgtcaac caagctctga   1620
tagagttggt caagaccaat gcggagcata tacgcccgga gccgcggcga tcctgcaagc   1680
tccggatgcc tccgctcgaa gtagcgcgtc tgctgctcca tacaagccaa ccacggcctc   1740
cagaagaaga tgttggcgac ctcgtattgg gaatccccga acatcgcctc gctccagtca   1800
atgaccgctg ttatgcggcc attgtccgtc aggacattgt tggagccgaa atccgcgtgc   1860
acgaggtgcc ggacttcggg gcagtcctcg gcccaaagca tcagctcatc gagagcctgc   1920
gcgacggacg cactgacggt gtcgtccatc acagtttgcc agtgatacac atggggatca   1980
gcaatcgcgc atatgaaatc acgccatgta gtgtattgac cgattccttg cggtccgaat   2040
gggccgaacc cgctcgtctg gctaagatcg gccgcagcga tcgcatccat agcctccgcg   2100
accggctgca gaacagcggg cagttcggtt tcaggcaggt cttgcaacgt gacaccctgt   2160
gcacggcggg agatgcaata ggtcaggctc tcgctgaatt ccccaatgtc aagcacttcc   2220
ggaatcggga gcgcggccga tgcaaagtgc cgataaacat aacgatcttt gtagaaacca   2280
tcggcgcagc tatttacccg caggacatat ccacgccctc ctacatcgaa gctgaaagca   2340
cgagattctt cgccctccga gagctgcatc aggtcggaga cgctgtcgaa cttttcgatc   2400
agaaacttct cgacagacgt cgcggtgagt tcaggctttt ccatgggtat atctccttct   2460
taaagttaaa caaaattatt tctagaggga aaccgttgtg gtctccctat agtgagtcgt   2520
```

attaattttcg cgggatcgag atcgatccaa ttccaatccc acaaaaatct gagcttaaca 2580
gcacagttgc tcctctcaga gcagaatcgg gtattcaaca ccctcatatc aactactacg 2640
ttgtgtataa cggtccacat gccggtatat acgatgactg gggttgtaca aaggcggcaa 2700
caaacggcgt tcccggagtt gcacacaaga aatttgccac tattacagag gcaagagcag 2760
cagctgacgc gtacacaaca agtcagcaaa cagacaggtt gaacttcatc cccaaaggag 2820
aagctcaact caagcccaag agctttgcta aggccctaac aagcccacca aagcaaaaag 2880
cccactggct cacgctagga accaaaaggc ccagcagtga tccagcccca aaagagatct 2940
cctttgcccc ggagattaca atggacgatt tcctctatct ttacgatcta ggaaggaagt 3000
tcgaaggtga aggtgacgac actatgttca ccactgataa tgagaaggtt agcctcttca 3060
atttcagaaa gaatgctgac ccacagatgg ttagagaggc ctacgcagca ggtctcatca 3120
agacgatcta cccgagtaac aatctccagg agatcaaata ccttcccaag aaggttaaag 3180
atgcagtcaa aagattcagg actaattgca tcaagaacac agagaaagac atatttctca 3240
agatcagaag tactattcca gtatggacga ttcaaggctt gcttcataaa ccaaggcaag 3300
taatagagat tggagtctct aaaaaggtag ttcctactga atctaaggcc atgcatggag 3360
tctaagattc aaatcgagga tctaacagaa ctcgccgtga agactggcga acagttcata 3420
cagagtcttt tacgactcaa tgacaagaag aaaatcttcg tcaacatggt ggagcacgac 3480
actctggtct actccaaaaa tgtcaaagat acagtctcag aagaccaaag ggctattgag 3540
acttttcaac aaaggataat ttcgggaaac ctcctcggat tccattgccc agctatctgt 3600
cacttcatcg aaaggacagt agaaaaggaa ggtggctcct acaaatgcca tcattgcgat 3660
aaaggaaagg ctatcattca agatgcctct gccgacagtg gtcccaaaga tggaccccca 3720
cccacgagga gcatcgtgga aaaagaagac gttccaacca cgtcttcaaa gcaagtggat 3780
tgatgtgaca tctccactga cgtaagggat gacgcacaat cccactatcc ttcgcaagac 3840
ccttcctcta tataaggaag ttcatttcat ttggagagga cacgctcgag ctcatttctc 3900
tattacttca gccataacaa aagaactctt ttctcttctt attaaaccat gaaaaagcct 3960
gaactcaccg cgacgtctgt cgagaagttt ctgatcgaaa agttcgacag cgtctccgac 4020
ctgatgcagc tctcggaggg cgaagaatct cgtgctttca gcttcgatgt aggagggcgt 4080
ggatatgtcc tgcgggtaaa tagctgcgcc gatggtttct acaaagatcg ttatgtttat 4140
cggcactttg catcggccgc gctcccgatt ccggaagtgc ttgacattgg ggaattcagc 4200
gagagcctga cctattgcat ctcccgccgt gcacagggtg tcacgttgca agacctgcct 4260
gaaaccgaac tgcccgctgt tctgcagccg gtcgcggagg ccatggatgc gatcgctgcg 4320
gccgatctta gccagacgag cgggttcggc ccattcggac cgcaaggaat cggtcaatac 4380
actacatggc gtgatttcat atgcgcgatt gctgatcccc atgtgtatca ctggcaaact 4440
gtgatggacg acaccgtcag tgcgtccgtc gcgcaggctc tcgatgagct gatgctttgg 4500
gccgaggact gccccgaagt ccggcacctc gtgcacgcgg atttcggctc caacaatgtc 4560
ctgacggaca atggccgcat aacagcggtc attgactgga gcgaggcgat gttcggggat 4620
tcccaatacg aggtcgccaa catcttcttc tggaggccgt ggttggcttg tatggagcag 4680
cagacgcgct acttcgagcg gaggcatccg gagcttgcag gatcgccgcg gctccgggcg 4740
tatatgctcc gcattggtct tgaccaactc tatcagagct tggttgacgg caatttcgat 4800
gatgcagctt gggcgcaggg tcgatgcgac gcaatcgtcc gatccggagc cgggactgtc 4860

```
gggcgtacac aaatcgcccg cagaagcgcg gccgtctgga ccgatggctg tgtagaagta   4920

ctcgccgata gtggaaaccg acgccccagc actcgtccga gggcaaagga atagtgaggt   4980

acctaaagaa ggagtgcgtc gaagcagatc gttcaaacat ttggcaataa agtttcttaa   5040

gattgaatcc tgttgccggt cttgcgatga ttatcatata atttctgttg aattacgtta   5100

agcatgtaat aattaacatg taatgcatga cgttatttat gagatgggtt tttatgatta   5160

gagtcccgca attatacatt taatacgcga tagaaaacaa aatatagcgc gcaaactagg   5220

ataaattatc gcgcgcggtg tcatctatgt tactagatcg atgtcga                 5267
```

```
<210> SEQ ID NO 84
<211> LENGTH: 1614
<212> TYPE: DNA
<213> ORGANISM: Arabidopsis thaliana

<400> SEQUENCE: 84

tctcgctatc aatcacacac atgcaacagt acaagatttg tcagagtcca cagaaatcga     60

tcttttcgag tcaagatttt cagctctgtt caggactccg gcggagatga agagtgtgtt    120

gcgtattgcg gcggcgatat tctggctttg gctgtttatc gtgttaggtg tgattgggag    180

tgggaatgtg agagatacag acgatgagat ctcgttactc gaaagtcaat tggtggtgac    240

atctccgtcg cagcttctta tggtgcctct cactttgatt caggctgctg cctccaaagg    300

agctgtgtgc ctggatggaa cactacctgg ttatcatcta caccctggtt ctggatcagg    360

agctaaccgg tggctcatcc aactcgaggg tggaggatgg tgcaacacac gtaggagctg    420

tatcttccgg aaaaccactc gccgtggttc atcaaatcat atggagaaag ttttggcctt    480

cactggaata ttgagcaata aatctaatga gaatcctgac ttcttcaact ggaacagagt    540

caaattgcgt tactgcgatg gtgcctcttt caccggcgat agtcaggatg agagctcaca    600

actttactat agaggacaac gaatctggca ttcagctatg gaagaactac tctctaaagg    660

catgcaaaaa gcagaacagg ctctactttc tggatgttca gctgggggat tagcttccat    720

cctacactgc gatcagttca aggaactatt tccgggcact acgacagtga aatgcttaag    780

tgatgctgga atgtttatgg atgcagtgga tgtctctggg ggccactcgc tccggaaaat    840

gttccaaggt gttgttacag tacagaacct ccaaaaggaa ctgtccactg cttgtacaaa    900

gcatttggat ccaacttcgt gcttctttcc ccagaacttg gtttcaggca ttaagactcc    960

aatgtttctt ctcaatgcag catatgacgc ttggcaggta caagagagtt tagctccacc   1020

atcagttgac ctaagcggct cttggaaggc atgcaaatct gatcactcgc attgtaattc   1080

atctcagatc cagttcttcc aagacttcag gactcatatg gtagatgctg taaagtcttt   1140

cgcgacatcg acacataacg gtgtgttcat aaactcatgc ttcgctcact gccaatctga   1200

aagacaggac acttggtatg caccagattc tcctactctt catggcaaga ccgttgctga   1260

atctgttggt gattggtact ttgacagaac aacagtgaaa gccattgact gtccttaccc   1320

ctgtgacaaa acatgtcaca atctcatctt caagtgagat gacaaatgac atatactctt   1380

caaactcaaa cagcttactt gattcttata ccatactacc attagtaaca acaattcctg   1440

aaaaaccgca tttcatcttt tacataatat gtgctatttt gactcaaata aagttagttt   1500

ttcgtgtgtt ttgtttaatc cttggattca ttgtattcta atacacaaag catcagactc   1560

tgcttttcat aaaagagtaa ctgattttat atgtgatttg tagaattggg tgct         1614
```

```
<210> SEQ ID NO 85
<211> LENGTH: 416
```

```
<212> TYPE: PRT
<213> ORGANISM: Arabidopsis thaliana

<400> SEQUENCE: 85

Met Lys Ser Val Leu Arg Ile Ala Ala Ala Ile Phe Trp Leu Trp Leu
1               5                   10                  15

Phe Ile Val Leu Gly Val Ile Gly Ser Gly Asn Val Arg Asp Thr Asp
            20                  25                  30

Asp Glu Ile Ser Leu Leu Glu Ser Gln Leu Val Val Thr Ser Pro Ser
        35                  40                  45

Gln Leu Leu Met Val Pro Leu Thr Leu Ile Gln Ala Ala Ala Ser Lys
    50                  55                  60

Gly Ala Val Cys Leu Asp Gly Thr Leu Pro Gly Tyr His Leu His Pro
65                  70                  75                  80

Gly Ser Gly Ser Gly Ala Asn Arg Trp Leu Ile Gln Leu Glu Gly Gly
                85                  90                  95

Gly Trp Cys Asn Thr Arg Arg Ser Cys Ile Phe Arg Lys Thr Thr Arg
            100                 105                 110

Arg Gly Ser Ser Asn His Met Glu Lys Val Leu Ala Phe Thr Gly Ile
        115                 120                 125

Leu Ser Asn Lys Ser Asn Glu Asn Pro Asp Phe Phe Asn Trp Asn Arg
    130                 135                 140

Val Lys Leu Arg Tyr Cys Asp Gly Ala Ser Phe Thr Gly Asp Ser Gln
145                 150                 155                 160

Asp Glu Ser Ser Gln Leu Tyr Tyr Arg Gly Gln Arg Ile Trp His Ser
                165                 170                 175

Ala Met Glu Glu Leu Leu Ser Lys Gly Met Gln Lys Ala Glu Gln Ala
            180                 185                 190

Leu Leu Ser Gly Cys Ser Ala Gly Gly Leu Ala Ser Ile Leu His Cys
        195                 200                 205

Asp Gln Phe Lys Glu Leu Phe Pro Gly Thr Thr Thr Val Lys Cys Leu
    210                 215                 220

Ser Asp Ala Gly Met Phe Met Asp Ala Val Asp Val Ser Gly Gly His
225                 230                 235                 240

Ser Leu Arg Lys Met Phe Gln Gly Val Val Thr Val Gln Asn Leu Gln
                245                 250                 255

Lys Glu Leu Ser Thr Ala Cys Thr Lys His Leu Asp Pro Thr Ser Cys
            260                 265                 270

Phe Phe Pro Gln Asn Leu Val Ser Gly Ile Lys Thr Pro Met Phe Leu
        275                 280                 285

Leu Asn Ala Ala Tyr Asp Ala Trp Gln Val Gln Glu Ser Leu Ala Pro
    290                 295                 300

Pro Ser Val Asp Leu Ser Gly Ser Trp Lys Ala Cys Lys Ser Asp His
305                 310                 315                 320

Ser His Cys Asn Ser Ser Gln Ile Gln Phe Phe Gln Asp Phe Arg Thr
                325                 330                 335

His Met Val Asp Ala Val Lys Ser Phe Ala Thr Ser Thr His Asn Gly
            340                 345                 350

Val Phe Ile Asn Ser Cys Phe Ala His Cys Gln Ser Glu Arg Gln Asp
        355                 360                 365

Thr Trp Tyr Ala Pro Asp Ser Pro Thr Leu His Gly Lys Thr Val Ala
    370                 375                 380

Glu Ser Val Gly Asp Trp Tyr Phe Asp Arg Thr Thr Val Lys Ala Ile
385                 390                 395                 400
```

```
Asp Cys Pro Tyr Pro Cys Asp Lys Thr Cys His Asn Leu Ile Phe Lys
                405                 410                 415


<210> SEQ ID NO 86
<211> LENGTH: 409
<212> TYPE: PRT
<213> ORGANISM: Glycine max

<400> SEQUENCE: 86

Met Lys Val Ile Leu Leu Leu Ile Ala Ala Ser Phe Ser Phe Val Ser
1               5                   10                  15

Val Leu Arg Ser Glu Ala Glu His Leu Phe Gln Asn Asp Ala Val Ser
            20                  25                  30

Leu Ala Val Glu Val Pro Pro Gly Pro Pro Pro Leu Met Val Pro Leu
        35                  40                  45

Thr Leu Ile Gln Gly Ala Ala Ser Lys Gly Ala Val Cys Leu Asp Gly
    50                  55                  60

Thr Leu Pro Gly Tyr His Phe His Pro Gly Phe Gly Ser Gly Ala Asn
65                  70                  75                  80

Ser Trp Leu Ile Gln Leu Glu Gly Gly Gly Trp Cys Asn Thr Ile Ser
                85                  90                  95

Ser Cys Val Phe Arg Lys Thr Thr Arg Arg Gly Ser Ser Lys Tyr Met
            100                 105                 110

Glu Lys Gln Leu Ala Phe Thr Gly Leu Leu Ser Asn Lys Ala Glu Glu
        115                 120                 125

Asn Pro Asp Phe Phe Asn Trp Asn Arg Val Lys Val Arg Tyr Cys Asp
    130                 135                 140

Gly Ala Ser Phe Ser Gly Asp Ser Gln Asn Glu Val Ala Gln Leu Gln
145                 150                 155                 160

Phe Arg Gly Gln Lys Ile Trp Gln Ala Ala Met Gln Glu Leu Leu Phe
                165                 170                 175

Lys Gly Met Gln Lys Ala Asn Gln Ala Leu Leu Ser Gly Cys Ser Ala
            180                 185                 190

Gly Gly Leu Ala Ser Ile Ile His Cys Asp Glu Phe Arg Ser Leu Phe
        195                 200                 205

Pro Thr Ser Thr Lys Val Lys Cys Leu Ser Asp Ala Gly Phe Phe Leu
    210                 215                 220

Asp Ala Val Asp Val Ser Gly Gly His Thr Leu Arg Asn Leu Phe Gly
225                 230                 235                 240

Gly Val Val Lys Leu Gln Glu Val Gln Lys Asn Leu Pro Asn Ser Cys
                245                 250                 255

Leu Asn Gln Leu Asp Pro Thr Ser Cys Phe Phe Pro Gln Asn Leu Ile
            260                 265                 270

Asn Tyr Val Glu Thr Pro Leu Phe Leu Leu Asn Ala Ala Tyr Asp Ala
        275                 280                 285

Trp Gln Val Gln Glu Ser Leu Val Pro His Ser Ala Asp Pro His Gly
    290                 295                 300

Ser Trp Asn Asp Cys Lys Ala Asn His Ala His Cys Asn Ser Ser Gln
305                 310                 315                 320

Ile Gln Phe Leu Gln Asp Phe Arg Asn Gln Met Leu Asn Asp Val Lys
                325                 330                 335

Gly Phe Ser Glu Thr Ser Gln Thr Gly Leu Phe Ile Asn Ser Cys Phe
            340                 345                 350

Ala His Cys Gln Ser Glu Arg Gln Asp Thr Trp Phe Ala Asp Asp Ser
```

```
        355                 360                 365

Pro Leu Ile Asn Asn Val Pro Val Ala Ile Ala Val Gly Asp Trp Phe
    370                 375                 380

Leu Asp Arg Lys Thr Val Lys Ala Ile Asp Cys Ala Tyr Pro Cys Asp
385                 390                 395                 400

Asn Thr Cys His Asn Leu Val Phe Lys
                405


<210> SEQ ID NO 87
<211> LENGTH: 375
<212> TYPE: PRT
<213> ORGANISM: Arabidopsis thaliana

<400> SEQUENCE: 87

Leu Val Val Thr Ser Pro Ser Gln Leu Leu Met Val Pro Leu Thr Leu
1               5                   10                  15

Ile Gln Ala Ala Ala Ser Lys Gly Ala Val Cys Leu Asp Gly Thr Leu
            20                  25                  30

Pro Gly Tyr His Leu His Pro Gly Ser Gly Ser Gly Ala Asn Arg Trp
        35                  40                  45

Leu Ile Gln Leu Glu Gly Gly Gly Trp Cys Asn Thr Arg Arg Ser Cys
    50                  55                  60

Ile Phe Arg Lys Thr Thr Arg Arg Gly Ser Ser Asn His Met Glu Lys
65                  70                  75                  80

Val Leu Ala Phe Thr Gly Ile Leu Ser Asn Lys Ser Asn Glu Asn Pro
                85                  90                  95

Asp Phe Phe Asn Trp Asn Arg Val Lys Leu Arg Tyr Cys Asp Gly Ala
            100                 105                 110

Ser Phe Thr Gly Asp Ser Gln Asp Glu Ser Ser Gln Leu Tyr Tyr Arg
        115                 120                 125

Gly Gln Arg Ile Trp His Ser Ala Met Glu Glu Leu Leu Ser Lys Gly
    130                 135                 140

Met Gln Lys Ala Glu Gln Ala Leu Leu Ser Gly Cys Ser Ala Gly Gly
145                 150                 155                 160

Leu Ala Ser Ile Leu His Cys Asp Gln Phe Lys Glu Leu Phe Pro Gly
                165                 170                 175

Thr Thr Thr Val Lys Cys Leu Ser Asp Ala Gly Met Phe Met Asp Ala
            180                 185                 190

Val Asp Val Ser Gly Gly His Ser Leu Arg Lys Met Phe Gln Gly Val
        195                 200                 205

Val Thr Val Gln Asn Leu Gln Lys Glu Leu Ser Thr Ala Cys Thr Lys
    210                 215                 220

His Leu Asp Pro Thr Ser Cys Phe Phe Pro Gln Asn Leu Val Ser Gly
225                 230                 235                 240

Ile Lys Thr Pro Met Phe Leu Leu Asn Ala Ala Tyr Asp Ala Trp Gln
                245                 250                 255

Val Gln Glu Ser Leu Ala Pro Pro Ser Val Asp Leu Ser Gly Ser Trp
            260                 265                 270

Lys Ala Cys Lys Ser Asp His Ser His Cys Asn Ser Ser Gln Ile Gln
        275                 280                 285

Phe Phe Gln Asp Phe Arg Thr His Met Val Asp Ala Val Lys Ser Phe
    290                 295                 300

Ala Thr Ser Thr His Asn Gly Val Phe Ile Asn Ser Cys Phe Ala His
305                 310                 315                 320
```

```
Cys Gln Ser Glu Arg Gln Asp Thr Trp Tyr Ala Pro Asp Ser Pro Thr
                325                 330                 335

Leu His Gly Lys Thr Val Ala Glu Ser Val Gly Asp Trp Tyr Phe Asp
            340                 345                 350

Arg Thr Thr Val Lys Ala Ile Asp Cys Pro Tyr Pro Cys Asp Lys Thr
        355                 360                 365

Cys His Asn Leu Ile Phe Lys
    370                 375


<210> SEQ ID NO 88
<211> LENGTH: 21
<212> TYPE: DNA
<213> ORGANISM: artificial sequence
<220> FEATURE:
<223> OTHER INFORMATION: DNA corresponding to the amiRNA used to silence
      esterase

<400> SEQUENCE: 88

tattacacca tcctcctccc t                                                21


<210> SEQ ID NO 89
<211> LENGTH: 21
<212> TYPE: DNA
<213> ORGANISM: artificial sequence
<220> FEATURE:
<223> OTHER INFORMATION: artificial star sequence

<400> SEQUENCE: 89

aggaaggagg atggtgtaat a                                                21


<210> SEQ ID NO 90
<211> LENGTH: 590
<212> TYPE: DNA
<213> ORGANISM: artificial sequence
<220> FEATURE:
<223> OTHER INFORMATION: microRNA 396b precursor
<220> FEATURE:
<221> NAME/KEY: misc_feature
<222> LOCATION: (539)..(541)
<223> OTHER INFORMATION: n is a, c, g, or t

<400> SEQUENCE: 90

gcggccgcgc gagaaacttt gtatgggcat ggttatttct cacttctcac cctcctttac      60

tttcttatgc taaatcctcc ttcccctata tctccaccct caaccccttt ttctcattat     120

aacttttggt gcctagatgg tgtgtgtgtg tgcgcgcgag agatctgagc tcaattttcc     180

tctctcaagt cctggtcatg cttttccaca gctttcttga acttcttatg catcttatat     240

ctctccacct ccaggatttt aagccctaga agctcaagaa agctgtggga gaatatggca     300

attcaggctt ttaattgctt tcatttggta ccatcacttg caagatttca gagtacaagg     360

tgaacacaca catcttcctc ttcatcaatt ctctagtttc atccttatct tttcattcac     420

ggtaactctc actaccctct ttcatcttat aagttatacc gggggtgtga tgttgatgag     480

tgtaaattaa atatatgtga tctctttctc tggaaaaatt ttcagtgtga tatacatann     540

natctcttaa tctagagatt ttatggcttt gttatatata aggcggccgc                590


<210> SEQ ID NO 91
<211> LENGTH: 605
<212> TYPE: DNA
<213> ORGANISM: artificial sequence
<220> FEATURE:
<223> OTHER INFORMATION: ready microRNA 396b precursor
<220> FEATURE:
```

<221> NAME/KEY: misc_feature
<222> LOCATION: (548)..(550)
<223> OTHER INFORMATION: n is a, c, g, or t

<400> SEQUENCE: 91
gcggccgcgc gagaaacttt gtatgggcat ggttatttct cacttctcac cctcctttac 60
tttcttatgc taaatcctcc ttcccctata tctccaccct caacccettt ttctcattat 120 aacttttggt gcctagatgg tgtgtgtgtg tgcgcgcgag agatctgagc tcaattttcc 180
tctctcaagt cctggtcatg ctgtttaaac cacagctttc ttgaacttct tatgcatctt 240
atatctctcc acctccagga ttttaagccc tagaagctca agaaagctgt gggagtttaa 300
actatggcaa ttcaggcttt taattgcttt catttggtac catcacttgc aagatttcag 360
agtacaaggt gaacacacac atcttcctct tcatcaattc tctagtttca tccttatctt 420
ttcattcacg gtaactctca ctaccctctt tcatcttata agttataccg gggtgtgat 480 gttgatgagt gtaaattaaa tatatgtgat ctctttctct ggaaaaattt tcagtgtgat 540
atacatannn atctcttaat ctagagattt tatggctttg ttatatataa ggaattcgcg 600
gccgc 605

<210> SEQ ID NO 92
<211> LENGTH: 8151
<212> TYPE: DNA
<213> ORGANISM: artificial sequence
<220> FEATURE:
<223> OTHER INFORMATION: ready microRNA 396b-KS126 plasmid
<220> FEATURE:
<221> NAME/KEY: misc_feature
<222> LOCATION: (546)..(548)
<223> OTHER INFORMATION: n is a, c, g, or t
<220> FEATURE:
<221> NAME/KEY: misc_feature
<222> LOCATION: (7239)..(7239)
<223> OTHER INFORMATION: n is a, c, g, or t

<400> SEQUENCE: 92
ggccgcgcga gaaactttgt atgggcatgg ttatttctca cttctcaccc tcctttactt 60
tcttatgcta aatcctcctt cccctatatc tccaccctca accccttttt ctcattataa 120
cttttggtgc ctagatggtg tgtgtgtgtg cgcgcgagag atctgagctc aattttcctc 180
tctcaagtcc tggtcatgct gtttaaacca cagctttctt gaacttctta tgcatcttat 240
atctctccac ctccaggatt ttaagcccta gaagctcaag aaagctgtgg gagtttaaac 300
tatggcaatt caggctttta attgctttca tttggtacca tcacttgcaa gatttcagag 360
tacaaggtga acacacacat cttcctcttc atcaattctc tagtttcatc cttatctttt 420
cattcacggt aactctcact accctctttc atcttataag ttataccggg ggtgtgatgt 480
tgatgagtgt aaattaaata tatgtgatct ctttctctgg aaaaattttc agtgtgatat 540
acatannnat ctcttaatct agagatttta tggctttgtt atatataagg aattcgcggc 600
cgcgacacaa gtgtgagagt actaaataaa tgctttggtt gtacgaaatc attacactaa 660
ataaaataat caaagcttat atatgccttc cgctaaggcc gaatgcaaag aaattggttc 720
tttctcgtta tcttttgcca cttttactag tacgtattaa ttactactta atcatctttg 780
tttacggctc attatatccg tcgacggcgc gcccgatcat ccggatatag ttcctccttt 840
cagcaaaaaa cccctcaaga cccgtttaga ggccccaagg ggttatgcta gttattgctc 900
agcggtggca gcagccaact cagcttcctt tcgggctttg ttagcagccg gatcgatcca 960
agctgtacct cactattcct ttgccctcgg acgagtgctg gggcgtcggt ttccactatc 1020
ggcgagtact tctacacagc catcggtcca gacggccgcg cttctgcggg cgatttgtgt 1080
acgcccgaca gtcccggctc cggatcggac gattgcgtcg catcgaccct gcgcccaagc 1140
tgcatcatcg aaattgccgt caaccaagct ctgatagagt tggtcaagac caatgcggag 1200
catatacgcc cggagccgcg gcgatcctgc aagctccgga tgcctccgct cgaagtagcg 1260
cgtctgctgc tccatacaag ccaaccacgg cctccagaag aagatgttgg cgacctcgta 1320
ttgggaatcc ccgaacatcg cctcgctcca gtcaatgacc gctgttatgc ggccattgtc 1380
cgtcaggaca ttgttggagc cgaaatccgc gtgcacgagg tgccggactt cggggcagtc 1440
ctcggcccaa agcatcagct catcgagagc ctgcgcgacg gacgcactga cggtgtcgtc 1500
catcacagtt tgccagtgat acacatgggg atcagcaatc gcgcatatga aatcacgcca 1560
tgtagtgtat tgaccgattc cttgcggtcc gaatgggccg aacccgctcg tctggctaag 1620
atcggccgca gcgatcgcat ccatagcctc cgcgaccggc tgcagaacag cgggcagttc 1680
ggtttcaggc aggtcttgca acgtgacacc ctgtgcacgg cgggagatgc aataggtcag 1740
gctctcgctg aattccccaa tgtcaagcac ttccggaatc gggagcgcgg ccgatgcaaa 1800
gtgccgataa acataacgat ctttgtagaa accatcggcg cagctattta cccgcaggac 1860
atatccacgc cctcctacat cgaagctgaa agcacgagat tcttcgccct ccgagagctg 1920
catcaggtcg gagacgctgt cgaacttttc gatcagaaac ttctcgacag acgtcgcggt 1980
gagttcaggc ttttccatgg gtatatctcc ttcttaaagt taaacaaaat tatttctaga 2040
gggaaaccgt tgtggtctcc ctatagtgag tcgtattaat ttcgcgggat cgagatcgat 2100
ccaattccaa tcccacaaaa atctgagctt aacagcacag ttgctcctct cagagcagaa 2160
tcgggtattc aacaccctca tatcaactac tacgttgtgt ataacggtcc acatgccggt 2220
atatacgatg actggggttg tacaaaggcg gcaacaaacg gcgttcccgg agttgcacac 2280
aagaaatttg ccactattac agaggcaaga gcagcagctg acgcgtacac aacaagtcag 2340
caaacagaca ggttgaactt catccccaaa ggagaagctc aactcaagcc caagagcttt 2400
gctaaggccc taacaagccc accaaagcaa aaagcccact ggctcacgct aggaaccaaa 2460
aggcccagca gtgatccagc cccaaaagag atctcctttg ccccggagat tacaatggac 2520
gatttcctct atctttacga tctaggaagg aagttcgaag gtgaaggtga cgacactatg 2580
ttcaccactg ataatgagaa ggttagcctc ttcaatttca gaaagaatgc tgacccacag 2640
atggttagag aggcctacgc agcaggtctc atcaagacga tctacccgag taacaatctc 2700
caggagatca aataccttcc caagaaggtt aaagatgcag tcaaaagatt caggactaat 2760
tgcatcaaga acacagagaa agacatattt ctcaagatca gaagtactat tccagtatgg 2820
acgattcaag gcttgcttca taaaccaagg caagtaatag agattggagt ctctaaaaag 2880
gtagttccta ctgaatctaa ggccatgcat ggagtctaag attcaaatcg aggatctaac 2940
agaactcgcc gtgaagactg gcgaacagtt catacagagt cttttacgac tcaatgacaa 3000
gaagaaaatc ttcgtcaaca tggtggagca cgacactctg gtctactcca aaaatgtcaa 3060
agatacagtc tcagaagacc aaagggctat tgagactttt caacaaagga taatttcggg 3120
aaacctcctc ggattccatt gcccagctat ctgtcacttc atcgaaagga cagtagaaaa 3180
ggaaggtggc tcctacaaat gccatcattg cgataaagga aaggctatca ttcaagatgc 3240
ctctgccgac agtggtccca aagatggacc cccacccacg aggagcatcg tggaaaaaga 3300
agacgttcca accacgtctt caaagcaagt ggattgatgt gacatctcca ctgacgtaag 3360

-continued ggatgacgca caatcccact atccttcgca agacccttcc tctatataag gaagttcatt 3420
tcatttggag aggacacgct cgagctcatt tctctattac ttcagccata acaaaagaac 3480
tcttttctct tcttattaaa ccatgaaaaa gcctgaactc accgcgacgt ctgtcgagaa 3540
gtttctgatc gaaaagttcg acagcgtctc cgacctgatg cagctctcgg agggcgaaga 3600
atctcgtgct ttcagcttcg atgtaggagg gcgtggatat gtcctgcggg taaatagctg 3660
cgccgatggt ttctacaaag atcgttatgt ttatcggcac tttgcatcgg ccgcgctccc 3720
gattccggaa gtgcttgaca ttggggaatt cagcgagagc ctgacctatt gcatctcccg 3780
ccgtgcacag ggtgtcacgt tgcaagacct gcctgaaacc gaactgcccg ctgttctgca 3840
gccggtcgcg gaggccatgg atgcgatcgc tgcggccgat cttagccaga cgagcgggtt 3900
cggcccattc ggaccgcaag gaatcggtca atacactaca tggcgtgatt tcatatgcgc 3960
gattgctgat ccccatgtgt atcactggca aactgtgatg gacgacaccg tcagtgcgtc 4020
cgtcgcgcag gctctcgatg agctgatgct ttgggccgag gactgccccg aagtccggca 4080
cctcgtgcac gcggatttcg gctccaacaa tgtcctgacg gacaatggcc gcataacagc 4140
ggtcattgac tggagcgagg cgatgttcgg ggattcccaa tacgaggtcg ccaacatctt 4200
cttctggagg ccgtggttgg cttgtatgga gcagcagacg cgctacttcg agcggaggca 4260
tccggagctt gcaggatcgc cgcggctccg ggcgtatatg ctccgcattg gtcttgacca 4320
actctatcag agcttggttg acggcaattt cgatgatgca gcttgggcgc agggtcgatg 4380
cgacgcaatc gtccgatccg gagccgggac tgtcgggcgt acacaaatcg cccgcagaag 4440
cgcggccgtc tggaccgatg gctgtgtaga agtactcgcc gatagtggaa accgacgccc 4500
cagcactcgt ccgagggcaa aggaatagtg aggtacctaa agaaggagtg cgtcgaagca 4560
gatcgttcaa acatttggca ataaagtttc ttaagattga atcctgttgc cggtcttgcg 4620
atgattatca tataatttct gttgaattac gttaagcatg taataattaa catgtaatgc 4680
atgacgttat ttatgagatg ggtttttatg attagagtcc cgcaattata catttaatac 4740
gcgatagaaa acaaaatata gcgcgcaaac taggataaat tatcgcgcgc ggtgtcatct 4800
atgttactag atcgatgtcg aatctgatca acctgcatta atgaatcggc caacgcgcgg 4860
ggagaggcgg tttgcgtatt gggcgctctt ccgcttcctc gctcactgac tcgctgcgct 4920
cggtcgttcg gctgcggcga gcggtatcag ctcactcaaa ggcggtaata cggttatcca 4980
cagaatcagg ggataacgca ggaaagaaca tgtgagcaaa aggccagcaa aaggccagga 5040
accgtaaaaa ggccgcgttg ctggcgtttt tccataggct ccgcccccct gacgagcatc 5100
acaaaaatcg acgctcaagt cagaggtggc gaaacccgac aggactataa agataccagg 5160
cgtttccccc tggaagctcc ctcgtgcgct ctcctgttcc gaccctgccg cttaccggat 5220
acctgtccgc ctttctccct tcgggaagcg tggcgctttc tcaatgctca cgctgtaggt 5280
atctcagttc ggtgtaggtc gttcgctcca agctgggctg tgtgcacgaa ccccccgttc 5340
agcccgaccg ctgcgcctta tccggtaact atcgtcttga gtccaacccg gtaagacacg 5400
acttatcgcc actggcagca gccactggta acaggattag cagagcgagg tatgtaggcg 5460
gtgctacaga gttcttgaag tggtggccta actacggcta cactagaagg acagtatttg 5520
gtatctgcgc tctgctgaag ccagttacct tcggaaaaag agttggtagc tcttgatccg 5580
gcaaacaaac caccgctggt agcggtggtt tttttgtttg caagcagcag attacgcgca 5640
gaaaaaaagg atctcaagaa gatcctttga tcttttctac ggggtctgac gctcagtgga 5700
acgaaaactc acgttaaggg attttggtca tgacattaac ctataaaaat aggcgtatca 5760

-continued cgaggccctt tcgtctcgcg cgtttcggtg atgacggtga aaacctctga cacatgcagc 5820
tcccggagac ggtcacagct tgtctgtaag cggatgccgg gagcagacaa gcccgtcagg 5880
gcgcgtcagc gggtgttggc gggtgtcggg gctggcttaa ctatgcggca tcagagcaga 5940
ttgtactgag agtgcaccat atggacatat tgtcgttaga acgcggctac aattaataca 6000
taaccttatg tatcatacac atacgattta ggtgacacta tagaacggcg cgccaagctt 6060
ggatcctcga agagaagggt taataacaca ctttttaac atttttaaca caaattttag 6120
ttatttaaaa atttattaaa aaatttaaaa taagaagagg aactctttaa ataaatctaa 6180
cttacaaaat ttatgatttt taataagttt tcaccaataa aaaatgtcat aaaaatatgt 6240
taaaaagtat attatcaata ttctctttat gataaataaa aagaaaaaaa aaataaaagt 6300
taagtgaaaa tgagattgaa gtgactttag gtgtgtataa atatatcaac cccgccaaca 6360
atttatttaa tccaaatata ttgaagtata ttattccata gcctttattt atttatatat 6420
ttattatata aaagctttat ttgttctagg ttgttcatga aatatttttt tggttttatc 6480
tccgttgtaa gaaaatcatg tgctttgtgt cgccactcac tattgcagct tttcatgca 6540 ttggtcagat tgacggttga ttgtattttt gtttttatg gttttgtgtt atgacttaag 6600
tcttcatctc tttatctctt catcaggttt gatggttacc taatatggtc catgggtaca 6660
tgcatggtta aattaggtgg ccaactttgt tgtgaacgat agaatttttt ttatattaag 6720
taaactattt ttatattatg aaataataat aaaaaaaata ttttatcatt attaacaaaa 6780
tcatattagt taatttgtta actctataat aaaagaaata ctgtaacatt cacattacat 6840
ggtaacatct ttccaccctt tcatttgttt tttgtttgat gacttttttt cttgtttaaa 6900
tttatttccc ttcttttaaa tttggaatac attatcatca tatataaact aaaatactaa 6960
aaacaggatt acacaaatga taaataataa cacaaatatt tataaatcta gctgcaatat 7020
atttaaacta gctatatcga tattgtaaaa taaaactagc tgcattgata ctgataaaaa 7080
aatatcatgt gctttctgga ctgatgatgc agtatacttt tgacattgcc tttattttat 7140
ttttcagaaa agctttctta gttctgggtt cttcattatt tgtttcccat ctccattgtg 7200
aattgaatca tttgcttcgt gtcacaaata caatttagnt aggtacatgc attggtcaga 7260
ttcacggttt attatgtcat gacttaagtt catggtagta cattacctgc cacgcatgca 7320
ttatattggt tagatttgat aggcaaattt ggttgtcaac aatataaata taaataatgt 7380
ttttatatta cgaaataaca gtgatcaaaa caaacagttt tatctttatt aacaagattt 7440
tgtttttgtt tgatgacgtt ttttaatgtt tacgctttcc cccttctttt gaatttagaa 7500
cactttatca tcataaaatc aaatactaaa aaaattacat atttcataaa taataacaca 7560
aatattttta aaaaatctga aataataatg aacaatatta catattatca cgaaaattca 7620
ttaataaaaa tattatataa ataaaatgta atagtagtta tatgtaggaa aaaagtactg 7680
cacgcataat atatacaaaa agattaaaat gaactattat aaataataac actaaattaa 7740
tggtgaatca tatcaaaata atgaaaaagt aaataaaatt tgtaattaac ttctatatgt 7800
attacacaca caaataataa ataatagtaa aaaaaattat gataaatatt taccatctca 7860
taagatattt aaaataatga taaaaatata gattattttt tatgcaacta gctagccaaa 7920
aagagaacac gggtatatat aaaaagagta cctttaaatt ctactgtact tcctttattc 7980
ctgacgtttt tatatcaagt ggacatacgt gaagatttta attatcagtc taaatatttc 8040
attagcactt aatacttttc tgttttattc ctatcctata agtagtcccg attctcccaa 8100
cattgcttat tcacacaact aactaagaaa gtcttccata gccccccaag c 8151

<210> SEQ ID NO 93
<211> LENGTH: 59
<212> TYPE: DNA
<213> ORGANISM: artificial sequence
<220> FEATURE:
<223> OTHER INFORMATION: primer 396b PAE-like primA

<400> SEQUENCE: 93
tctcaagtcc tggtcatgct ttattacacc atcctcctcc ctcttatgca tcttatatc 59

<210> SEQ ID NO 94
<211> LENGTH: 59
<212> TYPE: DNA
<213> ORGANISM: artificial sequence
<220> FEATURE:
<223> OTHER INFORMATION: primer 396b PAE-like primB

<400> SEQUENCE: 94
cctgaattgc catattctat tacaccatcc tccttcctct agggcttaaa atcctggag 59

<210> SEQ ID NO 95
<211> LENGTH: 125
<212> TYPE: DNA
<213> ORGANISM: artificial sequence
<220> FEATURE:
<223> OTHER INFORMATION: 396b-PAE-like in fusion ready microRNA sequence

<400> SEQUENCE: 95
tctcaagtcc tggtcatgct ttattacacc atcctcctcc ctcttatgca tcttatatct 60
ctccacctcc aggattttaa gccctagagg aaggaggatg gtgtaataga atatggcaat 120
tcagg 125

<210> SEQ ID NO 96
<211> LENGTH: 8135
<212> TYPE: DNA
<213> ORGANISM: artificial sequence
<220> FEATURE:
<223> OTHER INFORMATION: nucleotides sequence of the plasmid of
396b-PAE-like
<220> FEATURE:
<221> NAME/KEY: misc_feature
<222> LOCATION: (6642)..(6642)
<223> OTHER INFORMATION: n is a, c, g, or t

<400> SEQUENCE: 96
ggccgcgaca caagtgtgag agtactaaat aaatgctttg gttgtacgaa atcattacac 60
taaataaaat aatcaaagct tatatatgcc ttccgctaag gccgaatgca aagaaattgg 120
ttctttctcg ttatcttttg ccacttttac tagtacgtat taattactac ttaatcatct 180
ttgtttacgg ctcattatat ccgtcgacgg cgcgcccgat catccggata tagttcctcc 240
tttcagcaaa aaacccctca agacccgttt agaggcccca aggggttatg ctagttattg 300
ctcagcggtg gcagcagcca actcagcttc ctttcgggct ttgttagcag ccggatcgat 360
ccaagctgta cctcactatt cctttgccct cggacgagtg ctggggcgtc ggtttccact 420
atcggcgagt acttctacac agccatcggt ccagacggcc gcgcttctgc gggcgatttg 480
tgtacgcccg acagtcccgg ctccggatcg gacgattgcg tcgcatcgac cctgcgccca 540
agctgcatca tcgaaattgc cgtcaaccaa gctctgatag agttggtcaa gaccaatgcg 600
gagcatatac gcccggagcc gcggcgatcc tgcaagctcc ggatgcctcc gctcgaagta 660

-continued

```
gcgcgtctgc tgctccatac aagccaacca cggcctccag aagaagatgt tggcgacctc    720
gtattgggaa tccccgaaca tcgcctcgct ccagtcaatg accgctgtta tgcggccatt    780
gtccgtcagg acattgttgg agccgaaatc cgcgtgcacg aggtgccgga cttcggggca    840
gtcctcggcc caaagcatca gctcatcgag agcctgcgcg acggacgcac tgacggtgtc    900
gtccatcaca gtttgccagt gatacacatg gggatcagca atcgcgcata tgaaatcacg    960
ccatgtagtg tattgaccga ttccttgcgg tccgaatggg ccgaacccgc tcgtctggct   1020
aagatcggcc gcagcgatcg catccatagc ctccgcgacc ggctgcagaa cagcgggcag   1080
ttcggtttca ggcaggtctt gcaacgtgac accctgtgca cggcgggaga tgcaataggt   1140
caggctctcg ctgaattccc caatgtcaag cacttccgga atcgggagcg cggccgatgc   1200
aaagtgccga taaacataac gatctttgta gaaaccatcg gcgcagctat ttacccgcag   1260
gacatatcca cgccctccta catcgaagct gaaagcacga gattcttcgc cctccgagag   1320
ctgcatcagg tcggagacgc tgtcgaactt ttcgatcaga aacttctcga cagacgtcgc   1380
ggtgagttca ggcttttcca tggtgtatc tccttcttaa agttaaacaa aattatttct    1440
agagggaaac cgttgtggtc tccctatagt gagtcgtatt aatttcgcgg gatcgagatc   1500
gatccaattc caatcccaca aaaatctgag cttaacagca cagttgctcc tctcagagca   1560
gaatcgggta ttcaacaccc tcatatcaac tactacgttg tgtataacgg tccacatgcc   1620
ggtatatacg atgactgggg ttgtacaaag gcggcaacaa acggcgttcc cggagttgca   1680
cacaagaaat ttgccactat tacagaggca agagcagcag ctgacgcgta cacaacaagt   1740
cagcaaacag acaggttgaa cttcatcccc aaaggagaag ctcaactcaa gcccaagagc   1800
tttgctaagg ccctaacaag cccaccaaag caaaaagccc actggctcac gctaggaacc   1860
aaaaggccca gcagtgatcc agccccaaaa gagatctcct ttgccccgga gattacaatg   1920
gacgatttcc tctatcttta cgatctagga aggaagttcg aaggtgaagg tgacgacact   1980
atgttcacca ctgataatga gaaggttagc ctcttcaatt tcagaaagaa tgctgaccca   2040
cagatggtta gagaggccta cgcagcaggt ctcatcaaga cgatctaccc gagtaacaat   2100
ctccaggaga tcaaatacct tcccaagaag gttaaagatg cagtcaaaag attcaggact   2160
aattgcatca agaacacaga gaaagacata tttctcaaga tcagaagtac tattccagta   2220
tggacgattc aaggcttgct tcataaacca aggcaagtaa tagagattgg agtctctaaa   2280
aaggtagttc ctactgaatc taaggccatg catggagtct aagattcaaa tcgaggatct   2340
aacagaactc gccgtgaaga ctggcgaaca gttcatacag agtcttttac gactcaatga   2400
caagaagaaa atcttcgtca acatggtgga gcacgacact ctggtctact ccaaaaatgt   2460
caaagataca gtctcagaag accaaagggc tattgagact tttcaacaaa ggataatttc   2520
gggaaacctc ctcggattcc attgcccagc tatctgtcac ttcatcgaaa ggacagtaga   2580
aaaggaaggt ggctcctaca aatgccatca ttgcgataaa ggaaaggcta tcattcaaga   2640
tgcctctgcc gacagtggtc ccaaagatgg acccccaccc acgaggagca tcgtggaaaa   2700
agaagacgtt ccaaccacgt cttcaaagca agtggattga tgtgacatct ccactgacgt   2760
aagggatgac gcacaatccc actatccttc gcaagaccct tcctctatat aaggaagttc   2820
atttcatttg gagaggacac gctcgagctc atttctctat tacttcagcc ataacaaaag   2880
aactcttttc tcttcttatt aaaccatgaa aaagcctgaa ctcaccgcga cgtctgtcga   2940
gaagtttctg atcgaaaagt tcgacagcgt ctccgacctg atgcagctct cggagggcga   3000
agaatctcgt gctttcagct tcgatgtagg agggcgtgga tatgtcctgc gggtaaatag   3060
```

-continued ctgcgccgat ggtttctaca aagatcgtta tgtttatcgg cactttgcat cggccgcgct 3120
cccgattccg gaagtgcttg acattgggga attcagcgag agcctgacct attgcatctc 3180
ccgccgtgca cagggtgtca cgttgcaaga cctgcctgaa accgaactgc ccgctgttct 3240
gcagccggtc gcggaggcca tggatgcgat cgctgcggcc gatcttagcc agacgagcgg 3300
gttcggccca ttcggaccgc aaggaatcgg tcaatacact acatggcgtg atttcatatg 3360
cgcgattgct gatccccatg tgtatcactg gcaaactgtg atggacgaca ccgtcagtgc 3420
gtccgtcgcg caggctctcg atgagctgat gctttgggcc gaggactgcc ccgaagtccg 3480
gcacctcgtg cacgcggatt tcggctccaa caatgtcctg acggacaatg gccgcataac 3540
agcggtcatt gactggagcg aggcgatgtt cggggattcc caatacgagg tcgccaacat 3600
cttcttctgg aggccgtggt tggcttgtat ggagcagcag acgcgctact tcgagcggag 3660
gcatccggag cttgcaggat cgccgcggct ccgggcgtat atgctccgca ttggtcttga 3720
ccaactctat cagagcttgg ttgacggcaa tttcgatgat gcagcttggg cgcagggtcg 3780
atgcgacgca atcgtccgat ccggagccgg gactgtcggg cgtacacaaa tcgcccgcag 3840
aagcgcggcc gtctggaccg atggctgtgt agaagtactc gccgatagtg gaaaccgacg 3900
ccccagcact cgtccgaggg caaaggaata gtgaggtacc taaagaagga gtgcgtcgaa 3960
gcagatcgtt caaacatttg gcaataaagt ttcttaagat tgaatcctgt tgccggtctt 4020
gcgatgatta tcatataatt tctgttgaat tacgttaagc atgtaataat taacatgtaa 4080
tgcatgacgt tatttatgag atgggttttt atgattagag tcccgcaatt atacatttaa 4140
tacgcgatag aaaacaaaat atagcgcgca aactaggata aattatcgcg cgcggtgtca 4200
tctatgttac tagatcgatg tcgaatctga tcaacctgca ttaatgaatc ggccaacgcg 4260
cggggagagg cggtttgcgt attgggcgct cttccgcttc ctcgctcact gactcgctgc 4320
gctcggtcgt tcggctgcgg cgagcggtat cagctcactc aaaggcggta atacggttat 4380
ccacagaatc aggggataac gcaggaaaga acatgtgagc aaaaggccag caaaaggcca 4440
ggaaccgtaa aaaggccgcg ttgctggcgt ttttccatag gctccgcccc cctgacgagc 4500
atcacaaaaa tcgacgctca agtcagaggt ggcgaaaccc gacaggacta taaagatacc 4560
aggcgtttcc ccctggaagc tccctcgtgc gctctcctgt tccgaccctg ccgcttaccg 4620
gatacctgtc cgcctttctc ccttcgggaa gcgtggcgct ttctcaatgc tcacgctgta 4680
ggtatctcag ttcggtgtag gtcgttcgct ccaagctggg ctgtgtgcac gaaccccccg 4740
ttcagcccga ccgctgcgcc ttatccggta actatcgtct tgagtccaac ccggtaagac 4800
acgacttatc gccactggca gcagccactg gtaacaggat tagcagagcg aggtatgtag 4860
gcggtgctac agagttcttg aagtggtggc ctaactacgg ctacactaga aggacagtat 4920
ttggtatctg cgctctgctg aagccagtta ccttcggaaa aagagttggt agctcttgat 4980
ccggcaaaca aaccaccgct ggtagcggtg gtttttttgt ttgcaagcag cagattacgc 5040
gcagaaaaaa aggatctcaa gaagatcctt tgatcttttc tacggggtct gacgctcagt 5100
ggaacgaaaa ctcacgttaa gggattttgg tcatgacatt aacctataaa aataggcgta 5160
tcacgaggcc ctttcgtctc gcgcgtttcg gtgatgacgg tgaaaacctc tgacacatgc 5220
agctcccgga gacggtcaca gcttgtctgt aagcggatgc cgggagcaga caagcccgtc 5280
agggcgcgtc agcgggtgtt ggcgggtgtc ggggctggct taactatgcg gcatcagagc 5340
agattgtact gagagtgcac catatggaca tattgtcgtt agaacgcggc tacaattaat 5400

-continued

```
acataacctt atgtatcata cacatacgat ttaggtgaca ctatagaacg gcgcgccaag   5460
cttggatcct cgaagagaag ggttaataac acactttttt aacattttta acacaaattt   5520
tagttattta aaaatttatt aaaaaattta aaataagaag aggaactctt taaataaatc   5580
taacttacaa aatttatgat ttttaataag ttttcaccaa taaaaaatgt cataaaaata   5640
tgttaaaaag tatattatca atattctctt tatgataaat aaaaagaaaa aaaaaataaa   5700
agttaagtga aaatgagatt gaagtgactt taggtgtgta taaatatatc aaccccgcca   5760
acaatttatt taatccaaat atattgaagt atattattcc atagccttta tttatttata   5820
tatttattat ataaaagctt tatttgttct aggttgttca tgaaatattt ttttggtttt   5880
atctccgttg taagaaaatc atgtgctttg tgtcgccact cactattgca gctttttcat   5940
gcattggtca gattgacggt tgattgtatt tttgtttttt atggttttgt gttatgactt   6000
aagtcttcat ctctttatct cttcatcagg tttgatggtt acctaatatg gtccatgggt   6060
acatgcatgg ttaaattagg tggccaactt tgttgtgaac gatagaattt tttttatatt   6120
aagtaaacta tttttatatt atgaaataat aataaaaaaa atattttatc attattaaca   6180
aaatcatatt agttaatttg ttaactctat aataaaagaa atactgtaac attcacatta   6240
catggtaaca tctttccacc ctttcatttg tttttttgttt gatgactttt tttcttgttt   6300
aaatttattt cccttctttt aaatttggaa tacattatca tcatatataa actaaaatac   6360
taaaaacagg attacacaaa tgataaataa taacacaaat atttataaat ctagctgcaa   6420
tatatttaaa ctagctatat cgatattgta aaataaaact agctgcattg atactgataa   6480
aaaaatatca tgtgctttct ggactgatga tgcagtatac ttttgacatt gcctttattt   6540
tatttttcag aaaagctttc ttagttctgg gttcttcatt atttgtttcc catctccatt   6600
gtgaattgaa tcatttgctt cgtgtcacaa atacaattta gntaggtaca tgcattggtc   6660
agattcacgg tttattatgt catgacttaa gttcatggta gtacattacc tgccacgcat   6720
gcattatatt ggttagattt gataggcaaa tttggttgtc aacaatataa atataaataa   6780
tgtttttata ttacgaaata acagtgatca aaacaaacag ttttatcttt attaacaaga   6840
ttttgttttt gtttgatgac gttttttaat gtttacgctt tcccccttct tttgaattta   6900
gaacacttta tcatcataaa atcaaatact aaaaaaatta catatttcat aaataataac   6960
acaaatattt ttaaaaaatc tgaaataata atgaacaata ttacatatta tcacgaaaat   7020
tcattaataa aaatattata taaataaaat gtaatagtag ttatatgtag gaaaaaagta   7080
ctgcacgcat aatatataca aaaagattaa aatgaactat tataaataat aacactaaat   7140
taatggtgaa tcatatcaaa ataatgaaaa agtaaataaa atttgtaatt aacttctata   7200
tgtattacac acacaaataa taaataatag taaaaaaaat tatgataaat atttaccatc   7260
tcataagata tttaaaataa tgataaaaat atagattatt ttttatgcaa ctagctagcc   7320
aaaaagagaa cacgggtata tataaaaaga gtacctttaa attctactgt acttccttta   7380
ttcctgacgt ttttatatca agtggacata cgtgaagatt ttaattatca gtctaaatat   7440
ttcattagca cttaatactt ttctgtttta ttcctatcct ataagtagtc ccgattctcc   7500
caacattgct tattcacaca actaactaag aaagtcttcc atagcccccc aagcggccgc   7560
gcgagaaact ttgtatgggc atggttattt ctcacttctc accctccttt actttcttat   7620
gctaaatcct ccttccccta tatctccacc ctcaacccct ttttctcatt ataacttttg   7680
gtgcctagat ggtgtgtgtg tgtgcgcgcg agagatctga gctcaatttt cctctctcaa   7740
gtcctggtca tgctttatta caccatcctc ctccctctta tgcatcttat atctctccac   7800
```

ctccaggatt ttaagcccta gaggaaggag gatggtgtaa tagaatatgg caattcaggc 7860
ttttaattgc tttcatttgg taccatcact tgcaagattt cagagtacaa ggtgaacaca 7920
cacatcttcc tcttcatcaa ttctctagtt tcatccttat cttttcattc acggtaactc 7980
tcactaccct ctttcatctt ataagttata ccgggggtgt gatgttgatg agtgtaaatt 8040
aaatatatgt gatctctttc tctggaaaaa ttttcagtgt gatatacata ataatctctt 8100
aatctagaga ttttatggct ttgttatata taagc 8135

<210> SEQ ID NO 97
<211> LENGTH: 28
<212> TYPE: DNA
<213> ORGANISM: artificial sequence
<220> FEATURE:
<223> OTHER INFORMATION: primer

<400> SEQUENCE: 97
gcggccgcct ggctttggct gtttatcg 28

<210> SEQ ID NO 98
<211> LENGTH: 27
<212> TYPE: DNA
<213> ORGANISM: artificial sequence
<220> FEATURE:
<223> OTHER INFORMATION: primer

<400> SEQUENCE: 98
ctgcagggct ttcactgttg ttctgtc 27

<210> SEQ ID NO 99
<211> LENGTH: 30
<212> TYPE: DNA
<213> ORGANISM: artificial sequence
<220> FEATURE:
<223> OTHER INFORMATION: primer

<400> SEQUENCE: 99
ctgcagctgc atccataaac attccagcat 30

<210> SEQ ID NO 100
<211> LENGTH: 38
<212> TYPE: DNA
<213> ORGANISM: artificial sequence
<220> FEATURE:
<223> OTHER INFORMATION: gaattcgcggccgcaagagtgtgttgcgtattgcggcg

<400> SEQUENCE: 100
gaattcgcgg ccgcaagagt gtgttgcgta ttgcggcg 38

<210> SEQ ID NO 101
<211> LENGTH: 4193
<212> TYPE: DNA
<213> ORGANISM: artificial sequence
<220> FEATURE:
<223> OTHER INFORMATION: plasmid

<400> SEQUENCE: 101
aatcactagt gaattcgcgg ccgcctgcag gtcgaccata tgggagagct cccaacgcgt 60
tggatgcata gcttgagtat tctatagtgt cacctaaata gcttggcgta atcatggtca 120
tagctgtttc ctgtgtgaaa ttgttatccg ctcacaattc cacacaacat acgagccgga 180
agcataaagt gtaaagcctg gggtgcctaa tgagtgagct aactcacatt aattgcgttg 240

-continued

```
cgctcactgc ccgctttcca gtcgggaaac ctgtcgtgcc agctgcatta atgaatcggc    300
caacgcgcgg ggagaggcgg tttgcgtatt gggcgctctt ccgcttcctc gctcactgac    360
tcgctgcgct cggtcgttcg gctgcggcga gcggtatcag ctcactcaaa ggcggtaata    420
cggttatcca cagaatcagg ggataacgca ggaaagaaca tgtgagcaaa aggccagcaa    480
aaggccagga accgtaaaaa ggccgcgttg ctggcgtttt tccataggct ccgcccccct    540
gacgagcatc acaaaaatcg acgctcaagt cagaggtggc gaaacccgac aggactataa    600
agataccagg cgtttccccc tggaagctcc ctcgtgcgct ctcctgttcc gaccctgccg    660
cttaccggat acctgtccgc ctttctccct tcgggaagcg tggcgctttc tcatagctca    720
cgctgtaggt atctcagttc ggtgtaggtc gttcgctcca agctgggctg tgtgcacgaa    780
ccccccgttc agcccgaccg ctgcgcctta tccggtaact atcgtcttga gtccaacccg    840
gtaagacacg acttatcgcc actggcagca gccactggta acaggattag cagagcgagg    900
tatgtaggcg gtgctacaga gttcttgaag tggtggccta actacggcta cactagaaga    960
acagtatttg gtatctgcgc tctgctgaag ccagttacct tcggaaaaag agttggtagc   1020
tcttgatccg gcaaacaaac caccgctggt agcggtggtt tttttgtttg caagcagcag   1080
attacgcgca gaaaaaaagg atctcaagaa gatcctttga tcttttctac ggggtctgac   1140
gctcagtgga acgaaaactc acgttaaggg attttggtca tgagattatc aaaaaggatc   1200
ttcacctaga tccttttaaa ttaaaaatga agttttaaat caatctaaag tatatatgag   1260
taaacttggt ctgacagtta ccaatgctta atcagtgagg cacctatctc agcgatctgt   1320
ctatttcgtt catccatagt tgcctgactc cccgtcgtgt agataactac gatacgggag   1380
ggcttaccat ctggccccag tgctgcaatg ataccgcgag acccacgctc accggctcca   1440
gatttatcag caataaacca gccagccgga agggccgagc gcagaagtgg tcctgcaact   1500
ttatccgcct ccatccagtc tattaattgt tgccgggaag ctagagtaag tagttcgcca   1560
gttaatagtt tgcgcaacgt tgttgccatt gctacaggca tcgtggtgtc acgctcgtcg   1620
tttggtatgg cttcattcag ctccggttcc caacgatcaa ggcgagttac atgatccccc   1680
atgttgtgca aaaaagcggt tagctccttc ggtcctccga tcgttgtcag aagtaagttg   1740
gccgcagtgt tatcactcat ggttatggca gcactgcata attctcttac tgtcatgcca   1800
tccgtaagat gcttttctgt gactggtgag tactcaacca agtcattctg agaatagtgt   1860
atgcggcgac cgagttgctc ttgcccggcg tcaatacggg ataataccgc gccacatagc   1920
agaactttaa aagtgctcat cattggaaaa cgttcttcgg ggcgaaaact ctcaaggatc   1980
ttaccgctgt tgagatccag ttcgatgtaa cccactcgtg cacccaactg atcttcagca   2040
tcttttactt tcaccagcgt ttctgggtga gcaaaaacag gaaggcaaaa tgccgcaaaa   2100
aagggaataa gggcgacacg gaaatgttga atactcatac tcttcctttt tcaatattat   2160
tgaagcattt atcagggtta ttgtctcatg agcggataca tatttgaatg tatttagaaa   2220
aataaacaaa taggggttcc gcgcacattt ccccgaaaag tgccacctga tgcggtgtga   2280
aataccgcac agatgcgtaa ggagaaaata ccgcatcagg aaattgtaag cgttaatatt   2340
ttgttaaaat tcgcgttaaa tttttgttaa atcagctcat tttttaacca ataggccgaa   2400
atcggcaaaa tcccttataa atcaaaagaa tagaccgaga tagggttgag tgttgttcca   2460
gtttggaaca agagtccact attaaagaac gtggactcca acgtcaaagg gcgaaaaacc   2520
gtctatcagg gcgatggccc actacgtgaa ccatcaccct aatcaagttt tttggggtcg   2580
aggtgccgta aagcactaaa tcggaaccct aaagggagcc cccgatttag agcttgacgg   2640
```

ggaaagccgg cgaacgtggc gagaaaggaa gggaagaaag cgaaaggagc gggcgctagg 2700
gcgctggcaa gtgtagcggt cacgctgcgc gtaaccacca cacccgccgc gcttaatgcg 2760
ccgctacagg gcgcgtccat tcgccattca ggctgcgcaa ctgttgggaa gggcgatcgg 2820
tgcgggcctc ttcgctatta cgccagctgg cgaaaggggg atgtgctgca aggcgattaa 2880
gttgggtaac gccagggttt tcccagtcac gacgttgtaa aacgacggcc agtgaattgt 2940
aatacgactc actatagggc gaattgggcc cgacgtcgca tgctcccggc cgccatggcg 3000
gccgcgggaa ttcgattgcg gccgcctggc tttggctgtt tatcgtgtta ggtgtgattg 3060
ggagtgggaa tgtgagagat acagacgatg agatctcgtt actcgaaagt caattggtgg 3120
tgacatctcc gtcgcagctt cttatggtgc ctctcacttt gattcaggct gctgcctcca 3180
aaggagctgt gtgcctggat ggaacactac ctggttatca tctacaccct ggttctggat 3240
caggagctaa ccggtggctc atccaactcg agggtggagg atggtgcaac acacgtagga 3300
gctgtatctt ccggaaaacc actcgccgtg gttcatcaaa tcatatggag aaagttttgg 3360
ccttcactgg aatattgagc aataaatcta atgagaatcc tgacttcttc aactggaaca 3420
gagtcaaatt gcgttactgc gatggtgcct ctttcaccgg cgatagtcag gatgagagct 3480
cacaacttta ctatagagga caacgaatct ggcattcagc tatggaagaa ctactctcta 3540
aaggcatgca aaaagcagaa caggctctac tttctggatg ttcagctggg ggattagctt 3600
ccatcctaca ctgcgatcag ttcaaggaac tatttccggg cactacgaca gtgaaatgct 3660
taagtgatgc tggaatgttt atggatgcag tggatgtctc tgggggccac tcgctccgga 3720
aaatgttcca aggtgttgtt acagtacaga acctccaaaa ggaactgtcc actgcttgta 3780
caaagcattt ggatccaact tcgtgcttct ttccccagaa cttggtttca ggcattaaga 3840
ctccaatgtt tcttctcaat gcagcatatg acgcttggca ggtacaagag agtttagctc 3900
caccatcagt tgacctaagc ggctcttgga aggcatgcaa atctgatcac tcgcattgta 3960
attcatctca gatccagttc ttccaagact tcaggactca tatggtagat gctgtaaagt 4020
ctttcgcgac atcgacacat aacggtgtgt tcataaactc atgcttcgct cactgccaat 4080
ctgaaagaca ggacacttgg tatgcaccag attctcctac tcttcatggc aagaccgttg 4140
ctgaatctgt tggtgattgg tactttgaca gaacaacagt gaaagccctg cag 4193

<210> SEQ ID NO 102
<211> LENGTH: 3734
<212> TYPE: DNA
<213> ORGANISM: artificial sequence
<220> FEATURE:
<223> OTHER INFORMATION: plasmid

<400> SEQUENCE: 102
aatcactagt gaattcgcgg ccgcctgcag gtcgaccata tgggagagct cccaacgcgt 60
tggatgcata gcttgagtat tctatagtgt cacctaaata gcttggcgta atcatggtca 120
tagctgtttc ctgtgtgaaa ttgttatccg ctcacaattc cacacaacat acgagccgga 180
agcataaagt gtaaagcctg gggtgcctaa tgagtgagct aactcacatt aattgcgttg 240
cgctcactgc ccgctttcca gtcgggaaac ctgtcgtgcc agctgcatta atgaatcggc 300
caacgcgcgg ggagaggcgg tttgcgtatt gggcgctctt ccgcttcctc gctcactgac 360
tcgctgcgct cggtcgttcg gctgcggcga gcggtatcag ctcactcaaa ggcggtaata 420
cggttatcca cagaatcagg ggataacgca ggaaagaaca tgtgagcaaa aggccagcaa 480

-continued

```
aaggccagga accgtaaaaa ggccgcgttg ctggcgtttt tccataggct ccgcccccct    540
gacgagcatc acaaaaatcg acgctcaagt cagaggtggc gaaacccgac aggactataa    600
agataccagg cgtttccccc tggaagctcc ctcgtgcgct ctcctgttcc gaccctgccg    660
cttaccggat acctgtccgc ctttctccct tcgggaagcg tggcgctttc tcatagctca    720
cgctgtaggt atctcagttc ggtgtaggtc gttcgctcca agctgggctg tgtgcacgaa    780
ccccccgttc agcccgaccg ctgcgcctta tccggtaact atcgtcttga gtccaacccg    840
gtaagacacg acttatcgcc actggcagca gccactggta acaggattag cagagcgagg    900
tatgtaggcg gtgctacaga gttcttgaag tggtggccta actacggcta cactagaaga    960
acagtatttg gtatctgcgc tctgctgaag ccagttacct tcggaaaaag agttggtagc   1020
tcttgatccg gcaaacaaac caccgctggt agcggtggtt tttttgtttg caagcagcag   1080
attacgcgca gaaaaaaagg atctcaagaa gatcctttga tcttttctac ggggtctgac   1140
gctcagtgga acgaaaactc acgttaaggg attttggtca tgagattatc aaaaaggatc   1200
ttcacctaga tccttttaaa ttaaaaatga agttttaaat caatctaaag tatatatgag   1260
taaacttggt ctgacagtta ccaatgctta atcagtgagg cacctatctc agcgatctgt   1320
ctatttcgtt catccatagt tgcctgactc cccgtcgtgt agataactac gatacgggag   1380
ggcttaccat ctggccccag tgctgcaatg ataccgcgag acccacgctc accggctcca   1440
gatttatcag caataaacca gccagccgga agggccgagc gcagaagtgg tcctgcaact   1500
ttatccgcct ccatccagtc tattaattgt tgccgggaag ctagagtaag tagttcgcca   1560
gttaatagtt tgcgcaacgt tgttgccatt gctacaggca tcgtggtgtc acgctcgtcg   1620
tttggtatgg cttcattcag ctccggttcc caacgatcaa ggcgagttac atgatccccc   1680
atgttgtgca aaaaagcggt tagctccttc ggtcctccga tcgttgtcag aagtaagttg   1740
gccgcagtgt tatcactcat ggttatggca gcactgcata attctcttac tgtcatgcca   1800
tccgtaagat gcttttctgt gactggtgag tactcaacca agtcattctg agaatagtgt   1860
atgcggcgac cgagttgctc ttgcccggcg tcaatacggg ataataccgc gccacatagc   1920
agaactttaa aagtgctcat cattggaaaa cgttcttcgg ggcgaaaact ctcaaggatc   1980
ttaccgctgt tgagatccag ttcgatgtaa cccactcgtg cacccaactg atcttcagca   2040
tcttttactt tcaccagcgt ttctgggtga gcaaaaacag gaaggcaaaa tgccgcaaaa   2100
aagggaataa gggcgacacg gaaatgttga atactcatac tcttcctttt tcaatattat   2160
tgaagcattt atcagggtta ttgtctcatg agcggataca tatttgaatg tatttagaaa   2220
aataaacaaa taggggttcc gcgcacattt ccccgaaaag tgccacctga tgcggtgtga   2280
aataccgcac agatgcgtaa ggagaaaata ccgcatcagg aaattgtaag cgttaatatt   2340
ttgttaaaat tcgcgttaaa tttttgttaa atcagctcat tttttaacca ataggccgaa   2400
atcggcaaaa tcccttataa atcaaaagaa tagaccgaga tagggttgag tgttgttcca   2460
gtttggaaca agagtccact attaaagaac gtggactcca acgtcaaagg gcgaaaaacc   2520
gtctatcagg gcgatggccc actacgtgaa ccatcaccct aatcaagttt tttggggtcg   2580
aggtgccgta aagcactaaa tcggaaccct aaagggagcc cccgatttag agcttgacgg   2640
ggaaagccgg cgaacgtggc gagaaaggaa gggaagaaag cgaaaggagc gggcgctagg   2700
gcgctggcaa gtgtagcggt cacgctgcgc gtaaccacca cacccgccgc gcttaatgcg   2760
ccgctacagg gcgcgtccat tcgccattca ggctgcgcaa ctgttgggaa gggcgatcgg   2820
tgcgggcctc ttcgctatta cgccagctgg cgaaaggggg atgtgctgca aggcgattaa   2880
```

gttgggtaac gccagggttt tcccagtcac gacgttgtaa aacgacggcc agtgaattgt 2940
aatacgactc actatagggc gaattgggcc cgacgtcgca tgctcccggc cgccatggcg 3000
gccgcgggaa ttcgattctg cagctgcatc cataaacatt ccagcatcac ttaagcattt 3060
cactgtcgta gtgcccggaa atagttcctt gaactgatcg cagtgtagga tggaagctaa 3120
tcccccagct gaacatccag aaagtagagc ctgttctgct ttttgcatgc ctttagagag 3180
tagttcttcc atagctgaat gccagattcg ttgtcctcta tagtaaagtt gtgagctctc 3240
atcctgacta tcgccggtga aagaggcacc atcgcagtaa cgcaatttga ctctgttcca 3300
gttgaagaag tcaggattct cattagattt attgctcaat attccagtga aggccaaaac 3360
tttctccata tgatttgatg aaccacggcg agtggttttc cggaagatac agctcctacg 3420
tgtgttgcac catcctccac cctcgagttg gatgagccac cggttagctc ctgatccaga 3480
accagggtgt agatgataac caggtagtgt tccatccagg cacacagctc ctttggaggc 3540
agcagcctga atcaaagtga gaggcaccat aagaagctgc gacggagatg tcaccaccaa 3600
ttgactttcg agtaacgaga tctcatcgtc tgtatctctc acattcccac tcccaatcac 3660
acctaacacg ataaacagcc aaagccagaa tatcgccgcc gcaatacgca acacactctt 3720
gcggccgcga attc 3734

<210> SEQ ID NO 103
<211> LENGTH: 4096
<212> TYPE: DNA
<213> ORGANISM: artificial sequence
<220> FEATURE:
<223> OTHER INFORMATION: plasmid

<400> SEQUENCE: 103
ggaattcgat atcaagctta tcgataccgt cgacctcgag ggggggcccg gtacccaatt 60
cgccctatag tgagtcgtat tacaattcac tggccgtcgt tttacaacgt cgtgactggg 120
aaaaccctgg cgttacccaa cttaatcgcc ttgcagcaca tccccctttc gccagctggc 180
gtaatagcga agaggcccgc accgatcgcc cttcccaaca gttgcgcagc ctgaatggcg 240
aatgggacgc gccctgtagc ggcgcattaa gcgcggcggg tgtggtggtt acgcgcagcg 300
tgaccgctac acttgccagc gccctagcgc ccgctccttt cgctttcttc ccttcctttc 360
tcgccacgtt cgccggcttt ccccgtcaag ctctaaatcg ggggctccct ttagggttcc 420
gatttagtgc tttacggcac ctcgacccca aaaaacttga ttagggtgat ggttcacgta 480
gtgggccatc gccctgatag acggtttttc gccctttgac gttggagtcc acgttcttta 540
atagtggact cttgttccaa actggaacaa cactcaaccc tatctcggtc tattcttttg 600
atttataagg gattttgccg atttcggcct attggttaaa aaatgagctg atttaacaaa 660
aatttaacgc gaattttaac aaaatattaa cgcttacaat ttaggtggca cttttcgggg 720
aaatgtgcgc ggaaccccta tttgtttatt tttctaaata cattcaaata tgtatccgct 780
catgagacaa taaccctgat aaatgcttca ataatattga aaaaggaaga gtatgagtat 840
tcaacatttc cgtgtcgccc ttattccctt ttttgcggca ttttgccttc ctgtttttgc 900
tcacccagaa acgctggtga aagtaaaaga tgctgaagat cagttgggtg cacgagtggg 960
ttacatcgaa ctggatctca acagcggtaa gatccttgag agttttcgcc ccgaagaacg 1020
ttttccaatg atgagcactt ttaaagttct gctatgtggc gcggtattat cccgtattga 1080
cgccgggcaa gagcaactcg gtcgccgcat acactattct cagaatgact tggttgagta 1140

```
ctcaccagtc acagaaaagc atcttacgga tggcatgaca gtaagagaat tatgcagtgc   1200
tgccataacc atgagtgata acactgcggc caacttactt ctgacaacga tcggaggacc   1260
gaaggagcta accgcttttt tgcacaacat gggggatcat gtaactcgcc ttgatcgttg   1320
ggaaccggag ctgaatgaag ccataccaaa cgacgagcgt gacaccacga tgcctgtagc   1380
aatggcaaca acgttgcgca aactattaac tggcgaacta cttactctag cttcccggca   1440
acaattaata gactggatgg aggcggataa agttgcagga ccacttctgc gctcggccct   1500
tccggctggc tggtttattg ctgataaatc tggagccggt gagcgtgggt ctcgcggtat   1560
cattgcagca ctggggccag atggtaagcc ctcccgtatc gtagttatct acacgacggg   1620
gagtcaggca actatggatg aacgaaatag acagatcgct gagataggtg cctcactgat   1680
taagcattgg taactgtcag accaagttta ctcatatata ctttagattg atttaaaact   1740
tcatttttaa tttaaaagga tctaggtgaa gatccttttt gataatctca tgaccaaaat   1800
cccttaacgt gagttttcgt tccactgagc gtcagacccc gtagaaaaga tcaaaggatc   1860
ttcttgagat cctttttttc tgcgcgtaat ctgctgcttg caaacaaaaa aaccaccgct   1920
accagcggtg gtttgtttgc cggatcaaga gctaccaact ctttttccga aggtaactgg   1980
cttcagcaga gcgcagatac caaatactgt ccttctagtg tagccgtagt taggccacca   2040
cttcaagaac tctgtagcac cgcctacata cctcgctctg ctaatcctgt taccagtggc   2100
tgctgccagt ggcgataagt cgtgtcttac cgggttggac tcaagacgat agttaccgga   2160
taaggcgcag cggtcgggct gaacgggggg ttcgtgcaca cagcccagct tggagcgaac   2220
gacctacacc gaactgagat acctacagcg tgagctatga gaaagcgcca cgcttcccga   2280
agggagaaag gcggacaggt atccggtaag cggcagggtc ggaacaggag agcgcacgag   2340
ggagcttcca gggggaaacg cctggtatct ttatagtcct gtcgggtttc gccacctctg   2400
acttgagcgt cgatttttgt gatgctcgtc aggggggcgg agcctatgga aaaacgccag   2460
caacgcggcc tttttacggt tcctggcctt ttgctggcct tttgctcaca tgttctttcc   2520
tgcgttatcc cctgattctg tggataaccg tattaccgcc tttgagtgag ctgataccgc   2580
tcgccgcagc cgaacgaccg agcgcagcga gtcagtgagc gaggaagcgg aagagcgccc   2640
aatacgcaaa ccgcctctcc ccgcgcgttg gccgattcat taatgcagct ggcacgacag   2700
gtttcccgac tggaaagcgg gcagtgagcg caacgcaatt aatgtgagtt agctcactca   2760
ttaggcaccc caggctttac actttatgct tccggctcgt atgttgtgtg gaattgtgag   2820
cggataacaa tttcacacag gaaacagcta tgaccatgat tacgccaagc tcgaaattaa   2880
ccctcactaa agggaacaaa agctggagct ccaccgcggt ggcggccgcc tggctttggc   2940
tgtttatcgt gttaggtgtg attgggagtg ggaatgtgag agatacagac gatgagatct   3000
cgttactcga aagtcaattg gtggtgacat ctccgtcgca gcttcttatg gtgcctctca   3060
ctttgattca ggctgctgcc tccaaaggag ctgtgtgcct ggatggaaca ctacctggtt   3120
atcatctaca ccctggttct ggatcaggag ctaaccggtg gctcatccaa ctcgagggtg   3180
gaggatggtg caacacacgt aggagctgta tcttccggaa aaccactcgc cgtggttcat   3240
caaatcatat ggagaaagtt ttggccttca ctggaatatt gagcaataaa tctaatgaga   3300
atcctgactt cttcaactgg aacagagtca aattgcgtta ctgcgatggt gcctctttca   3360
ccggcgatag tcaggatgag agctcacaac tttactatag aggacaacga atctggcatt   3420
cagctatgga agaactactc tctaaaggca tgcaaaaagc agaacaggct ctactttctg   3480
gatgttcagc tgggggatta gcttccatcc tacactgcga tcagttcaag gaactatttc   3540
```

cgggcactac gacagtgaaa tgcttaagtg atgctggaat gtttatggat gcagtggatg 3600
tctctggggg ccactcgctc cggaaaatgt tccaaggtgt tgttacagta cagaacctcc 3660
aaaaggaact gtccactgct tgtacaaagc atttggatcc aacttcgtgc ttctttcccc 3720
agaacttggt ttcaggcatt aagactccaa tgtttcttct caatgcagca tatgacgctt 3780
ggcaggtaca agagagttta gctccaccat cagttgacct aagcggctct tggaaggcat 3840
gcaaatctga tcactcgcat tgtaattcat ctcagatcca gttcttccaa gacttcagga 3900
ctcatatggt agatgctgta aagtctttcg cgacatcgac acataacggt gtgttcataa 3960
actcatgctt cgctcactgc caatctgaaa gacaggacac ttggtatgca ccagattctc 4020
ctactcttca tggcaagacc gttgctgaat ctgttggtga ttggtacttt gacagaacaa 4080
cagtgaaagc cctgca 4096

<210> SEQ ID NO 104
<211> LENGTH: 4801
<212> TYPE: DNA
<213> ORGANISM: artificial sequence
<220> FEATURE:
<223> OTHER INFORMATION: plasmid

<400> SEQUENCE: 104
aattcgatat caagcttatc gataccgtcg acctcgaggg ggggcccggt acccaattcg 60
ccctatagtg agtcgtatta caattcactg gccgtcgttt tacaacgtcg tgactgggaa 120
aaccctggcg ttacccaact taatcgcctt gcagcacatc ccccttttcgc cagctggcgt 180 aatagcgaag aggcccgcac cgatcgccct tcccaacagt tgcgcagcct gaatggcgaa 240
tgggacgcgc cctgtagcgg cgcattaagc gcggcgggtg tggtggttac gcgcagcgtg 300
accgctacac ttgccagcgc cctagcgccc gctcctttcg ctttcttccc ttcctttctc 360
gccacgttcg ccggctttcc ccgtcaagct ctaaatcggg ggctcccttt agggttccga 420
tttagtgctt tacggcacct cgaccccaaa aaacttgatt agggtgatgg ttcacgtagt 480
gggccatcgc cctgatagac ggtttttcgc cctttgacgt tggagtccac gttctttaat 540
agtggactct tgttccaaac tggaacaaca ctcaacccta tctcggtcta ttcttttgat 600
ttataaggga ttttgccgat ttcggcctat tggttaaaaa atgagctgat ttaacaaaaa 660
tttaacgcga attttaacaa aatattaacg cttacaattt aggtggcact tttcggggaa 720
atgtgcgcgg aacccctatt tgtttatttt tctaaataca ttcaaatatg tatccgctca 780
tgagacaata accctgataa atgcttcaat aatattgaaa aaggaagagt atgagtattc 840
aacatttccg tgtcgccctt attccctttt ttgcggcatt ttgccttcct gtttttgctc 900
acccagaaac gctggtgaaa gtaaaagatg ctgaagatca gttgggtgca cgagtgggtt 960
acatcgaact ggatctcaac agcggtaaga tccttgagag ttttcgcccc gaagaacgtt 1020
ttccaatgat gagcactttt aaagttctgc tatgtggcgc ggtattatcc cgtattgacg 1080
ccgggcaaga gcaactcggt cgccgcatac actattctca gaatgacttg gttgagtact 1140
caccagtcac agaaaagcat cttacggatg gcatgacagt aagagaatta tgcagtgctg 1200
ccataaccat gagtgataac actgcggcca acttacttct gacaacgatc ggaggaccga 1260
aggagctaac cgcttttttg cacaacatgg gggatcatgt aactcgcctt gatcgttggg 1320
aaccggagct gaatgaagcc ataccaaacg acgagcgtga caccacgatg cctgtagcaa 1380
tggcaacaac gttgcgcaaa ctattaactg gcgaactact tactctagct tcccggcaac 1440

```
aattaataga ctggatggag gcggataaag ttgcaggacc acttctgcgc tcggcccttc   1500
cggctggctg gtttattgct gataaatctg gagccggtga gcgtgggtct cgcggtatca   1560
ttgcagcact ggggccagat ggtaagccct cccgtatcgt agttatctac acgacgggga   1620
gtcaggcaac tatggatgaa cgaaatagac agatcgctga gataggtgcc tcactgatta   1680
agcattggta actgtcagac caagtttact catatatact ttagattgat ttaaaacttc   1740
atttttaatt taaaaggatc taggtgaaga tcctttttga taatctcatg accaaaatcc   1800
cttaacgtga gttttcgttc cactgagcgt cagaccccgt agaaaagatc aaaggatctt   1860
cttgagatcc tttttttctg cgcgtaatct gctgcttgca aacaaaaaaa ccaccgctac   1920
cagcggtggt ttgtttgccg gatcaagagc taccaactct ttttccgaag gtaactggct   1980
tcagcagagc gcagatacca aatactgtcc ttctagtgta gccgtagtta ggccaccact   2040
tcaagaactc tgtagcaccg cctacatacc tcgctctgct aatcctgtta ccagtggctg   2100
ctgccagtgg cgataagtcg tgtcttaccg ggttggactc aagacgatag ttaccggata   2160
aggcgcagcg gtcgggctga acggggggtt cgtgcacaca gcccagcttg gagcgaacga   2220
cctacaccga actgagatac ctacagcgtg agctatgaga aagcgccacg cttcccgaag   2280
ggagaaaggc ggacaggtat ccggtaagcg gcagggtcgg aacaggagag cgcacgaggg   2340
agcttccagg gggaaacgcc tggtatcttt atagtcctgt cgggtttcgc cacctctgac   2400
ttgagcgtcg atttttgtga tgctcgtcag gggggcggag cctatggaaa aacgccagca   2460
acgcggcctt tttacggttc ctggcctttt gctggccttt tgctcacatg ttctttcctg   2520
cgttatcccc tgattctgtg gataaccgta ttaccgcctt tgagtgagct gataccgctc   2580
gccgcagccg aacgaccgag cgcagcgagt cagtgagcga ggaagcggaa gagcgcccaa   2640
tacgcaaacc gcctctcccc gcgcgttggc cgattcatta atgcagctgg cacgacaggt   2700
ttcccgactg gaaagcgggc agtgagcgca acgcaattaa tgtgagttag ctcactcatt   2760
aggcacccca ggctttacac tttatgcttc cggctcgtat gttgtgtgga attgtgagcg   2820
gataacaatt tcacacagga aacagctatg accatgatta cgccaagctc gaaattaacc   2880
ctcactaaag ggaacaaaag ctggagctcc accgcggtgg cggccgcctg gctttggctg   2940
tttatcgtgt taggtgtgat tgggagtggg aatgtgagag atacagacga tgagatctcg   3000
ttactcgaaa gtcaattggt ggtgacatct ccgtcgcagc ttcttatggt gcctctcact   3060
ttgattcagg ctgctgcctc caaaggagct gtgtgcctgg atggaacact acctggttat   3120
catctacacc ctggttctgg atcaggagct aaccggtggc tcatccaact cgagggtgga   3180
ggatggtgca acacacgtag gagctgtatc ttccggaaaa ccactcgccg tggttcatca   3240
aatcatatgg agaaagtttt ggccttcact ggaatattga gcaataaatc taatgagaat   3300
cctgacttct tcaactggaa cagagtcaaa ttgcgttact gcgatggtgc ctctttcacc   3360
ggcgatagtc aggatgagag ctcacaactt tactatagag gacaacgaat ctggcattca   3420
gctatggaag aactactctc taaaggcatg caaaaagcag aacaggctct actttctgga   3480
tgttcagctg gggattagc ttccatccta cactgcgatc agttcaagga actatttccg    3540
ggcactacga cagtgaaatg cttaagtgat gctggaatgt ttatggatgc agtggatgtc   3600
tctgggggcc actcgctccg gaaaatgttc caaggtgttg ttacagtaca gaacctccaa   3660
aaggaactgt ccactgcttg tacaaagcat ttggatccaa cttcgtgctt ctttccccag   3720
aacttggttt caggcattaa gactccaatg tttcttctca atgcagcata tgacgcttgg   3780
caggtacaag agagtttagc tccaccatca gttgacctaa gcggctcttg gaaggcatgc   3840
```

aaatctgatc actcgcattg taattcatct cagatccagt tcttccaaga cttcaggact 3900
catatggtag atgctgtaaa gtctttcgcg acatcgacac ataacggtgt gttcataaac 3960
tcatgcttcg ctcactgcca atctgaaaga caggacactt ggtatgcacc agattctcct 4020
actcttcatg gcaagaccgt tgctgaatct gttggtgatt ggtactttga cagaacaaca 4080
gtgaaagccc tgcagctgca tccataaaca ttccagcatc acttaagcat ttcactgtcg 4140
tagtgcccgg aaatagttcc ttgaactgat cgcagtgtag gatggaagct aatcccccag 4200
ctgaacatcc agaaagtaga gcctgttctg ctttttgcat gcctttagag agtagttctt 4260
ccatagctga atgccagatt cgttgtcctc tatagtaaag ttgtgagctc tcatcctgac 4320
tatcgccggt gaaagaggca ccatcgcagt aacgcaattt gactctgttc cagttgaaga 4380
agtcaggatt ctcattagat ttattgctca atattccagt gaaggccaaa actttctcca 4440
tatgatttga tgaaccacgg cgagtggttt tccggaagat acagctccta cgtgtgttgc 4500
accatcctcc accctcgagt tggatgagcc accggttagc tcctgatcca gaaccagggt 4560
gtagatgata accaggtagt gttccatcca ggcacacagc tcctttggag gcagcagcct 4620
gaatcaaagt gagaggcacc ataagaagct gcgacggaga tgtcaccacc aattgacttt 4680
cgagtaacga gatctcatcg tctgtatctc tcacattccc actcccaatc acacctaaca 4740
cgataaacag ccaaagccag aatatcgccg ccgcaatacg caacacactc ttgcggccgc 4800
g 4801

<210> SEQ ID NO 105
<211> LENGTH: 3453
<212> TYPE: DNA
<213> ORGANISM: artificial sequence
<220> FEATURE:
<223> OTHER INFORMATION: vector

<400> SEQUENCE: 105
tcttccatag ccccccaagc ggccgcgaca caagtgtgag agtactaaat aaatgctttg 60
gttgtacgaa atcattacac taaataaaat aatcaaagct tatatatgcc ttccgctaag 120
gccgaatgca aagaaattgg ttctttctcg ttatcttttg ccacttttac tagtacgtat 180
taattactac ttaatcatct ttgtttacgg ctcattatat ccgtcgacgg cgcgcccgat 240
catccggata tagttcctcc tttcagcaaa aaacccctca agacccgttt agaggcccca 300
aggggttatg ctagttattg ctcagcggtg gcagcagcca actcagcttc ctttcgggct 360
ttgttagcag ccggatcgat ccaagctgta cctcactatt cctttgccct cggacgagtg 420
ctggggcgtc ggtttccact atcggcgagt acttctacac agccatcggt ccagacggcc 480
gcgcttctgc gggcgatttg tgtacgcccg acagtcccgg ctccggatcg gacgattgcg 540
tcgcatcgac cctgcgccca agctgcatca tcgaaattgc cgtcaaccaa gctctgatag 600
agttggtcaa gaccaatgcg gagcatatac gcccggagcc gcggcgatcc tgcaagctcc 660
ggatgcctcc gctcgaagta gcgcgtctgc tgctccatac aagccaacca cggcctccag 720
aagaagatgt tggcgacctc gtattgggaa tccccgaaca tcgcctcgct ccagtcaatg 780
accgctgtta tgcggccatt gtccgtcagg acattgttgg agccgaaatc cgcgtgcacg 840
aggtgccgga cttcggggca gtcctcggcc caaagcatca gctcatcgag agcctgcgcg 900
acggacgcac tgacggtgtc gtccatcaca gtttgccagt gatacacatg gggatcagca 960
atcgcgcata tgaaatcacg ccatgtagtg tattgaccga ttccttgcgg tccgaatggg 1020

-continued

```
ccgaacccgc tcgtctggct aagatcggcc gcagcgatcg catccatagc ctccgcgacc   1080
ggctgcagaa cagcgggcag ttcggtttca ggcaggtctt gcaacgtgac accctgtgca   1140
cggcgggaga tgcaataggt caggctctcg ctgaattccc caatgtcaag cacttccgga   1200
atcgggagcg cggccgatgc aaagtgccga taaacataac gatctttgta gaaaccatcg   1260
gcgcagctat ttacccgcag gacatatcca cgccctccta catcgaagct gaaagcacga   1320
gattcttcgc cctccgagag ctgcatcagg tcggagacgc tgtcgaactt ttcgatcaga   1380
aacttctcga cagacgtcgc ggtgagttca ggcttttcca tgggtatatc tccttcttaa   1440
agttaaacaa aattatttct agagggaaac cgttgtggtc tccctatagt gagtcgtatt   1500
aatttcgcgg gatcgagatc tgatcaacct gcattaatga atcggccaac gcgcggggag   1560
aggcggtttg cgtattgggc gctcttccgc ttcctcgctc actgactcgc tgcgctcggt   1620
cgttcggctg cggcgagcgg tatcagctca ctcaaaggcg gtaatacggt tatccacaga   1680
atcaggggat aacgcaggaa agaacatgtg agcaaaaggc cagcaaaagg ccaggaaccg   1740
taaaaaggcc gcgttgctgg cgtttttcca taggctccgc ccccctgacg agcatcacaa   1800
aaatcgacgc tcaagtcaga ggtggcgaaa cccgacagga ctataaagat accaggcgtt   1860
tccccctgga agctccctcg tgcgctctcc tgttccgacc ctgccgctta ccggatacct   1920
gtccgccttt ctcccttcgg gaagcgtggc gctttctcaa tgctcacgct gtaggtatct   1980
cagttcggtg taggtcgttc gctccaagct gggctgtgtg cacgaacccc ccgttcagcc   2040
cgaccgctgc gccttatccg gtaactatcg tcttgagtcc aacccggtaa gacacgactt   2100
atcgccactg gcagcagcca ctggtaacag gattagcaga gcgaggtatg taggcggtgc   2160
tacagagttc ttgaagtggt ggcctaacta cggctacact agaaggacag tatttggtat   2220
ctgcgctctg ctgaagccag ttaccttcgg aaaaagagtt ggtagctctt gatccggcaa   2280
acaaaccacc gctggtagcg gtggtttttt tgtttgcaag cagcagatta cgcgcagaaa   2340
aaaaggatct caagaagatc ctttgatctt ttctacgggg tctgacgctc agtggaacga   2400
aaactcacgt taagggattt tggtcatgac attaacctat aaaaataggc gtatcacgag   2460
gccctttcgt ctcgcgcgtt tcggtgatga cggtgaaaac ctctgacaca tgcagctccc   2520
ggagacggtc acagcttgtc tgtaagcgga tgccgggagc agacaagccc gtcagggcgc   2580
gtcagcgggt gttggcgggt gtcggggctg gcttaactat gcggcatcag agcagattgt   2640
actgagagtg caccatatgg acatattgtc gttagaacgc ggctacaatt aatacataac   2700
cttatgtatc atacacatac gatttaggtg acactataga acggcgcgcc aagcttggat   2760
cctagcctaa gtacgtactc aaaatgccaa caaataaaaa aaaagttgct ttaataatgc   2820
caaaacaaat taataaaaca cttacaacac cggatttttt ttaattaaaa tgtgccattt   2880
aggataaata gttaatattt ttaataatta tttaaaaagc cgtatctact aaaatgattt   2940
ttatttggtt gaaaatatta atatgtttaa atcaacacaa tctatcaaaa ttaaactaaa   3000
aaaaaaataa gtgtacgtgg ttaacattag tacagtaata taagaggaaa atgagaaatt   3060
aagaaattga aagcgagtct aatttttaaa ttatgaacct gcatatataa aaggaaagaa   3120
agaatccagg aagaaaagaa atgaaaccat gcatggtccc ctcgtcatca cgagtttctg   3180
ccatttgcaa tagaaacact gaaacacctt tctctttgtc acttaattga gatgccgaag   3240
ccacctcaca ccatgaactt catgaggtgt agcacccaag gcttccatag ccatgcatac   3300
tgaagaatgt ctcaagctca gcaccctact tctgtgacgt gtccctcatt caccttcctc   3360
tcttccctat aaataaccac gcctcaggtt ctccgcttca caactcaaac attctctcca   3420
```

ttggtcctta aacactcatc agtcatcacc atg 3453

<210> SEQ ID NO 106
<211> LENGTH: 5326
<212> TYPE: DNA
<213> ORGANISM: artificial sequence
<220> FEATURE:
<223> OTHER INFORMATION: vector

<400> SEQUENCE: 106
ggccgcgaca caagtgtgag agtactaaat aaatgctttg gttgtacgaa atcattacac 60
taaataaaat aatcaaagct tatatatgcc ttccgctaag gccgaatgca aagaaattgg 120
ttctttctcg ttatcttttg ccacttttac tagtacgtat taattactac ttaatcatct 180
ttgtttacgg ctcattatat ccgtcgacgg cgcgcccgat catccggata tagttcctcc 240
tttcagcaaa aaacccctca agacccgttt agaggcccca aggggttatg ctagttattg 300
ctcagcggtg gcagcagcca actcagcttc ctttcgggct ttgttagcag ccggatcgat 360
ccaagctgta cctcactatt cctttgccct cggacgagtg ctggggcgtc ggtttccact 420
atcggcgagt acttctacac agccatcggt ccagacggcc gcgcttctgc gggcgatttg 480
tgtacgcccg acagtcccgg ctccggatcg gacgattgcg tcgcatcgac cctgcgccca 540
agctgcatca tcgaaattgc cgtcaaccaa gctctgatag agttggtcaa gaccaatgcg 600
gagcatatac gcccggagcc gcggcgatcc tgcaagctcc ggatgcctcc gctcgaagta 660
gcgcgtctgc tgctccatac aagccaacca cggcctccag aagaagatgt tggcgacctc 720
gtattgggaa tccccgaaca tcgcctcgct ccagtcaatg accgctgtta tgcggccatt 780
gtccgtcagg acattgttgg agccgaaatc cgcgtgcacg aggtgccgga cttcggggca 840
gtcctcggcc caaagcatca gctcatcgag agcctgcgcg acggacgcac tgacggtgtc 900
gtccatcaca gtttgccagt gatacacatg gggatcagca atcgcgcata tgaaatcacg 960
ccatgtagtg tattgaccga ttccttgcgg tccgaatggg ccgaacccgc tcgtctggct 1020
aagatcggcc gcagcgatcg catccatagc ctccgcgacc ggctgcagaa cagcgggcag 1080
ttcggtttca ggcaggtctt gcaacgtgac accctgtgca cggcgggaga tgcaataggt 1140
caggctctcg ctgaattccc caatgtcaag cacttccgga atcgggagcg cggccgatgc 1200
aaagtgccga taaacataac gatctttgta gaaaccatcg gcgcagctat ttacccgcag 1260
gacatatcca cgccctccta catcgaagct gaaagcacga gattcttcgc cctccgagag 1320
ctgcatcagg tcggagacgc tgtcgaactt ttcgatcaga aacttctcga cagacgtcgc 1380
ggtgagttca ggcttttcca tgggtatatc tccttcttaa agttaaacaa aattatttct 1440
agagggaaac cgttgtggtc tccctatagt gagtcgtatt aatttcgcgg gatcgagatc 1500
tgatcaacct gcattaatga atcggccaac gcgcggggag aggcggtttg cgtattgggc 1560
gctcttccgc ttcctcgctc actgactcgc tgcgctcggt cgttcggctg cggcgagcgg 1620
tatcagctca ctcaaaggcg gtaatacggt tatccacaga atcaggggat aacgcaggaa 1680
agaacatgtg agcaaaaggc cagcaaaagg ccaggaaccg taaaaaggcc gcgttgctgg 1740
cgtttttcca taggctccgc ccccctgacg agcatcacaa aaatcgacgc tcaagtcaga 1800
ggtggcgaaa cccgacagga ctataaagat accaggcgtt tccccctgga agctccctcg 1860
tgcgctctcc tgttccgacc ctgccgctta ccggatacct gtccgccttt ctcccttcgg 1920
gaagcgtggc gctttctcaa tgctcacgct gtaggtatct cagttcggtg taggtcgttc 1980

-continued

```
gctccaagct gggctgtgtg cacgaacccc ccgttcagcc cgaccgctgc gccttatccg   2040
gtaactatcg tcttgagtcc aacccggtaa gacacgactt atcgccactg gcagcagcca   2100
ctggtaacag gattagcaga gcgaggtatg taggcggtgc tacagagttc ttgaagtggt   2160
ggcctaacta cggctacact agaaggacag tatttggtat ctgcgctctg ctgaagccag   2220
ttaccttcgg aaaaagagtt ggtagctctt gatccggcaa acaaaccacc gctggtagcg   2280
gtggtttttt tgtttgcaag cagcagatta cgcgcagaaa aaaaggatct caagaagatc   2340
ctttgatctt ttctacgggg tctgacgctc agtggaacga aaactcacgt taagggattt   2400
tggtcatgac attaacctat aaaaataggc gtatcacgag gccctttcgt ctcgcgcgtt   2460
tcggtgatga cggtgaaaac ctctgacaca tgcagctccc ggagacggtc acagcttgtc   2520
tgtaagcgga tgccgggagc agacaagccc gtcagggcgc gtcagcgggt gttggcgggt   2580
gtcggggctg gcttaactat gcggcatcag agcagattgt actgagagtg caccatatgg   2640
acatattgtc gttagaacgc ggctacaatt aatacataac cttatgtatc atacacatac   2700
gatttaggtg acactataga acggcgcgcc aagcttggat cctagcctaa gtacgtactc   2760
aaaatgccaa caaataaaaa aaaagttgct ttaataatgc caaaacaaat taataaaaca   2820
cttacaacac cggatttttt ttaattaaaa tgtgccattt aggataaata gttaatattt   2880
ttaataatta tttaaaaagc cgtatctact aaaatgattt ttatttggtt gaaaatatta   2940
atatgtttaa atcaacacaa tctatcaaaa ttaaactaaa aaaaaaataa gtgtacgtgg   3000
ttaacattag tacagtaata taagaggaaa atgagaaatt aagaaattga aagcgagtct   3060
aatttttaaa ttatgaacct gcatatataa aaggaaagaa agaatccagg aagaaaagaa   3120
atgaaaccat gcatggtccc ctcgtcatca cgagtttctg ccatttgcaa tagaaacact   3180
gaaacacctt tctctttgtc acttaattga gatgccgaag ccacctcaca ccatgaactt   3240
catgaggtgt agcacccaag gcttccatag ccatgcatac tgaagaatgt ctcaagctca   3300
gcaccctact tctgtgacgt gtccctcatt caccttcctc tcttccctat aaataaccac   3360
gcctcaggtt ctccgcttca caactcaaac attctctcca ttggtcctta aacactcatc   3420
agtcatcacc atgtcttcca tagcccccca agcggccgcc tggctttggc tgtttatcgt   3480
gttaggtgtg attgggagtg ggaatgtgag agatacagac gatgagatct cgttactcga   3540
aagtcaattg gtggtgacat ctccgtcgca gcttcttatg gtgcctctca ctttgattca   3600
ggctgctgcc tccaaaggag ctgtgtgcct ggatggaaca ctacctggtt atcatctaca   3660
ccctggttct ggatcaggag ctaaccggtg gctcatccaa ctcgagggtg gaggatggtg   3720
caacacacgt aggagctgta tcttccggaa aaccactcgc cgtggttcat caaatcatat   3780
ggagaaagtt ttggccttca ctggaatatt gagcaataaa tctaatgaga atcctgactt   3840
cttcaactgg aacagagtca aattgcgtta ctgcgatggt gcctctttca ccggcgatag   3900
tcaggatgag agctcacaac tttactatag aggacaacga atctggcatt cagctatgga   3960
agaactactc tctaaaggca tgcaaaaagc agaacaggct ctactttctg gatgttcagc   4020
tgggggatta gcttccatcc tacactgcga tcagttcaag gaactatttc cgggcactac   4080
gacagtgaaa tgcttaagtg atgctggaat gtttatggat gcagtggatg tctctggggg   4140
ccactcgctc cggaaaatgt tccaaggtgt tgttacagta cagaacctcc aaaaggaact   4200
gtccactgct tgtacaaagc atttggatcc aacttcgtgc ttctttcccc agaacttggt   4260
ttcaggcatt aagactccaa tgtttcttct caatgcagca tatgacgctt ggcaggtaca   4320
agagagttta gctccaccat cagttgacct aagcggctct tggaaggcat gcaaatctga   4380
```

```
tcactcgcat tgtaattcat ctcagatcca gttcttccaa gacttcagga ctcatatggt   4440

agatgctgta aagtctttcg cgacatcgac acataacggt gtgttcataa actcatgctt   4500

cgctcactgc caatctgaaa gacaggacac ttggtatgca ccagattctc ctactcttca   4560

tggcaagacc gttgctgaat ctgttggtga ttggtacttt gacagaacaa cagtgaaagc   4620

cctgcagctg catccataaa cattccagca tcacttaagc atttcactgt cgtagtgccc   4680

ggaaatagtt ccttgaactg atcgcagtgt aggatggaag ctaatccccc agctgaacat   4740

ccagaaagta gagcctgttc tgctttttgc atgcctttag agagtagttc ttccatagct   4800

gaatgccaga ttcgttgtcc tctatagtaa agttgtgagc tctcatcctg actatcgccg   4860

gtgaaagagg caccatcgca gtaacgcaat ttgactctgt tccagttgaa gaagtcagga   4920

ttctcattag atttattgct caatattcca gtgaaggcca aaactttctc catatgattt   4980

gatgaaccac ggcgagtggt tttccggaag atacagctcc tacgtgtgtt gcaccatcct   5040

ccaccctcga gttggatgag ccaccggtta gctcctgatc cagaaccagg gtgtagatga   5100

taaccaggta gtgttccatc caggcacaca gctcctttgg aggcagcagc ctgaatcaaa   5160

gtgagaggca ccataagaag ctgcgacgga gatgtcacca ccaattgact ttcgagtaac   5220

gagatctcat cgtctgtatc tctcacattc ccactcccaa tcacacctaa cacgataaac   5280

agccaaagcc agaatatcgc cgccgcaata cgcaacacac tcttgc                  5326
```

<210> SEQ ID NO 107
<211> LENGTH: 16081
<212> TYPE: DNA
<213> ORGANISM: artificial sequence
<220> FEATURE:
<223> OTHER INFORMATION: vector

<400> SEQUENCE: 107

```
cgcgcctcga gtgggcggat cccccgggct gcaggaattc actggccgtc gttttacaac     60

gtcgtgactg ggaaaaccct ggcgttaccc aacttaatcg ccttgcagca catccccctt    120

tcgccagctg gcgtaatagc gaagaggccc gcaccgatcg cccttcccaa cagttgcgca    180

gcctgaatgg cgaatggatc gatccatcgc gatgtacctt ttgttagtca gcctctcgat    240

tgctcatcgt cattacacag taccgaagtt tgatcgatct agtaacatag atgacaccgc    300

gcgcgataat ttatcctagt ttgcgcgcta tattttgttt tctatcgcgt attaaatgta    360

taattgcggg actctaatca taaaaaccca tctcataaat aacgtcatgc attacatgtt    420

aattattaca tgcttaacgt aattcaacag aaattatatg ataatcatcg caagaccggc    480

aacaggattc aatcttaaga aactttattg ccaaatgttt gaacgatctg cttcgacgca    540

ctccttcttt actccaccat ctcgtcctta ttgaaaacgt gggtagcacc aaaacgaatc    600

aagtcgctgg aactgaagtt accaatcacg ctggatgatt tgccagttgg attaatcttg    660

cctttccccg catgaataat attgatgaat gcatgcgtga ggggtagttc gatgttggca    720

atagctgcaa ttgccgcgac atcctccaac gagcataatt cttcagaaaa atagcgatgt    780

tccatgttgt cagggcatgc atgatgcacg ttatgaggtg acggtgctag gcagtattcc    840

ctcaaagttt catagtcagt atcatattca tcattgcatt cctgcaagag agaattgaga    900

cgcaatccac acgctgcggc aaccttccgg cgttcgtggt ctatttgctc ttggacgttg    960

caaacgtaag tgttggatcg atccggggtg ggcgaagaac tccagcatga gatccccgcg   1020

ctggaggatc atccagccgg cgtcccggaa aacgattccg aagcccaacc tttcatagaa   1080
```

-continued

```
ggcggcggtg gaatcgaaat ctcgtgatgg caggttgggc gtcgcttggt cggtcatttc   1140
gaaccccaga gtcccgctca gaagaactcg tcaagaaggc gatagaaggc gatgcgctgc   1200
gaatcgggag cggcgatacc gtaaagcacg aggaagcggt cagcccattc gccgccaagc   1260
tcttcagcaa tatcacgggt agccaacgct atgtcctgat agcggtccgc cacacccagc   1320
cggccacagt cgatgaatcc agaaaagcgg ccattttcca ccatgatatt cggcaagcag   1380
gcatcgccat gggtcacgac gagatcctcg ccgtcgggca tgcgcgcctt gagcctggcg   1440
aacagttcgg ctggcgcgag cccctgatgc tcttcgtcca gatcatcctg atcgacaaga   1500
ccggcttcca tccgagtacg tgctcgctcg atgcgatgtt tcgcttggtg gtcgaatggg   1560
caggtagccg gatcaagcgt atgcagccgc cgcattgcat cagccatgat ggatactttc   1620
tcggcaggag caaggtgaga tgacaggaga tcctgccccg gcacttcgcc caatagcagc   1680
cagtcccttc ccgcttcagt gacaacgtcg agcacagctg cgcaaggaac gcccgtcgtg   1740
gccagccacg atagccgcgc tgcctcgtcc tgcagttcat tcagggcacc ggacaggtcg   1800
gtcttgacaa aaagaaccgg gcgcccctgc gctgacagcc ggaacacggc ggcatcagag   1860
cagccgattg tctgttgtgc ccagtcatag ccgaatagcc tctccaccca agcggccgga   1920
gaacctgcgt gcaatccatc ttgttcaatc atgcgaaacg atccccgcaa gcttggagac   1980
tggtgatttc agcgtgtcct ctccaaatga aatgaacttc cttatataga ggaagggtct   2040
tgcgaaggat agtgggattg tgcgtcatcc cttacgtcag tggagatatc acatcaatcc   2100
acttgctttg aagacgtggt tggaacgtct tctttttcca cgatgctcct cgtgggtggg   2160
ggtccatctt tgggaccact gtcggcagag gcatcttcaa cgatggcctt tcctttatcg   2220
caatgatggc atttgtagga gccaccttcc ttttccacta tcttcacaat aaagtgacag   2280
atagctgggc aatggaatcc gaggaggttt ccggatatta ccctttgttg aaaagtctca   2340
attgcccttt ggtcttctga gactgtatct ttgatatttt tggagtagac aagcgtgtcg   2400
tgctccacca tgttgacgaa gattttcttc ttgtcattga gtcgtaagag actctgtatg   2460
aactgttcgc cagtctttac ggcgagttct gttaggtcct ctatttgaat ctttgactcc   2520
atggcctttg attcagtggg aactaccttt ttagagactc caatctctat tacttgcctt   2580
ggtttgtgaa gcaagccttg aatcgtccat actggaatag tacttctgat cttgagaaat   2640
atatctttct ctgtgttctt gatgcagtta gtcctgaatc ttttgactgc atctttaacc   2700
ttcttgggaa ggtatttgat ctcctggaga ttattgctcg ggtagatcgt cttgatgaga   2760
cctgctgcgt aagcctctct aaccatctgt gggttagcat tctttctgaa attgaaaagg   2820
ctaatcttct cattatcagt ggtgaacatg gtatcgtcac cttctccgtc gaacttcctg   2880
actagatcgt agagatagag gaagtcgtcc attgtgatct ctggggcaaa ggagatctga   2940
attaattcga tatggtggat ttatcacaaa tgggacccgc cgccgacaga ggtgtgatgt   3000
taggccagga ctttgaaaat ttgcgcaact atcgtatagt ggccgacaaa ttgacgccga   3060
gttgacagac tgcctagcat ttgagtgaat tatgtgaggt aatgggctac actgaattgg   3120
tagctcaaac tgtcagtatt tatgtatatg agtgtatatt ttcgcataat ctcagaccaa   3180
tctgaagatg aaatgggtat ctgggaatgg cgaaatcaag gcatcgatcg tgaagtttct   3240
catctaagcc cccatttgga cgtgaatgta gacacgtcga aataaagatt tccgaattag   3300
aataatttgt ttattgcttt cgcctataaa tacgacggat cgtaatttgt cgttttatca   3360
aaatgtactt tcattttata ataacgctgc ggacatctac atttttgaat tgaaaaaaaa   3420
ttggtaatta ctctttcttt ttctccatat tgaccatcat actcattgct gatccatgta   3480
```

-continued

```
gatttcccgg acatgaagcc atttacaatt gaatatatcc tgccgccgct gccgctttgc   3540
acccggtgga gcttgcatgt tggtttctac gcagaactga gccggttagg cagataattt   3600
ccattgagaa ctgagccatg tgcaccttcc ccccaacacg gtgagcgacg gggcaacgga   3660
gtgatccaca tgggactttt aaacatcatc cgtcggatgg cgttgcgaga gaagcagtcg   3720
atccgtgaga tcagccgacg caccgggcag gcgcgcaaca cgatcgcaaa gtatttgaac   3780
gcaggtacaa tcgagccgac gttcacgcgg aacgaccaag caagctagct ttaatgcggt   3840
agtttatcac agttaaattg ctaacgcagt caggcaccgt gtatgaaatc taacaatgcg   3900
ctcatcgtca tcctcggcac cgtcaccctg gatgctgtag gcataggctt ggttatgccg   3960
gtactgccgg gcctcttgcg ggatatcgtc cattccgaca gcatcgccag tcactatggc   4020
gtgctgctag cgctatatgc gttgatgcaa tttctatgcg cacccgttct cggagcactg   4080
tccgaccgct ttggccgccg cccagtcctg ctcgcttcgc tacttggagc cactatcgac   4140
tacgcgatca tggcgaccac acccgtcctg tggtccaacc cctccgctgc tatagtgcag   4200
tcggcttctg acgttcagtg cagccgtctt ctgaaaacga catgtcgcac aagtcctaag   4260
ttacgcgaca ggctgccgcc ctgccctttt cctggcgttt tcttgtcgcg tgttttagtc   4320
gcataaagta gaatacttgc gactagaacc ggagacatta cgccatgaac aagagcgccg   4380
ccgctggcct gctgggctat gcccgcgtca gcaccgacga ccaggacttg accaaccaac   4440
gggccgaact gcacgcggcc ggctgcacca agctgttttc cgagaagatc accggcacca   4500
ggcgcgaccg cccggagctg gccaggatgc ttgaccacct acgccctggc gacgttgtga   4560
cagtgaccag gctagaccgc ctggcccgca gcacccgcga cctactggac attgccgagc   4620
gcatccagga ggccggcgcg ggcctgcgta gcctggcaga gccgtgggcc gacaccacca   4680
cgccggccgg ccgcatggtg ttgaccgtgt tcgccggcat tgccgagttc gagcgttccc   4740
taatcatcga ccgcacccgg agcgggcgcg aggccgccaa ggcccgaggc gtgaagtttg   4800
gcccccgccc taccctcacc ccggcacaga tcgcgcacgc ccgcgagctg atcgaccagg   4860
aaggccgcac cgtgaaagag gcggctgcac tgcttggcgt gcatcgctcg accctgtacc   4920
gcgcacttga gcgcagcgag gaagtgacgc ccaccgaggc caggcggcgc ggtgccttcc   4980
gtgaggacgc attgaccgag gccgacgccc tggcggccgc cgagaatgaa cgccaagagg   5040
aacaagcatg aaaccgcacc aggacggcca ggacgaaccg tttttcatta ccgaagagat   5100
cgaggcggag atgatcgcgg ccgggtacgt gttcgagccg cccgcgcacg tctcaaccgt   5160
gcggctgcat gaaatcctgg ccggtttgtc tgatgccaag ctggcggcct ggccggccag   5220
cttggccgct gaagaaaccg agcgccgccg tctaaaaagg tgatgtgtat ttgagtaaaa   5280
cagcttgcgt catgcggtcg ctgcgtatat gatgcgatga gtaaataaac aaatacgcaa   5340
gggaacgcat gaagttatcg ctgtacttaa ccagaaaggc gggtcaggca agacgaccat   5400
cgcaacccat ctagcccgcg ccctgcaact cgccggggcc gatgttctgt tagtcgattc   5460
cgatccccag ggcagtgccc gcgattgggc ggccgtgcgg gaagatcaac cgctaaccgt   5520
tgtcggcatc gaccgcccga cgattgaccg cgacgtgaag gccatcggcc ggcgcgactt   5580
cgtagtgatc gacggagcgc cccaggcggc ggacttggct gtgtccgcga tcaaggcagc   5640
cgacttcgtg ctgattccgg tgcagccaag cccttacgac atatgggcca ccgccgacct   5700
ggtggagctg gttaagcagc gcattgaggt cacggatgga aggctacaag cggcctttgt   5760
cgtgtcgcgg gcgatcaaag gcacgcgcat cggcggtgag gttgccgagg cgctggccgg   5820
```

-continued

```
gtacgagctg cccattcttg agtcccgtat cacgcagcgc gtgagctacc caggcactgc   5880
cgccgccggc acaaccgttc ttgaatcaga acccgagggc gacgctgccc gcgaggtcca   5940
ggcgctggcc gctgaaatta aatcaaaact catttgagtt aatgaggtaa agagaaaatg   6000
agcaaaagca caaacacgct aagtgccggc cgtccgagcg cacgcagcag caaggctgca   6060
acgttggcca gcctggcaga cacgccagcc atgaagcggg tcaactttca gttgccggcg   6120
gaggatcaca ccaagctgaa gatgtacgcg gtacgccaag gcaagaccat taccgagctg   6180
ctatctgaat acatcgcgca gctaccagag taaatgagca aatgaataaa tgagtagatg   6240
aattttagcg gctaaaggag gcggcatgga aaatcaagaa caaccaggca ccgacgccgt   6300
ggaatgcccc atgtgtggag gaacgggcgg ttggccaggc gtaagcggct gggttgtctg   6360
ccggccctgc aatggcactg gaacccccaa gcccgaggaa tcggcgtgag cggtcgcaaa   6420
ccatccggcc cggtacaaat cggcgcggcg ctgggtgatg acctggtgga gaagttgaag   6480
gccgcgcagg ccgcccagcg gcaacgcatc gaggcagaag cacgccccgg tgaatcgtgg   6540
caagcggccg ctgatcgaat ccgcaaagaa tcccggcaac cgccggcagc cggtgcgccg   6600
tcgattagga agccgcccaa gggcgacgag caaccagatt ttttcgttcc gatgctctat   6660
gacgtgggca cccgcgatag tcgcagcatc atggacgtgg ccgttttccg tctgtcgaag   6720
cgtgaccgac gagctggcga ggtgatccgc tacgagcttc cagacgggca cgtagaggtt   6780
tccgcagggc cggccggcat ggccagtgtg tgggattacg acctggtact gatggcggtt   6840
tcccatctaa ccgaatccat gaaccgatac cgggaaggga agggagacaa gcccggccgc   6900
gtgttccgtc cacacgttgc ggacgtactc aagttctgcc ggcgagccga tggcggaaag   6960
cagaaagacg acctggtaga aacctgcatt cggttaaaca ccacgcacgt tgccatgcag   7020
cgtacgaaga aggccaagaa cggccgcctg gtgacggtat ccgagggtga agccttgatt   7080
agccgctaca agatcgtaaa gagcgaaacc gggcggccgg agtacatcga gatcgagcta   7140
gctgattgga tgtaccgcga gatcacagaa ggcaagaacc cggacgtgct gacggttcac   7200
cccgattact ttttgatcga tcccggcatc ggccgttttc tctaccgcct ggcacgccgc   7260
gccgcaggca aggcagaagc cagatggttg ttcaagacga tctacgaacg cagtggcagc   7320
gccggagagt tcaagaagtt ctgtttcacc gtgcgcaagc tgatcgggtc aaatgacctg   7380
ccggagtacg atttgaagga ggaggcgggg caggctggcc cgatcctagt catgcgctac   7440
cgcaacctga tcgagggcga agcatccgcc ggttcctaat gtacggagca gatgctaggg   7500
caaattgccc tagcagggga aaaaggtcga aaaggtctct ttcctgtgga tagcacgtac   7560
attgggaacc caaagccgta cattgggaac cggaacccgt acattgggaa cccaaagccg   7620
tacattggga accggtcaca catgtaagtg actgatataa aagagaaaaa aggcgatttt   7680
tccgcctaaa actctttaaa acttattaaa actcttaaaa cccgcctggc ctgtgcataa   7740
ctgtctggcc agcgcacagc cgaagagctg caaaaagcgc ctacccttcg gtcgctgcgc   7800
tccctacgcc ccgccgcttc gcgtcggcct atcgcggccg ctggccgctc aaaaatggct   7860
ggcctacggc caggcaatct accagggcgc ggacaagccg cgccgtcgcc actcgaccgc   7920
cggcgcccac atcaaggcac cctgcctcgc gcgtttcggt gatgacggtg aaaacctctg   7980
acacatgcag ctcccggaga cggtcacagc ttgtctgtaa gcggatgccg ggagcagaca   8040
agcccgtcag ggcgcgtcag cgggtgttgg cgggtgtcgg ggcgcagcca tgacccagtc   8100
acgtagcgat agcggagtgt atactggctt aactatgcgg catcagagca gattgtactg   8160
agagtgcacc atatgcggtg tgaaataccg cacagatgcg taaggagaaa ataccgcatc   8220
```

-continued

```
aggcgctctt ccgcttcctc gctcactgac tcgctgcgct cggtcgttcg gctgcggcga   8280
gcggtatcag ctcactcaaa ggcggtaata cggttatcca cagaatcagg ggataacgca   8340
ggaaagaaca tgtgagcaaa aggccagcaa aaggccagga accgtaaaaa ggccgcgttg   8400
ctggcgtttt tccataggct ccgcccccct gacgagcatc acaaaaatcg acgctcaagt   8460
cagaggtggc gaaacccgac aggactataa agataccagg cgtttccccc tggaagctcc   8520
ctcgtgcgct ctcctgttcc gaccctgccg cttaccggat acctgtccgc ctttctccct   8580
tcgggaagcg tggcgctttc tcatagctca cgctgtaggt atctcagttc ggtgtaggtc   8640
gttcgctcca agctgggctg tgtgcacgaa ccccccgttc agcccgaccg ctgcgcctta   8700
tccggtaact atcgtcttga gtccaacccg gtaagacacg acttatcgcc actggcagca   8760
gccactggta acaggattag cagagcgagg tatgtaggcg gtgctacaga gttcttgaag   8820
tggtggccta actacggcta cactagaagg acagtatttg gtatctgcgc tctgctgaag   8880
ccagttacct tcggaaaaag agttggtagc tcttgatccg gcaaacaaac caccgctggt   8940
agcggtggtt tttttgtttg caagcagcag attacgcgca gaaaaaaagg atctcaagaa   9000
gatcctttga tcttttctac ggggtctgac gctcagtgga acgaaaactc acgttaaggg   9060
attttggtca tgagattatc aaaaaggatc ttcacctaga tccttttaaa ttaaaaatga   9120
agttttaaat caatctaaag tatatatgag taaacttggt ctgacagtta ccaatgctta   9180
atcagtgagg cacctatctc agcgatctgt ctatttcgtt catccatagt tgcctgactc   9240
cccgtcgtgt agataactac gatacgggag ggcttaccat ctggccccag tgctgcaatg   9300
ataccgcgag acccacgctc accggctcca gatttatcag caataaacca gccagccgga   9360
agggccgagc gcagaagtgg tcctgcaact ttatccgcct ccatccagtc tattaattgt   9420
tgccgggaag ctagagtaag tagttcgcca gttaatagtt tgcgcaacgt tgttgccatt   9480
gctacaggca tcgtggtgtc acgctcgtcg tttggtatgg cttcattcag ctccggttcc   9540
caacgatcaa ggcgagttac atgatccccc atgttgtgca aaaaagcggt tagctccttc   9600
ggtcctccga tcgttgtcag aagtaagttg gccgcagtgt tatcactcat ggttatggca   9660
gcactgcata attctcttac tgtcatgcca tccgtaagat gcttttctgt gactggtgag   9720
tactcaacca agtcattctg agaatagtgt atgcggcgac cgagttgctc ttgcccggcg   9780
tcaacacggg ataataccgc gccacatagc agaactttaa aagtgctcat cattggaaaa   9840
gacctgcagg gggggggggg cgctgaggtc tgcctcgtga agaaggtgtt gctgactcat   9900
accaggcctg aatcgcccca tcatccagcc agaaagtgag ggagccacgg ttgatgagag   9960
ctttgttgta ggtggaccag ttggtgattt tgaacttttg ctttgccacg gaacggtctg  10020
cgttgtcggg aagatgcgtg atctgatcct tcaactcagc aaaagttcga tttattcaac  10080
aaagccgccg tcccgtcaag tcagcgtaat gctctgccag tgttacaacc aattaaccaa  10140
ttctgattag aaaaactcat cgagcatcaa atgaaactgc aatttattca tatcaggatt  10200
atcaatacca tatttttgaa aaagccgttt ctgtaatgaa ggagaaaact caccgaggca  10260
gttccatagg atggcaagat cctggtatcg gtctgcgatt ccgactcgtc caacatcaat  10320
acaacctatt aatttcccct cgtcaaaaat aaggttatca agtgagaaat caccatgagt  10380
gacgactgaa tccggtgaga atggcaaaag cttatgcatt tctttccaga cttgttcaac  10440
aggccagcca ttacgctcgt catcaaaatc actcgcatca accaaaccgt tattcattcg  10500
tgattgcgcc tgagcgagac gaaatacgcg atcgctgtta aaggacaat tacaaacagg  10560
```

-continued

```
aatcgaatgc aaccggcgca ggaacactgc cagcgcatca acaatatttt cacctgaatc  10620
aggatattct tctaatacct ggaatgctgt tttcccgggg atcgcagtgg tgagtaacca  10680
tgcatcatca ggagtacgga taaaatgctt gatggtcgga agaggcataa attccgtcag  10740
ccagtttagt ctgaccatct catctgtaac atcattggca acgctacctt tgccatgttt  10800
cagaaacaac tctggcgcat cgggcttccc atacaatcga tagattgtcg cacctgattg  10860
cccgacatta tcgcgagccc atttataccc atataaatca gcatccatgt tggaatttaa  10920
tcgcggcctc gagcaagacg tttcccgttg aatatggctc ataacacccc ttgtattact  10980
gtttatgtaa gcagacagtt ttattgttca tgatgatata tttttatctt gtgcaatgta  11040
acatcagaga ttttgagaca caacgtggct ttcccccccc cccctgcagg tcaattcggt  11100
cgatatggct attacgaaga aggctcgtgc gcggagtccc gtgaactttc ccacgcaaca  11160
agtgaaccgc accgggtttg ccggaggcca tttcgttaaa atgcgcagcc atggctgctt  11220
cgtccagcat ggcgtaatac tgatcctcgt cttcggctgg cggtatattg ccgatgggct  11280
tcaaaagccg ccgtggttga accagtctat ccattccaag gtagcgaact cgaccgcttc  11340
gaagctcctc catggtccac gccgatgaat gacctcggcc ttgtaaagac cgttgatcgc  11400
ttctgcgagg gcgttgtcgt gctgtcgccg acgcttccga tagatggctc gatacctgct  11460
tctgccaacc gctcggaata gcgaaaggac acgtattgaa caccgcgatc cgagtgatgc  11520
actaggccgc catgagcggg acgccgatca tgatgagcct cctcgagggc atcgaggaca  11580
aagcctgcat gtgctgtccg gctcgcccgc catccgacaa tgcgacgggc gaagacgtcg  11640
atcacgaagg ccacgtagac gaagccctcc caagtggcga cataagtacg gacatgcgca  11700
aaggctttcc cggtttgtcg ctgatggtgc aagagacgct gaagcgcgat ccgatgcgca  11760
ggcatctgtt cgtcttccgc ggtcgtggcg gtggcctgat caaggtcact cgccgaagag  11820
ctgcatgatt ggctcgaaac cgagcggggg aaattgtcgc gcagttctcc cgtcgccgag  11880
gcgataaatt acatgctcaa gcgatgggat ggcattacgt cattcctcga tgacggcccg  11940
atttgcctga cgaacaatgc tgccgaacga acgctcagag gctatgtact cggcaggaag  12000
tcatggctgt ttgccggatc ggatcgttgt gctgaacgtg cggcgttcat ggcgacactg  12060
atcatgagcg ccaagctcaa taacatcgat ccgcaggcct ggcttgccga cgtccgcgcc  12120
gaccttgcgg acgctccgat cagcaggctt gagcaacagc tgccgtggaa ctggacatcc  12180
aagacactga gtgctcaggc ggcctgacct gcggccttca ccggatactt accccattat  12240
cgcagattgc gatgaagcat cagcgtcatt cagcaatctt gccaaagtat gcaggctcgc  12300
gagaatcgac gtgcgaaacc ggctggttgc gccaaagatc cgcttgcgga gcggtcgaac  12360
attcatgctg ggacttcaag aggtcgagta gaggaagaac cggaaaggtt gcaccggaaa  12420
atatgcgttc ctttggagag cgcctcatgg acgtgaacaa atcgcccgga ccaaggatgc  12480
cacggataca aaagctcgcg aagctcggtc ccgtgggtgt tctgtcgtct cgttgtacaa  12540
cgaaatccat tcccattccg cgctcaagat ggcttcccct cggcagttca tcagggctaa  12600
atcaatctag ccgacttgtc cggtgaaatg ggctgcactc caacagaaac aatcaaacaa  12660
acatacacag cgacttattc acacgagctc aaattacaac ggtatatatc ctgccagtca  12720
gcatcatcac accaaaagtt aggcccgaat agtttgaaat tagaaagctc gcaattgagg  12780
tctacaggcc aaattcgctc ttagccgtac aatattactc accggtgcga tgccccccat  12840
cgtaggtgaa ggtggaaatt aatgatccat cttgagacca caggcccaca acagctacca  12900
gtttcctcaa gggtccacca aaaacgtaag cgcttacgta catggtcgat aagaaaaggc  12960
```

aatttgtaga tgttaacatc caacgtcgct ttcagggatc gatccaatac gcaaaccgcc 13020
tctccccgcg cgttggccga ttcattaatg cagctggcac gacaggtttc ccgactggaa 13080
agcgggcagt gagcgcaacg caattaatgt gagttagctc actcattagg caccccaggc 13140
tttacacttt atgcttccgg ctcgtatgtt gtgtggaatt gtgagcggat aacaatttca 13200
cacaggaaac agctatgacc atgattacgc caagcttgca tgcctgcagg tcgactctag 13260
aggatctggc gcgccaagct tggatcctag cctaagtacg tactcaaaat gccaacaaat 13320
aaaaaaaaag ttgctttaat aatgccaaaa caaattaata aaacacttac aacaccggat 13380
tttttttaat taaaatgtgc catttaggat aaatagttaa tatttttaat aattatttaa 13440
aaagccgtat ctactaaaat gatttttatt tggttgaaaa tattaatatg tttaaatcaa 13500
cacaatctat caaaattaaa ctaaaaaaaa aataagtgta cgtggttaac attagtacag 13560
taatataaga ggaaaatgag aaattaagaa attgaaagcg agtctaattt ttaaattatg 13620
aacctgcata tataaaagga aagaaagaat ccaggaagaa aagaaatgaa accatgcatg 13680
gtcccctcgt catcacgagt ttctgccatt tgcaatagaa acactgaaac acctttctct 13740
ttgtcactta attgagatgc cgaagccacc tcacaccatg aacttcatga ggtgtagcac 13800
ccaaggcttc catagccatg catactgaag aatgtctcaa gctcagcacc ctacttctgt 13860
gacgtgtccc tcattcacct tcctctcttc cctataaata accacgcctc aggttctccg 13920
cttcacaact caaacattct ctccattggt ccttaaacac tcatcagtca tcaccatgtc 13980
ttccatagcc ccccaagcgg ccgcctggct ttggctgttt atcgtgttag gtgtgattgg 14040
gagtgggaat gtgagagata cagacgatga gatctcgtta ctcgaaagtc aattggtggt 14100
gacatctccg tcgcagcttc ttatggtgcc tctcactttg attcaggctg ctgcctccaa 14160
aggagctgtg tgcctggatg gaacactacc tggttatcat ctacaccctg gttctggatc 14220
aggagctaac cggtggctca tccaactcga gggtggagga tggtgcaaca cacgtaggag 14280
ctgtatcttc cggaaaacca ctcgccgtgg ttcatcaaat catatggaga aagttttggc 14340
cttcactgga atattgagca ataaatctaa tgagaatcct gacttcttca actggaacag 14400
agtcaaattg cgttactgcg atggtgcctc tttcaccggc gatagtcagg atgagagctc 14460
acaactttac tatagaggac aacgaatctg gcattcagct atggaagaac tactctctaa 14520
aggcatgcaa aaagcagaac aggctctact ttctggatgt tcagctgggg gattagcttc 14580
catcctacac tgcgatcagt tcaaggaact atttccgggc actacgacag tgaaatgctt 14640
aagtgatgct ggaatgttta tggatgcagt ggatgtctct gggggccact cgctccggaa 14700
aatgttccaa ggtgttgtta cagtacagaa cctccaaaag gaactgtcca ctgcttgtac 14760
aaagcatttg gatccaactt cgtgcttctt tccccagaac ttggtttcag gcattaagac 14820
tccaatgttt cttctcaatg cagcatatga cgcttggcag gtacaagaga gtttagctcc 14880
accatcagtt gacctaagcg gctcttggaa ggcatgcaaa tctgatcact cgcattgtaa 14940
ttcatctcag atccagttct tccaagactt caggactcat atggtagatg ctgtaaagtc 15000
tttcgcgaca tcgacacata acggtgtgtt cataaactca tgcttcgctc actgccaatc 15060
tgaaagacag gacacttggt atgcaccaga ttctcctact cttcatggca agaccgttgc 15120
tgaatctgtt ggtgattggt actttgacag aacaacagtg aaagccctgc agctgcatcc 15180
ataaacattc cagcatcact taagcatttc actgtcgtag tgcccggaaa tagttccttg 15240
aactgatcgc agtgtaggat ggaagctaat cccccagctg aacatccaga aagtagagcc 15300

-continued

```
tgttctgctt tttgcatgcc tttagagagt agttcttcca tagctgaatg ccagattcgt  15360

tgtcctctat agtaaagttg tgagctctca tcctgactat cgccggtgaa agaggcacca  15420

tcgcagtaac gcaatttgac tctgttccag ttgaagaagt caggattctc attagattta  15480

ttgctcaata ttccagtgaa ggccaaaact ttctccatat gatttgatga accacggcga  15540

gtggttttcc ggaagataca gctcctacgt gtgttgcacc atcctccacc ctcgagttgg  15600

atgagccacc ggttagctcc tgatccagaa ccagggtgta gatgataacc aggtagtgtt  15660

ccatccaggc acacagctcc tttggaggca gcagcctgaa tcaaagtgag aggcaccata  15720

agaagctgcg acggagatgt caccaccaat tgactttcga gtaacgagat ctcatcgtct  15780

gtatctctca cattcccact cccaatcaca cctaacacga taaacagcca aagccagaat  15840

atcgccgccg caatacgcaa cacactcttg cggccgcgac acaagtgtga gagtactaaa  15900

taaatgcttt ggttgtacga aatcattaca ctaaataaaa taatcaaagc ttatatatgc  15960

cttccgctaa ggccgaatgc aaagaaattg gttctttctc gttatctttt gccactttta  16020

ctagtacgta ttaattacta cttaatcatc tttgtttacg gctcattata tccgtcgacg  16080

g                                                                  16081
```

PLANT SEEDS WITH ALTERED STORAGE COMPOUND LEVELS, RELATED CONSTRUCTS AND METHODS INVOLVING GENES ENCODING PAE AND PAE-LIKE POLYPEPTIDES

FIELD OF THE INVENTION

This invention is in the field of plant molecular biology. More specifically, this invention pertains to isolated nucleic acid fragments encoding pectin acetyl esterase (PAE) and pectin acetyl esterase like (PAE-like) proteins in plants and seeds and the use of such fragments to modulate expression of a gene encoding PAE or PAE-like activity.

BACKGROUND OF THE INVENTION

At maturity, about 40% of soybean seed dry weight is protein and 20% extractable oil. These constitute the economically valuable products of the soybean crop. Plant oils for example are the most energy-rich biomass available from plants; they have twice the energy content of carbohydrates. It also requires very little energy to extract plant oils and convert them to fuels. Of the remaining 40% of seed weight, about 10% is soluble carbohydrate. The soluble carbohydrate portion contributes little to the economic value of soybean seeds and the main component of the soluble carbohydrate fraction, raffinosaccharides, are deleterious both to processing and to the food value of soybean meal in monogastric animals (Coon et al., (1988) Proceedings Soybean Utilization Alternatives, Univ. of Minnesota, pp. 203-211).

As the pathways of storage compound biosynthesis in seeds are becoming better understood it is clear that it may be possible to modulate the size of the storage compound pools in plant cells by altering the catalytic activity of specific enzymes in the oil, starch and soluble carbohydrate biosynthetic pathways (Taiz L., et al. *Plant Physiology*; The Benjamin/Cummings Publishing Company: New York, 1991). For example, studies investigating the over-expression of LPAT and DAGAT showed that the final steps acylating the glycerol backbone exert significant control over flux to lipids in seeds. Seed oil content could also be increased in oil-seed rape by overexpression of a yeast glycerol-3-phosphate dehydrogenase, whereas over-expression of the individual genes involved in de novo fatty acid synthesis in the plastid, such as acetyl-CoA carboxylase and fatty acid synthase, did not substantially alter the amount of lipids accumulated (Vigeolas H., et al. *Plant Biotechnology J.* 5, 431-441 (2007). A low-seed-oil mutant, wrinkled 1, has been identified in *Arabidopsis*. The mutation apparently causes a deficiency in the seed-specific regulation of carbohydrate metabolism (Focks, Nicole et al., Plant Physiol. (1998), 118(1), 91-101. There is a continued interest in identifying the genes that encode proteins that can modulate the synthesis of storage compounds, such as oil, protein, starch and soluble carbohydrates, in plants.

Serine hydrolase enzymes are abundant in nature and perform different biochemical roles in enzymes such as proteases, lipases, esterases and transferases. All these divergent enzymes share a serine residue in the active site that acts in the nucleophilic attack of the substrate thereby forming a covalent intermediate. Pectin Acetyl esterase (PAE) (EC 3.1.1.6) has been purified from plants and microorganisms. PAE specifically de-acetylates acetylated carbohydrate polymers, such as xylan and pectin. PAE has been shown to remove acetylester groups from, for example, sugar beet pectin at the C2 and/or C3 position of galacturonic acid residues (Nielsen, John E.; Christensen, Tove M. I. E. Distribution of pectin methyl esterase and acetylesterase in the genus Citrus visualized by tissue prints and chromatography. Plant Science (Shannon, Ireland) (2002), 162(5), 799-807.) Genes encoding PAE from plants have been cloned and sequenced (Christensen et al. Protein and cDNA sequences of orange fruit pectin acetylesterase, and uses thereof. PCT Int. Appl. (2000), 88 pp. CODEN: PIXXD2 WO 2000017368 A1 20000330). Large gene families encoding protein with similarity to PAE have been identified in every plant that was subjected to in-depth genome or EST sequencing. The divergent nature of sequences and expression pattern observed for the PAE gene family suggest a biochemical function for gene family members outside of the de-acetylation of polysaccharides. Few studies have been conducted on the possible role of these proteins with similarity to PAE. In view of the ubiquitous nature of genes encoding PAE-like proteins in plants further investigation of their role in plant growth and development and specifically in the regulation of storage compound content in seed is of great interest.

SUMMARY OF THE INVENTION

In a first embodiment the present invention concerns a transgenic plant comprising a recombinant DNA construct comprising a polynucleotide operably linked to at least one regulatory element, wherein said polynucleotide encodes a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85 and wherein seeds from said transgenic plant have an altered oil, protein, starch and/or soluble carbohydrate content when compared to seeds from a control plant not comprising said recombinant DNA construct.

In a second embodiment the present invention concerns transgenic seed comprising a recombinant DNA construct comprising a polynucleotide operably linked to at least one regulatory element, wherein said polynucleotide encodes a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85 and wherein said transgenic seed has an altered oil, protein, starch and/or soluble carbohydrate content when compared to a control seed not comprising said recombinant DNA construct.

In a third embodiment the present invention concerns transgenic seed comprising:

a recombinant DNA construct comprising: (a) a polynucleotide operably linked to at least one regulatory element, wherein said polynucleotide encodes a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85, or (b) a suppression DNA construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85, or (B) a full complement of the nucleic acid sequence of (b)(i)(A); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes an PAE-LIKE protein, and wherein said plant has an altered oil, protein, starch and/or soluble carbohydrate content when compared to a control plant not comprising said recombinant DNA construct.

In a fourth embodiment the invention concerns transgenic seed having an increased oil content of at least 4% on a dry-weight basis when compared to the oil content of a non-transgenic seed, wherein said transgenic seed comprises a recombinant DNA construct comprising: (a) all or part of the nucleotide sequence set forth in SEQ ID NO: 35, 37, 39, 41, 43, 45, 47, 49, 51, 53, 55, 57, 59, 61, 63, 65, 67, or 84; or (b) the full-length complement of (a): wherein (a) or (b) is of sufficient length to inhibit expression of endogenous activity in a transgenic plant and further wherein said seed has an increase in oil content of at least 4% on a dry-weight basis, as compared to seed obtained from a non-transgenic plant.

In a fifth embodiment the invention concerns transgenic seed comprising a recombinant DNA construct comprising: (a) all or part of the nucleotide sequence set forth in SEQ ID NO: 35, 37, 39, 41, 43, 45, 47, 49, 51, 53, 55, 57, 59, 61, 63, 65, 67, or 84; or (b) the full-length complement of (a): wherein (a) or (b) is of sufficient length to inhibit expression of endogenous PAE or PAE-LIKE proteins activity in a transgenic plant and further wherein said seed has an increase in oil content of at least 4% on a dry-weight basis, as compared to seed obtained from a non-transgenic plant.

In a sixth embodiment the present invention concerns a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70% sequence identity, based on the Clustal V method of alignment, when compared to SEQ ID NO: 35, 37, 39, 41, 43, 45, 47, 49, 51, 53, 55, 57, 59, 61, 63, 65, 67, or 84; and (b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

In a seventh embodiment this invention concerns a method for producing transgenic seed, the method comprising: (a) transforming a plant cell with a recombinant DNA construct comprising: (i) all or part of the nucleotide sequence set forth in SEQ ID NO: 35, 37, 39, 41, 43, 45, 47, 49, 51, 53, 55, 57, 59, 61, 63, 65, 67, or 84; or (ii) the full-length complement of (i); wherein (i) or (ii) is of sufficient length to inhibit expression of endogenous PAE or PAE-Like protein activity in a transgenic plant;

(b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

In an eighth embodiment, the present invention concerns a method for producing transgenic seed, the method comprising: (a) transforming a plant cell with a recombinant DNA construct comprising: (i) all or part of the nucleotide sequence set forth in SEQ ID NO: 35, 37, 39, 41, 43, 45, 47, 49, 51, 53, 55, 57, 59, 61, 63, 65, 67, or 84; or (ii) the full-length complement of (i); wherein (i) or (ii) is of sufficient length to inhibit expression of endogenous PAE or PAE-LIKE protein activity in a transgenic plant; (b) regenerating a transgenic plant from the transformed plant cell of (a); and (c) selecting a transgenic plant that produces a transgenic seed having an increase in oil content of at least 4% on a dry-weight basis, as compared to a transgenic seed obtained from a non-transgenic plant.

In a ninth embodiment the invention concerns a transgenic seed comprising: a recombinant DNA construct comprising: (a) a polynucleotide operably linked to at least one regulatory element, wherein said polynucleotide encodes a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85 or (b) a suppression DNA Construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85, or (B) a full complement of the nucleic acid sequence of (b)(i)(A); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes a PAE-LIKE protein, and wherein said plant has an altered, increased or decreased oil, protein, starch and/or soluble carbohydrate content when compared to a control plant not comprising said recombinant DNA construct.

In a tenth embodiment, the present invention includes an isolated polynucleotide comprising: (a) a nucleotide sequence encoding a polypeptide required for altering i.e. increasing or decreasing oil, protein, starch and/or soluble carbohydrate content, wherein the polypeptide has an amino acid sequence of at least 95% sequence identity when compared to SEQ ID NO:36 or 48, or (b) a full complement of the nucleotide sequence, wherein the full complement and the nucleotide sequence consist of the same number of nucleotides and are 100% complementary. The polypeptide may comprise the amino acid sequence of SEQ ID NO:36 or 48. The nucleotide sequence may comprise the nucleotide sequence of SEQ ID NO:35 or 47.

In another embodiment, the present invention concerns a recombinant DNA construct comprising any of the isolated polynucleotides of the present invention operably linked to at least one regulatory sequence, and a cell, a plant, and a seed comprising the recombinant DNA construct. The cell may be eukaryotic, e.g., a yeast, insect or plant cell, or prokaryotic, e.g., a bacterial cell.

Seeds obtained from monocot and dicot plants (such as for example maize and soybean, respectively) comprising the recombinant constructs of the invention are within the scope of the present invention. Also included are seed-specific or seed-preferred promoters driving the expression of the nucleic acid sequences of the invention. Embryo or endosperm specific promoters driving the expression of the nucleic acid sequences of the invention are also included. Furthermore the methods of the present inventions are useful for obtaining transgenic seeds from monocot plants (such as maize and rice) and dicot plants (such as soybean and canola).

Also within the scope of the invention are product(s) and/or by-product(s) obtained from the transgenic seed obtained from monocot or dicot plants, such as maize and soybean, respectively.

In another embodiment, this invention relates to a method for suppressing in a plant the level of expression of a gene encoding a polypeptide having PAE-LIKE protein activity, wherein the method comprises transforming a monocot or dicot plant with any of the nucleic acid fragments of the present invention.

BRIEF DESCRIPTION OF THE DRAWING AND SEQUENCE LISTING

The invention can be more fully understood from the following detailed description and the accompanying Drawing and Sequence Listing which form a part of this application.

Figure 1B:
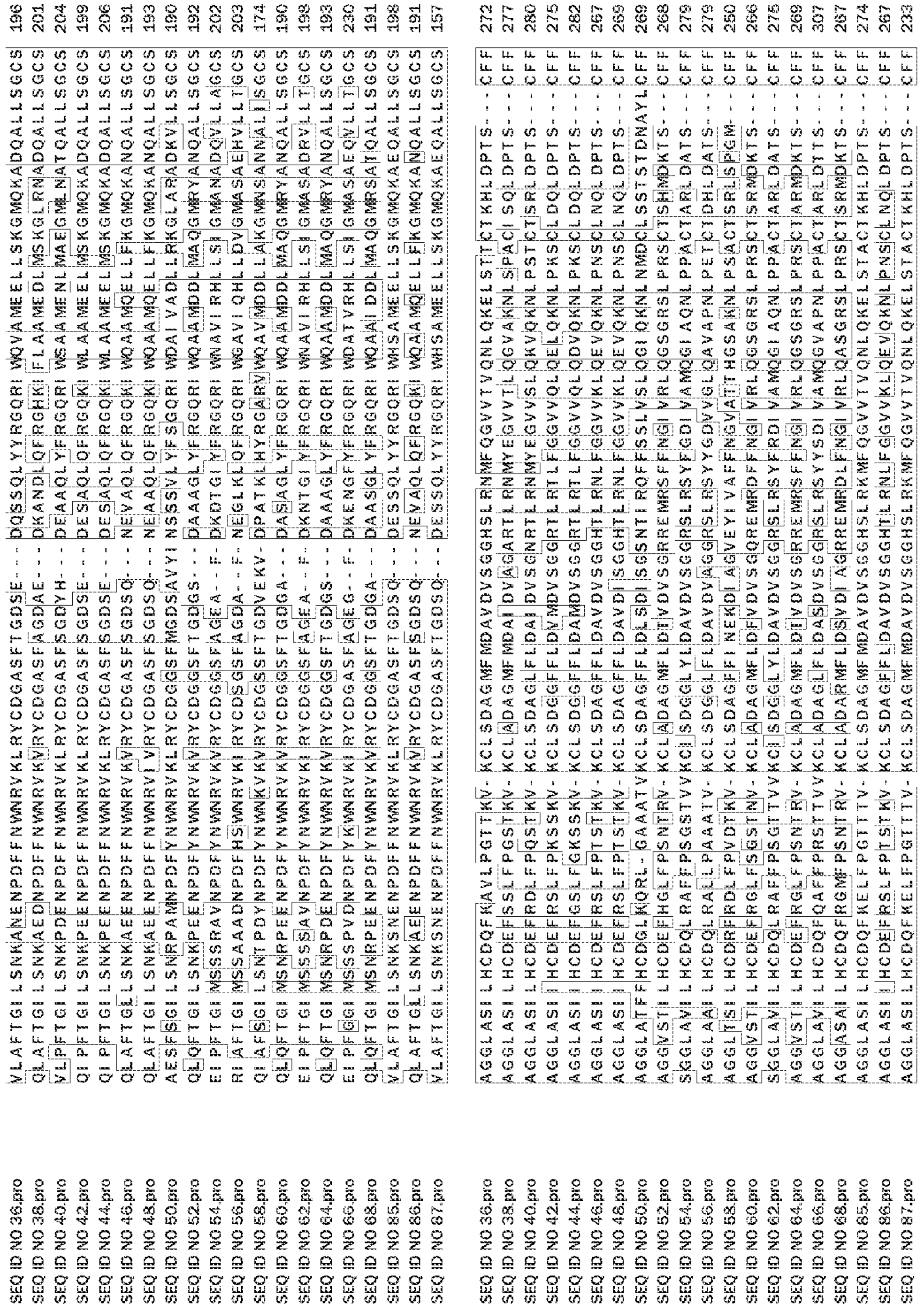
Figure 1C:
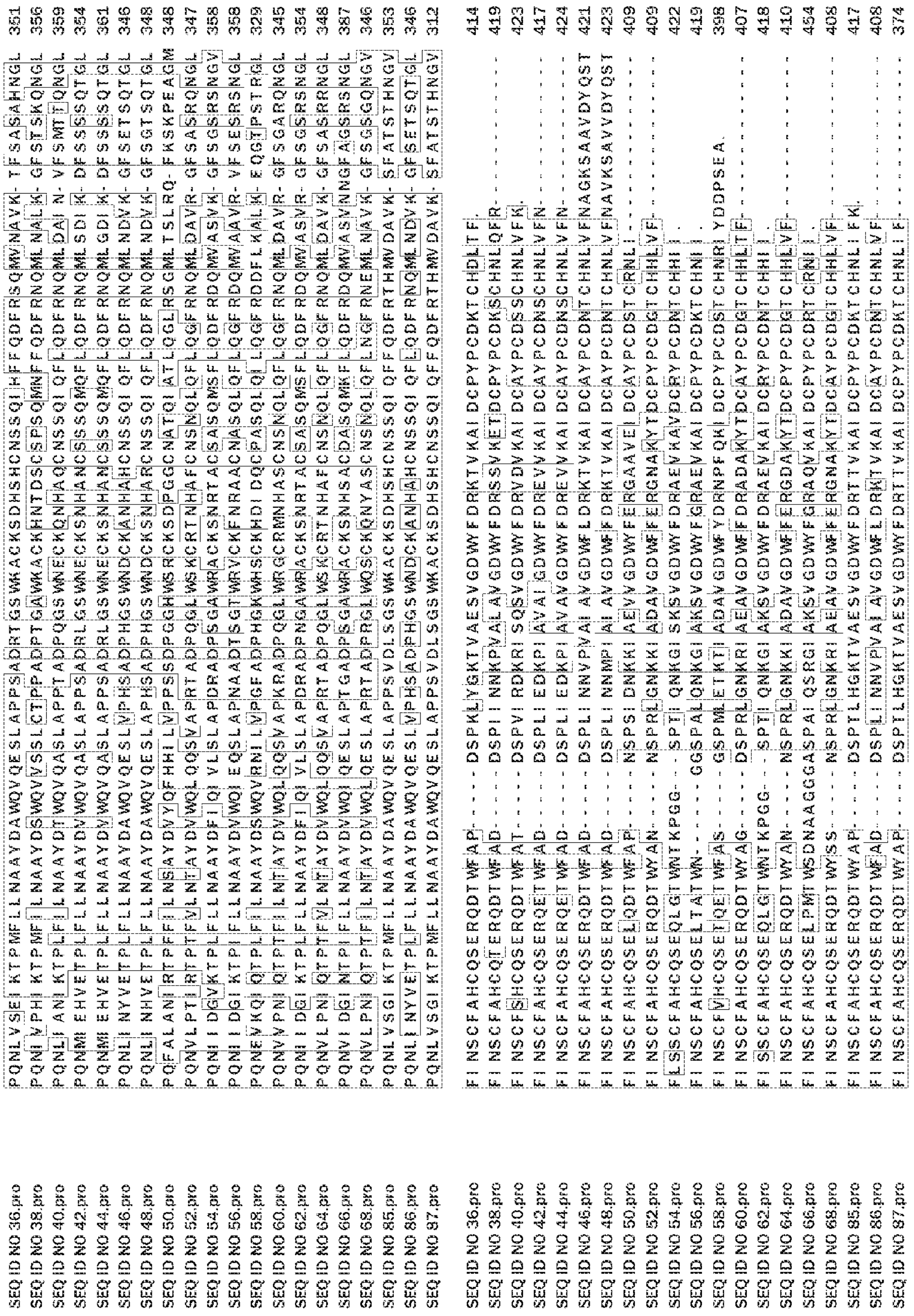

FIG. 1A-1D shows an alignment of the amino acid sequences of PAE and PAE-Like proteins encoded by the nucleotide sequences derived from the following: *Brassica rapa* (SEQ ID NO:36); *Helianthus annuus* (SEQ ID NO:38); *Ricinus communis* (SEQ ID NO:40); *Glycine max* (SEQ ID NO:42, 44, 46, and 48); *Zea mays* (SEQ ID NO:50, 52, and 54; *Oryza sativa* (SEQ ID NO:56, 58, and 60); *Sorghum bicolor* (SEQ ID NO:62, 64, and 66); *Triticum aestivum* (SEQ ID NO:68); *Arabidopsis thaliana* (SEQ ID NO:85, At2g46930); SEQ ID NO:86 corresponding to SEQ ID NO:53381 from US Patent Application US20100083407 (*Glycine max*); and SEQ ID NO:87 corresponding to SEQ ID NO:13822 of US Patent Application US20090094717 (*Arabidopsis thaliana*). For the alignment, amino acids which are conserved among all sequences at a given position, are boxed. Dashes are used by the program to maximize the alignment of the sequences.

FIG. 2 shows a chart of the percent sequence identity for each pair of amino acid sequences displayed in FIGS. 1A-1D.

The sequence descriptions and Sequence Listing attached hereto comply with the rules governing nucleotide and/or amino acid sequence disclosures in patent applications as set forth in 37 C.F.R. §1.821-1.825.

SEQ ID NO:1 Corresponds to the Nucleotide Sequence of Vector PHSbarENDS2.

SEQ ID NO:2 corresponds to the nucleotide sequence of a polylinker.

SEQ ID NO:3 corresponds to the nucleotide sequence of vector pKR85.

SEQ ID NO:4 corresponds to the nucleotide sequence of vector pKR278.

SEQ ID NO:5 corresponds to the nucleotide sequence of vector pKR407.

SEQ ID NO:6 corresponds to the nucleotide sequence of vector pKR1468.

SEQ ID NO:7 corresponds to the nucleotide sequence of vector pKR1475.

SEQ ID NO:8 corresponds to the nucleotide sequence of vector pKR92.

SEQ ID NO:9 corresponds to the nucleotide sequence of vector pKR1478.

SEQ ID NO:10 corresponds to SAIFF and genomic DNA of lo22730.

SEQ ID NO:11 corresponds to the forward primer PAE ORF FWD.

SEQ ID NO:12 corresponds to the reverse primer PAE ORF REV.

SEQ ID NO:13 corresponds to the nucleotide sequence of vector pENTR comprising PAE.

SEQ ID NO:14 corresponds to the nucleotide sequence of vector pKR1478-PAE.

SEQ ID NO:15 corresponds to the nucleotide sequence of PKR1481.

SEQ ID NO:16 corresponds to the AthLcc In forward primer.

SEQ ID NO:17 corresponds to the AthLcc In reverse primer.

SEQ ID NO:18 corresponds to the PCR product with the laccase intron.

SEQ ID NO:19 corresponds to the nucleotide sequence of PSM1318.

SEQ ID NO:20 corresponds to the nucleotide sequence of pMBL18 ATTR12 INT.

SEQ ID NO:21 corresponds to the nucleotide sequence of PSM1789.

SEQ ID NO:22 corresponds to the nucleotide sequence of pMBL18 ATTR12 INT ATTR21.

SEQ ID NO:23 corresponds to the SuSy-5' primer.

SEQ ID NO:24 corresponds to the SuSy-3' primer.

SEQ ID NO:25 corresponds to nucleotide sequence of pLF122.

SEQ ID NO:26 corresponds to the nucleotide sequence of pKR1142.

SEQ ID NO:27 corresponds to the nucleotide sequence of pKR1155.

SEQ ID NO:28 corresponds to the nucleotide sequence of KS294.

SEQ ID NO:29 corresponds to the nucleotide sequence of pKR627.

SEQ ID NO:30 corresponds to the nucleotide sequence of pKR132.

SEQ ID NO:31 corresponds to the nucleotide sequence of pKR278.

SEQ ID NO:32 corresponds to the nucleotide sequence of pKR1157.

SEQ ID NO:33 corresponds to the nucleotide sequence of pKR1479.

SEQ ID NO:34 corresponds to the nucleotide sequence of pKR1481-PAE.

Table 1 lists the polypeptides that are described herein, the designation of the clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire or functional protein derived from an FIS, a contig, an EST and PCR, or an FIS and PCR ("CGS").

TABLE 1

PAE-LIKE Proteins

| Protein (Plant Source) | Clone Designation | Status | SEQ ID NO: (Nucleotide) | SEQ ID NO: (Amino Acid) |
|---|---|---|---|---|
| PAE-LIKE (*Brassica rapa*) | PBR010399 | CGS | 35 | 36 |

TABLE 1-continued

| PAE-LIKE Proteins | | | | |
|---|---|---|---|---|
| | | | SEQ ID NO: | |
| Protein (Plant Source) | Clone Designation | Status | (Nucleotide) | (Amino Acid) |
| PAE-LIKE (*Helianthus annuus*) | TC19105 | CGS | 37 | 38 |
| PAE-LIKE (*Ricinus communis*) | XM002515114 | CGS | 39 | 40 |
| PAE-LIKE (*Glycine max*) | Glyma02g00930 | CGS | 41 | 42 |
| PAE-LIKE (*Glycine max*) | Glyma10g27960 | CGS | 43 | 44 |
| PAE-LIKE (*Glycine max*) | Glyma03g38430 | CGS | 45 | 46 |
| PAE-LIKE (*Glycine max*) | Glyma19g41030 | CGS | 47 | 48 |
| PAE-LIKE (*Zea mays*) | GRMZM2G117999 | CGS | 49 | 50 |
| PAE-LIKE (*Zea mays*) | GRMZM2G160569 | CGS | 51 | 52 |
| PAE-LIKE (*Zea mays*) | GRMZM2G164134 | CGS | 53 | 54 |
| PAE-LIKE (*Oryza sativa*) | Os01g21630 | CGS | 55 | 56 |
| PAE-LIKE (*Oryza sativa*) | Os02g47400 | CGS | 57 | 58 |
| PAE-LIKE (*Oryza sativa*) | Os07g44070 | CGS | 59 | 60 |
| PAE-LIKE (*Sorghum bicolor*) | Sb03g013080 | CGS | 61 | 62 |
| PAE-LIKE (*Sorghum bicolor*) | Sb02g040470 | CGS | 63 | 64 |
| PAE-LIKE (*Sorghum bicolor*) | Sb03g013070 | CGS | 65 | 66 |
| PAE-LIKE (*Triticum aestivum*) | TA80364 | CGS | 67 | 68 |

SEQ ID NO:69 is the nucleic acid sequence of the linker described in Example 18.

SEQ ID NO:70 is the nucleic acid sequence of vector pKS133 described in Example 19.

SEQ ID NO:71 corresponds to the single copy of ELVIS-LIVES.

SEQ ID NO:72 corresponds to two copies of ELVIS-LIVES.

SEQ ID NO:73 corresponds the primer described in Example 19.

SEQ ID NO:74 corresponds to the primer described in Example 19.

SEQ ID NO:75 corresponds to a synthetic PCR primer (SA 156).

SEQ ID NO:76 corresponds to a synthetic PCR primer (SA 157).

SEQ ID NO:77 corresponds to a synthetic PCR primer (SA 158).

SEQ ID NO:78 corresponds to a synthetic PCR primer (SA 159).

SEQ ID NO:79 corresponds to a synthetic PCR primer (SA 160).

SEQ ID NO:80 corresponds to the nucleotide sequence of pGemT-Easy D.

SEQ ID NO:81 corresponds to the nucleotide sequence of pGemT-Easy F.

SEQ ID NO:82 corresponds to the nucleotide sequence of pKS426.

SEQ ID NO:83 corresponds to the nucleotide sequence of pKS120.

SEQ ID NO:84 corresponds to the nucleotide sequence of At2g46930.

SEQ ID NO:85 corresponds to the amino acid sequence encoded by SEQ ID NO:84.

SEQ ID NO:86 corresponds to SEQ ID NO:53381 from US Patent Application US20100083407.

SEQ ID NO:87 corresponds to SEQ ID NO:13822 from US Patent Application US20090094717.

SEQ ID NO:88 represents the DNA corresponding to the amiRNA that was used to silence esterase.

SEQ ID NO:89 represents the DNA sequence corresponding to an artificial star sequence that was used to silence the desired target.

SEQ ID NO:90 represents the microRNA 396b precursor described in Example 23.

SEQ ID NO:91 represents the ready microRNA 396b precursor described in Example 23.

SEQ ID NO:92 represents the ready microRNA 396b-KS126 plasmid.

SEQ ID NO:93 corresponds to primer 396b PAE-like primA.

SEQ ID NO:94 corresponds to primer 396b PAE-like primB.

SEQ ID NO:95 corresponds to the 396b-PAE-like in fusion ready microRNA sequence.

SEQ ID NO:96 corresponds to the nucleotides sequence of the plasmid of 396b-PAE-like.

SEQ ID NO:97 corresponds to the nucleotide sequence of primer SA335.

SEQ ID NO:98 corresponds to the nucleotide sequence of primer SA336.

SEQ ID NO:99 corresponds to the nucleotide sequence of primer SA320.

SEQ ID NO:100 corresponds to the nucleotide sequence of primer SA319.

SEQ ID NO:101 corresponds to the nucleotide sequence of pGEM T easy A.

SEQ ID NO:102 corresponds to the nucleotide sequence of pGEM T easy B.

SEQ ID NO:103 corresponds to the nucleotide sequence of pBluescript-A.

SEQ ID NO:104 corresponds to the nucleotide sequence of pBluescript-AB.

SEQ ID NO:105 corresponds to the nucleotide sequence of KS442.

SEQ ID NO:106 corresponds to the nucleotide sequence of KS442-AB.

SEQ ID NO:107 corresponds to the nucleotide sequence of lo125.

The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. §1.822.

DETAILED DESCRIPTION OF THE INVENTION

All patents, patent applications, and publications cited throughout the application are hereby incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure a number of terms and abbreviations are used. The following definitions are provided.

"Open reading frame" is abbreviated ORF.

"Polymerase chain reaction" is abbreviated PCR.

"Triacylglycerols" are abbreviated TAGs.

"Co-enzyme A" is abbreviated CoA.

"pae" refers to the *Arabidopsis thaliana* locus, At2g46930 (SEQ ID NO:84).

"PAE" refers to the protein (SEQ ID NO:85) encoded by At2g46930 (SEQ ID NO:84).

"pae-like" refers to nucleotide homologs from different species, such as corn and soybean, of the *Arabidopsis thaliana* "pae" locus, At2g46930 (SEQ ID NO:84) and includes without limitation any of the nucleotide sequences of SEQ ID NOs:35, 37, 39, 41, 43, 45, 47, 49, 51, 53, 55, 57, 59, 61, 63, 65, and 67.

"PAE-like" refers to protein homologs from different species, such as corn and soybean, of the *Arabidopsis thaliana* "PAE" (SEQ ID NO:85) and includes without limitation any of the amino acid sequences of SEQ ID NOs: 36, 38, 40, 42, 44, 46, 48, 50, 52, 54, 56, 58, 60, 62, 64, 66, and 68.

The term "fatty acids" refers to long chain aliphatic acids (alkanoic acids) of varying chain length, from about $C_{12}$ to $C_{22}$ (although both longer and shorter chain-length acids are known). The predominant chain lengths are between $C_{16}$ and $C_{22}$. The structure of a fatty acid is represented by a simple notation system of "X:Y", where X is the total number of carbon (C) atoms in the particular fatty acid and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" have "double bonds" along their carbon backbones (which are most commonly in the cis-configuration). "Monounsaturated fatty acids" have only one "double bond" along the carbon backbone (e.g., usually between the $9^{th}$ and $10^{th}$ carbon atom as for palmitoleic acid (16:1) and oleic acid (18:1)), while "polyunsaturated fatty acids" (or "PUFAs") have at least two double bonds along the carbon backbone (e.g., between the $9^{th}$ and $10^{th}$, and $12^{th}$ and $13^{th}$ carbon atoms for linoleic acid (18:2); and between the $9^{th}$ and $10^{th}$, $12^{th}$ and $13^{th}$, and $15^{th}$ and $16^{th}$ for α-linolenic acid (18:3)).

The terms "triacylglycerol", "oil" and "TAGs" refer to neutral lipids composed of three fatty acyl residues esterified to a glycerol molecule (and such terms will be used interchangeably throughout the present disclosure herein). Such oils can contain long chain PUFAs, as well as shorter saturated and unsaturated fatty acids and longer chain saturated fatty acids. Thus, "oil biosynthesis" generically refers to the synthesis of TAGs in the cell.

The term "modulation" or "alteration" in the context of the present invention refers to increases or decreases of PAE OR PAE-LIKE protein expression, protein level or enzyme activity, as well as to an increase or decrease in the storage compound levels, such as oil, protein, starch or soluble carbohydrates.

The term "plant" includes reference to whole plants, plant parts or organs (e.g., leaves, stems, roots, etc.), plant cells, seeds and progeny of same. Plant cell, as used herein includes, without limitation, cells obtained from or found in the following: seeds, suspension cultures, embryos, meristematic regions, callus tissue, leaves, roots, shoots, gametophytes, sporophytes, pollen and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants.

Examples of monocots include, but are not limited to (corn) maize, wheat, rice, *sorghum*, millet, barley, palm, lily, Alstroemeria, rye, and oat.

Examples of dicots include, but are not limited to, soybean, rape, sunflower, canola, grape, guayule, columbine, cotton, tobacco, peas, beans, flax, safflower, and alfalfa.

Plant tissue includes differentiated and undifferentiated tissues or plants, including but not limited to, roots, stems, shoots, leaves, pollen, seeds, tumor tissue, and various forms of cells and culture such as single cells, protoplasm, embryos, and callus tissue.

The term "plant organ" refers to plant tissue or group of tissues that constitute a morphologically and functionally distinct part of a plant.

The term "genome" refers to the following: 1. The entire complement of genetic material (genes and non-coding sequences) is present in each cell of an organism, or virus or organelle. 2.A complete set of chromosomes inherited as a (haploid) unit from one parent. The term "stably integrated" refers to the transfer of a nucleic acid fragment into the genome of a host organism or cell resulting in genetically stable inheritance.

The terms "polynucleotide", "polynucleotide sequence", "nucleic acid", nucleic acid sequence", and "nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof.

The term "isolated" refers to materials, such as "isolated nucleic acid fragments" and/or "isolated polypeptides", which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "isolated nucleic acid fragment" is used interchangeably with "isolated polynucleotide" and is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of recombinant DNA constructs to produce the desired phenotype in a transformed plant. Recombinant DNA constructs can be designed for use in co-suppression or antisense by linking a nucleic acid fragment or subfragment thereof, whether or not it encodes an active enzyme, in the appropriate orientation relative to a plant promoter sequence.

"Cosuppression" refers to the production of sense RNA transcripts capable of suppressing the expression of identical or substantially similar native genes (U.S. Pat. No. 5,231,020). Cosuppression technology constitutes the subject matter of U.S. Pat. No. 5,231,020, which issued to Jorgensen et al. on Jul. 27, 1999. The phenomenon observed by Napoli et al. in petunia was referred to as "cosuppression" since expression of both the endogenous gene and the introduced transgene were suppressed (for reviews see Vaucheret et al., *Plant J.* 16:651-659 (1998); and Gura, *Nature* 404:804-808 (2000)).

Cosuppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al. (1998) *Plant J* 16:651-659; and Gura (2000) *Nature* 404:804-808). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication WO 99/53050 published on Oct. 21, 1999). This increases the frequency of co-suppression in the recovered transgenic plants. Another variation describes the use of plant viral sequences to direct the suppression, or "silencing", of proximal mRNA encoding sequences (PCT Publication WO 98/36083 published on Aug. 20, 1998). Both of these co-suppressing phenomena have not been elucidated mechanistically, although recent genetic evidence has begun to unravel this complex situation (Elmayan et al. (1998) *Plant Cell* 10:1747-1757).

In addition to cosuppression, antisense technology has also been used to block the function of specific genes in cells. Antisense RNA is complementary to the normally expressed RNA, and presumably inhibits gene expression by interacting with the normal RNA strand. The mechanisms by which the expression of a specific gene are inhibited by either antisense or sense RNA are on their way to being understood. However, the frequencies of obtaining the desired phenotype in a transgenic plant may vary with the design of the construct, the gene, the strength and specificity of its promoter, the method of transformation and the complexity of transgene insertion events (Baulcombe, *Curr. Biol.* 12(3):R82-84 (2002); Tang et al., *Genes Dev.* 17(1):49-63 (2003); Yu et al., *Plant Cell. Rep.* 22(3):167-174 (2003)). Cosuppression and antisense inhibition are also referred to as "gene silencing", "post-transcriptional gene silencing" (PTGS), RNA interference or RNAi. See for example U.S. Pat. No. 6,506,559.

MicroRNAs (miRNA) are small regulatory RNSs that control gene expression. miRNAs bind to regions of target RNAs and inhibit their translation and, thus, interfere with production of the polypeptide encoded by the target RNA. miRNAs can be designed to be complementary to any region of the target sequence RNA including the 3' untranslated region, coding region, etc. miRNAs are processed from highly structured RNA precursors that are processed by the action of a ribonuclease III termed DICER. While the exact mechanism of action of miRNAs is unknown, it appears that they function to regulate expression of the target gene. See, e.g., U.S. Patent Publication No. 2004/0268441 A1 which was published on Dec. 30, 2004.

The term "expression", as used herein, refers to the production of a functional end-product, be it mRNA or translation of mRNA into a polypeptide. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Overexpression" refers to the production of a functional end-product in transgenic organisms that exceeds levels of production when compared to expression of that functional end-product in a normal, wild type or non-transformed organism.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is using particle-accelerated or "gene gun" transformation technology (Klein et al. (1987) *Nature* (*London*) 327:70-73; U.S. Pat. No. 4,945,050), or an *Agrobacterium*-mediated method (Ishida Y. et al. (1996) *Nature Biotech.* 14:745-750). The term "transformation" as used herein refers to both stable transformation and transient transformation.

"Antisense inhibition" refers to the production of antisense RNA transcripts capable of suppressing the expression of the target protein.

As stated herein, "suppression" refers to the reduction of the level of enzyme activity or protein functionality detectable in a transgenic plant when compared to the level of enzyme activity or protein functionality detectable in a plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to the decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in the desired cell.

"Gene silencing," as used herein, is a general term that refers to decreasing mRNA levels as compared to wild-type plants, does not specify mechanism and is inclusive, and not limited to, anti-sense, cosuppression, viral-suppression, hairpin suppression and stem-loop suppression.

The terms "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. For example, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes that result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. It is therefore understood, as those skilled in the art will appreciate, that the invention encompasses more than the specific exemplary sequences.

Moreover, the skilled artisan recognizes that substantially similar nucleic acid sequences encompassed by this invention are also defined by their ability to hybridize, under moderately stringent conditions (for example, 1×SSC, 0.1% SDS, 60° C.) with the sequences exemplified herein, or to any portion of the nucleotide sequences reported herein and which are functionally equivalent to the gene or the promoter of the invention. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions involves a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions involves the use of higher temperatures in which the washes are identical to those above except for the temperature of the final two 30 min washes in 0.2×SSC, 0.5% SDS was increased to 60° C. Another preferred set of highly stringent conditions involves the use of two final washes in 0.1×SSC, 0.1% SDS at 65° C.

With respect to the degree of substantial similarity between the target (endogenous) mRNA and the RNA region in the construct having homology to the target mRNA, such sequences should be at least 25 nucleotides in length, preferably at least 50 nucleotides in length, more preferably at least 100 nucleotides in length, again more preferably at least 200 nucleotides in length, and most preferably at least 300 nucleotides in length; and should be at least 80% identical, preferably at least 85% identical, more preferably at least 90% identical, and most preferably at least 95% identical.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least 70% identical, preferably at least 80% identical to the amino acid sequences reported herein. Preferred nucleic acid fragments encode amino acid sequences that are at least 85% identical to the amino acid sequences reported herein. More preferred nucleic acid fragments encode amino acid sequences that are at least 90% identical to the amino acid sequences reported herein. Most preferred are nucleic acid fragments that encode amino acid sequences that are at least 95% identical to the amino acid sequences reported herein.

It is well understood by one skilled in the art that many levels of sequence identity are useful in identifying related polypeptide sequences. Useful examples of percent identities are 50%, 55%, 60%, 65%, 70%, 75%, 80%, 85%, 90%, or 95%, or any integer percentage from 55% to 100%.

Sequence alignments and percent similarity calculations may be determined using a variety of comparison methods designed to detect homologous sequences including, but not limited to, the Megalign program of the LASARGENE bioinformatics computing suite (DNASTAR Inc., Madison, Wis.). Unless stated otherwise, multiple alignment of the sequences provided herein were performed using the Clustal method of alignment (Higgins and Sharp (1989) CABIOS. 5:151-153) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain a "percent identity" by viewing the "sequence distances" table on the same program.

Unless otherwise stated, BLAST® (Basic Local Alignment Search Tool) sequence identity/similarity values provided herein refer to the value obtained using the BLAST® (Basic Local Alignment Search Tool) 2.0 suite of programs using default parameters (Altschul et al., *Nucleic Acids Res.* 25:3389-3402 (1997)). Software for performing BLAST® (Basic Local Alignment Search Tool) analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST® (Basic Local Alignment Search Tool algorithm parameters W, T, and X determine the sensitivity and speed of the alignment. The BLASTN program (BLAST® Basic Local Alignment Search Tool for nucleotide sequences) uses as defaults a wordlength (W) of 11, an expectation (E) of 10, a cutoff of 100, M=5, N=4, and a comparison of both strands. For amino acid sequences, the BLASTP program (BLAST® Basic Local Alignment Search Tool program) uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

"Sequence identity" or "identity" in the context of nucleic acid or polypeptide sequences refers to the nucleic acid bases or amino acid residues in the two sequences that are the same when aligned for maximum correspondence over a specified comparison window.

Thus, "Percentage of sequence identity" refers to the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90%, or 95%, or any integer percentage from 55% to 100%. These identities can be determined using any of the programs described herein.

Sequence alignments and percent identity or similarity calculations may be determined using a variety of comparison methods designed to detect homologous sequences including, but not limited to, the Megalign program of the LASARGENE bioinformatics computing suite (DNASTAR Inc., Madison, Wis.). Multiple alignment of the sequences are performed using the Clustal V method of alignment (Higgins, D. G. and Sharp, P. M. (1989) *Comput. Appl. Biosci.* 5:151-153; Higgins, D. G. et al. (1992) *Comput. Appl. Biosci.* 8:189-191) with the default parameters (GAP PENALTY=10, GAP LENGTH PENALTY=10). Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4.

It is well understood by one skilled in the art that many levels of sequence identity are useful in identifying polypeptides, from other plant species, wherein such polypeptides have the same or similar function or activity. Useful examples of percent identities include, but are not limited to, 50%, 55%, 60%, 65%, 70%, 75%, 80%, 85%, 90%, or 95%, or any integer percentage from 55% to 100%. Indeed, any integer amino acid identity from 50%-100% may be useful in describing the present invention. Also, of interest is any full or partial complement of this isolated nucleotide fragment.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

The terms "synthetic nucleic acid" or "synthetic genes" refer to nucleic acid molecules assembled either in whole or in part from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that is capable of directing expression a specific protein or functional RNA.

"Native gene" refers to a gene as found in nature with its own regulatory sequences.

"Chimeric gene" or "recombinant DNA construct" are used interchangeably herein, and refers to any gene that is not a native gene, comprising regulatory and coding sequences that are not found together in nature, or to an isolated native gene optionally modified and reintroduced into a host cell.

A chimeric gene may comprise regulatory sequences and coding sequences that are derived from different sources, or regulatory sequences and coding sequences derived from the same source, but arranged in a manner different than that found in nature. In one embodiment, a regulatory region and a coding sequence region are assembled from two different sources. In another embodiment, a regulatory region and a coding sequence region are derived from the same source but arranged in a manner different than that found in nature. In another embodiment, the coding sequence region is assembled from at least two different sources. In another embodiment, the coding region is assembled from the same source but in a manner not found in nature.

The term "endogenous gene" refers to a native gene in its natural location in the genome of an organism.

The term "foreign gene" refers to a gene not normally found in the host organism that is introduced into the host organism by gene transfer.

The term "transgene" refers to a gene that has been introduced into a host cell by a transformation procedure. Transgenes may become physically inserted into a genome of the host cell (e.g., through recombination) or may be maintained outside of a genome of the host cell (e.g., on an extrachromasomal array).

An "allele" is one of several alternative forms of a gene occupying a given locus on a chromosome. When the alleles present at a given locus on a pair of homologous chromosomes in a diploid plant are the same that plant is homozygous at that locus. If the alleles present at a given locus on a pair of homologous chromosomes in a diploid plant differ that plant is heterozygous at that locus. If a transgene is present on one of a pair of homologous chromosomes in a diploid plant that plant is hemizygous at that locus.

The term "coding sequence" refers to a DNA fragment that codes for a polypeptide having a specific amino acid sequence, or a structural RNA. The boundaries of a protein coding sequence are generally determined by a ribosome binding site (prokaryotes) or by an ATG start codon (eukaryotes) located at the 5' end of the mRNA and a transcription terminator sequence located just downstream of the open reading frame at the 3' end of the mRNA. A coding sequence can include, but is not limited to, DNA, cDNA, and recombinant nucleic acid sequences.

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be and are not limited to intracellular localization signals.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target isolated nucleic acid fragment (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

"Messenger RNA (mRNA)" refers to the RNA that is without introns and that can be translated into protein by the cell.

"cDNA" refers to a DNA that is complementary to and synthesized from a mRNA template using the enzyme reverse transcriptase. The cDNA can be single-stranded or converted into the double-stranded form using the Klenow fragment of DNA polymerase I.

"Sense" RNA refers to RNA transcript that includes the mRNA and can be translated into protein within a cell or in vitro.

"Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence.

"Functional RNA" refers to antisense RNA, ribozyme RNA, or other RNA that may not be translated, yet has an effect on cellular processes. The terms "complement" and "reverse complement" are used interchangeably herein with respect to mRNA transcripts, and are meant to define the antisense RNA of the message.

The term "recombinant DNA construct" refers to a DNA construct assembled from nucleic acid fragments obtained from different sources. The types and origins of the nucleic acid fragments may be very diverse.

A "recombinant expression construct" contains a nucleic acid fragment operably linked to at least one regulatory element, that is capable of effecting expression of the nucleic acid fragment. The recombinant expression construct may also affect expression of a homologous sequence in a host cell.

In one embodiment the choice of recombinant expression construct is dependent upon the method that will be used to transform host cells. The skilled artisan is well aware of the genetic elements that must be present on the recombinant expression construct in order to successfully transform, select and propagate host cells. The skilled artisan will also recognize that different independent transformation events may be screened to obtain lines displaying the desired expression level and pattern. Such screening may be accomplished by, but is not limited to, Southern analysis of DNA, Northern analysis of mRNA expression, Western analysis of protein expression, or phenotypic analysis.

The term "operably linked" refers to the association of nucleic acid fragments on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

"Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences.

"Promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of an isolated nucleic acid fragment in different tissues or cell types, or at different stages of development, or in response to different environmental conditions. Promoters which cause an isolated nucleic acid fragment to be expressed in most cell types at most times are commonly referred to as "constitutive promoters". New promoters of various types useful in plant cells are constantly being discovered; numerous examples may be found in the compilation by Okamuro and Goldberg, (1989) Biochemistry of Plants 15:1-82. It is further recognized that since in most cases the exact boundaries of regulatory sequences have not been completely defined, DNA fragments of some variation may have identical promoter activity.

Specific examples of promoters that may be useful in expressing the nucleic acid fragments of the invention include, but are not limited to, the oleosin promoter (PCT Publication WO99/65479, published Dec. 12, 1999), the maize 27 kD zein promoter (Ueda et al (1994) *Mol. Cell. Biol.* 14:4350-4359), the ubiquitin promoter (Christensen et al (1992) *Plant Mol. Biol.* 18:675-680), the SAM synthetase promoter (PCT Publication WO00/37662, published Jun. 29, 2000), the CaMV 35S (Odell et al (1985) *Nature* 313:810-812), and the promoter described in PCT Publication WO02/099063 published Dec. 12, 2002.

The "translation leader sequence" refers to a polynucleotide fragment located between the promoter of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Mol. Biotechnol.* 3:225-236).

An "intron" is an intervening sequence in a gene that does not encode a portion of the protein sequence. Thus, such sequences are transcribed into RNA but are then excised and are not translated. The term is also used for the excised RNA sequences.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) *Plant Cell* 1:671-680.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989. Transformation methods are well known to those skilled in the art and are described below.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

"Stable transformation" refers to the transfer of a nucleic acid fragment into a genome of a host organism, including nuclear and organellar genomes, resulting in genetically stable inheritance.

In contrast, "transient transformation" refers to the transfer of a nucleic acid fragment into the nucleus, or DNA-containing organelle, of a host organism resulting in gene expression without integration or stable inheritance.

Host organisms comprising the transformed nucleic acid fragments are referred to as "transgenic" organisms.

The term "amplified" means the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, D. H. Persing et al., Ed., American Society for Microbiology, Washington, D.C. (1993). The product of amplification is termed an amplicon.

The term "chromosomal location" includes reference to a length of a chromosome which may be measured by reference to the linear segment of DNA which it comprises. The chromosomal location can be defined by reference to two unique DNA sequences, i.e., markers.

The term "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

The present invention includes, inter alia, compositions and methods for altering or modulating (i.e., increasing or decreasing) the level of PAE OR PAE-LIKE polypeptides described herein in plants. The size of the oil, protein, starch and soluble carbohydrate pools in soybean seeds can be modulated or altered (i.e. increased or decreased) by altering the expression of a specific gene, encoding PAE OR PAE-LIKE protein.

In one embodiment, the present invention concerns a transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85 and wherein seed obtained from said transgenic plant has an altered oil, protein, starch and/or soluble carbohydrate content when compared to seed obtained from a control plant not comprising said recombinant DNA construct.

In a second embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85 and wherein said transgenic seed has an altered oil, protein, starch and/or soluble carbohydrate content when compared to a control plant not comprising said recombinant DNA construct.

In a third embodiment the present invention concerns a transgenic seed obtained from the transgenic plant comprising a recombinant DNA construct comprising a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85 and wherein said transgenic seed has an increased starch content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis when compared to a control seed not comprising said recombinant DNA construct.

In another embodiment, the present invention relates to a recombinant DNA construct comprising any of the isolated polynucleotides of the present invention operably linked to at least one regulatory sequence.

In another embodiment of the present invention, a recombinant construct of the present invention further comprises an enhancer.

In another embodiment, the present invention relates to a vector comprising any of the polynucleotides of the present invention.

In another embodiment, the present invention relates to an isolated polynucleotide fragment comprising a nucleotide sequence comprised by any of the polynucleotides of the present invention, wherein the nucleotide sequence contains at least 30, 40, 60, 100, 200, 300, 400, 500 or 600 nucleotides.

In another embodiment, the present invention relates to a method for transforming a cell comprising transforming a cell with any of the isolated polynucleotides of the present invention, and the cell transformed by this method. Advantageously, the cell is eukaryotic, e.g., a yeast or plant cell, or prokaryotic, e.g., a bacterium.

In yet another embodiment, the present invention relates to a method for transforming a cell, comprising transforming a cell with a polynucleotide of the present invention.

In another embodiment, the present invention relates to a method for producing a transgenic plant comprising transforming a plant cell with any of the isolated polynucleotides of the present invention and regenerating a transgenic plant from the transformed plant cell.

In another embodiment, a cell, plant, or seed comprising a recombinant DNA construct of the present invention.

In another embodiment, an isolated polynucleotide comprising: (i) a nucleic acid sequence encoding a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs (including suppression DNA constructs) of the present invention. Preferably the polypeptide is a PAE or PAE-like protein.

In another embodiment, an isolated polynucleotide comprising: (i) a nucleic acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85; or (ii) a full complement of the nucleic acid sequence of (i). Any of the foregoing isolated polynucleotides may be utilized in any recombinant DNA constructs (including suppression DNA constructs) of the present invention. Preferably, the polypeptide is an PAE or PAE-like protein.

In one aspect, the present invention includes recombinant DNA constructs (including suppression DNA constructs).

In another embodiment, the present invention relates to a method of selecting an isolated polynucleotide that alters, i.e. increases or decreases, the level of expression of a PAE OR PAE-LIKE protein gene, protein or enzyme activity in a host cell, preferably a plant cell, the method comprising the steps of: (a) constructing an isolated polynucleotide of the present invention or an isolated recombinant DNA construct of the present invention; (b) introducing the isolated polynucleotide or the isolated recombinant DNA construct into a host cell; (c) measuring the level of the PAE OR PAE-LIKE protein RNA, protein or enzyme activity in the host cell containing the isolated polynucleotide or recombinant DNA construct; (d) comparing the level of the PAE OR PAE-LIKE RNA, protein or enzyme activity in the host cell containing the isolated polynucleotide or recombinant DNA construct with the level of the PAE OR PAE-LIKE protein RNA, protein or enzyme activity in a host cell that does not contain the isolated polynucleotide or recombinant DNA construct, and selecting the isolated polynucleotide or recombinant DNA construct that alters, i.e., increases or decreases, the level of expression of the PAE OR PAE-LIKE protein gene, protein or enzyme activity in the plant cell.

In another embodiment, this invention concerns a method for suppressing the level of expression of a gene encoding a PAE OR PAE-LIKE protein having PAE OR PAE-LIKE protein activity in a transgenic plant, wherein the method comprises: (a) transforming a plant cell with a fragment of the isolated polynucleotide of the invention; (b) regenerating a transgenic plant from the transformed plant cell of 9a); and (c) selecting a transgenic plant wherein the level of expression of a gene encoding a polypeptide having PAE OR PAE-LIKE protein activity has been suppressed.

Preferably, the gene encodes a polypeptide having PAE OR PAE-LIKE protein activity, and the plant is a soybean plant.

In another embodiment, the invention concerns a method for producing transgenic seed, the method comprising: a) transforming a plant cell with the recombinant DNA construct of (i) all or part of the nucleotide sequence set forth in SEQ ID NO: 35, 37, 39, 41, 43, 45, 47, 49, 51, 53, 55, 57, 59, 61, 63, 65, 67, or 84, or (ii) the complement of (i); wherein (i) or (ii) is useful in co-suppression or antisense suppression of endogenous PAE OR PAE-LIKE protein activity in a transgenic plant; (b) regenerating a transgenic plant from the transformed plant cell of (a); and (c) selecting a transgenic plant that produces transgenic seeds having an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% compared to seed obtained from a non-transgenic plant. Preferably, the seed is a soybean plant.

In another embodiment, a plant comprising in its genome a recombinant DNA construct comprising: (a) a polynucleotide operably linked to at least one regulatory element, wherein said polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85 or (b) a suppression DNA construct comprising at least one regulatory element operably linked to: (i) all or part of: (A) a nucleic acid sequence encoding a polypeptide having an amino acid sequence of at least 70% sequence identity, based on the Clustal V method of alignment, when compared to SEQ ID NO: 36, 38, 40, 42, 44, 46, 48, 50, 52, 54, 56, 58, 60, 62, 64, 66, 68, or 85, or (B) a full complement of the nucleic acid sequence of (b)(iXA); or (ii) a region derived from all or part of a sense strand or antisense strand of a target gene of interest, said region having a nucleic acid sequence of at least 70% sequence identity, based on the Clustal V method of alignment, when compared to said all or part of a sense strand or antisense strand from which said region is derived, and wherein said target gene of interest encodes a PAE OR PAE-LIKE protein, and wherein said plant has an altered oil, protein, starch and/or soluble carbohydrate content, when compared to a control plant not comprising said recombinant DNA construct.

A transgenic seed having an increased oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% when compared to the oil content of a non-transgenic seed, wherein said transgenic seed comprises a recombinant DNA construct comprising: (a) all or part of the nucleotide sequence set forth in SEQ ID NO: 35, 37, 39, 41, 43, 45, 47, 49, 51, 53, 55, 57, 59, 61, 63, 65, 67, or 84;

or (b) the full-length complement of (a): wherein (a) or (b) is of sufficient length to inhibit expression of endogenous PAE OR PAE-LIKE protein activity in a transgenic plant and further wherein said seed has an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% on a dry-weight basis, as compared to seed obtained from a non-transgenic plant.

Yet another embodiment of the invention concerns a transgenic seed comprising a recombinant DNA construct comprising:

(a) all or part of the nucleotide sequence set forth in SEQ ID NO: 35, 37, 39, 41, 43, 45, 47, 49, 51, 53, 55, 57, 59, 61, 63, 65, 67, or 84; or (b) the full-length complement of (a): wherein (a) or (b) is of sufficient length to inhibit expression of endogenous PAE OR PAE-LIKE protein activity in a transgenic plant and further wherein said seed has an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% on a dry-weight basis, as compared to seed obtained from a non-transgenic plant.

In another embodiment, the invention concerns a method for producing a transgenic plant, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85; and (b) regenerating a plant from the transformed plant cell.

Another embodiment of the invention concerns, a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85; and (b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

Another embodiment of the invention concerns, a method for producing transgenic seeds, the method comprising: (a) transforming a plant cell with a recombinant DNA construct comprising a polynucleotide operably linked to at least one regulatory sequence, wherein the polynucleotide encodes a polypeptide having an amino acid sequence of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, based on the Clustal V method of alignment, when compared to SEQ ID NO: 36, 38, 40, 42, 44, 46, 48, 50, 52, 54, 56, 58, 60, 62, 64, 66, 68, or 85; and (b) regenerating a transgenic plant from the transformed plant cell of (a); and (c) selecting a transgenic plant that produces a transgenic seed having an increased starch content of at least 0.5%, 1%, 1.5%, 2%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0%, 10.5%, 11%, 11.5%, 12.0% 12.5%, 13.0, 13.5%. 14.0%, 14.5%, 15.0%, 15.5%, 15.0%, 16.5%, 17.0%, 17.5% 18.0%, 18.5%, 19.0%, 19.5%, 20.0%, 20.5%, 21.0%, 21.5%, 22.0%, 22.5%, 23.0%, 23.5%, 24.0%, 24.5%, 25.0%, 25.5%, 26.0%, 26.5%, 27.0%, 27.5%, 28.0%, 28.5%, 29%, 29.5%, 30.0%, 30.5%, 31.0%, 31.5%, 32.0%, 32.5%, 33.0%, 33.5%, 34.0%, 35.0%, 35.5%, 36.0%, 36.5%, 37.0%, 37.5%, 38.0%, 38.5%, 39.0%, 39.5%, 40.0%, 40.5%, 41.0%, 41.5%, 42.0%, 42.5%, 43.0%, 43.5%, 44.0%, 44.5%, 45.0%, 45.5%, 46.0%, 46.5%, 47.0%, 47.5%, 48.0%, 48.5%, 49.0%, 49.5%, or 50.0% on a dry weight basis as compared to a transgenic seed obtained from a non-transgenic plant.

In another embodiment, the invention concerns a method for producing transgenic seed, the method comprising: (a) transforming a plant cell with a recombinant DNA construct comprising: (i) all or part of the nucleotide sequence set forth in SEQ ID NO: 35, 37, 39, 41, 43, 45, 47, 49, 51, 53, 55, 57, 59, 61, 63, 65, 67, or 84; or (ii) the full-length complement of (i); wherein (i) or (ii) is of sufficient length to inhibit expression of endogenous PAE OR PAE-LIKE protein activity in a transgenic plant; (b) regenerating a transgenic plant from the transformed plant cell of (a); and (c) selecting a transgenic plant that produces a transgenic seed having an altered oil, protein, starch and/or soluble carbohydrate content, as compared to a transgenic seed obtained from a non-transgenic plant.

A method for producing transgenic seed, the method comprising: (a) transforming a plant cell with a recombinant DNA construct comprising: (i) all or part of the nucleotide sequence set forth in SEQ ID NO: 35, 37, 39, 41, 43, 45, 47, 49, 51, 53, 55, 57, 59, 61, 63, 65, 67, or 84; or (ii) the full-length complement of (i); wherein (i) or (ii) is of sufficient length to inhibit expression of endogenous PAE OR PAE-LIKE protein activity in a transgenic plant; (b) regenerating a transgenic plant from the transformed plant cell of (a); and (c) selecting a transgenic plant that produces a transgenic seed having an increase in oil content of at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30%, on a dry-weight basis, as compared to a transgenic seed obtained from a non-transgenic plant.

Soybeans can be processed into a number of products. For example, "soy protein products" can include, and are not limited to, those items listed in Table 2. "Soy protein products".

TABLE 2

Soy Protein Products Derived from Soybean Seeds[a]

| Whole Soybean Products | Processed Soy Protein Products |
|---|---|
| Roasted Soybeans | Full Fat and Defatted Flours |
| Baked Soybeans | Soy Grits |
| Soy Sprouts | Soy Hypocotyls |
| Soy Milk | Soybean Meal |
| | Soy Milk |
| | Soy Protein Isolates |
| **Specialty Soy Foods/Ingredients** | |
| Soy Milk | Soy Protein Concentrates |
| Tofu | Textured Soy Proteins |
| Tempeh | Textured Flours and Concentrates |
| Miso | Textured Concentrates |
| Soy Sauce | Textured Isolates |
| Hydrolyzed Vegetable Protein | |
| Whipping Protein | |

[a]See Soy Protein Products: Characteristics, Nutritional Aspects and Utilization (1987). Soy Protein Council.

"Processing" refers to any physical and chemical methods used to obtain the products listed in Table A and includes, and is not limited to, heat conditioning, flaking and grinding, extrusion, solvent extraction, or aqueous soaking and extraction of whole or partial seeds. Furthermore, "processing" includes the methods used to concentrate and isolate soy protein from whole or partial seeds, as well as the various traditional Oriental methods in preparing fermented soy food products. Trading Standards and Specifications have been established for many of these products (see National Oilseed Processors Association Yearbook and Trading Rules 1991-1992).

"White" flakes refer to flaked, dehulled cotyledons that have been defatted and treated with controlled moist heat to have a PDI (AOCS: Ba10-65) of about 85 to 90. This term can also refer to a flour with a similar PDI that has been ground to pass through a No. 100 U.S. Standard Screen size.

"Grits" refer to defatted, dehulled cotyledons having a U.S. Standard screen size of between No. 10 and 80.

"Soy Protein Concentrates" refer to those products produced from dehulled, defatted soybeans by three basic processes: acid leaching (at about pH 4.5), extraction with alcohol (about 55-80%), and denaturing the protein with moist heat prior to extraction with water. Conditions typically used to prepare soy protein concentrates have been described by Pass ((1975) U.S. Pat. No. 3,897,574; Campbell et al., (1985) in New Protein Foods, ed. by Altschul and Wilcke, Academic Press, Vol. 5, Chapter 10, *Seed Storage Proteins*, pp 302-338).

"Extrusion" refers to processes whereby material (grits, flour or concentrate) is passed through a jacketed auger using high pressures and temperatures as a means of altering the texture of the material. "Texturing" and "structuring" refer to extrusion processes used to modify the physical characteristics of the material. The characteristics of these processes, including thermoplastic extrusion, have been described previously (Atkinson (1970) U.S. Pat. No. 3,488,770, Horan (1985) In *New Protein Foods*, ed. by Altschul and Wilcke, Academic Press, Vol. 1A, Chapter 8, pp 367-414). Moreover, conditions used during extrusion processing of complex foodstuff mixtures that include soy protein products have been described previously (Rokey (1983) *Feed Manufacturing Technology III*, 222-237; McCulloch, U.S. Pat. No. 4,454,804).

TABLE 3

Generalized Steps for Soybean Oil and Byproduct Production

| Process Step | Process | Impurities Removed and/or By-Products Obtained |
|---|---|---|
| #1 | soybean seed | |
| #2 | oil extraction | meal |
| #3 | Degumming | lecithin |
| #4 | alkali or physical refining | gums, free fatty acids, pigments |
| #5 | water washing | soap |
| #6 | Bleaching | color, soap, metal |
| #7 | (hydrogenation) | |
| #8 | (winterization) | stearine |
| #9 | Deodorization | free fatty acids, tocopherols, sterols, volatiles |
| #10 | oil products | |

More specifically, soybean seeds are cleaned, tempered, dehulled, and flaked, thereby increasing the efficiency of oil extraction. Oil extraction is usually accomplished by solvent (e.g., hexane) extraction but can also be achieved by a combination of physical pressure and/or solvent extraction. The resulting oil is called crude oil. The crude oil may be degummed by hydrating phospholipids and other polar and neutral lipid complexes that facilitate their separation from the nonhydrating, triglyceride fraction (soybean oil). The resulting lecithin gums may be further processed to make commercially important lecithin products used in a variety of food and industrial products as emulsification and release (i.e., antisticking) agents. Degummed oil may be further refined for the removal of impurities (primarily free fatty acids, pigments and residual gums). Refining is accomplished by the addition of a caustic agent that reacts with free fatty acid to form soap and hydrates phosphatides and proteins in the crude oil. Water is used to wash out traces of soap formed during refining. The soapstock byproduct may be used directly in animal feeds or acidulated to recover the free fatty acids. Color is removed through adsorption with a bleaching earth that removes most of the chlorophyll and carotenoid compounds. The refined oil can be hydrogenated, thereby resulting in fats with various melting properties and textures. Winterization (fractionation) may be used to remove stearine from the hydrogenated oil through crystallization under carefully controlled cooling conditions. Deodorization (principally via steam distillation under vacuum) is the last step and is designed to remove compounds which impart odor or flavor to the oil. Other valuable byproducts such as tocopherols and sterols may be removed during the deodorization process. Deodorized distillate containing these byproducts may be sold for production of natural vitamin E and other high-value pharmaceutical products. Refined, bleached, (hydrogenated, fractionated) and deodorized oils and fats may be packaged and sold directly or further processed into more specialized products. A more detailed reference to soybean seed processing, soybean oil production, and byproduct utilization can be found in Erickson, Practical Handbook of Soybean Processing and Utilization, The American Oil Chemists' Society and United Soybean Board (1995). Soybean oil is liquid at room temperature because it is relatively low in saturated fatty acids when compared with oils such as coconut, palm, palm kernel, and cocoa butter.

For example, plant and microbial oils containing polyunsaturated fatty acids (PUFAs) that have been refined and/or purified can be hydrogenated, thereby resulting in fats with various melting properties and textures. Many processed fats (including spreads, confectionary fats, hard butters, margarines, baking shortenings, etc.) require varying degrees of solidity at room temperature and can only be produced through alteration of the source oil's physical properties. This is most commonly achieved through catalytic hydrogenation.

Hydrogenation is a chemical reaction in which hydrogen is added to the unsaturated fatty acid double bonds with the aid of a catalyst such as nickel. For example, high oleic soybean oil contains unsaturated oleic, linoleic, and linolenic fatty acids, and each of these can be hydrogenated. Hydrogenation has two primary effects. First, the oxidative stability of the oil is increased as a result of the reduction of the unsaturated fatty acid content. Second, the physical properties of the oil are changed because the fatty acid modifications increase the melting point resulting in a semi-liquid or solid fat at room temperature.

There are many variables which affect the hydrogenation reaction, which in turn alter the composition of the final product. Operating conditions including pressure, temperature, catalyst type and concentration, agitation, and reactor design are among the more important parameters that can be controlled. Selective hydrogenation conditions can be used to hydrogenate the more unsaturated fatty acids in preference to the less unsaturated ones. Very light or brush hydrogenation is often employed to increase stability of liquid oils. Further hydrogenation converts a liquid oil to a physically solid fat. The degree of hydrogenation depends on the desired performance and melting characteristics designed for the particular end product. Liquid shortenings (used in the manufacture of baking products, solid fats and shortenings used for commercial frying and roasting operations) and base stocks for margarine manufacture are among the myriad of possible oil and fat products achieved through hydrogenation. A more detailed description of hydrogenation and hydrogenated products can be found in Patterson, H. B. W., Hydrogenation of Fats and Oils: Theory and Practice. The American Oil Chemists' Society (1994).

Hydrogenated oils have become somewhat controversial due to the presence of trans-fatty acid isomers that result from the hydrogenation process. Ingestion of large amounts of trans-isomers has been linked with detrimental health effects including increased ratios of low density to high density lipoproteins in the blood plasma and increased risk of coronary heart disease.

In a another embodiment, the invention concerns a transgenic seed produced by any of the above methods. Preferably, the seed is a soybean seed.

The present invention concerns a transgenic soybean seed having increased total fatty acid content of at least 1%, 2%, 3%, 4%, 5%, 6%, 7%, 8%, 9%, 11%, 12%, 13%, 14%, 15%, 16%, 17%, 18%, 19%, 20%, 21%, 22%, 23%, 24%, 25%, 26%, 27%, 28%, 29%, or 30% when compared to the total fatty acid content of a non-transgenic, null segregant soybean seed. It is understood that any measurable increase in the total fatty acid content of a transgenic versus a non-transgenic, null segregant would be useful. Such increases in the total fatty acid content would include, but are not limited to, at least 1%, 2%, 3%, 4%, 5%, 6%, 7%, 8%, 9%, 11%, 12%, 13%, 14%, 15%, 16%, 17%, 18%, 19%, 20%, 21%, 22%, 23%, 24%, 25%, 26%, 27%, 28%, 29%, or 30%.

Regulatory sequences may include, and are not limited to, promoters, translation leader sequences, introns, and polyadenylation recognition sequences.

"Tissue-specific" promoters direct RNA production preferentially in particular types of cells or tissues. Promoters which cause a gene to be expressed in most cell types at most times are commonly referred to as "constitutive promoters". New promoters of various types useful in plant cells are constantly being discovered; numerous examples may be found in the compilation by Okamuro and Goldberg (*Biochemistry of Plants* 15:1-82 (1989)). It is further recognized that since in most cases the exact boundaries of regulatory sequences have not been completely defined, DNA fragments of some variation may have identical promoter activity.

A number of promoters can be used to practice the present invention. The promoters can be selected based on the desired outcome. The nucleic acids can be combined with constitutive, tissue-specific (preferred), inducible, or other promoters for expression in the host organism. Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al., *Nature* 313:810-812 (1985)); rice actin (McElroy et al., *Plant Cell* 2:163-171 (1990)); ubiquitin (Christensen et al., *Plant Mol. Biol.* 12:619-632 (1989) and Christensen et al., *Plant Mol. Biol.* 18:675-689 (1992)); pEMU (Last et al., *Theor. Appl. Genet.* 81:581-588 (1991)); MAS (Velten et al., *EMBO J.* 3:2723-2730 (1984)); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the invention, it may be desirable to use a tissue-specific or developmentally regulated promoter. A tissue-specific or developmentally regulated promoter is a DNA sequence which regulates the expression of a DNA sequence selectively in particular cells/tissues of a plant. Any identifiable promoter may be used in the methods of the present invention which causes the desired temporal and spatial expression.

Promoters which are seed or embryo specific and may be useful in the invention include patatin (potato tubers) (Rocha-Sosa, M., et al. (1989) EMBO J. 8:23-29), convicilin, vicilin, and legumin (pea cotyledons) (Rerie, W. G., et al. (1991) Mol. Gen. Genet 259:149-157; Newbigin, E. J., et al. (1990) Planta 180:461-470; Higgins, T. J. V., et al. (1988) Plant. Mol. Biol. 11:683-695), zein (maize endosperm) (Schemthaner, J. P., et al. (1988) EMBO J. 7:1249-1255), phaseolin (bean cotyledon) (Segupta-Gopalan, C., et al. (1985) Proc. Natl. Acad. Sci. U.S.A. 82:3320-3324), phytohemagglutinin (bean cotyledon) (Voelker, T. et al. (1987) EMBO J. 6:3571-3577), B-conglycinin and glycinin (soybean cotyledon) (Chen, Z-L, et al. (1988) EMBO J. 7:297-302), glutelin (rice endosperm), hordein (barley endosperm) (Marris, C., et al. (1988) Plant Mol. Biol. 10:359-366), glutenin and gliadin (wheat endosperm) (Colot, V., et al. (1987) EMBO J. 6:3559-3564), and sporamin (sweet potato tuberous root) (Hattori, T., et al. (1990) Plant Mol. Biol. 14:595-604). Promoters of seed-specific genes operably linked to heterologous coding regions in chimeric gene constructions maintain their temporal and spatial expression pattern in transgenic plants. Such examples include *Arabidopsis thaliana* 2S seed storage protein gene promoter to express enkephalin peptides in *Arabidopsis* and *Brassica napus* seeds (Vanderkerckhove et al., Bio/Technology 7:L929-932 (1989)). bean lectin and bean beta-phaseolin promoters to express luciferase (Riggs et al., Plant Sci. 63:47-57 (1989)), and wheat glutenin promoters to express chloramphenicol acetyl transferase (Colot et al., EMBO J 6:3559-3564 (1987)).

A plethora of promoters is described in WO 00/18963, published on Apr. 6, 2000, the disclosure of which is hereby incorporated by reference. Examples of seed-specific promoters include, and are not limited to, the promoter for soybean Kunitz trypsin inhibitor (Kti3, Jofuku and Goldberg, *Plant Cell* 1:1079-1093 (1989)) β-conglycinin (Chen et al., *Dev. Genet.* 10:112-122 (1989)), the napin promoter, and the phaseolin promoter.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention includes compositions, and methods for making, heterologous promoters and/or enhancers operably linked to a native, endogenous (i.e., non-heterologous) form of a polynucleotide of the present invention.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg, *Mol. Cell Biol.* 8:4395-4405 (1988); Callis et al., *Genes Dev.* 1:1183-1200 (1987)). Such intron enhancement of gene expression is typically greatest when placed near the 5' end of the transcription unit. Use of maize introns Adh1-S intron 1,2, and 6, the Bronze-1 intron are known in the art. See generally, *The Maize Handbook*, Chapter 116, Freeling and Walbot, Eds., Springer, New York (1994). A vector comprising the sequences from a polynucleotide of the present invention will typically comprise a marker gene which confers a selectable phenotype on plant cells. Typical vectors useful for expression of genes in higher plants are well known in the art and include vectors derived from the tumor-inducing (Ti) plasmid of *Agrobacterium tumefaciens* described by Rogers et al., *Meth. in Enzymol.* 153:253-277 (1987).

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

Preferred recombinant DNA constructs include the following combinations: a) a nucleic acid fragment corresponding to a promoter operably linked to at least one nucleic acid fragment encoding a selectable marker, followed by a nucleic acid fragment corresponding to a terminator, b) a nucleic acid fragment corresponding to a promoter operably linked to a nucleic acid fragment capable of producing a stem-loop structure, and followed by a nucleic acid fragment corresponding to a terminator, and c) any combination of a) and b) above. Preferably, in the stem-loop structure at least one nucleic acid fragment that is capable of suppressing expression of a native gene comprises the "loop" and is surrounded by nucleic acid fragments capable of producing a stem.

Preferred methods for transforming dicots and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al. (1996) *Plant Cell Rep.* 15:653-657, McKently et al. (1995) *Plant Cell Rep.* 14:699-703); *papaya* (Ling, K. et al. (1991) Bio/technology 9:752-758); and pea (Grant et al. (1995) *Plant Cell Rep.* 15:254-258). For a review of other commonly used methods of plant transformation see Newell, C. A. (2000) *Mol. Biotechnol.* 16:53-65. One of these methods of transformation uses *Agrobacterium rhizogenes* (Tepfler, M. and Casse-Delbart, F. (1987) *Microbiol. Sci.* 4:24-28). Transformation of soybeans using direct delivery of DNA has been published using PEG fusion (PCT publication WO 92/17598), electroporation (Chowrira, G. M. et al. (1995) *Mol. Biotechnol.* 3:17-23; Christou, P. et al. (1987) *Proc. Natl. Acad. Sci. U.S.A.* 84:3962-3966), microinjection, or particle bombardment (McCabe, D. E. et. Al. (1988) *BiolTechnology* 6:923; Christou et al. (1988) *Plant Physiol.* 87:671-674).

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants are well known in the art (Weissbach and Weissbach, (1988) In.: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. The regenerated plants may be self-pollinated. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide(s) is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook et al. (1989) Molecular Cloning: A Laboratory Manual, Cold Spring Harbor Press; Maliga et al. (1995) Methods in Plant Molecular Biology, Cold Spring Harbor Press; Birren et al. (1998) Genome Analysis: Detecting Genes, 1, Cold Spring Harbor, N.Y.; Birren et al. (1998) Genome Analysis: Analyzing DNA, 2, Cold Spring Harbor, N.Y.; Plant Molecular Biology: A Laboratory Manual, eds. Clark, Springer, New York (1997)).

Assays to detect proteins may be performed by SDS-polyacrylamide gel electrophoresis or immunological assays. Assays to detect levels of substrates or products of enzymes may be performed using gas chromatography or liquid chromatography for separation and UV or visible spectrometry or mass spectrometry for detection, or the like. Determining the levels of mRNA of the enzyme of interest may be accomplished using northern-blotting or RT-PCR techniques. Once plants have been regenerated, and progeny plants homozygous for the transgene have been obtained, plants will have a stable phenotype that will be observed in similar seeds in later generations.

In another aspect, this invention includes a polynucleotide of this invention or a functionally equivalent subfragment thereof useful in antisense inhibition or cosuppression of expression of nucleic acid sequences encoding proteins having cytosolic pyrophosphatase activity, most preferably in antisense inhibition or cosuppression of an endogenous PAE OR PAE-LIKE protein gene.

Protocols for antisense inhibition or co-suppression are well known to those skilled in the art.

The sequences of the polynucleotide fragments used for suppression do not have to be 100% identical to the sequences of the polynucleotide fragment found in the gene to be suppressed. For example, suppression of all the subunits of the soybean seed storage protein I-conglycinin has been accomplished using a polynucleotide derived from a portion of the gene encoding the a subunit (U.S. Pat. No. 6,362,399). β-conglycinin is a heterogeneous glycoprotein composed of varying combinations of three highly negatively charged subunits identified as α,α' and β. The polynucleotide sequences encoding the α and α' subunits are 85% identical to each other while the polynucleotide sequences encoding the β subunit are 75 to 80% identical to the α and α' subunits, respectively. Thus, polynucleotides that are at least 75% identical to a region of the polynucleotide that is target for suppression have been shown to be effective in suppressing the desired target. The polynucleotide may be at least 80% identical, at least 90% identical, at least 95% identical, or about 100% identical to the desired target sequence.

The isolated nucleic acids and proteins and any embodiments of the present invention can be used over a broad range of plant types, particularly dicots such as the species of the genus *Glycine.*

It is believed that the nucleic acids and proteins and any embodiments of the present invention can be with monocots as well including, but not limited to, Graminiae including *Sorghum bicolor* and *Zea mays.*

The isolated nucleic acid and proteins of the present invention can also be used in species from the following dicot genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Cichorium, Helianthus, Lactuca, Antirrhinum, Pelargonium, Ranunculus, Senecio, Salpiglossis, Cucumis, Browallia, Glycine, Pisum, Phaseolus*, and from the following monocot genera: *Bromus, Asparagus, Hemerocallis, Panicum, Pennisetum, Lolium, Oryza, Avena, Hordeum, Secale, Triticum, Bambusa, Dendrocalamus*, and *Melocanna.*

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Creation of an *Arabidopsis* Population with Activation-Tagged Genes

An 18.49-kb T-DNA based binary construct was created, pHSbarENDs2 (SEQ ID NO:1), that contains four multimerized enhancer elements derived from the Cauliflower Mosaic Virus 35S promoter (corresponding to sequences −341 to −64, as defined by Odell et al., *Nature* 313:810-812 (1985)). The construct also contains vector sequences (pUC9) and a poly-linker (SEQ ID NO:2) to allow plasmid rescue, transposon sequences (Ds) to remobilize the T-DNA, and the bar gene to allow for glufosinate selection of transgenic plants. In principle, only the 10.8-kb segment from the right border (RB) to left border (LB) inclusive will be transferred into the host plant genome. Since the enhancer elements are located near the RB, they can induce cis-activation of genomic loci following T-DNA integration.

*Arabidopsis* activation-tagged populations were created by whole plant *Agrobacterium* transformation. The pHSbarENDs2 (SEQ ID NO:1) construct was transformed into *Agrobacterium tumefaciens* strain C58, grown in lysogeny broth medium at 25° C. to OD600~1.0. Cells were then pelleted by centrifugation and resuspended in an equal volume of 5% sucrose/0.05% Silwet L-77 (OSI Specialties, Inc). At early bolting, soil grown *Arabidopsis thaliana* ecotype Col-0 were top watered with the *Agrobacterium* suspension. A week later, the same plants were top watered again with the same *Agrobacterium* strain in sucrose/Silwet. The plants were then allowed to set seed as normal. The resulting T1 seed were sown on soil, and transgenic seedlings were selected by spraying with glufosinate (FINALE®; AgrEvo; Bayer Environmental Science). A total of 100,000 glufosinate resistant T1 seedlings were selected. T2 seed from each line was kept separate. Small aliquots of T2 seed from independently generated activation-tagged lines were pooled. The pooled seed were planted in soil and plants were grown to maturity producing T3 seed pools each comprised of seed derived from 96 activation-tagged lines.

Example 2

Identification and Characterization of Mutant Line lo22730

A method for screening *Arabidopsis* seed density was developed based on Focks and Benning (1998) with significant modifications. *Arabidopsis* seeds can be separated according to their density. Density layers were prepared by a mixture of 1,6 dibromohexane (d=1.6), 1-bromohexane (d=1.17) and mineral oil (d=0.84) at different ratios. From the bottom to the top of the tube, 6 layers of organic solvents each comprised of 2 mL were added sequentially. The ratios of 1,6 dibromohexane:1-bromohexane:mineral oil for each layer were 1:1:0, 1:2:0, 0:1:0, 0:5:1, 0:3:1, 0:0:1. About 600 mg of T3 seed of a given pool of 96 activation-tagged lines corresponding to about 30,000 seeds were loaded on to the surface layer of a 15 ml glass tube containing said step gradient. After centrifugation for 5 min at 2000×g, seeds were separated according to their density. The seeds in the lower two layers of the step gradient and from the bottom of the tube were collected. Organic solvents were removed by sequential washing with 100% and 80% ethanol and seeds were sterilized using a solution of 5% hypochloride (NaOCl) in water. Seed were rinsed in sterile water and plated on MS-1 media comprised of 0.5×MS salts, 1% (W/V) sucrose, 0.05 MES/KOH (pH 5.8), 200 μg/mL, 10 g/L agar and 15 mg $L^{-1}$ glufosinate ammonium (Basta; Sigma Aldrich, USA). A total of 520 T3 pools each derived from 96 T2 activation-tagged lines were screened in this manner. Seed pool 475 when subjected to density gradient centrifugation as described above produced about 25 seed with increased density. These seed were sterilized and plated on selective media containing Basta. Basta-resistant seedlings were transferred to soil and plants were grown in a controlled environment (22° C., 16 h light/8 h dark, 100-200 μE $m^{-2}s^{-1}$). to maturity for about 8-10 weeks alongside four untransformed wild type plants of the Columbia ecotype. Oil content of T4 seed and control seed was measured by NMR as follows.

NMR Based Analysis of Seed Oil Content:

Seed oil content was determined using a Maran Ultra NMR analyzer (Resonance Instruments Ltd, Whitney, Oxfordshire, UK). Samples (e.g., batches of *Arabidopsis* seed ranging in weight between 5 and 200 mg) were placed into pre-weighed 2 mL polypropylene tubes (Corning Inc, Corning N.Y., USA; Part no. 430917) previously labeled with unique bar code identifiers. Samples were then placed into 96 place carriers and processed through the following series of steps by an ADEPT COBRA 600™ SCARA robotic system:

1. pick up tube (the robotic arm was fitted with a vacuum pickup devise);
2. read bar code;
3. expose tube to antistatic device (ensured that *Arabidopsis* seed were not adhering to the tube walls);
4. weigh tube (containing the sample), to 0.0001 g precision;
5. take NMR reading; measured as the intensity of the proton spin echo 1 msec after a 22.95 MHz signal had been applied to the sample (data was collected for 32 NMR scans per sample);
6. return tube to rack; and
7. repeat process with next tube.

Bar codes, tubes weights and NMR readings were recorded by a computer connected to the system. Sample weight was determined by subtracting the polypropylene tube weight from the weight of the tube containing the sample.

Seed oil content of soybeans seed or soybean somatic embryos was calculated as follows:

$$\%\text{ oil}(\%\text{ wt basis}) = \frac{(NMR\text{ signal}/\text{sample wt}(g)) - 70.58)}{351.45}$$

Calibration parameters were determined by precisely weighing samples of soy oil (ranging from 0.0050 to 0.0700 g at approximately 0.0050 g intervals; weighed to a precision of 0.0001 g) into Corning tubes (see above) and subjecting them to NMR analysis. A calibration curve of oil content (% seed wt basis; assuming a standard seed weight of 0.1500 g) to NMR value was established.

The relationship between seed oil contents measured by NMR and absolute oil contents measured by classical analytical chemistry methods was determined as follows. Fifty soybean seed, chosen to have a range of oil contents, were dried at 40° C. in a forced air oven for 48 h. Individual seeds were subjected to NMR analysis, as described above, and were then ground to a fine powder in a GenoGrinder (SPEX Centriprep (Metuchen, N.J., U.S.A.); 1500 oscillations per minute, for 1 minute). Aliquots of between 70 and 100 mg were weighed (to 0.0001 g precision) into 13×100 mm glass tubes fitted with Teflon® lined screw caps; the remainder of the powder from each bean was used to determine moisture content, by weight difference after 18 h in a forced air oven at 105° C. Heptane (3 mL) was added to the powders in the tubes and after vortex mixing samples were extracted, on an end-over-end agitator, for 1 h at room temperature. The extracts were centrifuged, 1500×g for 10 min, the supernatant decanted into a clean tube and the pellets were extracted two more times (1 h each) with 1 mL heptane. The supernatants from the three extractions were combined and 50 μL internal standard (triheptadecanoic acid; 10 mg/mL toluene) was added prior to evaporation to dryness at room temperature under a stream of nitrogen gas; standards containing 0, 0.0050, 0.0100, 0.0150, 0.0200 and 0.0300 g soybean oil, in 5 mL heptane, were prepared in the same manner. Fats were converted to fatty acid methyl esters (FAMEs) by adding 1 mL 5% sulfuric acid (v:v. in anhydrous methanol) to the dried pellets and heating them at 80° C. for 30 min, with occasional vortex mixing. The samples were allowed to cool to room temperature and 1 mL 25% aqueous sodium chloride was added followed by 0.8 mL heptane. After vortex mixing the phases were allowed to separate and the upper organic phase was transferred to a sample vial and subjected to GC analysis.

Plotting NMR determined oil contents versus GC determined oil contents resulted in a linear relationship between 9.66 and 26.27% oil (GC values; % seed wt basis) with a slope of 1.0225 and an $R^2$ of 0.9744; based on a seed moisture content that averaged 2.6+/−0.8%.

Seed oil content (on a % seed weight basis) of *Arabidopsis* seed was calculated as follows:

mg oil=(NMR signal−2.1112)/37.514;

% oil=[(mg oil)/1000]/[g of seed sample weight]×100.

Prior to establishing this formula, *Arabidopsis* seed oil was extracted as follows. Approximately 5 g of mature *Arabidopsis* seed (cv Columbia) were ground to a fine powder using a mortar and pestle. The powder was placed into a 33×94 mm paper thimble (Ahlstrom #7100-3394; Ahlstrom, Mount Holly Springs, Pa., USA) and the oil extracted during approximately 40 extraction cycles with petroleum ether (BP 39.9-51.7° C.) in a Soxhlet apparatus. The extract was allowed to cool and the crude oil was recovered by removing the solvent under vacuum in a rotary evaporator. Calibration parameters were determined by precisely weighing 11 standard samples of partially purified *Arabidopsis* oil (samples contained 3.6, 6.3, 7.9, 9.6, 12.8, 16.3, 20.3, 28.2, 32.1, 39.9 and 60 mg of partially purified *Arabidopsis* oil) weighed to a precision of 0.0001 g) into 2 mL polypropylene tubes (Corning Inc, Corning N.Y., USA; Part no. 430917) and subjecting them to NMR analysis. A calibration curve of oil content (% seed weight basis) to NMR value was established.

Table 4 shows that the seed oil content of T4 activation-tagged line with Bar code ID K22730 is only 87% of that of the average of four WT control plants grown in the same flat.

TABLE 4

Oil Content of T4 activation-tagged lines derived from T3 pool 500

| BARCODE | % Oil | T3 pool ID # | oil content % of WT |
|---|---|---|---|
| K22712 | 26.8 | 475 | 93.2 |
| K22713 | 30.2 | 475 | 105.0 |
| K22714 | 28.2 | 475 | 97.9 |
| K22715 | 28.9 | 475 | 100.5 |
| K22716 | 26.5 | 475 | 92.1 |
| K22717 | 28.2 | 475 | 98.1 |
| K22718 | 27.5 | 475 | 95.7 |
| K22720 | 34.9 | 475 | 121.5 |
| K22721 | 29.7 | 475 | 103.3 |
| K22722 | 30.7 | 475 | 106.7 |
| K22723 | 29.8 | 475 | 103.6 |
| K22724 | 33.3 | 475 | 115.8 |
| K22725 | 29.4 | 475 | 102.1 |
| K22726 | 34.1 | 475 | 118.5 |
| K22728 | 30.4 | 475 | 105.8 |
| K22729 | 28.0 | 475 | 97.3 |
| K22730 | 25.0 | 475 | 86.9 |
| K22731 | 30.7 | 475 | 106.6 |
| K22732 | 29.6 | 475 | 102.8 |
| K22733 | 28.4 | 475 | 98.8 |
| K22734 | 30.6 | 475 | 106.4 |
| K22735 | 29.0 | 475 | 100.7 |
| K22736 | 29.9 | 475 | 103.9 |
| K22737 | 30.5 | 475 | 106.1 |
| K22738 | 29.0 | 475 | 100.8 |
| K22739 | 29.3 | wt | |
| K22740 | 27.9 | wt | |
| K22741 | 28.4 | wt | |
| K22742 | 29.5 | wt | |

K22730 was renamed lo22730. T4 seed were plated on selective media and three glufosinate-resistant seedlings were planted in the same flat as four untransformed WT plants.

TABLE 5

Oil Content of T5 activation-tagged line lo22730

| BARCODE | T5 activation-tagged line ID | % Oil | Average % oil | oil content % of WT | Average oil content % of WT |
|---|---|---|---|---|---|
| K32033 | lo22730 | 34.6 | | 105.2 | |
| K32032 | lo22730 | 26.8 | | 81.4 | |
| K32031 | lo22730 | 25.6 | 29.0 | 77.8 | 88.1 |
| K32046 | wt | 34.6 | | | |
| K32045 | wt | 33.7 | | | |
| K32044 | wt | 33.2 | | | |
| K32048 | wt | 32.3 | | | |
| K32047 | wt | 30.7 | 32.9 | | |

Table 5 shows that the seed oil content of T5 activation-tagged line lo22730 is between 78 and 105% of that of WT control plants grown in the same flat. The average oil content of all T5 lines of lo22730 was 88.1% of the WT control plants. Twenty-four Basta-resistant T5 seedlings of lo22730 were planted in the same flat alongside 12 untransformed WT control plants of the Columbia ecotype. Plants were grown to maturity and seed was bulk-harvested from all 24 lo22730 and 12 WT plants. Oil content of lo22730 and WT seed was measured by NMR (Table 6).

TABLE 6

| Oil Content of T6 activation-tagged line lo22730 | | | |
|---|---|---|---|
| Barcode of WT | % Oil | Seed ID | oil content % |
| K35862 | 42.6 | lo22730 | 95.5 |
| K35883 | 44.6 | WT | |

T6 seed of lo22730 and WT seed produced under identical conditions were subjected to compositional analysis as described below. Seed weight was measured by determining the weight of 100 seed. This analysis was performed in triplicate.

Tissue Preparation:

*Arabidopsis* seed (approximately 0.5 g in a ½×2" polycarbonate vial) was ground to a homogeneous paste in a GENOGRINDER® (3×30 sec at 1400 strokes per minute, with a 15 sec interval between each round of agitation). After the second round of agitation the vials were removed and the *Arabidopsis* paste was scraped from the walls with a spatula prior to the last burst of agitation.

Determination of Protein Content:

Protein contents were estimated by combustion analysis on a Thermo FINNIGAN™ Flash 1112EA combustion analyzer running in the NCS mode (vanadium pentoxide was omitted) according to instructions of the manufacturer. Triplicate samples of the ground pastes, 4-8 mg, weighed to an accuracy of 0.001 mg on a METTLER-TOLEDO® MX5 micro balance, were used for analysis. Protein contents were calculated by multiplying % N, determined by the analyzer, by 6.25. Final protein contents were expressed on a % tissue weight basis.

Determination of Non-Structural Carbohydrate Content:

Sub-samples of the ground paste were weighed (to an accuracy of 0.1 mg) into 13×100 mm glass tubes; the tubes had TEFLON® lined screw-cap closures. Three replicates were prepared for each sample tested.

Lipid extraction was performed by adding 2 ml aliquots of heptane to each tube. The tubes were vortex mixed and placed into an ultrasonic bath (VWR Scientific Model 750D) filled with water heated to 60° C. The samples were sonicated at full-power (~360 W) for 15 min and were then centrifuged (5 min×1700 g). The supernatants were transferred to clean 13×100 mm glass tubes and the pellets were extracted 2 more times with heptane (2 ml, second extraction; 1 ml third extraction) with the supernatants from each extraction being pooled. After lipid extraction 1 ml acetone was added to the pellets and after vortex mixing, to fully disperse the material, they were taken to dryness in a Speedvac.

Non-Structural Carbohydrate Extraction and Analysis:

Two ml of 80% ethanol was added to the dried pellets from above. The samples were thoroughly vortex mixed until the plant material was fully dispersed in the solvent prior to sonication at 60° C. for 15 min. After centrifugation, 5 min×1700 g, the supernatants were decanted into clean 13×100 mm glass tubes. Two more extractions with 80% ethanol were performed and the supernatants from each were pooled. The extracted pellets were suspended in acetone and dried (as above). An internal standard β-phenyl glucopyranoside (100 μl of a 0.5000+/−0.0010 g/100 ml stock) was added to each extract prior to drying in a Speedvac. The extracts were maintained in a desiccator until further analysis.

The acetone dried powders from above were suspended in 0.9 ml MOPS (3-N[Morpholino]propane-sulfonic acid; 50 mM, 5 mM $CaCl_2$, pH 7.0) buffer containing 100 U of heat-stable α-amylase (from *Bacillus licheniformis*; Sigma A-4551). Samples were placed in a heat block (90° C.) for 75 min and were vortex mixed every 15 min. Samples were then allowed to cool to room temperature and 0.6 ml acetate buffer (285 mM, pH 4.5) containing 5 U amyloglucosidase (Roche 110 202 367 001) was added to each. Samples were incubated for 15-18 h at 55° C. in a water bath fitted with a reciprocating shaker; standards of soluble potato starch (Sigma S-2630) were included to ensure that starch digestion went to completion.

Post-digestion the released carbohydrates were extracted prior to analysis. Absolute ethanol (6 ml) was added to each tube and after vortex mixing the samples were sonicated for 15 min at 60° C. Samples were centrifuged (5 min×1700 g) and the supernatants were decanted into clean 13×100 mm glass tubes. The pellets were extracted 2 more times with 3 ml of 80% ethanol and the resulting supernatants were pooled. Internal standard (100 μl β-phenyl glucopyranoside, as above) was added to each sample prior to drying in a Speedvac.

Sample Preparation and Analysis:

The dried samples from the soluble and starch extractions described above were solubilized in anhydrous pyridine (Sigma-Aldrich P57506) containing 30 mg/ml of hydroxylamine HCl (Sigma-Aldrich 159417). Samples were placed on an orbital shaker (300 rpm) overnight and were then heated for 1 hr (75° C.) with vigorous vortex mixing applied every 15 min. After cooling to room temperature, 1 ml hexamethyldisilazane (Sigma-Aldrich H-4875) and 100 μl trifluoroacetic acid (Sigma-Aldrich T-6508) were added. The samples were vortex mixed and the precipitates were allowed to settle prior to transferring the supernatants to GC sample vials.

Samples were analyzed on an Agilent 6890 gas chromatograph fitted with a DB-17MS capillary column (15 m×0.32 mm×0.25 um film). Inlet and detector temperatures were both 275° C. After injection (2 μl, 20:1 split) the initial column temperature (150° C.) was increased to 180° C. at a rate of 3° C./min and then at 25° C.,/min to a final temperature of 320° C. The final temperature was maintained for 10 min. The carrier gas was $H_2$ at a linear velocity of 51 cm/sec. Detection was by flame ionization. Data analysis was performed using Agilent ChemStation software. Each sugar was quantified relative to the internal standard and detector responses were applied for each individual carbohydrate (calculated from standards run with each set of samples). Final carbohydrate concentrations were expressed on a tissue weight basis.

Carbohydrates were identified by retention time matching with authentic samples of each sugar run in the same chromatographic set and by GC-MS with spectral matching to the NIST Mass Spectral Library Version 2a, build Jul. 1, 2002.

TABLE 7

| Composition Analysis of lo22730 and WT Control Seed | | | | | |
|---|---|---|---|---|---|
| Genotype | Bar code ID | Oil (%, NMR) | Protein % | Seed Weight (μg) | fructose (μg $mg^{-1}$ seed) |
| lo22730 | K35862 | 42.6 | 18.01 | 23 | 0.38 |
| WT | K35863 | 44.6 | 18.07 | 20 | 0.43 |
| | Δ TG/WT % | −4.5 | −0.43 | +15 | −11.9 |

TABLE 7-continued

| Composition Analysis of lo22730 and WT Control Seed | | | | | |
|---|---|---|---|---|---|
| Genotype | Bar code ID | glucose (μg $mg^{-1}$ seed) | sucrose (μg $mg^{-1}$ seed) | raffinose (μg $mg^{-1}$ seed) | stachyose (μg $mg^{-1}$ seed) |
| lo22730 | K35882 | 9.02 | 26.46 | 0.64 | 3.98 |
| WT | K35883 | 9.59 | 32.46 | 0.72 | 3.58 |
| | Δ TG/WT % | −5.95 | −18.46 | −12.24 | +11.32 |

Table 7 shows that the oil decrease in seed oil content of lo22730 is associated with an increase in seed weight. The soluble carbohydrate profile of lo22730 differs from that of WT seed. The former shows decrease in soluble carbohydrates including fructose, glucose, sucrose and raffinose.

In summary the lo22730 contains a genetic locus that confers glufosinate herbicide resistance. Presence of this transgene is associated with a low oil trait (reduction in oil content of 5% compared to WT) that is accompanied by increased seed size, unchanged protein content and decreased levels of soluble carbohydrate in mature dry seed.

Example 3

Identification of Activation-Tagged Genes

Genes flanking the T-DNA insert in the lo22730 lines were identified using one, or both, of the following two standard procedures: (1) thermal asymmetric interlaced (TAIL) PCR (Liu et al., *Plant J.* 8:457-63 (1995)); and (2) SAIFF PCR (Siebert et al., *Nucleic Acids Res.* 23:1087-1088 (1995)). In lines with complex multimerized T-DNA inserts, TAIL PCR and SAIFF PCR may both prove insufficient to identify candidate genes. In these cases, other procedures, including inverse PCR, plasmid rescue and/or genomic library construction, can be employed.

A successful result is one where a single TAIL or SAIFF PCR fragment contains a T-DNA border sequence and *Arabidopsis* genomic sequence. Once a tag of genomic sequence flanking a T-DNA insert is obtained, candidate genes are identified by alignment to publicly available *Arabidopsis* genome sequence. Specifically, the annotated gene nearest the 35S enhancer elements/T-DNA RB are candidates for genes that are activated.

To verify that an identified gene is truly near a T-DNA and to rule out the possibility that the TAIL/SAIFF fragment is a chimeric cloning artifact, a diagnostic PCR on genomic DNA is done with one oligo in the T-DNA and one oligo specific for the candidate gene. Genomic DNA samples that give a PCR product are interpreted as representing a T-DNA insertion. This analysis also verifies a situation in which more than one insertion event occurs in the same line, e.g., if multiple differing genomic fragments are identified in TAIL and/or SAIFF PCR analyses.

Example 4

Identification of Activation-Tagged Genes in lo22730 Construction of pKR1478 for Seed Specific Overexpression of Genes in *Arabidopsis*

Plasmid pKR85 (SEQ ID NO:3; described in US Patent Application Publication US 2007/0118929 published on May 24, 2007) was digested with HindIII and the fragment containing the hygromycin selectable marker was re-ligated together to produce pKR278 (SEQ ID NO:4).

Plasmid pKR407 (SEQ ID NO:5; described in PCT Int. Appl. WO 2008/124048 published on Oct. 16, 2008) was digested with BamHI/HindIII and the fragment containing the Gy1 promoter/NotI/LegA2 terminator cassette was effectively cloned into the BamHI/HindIII fragment of pKR278 (SEQ ID NO:4) to produce pKR1468 (SEQ ID NO:6).

Plasmid pKR1468 (SEQ ID NO:6) was digested with NotI and the resulting DNA ends were filled using Klenow. After filling to form blunt ends, the DNA fragments were treated with calf intestinal alkaline phosphatase and separated using agarose gel electrophoresis. The purified fragment was ligated with cassette frmA containing a chloramphenicol resistance and ccdB genes flanked by attR1 and attR2 sites, using the Gateway® Vector Conversion System (Cat. No. 11823-029, Invitrogen Corporation) following the manufacturer's protocol to pKR1475 (SEQ ID NO:7).

Plasmid pKR1475 (SEQ ID NO:7) was digested with AscI and the fragment containing the Gy1 promoter/NotI/LegA2 terminator Gateway® L/R cloning cassette was cloned into the AscI fragment of binary vector pKR92 (SEQ ID NO:8; described in US Patent Application Publication US 2007/0118929 published on May 24, 2007) to produce pKR1478 (SEQ ID NO:9).

In this way, genes flanked by attL1 and attL2 sites could be cloned into pKR1478 (SEQ ID NO:9) using Gateway® technology (Invitrogen Corporation) and the gene could be expressed in *Arabidopsis* from the strong, seed-specific soybean Gy1 promoter in soy.

The activation tagged-line (lo22730) showing reduced oil content was further analyzed. DNA from the line was extracted, and genes flanking the T-DNA insert in the mutant line were identified using ligation-mediated PCR (Siebert et al., *Nucleic Acids Res.* 23:1087-1088 (1995)). A single amplified fragment was identified that contained a T-DNA border sequence and *Arabidopsis* genomic sequence. The sequence of this PCR product which contains part of the left border of the inserted T-DNA is set forth as SEQ ID NO:10. Once a tag of genomic sequence flanking a T-DNA insert was obtained, a candidate gene was identified by alignment of SEQ ID NO:10 to the completed *Arabidopsis* genome (NCBI). Specifically, the SAIFF PCR product generated with PCR primers corresponding to the left border sequence of the T-DNA present in pHSbarENDs2 aligns with sequence of the *Arabidopsis* genome that is 1406 bp upstream of the inferred start codon of At2g46930.

Validation of Candidate *Arabidopsis* Gene (At2g46930) Via Transformation into *Arabidopsis*

The gene At2g46930, specifically its inferred start codon is 1.4 kb upstream of the SAIFF sequence corresponding to sequence adjacent to the left T-DNA border in lo22730. This gene is annotated as encoding a member of the family of proteins with similarity to pectin acetyl esterases (PAE).

Primers PAE ORF FWD (SEQ ID NO:11) and PAE ORF REV (SEQ ID NO:12) were used to amplify the At2g46930 ORF from genomic DNA of *Arabidopsis* plants of the Columbia ecotype. The PCR product was cloned into pENTR (Invitrogen, USA) to give pENTR-PAE (SEQ ID NO:13). The At2g46930 ORF was inserted in the sense orientation downstream of the GY1 promoter in binary plant transformation vector pKR1478 using Gateway LR recombinase (Invitrogen, USA) using manufacturer instructions. The sequence of the resulting plasmid pKR1478-PAE is set forth as SEQ ID NO:14.

pKR1478-PAE (SEQ ID NO:14) was introduced into *Agrobacterium tumefaciens* NTL4 (Luo et al, *Molecular Plant-Microbe Interactions* (2001) 14(1):98-103) by electroporation. Briefly, 1 μg plasmid DNA was mixed with 100 μL of electro-competent cells on ice. The cell suspension was transferred to a 100 μL electroporation cuvette (1 mm gap width) and electroporated using a BIORAD electroporator set to 1 kV, 4005 and 25 μF. Cells were transferred to 1 mL LB medium and incubated for 2 h at 30° C. Cells were plated onto LB medium containing 50 μg/mL kanamycin. Plates were incubated at 30° C. for 60 h. Recombinant *Agrobacterium* cultures (500 mL LB, 50 μg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 cm² pot in METRO-MIX® 360 soil mixture for 4 weeks (22° C., 16 h light/8 h dark, 100 μE m$^{-2}$s$^{-1}$). Plants were repeatedly dipped into the *Agrobacterium* suspension harboring the binary vector pKR1478-PAE and kept in a dark, high humidity environment for 24 h. Post dipping, plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20×20 cm) containing 150 mL of sterile plant growth medium comprised of 0.5×MS salts, 0.53% (W/V) sorbitol, 0.05 MES/KOH (pH 5.8), 200 μg/mL TIMENTIN®, and 50 μg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. T1 Plants are grown to maturity alongside wt control plants and T2 seeds were harvested. A total of six wt plant were grown alongside the T1 plants and two bulk samples were generated by combining seed from three wt plants. Oil content was measured by NMR and is shown in Table 8

TABLE 8

Seed oil content of T1 plants generated with binary vector pKR1478-PAE for seed-specific over-expression of At2g46930

| Construct | BARCODE | % oil | oil content % of WT | avg. oil content % of WT |
|---|---|---|---|---|
| pKR1478-PAE | K18223 | 42.1 | 101.7 | |
| pKR1478-PAE | K18231 | 41.4 | 100.0 | |
| pKR1478-PAE | K18230 | 40.7 | 98.4 | |
| pKR1478-PAE | K18226 | 40.6 | 98.3 | |
| pKR1478-PAE | K18224 | 40.6 | 98.2 | |
| pKR1478-PAE | K18222 | 40.6 | 98.1 | |
| pKR1478-PAE | K18225 | 40.5 | 97.9 | |
| pKR1478-PAE | K18229 | 40.5 | 97.9 | |
| pKR1478-PAE | K17889 | 40.3 | 97.5 | |
| pKR1478-PAE | K17890 | 39.8 | 96.3 | |
| pKR1478-PAE | K18233 | 39.6 | 95.8 | |
| pKR1478-PAE | K18234 | 39.5 | 95.6 | |
| pKR1478-PAE | K18235 | 38.2 | 92.4 | |
| pKR1478-PAE | K18227 | 37.1 | 89.8 | |
| pKR1478-PAE | K18232 | 35.3 | 85.4 | |
| pKR1478-PAE | K18228 | 31.5 | 76.2 | 95.0 |
| wt | K17891 | 41.2 | | |
| wt | K17892 | 41.6 | | |

T2 seed of events K18232 and K18228 were plated on selective media and planted alongside untransformed wt control plants. Plants were gown to maturity. Seeds were harvested and oil content was measured by NMR (Table 9)

TABLE 9

Seed oil content of T2 plants generated with binary vector pKR1478-PAE for seed-specific over-expression of At2g46930

| Event ID | Construct | BAR-CODE | % oil | oil content % of WT | avg. oil content % of WT |
|---|---|---|---|---|---|
| K18232 | pKR1478-PAE | K45652 | 42.3 | 98.0 | |
| | | K45654 | 41.9 | 97.2 | |
| | | K45647 | 41.0 | 95.0 | |
| | | K45643 | 40.8 | 94.1 | |
| | | K45648 | 40.1 | 93.1 | |
| | | K45634 | 40.0 | 92.7 | |
| | | K45646 | 39.8 | 91.8 | |
| | | K45638 | 39.4 | 91.4 | |
| | | K45644 | 39.2 | 90.9 | |
| | | K45635 | 38.9 | 90.2 | |
| | | K45653 | 38.7 | 89.7 | |
| | | K45655 | 38.6 | 89.5 | |
| | | K45641 | 38.4 | 89.1 | |
| | | K45636 | 38.2 | 88.6 | |
| | | K45650 | 37.1 | 86.1 | |
| | | K45651 | 37.0 | 85.8 | |
| | | K45639 | 36.8 | 85.3 | |
| | | K45642 | 36.2 | 83.9 | |
| | | K45649 | 35.8 | 83.0 | |
| | | K45645 | 35.3 | 81.8 | |
| | | K45637 | 35.2 | 81.6 | 89.5 |
| | wt | K45666 | 44.9 | | |
| | | K45667 | 43.8 | | |
| | | K45660 | 43.8 | | |
| | | K45663 | 43.8 | | |
| | | K45664 | 43.8 | | |
| | | K45657 | 43.8 | | |
| | | K45658 | 43.5 | | |
| | | K45656 | 43.5 | | |
| | | K45665 | 42.5 | | |
| | | K45661 | 42.1 | | |
| | | K45659 | 41.6 | | |
| | | K45662 | 40.8 | | |
| K18228 | pKR1478-PAE | K45680 | 41.9 | 99.3 | |
| | | K45669 | 41.4 | 98.2 | |
| | | K45668 | 41.2 | 97.6 | |
| | | K45679 | 40.8 | 96.7 | |
| | | K45681 | 40.3 | 95.6 | |
| | | K45678 | 39.7 | 94.1 | |
| | | K45670 | 39.5 | 93.7 | |
| | | K45674 | 39.1 | 92.6 | |
| | | K45676 | 38.6 | 91.4 | |
| | | K45675 | 37.3 | 88.4 | |
| | | K45677 | 37.1 | 87.9 | |
| | | K45672 | 37.1 | 87.9 | |
| | | K45671 | 36.7 | 87.0 | |

TABLE 9-continued

| Seed oil content of T2 plants generated with binary vector pKR1478-PAE for seed-specific over-expression of At2g46930 | | | | | |
|---|---|---|---|---|---|
| Event ID | Construct | BAR-CODE | % oil | oil content % of WT | avg. oil content % of WT |
| | | K45682 | 36.5 | 86.4 | |
| | | K45673 | 34.4 | 81.4 | 91.9 |
| | | K45690 | 44.2 | | |
| | | K45685 | 43.1 | | |
| | | K45687 | 43.0 | | |
| | | K45686 | 42.9 | | |
| | | K45691 | 42.5 | | |
| | | K45688 | 42.4 | | |
| | | K45684 | 42.2 | | |
| | | K45692 | 41.5 | | |
| | | K45689 | 40.3 | | |
| | | K45683 | 39.8 | | |

T3 seed of lines K45642 and K45649 derived from event K18232 and lines K45672 and K45673 derived from event K18228 were plated on selective media and planted alongside untransformed wt control plants. Plants were gown to maturity. Seeds were harvested and oil content was measured by NMR (Table 10)

TABLE 10

| Seed oil content of T3 plants generated with binary vector pKR1478-PAE for seed-specific over-expression of At2g46930 | | | | | |
|---|---|---|---|---|---|
| Event ID | Construct | BAR-CODE | % oil | oil content % of WT | avg. oil content % of WT |
| K18232/K45642 | pKR1478-PAE | K49363 | 38.0 | 95.3 | |
| | pKR1478-PAE | K49370 | 37.5 | 94.1 | |
| | pKR1478-PAE | K49366 | 36.5 | 91.6 | |
| | pKR1478-PAE | K49374 | 36.4 | 91.3 | |
| | pKR1478-PAE | K49373 | 36.3 | 91.2 | |
| | pKR1478-PAE | K49378 | 36.2 | 91.0 | |
| | pKR1478-PAE | K49377 | 35.8 | 90.0 | |
| | pKR1478-PAE | K49371 | 35.4 | 88.9 | |
| | pKR1478-PAE | K49369 | 35.3 | 88.6 | |
| | pKR1478-PAE | K49365 | 35.0 | 87.8 | |
| | pKR1478-PAE | K49367 | 34.4 | 86.4 | |
| | pKR1478-PAE | K49375 | 33.7 | 84.5 | |
| | pKR1478-PAE | K49368 | 33.6 | 84.4 | |
| | pKR1478-PAE | K49364 | 32.8 | 82.4 | |
| | pKR1478-PAE | K49372 | 32.3 | 81.1 | 88.6 |
| | wt | K49378 | 42.0 | | |
| | wt | K49379 | 41.5 | | |
| | wt | K49382 | 40.6 | | |
| | wt | K49383 | 40.4 | | |
| | wt | K49385 | 40.1 | | |
| | wt | K49380 | 39.1 | | |
| | wt | K49381 | 37.8 | | |
| | wt | K49384 | 37.2 | | |
| K18232K45649 | PKR1478-PAE | K49715 | 41.8 | 109.5 | |

TABLE 10-continued

| Seed oil content of T3 plants generated with binary vector pKR1478-PAE for seed-specific over-expression of At2g46930 | | | | | |
|---|---|---|---|---|---|
| Event ID | Construct | BAR-CODE | % oil | oil content % of WT | avg. oil content % of WT |
| | pKR1478-PAE | K49704 | 38.3 | 100.2 | |
| | pKR1478-PAE | K49711 | 37.5 | 98.3 | |
| | pKR1478-PAE | K49718 | 36.9 | 96.6 | |
| | pKR1478-PAE | K49710 | 36.5 | 95.6 | |
| | pKR1478-PAE | K49717 | 35.5 | 92.9 | |
| | pKR1478-PAE | K49716 | 35.2 | 92.3 | |
| | pKR1478-PAE | K49707 | 34.8 | 91.0 | |
| | pKR1478-PAE | K49712 | 34.7 | 90.8 | |
| | pKR1478-PAE | K49708 | 34.4 | 90.0 | |
| | pKR1478-PAE | K49714 | 33.9 | 88.8 | |
| | pKR1478-PAE | K49709 | 32.4 | 84.8 | |
| | pKR1478-PAE | K49720 | 32.1 | 84.1 | |
| | pKR1478-PAE | K49721 | 32.1 | 84.1 | |
| | pKR1478-PAE | K49703 | 32.0 | 83.8 | |
| | pKR1478-PAE | K49713 | 31.8 | 83.2 | |
| | pKR1478-PAE | K49705 | 31.2 | 81.6 | |
| | pKR1478-PAE | K49708 | 29.5 | 77.4 | |
| | pKR1478-PAE | K49719 | 29.3 | 76.8 | 89.6 |
| | wt | K49723 | 39.7 | | |
| | wt | K49726 | 39.7 | | |
| | wt | K49724 | 39.4 | | |
| | wt | K49725 | 39.2 | | |
| | wt | K49722 | 39.0 | | |
| | wt | K49727 | 36.9 | | |
| | wt | K49729 | 36.5 | | |
| | wt | K49728 | 35.1 | | |
| K18228/K45672 | pKR1478-PAE | K49401 | 42.9 | 99.2 | |
| | pKR1478-PAE | K49391 | 38.6 | 89.4 | |
| | pKR1478-PAE | K49387 | 37.0 | 85.7 | |
| | pKR1478-PAE | K49388 | 36.1 | 83.6 | |
| | pKR1478-PAE | K49402 | 35.9 | 83.1 | |
| | pKR1478-PAE | K49390 | 35.8 | 82.8 | |
| | pKR1478-PAE | K49396 | 35.4 | 81.9 | |
| | pKR1478-PAE | K49400 | 35.0 | 81.1 | |
| | pKR1478-PAE | K49394 | 35.0 | 80.9 | |
| | pKR1478-PAE | K49399 | 34.4 | 79.7 | |
| | pKR1478-PAE | K49395 | 34.2 | 79.2 | |
| | pKR1478-PAE | K49393 | 34.0 | 78.8 | |
| | pKR1478-PAE | K49405 | 33.9 | 78.4 | |
| | pKR1478-PAE | K49397 | 33.7 | 78.1 | |
| | pKR1478-PAE | K49404 | 33.0 | 76.3 | |

TABLE 10-continued

Seed oil content of T3 plants generated with binary vector pKR1478-PAE for seed-specific over-expression of At2g46930

| Event ID | Construct | BAR-CODE | % oil | oil content % of WT | avg. oil content % of WT |
|---|---|---|---|---|---|
| | pKR1478-PAE | K49392 | 32.9 | 76.1 | |
| | pKR1478-PAE | K49403 | 32.4 | 75.1 | |
| | pKR1478-PAE | K49386 | 32.3 | 74.7 | |
| | pKR1478-PAE | K49389 | 32.1 | 74.3 | |
| | pKR1478-PAE | K49398 | 31.9 | 73.8 | 80.6 |
| | wt | K49410 | 44.2 | | |
| | wt | K49408 | 43.9 | | |
| | wt | K49407 | 43.3 | | |
| | wt | K49406 | 43.2 | | |
| | wt | K49409 | 41.4 | | |
| K18228/K45673 | pKR1478-PAE | K49427 | 41.2 | 100.9 | |
| | pKR1478-PAE | K49424 | 41.1 | 100.6 | |
| | pKR1478-PAE | K49419 | 40.8 | 100.0 | |
| | pKR1478-PAE | K49425 | 40.2 | 98.5 | |
| | pKR1478-PAE | K49412 | 40.0 | 97.9 | |
| | pKR1478-PAE | K49426 | 39.0 | 95.4 | |
| | pKR1478-PAE | K49423 | 38.8 | 95.0 | |
| | pKR1478-PAE | K49414 | 38.6 | 94.5 | |
| | pKR1478-PAE | K49422 | 35.5 | 86.9 | |
| | pKR1478-PAE | K49421 | 35.2 | 86.1 | |
| | pKR1478-PAE | K49415 | 34.7 | 85.0 | |
| | pKR1478-PAE | K49418 | 34.5 | 84.4 | |
| | pKR1478-PAE | K49420 | 34.2 | 83.6 | |
| | pKR1478-PAE | K49413 | 33.7 | 82.6 | |
| | pKR1478-PAE | K49411 | 33.5 | 81.9 | |
| | pKR1478-PAE | K49417 | 32.7 | 80.1 | 90.8 |
| | wt | K49430 | 42.3 | | |
| | wt | K49434 | 42.2 | | |
| | wt | K49431 | 41.6 | | |
| | wt | K49435 | 41.1 | | |
| | wt | K49432 | 40.4 | | |
| | wt | K49429 | 40.3 | | |
| | wt | K49428 | 40.0 | | |
| | wt | K49433 | 38.9 | | |

Tables 8-10 demonstrate that seed specific expression of At2g46930 leads to a decrease in oil content of 10-20%. The decrease in oil content associated with the transgene is heritable. This finding suggests that the low seed oil phenotype in lo22730 is related to increased expression of At2g46930 resulting from the nearby insertion of quadruple 35S enhancer sequence present in the pHSbarENDs2-derived T-DNA.

Example 5

Seed-Specific RNAi of At2g46930, Generation and Phenotypic Characterization of Transgenic Lines A binary plant transformation vector pKR1481 (SEQ ID NO:15) for generation of hairpin constructs facilitating seed-specific RNAi under control of the SUS2 promoter derived from the *Arabidopsis* gene At5g49190 was constructed. The RNAi-related expression cassette that can be used for cloning of a given DNA fragment flanked by ATTL sites in antisense and sense orientation downstream of the seed-specific promoter. The two gene fragments are interrupted by a spliceable intron sequence derived from the *Arabidopsis* gene At2g38080.

An intron of an *Arabidopsis* laccase gene (At2g38080) was amplified from genomic *Arabidopsis* DNA of ecotype Columbia using primers AthLcc IN FWD (SEQ ID NO:16) and AthLcc IN REV (SEQ ID NO:17). PCR products were cloned into pGEM T EASY (Promega, USA) according to manufacturer instructions and sequenced. The DNA sequence of the PCR product containing the laccase intron is set forth as SEQ ID NO:18. The PCR primers introduce an HpaI restriction site at the 5' end of the intron and restriction sites for NruI and SpeI at the 3' end of the intron. A three-way ligation of DNA fragments was performed as follows. XbaI digested, dephosphorylated DNA of pMBL18 (Nakano, Yoshio; Yoshida, Yasuo; Yamashita, Yoshihisa; Koga, Toshihiko. Construction of a series of pACYC-derived plasmid vectors. Gene (1995), 162(1), 157-8.) was ligated to the XbaI, EcoRV DNA fragment of PSM1318 (SEQ ID NO:19) containing ATTR12 sites a DNA Gyrase inhibitor gene (ccdB), a chloramphenicol acetyltransferase gene, an HpaI/SpeI restriction fragment excised from pGEM T EASY Lacc INT (SEQ ID NO:18) containing intron 1 of At2g38080. Ligation products were transformed into the DB 3.1 strain of *E. coli* (Invitrogen, USA). Recombinant clones were characterized by restriction digests and sequenced. The DNA sequence of the resulting plasmid pMBL18 ATTR12 INT is set forth as SEQ ID NO:20. DNA of pMBL18 ATTR12 INT was linearized with NruI, dephosphorylated and ligated to the XbaI, EcoRV DNA fragment of PSM1789 (SEQ ID NO: 21) containing ATTR12 sites and a DNA Gyrase inhibitor gene (ccdB). Prior to ligation ends of the PSM1789 restriction fragment had been filled in with T4 DNA polymerase (Promega, USA). Ligation products were transformed into the DB 3.1 strain of *E. coli* (Invitrogen, USA). Recombinant clones were characterized by restriction digests and sequenced. The DNA sequence of the resulting plasmid pMBL18 ATTR12 INT ATTR21 is set forth as SEQ ID NO:22.

Genomic DNA was isolated from 3 week-old wild-type *Arabidopsis* col-0 seedlings using the DNEASY® Plant Mini Kit (Qiagen, Valencia, Calif.) and following the manufacture's protocol. An *Arabidopsis* Sucrose Synthase ("At-SuSy"; "AtSUS2") promoter derived from gene At5g49190 was PCR-amplified from *Arabidopsis* genomic DNA using oligonucleotides SuSy-5 (SEQ ID NO:23) and SuSy-3 (SEQ ID NO:24) with the PHUSION™ High-Fidelity DNA Polymerase (Cat. No. F553S, Finnzymes Oy, Finland), following the manufacturer's protocol. The resulting DNA fragment was cloned into the pCR®-BLUNT® cloning vector using the ZERO BLUNT® PCR Cloning Kit (Invitrogen Corporation), following the manufacturer's protocol, to produce pLF122 (SEQ ID NO:25).

The BamHI/NotI fragment of pLF122 (SEQ ID NO:25), containing the AtSuSy promoter, was cloned into the BamHI/NotI fragment of pKR1142 (SEQ ID NO:26), containing the phaseolin terminator, to produce pKR1155 (SEQ ID NO:27).

Prior to this pKR1142 was constructed as follows: Plasmid KS294 (SEQ ID NO:28) contains a NotI site flanked by the SCP1 promoter and the phaseolin transcription terminator (SCP1Pro::NotI::PhasTerm). The SCP1 promoter is a synthetic constitutive promoter comprising a portion of the CaMV 35S promoter (Odell et al. (1985) Nature 313:810-812) and the Rsyn7-Syn II Core synthetic consensus promoter (U.S. Pat. Nos. 6,072,050 and 6,555,673, the contents of which are incorporated by reference). See also, for example, US20030226166, Table 13 (the contents of which are incorporated by reference). Downstream of this element is the Tobacco Mosaic Virus (TMV) omega 5'-UTR translational enhancer element (Gallie et al. (1992) Nucleic Acid Research 20:4631-4638), followed by the NotI site and the 3' transcription termination region of the phaseolin gene (Doyle et al., (1986) *J. Biol. Chem.* 261:9228-9238). The XbaI fragment of KS294 (SEQ ID NO:18), containing the SCP1Pro::NotI::PhasTerm cassette, was cloned into the XbaI site of pKR627 (SEQ ID NO:29) to produce pKR1142 (SEQ ID NO:26). Plasmid pKR627 was constructed earlier as disclosed below: Plasmid pKR132 (SEQ ID NO:30) which is described in PCT Publication No. WO 2004/071467 (the contents of which are incorporated by reference), was digested with BamHI/SalI and the fragment containing the soy albumin promoter was cloned into the BamHI/XhoI fragment of the pCR-Blunt® cloning vector (Invitrogen Corporation) to produce the starting vector pKR627 (SEQ ID NO:29).

The Asp718/BsiWI fragment of pKR1155 containing the AtSuSy promoter, was cloned into the BsiWI site of pKR278 (SEQ ID NO:4; described in U.S. Pat. Appl. Publ. 2008295204, the contents of which are incorporated by reference), to produce pKR1157 (SEQ ID NO:32).

Plasmid pMBL18 ATTR12 INT ATTR21 (SEQ ID NO:22) was digested with XbaI and after filling to blunt the XbaI site generated, the resulting DNA was digested with Ecl136II and the fragment containing the attR cassettes was cloned into the NotI/BsiWI (where NotI site was completely filled) fragment of pKR1155(SEQ ID NO:27), containing the SUS2 promoter, to produce pKR1479 (SEQ ID NO:33). pKR1479 (SEQ ID NO:33) was digested with AscI and the fragment containing the SUS2 promoter/attR cassettes was cloned into the AscI fragment of binary vector pKR92 to produce pKR1481 (SEQ ID NO:34).

5 μg of plasmid DNA of pENTR-PAE (SEQ ID NO:13). was digested with EcoRV/HpaI. A restriction fragment of 1300 bp (derived from pENTR-PAE) was excised from an agarose gel. The purified DNA fragment was inserted into vector pKR1481 using LR clonase (Invitrogen) according to the manufacturers instructions, to give pKR1481-PAE (SEQ ID NO:34)

pKR1481-PAE (SEQ ID NO:34) was introduced into *Agrobacterium tumefaciens* NTL4 (Luo et al, *Molecular Plant-Microbe Interactions* (2001) 14(1):98-103) by electroporation. Briefly, 1 μg plasmid DNA was mixed with 100 μL of electro-competent cells on ice. The cell suspension was transferred to a 100 μL electroporation cuvette (1 mm gap width) and electroporated using a BIORAD electroporator set to 1 kV, 400Ω and 25 μF. Cells were transferred to 1 mL LB medium and incubated for 2 h at 30° C. Cells were plated onto LB medium containing 50 μg/mL kanamycin. Plates were incubated at 30° C. for 60 h. Recombinant *Agrobacterium* cultures (500 mL LB, 50 μg/mL kanamycin) were inoculated from single colonies of transformed *agrobacterium* cells and grown at 30° C. for 60 h. Cells were harvested by centrifugation (5000×g, 10 min) and resuspended in 1 L of 5% (W/V) sucrose containing 0.05% (V/V) Silwet. *Arabidopsis* plants were grown in soil at a density of 30 plants per 100 $cm^2$ pot in METRO-MIX® 360 soil mixture for 4 weeks (22° C., 16 h light/8 h dark, 100 μE $m^{-2}s^{-1}$). Plants were repeatedly dipped into the *Agrobacterium* suspension harboring the binary vector pKR1481-PAE (SEQ ID NO:34) and kept in a dark, high humidity environment for 24 h. Plants were grown for three to four weeks under standard plant growth conditions described above and plant material was harvested and dried for one week at ambient temperatures in paper bags. Seeds were harvested using a 0.425 mm mesh brass sieve.

Cleaned *Arabidopsis* seeds (2 grams, corresponding to about 100,000 seeds) were sterilized by washes in 45 mL of 80% ethanol, 0.01% TRITON® X-100, followed by 45 mL of 30% (V/V) household bleach in water, 0.01% TRITON® X-100 and finally by repeated rinsing in sterile water. Aliquots of 20,000 seeds were transferred to square plates (20×20 cm) containing 150 mL of sterile plant growth medium comprised of 0.5×MS salts, 0.53% (W/V) sorbitol, 0.05 MES/KOH (pH 5.8), 200 μg/mL TIMENTIN®, and 50 μg/mL kanamycin solidified with 10 g/L agar. Homogeneous dispersion of the seed on the medium was facilitated by mixing the aqueous seed suspension with an equal volume of melted plant growth medium. Plates were incubated under standard growth conditions for ten days. Kanamycin-resistant seedlings were transferred to plant growth medium without selective agent and grown for one week before transfer to soil. Plants were grown to maturity and T2 seeds were harvested. A total of 21 events were generated with pKR1481-PAE (SEQ ID NO:34). Twelve wild-type (WT) control plants were grown in the same flat. WT seeds were bulk harvested and T2 seeds of individual transgenic lines were harvested and oil content was measured by NMR as described above.

TABLE 11

Seed oil content of T1 plants generated with binary vector pKR1481-PAE for seed specific gene suppression of At2g46930

| Construct | BARCODE | % oil | oil content % of WT | avg. oil content % of WT |
|---|---|---|---|---|
| pKR1481-PAE | K46661 | 43.0 | 106.9 | |
| pKR1481-PAE | K46663 | 42.9 | 106.8 | |
| pKR1481-PAE | K46666 | 42.6 | 106.0 | |
| pKR1481-PAE | K46657 | 42.0 | 104.4 | |
| pKR1481-PAE | K46654 | 41.8 | 104.1 | |
| pKR1481-PAE | K46667 | 41.5 | 103.3 | |
| pKR1481-PAE | K46671 | 41.3 | 102.8 | |
| pKR1481-PAE | K46658 | 41.2 | 102.4 | |
| pKR1481-PAE | K46670 | 41.1 | 102.3 | |
| pKR1481-PAE | K46662 | 41.0 | 101.9 | |
| pKR1481-PAE | K46669 | 40.9 | 101.9 | |
| pKR1481-PAE | K46675 | 40.9 | 101.8 | |

TABLE 11-continued

Seed oil content of T1 plants generated with binary vector pKR1481-PAE for seed specific gene suppression of At2g46930

| Construct | BARCODE | % oil | oil content % of WT | avg. oil content % of WT |
|---|---|---|---|---|
| pKR1481-PAE | K46656 | 40.8 | 101.6 | |
| pKR1481-PAE | K46655 | 40.7 | 101.3 | |
| pKR1481-PAE | K46674 | 40.6 | 101.0 | |
| pKR1481-PAE | K46673 | 40.5 | 100.7 | |
| pKR1481-PAE | K46672 | 40.2 | 100.0 | |
| pKR1481-PAE | K46666 | 40.1 | 99.7 | |
| pKR1481-PAE | K46664 | 39.6 | 98.5 | |
| pKR1481-PAE | K46659 | 39.2 | 97.5 | |
| pKR1481-PAE | K46676 | 38.1 | 94.8 | 101.9 |
| wt | K46685 | 41.6 | | |
| wt | K46679 | 41.1 | | |
| wt | K46677 | 40.9 | | |
| wt | K46686 | 40.4 | | |
| wt | K46684 | 40.4 | | |
| wt | K46688 | 40.2 | | |
| wt | K46680 | 40.2 | | |
| wt | K46681 | 40.1 | | |
| wt | K46687 | 39.9 | | |
| wt | K46682 | 39.5 | | |
| wt | K46678 | 39.4 | | |
| wt | K46683 | 38.4 | | |

Table 11 shows that seed-specific down regulation of At2g46930 leads to increased oil content in *Arabidopsis* seed.

T2 seed of events K46661 and K46663 that both carry transgenes pKR1481-PAE were plated on plant growth media containing kanamycin. Plants were grown to maturity alongside WT plants of the Columbia ecotype grown in the same flats. Oil content of T3 seed is depicted in Table 12. Table 12 demonstrates that an oil increase of about 4% associated with seed-specific down regulation of At2g46930 is observed in multiple events and that this oil increase is heritable.

TABLE 12

Seed oil content of T2 plants generated with binary vector pKR1481-PAE for seed specific gene suppression of At2g46930

| Event ID | Construct | BAR-CODE | % oil | oil content % of WT | avg. oil content % of WT |
|---|---|---|---|---|---|
| K46661 | pKR1481-PAE | K49933 | 42.6 | 110.1 | |
| | pKR1481-PAE | K49931 | 42.2 | 108.9 | |
| | pKR1481-PAE | K49947 | 41.7 | 107.7 | |
| | pKR1481-PAE | K49928 | 41.6 | 107.4 | |
| | pKR1481-PAE | K49944 | 41.6 | 107.4 | |
| | pKR1481-PAE | K49930 | 41.2 | 106.5 | |
| | pKR1481-PAE | K49935 | 41.1 | 106.3 | |
| | pKR1481-PAE | K49932 | 41.0 | 106.0 | |

TABLE 12-continued

Seed oil content of T2 plants generated with binary vector pKR1481-PAE for seed specific gene suppression of At2g46930

| Event ID | Construct | BAR-CODE | % oil | oil content % of WT | avg. oil content % of WT |
|---|---|---|---|---|---|
| | pKR1481-PAE | K49929 | 40.8 | 105.5 | |
| | pKR1481-PAE | K49941 | 40.8 | 105.3 | |
| | pKR1481-PAE | K49934 | 40.7 | 105.1 | |
| | pKR1481-PAE | K49945 | 40.4 | 104.3 | |
| | pKR1481-PAE | K49938 | 40.2 | 103.9 | |
| | pKR1481-PAE | K49948 | 40.0 | 103.4 | |
| | pKR1481-PAE | K49936 | 40.0 | 103.3 | |
| | pKR1481-PAE | K49940 | 40.0 | 103.2 | |
| | pKR1481-PAE | K49943 | 39.9 | 103.0 | |
| | pKR1481-PAE | K49950 | 39.7 | 102.5 | |
| | pKR1481-PAE | K49949 | 39.0 | 100.7 | |
| | pKR1481-PAE | K49942 | 38.6 | 99.8 | |
| | pKR1481-PAE | K49946 | 38.2 | 98.7 | |
| | pKR1481-PAE | K49937 | 38.2 | 98.6 | 104.4 |
| | pKR1481-PAE | K49939 | 36.9 | | |
| | wt | K49957 | 40.3 | | |
| | wt | K49954 | 40.1 | | |
| | wt | K49955 | 39.5 | | |
| | wt | K49951 | 38.0 | | |
| | wt | K49953 | 37.9 | | |
| | wt | K49952 | 37.7 | | |
| | wt | K49956 | 37.5 | | |
| K46663 | pKR1481-PAE | K49959 | 42.9 | 109.5 | |
| | pKR1481-PAE | K49958 | 42.2 | 107.8 | |
| | pKR1481-PAE | K49962 | 41.5 | 105.9 | |
| | pKR1481-PAE | K49964 | 41.3 | 105.5 | |
| | pKR1481-PAE | K49966 | 41.1 | 105.0 | |
| | pKR1481-PAE | K49961 | 41.1 | 104.8 | |
| | pKR1481-PAE | K49970 | 41.1 | 104.8 | |
| | pKR1481-PAE | K49972 | 40.8 | 104.1 | |
| | pKR1481-PAE | K49965 | 40.8 | 104.1 | |
| | pKR1481-PAE | K49969 | 40.8 | 104.0 | |
| | pKR1481-PAE | K49987 | 40.7 | 103.8 | |
| | pKR1481-PAE | K49968 | 40.4 | 103.2 | |
| | pKR1481-PAE | K49973 | 40.3 | 102.8 | |
| | pKR1481-PAE | K49963 | 39.8 | 101.6 | |
| | pKR1481-PAE | K49971 | 39.8 | 101.6 | |
| | pKR1481-PAE | K49960 | 39.6 | 101.0 | 104.3 |
| | wt | K49983 | 41.1 | | |
| | wt | K49978 | 40.9 | | |
| | wt | K49981 | 40.7 | | |
| | wt | K49974 | 40.3 | | |

TABLE 12-continued

| Seed oil content of T2 plants generated with binary vector pKR1481-PAE for seed specific gene suppression of At2g46930 | | | | | |
|---|---|---|---|---|---|
| Event ID | Construct | BAR-CODE | % oil | oil content % of WT | avg. oil content % of WT |
| | wt | K49976 | 40.0 | | |
| | wt | K49977 | 39.8 | | |
| | wt | K49982 | 39.6 | | |
| | wt | K49980 | 38.6 | | |
| | wt | K49979 | 36.6 | | |
| | wt | K49975 | 34.2 | | |

Example 6

Identification of Genes of *Brassica rapa* Closely-Related to At2g46930

A proprietary database *Brassica rapa* UniGene Dataset (July 2009), which was built from public *Brassica rapa* ESTs at NCBI was searched using the predicted amino acid sequence of At2g46930 and tBLASTn (BLAST® (Basic Local Alignment Search Tool). There is one gene PBR010399 which shares 86% amino acid sequence identity to At2g46930. This genes, its % identity to At2g46930 and SEQ ID NOs are listed in Table 13.

TABLE 13

| *Brassica rapa* gene closely realated to At2g46930 | | | |
|---|---|---|---|
| Gene name | % AA sequence identity to At2g46930 | SEQ ID NO: NT | SEQ ID NO: AA |
| PBR010399 | 86.2 | 35 | 36 |

Example 7

Identification of Genes of Sunflower Genes Closely-Related to At2g46930

The *Helianthus annuus* EST assembly version 4.0 (Jun. 17, 2006) from the Gene Index Project at Dana-Farber Cancer Institute. The assembly started with 93,807 public ESTs and expressed transcripts, and has a total of 36,743 sequences (12,285 assemblies and 24,458 singletons). The gene index site at the Dana-Farber Cancer institute was searched using the predicted amino acid sequence of At4g10750 and tBLASTn (BLAST® (Basic Local Alignment Search Tool). There is one gene TC19105 which shares 66.5% amino acid sequence identity to At2g46930. This gene, its % identity to At2g46930 and SEQ ID NOs are listed in Table 14.

TABLE 14

| Sunflower (*Helianthus annuus*) gene closely related to At2g46930 | | | |
|---|---|---|---|
| Gene name | % AA sequence identity to At2g46930 | SEQ ID NO: NT | SEQ ID NO: AA |
| TC19105 | 83.9 | 37 | 38 |

Example 8

Identification of Genes of Castor Genes Closely-Related to At2g46930

The Non-redundant protein data set from NCBI including non-redundant GenBank CDS translations+PDB+SwissProt+PIR+PRF protein sequences was searched using the predicted amino acid sequence of At4g10750 and tBLASTn (BLAST® (Basic Local Alignment Search Tool). There is one gene XM_002515114 which shares 66.5% amino acid sequence identity to At2g46930. This gene, its % identity to At2g46930 and SEQ ID NOs are listed in Table 15.

TABLE 15

| Castor (*Ricinus communis*) gene closely related to At2g46930 | | | |
|---|---|---|---|
| Gene name | % AA sequence identity to At2g46930 | SEQ ID NO: NT | SEQ ID NO: AA |
| XM_002515114 | 66.5 | 39 | 40 |

Example 9

Identification of Genes of Soybean (*Glycine max*) Closely-Related to At2g46930

Public DNA sequences (Soybean cDNAs Glyma1.01 (JGI) (N) Predicted cDNAs from Soybean JGI Glyma1.01 genomic sequence, FGENESH predictions, and EST PASA analysis.) were searched using the predicted amino acid sequence of At2g46930 and tBLASTn (BLAST® (Basic Local Alignment Search Tool). There are four genes that encode protein which share between 61.8% and 67.6% amino acid sequence identity with the predicted protein At2g46930. These genes, its properties and SEQ ID NO are listed in Table 16.

TABLE 16

| Soybean genes closely related to At2g46930 | | | |
|---|---|---|---|
| Gene name | % AA sequence identity to At2g46930 | SEQ ID NO: NT | SEQ ID NO: AA |
| Glyma02g00930 | 62.5 | 41 | 42 |
| Glyma10g27960 | 61.8 | 43 | 44 |
| Glyma03g38430 | 67.6 | 45 | 46 |
| Glyma19g41030 | 67.5 | 47 | 48 |

Example 10

Identification of Genes of Maize (*Zea mays*) Closely-Related to At2g46930

The filtered Gene Set cDNAs of the maize genome sequence at the MaizeSequence Release 4a.53-October 2009 was searched using the predicted amino acid sequence of At2g46930 and tBLASTn (BLAST® (Basic Local Alignment Search Tool). Predicted amino acid sequences derived from three cDNAs share between 49.8 and 57.8% sequence identity to At2g46930. These genes, its properties and SEQ ID NO are listed in Table 17.

TABLE 17

| Maize genes closely related to At2g46930 | | | |
|---|---|---|---|
| Gene name | % AA sequence identity to At2g46930 | SEQ ID NO: NT | SEQ ID NO: AA |
| GRMZM2G117999 | 49.8 | 49 | 50 |
| GRMZM2G160569 | 57.8 | 51 | 52 |
| GRMZM2G164134 | 52.8 | 53 | 54 |

Example 11

Identification of Genes of Rice (*Oryza Sativa*) Closely-Related to At2g46930

A public database of transcripts from rice gene models (*Oryza sativa* (*japonica* cultivar-group) MSU Rice Genome Annotation Project Osa1 release 6 (January 2009) which includes untranslated regions (UTR) but no introns was searched using the predicted amino acid sequence of At2g46930 and tBLASTn (BLAST® (Basic Local Alignment Search Tool). There are three genes that encode protein which share between 51.9% and 58.0% amino acid sequence identity with the predicted protein At2g46930. These genes, its properties and SEQ ID NO are listed in Table 18.

TABLE 18

| Rice genes closely related to At2g46930 | | | |
|---|---|---|---|
| Gene name | % AA sequence identity to At2g46930 | SEQ ID NO: NT | SEQ ID NO: AA |
| Os01g21630 | 55.9 | 55 | 56 |
| Os02g47400 | 51.9 | 57 | 58 |
| Os07g44070 | 58.0 | 59 | 80 |

Example 12

Identification of Genes of *Sorghum* (*Sorghum bicolor*) Closely-Related to At2g46930

The predicted coding sequences (mRNA) from the Sorghum JGI genomic sequence, version 1.4 were searched using the predicted amino acid sequence of At2g46930 and tBLASTn (BLAST® (Basic Local Alignment Search Tool). There are three genes that encode protein which share between 51.9% and 58.0% amino acid sequence identity with the predicted protein At2g46930. These genes, its properties and SEQ ID NO are listed in Table 19.

TABLE 19

| *Sorghum* genes closely related to At2g46930 | | | |
|---|---|---|---|
| Gene name | % AA sequence identity to At2g48930 | SEQ ID NO: NT | SEQ ID NO: AA |
| Sb03g013080 | 53.5 | 61 | 62 |
| Sb02g040470 | 57.3 | 63 | 64 |
| Sb03g013070 | 55.3 | 65 | 66 |

Example 13

Identification of a Gene of Wheat (*Triticum avestinum*) Closely-Related to At2g46930

TIGR Plant Transcript Assemblies from Wheat (*Triticum aestivum*). Release 2; (July 2007) were searched using the predicted amino acid sequence of At2g46930 and tBLASTn (BLAST® (Basic Local Alignment Search Tool). There is one gene, TA80364 that encodes a protein which shares 56.6% amino acid sequence identity with the predicted protein At2g46930. The genes, its properties and SEQ ID NO are listed in Table 20.

TABLE 20

| Wheat gene closely related to At2g46930 | | | |
|---|---|---|---|
| Gene name | % AA sequence identity to At2g46930 | SEQ ID NO: NT | SEQ ID NO: AA |
| TA80364 | 56.6 | 67 | 68 |

Example 14

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659-668). The embryos are kept in the dark at 27° C. Friable embryogenic callus consisting of undifferentiated masses of cells with somatic proembryoids and embryoids bore on suspensor structures proliferate from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810-812) and the 3' region of the nopaline synthase gene from the T-DNA of the Ti plasmid of *Agrobacterium tumefaciens*.

The particle bombardment method (Klein et al. (1987) *Nature* 327:70-73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi. Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833-839).

Example 15

Expression of Chimeric Genes in Dicot Cells

A seed-specific construct composed of the promoter and transcription terminator from the gene encoding the β subunit of the seed storage protein phaseolin from the bean *Phaseolus vulgaris* (Doyle et al. (1986) *J. Biol. Chem.* 261:9228-9238) can be used for expression of the instant polypeptides in transformed soybean. The phaseolin construct includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire construct is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed construct.

Soybean embryos may then be transformed with the expression vector comprising sequences encoding the instant polypeptides. To induce somatic embryos, cotyledons, 3-5 mm in length dissected from surface sterilized, immature seeds of the soybean cultivar A2872 can be cultured in the light or dark at 26° C. on an appropriate agar medium for 6-10 weeks. Somatic embryos which produce secondary embryos are then excised and placed into a suitable liquid medium. After repeated selection for clusters of somatic embryos which multiplied as early, globular staged embryos, the suspensions are maintained as described below. Soybean embryogenic suspension cultures can be maintained in 35 mL of liquid media on a rotary shaker, 150 rpm, at 26° C. with fluorescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70-73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810-812), the hygromycin phosphotransferase gene from plasmid pJR225 (from *E. coli*; Gritz et al. (1983) *Gene* 25:179-188) and the 3' region of the nopaline synthase gene from the T-DNA of the Ti plasmid of *Agrobacterium tumefaciens*. The seed construct comprising the phaseolin 5' region, the fragment encoding the instant polypeptides and the phaseolin 3' region can be isolated as a restriction fragment. This fragment can then be inserted into a unique restriction site of the vector carrying the marker gene. To 50 μL of a 60 mg/mL 1 μm gold particle suspension is added (in order): 5 μL DNA (1 μg/μL), 20 μL spermidine (0.1 M), and 50 μL $CaCl_2$ (2.5M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk. Approximately 300-400 mg of a two-week-old suspension culture is placed in an empty 60×1 5 mm petri dish and the residual liquid removed from the tissue with a pipette. For each transformation experiment, approximately 5-10 plates of tissue are normally bombarded. Membrane rupture pressure is set at 1100 psi and the chamber is evacuated to a vacuum of 28 inches of mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 16

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125-135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/mL ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis. For high level expression, a plasmid clone with the cDNA insert in the correct orientation relative to the T7 promoter can be transformed into *E. coli* strain BL21(DE3) (Studier et al. (1986) *J. Mol. Biol.* 189:113-130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25° C. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 17

Transformation of Somatic Soybean Embryo Cultures

Generic Stable Soybean Transformation Protocol:

Soybean embryogenic suspension cultures are maintained in 35 ml liquid media (SB55 or SBP6) on a rotary shaker, 150 rpm, at 28° C. with mixed fluorescent and incandescent lights on a 16:8 h day/night schedule. Cultures are subcultured every four weeks by inoculating approximately 35 mg of tissue into 35 ml of liquid medium.

TABLE 21

| | |
|---|---|
| Stock Solutions (g/L): | |
| MS Sulfate 100X Stock | |
| $MgSO_4$ $7H_2O$ | 37.0 |
| $MnSO_4$ $H_2O$ | 1.69 |
| $ZnSO_4$ $7H_2O$ | 0.86 |
| $CuSO_4$ $5H_2O$ | 0.0025 |
| MS Halides 100X Stock | |
| $CaCl_2$ $2H_2O$ | 44.0 |
| KI | 0.083 |
| $CoCl_2$ $6H_20$ | 0.00125 |
| $KH_2PO_4$ | 17.0 |
| $H_3BO_3$ | 0.62 |
| $Na_2MoO_4$ $2H_2O$ | 0.025 |
| MS FeEDTA 100X Stock | |
| $Na_2EDTA$ | 3.724 |
| $FeSO_4$ $7H_2O$ | 2.784 |
| B5 Vitamin Stock | |
| 10 g m-inositol | |
| 100 mg nicotinic acid | |
| 100 mg pyridoxine HCl | |
| 1 g thiamine | |
| SB55 (per Liter, pH 5.7) | |
| 10 mL each MS stocks | |
| 1 mL B5 Vitamin stock | |
| 0.8 g $NH_4NO_3$ | |

TABLE 21-continued

| |
|---|
| 3.033 g $KNO_3$ |
| 1 mL 2,4-D (10 mg/mL stock) |
| 60 g sucrose |
| 0.667 g asparagine |
| SBP6 |
| same as SB55 except 0.5 mL 2,4-D |
| SB103 (per Liter, pH 5.7) |
| 1X MS Salts |
| 6% maltose |
| 750 mg $MgCl_2$ |
| 0.2% Gelrite |
| SB71-1 (per Liter, pH 5.7) |
| 1X B5 salts |
| 1 ml B5 vitamin stock |
| 3% sucrose |
| 750 mg $MgCl_2$ |
| 0.2% Gelrite |

Soybean embryogenic suspension cultures are transformed with plasmid DNA by the method of particle gun bombardment (Klein et al (1987) Nature 327:70). A DuPont Biolistic PDS1000/HE instrument (helium retrofit) is used for these transformations.

To 50 ml of a 60 mg/ml 1 μm gold particle suspension is added (in order); 5 μL DNA (1 μg/μl), 20 μl spermidine (0.1 M), and 50 μl $CaCl_2$ (2.5 M). The particle preparation is agitated for 3 min, spun in a microfuge for 10 sec and the supernatant removed. The DNA-coated particles are then washed once in 400 μl 70% ethanol and re suspended in 40 μl of anhydrous ethanol. The DNA/particle suspension is sonicated three times for 1 sec each. Five μl of the DNA-coated gold particles are then loaded on each macro carrier disk. For selection, a plasmid conferring resistance to hygromycin phosphotransferase (HPT) may be co-bombarded with the silencing construct of interest.

Approximately 300-400 mg of a four week old suspension culture is placed in an empty 60×15 mm petri dish and the residual liquid removed from the tissue with a pipette. For each transformation experiment, approximately 5-10 plates of tissue are normally bombarded. Membrane rupture pressure is set at 1000 psi and the chamber is evacuated to a vacuum of 28 inches of mercury. The tissue is placed approximately 3.5 inches away from the retaining screen and bombarded three times. Following bombardment, the tissue is placed back into liquid and cultured as described above.

Eleven days post bombardment, the liquid media is exchanged with fresh SB55 containing 50 mg/ml hygromycin. The selective media is refreshed weekly. Seven weeks post bombardment, green, transformed tissue is observed growing from untransformed, necrotic embryogenic clusters. Isolated green tissue is removed and inoculated into individual flasks to generate new, clonally propagated, transformed embryogenic suspension cultures. Thus each new line is treated as an independent transformation event. These suspensions can then be maintained as suspensions of embryos maintained in an immature developmental stage or regenerated into whole plants by maturation and germination of individual somatic embryos.

Independent lines of transformed embryogenic clusters are removed from liquid culture and placed on a solid agar media (SB103) containing no hormones or antibiotics. Embryos are cultured for four weeks at 26° C. with mixed fluorescent and incandescent lights on a 16:8 h day/night schedule. During this period, individual embryos are removed from the clusters and screened for alterations in gene expression.

It should be noted that any detectable phenotype, resulting from the alterted expression of a target gene, can be screened at this stage. This would include, but not be limited to, alterations in oil content, protein content, carbohydrate content, growth rate, viability, or the ability to develop normally into a soybean plant.

Example 18

Plasmid DNAs for "Complementary Region" Co-Suppression

The plasmids in the following experiments are made using standard cloning methods well known to those skilled in the art (Sambrook et al (1989) *Molecular Cloning*, CSHL Press, New York). A starting plasmid pKS18HH (U.S. Pat. No. 5,846,784 the contents of which are hereby incorporated by reference) contains a hygromycin B phosphotransferase (HPT) obtained from *E. coli* strain W677 under the control of a T7 promoter and the 35S cauliflower mosaic virus promoter. Plasmid pKS18HH thus contains the T7 promoter/HPT/T7 terminator cassette for expression of the HPT enzyme in certain strains of *E. coli*, such as NovaBlue(DE3) [from Novagen], that are lysogenic for lambda DE3 (which carries the T7 RNA Polymerase gene under lacV5 control). Plasmid pKS18HH also contains the 35S/HPT/NOS cassette for constitutive expression of the HPT enzyme in plants, such as soybean. These two expression systems allow selection for growth in the presence of hygromycin to be used as a means of identifying cells that contain the plasmid in both bacterial and plant systems. pKS18HH also contains three unique restriction endonuclease sites suitable for the cloning other chimeric genes into this vector. Plasmid ZBL100 (PCT Application No. WO 00/11176 published on Mar. 2, 2000) is a derivative of pKS18HH with a reduced NOS 3' terminator. Plasmid pKS67 is a ZBL100 derivative with the insertion of a beta-conglycinin promoter, in front of a NotI cloning site, followed by a phaseolin 3' terminator (described in PCT Application No. WO 94/11516, published on May 26, 1994).

The 2.5 kb plasmid pKS17 contains pSP72 (obtained from Promega Biosystems) and the T7 promoter/HPT/T7 3' terminator region, and is the original vector into which the 3.2 kb BamHI-SalI fragment containing the 35S/HPT/NOS cassette was cloned to form pKS18HH. The plasmid pKS102 is a pKS17 derivative that is digested with XhoI and Sail, treated with mung-bean nuclease to generate blunt ends, and ligated to insert the following linker disclosed in SEQ ID NO:69.

The plasmid pKS83 has the 2.3 kb BamHI fragment of ML70 containing the Kti3 promoter/NotI/Kti3 3' terminator region (described in PCT Application No. WO 94/11516, published on May 26, 1994) ligated into the BamHI site of pKS17. Additional methods for suppression of endogenous genes are well know in the art and have been described in the detailed description of the instant invention and can be used to reduce the expression of endogenous plastidic HpaIL aldolase gene expression, protein or enzyme activity in a plant cell.

Example 19

Suppression by ELVISLIVES Complementary Region

Constructs can be made which have "synthetic complementary regions" (SCR). In this example the target sequence is placed between complementary sequences that are not known to be part of any biologically derived gene or genome (i.e. sequences that are "synthetic" or conjured up from the mind of the inventor). The target DNA would therefore be in the sense or antisense orientation and the complementary RNA would be unrelated to any known nucleic acid sequence. It is possible to design a standard "suppression vector" into which pieces of any target gene for suppression could be dropped. The plasmids pKS106, pKS124, and pKS133 (SEQ ID NO:70) exemplify this. One skilled in the art will appreciate that all of the plasmid vectors contain antibiotic selection genes such as, but not limited to, hygromycin phosphotransferase with promoters such as the T7 inducible promoter.

pKS106 uses the beta-conglycinin promoter while the pKS124 and pKS133 plasmids use the Kti promoter, both of these promoters exhibit strong tissue specific expression in the seeds of soybean. pKS106 uses a 3' termination region from the phaseolin gene, and pKS124 and pKS133 use a Kti 3' termination region. pKS106 and pKS124 have single copies of the 36 nucleotide EagI-ELVISLIVES sequence surrounding a NotI site (the amino acids given in parentheses are back-translated from the complementary strand): SEQ ID NO:71

```
EagIE  L  V  I  S  L  I   V   E  S  NotI
CGGCCG GAG CTG GTC ATC TCG CTC ATC GTC GAG TCG

GCGGCCGC

(S)  (E)  (V)  (I)  (L)  (S)  (I)  (V)  (L)  (E)  EagI
CGA CTC GAC GAT GAG CGA GAT GAC CAG CTC CGGCCG
```

pKS133 has 2× copies of ELVISLIVES surrounding the NotI site: SEQ ID NO:72

```
EagI E L V I S  L  I V E  S   EagI   E L V I S
cggccggagctggtcatctcgctcatcgtcgagtcg gcggccg

gagctggtcatctcg

L I V E S   NotI (S)(E (V)(I)(L)(S)(I)(V)(L)(E)
EagI
ctcatcgtcgagtcg gcggccgc

cgactcgacgatgagcgagatgaccagctc cggccgc

(S)(E)(V)(I)(L)(S)(I)(V)(L)(E) EagI
cgactcgacgatgagcgagatgaccagctc cggccg
```

The idea is that the single EL linker (SCR) can be duplicated to increase stem lengths in increments of approximately 40 nucleotides. A series of vectors will cover the SCR lengths between 40 bp and the 300 bp. Various target gene lengths can also be evaluated. It is believed that certain combinations of target lengths and complementary region lengths will give optimum suppression of the target, however, it is expected that the suppression phenomenon works well over a wide range of sizes and sequences. It is also believed that the lengths and ratios providing optimum suppression may vary somewhat given different target sequences and/or complementary regions.

The plasmid pKS106 is made by putting the EagI fragment of ELVISLIVES (SEQ ID NO:71) into the NotI site of pKS67. The ELVISLIVES fragment is made by PCR using two primers (SEQ ID NO:73 and SEQ ID NO:74) and no other DNA.

The product of the PCR reaction is digested with EagI (5'-CGGCCG-3') and then ligated into NotI digested pKS67. The term "ELVISLIVES" and "EL" are used interchangeably herein.

Additional plasmids can be used to test this example and any synthetic sequence, or naturally occurring sequence, can be used in an analogous manner.

Example 20

Screening of Transgenic Lines for Alterations in Oil, Protein, Starch and Soluble Carbohydrate Content Transgenic lines can be selected from soybean transformed with a suppression plasmid, such as those described in Example 15 and Example 18. Transgenic lines can be screened for down regulation of plastidic HpaIL aldolase in soybean, by measuring alteration in oil, starch, protein, soluble carbohydrate and/or seed weight. Compositional analysis including measurements of seed compositional parameters such as protein content and content of soluble carbohydrates of soybean seed derived from transgenic events that show seed-specific down-regulation of PAE genes is performed as follows:

Oil content of mature soybean seed or lyophilized soybean somatic embryos can be measured by NMR as described in Example 2.

Non-Structural Carbohydrate and Protein Analysis.

Dry soybean seed are ground to a fine powder in a GenoGrinder and subsamples are weighed (to an accuracy of 0.0001 g) into 13×100 mm glass tubes; the tubes have Teflon® lined screw-cap closures. Three replicates are prepared for each sample tested. Tissue dry weights are calculated by weighing sub-samples before and after drying in a forced air oven for 18 h at 105 C.

Lipid extraction is performed by adding 2 ml aliquots of heptane to each tube. The tubes are vortex mixed and placed into an ultrasonic bath (VWR Scientific Model 750D) filled with water heated to 60 C. The samples are sonicated at full-power (~360 W) for 15 min and were then centrifuged (5 min×1700 g). The supernatants are transferred to clean 13×100 mm glass tubes and the pellets are extracted 2 more times with heptane (2 ml, second extraction, 1 ml third extraction) with the supernatants from each extraction being pooled. After lipid extraction 1 ml acetone is added to the pellets and after vortex mixing, to fully disperse the material, they are taken to dryness in a Speedvac.

Non-Structural Carbohydrate Extraction and Analysis.

Two ml of 80% ethanol is added to the acetone dried pellets from above. The samples are thoroughly vortex mixed until the plant material was fully dispersed in the solvent prior to sonication at 60 C for 15 min. After centrifugation, 5 min×1700 g, the supernatants are decanted into clean 13×100 mm glass tubes. Two more extractions with 80% ethanol are performed and the supernatants from each are pooled. The extracted pellets are suspended in acetone and dried (as above). An internal standard ▯-phenyl glucopyranoside (100 ul of a 0.5000+/−0.0010 g/100 ml stock) is added to each extract prior to drying in a Speedvac. The extracts are maintained in a desiccator until further analysis.

The acetone dried powders from above were suspended in 0.9 ml MOPS (3-N[Morpholino]propane-sulfonic acid; 50 mM, 5 mM $CaCl_2$, pH 7.0) buffer containing 100 U of heat stable α-amylase (from *Bacillus licheniformis*; Sigma A-4551). Samples are placed in a heat block (90 C) for 75 min and were vortex mixed every 15 min. Samples are then allowed to cool to room temperature and 0.6 ml acetate buffer (285 mM, pH 4.5) containing 5 U amyloglucosidase (Roche 110 202 367 001) is added to each. Samples are incubated for 15-18 h at 55 C in a water bath fitted with a reciprocating shaker; standards of soluble potato starch (Sigma S-2630) are included to ensure that starch digestion went to completion.

Post-digestion the released carbohydrates are extracted prior to analysis. Absolute ethanol (6 ml) is added to each tube and after vortex mixing the samples were sonicated for 15 min at 60 C. Samples were centrifuged (5 min×1700 g) and the supernatants were decanted into clean 13×100 mm glass tubes. The pellets are extracted 2 more times with 3 ml of 80% ethanol and the resulting supernatants are pooled. Internal standard (100 ul β-phenyl glucopyranoside, as above) is added to each sample prior to drying in a Speed-vac.

Sample Preparation and Analysis

The dried samples from the soluble and starch extractions described above are solubilized in anhydrous pyridine (Sigma-Aldrich P57506) containing 30 mg/ml of hydroxylamine HCl (Sigma-Aldrich 159417). Samples are placed on an orbital shaker (300 rpm) overnight and are then heated for 1 hr (75 C) with vigorous vortex mixing applied every 15 min. After cooling to room temperature 1 ml hexamethyldisilazane (Sigma-Aldrich H-4875) and 100 ul trifluoroacetic acid (Sigma-Aldrich T-6508) are added. The samples are vortex mixed and the precipitates are allowed to settle prior to transferring the supernatants to GC sample vials. Samples are analyzed on an Agilent 6890 gas chromatograph fitted with a DB-17MS capillary column (15 m×0.32 mm×0.25 um film). Inlet and detector temperatures are both 275 C. After injection (2 ul, 20:1 split) the initial column temperature (150 C) is increased to 180 C at a rate 3 C/min and then at 25 C/min to a final temperature of 320 C. The final temperature is maintained for 10 min. The carrier gas is $H_2$ at a linear velocity of 51 cm/sec. Detection is by flame ionization. Data analysis is performed using Agilent ChemStation software. Each sugar is quantified relative to the internal standard and detector responses were applied for each individual carbohydrate (calculated from standards run with each set of samples). Final carbohydrate concentrations are expressed on a tissue dry weight basis.

Protein Analysis

Protein contents are estimated by combustion analysis on a Thermo Finnigan Flash 1112EA combustion analyzer. Samples, 4-8 mg, weighed to an accuracy of 0.001 mg on a Mettler-Toledo MX5 micro balance are used for analysis. Protein contents were calculated by multiplying % N, determined by the analyzer, by 6.25. Final protein contents are expressed on a % tissue dry weight basis.

Additionally, the composition of intact single seed and bulk quantities of seed or powders derived from them, may be measured by near-infrared analysis. Measurements of moisture, protein and oil content in soy and moisture, protein, oil and starch content in corn can be measured when combined with the appropriate calibrations.

Example 21

Screening of Transgenic Maize Lines for Alterations in Oil, Protein, Starch and Soluble Carbohydrate Content Transgenic maize lines prepared by the method described in Examples 11 can be screened essentially as described in Example 16. Embryo-specific downregulation of PAE or PAE-like protein expression is expected to lead to an increase in seed oil content. In contrast overexpression of PAE or PAE-like protein in the endosperm is expected to lead to an increase in seed starch content.

Example 22

Seed Specific RNAi of PAE-Like Genes in Soybean

A plasmid vector (pKS426) for generation of transgenic soybean events that show seed specific down-regulation of the soy PAE-like genes with similarity to Glyma02g00930, Glyma10g27960, Glyma03g38430 and Glyma19g41030 genes was constructed.

Briefly plasmid DNA of applicants EST clone sfp1n.pk031.o15 corresponding to Glyma03g38430 (SEQ ID NO:44) was used in a PCR reaction with Primers SA156 (SEQ ID NO:75) and SA157 (SEQ ID NO:76). A PCR product of 0.3 kb was gel purified and is henceforth known as product A. Plasmid DNA of applicants EST clone sfp1n.pk032.f12 corresponding to Glyma10g27960 (SEQ ID NO:42) was used in a PCR reaction with Primers SA158 (SEQ ID NO:77) and SA159 (SEQ ID NO:78). A PCR product of 0.55 kb was gel purified and is henceforth known as product B. Plasmid DNA of applicants EST clone sfp1n.pk032.f12 corresponding to Glyma10g27960 (SEQ ID NO:42) was used also used in a PCR reaction with Primers SA158 (SEQ ID NO:76) and SA160 (SEQ ID NO:79). A PCR product of 0.3 kb was gel purified and is henceforth known as product C. A mixture of 100 ng of PCR products A and B was used in a PCR reaction using PCR primers SA156 and SA159. A PCR product of approximately 0.86 kb was gel purified and is henceforth known as product D. A mixture of 100 ng of PCR products C and A was used in a PCR reaction using PCR primers SA156 and SA160. A PCR product of approximately 0.6 kb was gel purified and is henceforth known as product F. PCR products D and F were independently cloned into pGEM T-Easy (Promega, Wis., USA) according to instructions of the manufacturer. Sequences of pGEM T-Easy D and pGEM T-Easy F are set forth as SEQ ID NOs: 80 and 81, respectively.

pGEM T-Easy D was digested with NotI and SpeI a 0.9 kb was gel-purified. pGEM T-Easy F was digested with NotI and SpeI a 0.62 kb was gel-purified. The gel purified product were ligated using T4 ligase and subsequently digested with NotI. A 1.5 kb Noti fragment was gel purified and cloned in the sense orientation behind the Kti promoter of soybean expression vector KS126 (PCT Publication No. WO 04/071467) linearized with the restriction enzyme NotI to give pKS426 (SEQ ID NO:82).

Plasmid DNA of pKS426 can be used to generate transgenic somatic embryos or seed of soybean using hygromycin selection as described in Example 14. Composition of transgenic somatic embryos or soybean seed generated with pKS423 determined as described in Example 17.

The plasmid vector pKS123 is described in PCT Application No. WO 02/08269. Plasmid pKS120 (SEQ ID NO: 83) is identical to pKS123 (supra) with the exception that the HindIII fragment containing Bcon/NotI/Phas3' cassette was removed.

Generation of Transgenic Somatic Embryos:

Soybean somatic embryos soybean tissue was co-bombarded as described below with a plasmid DNA of pKS120 or pKS426

Culture Conditions:

Soybean embryogenic suspension cultures (cv. Jack) were maintained in 35 mL liquid medium SB196 (infra) on a rotary shaker, 150 rpm, 26° C. with cool white fluorescent lights on 16:8 h day/night photoperiod at light intensity of 60-85 μE/m2/s. Cultures were subcultured every 7 days to two weeks by inoculating approximately 35 mg of tissue into 35 mL of fresh liquid SB196 (the preferred subculture interval is every 7 days).

Soybean embryogenic suspension cultures were transformed with the soybean expression plasmids by the method of particle gun bombardment (Klein et al., *Nature* 327:70 (1987)) using a DuPont Biolistic PDS1000/HE instrument (helium retrofit) for all transformations.

Soybean Embryogenic Suspension Culture Initiation:

Soybean cultures were initiated twice each month with 5-7 days between each initiation. Pods with immature seeds from available soybean plants 45-55 days after planting were picked, removed from their shells and placed into a sterilized magenta box. The soybean seeds were sterilized by shaking them for 15 min in a 5% Clorox solution with 1 drop of ivory soap (i.e., 95 mL of autoclaved distilled water plus 5 mL Clorox and 1 drop of soap, mixed well). Seeds were rinsed using 2 1-liter bottles of sterile distilled water and those less than 4 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time, secondary embryos were cut and placed into SB196 liquid media for 7 days.

Preparation of DNA for Bombardment:

Plasmid DNA of pKS120 or pKS426 were used for bombardment.

A 50 μL aliquot of sterile distilled water containing 1 mg of gold particles was added to 5 μL of a 1 μg/μL plasmid DNA solution 50 μL 2.5M $CaCl_2$ and 20 μL of 0.1 M spermidine. The mixture was pulsed 5 times on level 4 of a vortex shaker and spun for 5 sec in a bench microfuge. After a wash with 150 μL of 100% ethanol, the pellet was suspended by sonication in 85 μL of 100% ethanol. Five μL of DNA suspension was dispensed to each flying disk of the Biolistic PDS1000/HE instrument disk. Each 5 μL aliquot contained approximately 0.058 mg gold particles per bombardment (i.e., per disk).

Tissue Preparation and Bombardment with DNA:

Approximately 100-150 mg of 7 day old embryonic suspension cultures were placed in an empty, sterile 60×15 mm petri dish and the dish was placed inside of an empty 150×25 mm Petri dish. Tissue was bombarded 1 shot per plate with membrane rupture pressure set at 650 PSI and the chamber was evacuated to a vacuum of 27-28 inches of mercury. Tissue was placed approximately 2.5 inches from the retaining/stopping screen.

Selection of Transformed Embryos:

Transformed embryos were selected using hygromycin as the selectable marker. Specifically, following bombardment, the tissue was placed into fresh SB196 media and cultured as described above. Six to eight days post-bombardment, the SB196 is exchanged with fresh SB196 containing 30 mg/L hygromycin. The selection media was refreshed weekly. Four to six weeks post-selection, green, transformed tissue was observed growing from untransformed, necrotic embryogenic clusters. Isolated, green tissue was removed and inoculated into multi-well plates to generate new, clonally propagated, transformed embryogenic suspension cultures.

Embryo Maturation:

Transformed embryogenic clusters were cultured for one-three weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 □E/m$^2$s. After this time embryo clusters were removed to a solid agar media, SB166, for 1 week. Then subcultured to medium SB103 for 3 weeks. Alternatively, embryo clusters were removed to SB228 (SHaM) liquid media, 35 mL in 250 mL Erlenmeyer flask, for 2-3 weeks. Tissue cultured in SB228 was maintained on a rotary shaker, 130 rpm, 26° C. with cool white fluorescent lights on 16:8 h day/night photoperiod at light intensity of 60-85 μE/m2/s. During this period, individual embryos were removed from the clusters and screened for alterations in their fatty acid compositions as described supra.

Media Recipes:

| SB 196 - FN Lite liquid Proliferation Medium (per liter) | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| $KNO_3$ | 2.83 gm |
| $(NH_4)_2SO_4$ | 0.463 gm |
| Asparagine | 1.0 gm |
| Sucrose (1%) | 10 gm |

pH 5.8

| FN Lite Stock Solutions | | | |
|---|---|---|---|
| Stock # | | 1000 ml | 500 ml |
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 Solid Medium (Per Liter)

1 package MS salts (Gibco/BRL—Cat. No. 11117-066)
1 mL B5 vitamins 1000× stock
31.5 g Glucose
2 mL 2,4-D (20 mg/L final concentration)
pH 5.7
8 g TC agar SB199 Solid Medium (Per Liter)

1 package MS salts (Gibco/BRL—Cat. No. 11117-066)
1 mL B5 vitamins 1000× stock
30 g Sucrose
4 ml 2,4-D (40 mg/L final concentration)

pH 7.0
2 gm Gelrite

SB 166 Solid Medium (Per Liter)

1 package MS salts (Gibco/BRL—Cat. No. 11117-066)
1 mL B5 vitamins 1000× stock
60 g maltose
750 mg $MgCl_2$ hexahydrate
5 g Activated charcoal
pH 5.7
2 g Gelrite SB 103 Solid Medium (Per Liter)

1 package MS salts (Gibco/BRL—Cat. No. 11117-066)
1 mL B5 vitamins 1000× stock
60 g maltose
750 mg MgCl2 hexahydrate
pH 5.7
2 g Gelrite SB 71-4 Solid Medium (Per Liter)

1 bottle Gamborg's B5 salts w/sucrose (Gibco/BRL—Cat. No. 21153-036)
pH 5.7
5 g TC agar 2.4-D Stock Obtain premade from Phytotech Cat. No. D 295—concentration 1 mg/mL B5 Vitamins Stock (Per 100 mL)

Store aliquots at −20° C.
10 g Myo-inositol
100 mg Nicotinic acid
100 mg Pyridoxine HCl
1 g Thiamine
If the solution does not dissolve quickly enough, apply a low level of heat via the hot stir plate.

| SB 228- Soybean Histodifferentiation & Maturation (SHaM) (per liter) | |
|---|---|
| DDI H2O | 600 mL |
| FN-Lite Macro Salts for SHaM 10X | 100 mL |
| MS Micro Salts 1000x | 1 mL |
| MS FeEDTA 100x | 10 mL |
| CaCl 100x | 6.82 mL |
| B5 Vitamins 1000x | 1 mL |
| L-Methionine | 0.149 g |
| Sucrose | 30 g |
| Sorbitol | 30 g |
| Adjust volume to 900 mL | |
| pH 5.8 | |
| Autoclave | |
| Add to cooled media (≤30° C.): | |
| *Glutamine (Final conc. 30 mM) 4% | 110 mL |

*Note:
Final volume will be 1010 mL after glutamine addition.

Because glutamine degrades relatively rapidly, it may be preferable to add immediately prior to using media. Expiration 2 weeks after glutamine is added; base media can be kept longer w/o glutamine.

| FN-lite Macro for SHAM 10X- Stock #1 (per liter) | |
|---|---|
| $(NH_4)2SO_4$ (Ammonium Sulfate) | 4.63 g |
| $KNO_3$ (Potassium Nitrate) | 28.3 g |
| $MgSO_4$*$7H_20$ (Magnesium Sulfate Heptahydrate) | 3.7 g |
| $KH_2PO_4$ (Potassium Phosphate, Monobasic) | 1.85 g |
| Bring to volume | |
| Autoclave | |
| **MS Micro 1000X- Stock #2 (per 1 liter)** | |
| $H_3BO_3$ (Boric Acid) | 6.2 g |
| $MnSO_4$*$H_2O$ (Manganese Sulfate Monohydrate) | 16.9 g |
| ZnSO4*7H20 (Zinc Sulfate Heptahydrate) | 8.6 g |
| $Na_2MoO_4$*2H20 (Sodium Molybdate Dihydrate) | 0.25 g |
| $CuSO_4$*$5H_20$ (Copper Sulfate Pentahydrate) | 0.025 g |
| $CoCl_2$*$6H_20$ (Cobalt Chloride Hexahydrate) | 0.025 g |
| KI (Potassium Iodide) | 0.8300 g |
| Bring to volume | |
| Autoclave | |
| **FeEDTA 100X- Stock #3 (per liter)** | |
| $Na_2EDTA$* (Sodium EDTA) | 3.73 g |
| $FeSO_4$*$7H_20$ (Iron Sulfate Heptahydrate) | 2.78 g |
| *EDTA must be completely dissolved before adding iron. | |
| Bring to Volume | |
| Solution is photosensitive. Bottle(s) should be wrapped in foil to omit light. | |
| Autoclave | |
| **Ca 100X- Stock #4 (per liter)** | |
| $CaCl_2$*$2H_20$ (Calcium Chloride Dihydrate) | 44 g |
| Bring to Volume | |
| Autoclave | |
| **B5 Vitamin 1000X- Stock #5 (per liter)** | |
| Thiamine*HCl | 10 g |
| Nicotinic Acid | 1 g |
| Pyridoxine*HCl | 1 g |
| Myo-Inositol | 100 g |
| Bring to Volume | |
| Store frozen | |
| **4% Glutamine- Stock #6 (per liter)** | |
| DDI water heated to 30° C. | 900 ml |
| L-Glutamine | 40 g |
| Gradually add while stirring and applying low heat. | |
| Do not exceed 35° C. | |
| Bring to Volume | |
| Filter Sterilize | |
| Store frozen * | |

* Note:
Warm thawed stock in 31° C. bath to fully dissolve crystals.

Oil Analysis:

Oil content of somatic embryos is measured using NMR. Briefly lyophilized soybean somatic embryo tissue is pulverized in genogrinder vial as described previously (Example 2). 20-200 mg of tissue powder were transferred to NMR tubes. Oil content of the somatic embryo tissue powder is calculated from the NMR signal as described in Example 2.

Example 23

Seed-Preferred Silencing of PAE-Like Genes in Soybean Using Artificial miRNAs The example describes the construction of a plasmid vector for soybean transformation. The plasmid provides seed-preferred expression of an artificial microRNA that targets soybean genes Glyma02g00930 (SEQ ID NO:41), Glyma10g27960 (SEQ ID NO:43), Glyma03g38430 (SEQ ID NO:45) and Glyma19g41030 (SEQ ID NO:47). Soybean somatic embryos transformed with this plasmid construct show increased oil content compared to embryos that harbor a control plasmid.

A vector was made to silence PAE-like genes using an artificial microRNA largely as described in U.S. patent application Ser. No. 12,335,717, filed Dec. 16, 2008. The following briefly explains the procedure.

Design of Artificial MicroRNA Sequences

Artificial microRNAs (amiRNAs) that would have the ability to silence the desired target genes were designed largely according to rules described in Schwab R, et al. (2005) *Dev Cell* 8: 517-27. To summarize, microRNA sequences are 21 nucleotides in length, start at their 5'-end with a "U", display 5' instability relative to their star sequence which is achieved by including a C or G at position 19, and their 10th nucleotide is either an "A" or an "U". An additional requirement for artificial microRNA design was that the amiRNA have a high free delta-G as calculated using the ZipFold algorithm (Markham, N. R. & Zuker, M. (2005) *Nucleic Acids Res.* 33: W577-W581.) The DNA sequence corresponding to the amiRNA that was used to silence esterase is represented by SEQ ID NO: 88).

Design of Artificial Star Sequences

"Star sequences" are those that base pair with the amiRNA sequences, in the precursor RNA, to form imperfect stem structures. To form a perfect stem structure the star sequence would be the exact reverse complement of the amiRNA. The soybean precursor sequence as described in "Novel and nodulation-regulated microRNAs in soybean roots" Subramanian S, Fu Y, Sunkar R, Barbazuk W B, Zhu J K, Yu O BMC Genomics. 9:160(2008) and accessed on mirBase (Conservation and divergence of microRNA families in plants" Dezulian T, Palatnik J F, Huson D H, Weigel D http://genomebiology.com/2005/6/11/p13 (2005)) was folded using mfold (M. Zuker (2003) *Nucleic Acids Res.* 31: 3406-15; and D. H. Mathews, J. et al. (1999) *J. Mol. Biol.* 288: 911-940). The miRNA sequence was then replaced with the amiRNA sequence and the endogenous star sequence was replaced with the exact reverse complement of the amiRNA. Changes in the artificial star sequence were introduced so that the structure of the stem would remain the same as the endogenous structure. The altered sequence was then folded with mfold and the original and altered structures were compared by eye. If necessary, further alterations to the artificial star sequence were introduced to maintain the original structure. The DNA sequences corresponding to the artificial star sequences that were used to silence the desired target genes are shown in SEQ ID NO:89.

Conversion of Genomic MicroRNA Precursors to Artificial MicroRNA Precursors

Genomic miRNA precursor genes can be converted to amiRNAs using overlapping PCR and the resulting DNAs are completely sequenced. These DNAs are then cloned downstream of an appropriate promoter in a vector capable of soybean transformation.

Alternatively, amiRNAs can be synthesized commercially, for example by Codon Devices, (Cambridge, Mass.). The synthesized DNA is then cloned downstream of an appropriate promoter in a vector capable of soybean transformation.

Alternatively, amiRNAs can be constructed using In-Fusion™ technology (Clontech, Mountain View, Calif.).

Conversion of Genomic MicroRNA Precursors to Artificial MicroRNA Precursors

Genomic miRNA precursor genes were converted to amiRNA precursors using In-Fusion™ as described above. In brief, the microRNA 396b precursor (SEQ ID NO:90) was altered to include Pme I sites immediately flanking the star and microRNA sequences to form the in-fusion ready microRNA 396b precursor (SEQ ID NO:91). This sequence was cloned into the Not I site of KS126 to form the in-fusion ready microRNA 396b-KS126 plasmid (SEQ ID NO:92). KS126 is described in PCT Publication No. WO 04/071467.

The microRNA 396b precursor (SEQ ID NO:90) was used as a PCR template. The primers (396b PAE-like primA, SEQ ID NO:93 and 396b PAE-like primB, SEQ ID NO:94) were designed according to the protocol provided by Clontech and do not leave any footprint of the Pme I sites after the In-Fusion recombination reaction. The sequence of resulting amplified DNAs is shown in SEQ ID NO:95.

The sequence of SEQ ID NO:95 was recombined into the in-fusion ready microRNA 396b-KS126 plasmid (SEQ ID NO:92) digested with Pme I. This was done using protocols provided with the In-Fusion™ kit. The resulting plasmid is shown in SEQ ID NO:96.

Plasmid DNA of 396b-PAE-like (SEQ ID NO: 96) and a control plasmid KS120 (SEQ ID NO:83) was used for transformation soybean cell suspensions and subsequent generation of soybean somatic embryos as described in Example 22. Oil content of soybean somatic embryos was measured by NMR and is summarized in Table 25.

TABLE 25

Oil content of soybean somatic embryos generate with a control plasmid (KS120) and 396b- PAE-like

| plasmid | event name | % oil (NMR) | all event average % oil |
|---|---|---|---|
| KS120 | MSE2698-19 | 8.6 | |
| | MSE2698-12 | 6.2 | |
| | MSE2698-9 | 5.0 | |
| | MSE2698-21 | 5.0 | |
| | MSE2698-15 | 5.0 | |
| | MSE2698-25 | 4.9 | |
| | MSE2698-1 | 4.8 | |
| | MSE2698-18 | 4.6 | |
| | MSE2698-3 | 4.3 | |
| | MSE2698-26 | 4.3 | |
| | MSE2698-8 | 4.2 | |
| | MSE2698-2 | 4.0 | |
| | MSE2698-7 | 3.9 | |
| | MSE2698-4 | 3.9 | |
| | MSE2698-14 | 3.8 | |
| | MSE2698-16 | 3.8 | |
| | MSE2698-5 | 3.7 | |
| | MSE2698-24 | 3.6 | |
| | MSE2698-20 | 3.5 | |
| | MSE2698-23 | 3.5 | |
| | MSE2698-22 | 3.4 | |
| | MSE2698-13 | 3.1 | |
| | MSE2698-11 | 3.1 | |
| | MSE2698-6 | 3.0 | |
| | MSE2698-17 | 2.6 | |
| | MSE2698-10 | 2.4 | 4.1 |
| 396b-ESTERASE | MSE2701-9 | 8.3 | |
| | MSE2701-1 | 7.5 | |
| | MSE2701-20 | 7.2 | |
| | MSE2701-11 | 7.1 | |
| | MSE2701-19 | 8.5 | |
| | MSE2701-30 | 6.3 | |
| | MSE2701-10 | 6.3 | |
| | MSE2701-8 | 5.9 | |
| | MSE2701-15 | 5.5 | |
| | MSE2701-29 | 5.5 | |
| | MSE2701-5 | 5.5 | |
| | MSE2701-13 | 5.4 | |
| | MSE2701-23 | 5.4 | |
| | MSE2701-16 | 5.3 | |
| | MSE2701-18 | 5.1 | |

TABLE 25-continued

Oil content of soybean somatic embryos generate with a control plasmid (KS120) and 396b- PAE-like

| plasmid | event name | % oil (NMR) | all event average % oil |
|---|---|---|---|
| | MSE2701-27 | 4.9 | |
| | MSE2701-21 | 4.9 | |
| | MSE2701-12 | 4.7 | |
| | MSE2701-28 | 4.4 | |
| | MSE2701-22 | 4.4 | |
| | MSE2701-3 | 4.3 | |
| | MSE2701-6 | 4.3 | |
| | MSE2701-2 | 4.2 | |
| | MSE2701-24 | 3.8 | |
| | MSE2701-26 | 3.7 | |
| | MSE2701-4 | 3.4 | |
| | MSE2701-7 | 3.3 | |
| | MSE2701-17 | 3.0 | |
| | MSE2701-14 | 2.8 | |
| | MSE2701-25 | 2.2 | 5.0 |

Example 24

Compositional Analysis of *Arabidopsis* Events Transformed with DNA Constructs for Seed Preferred Expression of PAE-Like Genes The example describes seed composition of transgenic events gene generated with pKR1478-PAE (SEQ ID NO:14). It demonstrates that transformation with DNA constructs for seed-preferred overexpression of genes encoding PAE-like genes leads to reduced oil content that is accompanied by an increase in seed storage protein content and (to a smaller extend an increase) in soluble carbohydrates.

T4 seed of transgenic events described in Example 4, Table 10 were subjected to compositional analysis of protein and soluble carbohydrates as described in Example 4.

The findings are summarized in Table 26.

TABLE 26

Seed composition of *arabidopsis* events transformed with DNA constructs for overexpression of PAE -like genes

| Genotype | Bar code ID | Oil (%, NMR) | Protein % | fructose (μg mg$^{-1}$ seed) | glucose (μg mg$^{-1}$ seed) |
|---|---|---|---|---|---|
| pKR1478-PAE (T4) | 45672 | 34.2 | 21.9 | 0.4 | 6.6 |
| WT | | 43.2 | 16.8 | 0.3 | 3.8 |
| | Δ TG/WT % | −20.8 | 30.0 | 9.1 | 72.9 |

| Genotype | Bar code ID | sucrose (μg mg$^{-1}$ seed) | raffinose (μg mg$^{-1}$ seed) | stachyose (μg mg$^{-1}$ seed) | total soluble CHO (μg mg$^{-1}$ seed) |
|---|---|---|---|---|---|
| pKR1478-PAE (T4) | 45672 | 16.2 | 0.5 | 1.2 | 25.1 |
| WT | | 15.8 | 0.4 | 1.6 | 22.2 |
| | Δ TG/WT % | 2.2 | 4.7 | −24.3 | 13.4 |

| Genotype | Bar code ID | Oil (%, NMR) | Protein % | fructose (μg mg$^{-1}$ seed) | glucose (μg mg$^{-1}$ seed) |
|---|---|---|---|---|---|
| pKR1478-PAE (T4) | 45642 | 35.3 | 21.9 | 0.2 | 4.1 |
| WT | | 39.8 | 18.0 | 0.3 | 4.0 |
| | Δ TG/WT % | −11.3 | 22.1 | −26.2 | 4.6 |

TABLE 26-continued

Seed composition of *arabidopsis* events transformed with DNA constructs for overexpression of PAE -like genes

| Genotype | Bar code ID | sucrose (μg mg$^{-1}$ seed) | raffinose (μg mg$^{-1}$ seed) | stachyose (μg mg$^{-1}$ seed) | total soluble CHO (μg mg$^{-1}$ seed) |
|---|---|---|---|---|---|
| pKR1478-PAE (T4) | 45642 | 15.1 | 0.6 | 2.3 | 24.8 |
| WT | | 16.6 | 0.4 | 1.7 | 23.4 |
| | Δ TG/WT % | −9.1 | 34.9 | 36.6 | 6.0 |

Table 26 demonstrates that the oil decrease associated with the presence of the pKR1478-PAE transgene (SEQ ID NO:14) is accompanied by an increase in seed protein content and a small increase in soluble carbohydrate content. The latter was calculated by summarizing the content of pinitol, sorbitol, fructose, glucose, myo-Inositol, sucrose, raffinose and stachyose.

Example 25

Compositional Analysis of *Arabidopsis* Events Transformed with DNA Constructs for Seed-Preferred Silencing of PAE-Like Genes The example describes seed composition of transgenic events gene generated with pKR1481-PAE (SEQ ID NO:34). It demonstrates that transformation with DNA constructs for seed-preferred overexpression of genes encoding PAE-like genes leads to increased oil content that is accompanied by decrease in seed storage protein content and, to a smaller extend, an decrease in soluble carbohydrates.

T4 seed of transgenic events described in Example 5, Table 12 were subjected to compositional analysis of protein and soluble carbohydrates as described in Example 4.

The findings are summarized in Table 27.

TABLE 27

Seed composition of *arabidopsis* events transformed with DNA constructs for seed preferred silencing of PAE -like genes

| Genotype | Bar code ID | Oil (%, NMR) | Protein % | fructose (μg mg$^{-1}$ seed) | glucose (μg mg$^{-1}$ seed) |
|---|---|---|---|---|---|
| pKR1481-PAE (T4) | K46661 | 45.3 | 15.9 | 0.3 | 4.0 |
| WT | | 42.5 | 18.0 | 0.3 | 4.2 |
| | Δ TG/WT % | 6.6 | −11.7 | 7.5 | −5.8 |

| Genotype | Bar code ID | sucrose (μg mg$^{-1}$ seed) | raffinose (μg mg$^{-1}$ seed) | stachyose (μg mg$^{-1}$ seed) | total soluble CHO (μg mg$^{-1}$ seed) |
|---|---|---|---|---|---|
| pKR1481-PAE (T4) | K46661 | 15.6 | 0.4 | 1.5 | 21.9 |
| WT | | 16.3 | 0.4 | 1.7 | 23.2 |
| | Δ TG/WT | −4.5 | −9.1 | −13.9 | −5.3 |

TABLE 27-continued

Seed composition of *arabidopsis* events transformed with DNA constructs for seed preferred silencing of PAE -like genes

| Genotype | % Bar code ID | Oil (%, NMR) | Protein % | fructose (μg $mg^{-1}$ seed) | glucose (μg $mg^{-1}$ seed) |
|---|---|---|---|---|---|
| pKR1481-PAE (T4) | K46663 | 44.8 | 15.9 | 0.3 | 3.0 |
| WT | | 42.1 | 18.2 | 0.3 | 4.6 |
| | Δ TG/WT % | 6.4 | −12.5 | −7.7 | −35.4 |

| Genotype | Bar code ID | sucrose (μg $mg^{-1}$ seed) | raffinose (μg $mg^{-1}$ seed) | stachyose (μg $mg^{-1}$ seed) | total soluble CHO (μg $mg^{-1}$ seed) |
|---|---|---|---|---|---|
| pKR1481-PAE (T4) | K46663 | 15.3 | 0.4 | 1.4 | 20.5 |
| WT | | 16.1 | 0.4 | 1.7 | 23.3 |
| | Δ TG/WT % | −4.8 | −11.1 | −18.4 | −11.8 |

Table 27 demonstrates that the oil increase associated with the presence of the pKR1481-PAE transgene (SEQ ID NO:28) is accompanied by a reduction in seed protein content and a small reduction in soluble carbohydrate content. The latter was calculated by summarizing the content of pinitol, sorbitol, fructose, glucose, myo-Inositol, sucrose, raffinose and stachyose.

Example 26

Characterization of *Arabidopsis* Events Transformed with a DNA Construct that Contains an Intron-Less Inverted Repeat Construct Derived from Sequences of the At2g46930 (PAE) Gene A plasmid vector lo125 for generation of transgenic *arabidopsis* events that show seed specific down-regulation of the PAE gene corresponding to At2g46930 was constructed.

Briefly, plasmid DNA isolated from a pooled *Arabidopsis* cDNA library was used in two PCR reactions with either primers SA335 (SEQ ID NO:97) and SA336 (SEQ ID NO:98) or SA320 (SEQ ID NO:99) and SA319 (SEQ ID NO:100). A PCR product of 1.18 kb was generated with SA335 (SEQ ID NO:97) and SA336 (SEQ ID NO:98). It was gel purified and is henceforth known as product A. A PCR product of 0.7 kb was generated with SA320 (SEQ ID NO:99) and SA319 (SEQ ID NO:100). It was gel purified and is henceforth known as product B. PCR products A and B were cloned into pGEM T easy using instructions of the manufacturer which generated plasmids pGEM T easy A (SEQ ID NO:101) and pGEM T easy B (SEQ ID NO: 102). A restriction fragment of 1.18 bp was excised from pGEM T easy A with NotI and PstI and cloned into pBluesript SK+ (Stratagene, USA). The resulting plasmid pBluescript-A (SEQ ID NO:103) was linearized with PstI and EcoRI and ligated to a 0.7 kb fragment excised from pGEM T easy B with PstI and EcoRI. A fragment of 1.9 kb was excised from pBluescript-AB (SEQ ID NO:104) with NotI and ligated to NotI linearized KS442 (SEQ ID NO:105) to give KS442-AB (SEQ ID NO: 106).

Prior to this KS442 was constructed as follows. KS121 (PCT Application No. WO 02/00904) was digested with BamHI and XmnI and ligated to a fragment comprising the soybean GYI promoter. The GYI promoter was obtained from KS349 (US 20080295204 A1, published Nov. 27, 2008). Briefly, KS349 was digested with NcoI, overhangs were filled in with Klenow DNA polymerase (NEB, USA) according to manufacturer instructions. The linearized KS349 plasmid was digested with BamHI thus releasing the GYI promoter used for construction of KS442 (SEQ ID NO:105).

KS442-AB (SEQ ID NO:106) was digested with AscI and a DNA fragment of 1.9 kb was ligated to Asc-linearized pKR92 (SEQ ID NO:8) to give lo125 (SEQ ID NO:107).

Plasmid DNA of lo125 (SEQ ID NO:107) was used for *agrobacterium*-mediated transformation of *Arabidopsis* as described in Example 4. A total of 22 events were generated with lo125. T1 plants of these events were grown to maturity alongside WT control plants. Seed were harvested and oil content was measured by NMR as described in Example 2. The results of this analysis are summarized in Table 28.

TABLE 28

Seed oil content of T1 plants generated with binary vector lo125 for seed-specific silencing of At2g46930

| construct/genotype | event ID | % oil | oil content % of WT avg | avg oil content % of WT |
|---|---|---|---|---|
| ARALO 125 | K60334 | 41.8 | 114.1 | |
| ARALO 125 | K60333 | 41.2 | 112.5 | |
| ARALO 125 | K60344 | 40.3 | 110.0 | |
| ARALO 125 | K60345 | 40.1 | 109.6 | |
| ARALO 125 | K60332 | 39.0 | 106.7 | |
| ARALO 125 | K60351 | 38.5 | 105.3 | |
| ARALO 125 | K60338 | 38.5 | 105.2 | |
| ARALO 125 | K60342 | 38.4 | 105.0 | |
| ARALO 125 | K60346 | 38.3 | 104.7 | |
| ARALO 125 | K60341 | 37.8 | 103.4 | |
| ARALO 125 | K60343 | 37.6 | 102.8 | |
| ARALO 125 | K60352 | 37.4 | 102.2 | |
| ARALO 125 | K60340 | 37.3 | 102.0 | |
| ARALO 125 | K60348 | 37.1 | 101.3 | |
| ARALO 125 | K60335 | 37.0 | 101.3 | |
| ARALO 125 | K60339 | 36.8 | 100.6 | |
| ARALO 125 | K60349 | 36.8 | 100.6 | |
| ARALO 125 | K60336 | 36.7 | 100.4 | |
| ARALO 125 | K60350 | 36.6 | 100.1 | |
| ARALO 125 | K60353 | 36.4 | 99.6 | |
| ARALO 125 | K60337 | 35.2 | 96.1 | |
| ARALO 125 | K60347 | 34.5 | 94.2 | 103.5 |
| col | | 38.7 | | |
| col | | 37.5 | | |
| col | | 37.4 | | |
| col | | 37.1 | | |
| col | | 36.7 | | |
| col | | 36.4 | | |
| col | | 34.5 | WT avg % oil | |
| col | | 34.4 | 36.6 | |

T2 seed of events K60333, K60344, K60345 and K60332 were germinated on selective plant growth media containing kanamycin, planted in soil alongside WT plants and grown to maturity. T3 seed oil content was measured by NMR. The results of this analysis are summarized in Table 29.

TABLE 29

Seed oil content of T2 plants generated with binary vector lo125 for seed preferred silencing of At2g46930

| event ID/genotype | Line ID | % oil | oil content % of WT avg | avg oil content % of WT |
|---|---|---|---|---|
| K60333 | K63263 | 46.4 | 112.5 | |
| | K63258 | 46.4 | 112.4 | |
| | K63264 | 45.5 | 110.4 | |
| | K63266 | 45.3 | 109.9 | |
| | K63257 | 45.0 | 109.1 | |
| | K63265 | 45.0 | 109.1 | |
| | K63268 | 44.9 | 108.8 | |
| | K63270 | 44.9 | 108.8 | |
| | K63255 | 44.8 | 108.5 | |
| | K63252 | 44.6 | 108.2 | |
| | K63259 | 44.0 | 106.8 | |
| | K63262 | 44.0 | 106.6 | |
| | K63261 | 43.8 | 106.3 | |
| | K63260 | 43.8 | 106.3 | |
| | K63256 | 43.7 | 106.1 | |
| | K63269 | 43.7 | 106.0 | |
| | K63272 | 43.6 | 105.8 | |
| | K63275 | 43.4 | 105.3 | |
| | K63253 | 43.2 | 104.7 | |
| | K63254 | 42.9 | 104.2 | |
| | K63273 | 42.7 | 103.6 | |
| | K63267 | 42.6 | 103.2 | |
| | K63271 | 41.7 | 101.1 | |
| | K63274 | 41.4 | 100.5 | 106.8 |
| Col | K63286 | 43.8 | | |
| | K63278 | 42.9 | | |
| | K63284 | 42.7 | | |
| | K63277 | 41.9 | | |
| | K63276 | 41.6 | | |
| | K63282 | 41.2 | | |
| | K63279 | 40.9 | | |
| | K63281 | 40.6 | | |
| | K63283 | 40.1 | | |
| | K63280 | 39.8 | WT avg % oil | |
| | K63285 | 38.1 | 41.2 | |
| K60344 | K62351 | 43.1 | 109.2 | |
| | K62352 | 43.1 | 109.1 | |
| | K62338 | 42.9 | 108.7 | |
| | K62335 | 42.9 | 108.6 | |
| | K62354 | 42.8 | 108.5 | |
| | K62344 | 42.6 | 107.9 | |
| | K62355 | 42.5 | 107.7 | |
| | K62347 | 42.3 | 107.3 | |
| | K62346 | 42.3 | 107.2 | |
| | K62339 | 42.3 | 107.2 | |
| | K62333 | 42.1 | 106.6 | |
| | K62340 | 42.0 | 106.4 | |
| | K62348 | 41.7 | 105.6 | |
| | K62342 | 41.6 | 105.4 | |
| | K62336 | 41.5 | 105.1 | |
| | K62334 | 41.3 | 104.7 | |
| | K62353 | 41.2 | 104.5 | |
| | K62337 | 41.1 | 104.1 | |
| | K62350 | 41.0 | 104.0 | |
| | K62356 | 40.5 | 102.5 | |
| | K62349 | 40.3 | 102.1 | |
| | K62341 | 39.6 | 100.3 | |
| | K62343 | 37.7 | 95.5 | |
| | K62345 | 37.1 | 93.9 | 105.1 |
| Col | K62357 | 42.4 | | |
| | K62366 | 42.2 | | |
| | K62359 | 40.5 | | |
| | K62367 | 39.7 | | |
| | K62362 | 39.5 | | |
| | K62363 | 39.3 | | |
| | K62365 | 39.1 | | |
| | K62358 | 39.0 | | |
| | K62368 | 38.6 | | |
| | K62361 | 38.5 | | |
| | K62360 | 38.4 | WT avg % oil | |
| | K62364 | 36.3 | 39.5 | |
| K60345 | K63204 | 45.1 | 110.0 | |
| | K63206 | 45.0 | 109.8 | |

TABLE 29-continued

Seed oil content of T2 plants generated with binary vector lo125 for seed preferred silencing of At2g46930

| event ID/genotype | Line ID | % oil | oil content % of WT avg | avg oil content % of WT |
|---|---|---|---|---|
| | K63193 | 44.4 | 108.4 | |
| | K63198 | 44.4 | 108.4 | |
| | K63188 | 44.0 | 107.4 | |
| | K63186 | 43.9 | 107.3 | |
| | K63191 | 43.8 | 107.0 | |
| | K63205 | 43.7 | 106.7 | |
| | K63199 | 43.5 | 106.3 | |
| | K63196 | 43.5 | 106.2 | |
| | K63195 | 43.3 | 105.7 | |
| | K63190 | 43.0 | 105.0 | |
| | K63207 | 43.0 | 105.0 | |
| | K63197 | 42.8 | 104.5 | |
| | K63201 | 42.7 | 104.2 | |
| | K63203 | 42.2 | 103.1 | |
| | K63192 | 42.2 | 103.0 | |
| | K63189 | 42.1 | 102.7 | |
| | K63208 | 41.7 | 102.0 | |
| | K63202 | 41.7 | 101.9 | |
| | K63200 | 41.4 | 101.1 | |
| | K63187 | 40.1 | 98.0 | |
| | K63194 | 39.1 | 95.4 | 104.7 |
| Col | K63210 | 44.9 | | |
| | K63212 | 42.6 | | |
| | K63216 | 42.1 | | |
| | K63217 | 42.0 | | |
| | K63218 | 41.8 | | |
| | K63215 | 41.5 | | |
| | K63211 | 39.1 | | |
| | K63209 | 38.6 | | |
| | K63213 | 38.5 | WT avg % oil | |
| | K63214 | 38.4 | 40.9 | |
| K60332 | K63173 | 46.6 | 112.7 | |
| | K63154 | 45.2 | 109.4 | |
| | K63153 | 44.7 | 108.1 | |
| | K63172 | 44.1 | 106.7 | |
| | K63171 | 44.0 | 106.4 | |
| | K63163 | 43.9 | 106.3 | |
| | K63168 | 43.9 | 106.2 | |
| | K63157 | 43.8 | 105.6 | |
| | K63152 | 43.5 | 105.2 | |
| | K63158 | 43.5 | 105.1 | |
| | K63166 | 43.1 | 104.2 | |
| | K63167 | 42.9 | 103.7 | |
| | K63159 | 42.7 | 103.4 | |
| | K63169 | 42.7 | 103.3 | |
| | K63156 | 42.5 | 102.8 | |
| | K63162 | 42.3 | 102.3 | |
| | K63160 | 41.6 | 100.7 | |
| | K63165 | 41.6 | 100.6 | |
| | K63170 | 41.4 | 100.2 | |
| | K63161 | 41.0 | 99.2 | |
| | K63155 | 40.0 | 96.9 | 104.2 |
| Col | K63185 | 43.9 | | |
| | K63177 | 43.6 | | |
| | K63181 | 43.1 | | |
| | K63180 | 42.2 | | |
| | K63176 | 42.0 | | |
| | K63178 | 41.4 | | |
| | K63183 | 41.3 | | |
| | K63175 | 41.0 | | |
| | K63174 | 40.5 | | |
| | K63182 | 40.3 | | |
| | K63179 | 39.8 | WT avg % oil | |
| | K63184 | 36.7 | 41.3 | |

Tables 28 and 29 show that silencing of PAE genes such as At2g46930 using hairpin constructs that contain an intron-less inverted repeat lead to a heritable oil increase. In T3 lines that still segregate for the lo125 derived T-DNA insertion the average oil content was between 4.2 and 6.8% higher than that of WT control plants.

What is claimed is:

1. A method for producing a transgenic soybean plant wherein the seeds of said plant exhibit decreased oil content when compared to seeds from a control plant not comprising said recombinant DNA construct, the method comprising:

(a) transforming a soybean plant cell with a recombinant DNA construct comprising a polynucleotide operably linked to at least one regulatory sequence, wherein the polynucleotide encodes a polypeptide having an amino acid sequence of at least 95% sequence identity, based on the Clustal V method of alignment, when compared to SEQ ID NOs:42, 44, 46, or 48; and (b) regenerating a soybean plant from the transformed plant cell wherein said plant comprises in its genome the recombinant DNA construct, and seed obtained from said plant exhibit decreased oil content when compared to seeds from a control plant not comprising said recombinant DNA construct.

2. A method for producing a transgenic soybean seed having an increased or decreased oil content when compared to a seed from a control plant not comprising said recombinant DNA construct, the method comprising:

(a) transforming a soybean plant cell with a recombinant DNA construct comprising a polynucleotide operably linked to at least one regulatory sequence, wherein the polynucleotide encodes a polypeptide having an amino acid sequence of at least 95% sequence identity, based on the Clustal V method of alignment, when compared to SEQ ID NOs:42, 44, 46, or 48; or (a') transforming a plant cell with a recombinant DNA construct comprising a seed-specific or seed-preferred promoter operably linked to: (i) all or part of the nucleotide sequence set forth in SEQ ID NOs:41, 43, 45, or 47, or (ii) the full-length complement of (i): wherein (i) or (ii) is 21 or more contiguous nucleotides in length sufficient to inhibit expression of SEQ ID NOs:42, 44, 46 or 48 in a transgenic soybean plant;

(b) regenerating a transgenic plant from the transformed plant cell of (a) or (a'); and (c) selecting a transgenic plant that produces a transgenic soybean seed having an increased or decreased oil content when compared to a seed from a control plant not comprising said recombinant DNA construct.

3. A transgenic soybean plant comprising a recombinant DNA construct, the recombinant DNA construct comprising:

(a) a polynucleotide operably linked to at least one regulatory element, wherein said polynucleotide encodes a polypeptide having an amino acid sequence of at least 95% sequence identity, based on the Clustal V method of alignment, when compared to SEQ ID NO: 42, 44, 46, or 48; or (b) the full complement of the nucleotide sequence of (a), wherein seed obtained from said transgenic soybean plant has decreased oil content when compared to a seed from a control plant not comprising said recombinant DNA construct.

4. A transgenic soybean seed comprising a recombinant DNA construct, the recombinant construct comprising a suppression construct comprising at least one regulatory element operably linked to:

all or part of (A) a nucleic acid sequence of SEQ ID NOs:41, 43, 45, or 47, which part is 21 or more contiguous nucleotides in length, or (B) a full complement of the nucleic acid sequence of (A); wherein said suppression construct inhibits expression of at least one of SEQ ID NOs: 42, 44, 46 or 48 in the soybean seed, wherein said soybean seed has an increased oil content when compared to a seed from a control plant not comprising said recombinant DNA construct, and wherein said regulatory element comprises a seed-specific or seed-preferred promoter.

5. The transgenic seed of claim 4, wherein said transgenic seed has an increased oil content of at least 4% when compared to the oil content of the seed of the control plant.

6. The method of claim 1, wherein the at least one regulatory element is a seed-specific or seed-preferred promoter.

7. A product or by-product obtained from the transgenic seed of claim 4 and comprising at least one cell of the seed, which cell comprises the recombinant construct.

8. The soybean seed obtained from the plant produced by the method claim 1, wherein the seed comprises the recombinant construct.

9. The soybean seed obtained by the method of claim 2, wherein the seed comprises the recombinant construct in step (a).

10. The soybean seed obtained by the method of claim 2, wherein the seed comprises the recombinant construct in step (a').

11. The soybean seed of claim 10, wherein the seed has an increased oil content of at least 4% when compared to the oil content of the seed of the control plant.

12. The method of claim 2, wherein the at least one regulatory sequence is a seed-specific or seed-preferred promoter.

* * * * *